United States Patent
Haeggström et al.

(10) Patent No.: US 7,590,494 B1
(45) Date of Patent: Sep. 15, 2009

(54) DRUG DESIGN BASED ON THE STRUCTURE OF LTA$_4$ HYDROLASE

(76) Inventors: Jesper Z. Haeggström, Valhallavägen 145, SE-115 31 Stockholm (SE); Pär Nordlund, Gruvbacken 2, SE-116 34 Stockholm (SE); Marjolein Thunissen, Svinningevägen 26, SE-184 92 Åkersberga (SE)

( * ) Notice: Subject to any disclaimer, the term of this patent is extended or adjusted under 35 U.S.C. 154(b) by 0 days.

(21) Appl. No.: 09/914,451

(22) PCT Filed: Feb. 28, 2000

(86) PCT No.: PCT/SE00/00384
§ 371 (c)(1),
(2), (4) Date: Dec. 20, 2001

(87) PCT Pub. No.: WO00/50577
PCT Pub. Date: Aug. 31, 2000

Related U.S. Application Data

(60) Provisional application No. 60/122,110, filed on Feb. 26, 1999.

(30) Foreign Application Priority Data

Feb. 26, 1999 (SE) .................................. 9900722

(51) Int. Cl.
*G01N 31/00* (2006.01)
*C12N 9/14* (2006.01)
*G06G 7/58* (2006.01)

(52) U.S. Cl. ........................... 702/27; 435/195; 703/11

(58) Field of Classification Search ....................... None
See application file for complete search history.

(56) References Cited

U.S. PATENT DOCUMENTS 5,579,250 A * 11/1996 Balaji et al. .................... 702/19
2004/0137518 A1 * 7/2004 Lambert et al. .............. 435/7.1

OTHER PUBLICATIONS

Minami et al., Molecular Cloning of a cDNA Coding for Human Leukotriene A4 Hydrolase, 1987, The Journal of Biological Chemistry, vol. 262, pp. 13873-13876.*

Minami et al., Expression of human leukotriene A4 hydrolase cDNA in *Escherichia coli*, 1988, FEBS Letters, vol. 229, pp. 279-282.*

(Continued)

*Primary Examiner*—Suzanne M. Noakes
*Assistant Examiner*—Alexander D Kim
(74) *Attorney, Agent, or Firm*—Lahive & Cockfield, LLP; Giulio A. DeConti, Jr., Esq.; Maneesh Gulati, Esq.

(57) ABSTRACT

The present invention relates to an isolated leukotriene A$_4$ (LTA$_4$) hydrolase, which LTA$_4$ hydrolase is present in its naturally occurring three dimensional form. It is the first three-dimensional structure of any protein component of the leukotriene cascade and enables a description of the structural basis and molecular mechanisms for the two catalytic activities of LTA$_4$ hydrolase. Further, the invention also relates to LTA$_4$ hydrolase complexed with an inhibitor. The structural information provided by the present invention will make possible rational design of enzyme inhibitors, which may be developed into clinically useful anti-inflammatory drugs.

7 Claims, 14 Drawing Sheets

OTHER PUBLICATIONS

Kuntz et al. Science, vol. 257, pp. 1078-1082, 1992.*

Giege et al., Crystallogenesis of Biological Macromolecule: Facts and Perspectives, (1994) Acta Cryst., vol. D50, pp. 339-350.*

Branden et al., Introduction to Protein Structure, Second Edition, Garland Publishing Inc., New York, (1999) pp. 374-375 and 382.*

Drenth, Principles of Protein X-ray Crystallography (1995) Springer, New York, p. 1.*

Kierzek et al., Models of protein crystal growth, (2001) Biophys Chem, 91:1-20.*

Wiencek, New Strategies for Protein Crystal Growth, (1999) Ann Rev Biomed Eng., 1:505-534.*

Andberg, M. et al. "Mutation of tyrosine 383 in leukotriene $A_4$ hydrolase allows conversion of leukotriene $A_4$ into 5S,6S-dihydroxy-7,9-trans-11,14-cis-eicosatetraenoic acid. Implications for the epoxide hydrolase mechanism," *J. Biol. Chem.* Sep. 12, 1997;272(37):23057-63.

Barrett, A.J. et al. Eds. "336. Introduction: family M1 of membrane alanyl aminopeptidase," in Handbook of proteolytic enzymes Oct. 1998; pp. 994-996.

Blomster, M. et al. "Evidence for a catalytic role of tyrosine 383 in the peptidase reaction of leukotriene $A_4$ hydrolase," *Eur. J. Biochem.* Aug. 1, 1995;231(3):528-34.

Byrum, R.S. et al. "Determination of the contribution of cysteinyl leukotrienes and leukotriene $B_4$ in acute inflammatory responses using 5-lipoxygenase- and leukotriene $A_4$ hydrolase-deficient mice," *J. Immunol.* Dec. 15, 1999;163(12):6810-9.

Chen, X-S. et al. "Role of leukotrienes revealed by targeted disruption of the 5-lipoxygenase gene," *Nature* Nov. 1994;372:179-182.

Crameri, A. et al. "DNA shuffling of a family of genes from diverse species accelerates directed evolution," *Nature* Jan. 15, 1998;391(6664):288-91.

Devchand, P.R. et al. "The PPARalpha-leukotriene $B_4$ pathway to inflammation control," *Nature* Nov. 7, 1996;384(6604):39-43.

Dittman, K.H. et al. "MK-886, a leukotriene biosynthesis inhibitor, induces antiproliferative effects and apoptosis in HL-60 cells," *Leuk. Res.* Jan. 1998;22(1):49-53.

Drazen, J.M. et al. "Treatment of asthma with drugs modifying the leukotriene pathway," *N. Engl. J. Med.* Jan. 21, 1999;340(3):197-206.

Evans, J.F. "Leukotriene $A_3$. A poor substrate but a potent inhibitor of rat and human neutrophil leukotriene $A_4$ hydrolase," *J. Biol. Chem.* Sep. 15, 1985;260(20):10966-70.

Ford-Hutchinson, A.W. et al. "Leukotriene B, a potent chemokinetic and aggregating substance released from polymorphonuclear leukocytes," *Nature* Jul. 17, 1980;286:264-65.

Funk, C.D. et al. "Molecular cloning and amino acid sequence of leukotriene $A_4$ hydrolase," *Proc. Natl. Acad. Sci. USA* Oct. 1987;84(19):6677-81.

Griffiths, R.J. et al. "Leukotriene $B_4$ plays a critical role in the progression of collagen-induced arthritis," *Proc. Natl. Acad. Sci. USA* Jan. 17, 1995;92(2):517-21.

Griffiths, R.J. et al. "Collagen-induced arthritis is reduced in 5-lipoxygenase-activating protein-deficient mice," *J. Exp. Med.* Mar. 17, 1997;185(6):1123-9.

Haeggström, J.Z. et al. "Leukotriene $A_4$ hydrolase: structural and functional properties of the active center," *J. Lipid Mediat.* Mar.-Apr. 1993;6(1-3):1-13.

Hogg, J.H. et al. "Probing the activities and mechanisms of leukotriene $A_4$ hydrolase with synthetic inhibitors," *Chem. Eur. J.* 1998;4(9)1698-1713.

Kuchner, O. et al. "Directed evolution of enzyme catalysts," *Trends Biotechnol.* Dec. 1997;15(12):523-30.

Labaudinière, R. et al. "ω-[(ω-Arylalkyl)thienyl]alkanoic acids: from specific $LTA_4$ hydrolase inhibitors to $LTB_4$ receptor antagonists," *J. Med. Chem.* Aug. 21, 1992;35(17):3170-9.

Lewis, R.A. et al. "Leukotrienes and other products of the 5-lipoxygenase pathway. Biochemistry and relation to pathobiology in human diseases," *N. Engl. J. Med.* Sep. 6, 1990;323(10):645-55.

Lorsch, J.R. et al. "In vitro evolution of new ribozymes with polynucleotides kinase activity," *Nature* Sep. 1, 1994;371(6492):31-6.

Medina, J.F. et al. "Leukotriene $A_4$ hydrolase: determination of the three zinc-binding ligands by site-directed mutagenesis and zinc analysis," *Proc. Natl. Acad. Sci. USA* Sep. 1, 1991;88(17):7620-4.

Ménard, A. et al. "The cytotoxic activity of *Bacillus anthracis* lethal factor is inhibited by leukotriene $A_4$ hydrolase and metallopeptidase inhibitors," *Biochem. J.* Dec. 1, 1996;320 ( Pt 2):687-91.

Mueller, M.J. et al. "Leukotriene $A_4$ hydrolase; mapping of a henicosapeptide involved in mechanism-based inactivation," *Proc. Natl. Acad. Sci. USA* Aug. 29, 1995;92(18):8383-7.

Mueller, M.J. et al. "Leukotriene $A_4$ hydrolase: protection from mechanism-based inactivation by mutation of tyrosine-378," *Proc. Natl. Acad. Sci. USA* Jun. 11, 1996;93(12):5931-5.

Mueller, M.J. et al. "Leukotriene $A_4$ hydrolase, mutation of tyrosine 378 allows conversion of leukotriene $A_4$ into an isomer of leukotriene $B_4$," *J. Biol. Chem.* Oct. 4, 1996;271(40):24345-8.

Nord, K. et al. "Binding proteins selected from combinational libraries of an alpha-helical bacterial receptor domain," *Nat. Biotechnol.* Aug. 1997;15(8):772-7.

Orning, L. et al. "Inhibition of leukotriene $A_4$ hydrolase/aminopeptidase by captopril," *J. Biol. Chem.* Sep. 5, 1991;266(25):16507-11.

Orning, L. et al. "The bifunctional enzyme leukotriene-$A_4$ hydrolase is an arginine aminopeptidase of high efficiency and specificity," *J. Biol. Chem.* Apr. 15, 1994;269(15):11269-73.

Owman, C. et al. "The leukotriene $B_4$ recepto functions as a novel type coreceptor mediating entry of primary HIV-1 isolates into CD4-positive cells," *PNAS. USA* Aug. 4, 1998;95(16):9530-4.

Rola-Pleszczynski, M. et al. "Leukotrienes augment interleukin 1 production by human monocytes," *J. Immunol.* Dec. 1985;135(6):3958-61.

Samuelsson, B. "Leukotrienes: mediators of immediate hypersensitivity reactions and inflammation," *Science* May 6, 1983;220(4597):568-75.

Samuelsson, B. et al. "Leukotrienes and lipoxins: structures, biosynthesis, and biological effects," *Science* Sep. 4, 1987;237(4819):1171-6.

Serhan, C.H. et al. "Lipid mediator networks in cell signaling: update and impact of cytokines," *FASEB J.* Aug. 1996;10:1-12.

Tsuge, H. et al., "Crystallization and preliminary X-ray crystallographic studies of recombinant human leukotriene $A_4$ hydrolase complexed with bestatin," *J. Mol. Biol.* May 20, 1994;238(5):854-6.

Vallee, B.L. et al. "Active-site zinc ligands and activated $H_2O$ of zinc enzymes," *Proc. Natl. Acad. Sci. USA* Jan. 1990;87(1):220-4.

Wetterholm, A. et al. "Recombinant mouse leukotriene $A_4$ hydrolase: a zinc metalloenzyme with dual enzymatic activities," *Biochim. Biophys. Acta* Oct. 25, 1991;1080(2):96-102.

Wetterholm, A. et al. "Leukotriene $A_4$ hydrolase: abrogation of the peptidase activity by mutation of glutamic acid-296," *Proc. Natl. Acad. Sci. USA* Oct. 1, 1992;89(19):9141-5.

Wetterholm, A. et al. "Potent and selective inhibitors of leukotriene $A_4$ hydrolase: effects on purified enzyme and human polymorphonuclear leukocytes," *J. Pharmacol. Exp. Ther.* Oct. 1995;275(1):31-7.

Yamaoka, K.A. et al. "Leukotriene $B_4$ enhances activation, proliferation, and differentiation of human B lymphocytes," *J. Immunol.* Sep. 15, 1989;143(6):1996-2000.

Yokomizo, T. et al. "A G-protein-coupled receptor for leukotriene $B_4$ that mediates chemotaxis," *Nature* Jun. 5, 1997;387(6633):620-4.

Yokomizo, T. et al. "A second leukotriene $B_4$ receptor, BLT2. A new therapeutic target in inflammation and immunological disorders," *J. Exp. Med.* Aug. 7, 2000;192(3):421-32.

Yuan, W. et al. "Novel tight-binding inhibitors of leukotriene $A_4$ hydrolase," *J. Am. Chem. Soc.* Apr. 1992;114:6552-53.

GenPept Acc. No. S65947; leukotriene-A4 hydrolase (EC 3.3.2.6) long isoform—human.

Wetterholm, Anders, et al., "Leukotriene $A_4$ hydrolase: Abrogation of the peptidase activity by mutation of glutamic acid-296," *Proc. Natl. Acad. Sci. USA*, vol. 89:9141-9145 (1992).

Minami, Michiko, et al., "Leukotriene $A_4$ hydrolase, a bifuctional enzyme. Distinction of leukotriene $A_4$ hydrolase and aminopeptidase activities by site-directed mutagenesis at Glu-297," *FEBS*, vol. 309(3):353-357 (1992).

Medina, Juan F., et al., "Leukotriene $A_4$ hydrolase: Determination of the three zinc-binding ligands by site-directed mutagenesis and zinc analysis," *Proc. Natl. Acad. Sci. USA*, vol. 88:7620-7624 (1991).

Toh, Hiroyuki, et al., "Molecular Evolution and Zinc Ion Binding Motif of Leukotriene $A_4$Hydrolase," *Biochemical and Biophysical Research Communications*, vol. 171(1):216-221 (1990).

Haeggstrom, Jesper Z., et al., "Leukotriene $A_4$ Hydrolase: A Zinc Metalloenzyme," *Biochemical and Biophysical Research Communications*, vol. 172(3):965-970 (1990).

Funk, Colin D., et al., "Molecular cloning and amino acid sequence of leukotriene $A_4$ hydrolase," *Proc. Natl. Acad. Sci. USA*, vol. 84:6677-6681 (1987).

Thunnissen, Marjolein M.G.M., et al., "Crystal structure of human leukotriene $A_4$hydrolase, a bifunctional enzyme in inflammation," *Nature Structural Biology*, vol. 8(2):131-135 (2001).

Rudberg, Peter C., et al., "Leukotriene $A_4$ Hydrolase/Aminopeptidase," *The Journal of Biological Chemistry*, vol. 277(2):1398-1404 (2002).

Mammalian Gene Collection (MGC) Program Team, "Generation and initial analysis of more then 15,000 full-length human and mouse cDNA sequences," *PNAS*, vol. 99(26):16899-16903 (2002).

Odlander, Bjorn, et al., "Leukotriene $A_4$ Hydrolase in the Human B-Lymphocytic Cell Line *Raji:* Indications of Catalytically Divergent Forms of the Enzyme," *Archives of Biochemistry and Biophysics*, vol. 287(1):167-174 (1991).

Minami, Michiko, et al., "Molecular Cloning of a cDNA Coding for Human Leukotriene $A_4$ Hydrolase," *The Journal for Biological Chemistry*, vol. 262(29):13873-13876 (1987).

Radmark, Olof, et al., "Leukotriene $A_4$ Hydrolase in Human Leukocytes," *The Journal of Biological Chemistry*, vol. 259(20):12339-12345 (1984).

Mancini, Joseph A., et al., "Cloning and characterizations of the human leukotriene $A_4$ hydrolase gene," *Eur. J. Biochem.*, vol. 231:65-17 (1995).

Jendraschak, Ellen, et al., "The human leukotriene $A_4$ hydrolase gene is expressed in two alternatively spliced mRNA forms," *Biochem J.*, vol. 314:733-737 (1996).

Nasr, F., et al., "The Sequence of 12-8 kb from the Left Arm of Chromosome XIV Reveals a Sigma Element, a pro-tRNA and Six Complete Open Reading Frames, One of Which Encodes a Protein Similar to the Human Leukotriene $A_4$ Hydrolase," *Yeast*, vol. 12:493-499 (1996).

\* cited by examiner

SEQUENCE LISTING

<160> NUMBER OF SEQ ID NOS: 1

<210> SEQ ID NO 1
<211> LENGTH: 610
<212> TYPE: PRT
<213> ORGANISM: Homo sapiens

<400> SEQUENCE: 1

```
Pro Glu Ile Val Asp Thr Cys Ser Leu Ala Ser Pro Ala Ser Val Cys
  1               5                  10                  15

Arg Thr Lys His Leu His Leu Arg Cys Ser Val Asp Phe Thr Arg Arg
             20                  25                  30

Thr Leu Thr Gly Thr Ala Ala Leu Thr Val Gln Ser Gln Glu Asp Asn
         35                  40                  45

Leu Arg Ser Leu Val Leu Asp Thr Lys Asp Leu Thr Ile Glu Lys Val
 50                  55                  60

Val Ile Asn Gly Gln Glu Val Lys Tyr Ala Leu Gly Glu Arg Gln Ser
 65                  70                  75                  80

Tyr Lys Gly Ser Pro Met Glu Ile Ser Leu Pro Ile Ala Leu Ser Lys
                 85                  90                  95

Asn Gln Glu Ile Val Ile Glu Ile Ser Phe Glu Thr Ser Pro Lys Ser
            100                 105                 110

Ser Ala Leu Gln Trp Leu Thr Pro Glu Gln Thr Ser Gly Lys Glu His
        115                 120                 125

Pro Tyr Leu Phe Ser Gln Cys Gln Ala Ile His Cys Arg Ala Ile Leu
130                 135                 140

Pro Cys Gln Asp Thr Pro Ser Val Lys Leu Thr Tyr Thr Ala Glu Val
145                 150                 155                 160

Ser Val Pro Lys Glu Leu Val Ala Leu Met Ser Ala Ile Arg Asp Gly
                165                 170                 175

Glu Thr Pro Asp Pro Glu Asp Pro Ser Arg Lys Ile Tyr Lys Phe Ile
            180                 185                 190

Gln Lys Val Pro Ile Pro Cys Tyr Leu Ile Ala Leu Val Val Gly Ala
        195                 200                 205

Leu Glu Ser Arg Gln Ile Gly Pro Arg Thr Leu Val Trp Ser Glu Lys
210                 215                 220

Glu Gln Val Glu Lys Ser Ala Tyr Glu Phe Ser Glu Thr Glu Ser Met
225                 230                 235                 240

Leu Lys Ile Ala Glu Asp Leu Gly Gly Pro Tyr Val Trp Gly Gln Tyr
                245                 250                 255

Asp Leu Leu Val Leu Pro Pro Ser Phe Pro Tyr Gly Gly Met Glu Asn
            260                 265                 270

Pro Cys Leu Thr Phe Val Thr Pro Thr Leu Leu Ala Gly Asp Lys Ser
        275                 280                 285

Leu Ser Asn Val Ile Ala His Glu Ile Ser His Ser Trp Thr Gly Asn
290                 295                 300

Leu Val Thr Asn Lys Thr Trp Asp His Phe Trp Leu Asn Glu Gly His
305                 310                 315                 320

Thr Val Tyr Leu Glu Arg His Ile Cys Gly Arg Leu Phe Gly Glu Lys
                325                 330                 335

Phe Arg His Phe Asn Ala Leu Gly Gly Trp Gly Glu Leu Gln Asn Ser
            340                 345                 350

Val Lys Thr Phe Gly Glu Thr His Pro Phe Thr Lys Leu Val Val Asp
```

-continued

```
                355                 360                 365
Leu Thr Asp Ile Asp Pro Asp Val Ala Tyr Ser Ser Val Pro Tyr Glu
        370                 375                 380

Lys Gly Phe Ala Leu Leu Phe Tyr Leu Glu Gln Leu Leu Gly Gly Pro
385                 390                 395                 400

Glu Ile Phe Leu Gly Phe Leu Lys Ala Tyr Val Glu Lys Phe Ser Tyr
                405                 410                 415

Lys Ser Ile Thr Thr Asp Asp Trp Lys Asp Phe Leu Tyr Ser Tyr Phe
                420                 425                 430

Lys Asp Lys Val Asp Val Leu Asn Gln Val Asp Trp Asn Ala Trp Leu
            435                 440                 445

Tyr Ser Pro Gly Leu Pro Pro Ile Lys Pro Asn Tyr Asp Met Thr Leu
        450                 455                 460

Thr Asn Ala Cys Ile Ala Leu Ser Gln Arg Trp Ile Thr Ala Lys Glu
465                 470                 475                 480

Asp Asp Leu Asn Ser Phe Asn Ala Thr Asp Leu Lys Asp Leu Ser Ser
                485                 490                 495

His Gln Leu Asn Glu Phe Leu Ala Gln Thr Leu Gln Arg Ala Pro Leu
            500                 505                 510

Pro Leu Gly His Ile Lys Arg Met Gln Glu Val Tyr Asn Phe Asn Ala
        515                 520                 525

Ile Asn Asn Ser Glu Ile Arg Phe Arg Trp Leu Arg Leu Cys Ile Gln
    530                 535                 540

Ser Lys Trp Glu Asp Ala Ile Pro Leu Ala Leu Lys Met Ala Thr Glu
545                 550                 555                 560

Gln Gly Arg Met Lys Phe Thr Arg Pro Leu Phe Lys Asp Leu Ala Ala
                565                 570                 575

Phe Asp Lys Ser His Asp Gln Ala Val Arg Thr Tyr Gln Glu His Lys
                580                 585                 590

Ala Ser Met His Pro Val Thr Ala Met Leu Val Gly Lys Asp Leu Lys
            595                 600                 605

Val Asp
    610
```

DRUG DESIGN BASED ON THE STRUCTURE OF LTA$_4$ HYDROLASE

The present application is a 35 U.S.C. § 371 national stage filing of International Application No. PCT/SE00/00384, filed Feb. 28, 2000, now abandoned, which claims priority to Swedish Application No. 9900722-1, filed Feb. 26, 1999, now abandoned, and U.S. Provisional Application No. 60/122,110, filed Feb. 26, 1999, now expired.

1. BACKGROUND

1.1 Technical Field

The present invention relates to methods of design or identification of biologically active compounds which methods are based on the first definition ever of a three-dimensional structure of a protein involved in the leukotriene cascade. Further, the invention relates to novel compounds obtained by said methods, to advantageous uses of such compounds as well as to processes for the preparation thereof.

1.2 Prior art

Leukotriene A$_4$ (LTA$_4$) hydrolase is a pivotal enzyme in the biosynthesis of leukotrienes, a family of paracrine hormones implicated in the pathophysiology of inflammatory and allergic disorders, in particular bronchial asthma (Samuelsson, B. *Science* 220, 568-75 (1983); and Lewis, R. A., Austen, K. F. & Soberman, R. J. *N Engl J Med* 323, 645-55 (1990)). Leukotrienes are formed by immunocompetent cells including neutrophils, eosinophils, basophils, mast cells, and macrophages, in response to a variety of immunological as well as non-immunological stimuli. These lipid mediators are divided into two major classes exemplified by the chemotaxin LTB$_4$, and the spasmogenic cysteinyl-leukotrienes (LTC$_4$, LTD$_4$, and LTE$_4$). Leukotriene biosynthesis is initiated by the enzyme 5-lipoxygenase which converts arachidonic acid into the unstable epoxide LTA$_4$, a central intermediate in the leukotriene cascade. LTA$_4$ may in turn be hydrolyzed into LTB$_4$ by the enzyme LTA$_4$ hydrolase, or conjugated with GSH to form LTC$_4$, a reaction catalyzed by a specific LTC$_4$ synthase. During cellular activation, all key enzymes in leukotriene biosynthesis, except LTA$_4$ hydrolase, form a biosynthetic complex assembled at the nuclear membrane, suggesting that leukotrienes may have unknown intranuclear functions related to gene regulation or cell growth (Serhan, C. N., Haeggstrom, J. Z. & Leslie, C. C. *Faseb J* 10, 1147-58 (1996)).

Leukotriene B$_4$, the natural product of LTA$_4$ hydrolase, is one of the most powerful chemotactic agents known to date and triggers leukocyte adherence and aggregation at only nM concentrations (Ford-Hutchinson, A. W., Bray, M. A., Doig, M. V., Shipley, M. E. & Smith, M. J. H. *Nature* 286, 264-265 (1980)). Hence, this molecule is regarded as a key mediator of inflammation, and has been implicated in a number of diseases, including arthritis, psoriasis, inflammatory bowel disease (IBD), and chronic obstructive pulmonary disease (COPD). Furthermore, the role of LTB$_4$ in inflammation has been well corroborated by the anti-inflammatory properties of LTA$_4$ hydrolase inhibitors, particularly in combination with a cyclooxygenase inhibitor, and specific LTB$_4$ receptor antagonists, as well as the reduced inflammatory reactions observed in several animal models of leukotriene deficiency (Tsuji, F., Miyake, Y., Enomoto, H., Horiuchi, M., Mita, S. *Eur. J. Pharmacol.* 346, 81-85, (1998); Chen, X. S., Sheller, J. R., Johnson, E. N. & Funk, C. D. *Nature* 372, 179-182 (1994); Griffiths, R. J., et al. *Proc Natl Acad Sci USA* 92, 517-21 (1995); and Griffiths, R. J., et al. *J Exp Med* 185, 1123-9 (1997)). In addition, LTB$_4$ modulates the immune response, e.g., by interference with specific subsets of lymphocytes, production of cytokines, as well as liberation of immunoglobulins from B-lymphocytes (Payan, D. G., Missirian-Bastian, A. & Goetzl, E. J. *Proc Natl Acad Sci USA* 81, 3501-5 (1984); Rola-Pleszczynski, M. & Lemaire, I. *J Immunol* 135, 3958-61 (1985); and Yamaoka, K. A., Claesson, H. E. & Rosen, A. *J Immunol* 143, 1996-2000 (1989)). Recent data also indicate that LTB$_4$ stimulates, and thus has a crucial role in the regulation of, cell proliferation and cell survival in HL-60 cells, suggesting that LTA$_4$ hydrolase inhibitors may have an antiproliferative effect. (Dittman, K. H., Mayer, C., Rodemann, H. P., Petrides, P. E., and Denzlinger, C. *Leuk Res.* 22, 49-53 (1998)). The cell surface receptor for LTB$_4$ (BLTR) was recently cloned and found to be abundantly expressed in the immune system, including lymphocytes, spleen and thymus (Yokomizo, T., Izumi, T., Chang, K., Takuwa, Y. & Shimuzu, T. *Nature* 387, 620-624 (1997)). BLTR belongs to a family of chemokine receptors and, interestingly, together with CD4 it was found to be an efficient coreceptor for HIV-1 infection (Owman, C., et al. *Proc Natl Acad Sci USA* 95, 9530-4 (1998)). Moreover, LTB$_4$ is also a natural ligand to the nuclear orphan receptor PPARα, suggesting that LTB$_4$ may have intranuclear functions possibly related to lipid homeostasis (Devchand, P. R., et al. *Nature* 384, 39-43 (1996)).

LTA$_4$ hydrolase is a cytosolic 69 kDa enzyme without any similarity to other soluble or membrane bound xenobiotic epoxide hydrolases (Funk, C. D., et al. *Proc Natl Acad Sci USA* 84, 6677-81 (1987)). The enzyme's epoxide hydrolase activity, which generates LTB$_4$, is highly substrate selective accepting only LTA$_4$ and to a small extent the double bond isomers LTA$_3$ and LTA$_5$. Typically, LTA$_4$ hydrolase undergoes suicide inactivation and covalent modification when exposed to LTA$_4$ (Evans, J. F., Nathaniel, D. J., Zamboni, R. J. & Ford-Hutchinson, A. W. *J. Biol. Chem.* 260, 10966-10970 (1985)). During this process, LTA$_4$ apparently binds to Tyr-378, a residue which also seems to play a role for the formation of the critical cis-trans-trans geometry in the conjugated triene structure of LTB$_4$ (Mueller, M. J., et al. *Proc Natl Acad Sci USA* 93, 5931-5935 (1996); and Mueller, M., Andberg, M., Samuelsson, B. & Haeggstrom, J. Z. *J. Biol. Chem.* 271, 24345-24348 (1996)).

From sequence comparisons with certain metalloproteases and aminopeptidases, a zinc binding motif (HEXXH-X$_{18}$-E) was unexpectedly found in LTA$_4$ hydrolase (Vallee, B. L. & Auld, D. S. *Proc. Natl. Acad. Sci. USA* 87, 220-224 (1990)). Further studies demonstrated that the enzyme indeed contains one catalytic zinc atom complexed to His295, His299, and Glu318 (Medina, J. F., et al. *Proc. Natl. Acad. Sci. USA* 88, 7620-7624 (1991)). In addition, a previously unknown peptide cleaving activity was discovered which requires the presence of anions, particularly chloride (Haeggström, J. Z., Wetterholm, A., Medina, J. F. & Samuelsson, B. *J Lipid Mediator* 6, 1-13 (1993)). Although the endogenous physiological peptidase substrate(s) has not yet been identified, LTA$_4$ hydrolase cleaves certain arginyl di- and tripeptides with very high efficiency (Örning, L., Gierse, J. K. & Fitzpatrick, F. A. *J. Biol. Chem.* 269, 11269-11273 (1994)). Hence, LTA$_4$ hydrolase can be described as a bifunctional zinc metalloenzyme with the unique ability to accept both lipid and peptide substrates. Using site-directed mutagenesis, Glu296 and Tyr383 were found to be critical for the peptidase reaction, presumably as a general base and proton donor, respectively (Blomster, M., Wetterholm, A., Mueller, M. J. & Haeggström, J. Z. *Eur. J. Biochem.* 231, 528-534 (1995); and Wetterholm, A., et al. *Proc Natl Acad Sci USA* 89, 9141-9145 (1992)). Since the enzyme's ability to convert LTA$_4$ into LTB$_4$ was not affected by the mutations, the two enzyme activities of LTA$_4$ hydrolase are exerted via non-identical but overlapping active sites. Notably, unlike other enzymes in the leukotriene cascade, LTA$_4$ hydrolase is ubiquitous in mammalian cells and tissues suggesting that it may have other functions presumably related to its peptide cleaving activity.

As a consequence of the identification of LTA$_4$ hydrolase as a zinc metalloenzyme with a peptidase activity, it was observed that LTA$_4$ hydrolase is inhibited by bestatin, a general aminopeptidase inhibitor, and captopril, an inhibitor of angiotensin converting enzyme (Örning, L., et al. *J. Biol. Chem.* 266, 16507-16511 (1991)).

Tsuge et al., (*J. Mol. Biol.* 238, 854-856 (1994)), have described the crystallization of LTA$_4$ hydrolase. However, despite the well recognized need thereof, the three-dimensional structure of LTA$_4$ hydrolase has not yet been disclosed. More specifically, the problems that need to be overcome in order to provide such a determination may in brief be explained as follows. There are two major difficulties in obtaining a three-dimensional structure of a protein molecule. The first one is to grow crystals of good quality that are reproducible and diffract to atomic resolution (beyond 2.5 Å). This means a thorough and cumbersome investigation of parameters that influence the crystal growth such as pH, temperature, nature of buffers, nature of precipitant, just to mention a few. The addition of ligands such as substrate analogues or inhibitors or the addition of other molecules can be important for obtaining good crystals. There is only little understanding of the physical background of the crystallisation process which means that the search for suitable crystallisation conditions for a certain protein is unique, requires creativity and intuition, and is governed by trial and error procedures. The purity of the protein is also a crucial parameter in the crystallisation and a suitable degree of purity can be hard, or even impossible, to achieve. The second major difficulty is associated with overcoming the phase-problem which is inherent to X-ray diffraction methods. To be able to overcome this problem it is necessary to substitute the protein with suitable heavy atom substance such as e.g. mercury, gold or platinum compounds. Crystals often cannot withstand the treatment with these compounds and the search for suitable substitutions is not straight forward and may become very exhaustive. Another option is to substitute all methionines by seleno-methionine (Se-Met) residues. This method requires production of recombinant protein in special strains of *E. coli* under non-standard conditions, followed by a new purification and recrystallisation of the Se-Met containing protein. Although Tsuge et al reported the crystallisation of LTA$_4$ hydrolase, their crystals only diffracted to medium resolution and the phase-problem was not solved. Thus, as a reliable definition of the three-dimensional structure of LTA$_4$ hydrolase would enable e.g. a display in visual form on a computer screen of the shape of the molecule, then, could the above mentioned problems be solved, a whole range of possibilities would be opened, such as rational structure-based drug design, e.g. in combination with combinatorial chemistry, aimed at production of novel medicaments useful in disorders associated with the leukotriene cascade, as well as protein-engineering to create novel variants of the enzyme with altered, but yet useful, catalytic properties.

As LTA$_4$ hydrolase is a recognized important drug target, some inhibitors thereof have been synthesized (Wetterholm, A., et al. *J Pharmacol Exp Ther* 275, 31-7 (1995); and Yuan, W., Wong, C., Haeggstrom, J. Z., Wetterholm, A. & Samuelsson, B. *J. Am. Chem. Soc.*, 114, 6552-6553 (1992)). Interestingly, certain inhibitors of LTA$_4$ hydrolase were reported to act also as LTB$_4$ receptor antagonists (Labaudinière R, Hilboll G, Leon-Lomeli A, Terlain B, Cavy F, Parnham M, Kuhl P, and Dereu N. *J. Med. Chem.* 35, 3170-3179 (1992)). Due to the absence of any available information regarding the three-dimensional structure of LTA$_4$ hydrolase, as discussed above, none of the previously described inhibitors have been designed based on the exact structure thereof. Accordingly, there is a need within this field of determining the three-dimensional structure of LTA$_4$ hydrolase in order to design more potent and selective inhibitors of LTA$_4$ hydrolase as well as modified structures exhibiting even more advantageous pharmaceutical properties.

2. THE PRESENT INVENTION

As the following chapter includes a substantial amount of text, it has herein been divided into separate sections, each one of which disclose separate aspects of the present invention.

Index Chapter 2

2.1 Summary of the invention
2.2 Brief description of the drawings
2.3 Definitions
2.4 Detailed description of the invention
2.4.1 LTA$_4$ hydrolase, subsequences and analogues thereof
2.4.2 Compounds complementary to LTA$_4$ hydrolase
2.4.3 A complex of LTA$_4$ hydrolase and acomplementary compound
2.4.4 Advantageous uses of LTA hydrolase, complementary compounds and complexes thereof
2.4.5 Screening for LTA$_4$ hydrolase analogues
2.4.5 (a) Method
2.4.5 (b) Analogues obtainable by the present screening method
2.4.5 (c) Mutated forms of LTA$_4$ hydrolase obtainable by the present screening method
2.4.5 (d) Nucleic acids encoding the novel compounds
2.4.6 (a) Production and purification of genetically modified forms of LTA$_4$ hydrolase
2.4.6 (b) Purified LTA$_4$ hydrolase
2.4.7 Identification of LTA$_4$ hydrolase binding compounds
2.4.7 (a) Method
2.4.7 (b) Identified binding compounds
2.4.8 Protein engineering
2.4.8 (a) Method
2.4.8. (b) Novel specifically designed proteins
2.4.8. (c) Use of genetically modified LTA$_4$ hydrolase
2.4.9 Pharmaceutical applications of the present invention
2.4.9 (a) First medical indication
2.4.9 (b) Second medical indication and pharmaceutical methods
2.4.9.(c) Methods of treatment
2.5 Production of the novel molecules
2.6 Detailed description of the drawings

2.1 SUMMARY OF THE INVENTION

The object of the present invention is to fulfill the above defined need. This has been achieved by the crystallization and determination of the three-dimensional structure of LTA$_4$ hydrolase complexed with the competitive inhibitor bestatin and subsequent structure determination of complexes between LTA$_4$ hydrolase and two specific inhibitors. It is the first three-dimensional structure of any protein component of the leukotriene cascade and enables a description of the structural basis and molecular mechanisms of various enzyme functions, such as the two catalytic activities of LTA$_4$ hydrolase. In addition, the structural information will now make possible rational design of enzyme inhibitors, which may be developed into clinically useful anti-inflammatory drugs.

2.2 BRIEF DESCRIPTION OF THE DRAWINGS

FIG. 9 (b) is a schematic presentation for the proposed binding of $LTA_4$ into the cavity.

2.3 DEFINITIONS

Figure 1:
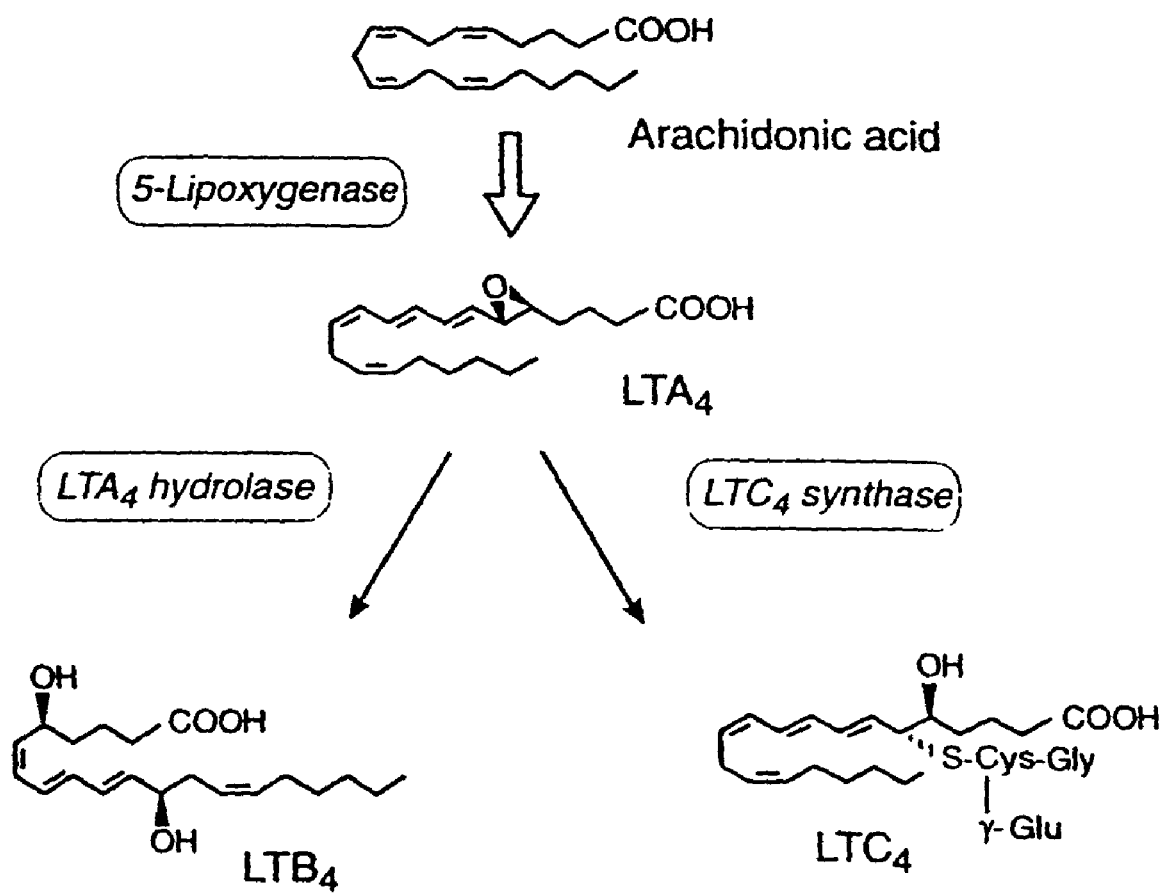
FIG. 1 shows the key enzymes and intermediates in leukotriene biosynthesis.

In the present context the term "the three-dimensional form adopted thereof in nature" is to be understood as the conformational structure, defined by the parameters x, y and z in a conventional coordinate system, that a naturally occurring molecule adapt under conditions where it is capable of exerting its biological activities.

The specific conditions during which the herein presented data were collected are detailed in the section "Experimental".

The term "isolated" and variations thereof when used in connection with a molecule, such as protein, a polypeptide or a nucleic acid, means that said molecule is isolated from other substances, such as other proteins, DNA etc normally accompanying it in its natural environment.

The term "leukotriene $A_4$ ($LTA_4$) hydrolase" as used herein is to be understood to include any mammalian or other $LTA_4$ hydrolase which comprises the same backbone as the human form specifically disclosed in the present application, irrespective of source. The amino acid sequences of mammalian $LTA_4$ hydrolase have been shown to be identical to about 90%. Thus, the three-dimensional structures thereof may be suspected to be identical to approximately the same extent.

"Thiolamine" and "hydroxamic acid" are used herein to denote the compounds exemplified in the Experimental section of the present specification.

A "complementary compound" means any compound, the structure of which enables a binding thereof to a specified protein, i.e a compound having a conformation or structure enabling such a suitable fit as to provide an energetically favorable interaction between protein-complementary compound.

"Analogue" means, as used herein, a chemically altered molecule which shares the backbone with, or at least structurally resembles, a "parent molecule". In the present specification, such a "parent molecule" may be $LTA_4$ hydrolase or an inhibitor thereof.

In the present application, the term "active site" is to be understood to include any region capable of binding a substrate and converting it into product.

The term "nucleic acid" refers to a deoxyribonucleotide or ribonucleotide polymer in either single- or double-stranded form, and unless otherwise limited, encompasses known analogs of nucleotides, that can function in a similar manner as naturally occurring nucleotides.

The phrase "hybridising specifically to" refers to the binding, duplexing, or hybridising of a molecule only to a particular nucleotide sequence under stringent conditions when that sequence is present in a complex mixture (e.g., total cellular) of DNA or RNA. The term "stringent conditions" refers to conditions under which a probe will hybridise to its target subsequence, but to no other sequences. Stringent conditions are sequence-dependent and will be different in different circumstances. Longer sequences hybridise specifically at higher temperatures. Generally, stringent conditions are selected to be about 5° C. lower than the thermal melting point Tm for the specific sequence at a defined ionic strength and pH. The Tm is the temperature (under defined ionic strength, pH, and nucleic acid concentration) at which 50% of the probes complementary to the target sequence hybridise to the target sequence at equilibrium. (As the target sequences are generally present in excess, at Tm, 50% of the probes are occupies at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

"Essentially pure" means herein a purity of at least about 80%, especially at least about 90% and preferably at least about 95%, such as 98-99%. The purity of $LTA_4$ hydrolase, an analogue or inhibitor thereof is according to the present invention preferably determined by general biochemical and biophysical methods well-known to the skilled in this field. For proteins, SDS polyacrylamide gel electrophoresis (SDS-PAGE) with Coomassie and silver staining or amino acid sequence analysis can be used, whereas high-pressure liquid chromatography (HPLC), gas chromatography coupled to mass spectrometry (GC-MS), and nuclear magnetic resonance spectroscopy (NMR) are suitable methods for small organic molecules (peptides, lipids, or carbohydrates, or combinations of these classes of substances).

2.4 DETAILED DESCRIPTION OF THE INVENTION

2.4.1 $LTA_4$ Hydrolase, Subsequences and Analogues Thereof

In a first aspect, the present invention relates to an isolated protein comprising at least a subsequence of the amino acid sequence of leukotriene $A_4$ ($LTA_4$) hydrolase, which subsequence has the corresponding three-dimensional form adopted thereof in nature. The protein according to invention as discussed below and elsewhere in this application is also understood to encompass any other functionally equivalent part, derivative or conformational analogue thereof. More specifically, the invention relates to the above disclosed protein which comprises a subsequence of the amino acid sequence of leukotriene $A_4$ ($LTA_4$) hydrolase, which is able to participate in, and influence, e.g. by providing enzymatic activity, the leukotriene cascade. Most preferably, the protein according to the invention is capable of controlling said cascade by exerting an enzymatic activity and thus regulate the production of leukotriene $B_4$ ($LTB_4$). In a particular embodiment, the protein is comprised of essentially all of the amino acid sequence of leukotriene $A_4$ ($LTA_4$) hydrolase as disclosed in SEQ ID NO 1, or a functionally equivalent part, derivative or conformational analogue thereof.

Thus, the present invention relates to an isolated $LTA_4$ hydrolase in its naturally occurring three-dimensional form. More specifically, the present application provides a listing illustrating, for the first time, the coordinates defining human $LTA_4$ hydrolase complexed to an inhibitor thereof. Thus, the coordinates defining the conformation of $LTA_4$ hydrolase have been determined by the present inventors as complexed with bestatin, thiolamine and hydroxamic acid, respectively. Bestatin is a universal inhibitor of amino peptidase activity (see e.g. Mathé, G. *Biochem. Pharmacol.* 45, 49-54 (1991)), while the last mentioned two are specific inhibitors of LTA hydrolase. Based on these different activities, said inhibitors may be used as models in the design of novel molecules having desired properties. Methods for such design will be discussed in further detail below as a further advantageous aspect of the invention. For reasons of convenience for the reader of the present specification, the data collection comprising the novel coordinates according to the invention is included in the present description as a separate section denoted "X-ray data", as Table 9, immediately preceding the claims. In said table, atom no 1 to atom no 4876 define the LTA hydrolase part of the complex. (protein part), atom no 4877 refers to Zn, atom nos. 48784880 refer to Yb, atom nos. 4881-4885 refer to imidazole, atom nos. 4886-4889 refer to acetate, atom nos 4890-4908 refer to thiolamine while atom nos. 4909-5160 refer to water. Thus, the intervening atoms relate to the metals that bind in LTA hydrolase, i.e. the active site Zn atom and the Yb atoms that were crucial for the present structure determination. The conditions prevailing at the determination thereof will be described in detail in the Experimental section below. As the skilled in this field realises, such coordinates usually exhibit a certain degree of variation, due to e.g. thermal motion and slight differences in crystal packing. Thus, any references herein to Table 9 in connection with the proteins and other molecules are merely intended to illustrate an average value for each of the coordinates defining the conformation of the molecules under identical conditions, as determined by use of the same apparatus and method. Accordingly, this embodiment of the invention is not limited to a molecule having exactly the specified coordinates, but rather to molecules capable of adopting such a structure. For example, a human $LTA_4$ hydrolase according to the invention will exhibit a strong bit a conformational similarity with the coordinates presented by atom nos 1-4876 of Table 9, wherein a variation of about 1%, or 0.5 Å, may be expected. Accordingly, any such variants are within the scope of the present invention.

As regards amino acid sequence, in a specific embodiment, the protein according to the invention is identical, by direct sequence comparison, to at least about 500%, more specifically, at least about 70%, such as at least about 90%, to the $LTA_4$ hydrolase as defined by SEQ ID NO. 1 while in the three-dimensional form adopted thereof in nature. In this context, it is noted that the amino acid sequence of $LTA_4$ hydrolase also appears from the data of Table 9, but is also included as a separate sequence listing for reasons of clarity. The protein of this embodiment of the invention are e.g. variants originating from any species, preferably mammals, such as humans, mice or other rodents, etc. Alternatively, the variants including subsequences of the human sequence are mutated forms, resulting from either spontaneous mutations or deliberately produced mutations, as discussed in more detail below.

One preferred embodiment of the present invention is a protein which comprises at least one of the regions defined below in Tables 1-3 below as active sites.

TABLE 1

| | Residues lining the big cavity from outsite to insite | |
|---|---|---|
| | Left wall | Right wall |
| 1 | | Lys608, Asp606, Lys605, Lys354, Thr355 |
| 2 | Phe356, Phe362 | Gln544, Asp573, Lys572, Arg568 |
| 3 | Val376 | Lys565, Arg540, Leu507 |
| 4 | Ser380, Ser352, Glu348 | Pro569 |
| 5 | Tyr378, Glu348 | Arg563, Glu533, Phe536, Arg537, Tyr267 |
| 6 | Tyr383, Phe314, Glu318, Glu384, Arg326 | |
| 7 | Gly268, Gly269, Met270 | His295, Asn341, Phe340 |
| 8 | Ser288, His497 | Glu325, Asn291 |

In Table 1, Lys565, Ser380, Pro569, Glu533, Tyr383, Phe314, Glu318, Glu384, Arg326, Gly269, Gly269, Met270, His295, Phe340, Ser288, and Glu325 are strictly conserved amino acids, while Lys608, Phe356, Phe362, Lys572, Arg568, Tyr378, Phe536, Tyr 267, and Asn291 are conserved in nature.

Table 2

Amino-Acids in the Bestatin Binding Site ("Basic" Amino-Peptidase Site)

The binding of bestatin to $LTA_4$ hydrolase may also be described by way of coordinates. Below follows the specific amino acids involved in the binding of bestatin and similar structures, as defined according to the invention.

Gln136; Ala137; Tyr267; Gly268; Gly269; Met270; Glu271; Val292; His295; Glu296; His299; Glu318; Tyr378; Tyr383; Arg563; Lys565.

Table 3

Amino Acids in the Leukotriene Binding Site

The present amino acids define the site binding leukotriene-based inhibitors, such as thiolamine and hydroxamic acid, as shown in Table 9 for thiolamine.

Gln136; Ala137; Tyr267; Gly268; Gly269; Met270; Glu271; Val292; His295; Glu296; His299; Trp315; Glu318; Val322; Phe362; Val367; Leu369; Pro374; Asp375; Ile372; Ala377; Pro382; Tyr378; Tyr383; Arg563; Lys565.

In Tables 1-3 above, the enumeration of the amino acid sequence of $LTA_4$ hydrolase begin without the initial Met. Thus, compared to SEQ ID NO 1, which includes the initial Met, the amino acid enumeration above is lowered by one.

Accordingly, Gln136 above corresponds to Gln 137 of SED ID NO 1, Ala137 above corresponds to Ala 138 of SEQ ID NO 1, etc.

Table 4

General Catalytic Domain for the M1 Class of Enzymes

Amino acids no. 210450.

The present region will provide a basis for the development of enzyme inhibitors useful in the control other biological pathways than the leukotriene cascade.

Thus, as regards the above defined region of aminopeptidase activity of LTA hydrolase, the present inventors have surprisingly observed, that said region is in fact universal for all enzymes belonging to the metallohydrolase family denoted M1.

Thus, this specific subsequence of $LTA_4$ hydrolase is encompassed by the present invention as a novel protein per se. In addition to the various advantageous uses of subsequences of $LTA_4$ hydrolase described herein in connection with the leukotriene cascade, this region, which is shared between all M1 enzymes, will find several further applications in connection with other enzymatic pathways. For example, the present region, herein denoted the "M1 region" in order to clarify that it is shared between the M1 enzymes, may advantageously be used to produce synthetic inhibitors, or identify natural inhibitors, of any one of the other M1 enzymes. Such M1 inhibitors will be discussed below when compounds complementary to $LTA_4$ hydrolase are disclosed.

The above disclosed proteins and peptides comprising subunits of $LTA_4$ hydrolase are advantageously used e.g. as enzymes or more preferably in methods wherein novel inhibitors of enzymatic activities are identified and/or designed.

2.4.2 Compounds Complementary to $LTA_4$ Hydrolase

In a second aspect, the present invention relates to a novel compound defined by a structure substantially complementary to the above described protein, preferably identified by use of the novel $LTA_4$ hydrolase conformation according to the present invention. The complementary compound is a naturally occurring or synthetic protein, peptide, lipid, carbohydrate or any other organic or inorganic compound. In relation to naturally occurring compounds, it is to be understood that the present invention relates to such compounds as isolated from their natural environment, preferably identifiable by aid of the novel coordinates defining structures according to the invention, as exemplified by the complementary compounds used in the complexes shown in Table 9.

In a first embodiment, the present complementary compound is substantially complementary to an enzymatically active site of the protein and is advantageously capable of specifically inhibiting an enzymatic activity of said protein. Thus, in one embodiment, the present compound is substantially complementary to parts, or all, of the "basic" aminopeptidase binding site defined in Table 2 above. Thus, the present compound is an inhibitor capable of specifically inhibiting an aminopeptidase activity of an enzyme, preferably of $LTA_4$ hydrolase. In an alternative embodiment, the present compound is substantially complementary to parts, or all, of the leukotriene binding site as defined in Table 3 above. Thus, the present compound is an inhibitor capable of specifically inhibiting an epoxide hydrolase activity of an enzyme, preferably of $LTA_4$ hydrolase. (The inhibition of both aminopeptidase and epoxidase hydrolase is discussed in detail below in the experimental section.) As the present two binding sites of $LTA_4$ hydrolase overlap in part, a further embodiment is a compound which is complementary to essential parts of both of the above discussed two binding sites, in part or partially, which thus preferably is an inhibitor of both the discussed activities.

As already mentioned above, one compound which is complementary to an enzymatically active site of $LTA_4$ hydrolase is a compound complementary to the M1 region thereof and thus capable of partial or total inhibition of the enzymatic activity of $LTA_4$ hydrolase or any other metallohydrolase belonging to the M1 family. In the present application, such inhibitors will be denoted M1 inhibitors.

As the skilled in this field will realise, the present inhibitors disclosed above need not be compound that inhibit a biological activity completely, but may be capable of exerting a partially inhibiting activity, i.e, lowering the enzymatic activity.

In another embodiment, the present complementary compound is a compound which is also capable of binding to the receptor for the product of an $LTA_4$ hydrolase, i.e. an $LTB_4$ receptor, e.g. on a cell, such as a polymorphonuclear leukocyte. Thus, such a compound may be useful as an $LTB_4$ antagonist whereby the biological effect of $LTA_4$ hydrolase activity may be regulated. Accordingly, any such $LTB_4$ antagonist designed and/or identified using the coordinates of LTA hydrolase as presented herein are also encompassed by the present invention.

In another embodiment, the present complementary compound is a compound which, apart from being capable of binding to an active site of $LTA_4$ hydrolase, is also capable of binding to an active site of $LTC_4$ synthase which binds the same substrate as $LTA_4$ hydrolase, i.e. $LTA_4$, and turns it over into $LTC_4$ (cf. FIG. 1) and is thus expected to share important structural features with the active site of $LTA_4$ hydrolase. Such a compound may be useful as an inhibitor of $LTC_4$ biosynthesis, whereby the production thereof may be regulated. Accordingly, any such $LTC_4$ synthase inhibitor, designed and/or identified using the coordinates of $LTA_4$ hydrolase, are also encompassed by the present invention.

The specific properties and advantageous uses of the present compounds as well as the design and production of novel $LTA_4$ hydrolase inhibitors will be described in further detail below in relation to the various methods.

2.4.3 A Complex of $LTA_4$ Hydrolase and a Complementary Compound

In a third aspect, the present invention relates to an isolated complex comprised of a protein as described above and a compound complementary to said protein. Said complementary compound may thus be an inhibitor of one or more of the protein's enzymatic activities, such as an aminopeptidase and/or epoxide hydrolase activity, such as bestatin, hydroxamic acid or thiolamine, or leukotriene $B_4$ or any analogue thereof, or $LTC_4$ or any analogue thereof. Examples of complementary compounds are bestatin, thiolamine or hydroxamic acid. In the present context, it is to be understood that the invention also relates to specific regions of said inhibitors, that have never been specifically disclosed for the present purpose, as well as novel inhibitors identified by aid of the present invention. In specific embodiments, the complex according to the invention is composed of $LTA_4$ hydrolase complexed with bestatin, thiolamine or hydroxamic acid, respectively, wherein the LTA$_4$ hydrolase is as defined by the coordinates presented in Table 9, or any functional fragment, derivative or analogue thereof. As bestatin is aminopeptidase based, further similar and advantageous inhibitors may be developed based on the structural information for LTA$_4$ hydrolase complexed with bestatin, preferably combined with the specification of the binding site of Table 2. Further, as both thiolamine is leukotriene based, the information provided in Table 9, preferably combined with the specification of binding site of Table 3, will prove to be an advantageous tool in order to gain more information about such enzymatic binding and thus the development of further novel inhibitors, the same principles applying to hydroxamic acid, which is also leukotriene based.

Accordingly, the present invention presents for the first time the coordinates defining the three-dimensional structure of a complex of LTA$_4$ hydrolase and an inhibitor thereof as determined by X-ray crystallography, e.g. as illustrated in Table 9. In fact, this is the first time ever to disclose the exact parameters defining the three-dimensional structure of a protein component of the leukotriene cascade. Due to these novel reliable parameters, the complex as well as the components thereof are readily distinguished from the prior art. Together with biochemical and mutagenetic data, the novel structures will provide the basis for understanding the molecular mechanisms of the aminopeptidase and epoxide hydrolase activities, as well as the enzyme's suicide inhibition. Accordingly, the present invention will open a whole range of new possibilities as regards e.g. identification and/or design of novel biologically active molecules and methods of controlling said cascade, in vivo or in vitro. Consequently, novel advantageous drugs, such as medicaments for the treatment and/or prevention of inflammatory and/or allergic diseases, may be designed, as will be discussed in further detail below.

In the present context, it is to be understood that proteins according to the invention include the naturally occurring three dimensional forms thereof, separated and isolated from its natural environments, as well as any such protein, wherein deletions, additions and/or substitutions of the amino acid sequence have been made, provided that the three dimensional structure is substantially maintained, as the exerted biological activity is critically dependent upon the particular three-dimensional folding of the protein. The present invention also encompasses any derivative or conformational analogue of the above disclosed proteins, which has a three-dimensional structure essentially as disclosed above, or an effective part thereof having the biological activities discussed in detail below.

2.4.4 Advantageous Uses of LTA$_4$ Hydrolase, Complementary Compounds and Complexes Thereof A fourth aspect of the present invention is the use of a protein, a complementary compound or a complex according to the invention in drug design, such as in molecular modeling, direct structure-based design and/or combinatorial chemistry. Such methods will be disclosed in detail below. The drugs designed using the above mentioned compounds may be suitable for the treatment and/or prevention of disorders involving acute and chronic inflammatory symptoms, said disorder being selected from the group consisting of arthritis, inflammatory bowel disease (IBD), psoriasis, chronic obstructive pulmonary disease (COPD), and acquired immune deficiency syndrome (AIDS). Further, such a drug may be used for the treatment and/or prevention of proliferative disorders, such as neoplasias and/or cancer. Alternatively, a drug may be designed which is effective for the treatment and/or prevention of an inflammatory and/or allergic disorders caused by the lethal factor of *Bacillus anthracis*, e.g. anthrax. However, the above mentioned diseases are exemplary and other diseases or conditions not mentioned herein may also be contemplated.

In a further aspect, the present invention relates to the use of a protein having a structure substantially as defined for the LTA hydrolase of the invention, or a part, analogue or derivative thereof for screening a compound for possible medicinal activity. In the pharmaceutical industry, new or known compounds are routinely screened for new uses employing a variety of known in vitro or in vivo screens. Often such screens involve complex natural substances and are consequently expensive to carry out, and the results may be difficult to interpret. However, the knowledge of the three-dimensional protein structure according to the invention allows a preliminary screening to be carried out on the basis of the three-dimensional structure of a region thereof, and the structural similarity of a molecule which is being screened. Such screening can conveniently be carried out using computer modelling techniques, which match the three-dimensional structure of the protein or part thereof with the structure of the molecule being screened. Potential agonist or inhibitor activity may be predicted. As a result, the production efficiency, bioavailability, immunogenicity, stability etc. may be favourably changed with respect to their therapeutic application.

As regards the above disclosed M1 inhibitors, these compounds will presumably find a broader field of application than the other novel inhibitors according to the invention. Thus, the novel general M1 inhibitors are advantageously used e.g. in models to disclose in further detail other enzymatic pathways. Further, they may also be used in the above mentioned type of methods of drug design etc.

2.4.5 Screening for LTA$_4$ Hydrolase Analogues

2.4.5 (a) Method

Accordingly, in another aspect, the invention relates to a method for screening LTA$_4$ hydrolase analogues that mimic at least a part of the three dimensional structure of LTA$_4$ hydrolase, which comprises the steps of
(a) producing a multiplicity of analogue structures of the LTA$_4$ hydrolase
(b) selecting an analogue structure represented by a three-dimensional representation wherein the three-dimensional configuration and spatial arrangement of specific regions, preferably involved in ligand binding of said LTA$_4$ hydrolase, remain substantially preserved.

The coordinates used are general for LTA$_4$ hydrolase are essentially as illustrated in Table 9, as defined by atom nos. 1-4876.

More specifically, analogue structures of LTA$_4$ hydrolase may be screened by their ability to catalyze a particular reaction which may be monitored by chemical physical or immunological means. Furthermore, the analogue structure may be selected from its ability to produce receptor ligands or inhibitors of secondary reactions, which may be monitored directly, as examplified above, via binding assays, enzyme assays, chemical assays, or functional bioassays.

Thus, in one embodiment, the invention relates to a method of screening, wherein one or more analogues exhibiting epoxide hydrolase activity, are screened for. Thus, such a method may be based on the data of Table 9, wherein the binding of thiolamine to LTA$_4$ hydrolase is shown, preferably combined with the information of Table 3 regarding the active site of LTA$_4$ hydrolase. In one embodiment, the invention relates to a method of screening, wherein one or more analogues exhibiting epoxide hydrolase activity, are screened for. In an alternative embodiment, the present method is used to screen for analogues exhibiting aminopeptidase activity, which method e.g. is based data concerning the binding of bestatin to LTA$_4$ hydrolase is used, preferably combined with the information of Table 2 regarding the active site of LTA$_4$ hydrolase. Thus, the present analogues will comprise a region which is essentially analogue with the regions of LTA$_4$ hydrolase exhibiting aminopeptidase activity, and/or analogues exhibiting epoxide hydrolase activity are selected.

In an advantageous embodiment of the screening method according to the invention, one or more analogues comprising one or more genetic modifications, as compared to the naturally occurring form of LTA hydrolase, are selected.

2.4.5 (b) Analogues Obtainable by the Present Screening Method

Further, the invention also relates to a novel analogue obtainable by the method according to the invention, such as an analogue exhibiting an increased or improved or otherwise modified catalytic activity when compared to the naturally occurring form of LTA hydrolase. Preferably, said catalytic activity is an epoxide hydrolase and/or aminopeptidase activity. Further, the invention relates to an analogue obtainable by the present method and capable of acting as a metallohydrolase, preferably belonging to the M1 class of metallohydrolases.

2.4.5 (c) Mutated Forms of LTA$_4$ Hydrolase Obtainable by the Present Screening Method In one advantageous embodiment, the present invention relates to a specified analogue which is a mutated form of LTA$_4$ hydrolase, which analogue comprises one or more of the mutations defined in the following Tables 5-7, wherein amino acids are given in single letter code. Thus, Q134G/AN/L/I/S/T/DIE/N/R/H/K/P/C/M/F/Y/W indicates that residue glutamine 134, using the LTA$_4$ hydrolase numbering scheme, is modified to an alanine, valine, a leucine and so forth.

TABLE 5

| Mutations in the active site | |
|---|---|
| Q134G/A/V/L/I/S/T/D/E/N/R/H/K/P/C/M/F/Y/W | 5(1) |
| Q136G/A/V/L/I/S/T/D/E/N/R/H/K/P/C/M/F/Y/W | 5(2) |
| A137G/V/L/I/S/T/D/E/N/Q/R/H/K/P/C/M/F/Y/W | 5(3) |
| Y267G/A/V/L/I/S/T/D/E/N/Q/R/H/K/P/C/M/F/W | 5(4) |
| G268A/V/L/I/S/T/D/E/N/Q/R/H/K/P/C/M/F/Y/W | 5(5) |
| G269A/V/L/I/S/T/D/E/N/Q/R/H/K/P/C/M/F/Y/W | 5(6) |
| M270G/A/V/L/I/S/T/D/E/N/Q/R/H/K/P/C/F/Y/W | 5(7) |
| E271G/A/V/L/I/S/T/D/N/Q/R/H/K/P/C/M/F/Y/W | 5(8) |
| V292G/A/L/I/S/T/D/E/N/Q/R/H/K/P/C/M/F/Y/W | 5(9) |
| H295G/A/V/L/I/S/T/D/E/N/Q/R/K/P/C/M/F/Y/W | 5(10) |
| E296/G/A/V/L/I/S/T/D/N/Q/R/H/K/P/C/M/F/Y/W | 5(11) |
| H299G/A/V/L/I/S/T/D/E/N/Q/R/K/P/C/M/F/Y/W | 5(12) |
| W311G/A/V/L/I/S/T/D/E/N/Q/R/H/K/P/C/M/F/Y | 5(13) |
| F314G/A/V/L/I/S/T/D/E/N/Q/R/H/K/P/C/M/Y/W | 5(14) |
| W315G/A/V/L/I/S/T/D/E/N/Q/R/H/K/P/C/M/F/Y | 5(15) |
| E318G/A/V/L/I/S/T/D/N/Q/R/H/K/P/C/M/F/Y/W | 5(16) |
| V322G/A/L/I/S/T/D/E/N/Q/R/H/K/P/C/M/F/Y/W | 5(17) |
| F362G/A/V/L/I/S/T/D/E/N/Q/R/H/K/P/C/M/Y/W | 5(18) |
| V367G/A/L/I/S/T/D/E/N/Q/R/H/K/P/C/M/F/Y/W | 5(19) |
| L369G/A/V/I/S/T/D/E/N/Q/R/H/K/P/C/M/F/Y/W | 5(20) |
| I372G/A/V/L/S/T/D/E/N/Q/R/H/K/P/C/M/F/Y/W | 5(21) |
| P374G/A/V/L/I/S/T/D/E/N/Q/R/H/K/C/M/F/Y/W | 5(22) |
| D375G/A/V/L/I/S/T/E/N/Q/R/H/K/P/C/M/F/Y/W | 5(23) |

TABLE 5-continued

| Mutations in the active site | |
|---|---|
| A377G/V/L/I/S/T/D/E/N/Q/R/H/K/P/C/M/F/Y/W | 5(24) |
| Y378G/A/V/L/I/S/T/D/E/N/Q/R/H/K/P/C/M/F/W | 5(25) |
| P382G/A/V/L/I/S/T/D/E/N/Q/R/H/K/C/M/F/Y/W | 5(26) |
| Y383G/A/V/L/I/S/T/D/E/N/Q/R/H/K/P/C/M/F/W | 5(27) |
| R563G/A/V/L/I/S/T/D/E/N/Q/H/K/P/C/M/F/Y/W | 5(28) |

More specifically, this embodiment relates to an analogue comprising any combination of at least two mutated amino acids, or any one of the above mentioned sequences of mutations, or any separate one amino acid mutation selected from the group consisting of sequences nos 1-9, 13-15, 17-24, 26 and 28, which are all novel mutations that have never been published before the present application. As two specific embodiments of the present mutations according to the invention, E271Q and D375N are mentioned, which have shown to be especially advantageous. However, the other sequences not specified above are novel in the present context and thus such specific uses thereof are within the scope of the present invention.

TABLE 6

| Mutations of the curved outside of the N-terminal domain | |
|---|---|
| R17 G/A/V/L/I/S/T/D/N/E/Q/H/K/P/C/M/F/Y/W | 6(1) |
| K19 G/A/V/L/I/S/T/D/N/E/Q/R/H/P/C/M/F/Y/W | 6(2) |
| H20 G/A/V/L/I/S/T/D/N/E/Q/R/K/P/C/M/F/Y/W | 6(3) |
| H22 G/A/V/L/I/S/T/D/N/E/Q/R/K/P/C/M/F/Y/W | 6(4) |
| R24 G/A/V/L/I/S/T/D/N/E/Q/H/K/P/C/M/F/Y/W | 6(5) |
| D28 G/A/V/L/I/S/T/N/E/Q/R/H/K/P/C/M/F/Y/W | 6(6) |
| T33 G/A/V/L/I/S/D/N/E/Q/R/H/K/P/C/M/F/Y/W | 6(7) |
| T35 G/A/V/L/I/S/D/N/E/Q/R/H/K/P/C/M/F/Y/W | 6(8) |
| G36/A/V/L/I/S/T/D/N/E/Q/R/H/K/P/C/M/F/Y/W | 6(9) |
| T37 G/A/V/L/I/S/D/N/E/Q/R/H/K/P/C/M/F/Y/W | 6(10) |
| A39 G/V/L/I/S/T/D/N/E/Q/R/H/K/P/C/M/F/Y/W | 6(11) |
| T41 G/A/V/L/I/S/D/N/E/Q/R/H/K/P/C/M/F/Y/W | 6(12) |
| Q43 G/A/V/L/I/S/T/D/N/E/R/H/K/P/C/M/F/Y/W | 6(13) |
| K63 G/A/V/L/I/S/T/D/N/E/Q/R/H/P/C/M/F/Y/W | 6(14) |
| V65 G/A/L/I/S/T/D/N/E/Q/R/H/K/P/C/M/F/Y/W | 6(15) |
| N67 G/A/V/L/I/S/T/D/E/Q/R/H/K/P/C/M/F/Y/W | 6(16) |
| N97 G/A/V/L/I/S/T/D/E/Q/R/H/K/P/C/M/F/Y/W | 6(17) |
| E99 G/A/V/L/I/S/T/D/N/Q/R/H/K/P/C/M/F/Y/W | 6(18) |
| V101 G/A/L/I/S/T/D/N/E/Q/R/H/K/P/C/M/F/Y/W | 6(19) |
| E103 G/A/V/L/I/S/T/D/N/Q/R/H/K/P/C/M/F/Y/W | 6(20) |
| S105 G/A/V/L/I/T/D/N/E/Q/R/H/K/P/C/M/F/Y/W | 6(21) |
| E107 G/A/V/L/I/S/T/D/N/Q/R/H/K/P/C/M/F/Y/W | 6(22) |
| K153 G/A/V/L/I/S/T/D/N/E/Q/R/H/P/C/M/F/Y/W | 6(23) |
| T155 G/A/V/L/I/S/D/N/E/Q/R/H/K/P/C/M/F/Y/W | 6(24) |
| T157 G/A/V/L/I/S/D/N/E/Q/R/H/K/P/C/M/F/Y/W | 6(25) |
| E159 G/A/V/L/I/S/T/D/N/Q/R/H/K/P/C/M/F/Y/W | 6(26) |
| S161 G/A/V/L/I/T/D/N/E/Q/R/H/K/P/C/M/F/Y/W | 6(27) |
| D175 G/A/V/L/I/S/T/N/E/Q/R/H/K/P/C/M/F/Y/W | 6(28) |
| E177 G/A/V/L/I/S/T/D/N/Q/R/H/K/P/C/M/F/Y/W | 6(29) |
| T178 G/A/V/L/I/S/D/N/E/Q/R/H/K/P/C/M/F/Y/W | 6(30) |
| D180 G/A/V/L/I/S/T/N/E/Q/R/H/K/P/C/M/F/Y/W | 6(31) |
| R186 G/A/V/L/I/S/T/D/N/E/Q/H/K/P/C/M/F/Y/W | 6(32) |
| I188 G/A/V/L/S/T/D/N/E/Q/R/H/K/P/C/M/F/Y/W | 6(33) |
| K190 G/A/V/L/I/S/T/D/N/E/Q/R/H/P/C/M/F/Y/W | 6(34) |
| I192 G/A/V/L/S/T/D/N/E/Q/R/H/K/P/C/M/F/Y/W | 6(35) |
| K194 G/A/V/L/I/S/T/D/N/E/Q/R/H/P/C/M/F/Y/W | 6(36) |

TABLE 7

| Mutations at the proline rich region | |
|---|---|
| T359 G/A/V/L/I/S/D/N/E/Q/R/H/K/P/C/M/F/Y/W | 7(1) |
| E358 G/A/V/L/I/S/T/D/N/Q/R/H/K/P/C/M/F/Y/W | 7(2) |
| D443 G/A/V/L/I/S/T/N/E/Q/R/H/K/P/C/M/F/Y/W | 7(3) |
| A446 G/V/L/I/S/T/D/N/E/Q/R/H/K/P/C/M/F/Y/W | 7(4) |

TABLE 7-continued

| Mutations at the proline rich region | |
|---|---|
| Y449 G/A/V/L/I/S/T/D/N/E/Q/R/H/K/P/C/M/F/W | 7(5) |
| S450 G/A/V/L/I/T/D/N/E/Q/R/H/K/P/C/M/F/Y/W | 7(6) |
| P451 G/A/V/L/I/S/T/D/N/E/Q/R/H/K/C/M/F/Y/W | 7(7) |
| G452 /A/V/L/I/S/T/D/N/E/Q/R/H/K/P/C/M/F/Y/W | 7(8) |
| L453 G/A/V/I/S/T/D/N/E/Q/R/H/K/P/C/M/F/Y/W | 7(9) |
| P454 G/A/V/L/I/S/T/D/N/E/Q/R/H/K/C/M/F/Y/W | 7(10) |
| P455 G/A/V/L/I/S/T/D/N/E/Q/R/H/K/C/M/F/Y/W | 7(11) |
| I456 G/A/V/L/S/T/D/N/E/Q/R/H/K/P/C/M/F/Y/W | 7(12) |
| K457 G/A/V/L/I/S/T/D/N/E/Q/R/H/P/C/M/F/Y/W | 7(13) |
| P458 G/A/V/L/I/S/T/D/N/E/Q/R/H/K/C/M/F/Y/W | 7(14) |
| N459 G/A/V/L/I/S/T/D/E/Q/R/H/K/P/C/M/F/Y/W | 7(15) |
| Y460 G/A/V/L/I/S/T/D/N/E/Q/R/H/K/P/C/M/F/W | 7(16) |
| D461 G/A/V/L/I/S/T/N/E/Q/R/H/K/P/C/M/F/Y/W | 7(17) |

2.4.5 (d) Nucleic Acids Encoding the Novel Compounds

Further, the invention also relates to an isolated nucleic acid encoding a novel analogue as defined above, that is, including a combination of any at least two of said mutations or one of the novel mutations, as well as a nucleic acid capable of specifically hybridising to a such a nucleic acid. The conditions of specific hybridisation are defined above in the section "Definitions". Further, the invention also relates to any vector or carrier comprising such a nucleotide, such as plasmids, viral vectors, e.g. retrovirus, oligonucleotides etc. Thus, any cell including such a nucleic acid or vector are also within the scope of the present invention and may e.g. be a mammalian cell, such as a human cell, or any other eucaryotic cell, or a procaryotic cell, such as a bacterium. The above mentioned elements may be used in the design of model systems useful in the study of the diseases discussed elsewhere in this application, which systems may be cell cultures, animal models, such as mice, etc.

2.4.6 (a) Production and Purification of Genetically Modified Forms of LTA$_4$ Hydrolase Yet another aspect of the present invention is a process for the production of a novel genetically modified form of LTA$_4$ hydrolase identified or designed according to the present invention. Thus, the present process involves, after conventional steps of insertion a gene encoding the desired product in a host cell and expression thereof, a purification procedure, which includes a hydroxyapatite-based chromatography and a subsequent anion exchange chromatography. These last two steps have been shown to be especially advantageous, in fact, even crucial, for obtaining a satisfying purity of the novel LTA$_4$ hydrolase forms according to the invention. The preceding steps are conventional as disclosed in literature and are easily performed by the skilled in this field.

Thus, in more detail, the invention relates to a method for purification of LTA$_4$ hydrolase comprised of (i) precipitation with ammonium sulphate, followed by (ii) separations on FPLC using anion exchange, hydrophobic interaction, and chromatofocusing resins, essentially as described (Wetterholm A., Medina J. F., Rådmark O., Shapiro R., Haeggström J. Z., Vallee B. L., Samuelsson B. *Biochim. Biophys. Acta.* 1080, 96-102 (1991)). To achieve a purity suitable for crystallography, we used (iii) chromatography on hydroxyapatite, e.g., on a TSKgel HA-1000, Tosohaas, followed by (iv) a step of anion-exchange chromatography on e.g., Mono-Q HR5/5.

Further, example 4 below describes in detail a purification of LTA$_4$ hydrolase according to the invention. Said example may be generalised to describe further the purification according to the invention.

2.4.6 (b) Purified LTA$_4$ Hydrolase

Further, the invention also relates to an essentially pure form of LTA$_4$ hydrolase obtained by the process described above.

2.4.7 Identification of LTA$_4$ Hydrolase Binding Compounds

2.4.7 (a) Method

In yet a further aspect, the present invention relates to a method for screening LTA$_4$ hydrolase binding compounds complementary to a region, preferably an enzymatically active site, e.g. as defined in Tables 1-3, of the LTA$_4$ hydrolase molecule, which comprises the steps of
(a) producing a multiplicity of possible complementary structures and
(b) selecting a structure represented by a three-dimensional representation, wherein the three-dimensional configuration and spatial arrangement of regions of LTA$_4$ hydrolase involved in binding remain substantially preserved, which selection is based on the three-dimensional structure of LTA$_4$ hydrolase and/or LTA$_4$ hydrolase complexed to an inhibitor thereof, e.g. as defined by the coordinates of Table 9.

More specifically, the method according to the invention will advantageously be used to select compounds capable of inhibiting epoxide hydrolase activity and/or aminopeptidase activity, LTB$_4$ receptor antagonists or inhibitors of LTC$_4$ synthases or inhibitors of any member of the M1 class of metallohydrolases. In one preferred embodiment, general enzyme inhibitors are screened for, which inhibitors are useful in the control of any one of a plurality of enzymatic pathways, wherein a metallohydrolase of the M1 type is participating. These general metallohydrolase inhibitors are herein denoted M1 inhibitors.

Structure-Based Design of Inhibitors

In a further embodiment, the present invention relates to a method of structure-based design of LTA$_4$ hydrolase inhibitors. Such methods are based on the use of the present coordinates, or preferably the coordinates defining a selected region, as templates in order to synthesize advantageous inhibitors with strong and specific binding properties. More specifically, said method first uses a conventional organic synthesis, alone or combined with combinatorial chemistry, wherein the structure of the product of the synthesis is then further refined by cycles of crystallisation of enzyme and inhibitor, followed by another chemical synthesis, the product of which is again refined, etc.

Example 2 describes such a design, wherein it is noted that the removal of an extra carbon atom could yield a compound, which is a better inhibitor than this hydroxamic acid compound. Thus, similar conclusions will be drawn from the present method and result in inhibitors with superior properties compared to any prior art inhibitors.

2.4.7 (b) Identified Binding Compounds

Further, the present invention also relates to any novel compounds identifiable by the present method. Advantageous and desired properties as well as other features of such compounds, e.g. as inhibitors, is discussed above in relation to complementary compounds, analogues etc. In one preferred embodiment of the invention, such an identified compound is an inhibitor of another M1 enzyme than LTA hydrolase, such as. The medicinal aspects of the present compounds will be discussed below.

Protein Engineering 2.4.8 (a) Method

In a further aspect, the present invention relates to a method of engineering a protein, which method comprises the steps of
identification of a suitable set of mutation sites based on the structure of $LTA_4$ hydrolase according to the invention,
generation of a library of genes which contains the suitable sequence variations;
selection of clones encoding a $LTA_4$ analogue with a desired activity;
wherein said desired activity is the capability of efficiently producing organic compounds of interest.

The present method is based on recent techniques available for generating large libraries of mutated genes (>1 billion variants) which can be attributed to a selection process of individual genes in the laboratory. Such directed evolution schemes have enormous potential for the design of new proteins, including new substrate specificity for enzymes as well as improving enzyme activities.

Directed evolution, or combinatorial engineering schemes have been successfully applied in evolving RNA molecules with improved binding and catalytic activities (Lorsch and Szostak, 1994). Also binding proteins (and peptides) with good affinities can now routinely be evolved based on a range of different protein folds (Nord et al, 1997). The present methods may be used to perform such a directed evolution of advantageous enzyme activity and specificity and may be performed by someone skilled in this field with reference to the literature, see e.g. O. Kuchner and F. H. Arnold (1997); A. Crameri, S. A. Raillard, E. Bermudez and W. P. C. Stemmer (1998).) In this context, see also the descriptions provided in U.S. Pat. No. 5,873,082, Noguchi, wherein a list processing system for managing and processing lists of data is disclosed; U.S. Pat. No. 5,869,295, LaBean et al., disclosing methods and materials for producing gene libraries; and U.S. Pat. No. 5,856,928, disclosing a process for gene and protein representation, characterization and interpretation thereof.

In general, major difficulties in this kind of process are to search the sequence space: find the suitable sequence variations for a large but limited number of mutations (for the same protein fold an immense number of variations can be made e.g. 10 resides protein, $20^{100}$ variants are in theory possible). It is therefor very important to identify the residues in the protein structure which could effect the activity the most, i.e. the residues near the active site area. Thus, in order to enable a successful performance of a method for engineering proteins with properties relevant in the present field, the data disclosed above, more specifically, in Tables 2-4, is crucial.

Further references which are relevant in the context of protein engineering are K. Nord, E. Gunneriusson, J. Ringdahl, S. Stahl, M. Uhlen, P. A. Nygren (1997): "Binding proteins selected from combinatorial libraries of an alpha-helical bacterial receptor domain", *Nature Biotechnology*, 15, 772-777 (1997); R. Lorsch and J. W. Szostak (1994): "In vitro evolution of new ribozymes with polynucleotide kinase activity", *Nature,* 371, 31-36; A. Crameri, S. A. Raillard, E. Bermudez and W. P. C. Stemmer (1998): "DNA shuffling of a family of genes from diverse species accelerates directed evolution", *Nature,* 391, 288-291; and O. Kuchner and F. H. Arnold (1997): "Directed evolution of enzyme catalysts", *Trends in Biotechnology,* 15, 523-530.

In an advantageous embodiment, the present method is used to engineer $LTA_4$ hydrolase inhibitors and/or analogues. In a specific embodiment of said method, a compound capable of mimicking the suicidal mode of $LTA_4$ hydrolase catalysis, thus acting as a mechanism-based suicide inhibitor, or otherwise capable of regulating the production of $LTB_4$ is engineered. In an alternative embodiment, an inhibitor of $LTC_4$ synthase or an $LTB_4$ receptor antagonist is designed.

2.4.8 (b) Novel Specifically Designed Proteins

Further, the present invention also relates to any novel protein designed by use of the above described method. Once specified, such proteins may be produced by any conventional method well known to the skilled in this field, some of which are examplified below. In Example 2 below, the binding of hydroxamic acid to LTA4 hydrolase is discussed. Thus, such a modified hydroxamic is one example of a novel inhibitor specifically designed according to the invention, and the reasoning in the example may be used as a basis for the way of reasoning that is used in the present design.

Accordingly, novel enzymes may be produced, which are capable of any different chemical activity. For example, enzymes capable of novel catalytic properties, enzymes that in turn produce enzymes, etc., may be produced according to the present invention.

2.4.8 (c) Use of Genetically Modified $LTA_4$ Hydrolase

The invention also encompasses the use of a genetically modified $LTA_4$ hydrolase, obtained by any method according to the invention, with altered catalytic properties, e.g., increased ability to synthesize $LTB_4$. The modified enzyme may thus be used for production of $LTB_4$, or any analogues substances, a biomedical reagent which in turn may be used in, e.g., studies of leukotriene metabolism, induction of chemotaxis, as a reference compound in analysis of leukotrienes etc.

2.4.9 Pharmaceutical Applications of the Present Invention 2.4.9 (a) First Medical Indication Further, the invention also encompasses a compound obtainable by the method of screening $LTA_4$ hydrolase binding compounds, structure-based drug design, or the protein engineering methods described above, and more preferably, said compound for use as a medicament. One specifically advantageous embodiment is the herein disclosed novel M1 inhibitor for use as a medicament.

In an advantageous embodiment, the present compounds are used in the manufacture of a medicament for the treatment and/or prevention of acute and chronic inflammatory disorders, said disorder being selected from the group consisting of arthritis, inflammatory bowel disease (IBD), psoriasis and chronic obstructive pulmonary disease (COPD); neoplasias and/or cancer; or disorders caused by the lethal factor of *Bacillus anthracis*, e.g. anthrax. Alternatively, the use may relate to the manufacture of a medicament for the treatment and/or prevention of an inflammatory and/or allergenic disorder, such as bronchial asthma, allergic rhinitis, conjunctivitis etc. Yet an alternative use is in the manufacture of a medicament for the treatment and/or prevention of infection caused be human immunodeficiency virus (HIV). The novel M1 inhibitor are preferably used in medicaments for the treatment and/or prevention of such various diseases as cancer and/or endocrinological disturbances.

2.4.9 (b) Second Medical Indication and Pharmaceutical Methods

Thus, the present invention relates to the above mentioned molecules prepared by the method according to the invention for use in the manufacture of various medicaments for the above defined conditions. The invention also encompasses pharmaceutical preparations containing these molecules together with pharmaceutically acceptable carriers. Methods for the preparation of pharmaceutical preparations are e.g. found in Remington's Pharmaceutical Sciences, Mack Publishing Company, Philadelphia, Pa., $17^{th}$ ed. (1985). For a review of drug delivery, see Langer, Science 249:1527-1533 (1990). As those skilled in this field easily realise, the form of such a pharmaceutical preparation, the mode of administration thereof as well as suitable dosages will depend on the specific disease to be treated, the nature of the active substance used, the patient's age, body weight etc.

2.4.9 c) Methods of Treatment

The present invention also encompasses any method of treatment for the above defined purposes. Exact details regarding such methods are determined by the practitioner depending on the specific circumstances from case to case.

2.5 PRODUCTION OF NOVEL PROTEINACEOUS COMPOUNDS

The compounds, which may be proteins, polypeptides, peptides or any other organic molecules, prepared according to the methods according to the invention may be synthesized chemically by methods well known to those of skill in this field or they may be prepared by use of recombinant DNA technology by any suitable method well known to those of skill in this field. General methods of synthesis are e.g. found in Berger and Kimmel, Guide to Molecular Cloning Techniques, Methods in Enzymology, vol. 152, Academic Press, Inc., San Diego, Calif.; Sambrook et al., Molecular Cloning, A Laboratory Manual, $2^{nd}$ Ed., vol. 1-3, Cold Spring Harbor Laboratory, Cold Spring Harbor, N.Y., 1989; and Current Protocols in Molecular Biology, F. M. Ausbel et al., Current Protocols (1994). Methods of reducing and denaturing proteins and inducing re-folding are well known to those of skill in the art, see e.g. Debinski et al., J. Biol. Chem., 268: 14065-14070 (1993); Kreitman and Pastan, Bioconjug. Chem., 4: 581-585 (1993); and Buchner et al., Anal. Biochem., 205: 263-270 (1992).

2.6 DETAILED DESCRIPTION OF THE DRAWINGS

FIG. 1 shows key enzymes and intermediates in leukotriene biosynthesis.

Figure 2:
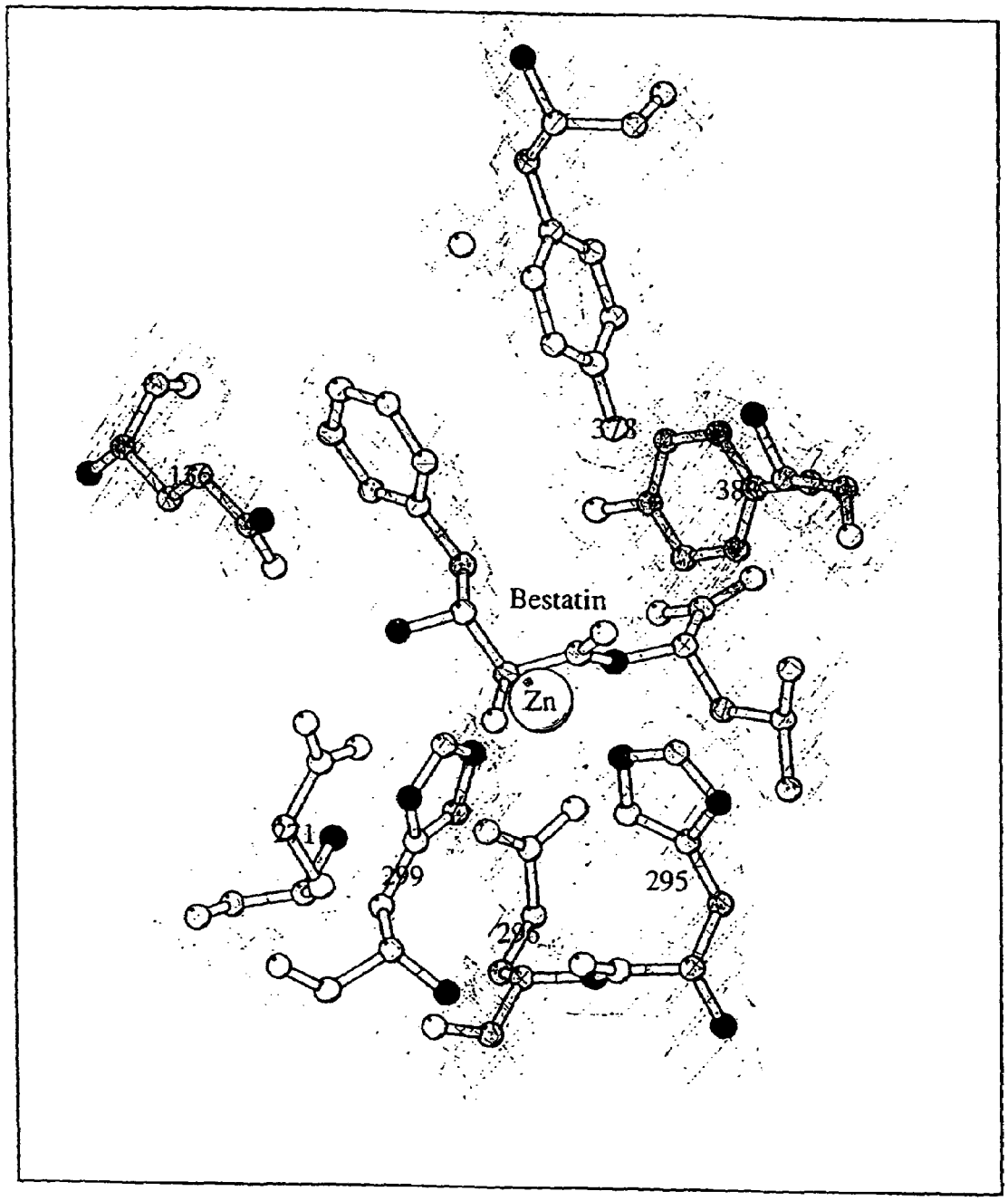
FIG. 2 shows 2Fo-Fc density contoured at 1.1 s. Part of the active site in the neighborhood of the bestatin molecules is shown.

FIG. 2 shows 2Fo-Fc density contoured at 1.1 σ. Part of the active site in the neighborhood of the bestatin molecules is shown. Figures are created using a modified version of Molscript48,49.

Figure 3:
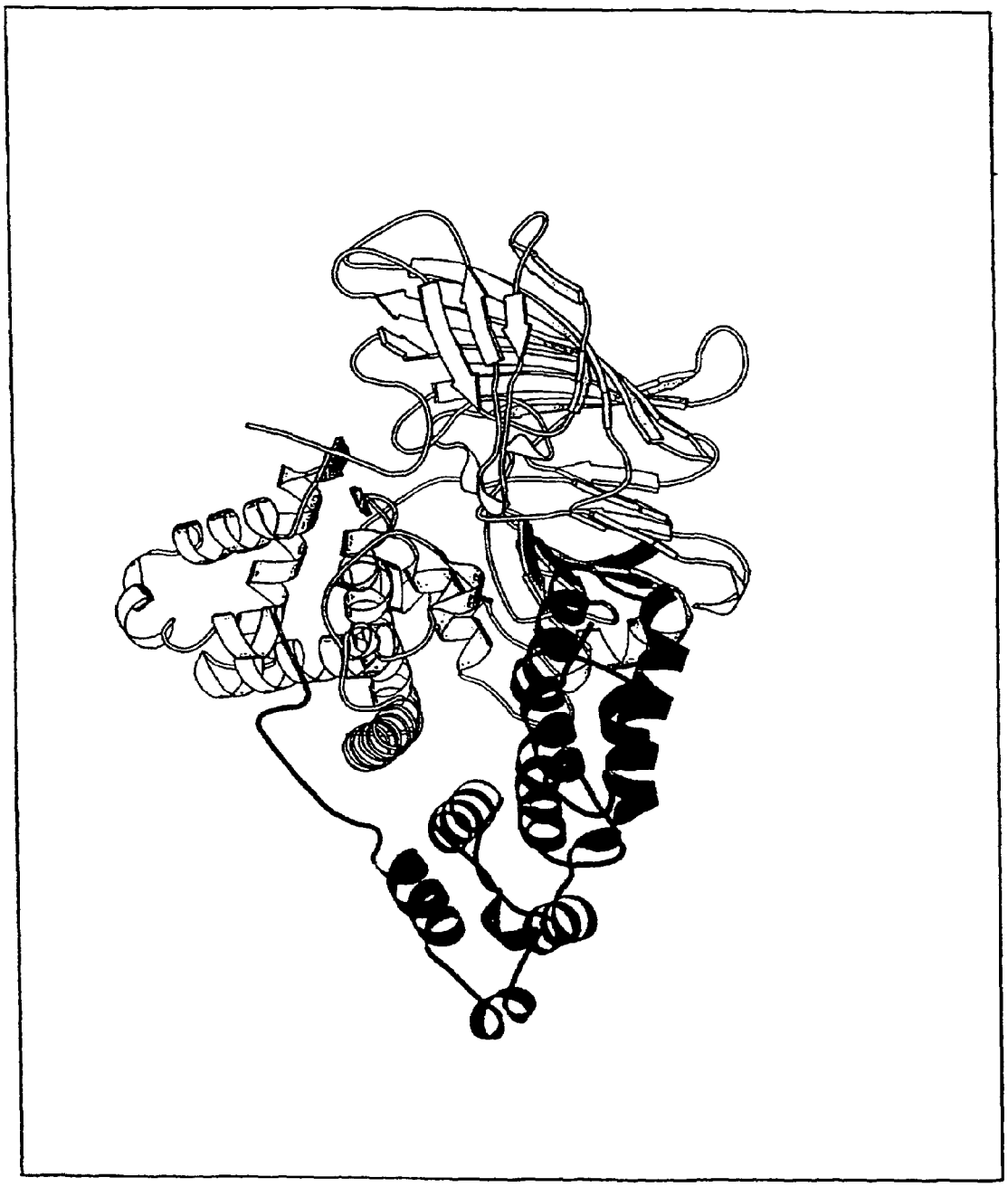
FIG. 3 is a ribbon diagram of the tertiary structure of leukotriene $A_4$ hydrolase.

FIG. 3 is a ribbon diagram of the tertiary structure of $LTA_4$ hydrolase. The N-terminal domain at the top of the diagram is rich in β-strands and connects to the catalytic domain to the left in the figure which is more α-helical and extends into the central part of the molecule. The C-terminal domain, illustrated at the bottom of the ribbon diagram, extends towards the right side of the catalytic domain.

FIG. 4 (a) is a ribbon diagram of the N-terminal domain with its layers of β-strands, while (b) is a superimposition of the Cα trace of the N-terminal domain on the Cα trace of bacteriochlorophyll a. The N-terminal domain covers approx. half of the bacteriochlorophyll a structure (the right and bottom part of the diagram).

Figure 5A:
FIG. 5 shows ribbon diagrams of the catalytic domain of $LTA_4$ hydrolase and thermolysin.
Figure 5B:
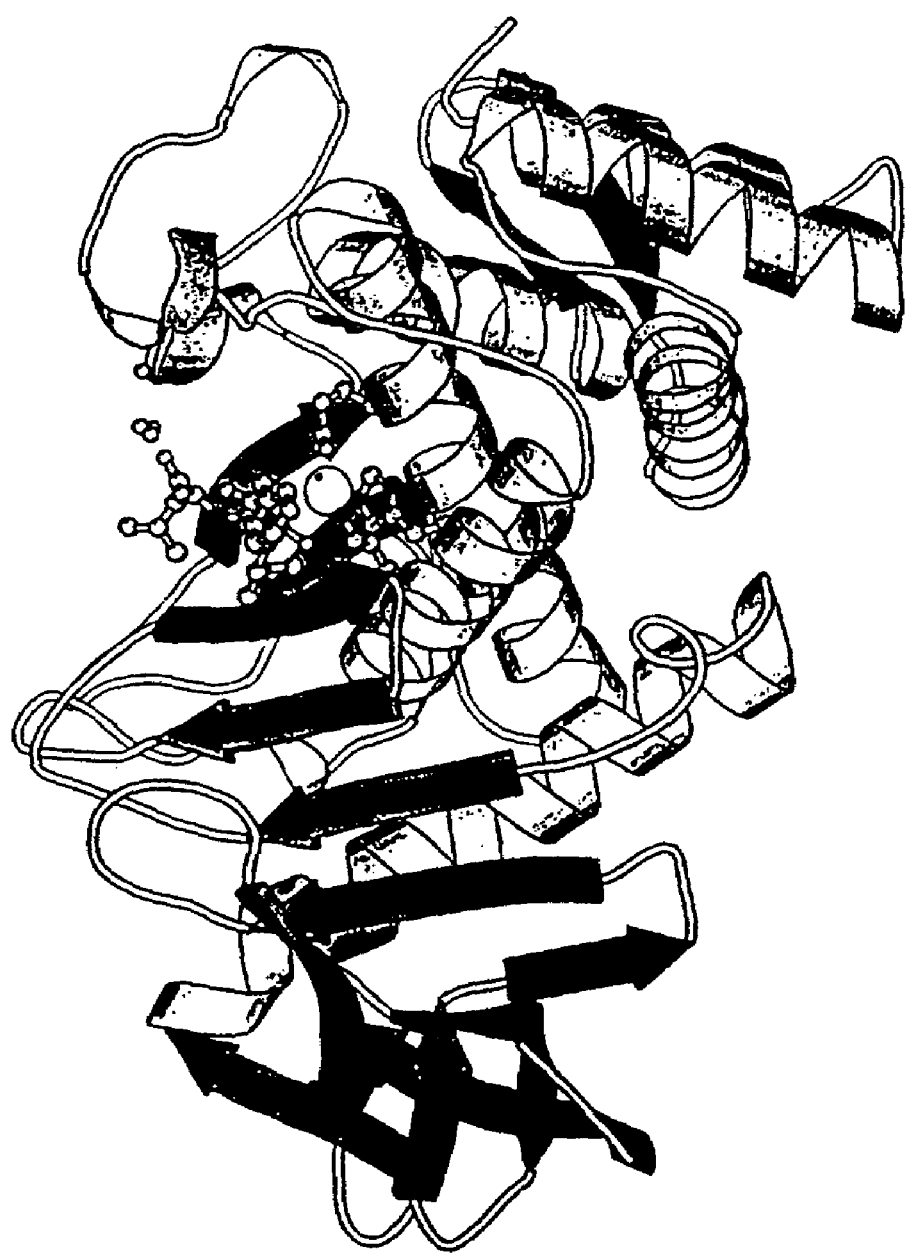

FIG. 5 (a) is a ribbon diagram of the catalytic domain. In the center of the diagram, the three zinc binding ligands, His295, His299, and Glu318, as well as the inhibitor bestatin are depicted in ball and stick representation. The zinc ion is shown as a CPK model. The diagram in (b) shows the structure of thermolysin in the same orientation as the catalytic domain of $LTA_4$ hydrolase. The three zinc ligands, His142, His146, and Glu166, as well as the inhibitor Cbz-GlyP-(O)-Leu-Leu50 are depicted in ball- and stick representation. The zinc ion is shown as a CPK model.

Figure 6:
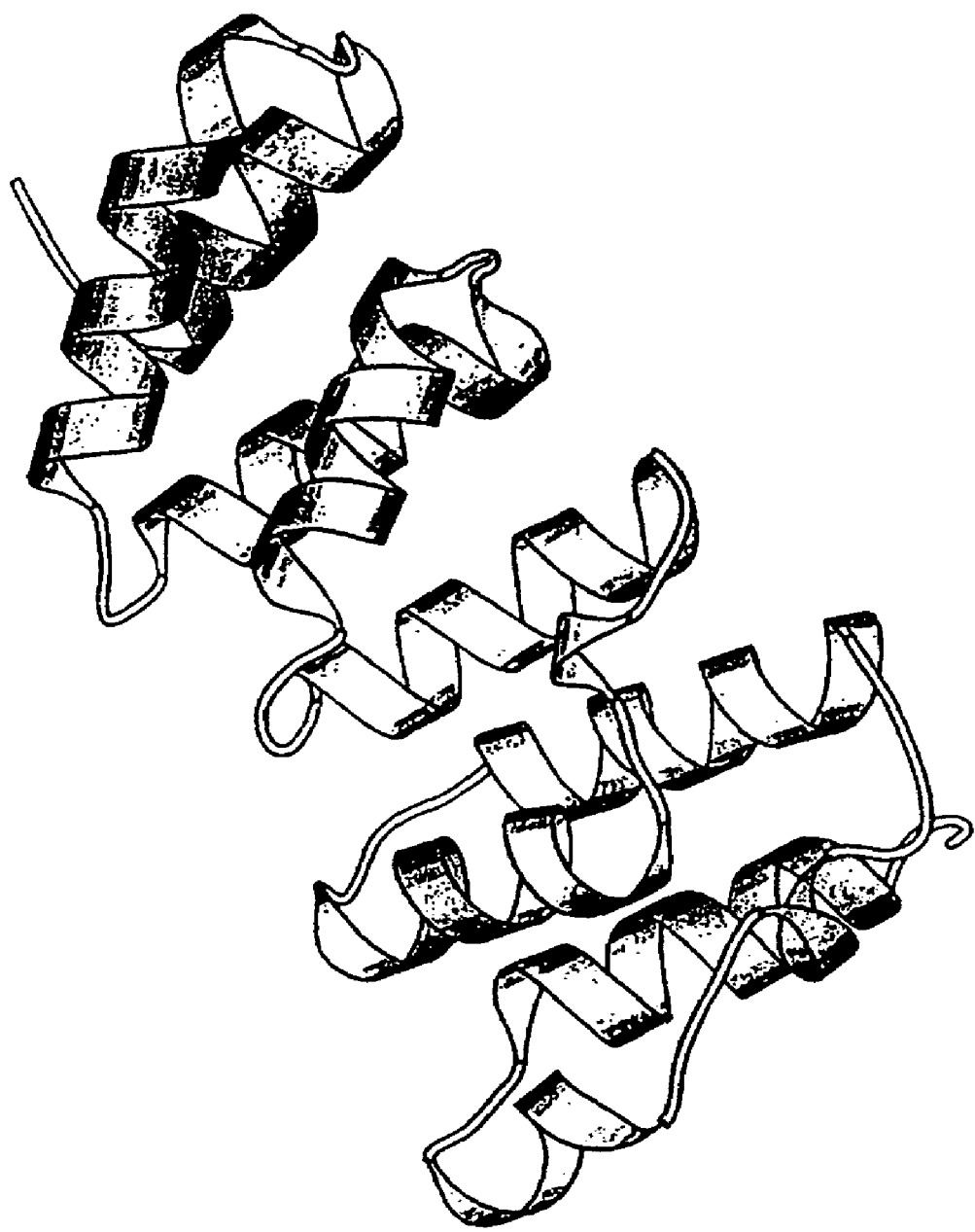
FIG. 6 shows the structure of the C-terminal domain.

FIG. 6 shows the structure of the C-terminal domain.

Figure 7:
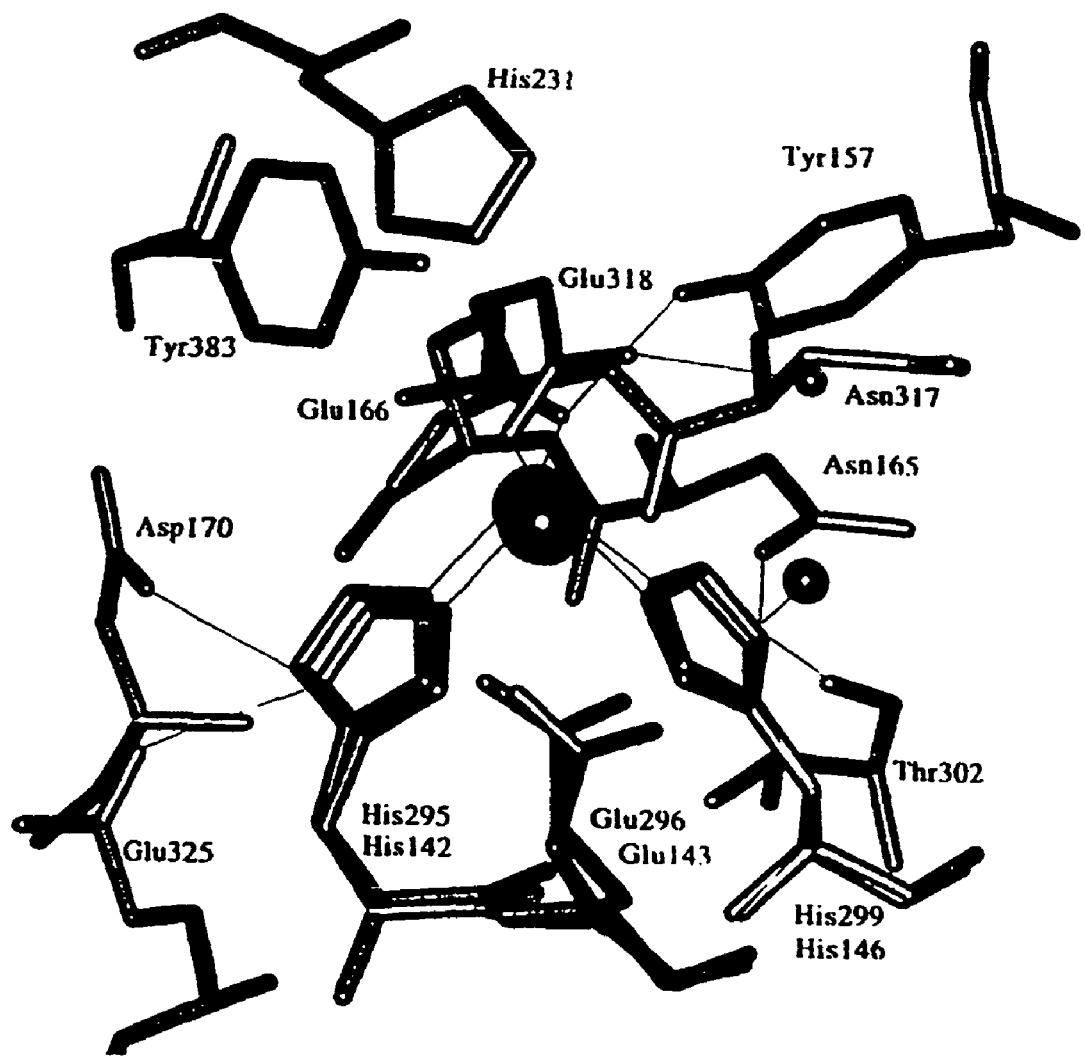
FIG. 7 illustrates zinc binding ligands in $LTA_4$ hydrolase.

FIG. 7 shows the zinc binding ligands in $LTA_4$ hydrolase, His295, His299, and Glu318, superimposed on those in thermolysin, His142, His146, and Glu-166. Other catalytic or neighboring residues in the two enzymes are Tyr383, Glu325, Glu296, Thr302, and Asn317 in $LTA_4$ hydrolase which correspond to His231, Asp170, Glu143, Asn165, and Tyr157 in thermolysin.

FIG. 8 (a) is a Ball-and-Stick presentation of the binding of bestatin in $LTA_4$ hydrolase.

FIG. 8 (b) is a schematic overview of bestatin binding in $LTA_4$ hydrolase.

FIG. 9 (a) is a wire representation of the cavity found in $LTA_4$ hydrolase (shown as Cα-trace).

FIG. 9 (b) is a schematic presentation for the proposed binding of $LTA_4$ into the cavity.

Figure 10:
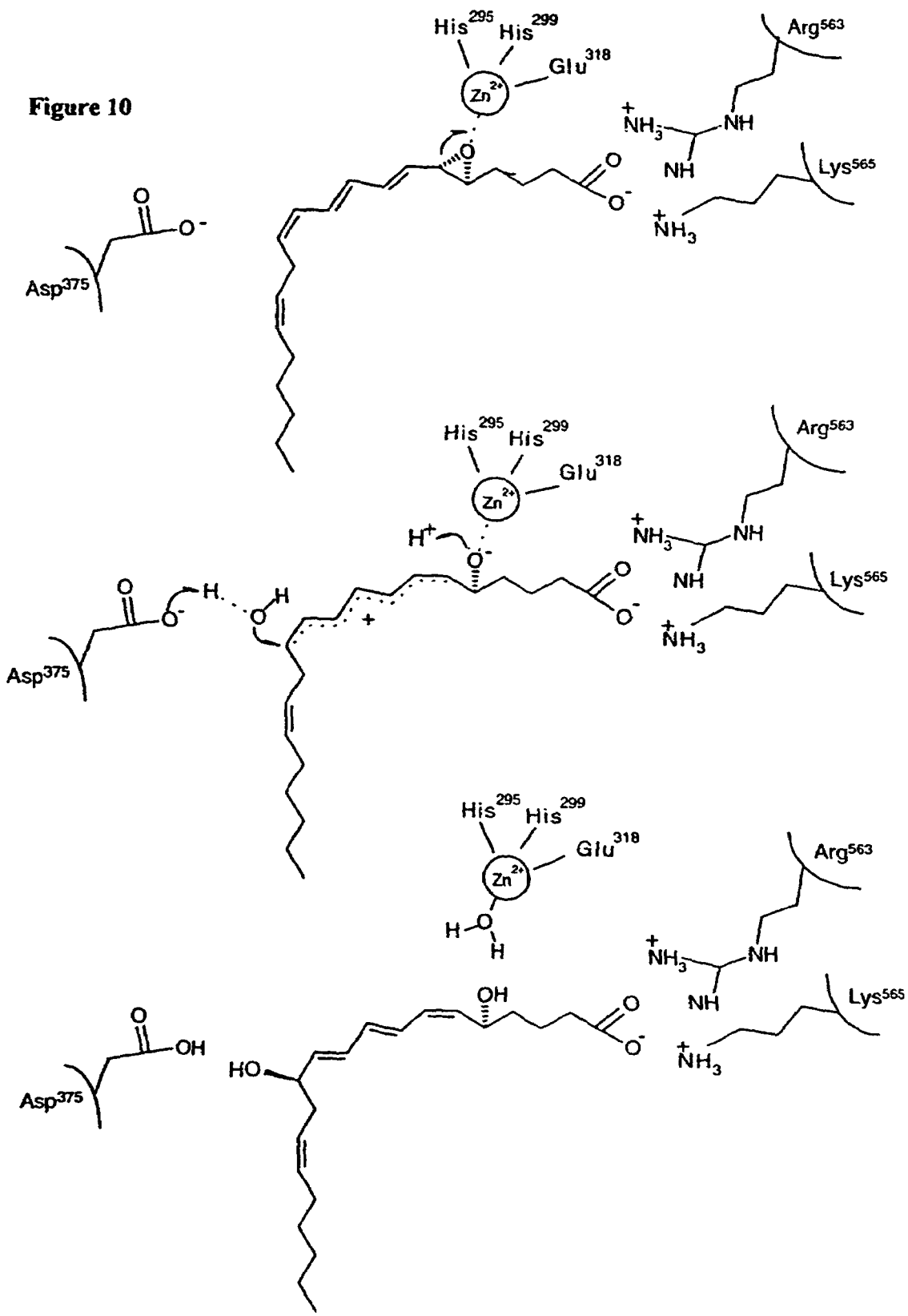
FIG. 10 is a schematic representation for the proposed reaction mechanism of the epoxide hydrolase.

FIG. 10 is a schematic representation for the proposed epoxide hydrolase reaction mechanism. The catalytic zinc acts as a Lewis acid and activates the epoxide to form a carbocation intermediate according to an $S_N1$ reaction. Water is added at C12 in a stereospecific manner, presumably directed by Asp375. The double bond geometry is controlled by the binding conformation of $LTA_4$. Further details are given elsewhere in the present description.

3. EXPERIMENTAL

The following examples are intended for illustrating purposes only and should not in any way be used to construe the scope of the protection of the present invention as defined by the appended claims. All the references given below, and previously in this specification, are hereby included herein by reference.

3.1 Examples

Example 1

Binding of the Thiol-Compound (I)

The thiol group of the compound is ligated to the $Zn^{2+}$ ion, that has a tetra-hedral configuration. Both the phenyl-groups are making extensive hydrophobic interactions. The first one makes aromatic stacking interactions with Phe314 and Trp311. Further hydrophobic interactions are made with Pro374 and Leu369. The other phenyl ring is making stacking interactions with Tyr267 and Tyr378. Met270 and Gln136 provide additional hydrophobic interactions. The ether-oxygen in the linker between the two phenyl rings makes a hydrogen bond to the backbone nitrogen of Ala137 and also with a water molecule which is linked to Asp375. The amine group makes interactions to the Oε1 of Gln136 and the Oε1 of Glu271.

Formula (I)

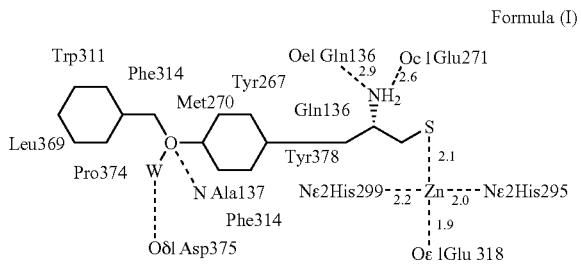

Example 2

Binding of the Hydroxamic Acid Compound (II)

The binding of this compound is very similar to the binding of the thiol compound described above. The manner in which the phenyl-moieties, the linker region and the amine group are bound is identical. The manner in which the hydroxamic acid part is bound is different in comparison with other complexes such as thermolysin-HA complexes and $LTA_4$-hydrolase-bestatin complex. Instead of a double interaction of the hydroxyl and carbonyl oxygens and the Zn ion resulting in a pentavalent co-ordination, here only one of the oxygens (the hydroxyl) is making an interaction with the Zn ion giving a tetrahedral co-ordination. The other oxygens make an interaction to Asp296 and the backbone nitrogen of Gly268. This difference is probably due to the tight binding of the phenyl rings and the amine group. The linkage between the amine group and the hydroxamic acid group contains one more carbon atom than in a normal or modified peptide-linkage. Since the binding site for substrates is rather narrow near the Zn ion, the conformation of compounds which bind in this area is rather restricted. Therefore one of the otherwise binding oxygens is pushed out and can no longer make an interaction with the $Zn^{2+}$ ion. Removal of this extra carbon atom could yield a compound which is a better inhibitor than this hydroxamic acid compound. The acid group at the other end of the compound is fixed by making a double interaction with the Ns and the Nh2 of Arg563.

Example 3

Structure Determination of Two Specific Inhibitor-$LTA_4$ Hydrolase Complexes Crystals, grown as described above, were soaked in 1 mM solution of thiolamine (Yuan et al., 1993) or 0.5 mM solution of hydroxamic acid (Hogg et al., 1995) in 15% PEG8000, 50 mM Imidazol pH 6.7, 25 mM acetate and 2.5 mM $YbCl_3$. After at least 24 hours, the crystals were transferred to a solution that contained a cryoprotectant (see above) and subsequently flash frozen in liquid nitrogen. The data for the crystal soaked with thiolamine was obtained at BM14B at the EMBL-outstation in DESY, Hamburg. The data for the hydroxamic acid was collected at beamline 7/11 at MAX-lab, Lund. Statistics from the data collections are shown in the table. The data were processed using MOSFLM, merging and other manipulations were performed by programs from CCP4 and the BIOMOL packages. The refinement procedures for both datasets were very similar. First rigid body refinement using TNT was performed. As a starting model for refinement and model building the structure of $LTA_4$ hydrolase complexed with bestatin was used. The bestatin molecule and all water molecules were deleted from the model. After this initial refinement it was possible to build the inhibitors into the protein. For evaluation of the density maps and model-building the program QUANTA (Molecular Simulations Inc., Burlington, Mass.) was used. The refinement was continued using TNT and was combined with sessions of model-building. In all rounds no sigma cut-offs were used and the resolution was slowly increased during the procedure. Water molecules were identified and incorporated into the models. During these procedures the $R_{free}$ was carefully monitored. When refinement had converged, it was finished with one round in which all reflections, including those who were used for the calculations of the $R_{free}$, were incorporated. Statistics about refinement and quality of the models can be found in Table 5.

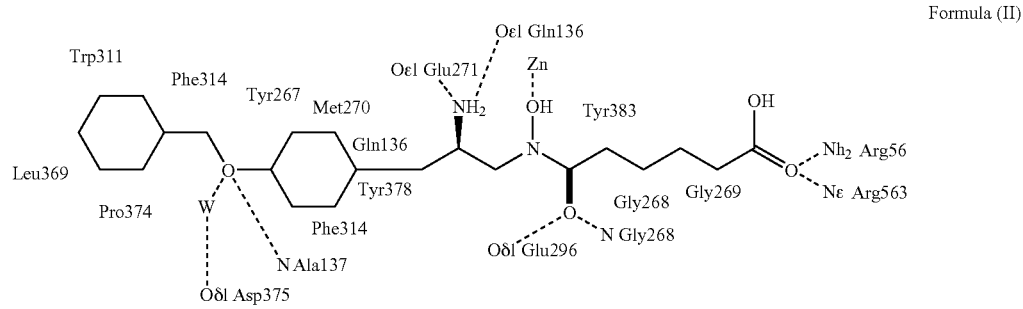

Formula (II)

TABLE 8

Statistics of refinement and quality of the model

| | Thiolamine (Thiol) | Hydroxamic acid (HA) |
|---|---|---|
| Resolution | 15-2.5 Å | 15-1.8 Å |
| Rfactor | 17.8% | 24.2% |
| Rfree | 24.4 | 29.7% |
| Bond Lengths | 0.011 Å | 0.012 Å |
| Angles | 1.9° | 2.0° |
| Trigonal groups | 0.005 Å | 0.006 Å |
| Planar groups | 0.009 Å | 0.010 Å |
| Contacts | 0.026 Å | 0.041 Å |
| No. of Waters | 252 | 127 |

Example 4

Purification of LTA$_4$ Hydrolase

For adsorption chromatography on hydroxyapatite, a TSK-gel HA-1000 column (Tosohaas) was equilibrated in 10 mM potassium phosphate buffer, pH 7.1, supplemented with 0.2 mM CaCl$_2$. The enzyme sample was applied and a linear gradient of increasing phosphate (10-400 mM) was developed by mixing the starting buffer with 400 mM potassium phosphate buffer, pH 6.8, supplemented with 10 µM CaCl$_2$. Active fractions containing LTA$_4$ hydrolase were eluted between 150-190 mM potassium phosphate.

Anion exchange chromatography was performed on a Mono-Q HR 5/5 column (Pharmacia Biotech) equilibrated with the loading buffer 10 mM Tris-Cl, pH 8. The pure protein was eluted using a linear gradient of KCl (0-500 mM) and was recovered at 110-140 mM KCl.

Example 5

Enzyme Engineering

The present inventors have shown, that when Tyr-378 in LTA$_4$ hydrolase was exchanged for a Phe residue, the resulting mutated enzyme was no longer suicide inhibited by LTA$_4$ and exhibited a substantially increased catalytic efficiency. Furthermore, the mutated enzyme was capable of converting LTA$_4$ not only into the natural product LTB$_4$, but also into a novel metabolite, 6-trans-8-cis-LTB$_4$. (Mueller, M. J., et al. *Proc Natl Acad Sci USA* 93, 5931-5935 (1996)).

Example 6

Enzyme-Engineering

Tyr-383 in mouse LTA$_4$ hydrolase was exchanged for Gln residue, which resulted in a mutated enzyme capable of forming the unnatural product 5S, 6S-dihydroxy-7,9-trans-11, 14-cis-eicosatetraenoic acid from LTA$_4$ (Andberg, M., Hamberg, M. & Haeggstrom, J. Z. *J. Biol. Chem.* 272, 23057-23063 (1997)).

Example 7

Crystallisation of LTA$_4$ Hydrolase

LTA$_4$ hydrolase was crystallised using YbCl$_3$ as an additive, 15% PEG and 50 mM Na-acetate as precipitant and 50 mM imidazole, pH 6.7, as buffer. Liquid-liquid-diffusion in capillaries were used as crystallisation set-ups.

3.2 Materials and Methods

Enzyme purification. Human recombinant LTA$_4$ hydrolase was expressed in *E. coli* and purified to homogeneity in four chromatographic steps on FPLC using anion exchange, hydrophobic interaction, chromatofocusing, and hydroxyapatite resins, essentially as described (Wetterholm A., Medina J. F., Rådmark O., Shapiro R., Haeggstrom J. Z., Vallee B. L., Samuelsson B. Recombinant mouse leukotriene A$_4$ hydrolase: a zinc metalloenzyme with dual enzymatic activities. *Biochim. Biophys. Aca.* 1080, 96-102 (1991)).

Crystallization Conditions. The chemicals used for the crystallization experiments were purchased from Merck and were of highest purity available. The sparse matrix kit was obtained from Hampton Research. Crystallization conditions for the protein were initially sought by using the sparse matrix approach (Jancarik, J. & Kim, S.-H. *J. Appl. Crystallogr.* 24, 409-411 (1991)) in hanging drop vapor diffusion set-ups in cell culture plates at room temperature. Under condition 28, (30% PEG8000, 0.2 M sodium-acetate, 0.1 M cacodylate buffer, pH 6.5) needles grew. They were subsequently reproduced and optimized using a finer grid search, different temperatures for the equilibration and testing of additives. Crystals were only obtained when the inhibitor bestatin was present in the crystallization set-ups. Using YbCl$_3$ as an additive and switching to liquid-liquid diffusion in capillaries, allowed plate-like crystals to grow. Thus, 5 µl 28% PEG8000, 0.1 M Na-acetate, 0.1 M imidazole buffer, pH 6.8, 5 mM YbCl3 is injected into the bottom of a melting point capillary and an equal volume of LTA$_4$ hydrolase (5 mg/ml) in 10 mM Tris-Cl, pH 8, supplemented with 1 mM bestatin, is layered on top. Finally, the capillary is closed and stored at 22° C. Crystals with an average size of 0.6×0.4×0.05 mm$^3$ appear in 3 to 4 weeks.

Crystal properties. The plate-like crystals diffract beyond 2 Å using synchrotron radiation. They belong to space-group P2$_1$2$_1$2 with cell dimensions a=67.59 Å, b=133.51 Å, c=83.40 Å, a=b=g=90° at 100 K. As a cryo-solution, a mixture of 15% PEG 8000, 50 mM Na-acetate, 50 mM imidazole buffer, pH 6.8, 2.5 mM YbCl$_3$, and 25% glycerol was used. Assuming one molecule per asymmetric unit the solvent content of the crystals is 48%.

Structure determination. The structure was determined by using multiple anomalous dispersion measurements on the LIII edge of Ytterbium (λ=1.3862 Å) at beam line BM14 at the European Synchrotron Radiation Facility (ESRF), Grenoble. Three datasets, peak (PK), point of inflection (PI) and remote (RM), were collected to 2.5 Å resolution from the same crystal. The crystal was aligned such that Bijvoet equivalent reflections could be collected in one pass of 90° for each wavelength. For RM a subsequent dataset to 2.15 Å was collected. A second crystal was used for obtaining a dataset to 1.95 Å. (For statistics on data-collection and quality, see table 1). Data were integrated using the program Denzo, scaled to each other using Scalepack (Otwinowski, Z. *Data collection and Processing. Proceedings of the ccp4 study weekend.* SERC Daresbury Laboratory, Warrington, UK., 56-62 (1993)) and further analyzed using programs from the CCP4 package (Collaborative Computing Project Number 4. *Acta Crystallogr. Sect. D* 50, 760-763 (1994)).

From Patterson functions one major and one minor Yb position could readily be identified, a third position was identified during heavy atom refinement in difference Fourier maps. The heavy atom parameters were refined using MLPHARE (Otwinowski, Z. *Isomorphous replacement anomalous scattering. Proceedings of the CCP4 study weekend.* SERC Daresbury Laboratory, Warrington, UK, 80-85

(1991)) and SHARP (de La Fortelle, E. & Bricogne, G. *Met. Enzymol.* 276, 472-494 (1997)). The final figures of merit was 0.57 to 2.15 Å. Phase information was further improved to 2.15 Å by solvent flattening using SOLOMON (Abrahams, J. P. & Leslie, A. G. W. *Acta Crystallographica* D52, 30-42 (1996)) with a solvent content of 43%. The quality of the maps was very good and the entire protein molecule (residue 1-610) could be traced unambiguously. All model building was performed using QUANTA (Molecular simulations). Refinement was started by a run of slow-cooling molecular dynamics in XPLOR (Brünger, A. T., Kuriyan, J. & Karplus, M. *Science* 235, 458-460 (1987)) using the RM dataset to 2.7 Å. The three Yb ions were included into the refinement with full occupancy for the first Yb and half occupancy for the two other ions. All subsequent refinement was performed with TNT (Tronrud, D. E., ten Eyk, L. F. & Matthews, B. W. *Acta Crystallogr. Sect. A* 43, 481-501 (1987)). The same set of reflections (4% of total amount from 25-1.95 Å) for the calculation of $R_{free}$ (Brünger, A. T. *Nature* 355, 472-475 (1992)) was maintained throughout all refinement procedures. The resolution was slowly improved by alternating sessions of model-building and refinement. The data for the second crystal to 1.95 Å were used for further refinement during which a Zn ion, bestatin, an acetate and an imidazole molecule were identified. Judged from the B-factors these molecules are all fully occupied. 540 water molecules were added to the coordinates. The $R_{free}$ was 24.7% and the working R-factor was 18.8% for all data between 25-1.95 Å. In a final round of refinement all data between 25-1.95 Å were included, yielding a final R-factor of 18.5% for residues 1-610, 3 Yb ions, 1 Zn, 1 bestatin, 1 imidazole, 1 acetate and 540 water molecules. Most of the model is in good density (FIG. 2) except a loop encompassing residues 179 to 184 for which only poor density was obtained. The model has good stereo-chemical parameters (r.m.s bonds=0.010 Å, r.m.s angles=2.2°) and 91.7% of the residues lie in the most favored part of the Ramachandran plot.

4. RESULTS AND DISCUSSION

4.1 Overall Structure and Domain Organization

The leukotriene $A_4$ hydrolase molecule is folded into three domains; an N-terminal domain, a catalytic domain and a C-terminal domain which together form a flat triangular arrangement with approximate dimensions of 85×65×50 Å³. The overall structure of the enzyme is depicted in FIG. 3. Although the three domains pack closely and make contact with each other, a deep cleft is formed in between.

4.2 The N-Terminal Domain is Structurally Related to Bacteriochlorophyll a

Figure 4A:
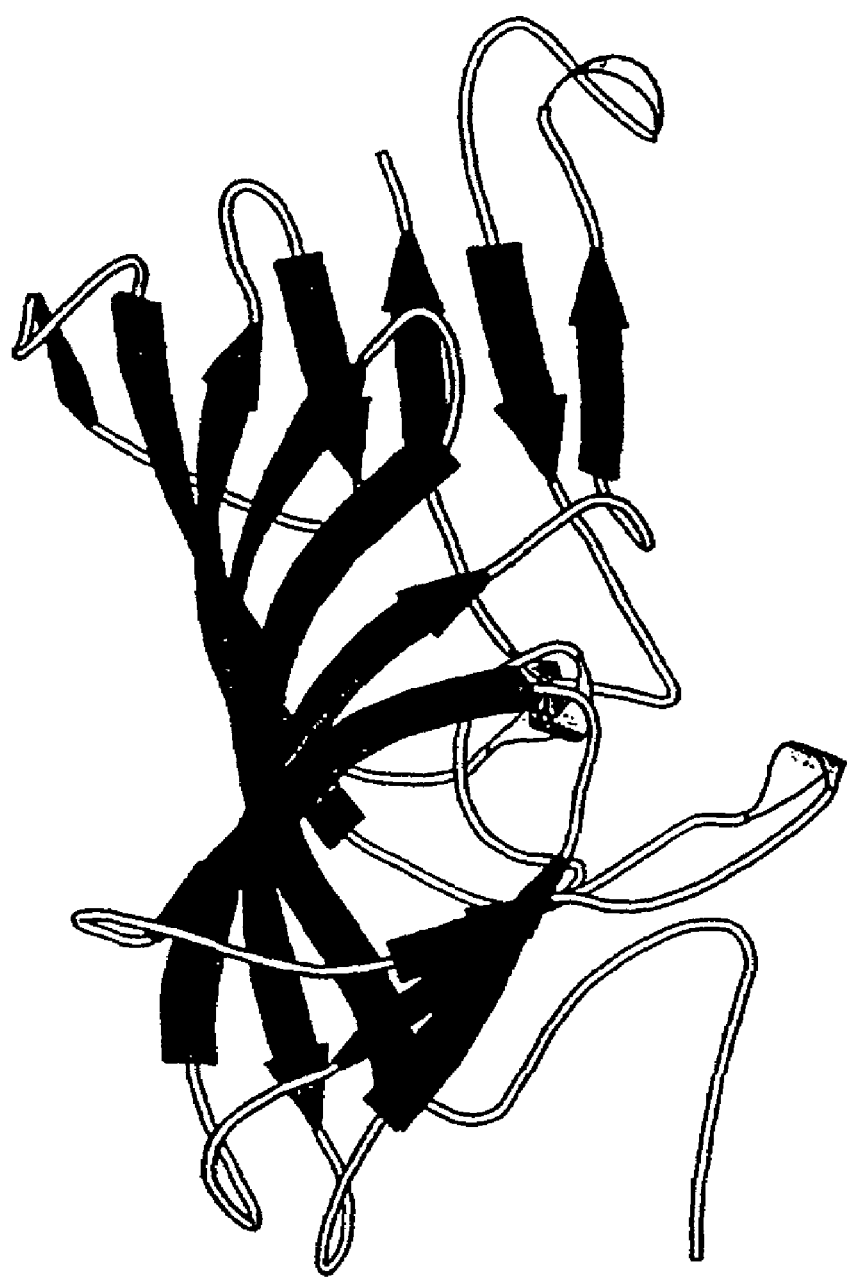
FIG. 4 shows ribbon diagrams of the N-terminal domains of. $LTA_4$ hydrolase.
Figure 4B:
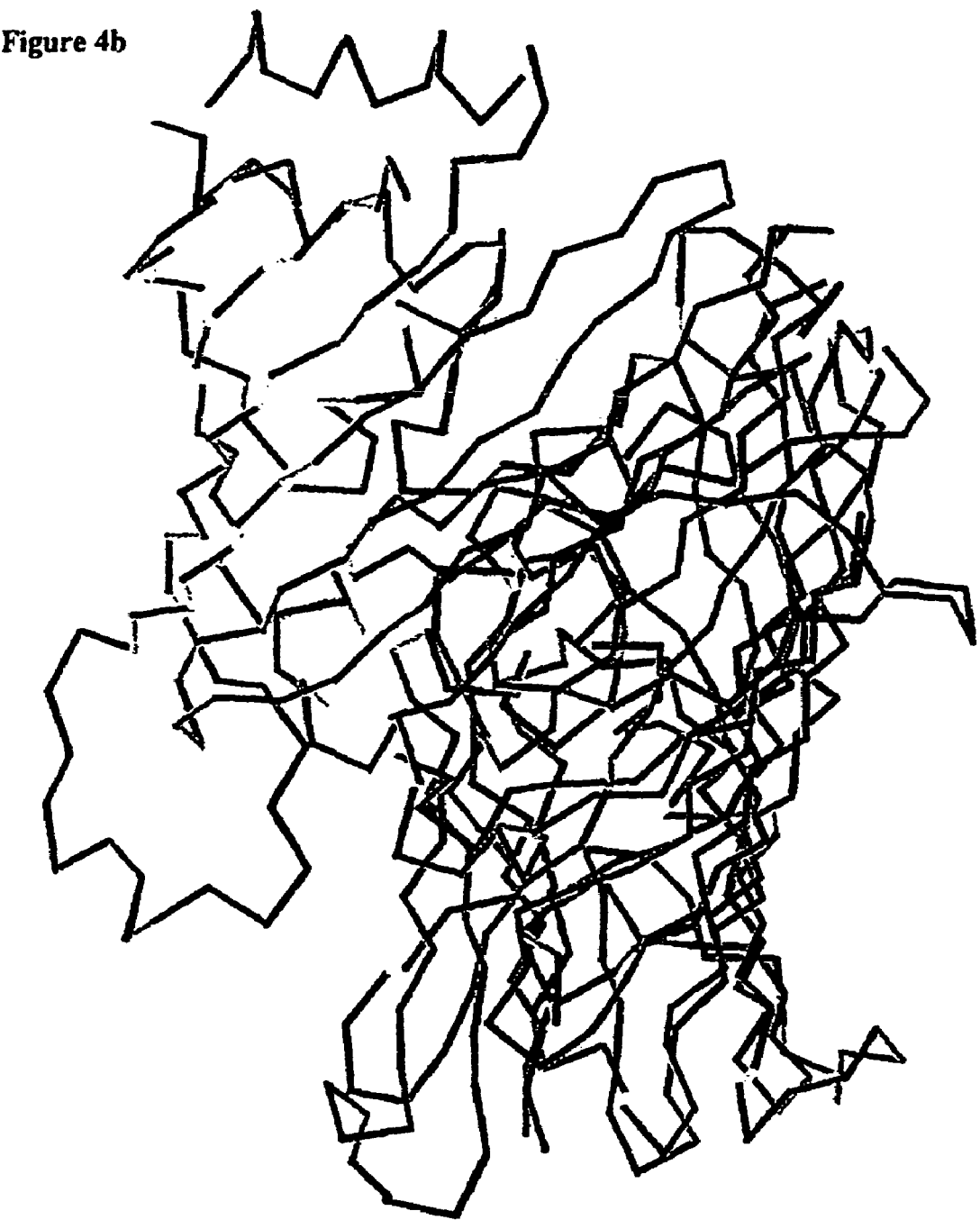

The N-terminal domain (residue 1-209) is composed of one 7 stranded mixed b-sheet, one 4 and one 3 stranded antiparallel β-sheet. Strands from the larger β-sheet continue into the two smaller β-sheets that pack on the edges of the same side of the larger sheet so that a kind of envelope is formed (FIGS. 4a & b). The two small β-sheets are turned towards the inside of the whole protein while the larger β-sheet is exposed to solvent and forms a large concave surface area. Loops connecting the other strands and hydrophobic residues fill the core of this domain. The N-terminal domain of $LTA_4$ hydrolase shares important structural features with the chlorophyll-containing enzyme bacteriochlorophyll (Bchl) a (Matthews, B., Fenna, R., Bolognesi, M., Schmid, M. & Olson, J. *J. Mol. Biol.* 131, 259-285 (1979)). Thus, 111 Cα positions have equivalent positions in the two proteins despite the absence of any sequence identity (FIG. 4b). The domain is about half the size of Bchl a which has a single domain structure without major extensions. Like Bchl a, the shape of the N-terminal domain resembles an envelope (or Taco) with a hollow inside and in Bchl a, 7 bacteriochlorophylls are buried in this cavity. However, the domain is not as hollow as BChl a since loop 135-155, which contains a small helical segment, is turned inwards and fills up the core. In BChl a the equivalent loop (290-305) is positioned more towards the exterior of the protein, thereby leaving space for some of the tertrapyrroles of the bacteriochlorophylls. The large sheet (17 strands) of Bchl a is truncated to only 7 strands in $LTA_4$ hydrolase. Especially the region between residue 35 and 263 of Bchl a has been replaced by a much shorter region in $LTA_4$ hydrolase (res. 45 to 98) that forms the 3 stranded small β-sheet and the edge strand of the larger 7 stranded β-sheet. The structure of the other half of the molecule is almost completely conserved, except the insertion of two extra strands instead of loops in $LTA_4$ hydrolase. The structural homology between Bchl a, a protein involved in light harvesting, and $LTA_4$ hydrolase was certainly unexpected. In $LTA_4$ hydrolase, the function of the N-terminal domain is not yet known, but one may speculate that it participates in binding to hydrophobic molecules or surfaces with a possible regulatory function. In mammalian 15-lipoxygenase, a similar function was proposed for an N-terminal β-barrel domain with structural homology to a corresponding C-terminal domain in mammalian lipases (Gilimor, S. A., Villasenor, A., Fletterick, R., Sigal, E. & Browner, M. F. *Nature Struc. Biol.* 4, 1003-1009 (1997)).

The connection from the N-terminal to the catalytic domain is very short, a strand from the 4 stranded β-sheet connects into a strand of a 5-stranded anti-parallel β-sheet of the catalytic domain. The two sheets are closely packed and the interface is mainly hydrophobic in character with 14 hydrophobic residues contributing from the N-terminal domain and 11 from the catalytic domain. Hydrogen bonds occur between Gln116 and Ser264, Ser124 and Gln226, the backbone of Ser124 and Glu223, the backbone of Ser151 and Lys309, Lys153 and the backbone of Leu305 and indirectly through a water molecule between Tyr130 and the backbone of Val260. Two salt-bridges between His139 and Asp375 and between Arg174 and Asp257 complete the interactions made in this interface.

4.3 The Catalytic Domain Contains the Zinc Binding Site and is Structurally Similar to Thermolysin The structure of the catalytic domain (res. 210-450) is surprisingly similar to the structure of thermolysin (FIGS. 5a & b) (Holmes, M. & Matthews, B. *J. Mol. Biol.* 160, 623-639 (1982)). When the amino acid sequence in this domain was compared with that of thermolysin, the sequence identity was found to be very low (essentially confined to the zinc binding motifs). However, the structural homology stretches out over the whole domain. Thus, no less than 146 Ca positions overlap with an r.m.s. deviation of 1.946 Å. Like thermolysin, the catalytic domain consists of two lobes, one mainly a-helical and one mixed a/b lobe. The a-lobe consists of 6 major helices interconnected by long loops containing smaller helical segments, while the a/b lobe has a 5 stranded mixed β-sheet lined with 3 helices on one side. The zinc binding site is found in between the two lobes. Since this domain contains only 245 amino acids and thermolysin contains 314 residues, some truncations have taken place, especially in the a/b lobe in which the N-terminal extended b structure is truncated and only a mixed 5 stranded β-sheet remains. The changes in the a-lobe are smaller. Here the long meandering loop 181 to 221 has been replaced by a long a-helix and the b-hairpin from 245 to 258 has been deleted.

A loop in extended conformation on the surface of the protein from 451 to 463 connects the catalytic domain with the C-terminal domain. Interestingly, this segment contains a highly conserved proline rich motif P451-G-f-P-P-x-K-P-x-Y460 which bears some resemblance to an SH3 domain recognition sequence. However, the canonical arginine residue is not present on either side of the proline motif. Nevertheless, since this stretch of amino acids is exposed on the surface of the protein, it is still possible that it could serve as an anchoring site for protein-protein interactions.

The C-terminal domain (464-610) is composed of 9 a-helices that form an unusual coil of helices reminiscent of the ones found in lytic transglycosylase[40] and recently in the armadillo repeat region of b-catenin (Huber, A. H., Nelson, W. J. & Weis, W. I. *Cell* 90, 871-882 (1997)) (FIG. 6). The helices pack into two layers of parallel helices (5 inner and 4 outer helices) and in an anti-parallel manner between the two layers. The arrangements found in the two other proteins are much larger and form super-helical structures. In the C-terminal domain of $LTA_4$ hydrolase, the arrangement is more straight and has a very compact shape. One of the helices is deformed and one of the interconnecting loops is long and contains a small 310 helix. The domain makes contacts with both the a-lobe of the catalytic domain and one of the edges of the N-terminal domain. It is positioned in a way such that the helices lie perpendicular to the 7 stranded b-sheet of the N-terminal domain and to most of the helices in the catalytic domain. The helices are amphipatic in character, with the hydrophobic sides towards the middle of the domain and hydrophilic residues pointing towards the solvent and into the deep cleft in the middle of the whole molecule. This side of the cleft is highly polar; 10 Arg and Lys residues and 4 Asp and Glu residues are positioned on this side.

4.4 Zinc Coordination

Figure 8A:
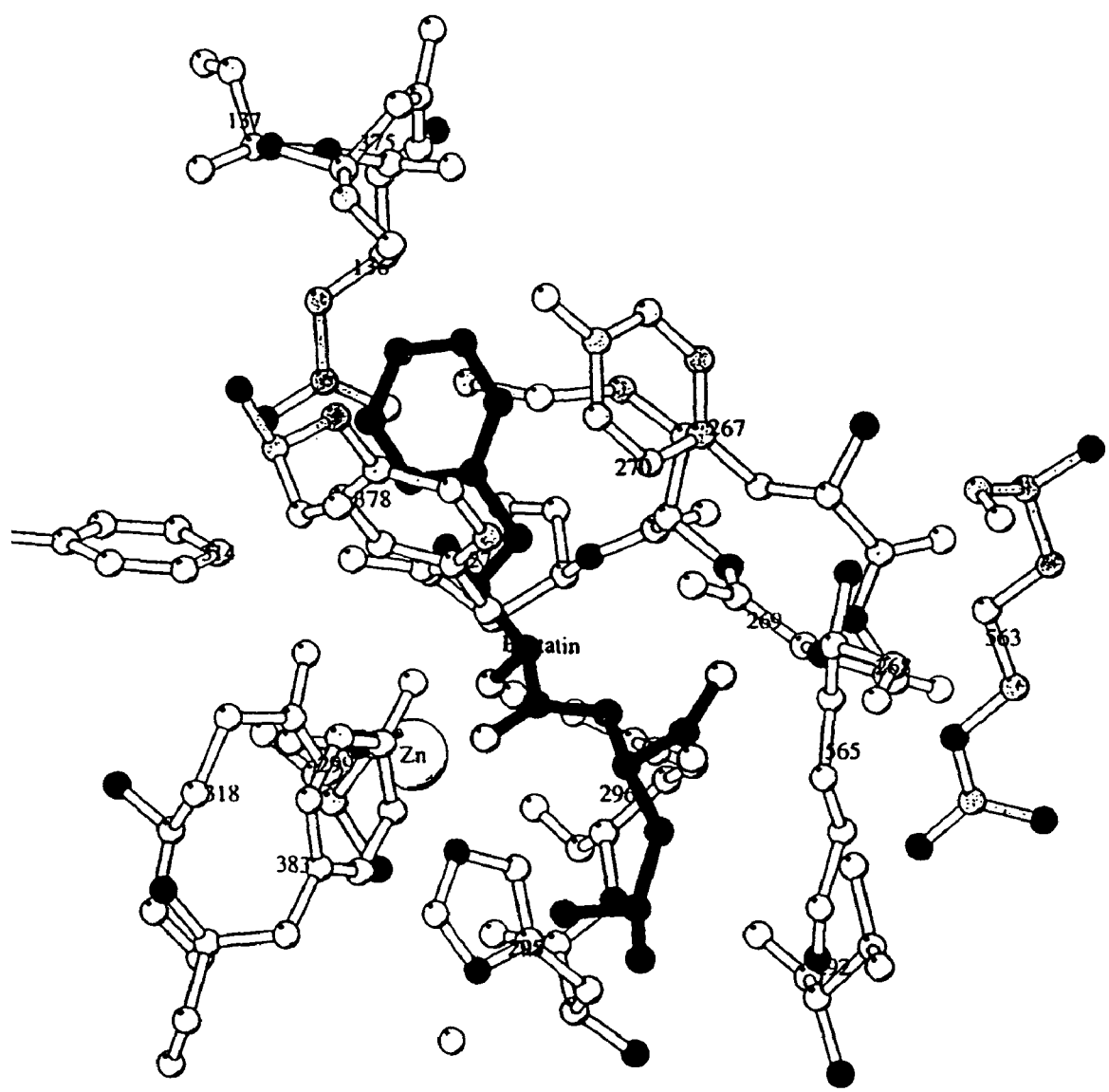
FIG. 8 (a) is a Ball-and-Stick presentation of the binding of bestatin in $LTA_4$ hydrolase, while FIG. 8 (b) is a schematic overview of bestatin binding in $LTA_4$ hydrolase.
Figure 8B:
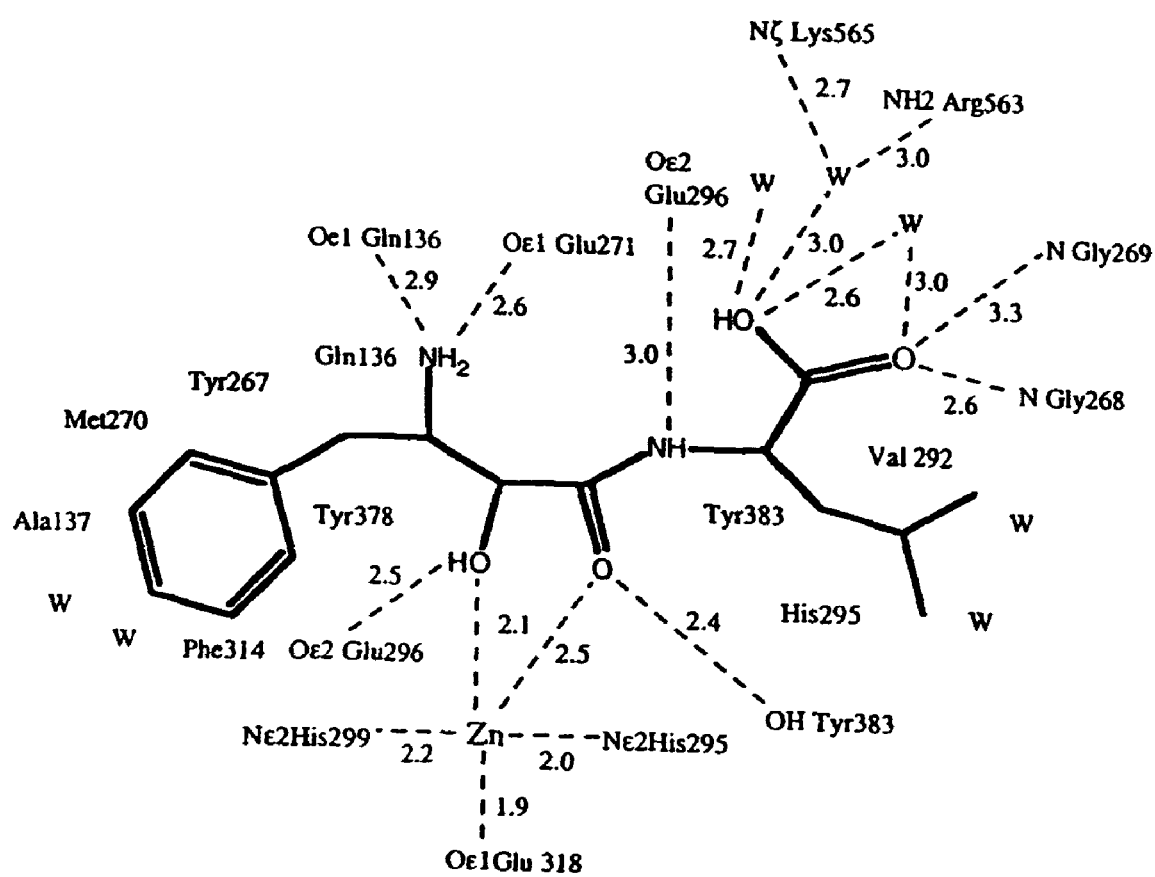

The immediate surroundings of the active site $Zn^{2+}$ ion are very similar in thermolysin and $LTA_4$ hydrolase. The $Zn^{2+}$ is bound between the two lobes and is coordinated by His295, His299, one carboxylic oxygen of Glu318 and the carbonyl and hydroxyloxygens of the inhibitor bestatin so that a square based pyramid is formed. The two histidines originate from a long a-helix and the glutamate from a neighboring a-helix, all in the a-lobe. Glu296 and Tyr383, two residues implicated in the reaction mechanism for the peptide cleaving activity, are located near the Zn ion. Glu296, the putative general base, is positioned next to the metal ligand His295 and bends over the bestatin molecule and Tyr383, which was described as a proton donor, also makes contact with the bestatin molecule (FIG. 8a).

Interestingly, the second layer around the Zn ion shows differences between thermolysin and $LTA_4$ hydrolase. In both enzymes the orientation of the zinc binding ligands is fixed by hydrogen bonds, however the hydrogen bond acceptors are positioned differently. In thermolysin, the Nd1 of His142 is hydrogen bonded to the Od2 of Asp170, while in $LTA_4$ hydrolase the Nd1 of His295 is hydrogen bonded to the Oe1 of Glu325. This residue comes from a structural equivalent to the helix carrying Asp170 in thermolysin, but is shifted half a turn outwards. The Nd1 of His146 in thermolysin is hydrogen bonded to the Od1 of Asn165. This residue is part of the zinc binding signature and is conserved between the two enzymes. However, in $LTA_4$ hydrolase the helix in which this conserved residue is placed has been rotated slightly and Asn317 is no longer making a hydrogen bond to His299. The orientation of His299 is now fixed by a hydrogen bond from the Nd1 to the carbonyl backbone oxygen of Thr302. The Od1 of Asn317 makes instead a hydrogen bond to the backbone amide of Asn381 while the Nd2 makes a hydrogen bond to the hydroxyl group of Tyr200. The last protein-ligand, Glu166 is in thermolysin hydrogen bonded to Tyr157 and a water molecule, in $LTA_4$ hydrolase, Glu318 is only hydrogen bonded to a water molecule (FIG. 7).

4.5 Bestatin Binding

Although the zinc binding site is formed by residues only from the catalytic domain and most catalytic residues also come from this domain, the active site itself is surrounded by loops from all three domains. The binding of bestatin reflects this, since it makes interactions with residues from all three domains. The main interactions of bestatin are made through the carbonyl and hydroxyl oxygens to the Zn atom. Hydrophobic interactions are made between the phenyl moiety and the phenyl rings of Tyr267, Phe316, Tyr378 and Tyr383. Also, Met270 and Gln136 are involved (FIG. 8a). The other end of the inhibitor is pointing towards the solvent, the leucine moiety makes interactions with Val292 and His295, while the carboxylic oxygens make interactions with Arg563 and Lys565 through water molecules as well as hydrogen bonds to the backbone nitrogen atoms of Gly268 and Gly269. Hydrogen bonds are formed between the peptidyl N of bestatin and Oe2 of Glu296 and between the terminal $NH_2$ and the Oe1 of Glu271 and Oe1 of Gln136. The hydroxyloxygen makes apart from the interaction with the Zn ion also an interaction to the OH of Tyr383. (For schematic overview see FIG. 8b). Tyr378 which gets modified during suicide inactivation sits slightly further away, but makes a hydrogen bond to Tyr383 and some hydrophobic interactions with the phenyl ring of the inhibitor. These two tyrosine are both found on the same stretch of amino-acids that in thermolysin form a long a helix, however in leukotriene hydrolase this helix is interrupted and two turns of the helix are replaced by three residues (378-380) in an extended conformation. The binding of bestatin is quite different as was found in the complex between bestatin and bovine lens leucine amino-peptidase (blLAP) (Burley, S., David, P., Sweet, R., Taylor, A. & Lipscomb, W. *J. Mol. Biol.* 224, 113-140 (1992)). In that complex, bestatin was bound to the Zn by both the terminal nitrogen and the nonproteinaceous P1 hydroxyl oxygen, while in $LTA_4$ hydrolase the bestatin is bound by the hydroxyl and carbonyl oxygens. The terminal nitrogen is involved in hydrogen bonding to Glu271 and Gln136. These differences could stem from the fact the blLAP is a bimetal protein with a different reaction mechanism. Moreover the binding of bestatin as seen in $LTA_4$ hydrolase is similar with the complexes formed between thermolysin and hydroxamates which also act as bidentate ligands by the hydroxyl and carbonyl oxygens (Holmes, M. & Matthews, B. *Biochemistry* 20 (1981)).

Figure 9A:
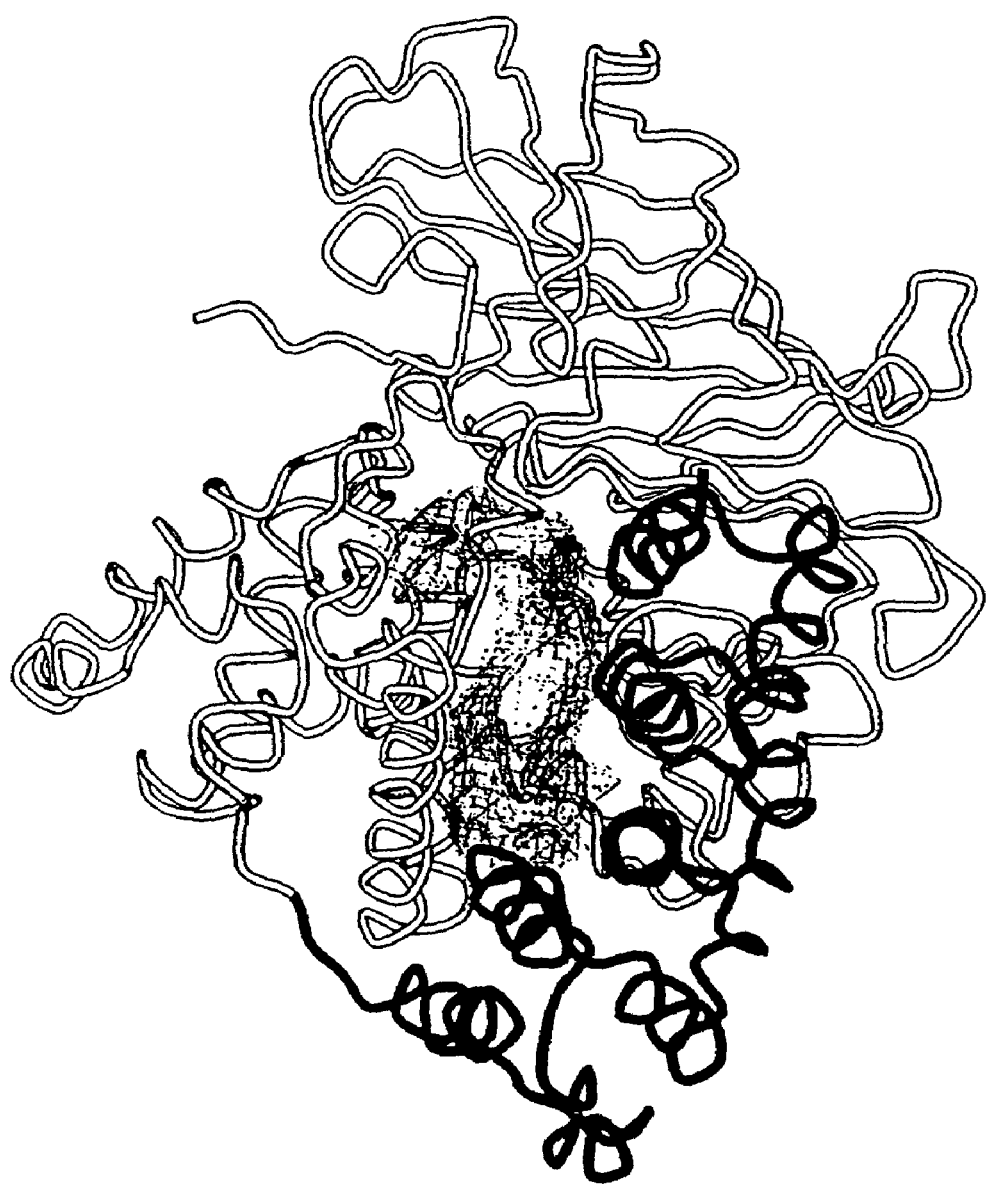
FIG. 9 (a) is a wire representation of the central cavity found in $LTA_4$ hydrolase (shown as Cα-trace).

Behind the pocket in which the phenyl ring of bestatin binds, there is a cavity that stretches 15 Å deeper into the protein and is approximately 6 to 7 Å wide. In the present structure this cavity is filled with water molecules. It has however a very hydrophobic nature and is lined with Trp311, Phe314, Trp315 Phe362, Leu365, Val367, Leu369, Pro374, Ala377, Tyr378, and Pro382. Most of these residues are strictly conserved or conserved in nature in all $LTA_4$ hydrolase sequences known up until now, with the exception of Val367, which is replaced by a Gln in the yeast and *C. elegans* sequences. Interestingly space for this cavity is partly created by the interruption by the extended conformation in the stretch where Tyr378 and Tyr383 are found. One patch of this binding site is quite hydrophilic with Asn134, Asp375 and the OH of Tyr267 clustering together. This bigger cavity could be a binding site for the LTA$_4$ substrate molecule. If the epoxide moiety would bind in a similar way as the carbonyl oxygen of bestatin to the Zn ion, then the hydrophobic tail would fit snugly into the binding site now occupied by the phenyl group of bestatin and would continue into the deeper hydrophobic cavity (FIG. 9a). The other tail would sit in the pocket that is now occupied by the carboxy group of bestatin and it would be long enough for the carboxylic acid to make direct electrostatic interactions with the conserved Arg563 and Lys565.

The replacement of Val367 by Gln as seen in the enzyme from yeast would make the hydrophobic channel shorter and this might be one of the reasons why the yeast enzyme has a poor leukotriene A$_4$ epoxide hydrolase activity. The manner in which the leukotriene molecule would bind is similar as what is proposed for binding of arachidonic acid in 15-lipoxygenase (Gillmor, S. A., Villasenor, A., Fletterick, R., Sigal, E. & Browner, M. F. *Nature Struc. Biol.* 4, 1003-1009 (1997)) with the hydrophobic end buried inside the protein and the carboxylic acid more towards the surface making interactions with Arg and Lys residues.

The binding of bestatin acts also as a guide for the binding of peptide substrate molecules. From systematic binding studies with tri-peptides it was shown that the enzyme has a strong preference for an arginine residue as the N-terminal residue and for several tri-peptides the enzyme has a kcat/Km ratio 10-fold the kcat/Km for LTA$_4$ (Örning, L., Gierse, J. K. & Fitzpatrick, F. A. *J. Biol. Chem.* 269, 11269-11273 (1994). If we roughly model a peptide in the active site with an N-terminal Arg with the carbonyl oxygen sitting on the place of the hydroxyl group of bestatin, then the Arg side-chain of this residue would sit in the same place as the phenyl group of the bestatin with the guanidinium headgroup interacting with the conserved Asp375 and the OH of Tyr267 and the more hydrophobic Cb, Cd and Cg atoms making similar interactions as the phenyl ring. The terminal aminogroup could make the same electrostatic interaction as the terminal aminogroup of bestatin with Asp271 and Gln136. This mode of binding of bestatin is in contrast with the mode proposed by Örning, since the phenyl ring seems to occupy the S1 pocket. We also propose that the LTA$_4$ substrate molecule is occupying all three pockets, S1, S'1 and S'2.

If the binding mode of peptides in LTA$_4$ hydrolase is compared with the one described for thermolysin, a number of differences are observed. In thermolysin, the peptide molecule is held in place by many interactions to the main chain atoms provided by Asn112, Ala203, Arg203 and Trp115. None of these residues or equivalent residues can be found in the binding site in LTA$_4$ hydrolase. Furthermore, although binding pockets S1 and S'1 are at similar positions as in thermolysin, site S'2 has to be different since its space is occupied by Tyr378 in LTA$_4$ hydrolase. Glu271 and Gln136 and the N-terminal domain are fining up the space into which in thermolysin the upstream peptide binds contributing to the exo-peptidase function instead of an endo-peptidase function as in thermolysin.

4.6 Putative Phosphorylation Site

Recently specific phosphorylation by a yet unknown specific kinase of Ser415 has been described as means of regulation of LTA$_4$ hydrolase activity in endothelial cells (Rybina, I. V., Liu, H., Gor, Y. & Feinmark, S. J. *J Biol Chem* 272, 31865-71 (1997)). This residue is conserved in all mammalian LTA$_4$ hydrolases and is embedded in a highly homologous stretch of residues. Phosphorylation of this residue seems to inhibit the epoxide hydrolase activity but not the amino-peptidase activity. In the structure this residue is located in a loop connecting two a-helices that lie on the surface of the molecule. The loop itself is located at the back of the enzyme.

4.7 Aminopeptidase Activity

The amino-peptidase activity catalyzed by this enzyme has been well studied and many of the important residues have been target for site-directed mutagenesis work. This lead to a proposal in which Glu296 would act as a general base (Wetterholm, A., et al. *Proc Natl Acad Sci USA* 89, 9141-9145 (1992)) and Tyr383 as a putative proton donor (Blomster, M., Wetterholm, A., Mueller, M. J. & Haeggstrom, J. Z. *Eur. J. Biochem.* 231, 528-534 (1995)). In the current complex, these residues are involved in hydrogen bonds with the bestatin molecule. If bestatin binding is seen as a rough analog for the transition state binding, then the interaction of Glu296 with the hydroxyl oxygen of bestatin indicates that this residue could indeed activate a water-molecule for the nucleophilic attack. The role of Tyr383 cannot so easily be confirmed, however its position strongly suggest the role of proton donor. In thermolysin the proton donor is His231 and although the Ca position of this residue is 4.1 Å removed from the Ca position of Tyr383 in LTA$_4$ hydrolase, the Nd1 is only 1 Å removed from the OH position of Tyr383. The conserved Glu271 could be involved in the exo-protease activity of the protein. Recently, the analogous Glu350 in aminopeptidase N and Glu352 in aminopeptidase A were subject to site-directed mutagenesis work (Luciani, N., et al. *Biochemistry* 37, 686-692 (1998); and Vazeux, G., Iturrioz, X., Corvol, P. & Llorenz-Cortez, C. *Biochem. J.* 334, 407-413 (1998)) and it was observed that mutations of this residue lead to large decreases in the activity in the case of substitutions by conserved amino-acids such as aspartate and glutamine and absence of activity in substitution by alanine. It was concluded that Glu350 belonged to the anionic binding site in that protein. A mechanism based on thermolysin was proposed for aminopeptidase N with a pentavalent transition state with an additional interaction between the free a-aminogroup and Glu350. In this structure we can observe such an interaction between Glu271 and the free aminogroup of bestatin. Furthermore the penta-valent coordination of Zn by the His295, His299, Glu318 and the carbonyl and hydroxyl groups of bestatin indicates that this is an equivalent transition state analog complex as determined previously for thermolysin.

From careful sequence alignments and structural insight we can conclude that the enzymes in the M1 family of proteases will share a highly conserved catalytic domain that includes part of the N-terminal domain as we see it in LTA$_4$ hydrolase and the thermolysin-like domain. There is no homology for residues in the C-terminal domain and we believe that this domain is unique for LTA$_4$ hydrolases. According to the present invention, it is suggested that all proteases belonging to class M1 with the signature HExxH and a Glu 18 residues downstream will function in a similar way to thermolysin.

4.8 Epoxide Hydrolase Activity

Concerning the epoxide hydrolase activity, much less is known about the functional elements and mechanisms of catalysis. In fact, the prosthetic zinc is the only critical component identified thus far and may potentially assist in the introduction of a water molecule at C12 or in the activation of the epoxide. Although Tyr378 and Tyr383 are important active side residues, none of them is essential for catalysis. A mutation of Tyr378 to Phe protects the enzyme against suicide inhibition, however the specificity of the double bond configuration is partly lost (Mueller, M., Andberg, M., Samuelsson, B. & Haeggstrom, J. *J. Biol. Chem.* 271, 24345-24348 (1996)) since a novel metabolite with a cis-trans-cis conjugated system can be detected. Thus, Tyr378 is a major binding site for $LTA_4$ during suicide inactivation and seems to play a role for the formation of the correct double bond geometry in the product $LTB_4$. Mutations of Tyr383 abolish the amino-peptidase activity where it has a role as potential proton donor (vide supra) but the epoxide hydrolase activity is only decreased compared to wild-type. It is however implicated in the stereospecific introduction of water during the hydrolysis of $LTA_4$ to $LTB_4$ since these mutants convert $LTA_4$ in both $LTB_4$ and 5 [S],6 [S]-DHETE (Andberg, M., Hamberg, M. & Haeggstrom, J. *J. Biol. Chem.* 272, 23057-23063 (1997)). Moreover careful analysis of the catalytic properties of enzymes mutated in pos. 383, viz [Y383F], [Y383H] and [Y383Q]$LTA_4$ hydrolase have indicated that the epoxide hydrolase reaction follows an SN1 mechanism.

Figure 9B:
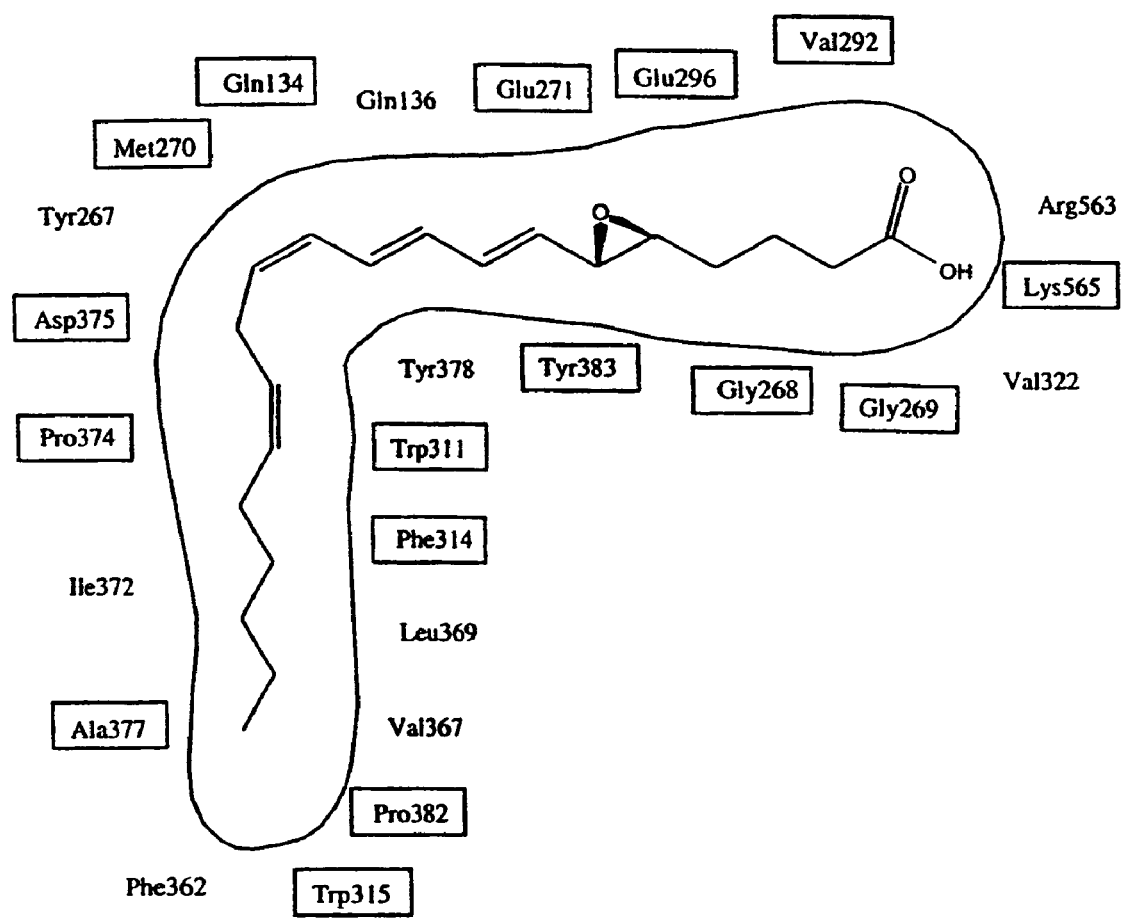

If one considers the chemistry carried out by $LTA_4$ hydrolase, the enzyme has two major tasks during the hydrolysis of $LTA_4$ to $LTB_4$. First introduction of a water molecule stereospecific at C12 and second to generate a cis-double bond AE6 in the resulting conjugated triene system [cf. FIG. 1]. If $LTA_4$ is modeled into the putative substrate binding pocket as indicated in FIG. 9b, the catalytic zinc gets close to the epoxide and not C12 of the substrate. Therefore the most likely role of the Zn ion is to act directly as a Lewis acid to activate and open the epoxide ring. This would generate a carbocation, whose charge will be delocalised over the conjugated triene system from C7 to C12. Since this intermediate has an sp2 hybridized planar configuration at C12, it is in principle open for nucleophilic attack from either side of the molecule. The conserved Asp375 is positioned in such a way that a water molecule bound to it is in "attacking" distance of C12 of a modeled $LTA_4$ molecule, the position into which a hydroxyl group is inserted during the reaction. This will account for the proper stereo-chemical and positional insertion of the hydroxyl-group at C12 in R configuration.

The shape and curvature of the $LTA_4$ binding pocket also gives a clue as to how the enzyme creates the cis double bond at AE6. Since there is free rotation between the c6 and c7 of $LTA_4$, this bond may be kept in a "pro-cis" configuration in the transition state, which in turn would facilitate the formation of a AE6-cis double bond form the carbocation intermediate. If $LTA_4$ is modeled in this way, the entire molecule adopts a bent shape, fitting very well with the architecture of the binding pocket (FIG. 9b). Hence, the critical double bond geometry at AE6 of $LTB_4$ is probably guaranteed by the exact binding conformation of $LTA_4$ at the active side which in turn is governed by all the structural elements participating in substrate binding, including the carboxylate recognition sites, Arg56 and Lys565, the catalytic zinc and the hydrophobic residues lining the pocket. The putative binding cleft for the leukotriene molecule is narrow and bend and thereby favoring $LTA_4$ over other epoxides. The two tyrosines are positioned such that they are in contact with the triple double bond configuration of a modeled $LTA_4$ molecule at the bent of the putative binding pocket and they are hydrogen-bonded to each other. Therefore their position is ideal for guidance in stereo-specificity of the double bond configuration. The loss of specificity for the hydroxyl-incorporation at the C12 position in case of the Tyr383 position can be explained that mutations at this position would possibly create extra space for a water molecule that could attack at the C6 position and thereby form 5 [S],6 [S]-DHETE.

The position of Tyr378 is such that it is in contact with the C6 atom of the modeled $LTA_4$ molecule. If after opening of the epoxide ring the hydroxyl group of Tyr378 instead of a water molecule would attack the carbon-cation at the C6 position, a covalently attached molecule is formed which forms the suicide inhibited complex. In order to check this hypothesis and to obtain more information about the binding-site for leukotriene $A_4$, the structure of this inhibited species would be essential.

In order to exclude the possibility that residues near the active site might have further catalytic roles in the epoxide hydrolase reaction, a thorough investigation of these residues, such as Glu271 and Gln136 has to be started. Furthermore the proposed role of Asp375 in activating a water molecule for the stereospecific attack at C12 has to be investigated.

Accordingly, the present invention has solved the first specific leukotriene converting enzyme, which for the first time reveals the binding mode for leukotriene molecules. Furthermore, insight is provided in a unique active site that harbours two activities using different amino-acids to catalyze different reactions.

5. CONFORMATIONAL DATA

TABLE 9

Structure coordinates of $LTA_4$ hydrolase-thiolamine complex
(The amino acid sequence set forth as residues 1-610 below correspond to SEQ ID NO:1.)

| | | | | | | | | |
|---|---|---|---|---|---|---|---|---|
| CRYST | | 68.560 | 132.150 | 83.270 | 90.00 | 90.00 | 90.00 | P21212 |
| | SCALE1 | 0.01459 | | 0.00000 | | 0.00000 | | 0.00000 |
| | SCALE2 | 0.00000 | | 0.00757 | | 0.00000 | | 0.00000 |
| | SCALE3 | 0.00000 | | 0.00000 | | 0.01201 | | 0.00000 |

| | | Atom | res. | | Chain | No. | x | y | z | occ | B-factor |
|---|---|---|---|---|---|---|---|---|---|---|---|
| ATOM | 1 | N | PRO | A | | 1 | −0.593 | 16.387 | 63.494 | 1.00 | 97.99 |
| ATOM | 2 | CA | PRO | A | | 1 | −1.890 | 16.918 | 63.874 | 1.00 | 97.22 |
| ATOM | 3 | C | PRO | A | | 1 | −2.210 | 18.371 | 63.525 | 1.00 | 100.00 |
| ATOM | 4 | O | PRO | A | | 1 | −2.402 | 18.667 | 62.342 | 1.00 | 100.00 |
| ATOM | 5 | CB | PRO | A | | 1 | −2.130 | 16.551 | 65.332 | 1.00 | 97.81 |
| ATOM | 6 | CG | PRO | A | | 1 | −1.221 | 15.355 | 65.583 | 1.00 | 100.00 |
| ATOM | 7 | CD | PRO | A | | 1 | −0.290 | 15.233 | 64.369 | 1.00 | 97.05 |
| ATOM | 8 | N | GLU | A | | 2 | −2.216 | 19.272 | 64.556 | 1.00 | 96.95 |
| ATOM | 9 | CA | GLU | A | | 2 | −2.569 | 20.678 | 64.314 | 1.00 | 95.71 |

TABLE 9-continued

Structure coordinates of LTA₄ hydrolase-thiolamine complex
(The amino acid sequence set forth as residues 1-610 below correspond to SEQ ID NO:1.)

| ATOM | 10 | C | GLU | A | 2 | −2.188 | 21.701 | 65.386 | 1.00 | 94.33 |
|---|---|---|---|---|---|---|---|---|---|---|
| ATOM | 11 | O | GLU | A | 2 | −2.512 | 21.542 | 66.562 | 1.00 | 93.21 |
| ATOM | 12 | CB | GLU | A | 2 | −4.105 | 20.768 | 64.214 | 1.00 | 97.26 |
| ATOM | 13 | CG | GLU | A | 2 | −4.587 | 21.732 | 63.125 | 1.00 | 100.00 |
| ATOM | 14 | CD | GLU | A | 2 | −4.351 | 21.139 | 61.767 | 1.00 | 100.00 |
| ATOM | 15 | OE1 | GLU | A | 2 | −3.301 | 21.261 | 61.152 | 1.00 | 100.00 |
| ATOM | 16 | OE2 | GLU | A | 2 | −5.361 | 20.398 | 61.368 | 1.00 | 100.00 |
| ATOM | 17 | N | ILE | A | 3 | −1.550 | 22.799 | 64.944 | 1.00 | 86.29 |
| ATOM | 18 | CA | ILE | A | 3 | −1.148 | 23.905 | 65.820 | 1.00 | 81.53 |
| ATOM | 19 | C | ILE | A | 3 | −2.006 | 25.154 | 65.661 | 1.00 | 75.68 |
| ATOM | 20 | O | ILE | A | 3 | −2.835 | 25.288 | 64.763 | 1.00 | 76.97 |
| ATOM | 21 | CB | ILE | A | 3 | 0.308 | 24.324 | 65.707 | 1.00 | 83.45 |
| ATOM | 22 | CG1 | ILE | A | 3 | 0.452 | 25.521 | 64.759 | 1.00 | 83.63 |
| ATOM | 23 | CG2 | ILE | A | 3 | 1.198 | 23.160 | 65.300 | 1.00 | 84.76 |
| ATOM | 24 | CD1 | ILE | A | 3 | −0.184 | 25.361 | 63.375 | 1.00 | 91.36 |
| ATOM | 25 | N | VAL | A | 4 | −1.725 | 26.099 | 66.523 | 1.00 | 61.54 |
| ATOM | 26 | CA | VAL | A | 4 | −2.477 | 27.303 | 66.482 | 1.00 | 56.32 |
| ATOM | 27 | C | VAL | A | 4 | −1.658 | 28.552 | 66.623 | 1.00 | 50.98 |
| ATOM | 28 | O | VAL | A | 4 | −0.803 | 28.694 | 67.512 | 1.00 | 47.84 |
| ATOM | 29 | CB | VAL | A | 4 | −3.514 | 27.318 | 67.595 | 1.00 | 58.99 |
| ATOM | 30 | CG1 | VAL | A | 4 | −3.735 | 28.754 | 68.047 | 1.00 | 58.40 |
| ATOM | 31 | CG2 | VAL | A | 4 | −4.819 | 26.691 | 67.131 | 1.00 | 58.56 |
| ATOM | 32 | N | ASP | A | 5 | −2.012 | 29.486 | 65.732 | 1.00 | 39.38 |
| ATOM | 33 | CA | ASP | A | 5 | −1.403 | 30.782 | 65.763 | 1.00 | 32.64 |
| ATOM | 34 | C | ASP | A | 5 | −2.308 | 31.596 | 66.634 | 1.00 | 36.35 |
| ATOM | 35 | O | ASP | A | 5 | −3.343 | 32.051 | 66.171 | 1.00 | 38.30 |
| ATOM | 36 | CB | ASP | A | 5 | −1.252 | 31.492 | 64.400 | 1.00 | 30.79 |
| ATOM | 37 | CG | ASP | A | 5 | −0.251 | 32.581 | 64.563 | 1.00 | 29.96 |
| ATOM | 38 | OD1 | ASP | A | 5 | −0.069 | 33.123 | 65.635 | 1.00 | 35.01 |
| ATOM | 39 | OD2 | ASP | A | 5 | 0.457 | 32.831 | 63.493 | 1.00 | 29.81 |
| ATOM | 40 | N | THR | A | 6 | −1.931 | 31.745 | 67.903 | 1.00 | 32.32 |
| ATOM | 41 | CA | THR | A | 6 | −2.710 | 32.507 | 68.842 | 1.00 | 32.08 |
| ATOM | 42 | C | THR | A | 6 | −2.701 | 34.011 | 68.557 | 1.00 | 40.63 |
| ATOM | 43 | O | THR | A | 6 | −3.484 | 34.759 | 69.132 | 1.00 | 46.68 |
| ATOM | 44 | CB | THR | A | 6 | −2.357 | 32.171 | 70.295 | 1.00 | 44.71 |
| ATOM | 45 | OG1 | THR | A | 6 | −0.967 | 32.322 | 70.505 | 1.00 | 51.05 |
| ATOM | 46 | CG2 | THR | A | 6 | −2.789 | 30.741 | 70.604 | 1.00 | 35.79 |
| ATOM | 47 | N | CYS | A | 7 | −1.842 | 34.480 | 67.656 | 1.00 | 32.51 |
| ATOM | 48 | CA | CYS | A | 7 | −1.797 | 35.923 | 67.335 | 1.00 | 28.92 |
| ATOM | 49 | C | CYS | A | 7 | −2.627 | 36.329 | 66.129 | 1.00 | 31.49 |
| ATOM | 50 | O | CYS | A | 7 | −2.780 | 37.523 | 65.875 | 1.00 | 25.42 |
| ATOM | 51 | CB | CYS | A | 7 | −0.362 | 36.410 | 67.107 | 1.00 | 27.38 |
| ATOM | 52 | SG | CYS | A | 7 | 0.686 | 35.944 | 68.518 | 1.00 | 32.02 |
| ATOM | 53 | N | SER | A | 8 | −3.140 | 35.315 | 65.383 | 1.00 | 34.03 |
| ATOM | 54 | CA | SER | A | 8 | −3.940 | 35.508 | 64.158 | 1.00 | 32.97 |
| ATOM | 55 | C | SER | A | 8 | −5.410 | 35.136 | 64.264 | 1.00 | 33.52 |
| ATOM | 56 | O | SER | A | 8 | −5.744 | 34.137 | 64.866 | 1.00 | 32.89 |
| ATOM | 57 | CB | SER | A | 8 | −3.363 | 34.754 | 62.980 | 1.00 | 34.07 |
| ATOM | 58 | OG | SER | A | 8 | −4.017 | 35.182 | 61.798 | 1.00 | 36.65 |
| ATOM | 59 | N | LEU | A | 9 | −6.289 | 35.921 | 63.635 | 1.00 | 30.79 |
| ATOM | 60 | CA | LEU | A | 9 | −7.724 | 35.649 | 63.672 | 1.00 | 31.91 |
| ATOM | 61 | C | LEU | A | 9 | −8.198 | 35.009 | 62.377 | 1.00 | 36.07 |
| ATOM | 62 | O | LEU | A | 9 | −9.359 | 34.626 | 62.216 | 1.00 | 38.61 |
| ATOM | 63 | CB | LEU | A | 9 | −8.514 | 36.958 | 63.874 | 1.00 | 32.47 |
| ATOM | 64 | CG | LEU | A | 9 | −8.306 | 37.688 | 65.212 | 1.00 | 35.39 |
| ATOM | 65 | CD1 | LEU | A | 9 | −9.113 | 38.983 | 65.193 | 1.00 | 32.27 |
| ATOM | 66 | CD2 | LEU | A | 9 | −8.746 | 36.816 | 66.397 | 1.00 | 33.25 |
| ATOM | 67 | N | ALA | A | 10 | −7.273 | 34.933 | 61.443 | 1.00 | 28.63 |
| ATOM | 68 | CA | ALA | A | 10 | −7.545 | 34.408 | 60.147 | 1.00 | 27.14 |
| ATOM | 69 | C | ALA | A | 10 | −7.643 | 32.921 | 60.090 | 1.00 | 34.34 |
| ATOM | 70 | O | ALA | A | 10 | −7.296 | 32.173 | 61.005 | 1.00 | 37.34 |
| ATOM | 71 | CB | ALA | A | 10 | −6.551 | 34.936 | 59.100 | 1.00 | 27.72 |
| ATOM | 72 | N | SER | A | 11 | −8.130 | 32.503 | 58.959 | 1.00 | 32.08 |
| ATOM | 73 | CA | SER | A | 11 | −8.256 | 31.115 | 58.708 | 1.00 | 32.03 |
| ATOM | 74 | C | SER | A | 11 | −6.838 | 30.519 | 58.656 | 1.00 | 32.67 |
| ATOM | 75 | O | SER | A | 11 | −5.927 | 31.028 | 57.986 | 1.00 | 29.29 |
| ATOM | 76 | CB | SER | A | 11 | −9.013 | 30.934 | 57.401 | 1.00 | 38.42 |
| ATOM | 77 | OG | SER | A | 11 | −10.391 | 30.728 | 57.648 | 1.00 | 44.17 |
| ATOM | 78 | N | PRO | A | 12 | −6.651 | 29.440 | 59.387 | 1.00 | 29.14 |
| ATOM | 79 | CA | PRO | A | 12 | −5.370 | 28.786 | 59.476 | 1.00 | 26.83 |
| ATOM | 80 | C | PRO | A | 12 | −4.935 | 28.176 | 58.173 | 1.00 | 32.64 |
| ATOM | 81 | O | PRO | A | 12 | −5.737 | 28.007 | 57.284 | 1.00 | 35.89 |
| ATOM | 82 | CB | PRO | A | 12 | −5.544 | 27.698 | 60.540 | 1.00 | 28.28 |
| ATOM | 83 | CG | PRO | A | 12 | −7.029 | 27.571 | 60.843 | 1.00 | 32.92 |
| ATOM | 84 | CD | PRO | A | 12 | −7.731 | 28.587 | 59.952 | 1.00 | 30.42 |
| ATOM | 85 | N | ALA | A | 13 | −3.645 | 27.836 | 58.063 | 1.00 | 30.63 |

TABLE 9-continued

Structure coordinates of LTA₄ hydrolase-thiolamine complex
(The amino acid sequence set forth as residues 1-610 below correspond to SEQ ID NO:1.)

| ATOM | 86 | CA | ALA | A | 13 | −3.066 | 27.236 | 56.855 | 1.00 | 28.36 |
|---|---|---|---|---|---|---|---|---|---|---|
| ATOM | 87 | C | ALA | A | 13 | −3.644 | 25.852 | 56.576 | 1.00 | 33.99 |
| ATOM | 88 | O | ALA | A | 13 | −3.455 | 25.240 | 55.528 | 1.00 | 31.60 |
| ATOM | 89 | CB | ALA | A | 13 | −1.561 | 27.133 | 57.050 | 1.00 | 27.68 |
| ATOM | 90 | N | SER | A | 14 | −4.338 | 25.352 | 57.571 | 1.00 | 31.10 |
| ATOM | 91 | CA | SER | A | 14 | −4.919 | 24.069 | 57.469 | 1.00 | 30.66 |
| ATOM | 92 | C | SER | A | 14 | −6.242 | 24.133 | 56.753 | 1.00 | 37.86 |
| ATOM | 93 | O | SER | A | 14 | −6.768 | 23.118 | 56.328 | 1.00 | 45.79 |
| ATOM | 94 | CB | SER | A | 14 | −5.005 | 23.386 | 58.825 | 1.00 | 34.33 |
| ATOM | 95 | OG | SER | A | 14 | −6.006 | 23.978 | 59.621 | 1.00 | 41.01 |
| ATOM | 96 | N | VAL | A | 15 | −6.785 | 25.327 | 56.630 | 1.00 | 32.80 |
| ATOM | 97 | CA | VAL | A | 15 | −8.036 | 25.529 | 55.917 | 1.00 | 31.81 |
| ATOM | 98 | C | VAL | A | 15 | −7.777 | 26.107 | 54.507 | 1.00 | 34.70 |
| ATOM | 99 | O | VAL | A | 15 | −8.241 | 25.576 | 53.494 | 1.00 | 31.96 |
| ATOM | 100 | CB | VAL | A | 15 | −9.033 | 26.336 | 56.720 | 1.00 | 33.07 |
| ATOM | 101 | CG1 | VAL | A | 15 | −10.272 | 26.638 | 55.861 | 1.00 | 33.31 |
| ATOM | 102 | CG2 | VAL | A | 15 | −9.412 | 25.538 | 57.949 | 1.00 | 30.32 |
| ATOM | 103 | N | CYS | A | 16 | −6.990 | 27.183 | 54.453 | 1.00 | 33.85 |
| ATOM | 104 | CA | CYS | A | 16 | −6.602 | 27.826 | 53.189 | 1.00 | 38.27 |
| ATOM | 105 | C | CYS | A | 16 | −5.206 | 28.388 | 53.265 | 1.00 | 37.14 |
| ATOM | 106 | O | CYS | A | 16 | −4.616 | 28.534 | 54.322 | 1.00 | 39.70 |
| ATOM | 107 | CB | CYS | A | 16 | −7.589 | 28.870 | 52.581 | 1.00 | 42.09 |
| ATOM | 108 | SG | CYS | A | 16 | −7.844 | 30.418 | 53.540 | 1.00 | 47.38 |
| ATOM | 109 | N | ARG | A | 17 | −4.679 | 28.722 | 52.132 | 1.00 | 32.10 |
| ATOM | 110 | CA | ARG | A | 17 | −3.349 | 29.262 | 52.101 | 1.00 | 32.54 |
| ATOM | 111 | C | ARG | A | 17 | −3.210 | 30.307 | 51.005 | 1.00 | 34.56 |
| ATOM | 112 | O | ARG | A | 17 | −3.511 | 30.065 | 49.842 | 1.00 | 35.07 |
| ATOM | 113 | CB | ARG | A | 17 | −2.371 | 28.152 | 51.758 | 1.00 | 36.83 |
| ATOM | 114 | CG | ARG | A | 17 | −1.779 | 27.391 | 52.915 | 1.00 | 40.61 |
| ATOM | 115 | CD | ARG | A | 17 | −1.472 | 25.970 | 52.503 | 1.00 | 27.18 |
| ATOM | 116 | NE | ARG | A | 17 | −1.963 | 25.026 | 53.501 | 1.00 | 52.41 |
| ATOM | 117 | CZ | ARG | A | 17 | −1.244 | 24.036 | 54.035 | 1.00 | 69.41 |
| ATOM | 118 | NH1 | ARG | A | 17 | 0.020 | 23.812 | 53.683 | 1.00 | 54.86 |
| ATOM | 119 | NH2 | ARG | A | 17 | −1.810 | 23.246 | 54.952 | 1.00 | 49.68 |
| ATOM | 120 | N | THR | A | 18 | −2.711 | 31.454 | 51.378 | 1.00 | 27.06 |
| ATOM | 121 | CA | THR | A | 18 | −2.489 | 32.477 | 50.428 | 1.00 | 26.12 |
| ATOM | 122 | C | THR | A | 18 | −1.250 | 32.110 | 49.653 | 1.00 | 30.83 |
| ATOM | 123 | O | THR | A | 18 | −0.174 | 31.964 | 50.194 | 1.00 | 29.06 |
| ATOM | 124 | CB | THR | A | 18 | −2.276 | 33.810 | 51.134 | 1.00 | 34.27 |
| ATOM | 125 | OG1 | THR | A | 18 | −3.481 | 34.261 | 51.738 | 1.00 | 32.95 |
| ATOM | 126 | CG2 | THR | A | 18 | −1.730 | 34.839 | 50.156 | 1.00 | 35.91 |
| ATOM | 127 | N | LYS | A | 19 | −1.408 | 31.955 | 48.365 | 1.00 | 31.55 |
| ATOM | 128 | CA | LYS | A | 19 | −0.298 | 31.615 | 47.511 | 1.00 | 31.74 |
| ATOM | 129 | C | LYS | A | 19 | 0.359 | 32.848 | 46.906 | 1.00 | 33.90 |
| ATOM | 130 | O | LYS | A | 19 | 1.513 | 32.834 | 46.520 | 1.00 | 34.57 |
| ATOM | 131 | CB | LYS | A | 19 | −0.795 | 30.697 | 46.398 | 1.00 | 36.08 |
| ATOM | 132 | CG | LYS | A | 19 | −1.332 | 29.368 | 46.924 | 1.00 | 62.54 |
| ATOM | 133 | CD | LYS | A | 19 | −0.281 | 28.257 | 47.057 | 1.00 | 82.23 |
| ATOM | 134 | CE | LYS | A | 19 | 0.093 | 27.880 | 48.496 | 1.00 | 77.50 |
| ATOM | 135 | NZ | LYS | A | 19 | 1.553 | 27.849 | 48.745 | 1.00 | 55.63 |
| ATOM | 136 | N | HIS | A | 20 | −0.387 | 33.928 | 46.810 | 1.00 | 31.40 |
| ATOM | 137 | CA | HIS | A | 20 | 0.160 | 35.122 | 46.198 | 1.00 | 29.22 |
| ATOM | 138 | C | HIS | A | 20 | −0.655 | 36.345 | 46.517 | 1.00 | 34.68 |
| ATOM | 139 | O | HIS | A | 20 | −1.833 | 36.239 | 46.846 | 1.00 | 35.34 |
| ATOM | 140 | CB | HIS | A | 20 | 0.123 | 34.956 | 44.666 | 1.00 | 26.47 |
| ATOM | 141 | CG | HIS | A | 20 | 0.865 | 36.022 | 43.970 | 1.00 | 26.77 |
| ATOM | 142 | ND1 | HIS | A | 20 | 2.249 | 36.046 | 43.980 | 1.00 | 28.92 |
| ATOM | 143 | CD2 | HIS | A | 20 | 0.415 | 37.091 | 43.280 | 1.00 | 27.43 |
| ATOM | 144 | CE1 | HIS | A | 20 | 2.622 | 37.126 | 43.301 | 1.00 | 28.21 |
| ATOM | 145 | NE2 | HIS | A | 20 | 1.536 | 37.781 | 42.865 | 1.00 | 28.18 |
| ATOM | 146 | N | LEU | A | 21 | 0.000 | 37.492 | 46.390 | 1.00 | 30.14 |
| ATOM | 147 | CA | LEU | A | 21 | −0.596 | 38.782 | 46.610 | 1.00 | 31.02 |
| ATOM | 148 | C | LEU | A | 21 | −0.134 | 39.786 | 45.562 | 1.00 | 38.34 |
| ATOM | 149 | O | LEU | A | 21 | 1.073 | 39.952 | 45.312 | 1.00 | 37.30 |
| ATOM | 150 | CB | LEU | A | 21 | −0.342 | 39.363 | 47.999 | 1.00 | 31.30 |
| ATOM | 151 | CG | LEU | A | 21 | −0.611 | 40.880 | 48.047 | 1.00 | 32.33 |
| ATOM | 152 | CD1 | LEU | A | 21 | −2.088 | 41.192 | 48.324 | 1.00 | 27.10 |
| ATOM | 153 | CD2 | LEU | A | 21 | 0.277 | 41.522 | 49.100 | 1.00 | 32.86 |
| ATOM | 154 | N | HIS | A | 22 | −1.127 | 40.442 | 44.951 | 1.00 | 35.47 |
| ATOM | 155 | CA | HIS | A | 22 | −0.895 | 41.452 | 43.920 | 1.00 | 34.24 |
| ATOM | 156 | C | HIS | A | 22 | −1.249 | 42.742 | 44.550 | 1.00 | 33.99 |
| ATOM | 157 | O | HIS | A | 22 | −2.402 | 42.957 | 44.905 | 1.00 | 35.72 |
| ATOM | 158 | CB | HIS | A | 22 | −1.720 | 41.244 | 42.624 | 1.00 | 33.38 |
| ATOM | 159 | CG | HIS | A | 22 | −1.350 | 42.256 | 41.615 | 1.00 | 35.97 |
| ATOM | 160 | ND1 | HIS | A | 22 | −0.030 | 42.576 | 41.384 | 1.00 | 38.81 |
| ATOM | 161 | CD2 | HIS | A | 22 | −2.125 | 43.043 | 40.830 | 1.00 | 39.07 |

TABLE 9-continued

Structure coordinates of LTA₄ hydrolase-thiolamine complex
(The amino acid sequence set forth as residues 1-610 below correspond to SEQ ID NO:1.)

| ATOM | 162 | CE1 | HIS | A | 22 | −0.019 | 43.534 | 40.462 | 1.00 | 38.66 |
|---|---|---|---|---|---|---|---|---|---|---|
| ATOM | 163 | NE2 | HIS | A | 22 | −1.262 | 43.829 | 40.103 | 1.00 | 39.13 |
| ATOM | 164 | N | LEU | A | 23 | −0.235 | 43.539 | 44.757 | 1.00 | 30.17 |
| ATOM | 165 | CA | LEU | A | 23 | −0.416 | 44.793 | 45.405 | 1.00 | 33.32 |
| ATOM | 166 | C | LEU | A | 23 | −0.203 | 45.949 | 44.440 | 1.00 | 44.46 |
| ATOM | 167 | O | LEU | A | 23 | 0.828 | 46.068 | 43.761 | 1.00 | 44.06 |
| ATOM | 168 | CB | LEU | A | 23 | 0.446 | 44.882 | 46.680 | 1.00 | 33.72 |
| ATOM | 169 | CG | LEU | A | 23 | −0.141 | 45.682 | 47.871 | 1.00 | 33.15 |
| ATOM | 170 | CD1 | LEU | A | 23 | 0.780 | 46.835 | 48.172 | 1.00 | 26.07 |
| ATOM | 171 | CD2 | LEU | A | 23 | −1.539 | 46.213 | 47.609 | 1.00 | 35.39 |
| ATOM | 172 | N | ARG | A | 24 | −1.256 | 46.765 | 44.395 | 1.00 | 42.83 |
| ATOM | 173 | CA | ARG | A | 24 | −1.406 | 47.964 | 43.596 | 1.00 | 41.79 |
| ATOM | 174 | C | ARG | A | 24 | −1.930 | 49.005 | 44.562 | 1.00 | 39.15 |
| ATOM | 175 | O | ARG | A | 24 | −3.025 | 48.859 | 45.107 | 1.00 | 39.85 |
| ATOM | 176 | CB | ARG | A | 24 | −2.458 | 47.716 | 42.504 | 1.00 | 46.35 |
| ATOM | 177 | CG | ARG | A | 24 | −2.054 | 46.750 | 41.382 | 1.00 | 50.50 |
| ATOM | 178 | CD | ARG | A | 24 | −2.754 | 47.058 | 40.043 | 1.00 | 80.27 |
| ATOM | 179 | NE | ARG | A | 24 | −4.200 | 46.798 | 40.062 | 1.00 | 95.12 |
| ATOM | 180 | CZ | ARG | A | 24 | −5.152 | 47.703 | 39.826 | 1.00 | 100.00 |
| ATOM | 181 | NH1 | ARG | A | 24 | −4.863 | 48.973 | 39.483 | 1.00 | 100.00 |
| ATOM | 182 | NH2 | ARG | A | 24 | −6.432 | 47.326 | 39.865 | 1.00 | 100.00 |
| ATOM | 183 | N | CYS | A | 25 | −1.164 | 50.028 | 44.844 | 1.00 | 32.39 |
| ATOM | 184 | CA | CYS | A | 25 | −1.698 | 50.969 | 45.813 | 1.00 | 33.30 |
| ATOM | 185 | C | CYS | A | 25 | −1.061 | 52.325 | 45.724 | 1.00 | 34.82 |
| ATOM | 186 | O | CYS | A | 25 | −0.012 | 52.514 | 45.076 | 1.00 | 31.03 |
| ATOM | 187 | CB | CYS | A | 25 | −1.503 | 50.440 | 47.257 | 1.00 | 34.67 |
| ATOM | 188 | SG | CYS | A | 25 | 0.231 | 50.529 | 47.798 | 1.00 | 38.07 |
| ATOM | 189 | N | SER | A | 26 | −1.711 | 53.257 | 46.418 | 1.00 | 34.39 |
| ATOM | 190 | CA | SER | A | 26 | −1.196 | 54.601 | 46.437 | 1.00 | 36.77 |
| ATOM | 191 | C | SER | A | 26 | −0.963 | 55.133 | 47.821 | 1.00 | 39.85 |
| ATOM | 192 | O | SER | A | 26 | −1.738 | 54.853 | 48.757 | 1.00 | 37.56 |
| ATOM | 193 | CB | SER | A | 26 | −1.889 | 55.600 | 45.530 | 1.00 | 42.70 |
| ATOM | 194 | OG | SER | A | 26 | −0.899 | 56.330 | 44.824 | 1.00 | 61.74 |
| ATOM | 195 | N | VAL | A | 27 | 0.133 | 55.897 | 47.886 | 1.00 | 39.43 |
| ATOM | 196 | CA | VAL | A | 27 | 0.624 | 56.583 | 49.081 | 1.00 | 41.31 |
| ATOM | 197 | C | VAL | A | 27 | 0.209 | 58.043 | 49.082 | 1.00 | 44.32 |
| ATOM | 198 | O | VAL | A | 27 | 0.562 | 58.799 | 48.187 | 1.00 | 45.24 |
| ATOM | 199 | CB | VAL | A | 27 | 2.135 | 56.531 | 49.207 | 1.00 | 46.35 |
| ATOM | 200 | CG1 | VAL | A | 27 | 2.524 | 57.207 | 50.522 | 1.00 | 45.62 |
| ATOM | 201 | CG2 | VAL | A | 27 | 2.592 | 55.079 | 49.178 | 1.00 | 47.20 |
| ATOM | 202 | N | ASP | A | 28 | −0.553 | 58.417 | 50.093 | 1.00 | 37.94 |
| ATOM | 203 | CA | ASP | A | 28 | −1.040 | 59.764 | 50.237 | 1.00 | 35.28 |
| ATOM | 204 | C | ASP | A | 28 | −0.595 | 60.366 | 51.538 | 1.00 | 33.85 |
| ATOM | 205 | O | ASP | A | 28 | −1.181 | 60.099 | 52.598 | 1.00 | 28.52 |
| ATOM | 206 | CB | ASP | A | 28 | −2.559 | 59.807 | 50.189 | 1.00 | 37.09 |
| ATOM | 207 | CG | ASP | A | 28 | −3.055 | 61.205 | 50.095 | 1.00 | 55.20 |
| ATOM | 208 | OD1 | ASP | A | 28 | −2.611 | 62.119 | 50.767 | 1.00 | 59.17 |
| ATOM | 209 | OD2 | ASP | A | 28 | −3.993 | 61.335 | 49.192 | 1.00 | 61.41 |
| ATOM | 210 | N | PHE | A | 29 | 0.436 | 61.174 | 51.405 | 1.00 | 36.42 |
| ATOM | 211 | CA | PHE | A | 29 | 1.044 | 61.888 | 52.512 | 1.00 | 43.07 |
| ATOM | 212 | C | PHE | A | 29 | 0.105 | 62.928 | 53.077 | 1.00 | 51.14 |
| ATOM | 213 | O | PHE | A | 29 | 0.161 | 63.279 | 54.257 | 1.00 | 51.35 |
| ATOM | 214 | CB | PHE | A | 29 | 2.410 | 62.517 | 52.143 | 1.00 | 47.77 |
| ATOM | 215 | CG | PHE | A | 29 | 3.519 | 61.485 | 52.079 | 1.00 | 50.86 |
| ATOM | 216 | CD1 | PHE | A | 29 | 4.066 | 60.957 | 53.247 | 1.00 | 52.08 |
| ATOM | 217 | CD2 | PHE | A | 29 | 3.996 | 61.001 | 50.863 | 1.00 | 53.94 |
| ATOM | 218 | CE1 | PHE | A | 29 | 5.075 | 59.995 | 53.215 | 1.00 | 52.83 |
| ATOM | 219 | CE2 | PHE | A | 29 | 5.013 | 60.046 | 50.813 | 1.00 | 56.46 |
| ATOM | 220 | CZ | PHE | A | 29 | 5.559 | 59.538 | 51.992 | 1.00 | 53.39 |
| ATOM | 221 | N | THR | A | 30 | −0.766 | 63.420 | 52.220 | 1.00 | 47.10 |
| ATOM | 222 | CA | THR | A | 30 | −1.718 | 64.386 | 52.654 | 1.00 | 45.48 |
| ATOM | 223 | C | THR | A | 30 | −2.788 | 63.715 | 53.509 | 1.00 | 48.41 |
| ATOM | 224 | O | THR | A | 30 | −3.045 | 64.082 | 54.649 | 1.00 | 48.64 |
| ATOM | 225 | CB | THR | A | 30 | −2.283 | 65.097 | 51.434 | 1.00 | 54.06 |
| ATOM | 226 | OG1 | THR | A | 30 | −1.428 | 66.186 | 51.107 | 1.00 | 50.68 |
| ATOM | 227 | CG2 | THR | A | 30 | −3.697 | 65.568 | 51.745 | 1.00 | 60.28 |
| ATOM | 228 | N | ARG | A | 31 | −3.392 | 62.683 | 52.978 | 1.00 | 46.66 |
| ATOM | 229 | CA | ARG | A | 31 | −4.404 | 61.987 | 53.734 | 1.00 | 47.88 |
| ATOM | 230 | C | ARG | A | 31 | −3.826 | 60.999 | 54.750 | 1.00 | 45.46 |
| ATOM | 231 | O | ARG | A | 31 | −4.590 | 60.468 | 55.551 | 1.00 | 41.52 |
| ATOM | 232 | CB | ARG | A | 31 | −5.335 | 61.214 | 52.805 | 1.00 | 56.73 |
| ATOM | 233 | CG | ARG | A | 31 | −5.950 | 62.065 | 51.700 | 1.00 | 84.16 |
| ATOM | 234 | CD | ARG | A | 31 | −7.338 | 61.568 | 51.284 | 1.00 | 100.00 |
| ATOM | 235 | NE | ARG | A | 31 | −7.344 | 60.450 | 50.327 | 1.00 | 100.00 |
| ATOM | 236 | CZ | ARG | A | 31 | −8.148 | 60.371 | 49.251 | 1.00 | 100.00 |
| ATOM | 237 | NH1 | ARG | A | 31 | −9.034 | 61.324 | 48.944 | 1.00 | 100.00 |

TABLE 9-continued

Structure coordinates of LTA₄ hydrolase-thiolamine complex
(The amino acid sequence set forth as residues 1-610 below correspond to SEQ ID NO:1.)

| ATOM | 238 | NH2 | ARG | A | 31 | −8.062 | 59.298 | 48.460 | 1.00 | 100.00 |
|---|---|---|---|---|---|---|---|---|---|---|
| ATOM | 239 | N | ARG | A | 32 | −2.489 | 60.752 | 54.683 | 1.00 | 39.71 |
| ATOM | 240 | CA | ARG | A | 32 | −1.751 | 59.798 | 55.531 | 1.00 | 39.09 |
| ATOM | 241 | C | ARG | A | 32 | −2.324 | 58.411 | 55.379 | 1.00 | 39.62 |
| ATOM | 242 | O | ARG | A | 32 | −2.495 | 57.655 | 56.337 | 1.00 | 33.10 |
| ATOM | 243 | CB | ARG | A | 32 | −1.523 | 60.115 | 57.022 | 1.00 | 37.14 |
| ATOM | 244 | CG | ARG | A | 32 | −1.197 | 61.569 | 57.337 | 1.00 | 71.25 |
| ATOM | 245 | CD | ARG | A | 32 | 0.277 | 61.834 | 57.686 | 1.00 | 100.00 |
| ATOM | 246 | NE | ARG | A | 32 | 0.703 | 61.299 | 58.986 | 1.00 | 100.00 |
| ATOM | 247 | CZ | ARG | A | 32 | 1.284 | 62.005 | 59.961 | 1.00 | 79.51 |
| ATOM | 248 | NH1 | ARG | A | 32 | 1.522 | 63.308 | 59.831 | 1.00 | 55.73 |
| ATOM | 249 | NH2 | ARG | A | 32 | 1.626 | 61.387 | 61.098 | 1.00 | 44.96 |
| ATOM | 250 | N | THR | A | 33 | −2.612 | 58.068 | 54.139 | 1.00 | 39.83 |
| ATOM | 251 | CA | THR | A | 33 | −3.162 | 56.752 | 53.902 | 1.00 | 39.31 |
| ATOM | 252 | C | THR | A | 33 | −2.543 | 56.010 | 52.760 | 1.00 | 41.13 |
| ATOM | 253 | O | THR | A | 33 | −1.853 | 56.574 | 51.926 | 1.00 | 42.93 |
| ATOM | 254 | CB | THR | A | 33 | −4.635 | 56.835 | 53.641 | 1.00 | 43.44 |
| ATOM | 255 | OG1 | THR | A | 33 | −4.798 | 57.636 | 52.468 | 1.00 | 40.17 |
| ATOM | 256 | CG2 | THR | A | 33 | −5.245 | 57.468 | 54.880 | 1.00 | 38.71 |
| ATOM | 257 | N | LEU | A | 34 | −2.822 | 54.717 | 52.762 | 1.00 | 35.26 |
| ATOM | 258 | CA | LEU | A | 34 | −2.372 | 53.799 | 51.745 | 1.00 | 35.20 |
| ATOM | 259 | C | LEU | A | 34 | −3.632 | 53.293 | 51.098 | 1.00 | 32.49 |
| ATOM | 260 | O | LEU | A | 34 | −4.474 | 52.670 | 51.751 | 1.00 | 30.96 |
| ATOM | 261 | CB | LEU | A | 34 | −1.522 | 52.651 | 52.322 | 1.00 | 37.07 |
| ATOM | 262 | CG | LEU | A | 34 | −0.149 | 52.571 | 51.685 | 1.00 | 42.99 |
| ATOM | 263 | CD1 | LEU | A | 34 | 0.648 | 51.425 | 52.285 | 1.00 | 40.58 |
| ATOM | 264 | CD2 | LEU | A | 34 | −0.360 | 52.302 | 50.208 | 1.00 | 50.83 |
| ATOM | 265 | N | THR | A | 35 | −3.800 | 53.632 | 49.838 | 1.00 | 28.72 |
| ATOM | 266 | CA | THR | A | 35 | −5.017 | 53.228 | 49.198 | 1.00 | 31.26 |
| ATOM | 267 | C | THR | A | 35 | −4.838 | 52.329 | 48.013 | 1.00 | 36.54 |
| ATOM | 268 | O | THR | A | 35 | −3.940 | 52.546 | 47.187 | 1.00 | 34.70 |
| ATOM | 269 | CB | THR | A | 35 | −5.877 | 54.427 | 48.813 | 1.00 | 44.88 |
| ATOM | 270 | OG1 | THR | A | 35 | −5.484 | 55.549 | 49.579 | 1.00 | 58.59 |
| ATOM | 271 | CG2 | THR | A | 35 | −7.324 | 54.094 | 49.109 | 1.00 | 49.42 |
| ATOM | 272 | N | GLY | A | 36 | −5.726 | 51.329 | 47.950 | 1.00 | 32.57 |
| ATOM | 273 | CA | GLY | A | 36 | −5.696 | 50.405 | 46.837 | 1.00 | 33.89 |
| ATOM | 274 | C | GLY | A | 36 | −6.418 | 49.074 | 46.993 | 1.00 | 34.50 |
| ATOM | 275 | O | GLY | A | 36 | −7.441 | 48.919 | 47.678 | 1.00 | 31.78 |
| ATOM | 276 | N | THR | A | 37 | −5.836 | 48.103 | 46.293 | 1.00 | 35.93 |
| ATOM | 277 | CA | THR | A | 37 | −6.327 | 46.723 | 46.281 | 1.00 | 36.12 |
| ATOM | 278 | C | THR | A | 37 | −5.268 | 45.696 | 46.473 | 1.00 | 35.67 |
| ATOM | 279 | O | THR | A | 37 | −4.155 | 45.795 | 45.964 | 1.00 | 33.86 |
| ATOM | 280 | CB | THR | A | 37 | −7.119 | 46.306 | 45.050 | 1.00 | 42.21 |
| ATOM | 281 | OG1 | THR | A | 37 | −6.507 | 46.804 | 43.870 | 1.00 | 30.98 |
| ATOM | 282 | CG2 | THR | A | 37 | −8.547 | 46.793 | 45.229 | 1.00 | 50.03 |
| ATOM | 283 | N | ALA | A | 38 | −5.687 | 44.705 | 47.220 | 1.00 | 32.95 |
| ATOM | 284 | CA | ALA | A | 38 | −4.886 | 43.570 | 47.533 | 1.00 | 33.45 |
| ATOM | 285 | C | ALA | A | 38 | −5.481 | 42.374 | 46.824 | 1.00 | 35.47 |
| ATOM | 286 | O | ALA | A | 38 | −6.580 | 41.906 | 47.151 | 1.00 | 32.91 |
| ATOM | 287 | CB | ALA | A | 38 | −4.845 | 43.341 | 49.044 | 1.00 | 33.72 |
| ATOM | 288 | N | ALA | A | 39 | −4.764 | 41.874 | 45.834 | 1.00 | 32.70 |
| ATOM | 289 | CA | ALA | A | 39 | −5.274 | 40.702 | 45.140 | 1.00 | 31.59 |
| ATOM | 290 | C | ALA | A | 39 | −4.692 | 39.464 | 45.770 | 1.00 | 32.11 |
| ATOM | 291 | O | ALA | A | 39 | −3.514 | 39.147 | 45.608 | 1.00 | 32.46 |
| ATOM | 292 | CB | ALA | A | 39 | −4.934 | 40.729 | 43.662 | 1.00 | 32.13 |
| ATOM | 293 | N | LEU | A | 40 | −5.505 | 38.774 | 46.508 | 1.00 | 27.06 |
| ATOM | 294 | CA | LEU | A | 40 | −5.001 | 37.593 | 47.155 | 1.00 | 29.04 |
| ATOM | 295 | C | LEU | A | 40 | −5.331 | 36.322 | 46.364 | 1.00 | 36.88 |
| ATOM | 296 | O | LEU | A | 40 | −6.485 | 36.100 | 45.963 | 1.00 | 28.89 |
| ATOM | 297 | CB | LEU | A | 40 | −5.587 | 37.451 | 48.600 | 1.00 | 29.39 |
| ATOM | 298 | CG | LEU | A | 40 | −5.303 | 38.598 | 49.559 | 1.00 | 31.39 |
| ATOM | 299 | CD1 | LEU | A | 40 | −5.435 | 38.063 | 50.970 | 1.00 | 32.62 |
| ATOM | 300 | CD2 | LEU | A | 40 | −3.879 | 39.019 | 49.355 | 1.00 | 31.60 |
| ATOM | 301 | N | THR | A | 41 | −4.310 | 35.470 | 46.165 | 1.00 | 42.40 |
| ATOM | 302 | CA | THR | A | 41 | −4.523 | 34.210 | 45.488 | 1.00 | 43.93 |
| ATOM | 303 | C | THR | A | 41 | −4.548 | 33.155 | 46.552 | 1.00 | 43.75 |
| ATOM | 304 | O | THR | A | 41 | −3.510 | 32.827 | 47.115 | 1.00 | 45.22 |
| ATOM | 305 | CB | THR | A | 41 | −3.511 | 33.892 | 44.402 | 1.00 | 55.44 |
| ATOM | 306 | OG1 | THR | A | 41 | −3.604 | 34.885 | 43.418 | 1.00 | 55.57 |
| ATOM | 307 | CG2 | THR | A | 41 | −3.872 | 32.544 | 43.802 | 1.00 | 47.78 |
| ATOM | 308 | N | VAL | A | 42 | −5.755 | 32.688 | 46.848 | 1.00 | 33.25 |
| ATOM | 309 | CA | VAL | A | 42 | −5.946 | 31.720 | 47.893 | 1.00 | 32.21 |
| ATOM | 310 | C | VAL | A | 42 | −6.166 | 30.312 | 47.380 | 1.00 | 40.56 |
| ATOM | 311 | O | VAL | A | 42 | −6.827 | 30.105 | 46.376 | 1.00 | 42.56 |
| ATOM | 312 | CB | VAL | A | 42 | −7.017 | 32.153 | 48.920 | 1.00 | 36.45 |
| ATOM | 313 | CG1 | VAL | A | 42 | −6.817 | 31.451 | 50.266 | 1.00 | 36.89 |

TABLE 9-continued

Structure coordinates of LTA$_4$ hydrolase-thiolamine complex
(The amino acid sequence set forth as residues 1-610 below correspond to SEQ ID NO:1.)

| ATOM | 314 | CG2 | VAL | A | 42 | −6.963 | 33.665 | 49.170 | 1.00 | 36.10 |
|------|-----|-----|-----|---|----|--------|--------|--------|------|-------|
| ATOM | 315 | N | GLN | A | 43 | −5.590 | 29.357 | 48.117 | 1.00 | 35.91 |
| ATOM | 316 | CA | GLN | A | 43 | −5.678 | 27.945 | 47.838 | 1.00 | 31.59 |
| ATOM | 317 | C | GLN | A | 43 | −6.346 | 27.244 | 48.988 | 1.00 | 38.98 |
| ATOM | 318 | O | GLN | A | 43 | −5.916 | 27.317 | 50.144 | 1.00 | 40.92 |
| ATOM | 319 | CB | GLN | A | 43 | −4.305 | 27.319 | 47.568 | 1.00 | 30.50 |
| ATOM | 320 | CG | GLN | A | 43 | −4.362 | 25.800 | 47.259 | 1.00 | 53.80 |
| ATOM | 321 | CD | GLN | A | 43 | −2.986 | 25.177 | 47.099 | 1.00 | 62.47 |
| ATOM | 322 | OE1 | GLN | A | 43 | −2.569 | 24.842 | 45.978 | 1.00 | 57.34 |
| ATOM | 323 | NE2 | GLN | A | 43 | −2.274 | 25.037 | 48.224 | 1.00 | 43.72 |
| ATOM | 324 | N | SER | A | 44 | −7.423 | 26.555 | 48.664 | 1.00 | 33.83 |
| ATOM | 325 | CA | SER | A | 44 | −8.166 | 25.839 | 49.678 | 1.00 | 31.38 |
| ATOM | 326 | C | SER | A | 44 | −7.495 | 24.557 | 50.117 | 1.00 | 42.10 |
| ATOM | 327 | O | SER | A | 44 | −6.955 | 23.814 | 49.292 | 1.00 | 42.78 |
| ATOM | 328 | CB | SER | A | 44 | −9.576 | 25.530 | 49.226 | 1.00 | 28.60 |
| ATOM | 329 | OG | SER | A | 44 | −10.234 | 24.785 | 50.224 | 1.00 | 34.57 |
| ATOM | 330 | N | GLN | A | 45 | −7.579 | 24.286 | 51.423 | 1.00 | 38.84 |
| ATOM | 331 | CA | GLN | A | 45 | −7.007 | 23.082 | 51.994 | 1.00 | 37.05 |
| ATOM | 332 | C | GLN | A | 45 | −8.082 | 22.050 | 52.269 | 1.00 | 47.57 |
| ATOM | 333 | O | GLN | A | 45 | −7.801 | 20.917 | 52.678 | 1.00 | 42.94 |
| ATOM | 334 | CB | GLN | A | 45 | −6.247 | 23.411 | 53.280 | 1.00 | 36.10 |
| ATOM | 335 | CG | GLN | A | 45 | −5.246 | 24.539 | 53.034 | 1.00 | 54.73 |
| ATOM | 336 | CD | GLN | A | 45 | −4.323 | 24.206 | 51.888 | 1.00 | 45.43 |
| ATOM | 337 | OE1 | GLN | A | 45 | −4.257 | 24.888 | 50.833 | 1.00 | 39.23 |
| ATOM | 338 | NE2 | GLN | A | 45 | −3.621 | 23.121 | 52.092 | 1.00 | 29.80 |
| ATOM | 339 | N | GLU | A | 46 | −9.330 | 22.459 | 52.048 | 1.00 | 50.54 |
| ATOM | 340 | CA | GLU | A | 46 | −10.454 | 21.573 | 52.283 | 1.00 | 50.99 |
| ATOM | 341 | C | GLU | A | 46 | −11.496 | 21.583 | 51.179 | 1.00 | 54.49 |
| ATOM | 342 | O | GLU | A | 46 | −11.518 | 22.406 | 50.261 | 1.00 | 54.00 |
| ATOM | 343 | CB | GLU | A | 46 | −11.139 | 21.793 | 53.657 | 1.00 | 51.61 |
| ATOM | 344 | CG | GLU | A | 46 | −10.581 | 22.979 | 54.454 | 1.00 | 55.93 |
| ATOM | 345 | CD | GLU | A | 46 | −11.427 | 23.329 | 55.646 | 1.00 | 78.67 |
| ATOM | 346 | OE1 | GLU | A | 46 | −12.563 | 23.765 | 55.543 | 1.00 | 69.56 |
| ATOM | 347 | OE2 | GLU | A | 46 | −10.814 | 23.129 | 56.796 | 1.00 | 75.10 |
| ATOM | 348 | N | ASP | A | 47 | −12.387 | 20.630 | 51.300 | 1.00 | 48.90 |
| ATOM | 349 | CA | ASP | A | 47 | −13.450 | 20.549 | 50.362 | 1.00 | 49.03 |
| ATOM | 350 | C | ASP | A | 47 | −14.591 | 21.425 | 50.846 | 1.00 | 55.15 |
| ATOM | 351 | O | ASP | A | 47 | −14.760 | 21.631 | 52.044 | 1.00 | 56.66 |
| ATOM | 352 | CB | ASP | A | 47 | −13.913 | 19.099 | 50.227 | 1.00 | 50.20 |
| ATOM | 353 | CG | ASP | A | 47 | −13.083 | 18.376 | 49.218 | 1.00 | 66.88 |
| ATOM | 354 | OD1 | ASP | A | 47 | −12.340 | 18.945 | 48.434 | 1.00 | 66.27 |
| ATOM | 355 | OD2 | ASP | A | 47 | −13.235 | 17.081 | 49.284 | 1.00 | 76.37 |
| ATOM | 356 | N | ASN | A | 48 | −15.391 | 21.941 | 49.929 | 1.00 | 50.25 |
| ATOM | 357 | CA | ASN | A | 48 | −16.519 | 22.755 | 50.339 | 1.00 | 48.45 |
| ATOM | 358 | C | ASN | A | 48 | −16.115 | 24.000 | 51.115 | 1.00 | 43.07 |
| ATOM | 359 | O | ASN | A | 48 | −16.699 | 24.351 | 52.138 | 1.00 | 39.78 |
| ATOM | 360 | CB | ASN | A | 48 | −17.559 | 21.909 | 51.117 | 1.00 | 51.19 |
| ATOM | 361 | CG | ASN | A | 48 | −18.985 | 22.417 | 51.005 | 1.00 | 76.39 |
| ATOM | 362 | OD1 | ASN | A | 48 | −19.594 | 22.348 | 49.929 | 1.00 | 85.15 |
| ATOM | 363 | ND2 | ASN | A | 48 | −19.515 | 22.928 | 52.115 | 1.00 | 68.29 |
| ATOM | 364 | N | LEU | A | 49 | −15.113 | 24.688 | 50.628 | 1.00 | 35.36 |
| ATOM | 365 | CA | LEU | A | 49 | −14.728 | 25.874 | 51.335 | 1.00 | 34.40 |
| ATOM | 366 | C | LEU | A | 49 | −15.601 | 27.009 | 50.851 | 1.00 | 47.38 |
| ATOM | 367 | O | LEU | A | 49 | −15.421 | 27.515 | 49.734 | 1.00 | 45.47 |
| ATOM | 368 | CB | LEU | A | 49 | −13.239 | 26.152 | 51.173 | 1.00 | 31.04 |
| ATOM | 369 | CG | LEU | A | 49 | −12.781 | 27.394 | 51.885 | 1.00 | 29.82 |
| ATOM | 370 | CD1 | LEU | A | 49 | −12.725 | 27.137 | 53.385 | 1.00 | 28.15 |
| ATOM | 371 | CD2 | LEU | A | 49 | −11.394 | 27.753 | 51.368 | 1.00 | 30.24 |
| ATOM | 372 | N | ARG | A | 50 | −16.568 | 27.363 | 51.699 | 1.00 | 50.49 |
| ATOM | 373 | CA | ARG | A | 50 | −17.560 | 28.392 | 51.401 | 1.00 | 52.83 |
| ATOM | 374 | C | ARG | A | 50 | −17.169 | 29.838 | 51.702 | 1.00 | 55.57 |
| ATOM | 375 | O | ARG | A | 50 | −17.627 | 30.760 | 51.011 | 1.00 | 53.89 |
| ATOM | 376 | CB | ARG | A | 50 | −18.928 | 28.028 | 51.986 | 1.00 | 58.35 |
| ATOM | 377 | CG | ARG | A | 50 | −19.863 | 27.354 | 50.980 | 1.00 | 74.76 |
| ATOM | 378 | CD | ARG | A | 50 | −20.438 | 26.024 | 51.462 | 1.00 | 81.60 |
| ATOM | 379 | NE | ARG | A | 50 | −21.214 | 25.355 | 50.415 | 1.00 | 94.37 |
| ATOM | 380 | CZ | ARG | A | 50 | −22.465 | 24.888 | 50.538 | 1.00 | 100.00 |
| ATOM | 381 | NH1 | ARG | A | 50 | −23.151 | 24.990 | 51.687 | 1.00 | 100.00 |
| ATOM | 382 | NH2 | ARG | A | 50 | −23.046 | 24.297 | 49.471 | 1.00 | 74.34 |
| ATOM | 383 | N | SER | A | 51 | −16.331 | 30.006 | 52.743 | 1.00 | 54.71 |
| ATOM | 384 | CA | SER | A | 51 | −15.823 | 31.297 | 53.224 | 1.00 | 53.49 |
| ATOM | 385 | C | SER | A | 51 | −14.495 | 31.156 | 53.955 | 1.00 | 53.57 |
| ATOM | 386 | O | SER | A | 51 | −14.146 | 30.062 | 54.420 | 1.00 | 52.93 |
| ATOM | 387 | CB | SER | A | 51 | −16.788 | 31.900 | 54.232 | 1.00 | 54.03 |
| ATOM | 388 | OG | SER | A | 51 | −16.871 | 31.048 | 55.373 | 1.00 | 45.15 |
| ATOM | 389 | N | LEU | A | 52 | −13.796 | 32.298 | 54.067 | 1.00 | 47.19 |

TABLE 9-continued

Structure coordinates of LTA$_4$ hydrolase-thiolamine complex
(The amino acid sequence set forth as residues 1-610 below correspond to SEQ ID NO:1.)

| ATOM | 390 | CA | LEU | A | 52 | −12.519 | 32.422 | 54.762 | 1.00 | 45.66 |
|------|-----|-----|-----|---|----|---------|--------|--------|------|-------|
| ATOM | 391 | C | LEU | A | 52 | −12.415 | 33.671 | 55.640 | 1.00 | 50.43 |
| ATOM | 392 | O | LEU | A | 52 | −13.145 | 34.633 | 55.471 | 1.00 | 52.64 |
| ATOM | 393 | CB | LEU | A | 52 | −11.235 | 32.117 | 53.923 | 1.00 | 44.20 |
| ATOM | 394 | CG | LEU | A | 52 | −10.896 | 33.044 | 52.745 | 1.00 | 43.98 |
| ATOM | 395 | CD1 | LEU | A | 52 | −11.739 | 32.687 | 51.554 | 1.00 | 42.82 |
| ATOM | 396 | CD2 | LEU | A | 52 | −11.128 | 34.501 | 53.094 | 1.00 | 44.71 |
| ATOM | 397 | N | VAL | A | 53 | −11.483 | 33.658 | 56.579 | 1.00 | 44.97 |
| ATOM | 398 | CA | VAL | A | 53 | −11.271 | 34.781 | 57.455 | 1.00 | 41.69 |
| ATOM | 399 | C | VAL | A | 53 | −9.859 | 35.309 | 57.339 | 1.00 | 44.25 |
| ATOM | 400 | O | VAL | A | 53 | −8.866 | 34.551 | 57.302 | 1.00 | 45.42 |
| ATOM | 401 | CB | VAL | A | 53 | −11.565 | 34.420 | 58.906 | 1.00 | 45.48 |
| ATOM | 402 | CG1 | VAL | A | 53 | −11.223 | 35.554 | 59.853 | 1.00 | 44.94 |
| ATOM | 403 | CG2 | VAL | A | 53 | −13.030 | 34.073 | 59.050 | 1.00 | 45.79 |
| ATOM | 404 | N | LEU | A | 54 | −9.796 | 36.627 | 57.166 | 1.00 | 35.12 |
| ATOM | 405 | CA | LEU | A | 54 | −8.555 | 37.333 | 57.080 | 1.00 | 34.14 |
| ATOM | 406 | C | LEU | A | 54 | −8.377 | 38.207 | 58.326 | 1.00 | 38.92 |
| ATOM | 407 | O | LEU | A | 54 | −9.281 | 38.457 | 59.108 | 1.00 | 37.45 |
| ATOM | 408 | CB | LEU | A | 54 | −8.461 | 38.216 | 55.831 | 1.00 | 34.73 |
| ATOM | 409 | CG | LEU | A | 54 | −8.539 | 37.469 | 54.510 | 1.00 | 40.25 |
| ATOM | 410 | CD1 | LEU | A | 54 | −8.416 | 38.488 | 53.374 | 1.00 | 40.69 |
| ATOM | 411 | CD2 | LEU | A | 54 | −7.424 | 36.428 | 54.415 | 1.00 | 39.64 |
| ATOM | 412 | N | ASP | A | 55 | −7.192 | 38.674 | 58.524 | 1.00 | 35.02 |
| ATOM | 413 | CA | ASP | A | 55 | −6.918 | 39.526 | 59.627 | 1.00 | 31.65 |
| ATOM | 414 | C | ASP | A | 55 | −6.956 | 40.941 | 59.078 | 1.00 | 40.38 |
| ATOM | 415 | O | ASP | A | 55 | −6.754 | 41.151 | 57.886 | 1.00 | 39.98 |
| ATOM | 416 | CB | ASP | A | 55 | −5.494 | 39.232 | 60.075 | 1.00 | 30.92 |
| ATOM | 417 | CG | ASP | A | 55 | −5.397 | 38.103 | 61.037 | 1.00 | 35.96 |
| ATOM | 418 | OD1 | ASP | A | 55 | −6.049 | 38.074 | 62.066 | 1.00 | 38.49 |
| ATOM | 419 | OD2 | ASP | A | 55 | −4.491 | 37.205 | 60.682 | 1.00 | 36.53 |
| ATOM | 420 | N | THR | A | 56 | −7.196 | 41.900 | 59.963 | 1.00 | 42.93 |
| ATOM | 421 | CA | THR | A | 56 | −7.243 | 43.334 | 59.661 | 1.00 | 41.75 |
| ATOM | 422 | C | THR | A | 56 | −7.101 | 44.128 | 60.967 | 1.00 | 37.46 |
| ATOM | 423 | O | THR | A | 56 | −7.517 | 43.687 | 62.049 | 1.00 | 36.98 |
| ATOM | 424 | CB | THR | A | 56 | −8.514 | 43.825 | 58.894 | 1.00 | 37.17 |
| ATOM | 425 | OG1 | THR | A | 56 | −9.587 | 43.957 | 59.805 | 1.00 | 31.84 |
| ATOM | 426 | CG2 | THR | A | 56 | −8.910 | 42.943 | 57.714 | 1.00 | 33.58 |
| ATOM | 427 | N | LYS | A | 57 | −6.513 | 45.304 | 60.863 | 1.00 | 26.63 |
| ATOM | 428 | CA | LYS | A | 57 | −6.363 | 46.134 | 62.020 | 1.00 | 25.64 |
| ATOM | 429 | C | LYS | A | 57 | −6.585 | 47.539 | 61.547 | 1.00 | 30.08 |
| ATOM | 430 | O | LYS | A | 57 | −5.854 | 48.012 | 60.711 | 1.00 | 25.68 |
| ATOM | 431 | CB | LYS | A | 57 | −4.991 | 45.983 | 62.641 | 1.00 | 27.34 |
| ATOM | 432 | CG | LYS | A | 57 | −4.907 | 46.387 | 64.100 | 1.00 | 35.83 |
| ATOM | 433 | CD | LYS | A | 57 | −3.514 | 46.904 | 64.471 | 1.00 | 35.57 |
| ATOM | 434 | CE | LYS | A | 57 | −2.901 | 46.225 | 65.689 | 1.00 | 50.54 |
| ATOM | 435 | NZ | LYS | A | 57 | −2.521 | 47.180 | 66.757 | 1.00 | 55.43 |
| ATOM | 436 | N | ASP | A | 58 | −7.617 | 48.188 | 62.065 | 1.00 | 32.68 |
| ATOM | 437 | CA | ASP | A | 58 | −7.895 | 49.545 | 61.665 | 1.00 | 35.27 |
| ATOM | 438 | C | ASP | A | 58 | −7.894 | 49.710 | 60.149 | 1.00 | 38.24 |
| ATOM | 439 | O | ASP | A | 58 | −7.289 | 50.627 | 59.571 | 1.00 | 35.86 |
| ATOM | 440 | CB | ASP | A | 58 | −6.968 | 50.550 | 62.386 | 1.00 | 37.22 |
| ATOM | 441 | CG | ASP | A | 58 | −7.041 | 50.393 | 63.880 | 1.00 | 50.71 |
| ATOM | 442 | OD1 | ASP | A | 58 | −8.073 | 50.136 | 64.478 | 1.00 | 57.20 |
| ATOM | 443 | OD2 | ASP | A | 58 | −5.878 | 50.562 | 64.463 | 1.00 | 45.82 |
| ATOM | 444 | N | LEU | A | 59 | −8.604 | 48.796 | 59.516 | 1.00 | 37.68 |
| ATOM | 445 | CA | LEU | A | 59 | −8.720 | 48.813 | 58.079 | 1.00 | 39.36 |
| ATOM | 446 | C | LEU | A | 59 | −10.077 | 49.243 | 57.555 | 1.00 | 45.51 |
| ATOM | 447 | O | LEU | A | 59 | −11.146 | 48.946 | 58.120 | 1.00 | 44.18 |
| ATOM | 448 | CB | LEU | A | 59 | −8.265 | 47.506 | 57.422 | 1.00 | 38.42 |
| ATOM | 449 | CG | LEU | A | 59 | −6.762 | 47.475 | 57.218 | 1.00 | 37.40 |
| ATOM | 450 | CD1 | LEU | A | 59 | −6.392 | 46.173 | 56.526 | 1.00 | 36.39 |
| ATOM | 451 | CD2 | LEU | A | 59 | −6.321 | 48.655 | 56.361 | 1.00 | 36.57 |
| ATOM | 452 | N | THR | A | 60 | −9.984 | 49.949 | 56.437 | 1.00 | 42.59 |
| ATOM | 453 | CA | THR | A | 60 | −11.132 | 50.483 | 55.734 | 1.00 | 42.63 |
| ATOM | 454 | C | THR | A | 60 | −11.357 | 49.705 | 54.463 | 1.00 | 38.18 |
| ATOM | 455 | O | THR | A | 60 | −10.632 | 49.856 | 53.454 | 1.00 | 34.33 |
| ATOM | 456 | CB | THR | A | 60 | −11.030 | 52.028 | 55.532 | 1.00 | 65.15 |
| ATOM | 457 | OG1 | THR | A | 60 | −11.806 | 52.736 | 56.504 | 1.00 | 67.56 |
| ATOM | 458 | CG2 | THR | A | 60 | −11.345 | 52.480 | 54.104 | 1.00 | 56.89 |
| ATOM | 459 | N | ILE | A | 61 | −12.360 | 48.847 | 54.571 | 1.00 | 33.39 |
| ATOM | 460 | CA | ILE | A | 61 | −12.753 | 47.975 | 53.482 | 1.00 | 35.89 |
| ATOM | 461 | C | ILE | A | 61 | −13.726 | 48.634 | 52.533 | 1.00 | 41.05 |
| ATOM | 462 | O | ILE | A | 61 | −14.913 | 48.706 | 52.840 | 1.00 | 40.08 |
| ATOM | 463 | CB | ILE | A | 61 | −13.403 | 46.670 | 53.944 | 1.00 | 39.71 |
| ATOM | 464 | CG1 | ILE | A | 61 | −12.482 | 45.826 | 54.832 | 1.00 | 39.90 |
| ATOM | 465 | CG2 | ILE | A | 61 | −13.788 | 45.900 | 52.691 | 1.00 | 38.96 |

TABLE 9-continued

Structure coordinates of LTA₄ hydrolase-thiolamine complex
(The amino acid sequence set forth as residues 1-610 below correspond to SEQ ID NO:1.)

| ATOM | 466 | CD1 | ILE | A | 61 | −11.027 | 45.851 | 54.358 | 1.00 | 49.61 |
|------|-----|-----|-----|---|----|---------|--------|--------|------|-------|
| ATOM | 467 | N | GLU | A | 62 | −13.219 | 49.080 | 51.391 | 1.00 | 40.23 |
| ATOM | 468 | CA | GLU | A | 62 | −14.040 | 49.700 | 50.365 | 1.00 | 41.73 |
| ATOM | 469 | C | GLU | A | 62 | −14.986 | 48.633 | 49.826 | 1.00 | 47.09 |
| ATOM | 470 | O | GLU | A | 62 | −16.207 | 48.726 | 49.926 | 1.00 | 47.52 |
| ATOM | 471 | CB | GLU | A | 62 | −13.138 | 50.272 | 49.239 | 1.00 | 44.08 |
| ATOM | 472 | CG | GLU | A | 62 | −13.765 | 51.406 | 48.381 | 1.00 | 64.08 |
| ATOM | 473 | CD | GLU | A | 62 | −14.686 | 50.946 | 47.256 | 1.00 | 100.00 |
| ATOM | 474 | OE1 | GLU | A | 62 | −15.458 | 50.002 | 47.376 | 1.00 | 100.00 |
| ATOM | 475 | OE2 | GLU | A | 62 | −14.591 | 51.670 | 46.146 | 1.00 | 75.11 |
| ATOM | 476 | N | LYS | A | 63 | −14.399 | 47.580 | 49.267 | 1.00 | 43.46 |
| ATOM | 477 | CA | LYS | A | 63 | −15.168 | 46.474 | 48.746 | 1.00 | 40.53 |
| ATOM | 478 | C | LYS | A | 63 | −14.250 | 45.307 | 48.489 | 1.00 | 45.38 |
| ATOM | 479 | O | LYS | A | 63 | −13.046 | 45.500 | 48.362 | 1.00 | 43.51 |
| ATOM | 480 | CB | LYS | A | 63 | −15.818 | 46.830 | 47.428 | 1.00 | 40.46 |
| ATOM | 481 | CG | LYS | A | 63 | −14.789 | 46.959 | 46.321 | 1.00 | 20.53 |
| ATOM | 482 | CD | LYS | A | 63 | −15.367 | 47.555 | 45.054 | 1.00 | 28.36 |
| ATOM | 483 | CE | LYS | A | 63 | −14.315 | 48.158 | 44.139 | 1.00 | 40.61 |
| ATOM | 484 | NZ | LYS | A | 63 | −14.588 | 47.938 | 42.711 | 1.00 | 54.71 |
| ATOM | 485 | N | VAL | A | 64 | −14.862 | 44.116 | 48.441 | 1.00 | 45.57 |
| ATOM | 486 | CA | VAL | A | 64 | −14.190 | 42.844 | 48.171 | 1.00 | 44.90 |
| ATOM | 487 | C | VAL | A | 64 | −14.666 | 42.263 | 46.841 | 1.00 | 46.44 |
| ATOM | 488 | O | VAL | A | 64 | −15.826 | 41.917 | 46.700 | 1.00 | 45.81 |
| ATOM | 489 | CB | VAL | A | 64 | −14.505 | 41.748 | 49.192 | 1.00 | 46.24 |
| ATOM | 490 | CG1 | VAL | A | 64 | −13.864 | 40.471 | 48.669 | 1.00 | 44.81 |
| ATOM | 491 | CG2 | VAL | A | 64 | −14.040 | 42.048 | 50.627 | 1.00 | 44.77 |
| ATOM | 492 | N | VAL | A | 65 | −13.793 | 42.099 | 45.875 | 1.00 | 43.10 |
| ATOM | 493 | CA | VAL | A | 65 | −14.240 | 41.537 | 44.604 | 1.00 | 41.42 |
| ATOM | 494 | C | VAL | A | 65 | −13.707 | 40.156 | 44.282 | 1.00 | 42.13 |
| ATOM | 495 | O | VAL | A | 65 | −12.605 | 39.787 | 44.660 | 1.00 | 42.64 |
| ATOM | 496 | CB | VAL | A | 65 | −13.856 | 42.462 | 43.484 | 1.00 | 44.58 |
| ATOM | 497 | CG1 | VAL | A | 65 | −14.520 | 42.037 | 42.189 | 1.00 | 42.79 |
| ATOM | 498 | CG2 | VAL | A | 65 | −14.264 | 43.874 | 43.883 | 1.00 | 45.05 |
| ATOM | 499 | N | ILE | A | 66 | −14.515 | 39.402 | 43.556 | 1.00 | 38.68 |
| ATOM | 500 | CA | ILE | A | 66 | −14.179 | 38.053 | 43.113 | 1.00 | 39.98 |
| ATOM | 501 | C | ILE | A | 66 | −14.899 | 37.774 | 41.802 | 1.00 | 44.86 |
| ATOM | 502 | O | ILE | A | 66 | −16.136 | 37.735 | 41.729 | 1.00 | 42.69 |
| ATOM | 503 | CB | ILE | A | 66 | −14.520 | 36.947 | 44.113 | 1.00 | 44.28 |
| ATOM | 504 | CG1 | ILE | A | 66 | −13.813 | 37.127 | 45.445 | 1.00 | 47.27 |
| ATOM | 505 | CG2 | ILE | A | 66 | −14.141 | 35.578 | 43.550 | 1.00 | 42.84 |
| ATOM | 506 | CD1 | ILE | A | 66 | −14.352 | 36.169 | 46.514 | 1.00 | 38.79 |
| ATOM | 507 | N | ASN | A | 67 | −14.120 | 37.549 | 40.759 | 1.00 | 42.94 |
| ATOM | 508 | CA | ASN | A | 67 | −14.715 | 37.266 | 39.472 | 1.00 | 44.24 |
| ATOM | 509 | C | ASN | A | 67 | −15.541 | 38.444 | 39.008 | 1.00 | 54.25 |
| ATOM | 510 | O | ASN | A | 67 | −16.743 | 38.344 | 38.768 | 1.00 | 57.56 |
| ATOM | 511 | CB | ASN | A | 67 | −15.595 | 36.007 | 39.507 | 1.00 | 40.72 |
| ATOM | 512 | CG | ASN | A | 67 | −14.788 | 34.759 | 39.745 | 1.00 | 57.39 |
| ATOM | 513 | OD1 | ASN | A | 67 | −13.581 | 34.711 | 39.454 | 1.00 | 52.63 |
| ATOM | 514 | ND2 | ASN | A | 67 | −15.446 | 33.760 | 40.317 | 1.00 | 44.54 |
| ATOM | 515 | N | GLY | A | 68 | −14.876 | 39.574 | 38.899 | 1.00 | 50.43 |
| ATOM | 516 | CA | GLY | A | 68 | −15.517 | 40.796 | 38.462 | 1.00 | 48.89 |
| ATOM | 517 | C | GLY | A | 68 | −16.807 | 41.115 | 39.194 | 1.00 | 48.77 |
| ATOM | 518 | O | GLY | A | 68 | −17.523 | 42.018 | 38.803 | 1.00 | 51.39 |
| ATOM | 519 | N | GLN | A | 69 | −17.129 | 40.385 | 40.244 | 1.00 | 40.06 |
| ATOM | 520 | CA | GLN | A | 69 | −18.348 | 40.716 | 40.928 | 1.00 | 40.02 |
| ATOM | 521 | C | GLN | A | 69 | −18.031 | 41.059 | 42.364 | 1.00 | 50.45 |
| ATOM | 522 | O | GLN | A | 69 | −16.943 | 40.748 | 42.855 | 1.00 | 50.53 |
| ATOM | 523 | CB | GLN | A | 69 | −19.415 | 39.602 | 40.829 | 1.00 | 40.78 |
| ATOM | 524 | CG | GLN | A | 69 | −19.966 | 39.367 | 39.414 | 1.00 | 23.77 |
| ATOM | 525 | CD | GLN | A | 69 | −20.513 | 40.646 | 38.831 | 1.00 | 56.53 |
| ATOM | 526 | OE1 | GLN | A | 69 | −19.974 | 41.198 | 37.859 | 1.00 | 55.28 |
| ATOM | 527 | NE2 | GLN | A | 69 | −21.588 | 41.134 | 39.437 | 1.00 | 62.26 |
| ATOM | 528 | N | GLU | A | 70 | −18.975 | 41.718 | 43.028 | 1.00 | 49.43 |
| ATOM | 529 | CA | GLU | A | 70 | −18.766 | 42.094 | 44.407 | 1.00 | 50.67 |
| ATOM | 530 | C | GLU | A | 70 | −19.296 | 40.996 | 45.288 | 1.00 | 57.90 |
| ATOM | 531 | O | GLU | A | 70 | −20.272 | 40.367 | 44.909 | 1.00 | 63.90 |
| ATOM | 532 | CB | GLU | A | 70 | −19.449 | 43.434 | 44.732 | 1.00 | 52.26 |
| ATOM | 533 | CG | GLU | A | 70 | −18.824 | 44.624 | 43.970 | 1.00 | 64.80 |
| ATOM | 534 | CD | GLU | A | 70 | −19.181 | 45.967 | 44.555 | 1.00 | 91.82 |
| ATOM | 535 | OE1 | GLU | A | 70 | −19.749 | 46.108 | 45.629 | 1.00 | 100.00 |
| ATOM | 536 | OE2 | GLU | A | 70 | −18.814 | 46.963 | 43.785 | 1.00 | 76.01 |
| ATOM | 537 | N | VAL | A | 71 | −18.655 | 40.742 | 46.433 | 1.00 | 47.28 |
| ATOM | 538 | CA | VAL | A | 71 | −19.119 | 39.685 | 47.335 | 1.00 | 43.84 |
| ATOM | 539 | C | VAL | A | 71 | −19.434 | 40.153 | 48.768 | 1.00 | 41.62 |
| ATOM | 540 | O | VAL | A | 71 | −18.983 | 41.206 | 49.254 | 1.00 | 35.70 |
| ATOM | 541 | CB | VAL | A | 71 | −18.308 | 38.361 | 47.273 | 1.00 | 46.05 |

TABLE 9-continued

Structure coordinates of LTA₄ hydrolase-thiolamine complex
(The amino acid sequence set forth as residues 1-610 below correspond to SEQ ID NO:1.)

| ATOM | 542 | CG1 | VAL | A | 71 | −18.062 | 37.923 | 45.827 | 1.00 | 45.19 |
|---|---|---|---|---|---|---|---|---|---|---|
| ATOM | 543 | CG2 | VAL | A | 71 | −16.979 | 38.460 | 48.017 | 1.00 | 45.24 |
| ATOM | 544 | N | LYS | A | 72 | −20.239 | 39.343 | 49.431 | 1.00 | 39.34 |
| ATOM | 545 | CA | LYS | A | 72 | −20.610 | 39.594 | 50.792 | 1.00 | 42.40 |
| ATOM | 546 | C | LYS | A | 72 | −19.347 | 39.466 | 51.668 | 1.00 | 56.92 |
| ATOM | 547 | O | LYS | A | 72 | −18.399 | 38.729 | 51.334 | 1.00 | 59.27 |
| ATOM | 548 | CB | LYS | A | 72 | −21.719 | 38.629 | 51.211 | 1.00 | 45.76 |
| ATOM | 549 | CG | LYS | A | 72 | −22.378 | 38.960 | 52.557 | 1.00 | 86.98 |
| ATOM | 550 | CD | LYS | A | 72 | −23.898 | 38.767 | 52.606 | 1.00 | 100.00 |
| ATOM | 551 | CE | LYS | A | 72 | −24.656 | 40.012 | 53.077 | 1.00 | 100.00 |
| ATOM | 552 | NZ | LYS | A | 72 | −26.011 | 39.730 | 53.592 | 1.00 | 100.00 |
| ATOM | 553 | N | TYR | A | 73 | −19.332 | 40.210 | 52.780 | 1.00 | 55.45 |
| ATOM | 554 | CA | TYR | A | 73 | −18.236 | 40.226 | 53.747 | 1.00 | 53.31 |
| ATOM | 555 | C | TYR | A | 73 | −18.636 | 40.884 | 55.068 | 1.00 | 50.87 |
| ATOM | 556 | O | TYR | A | 73 | −19.552 | 41.703 | 55.139 | 1.00 | 47.82 |
| ATOM | 557 | CB | TYR | A | 73 | −16.891 | 40.741 | 53.214 | 1.00 | 52.73 |
| ATOM | 558 | CG | TYR | A | 73 | −16.765 | 42.244 | 53.227 | 1.00 | 51.76 |
| ATOM | 559 | CD1 | TYR | A | 73 | −16.539 | 42.946 | 54.416 | 1.00 | 52.82 |
| ATOM | 560 | CD2 | TYR | A | 73 | −16.927 | 42.967 | 52.039 | 1.00 | 53.30 |
| ATOM | 561 | CE1 | TYR | A | 73 | −16.439 | 44.340 | 54.422 | 1.00 | 52.71 |
| ATOM | 562 | CE2 | TYR | A | 73 | −16.804 | 44.359 | 52.026 | 1.00 | 55.39 |
| ATOM | 563 | CZ | TYR | A | 73 | −16.592 | 45.044 | 53.229 | 1.00 | 63.45 |
| ATOM | 564 | OH | TYR | A | 73 | −16.471 | 46.404 | 53.215 | 1.00 | 69.53 |
| ATOM | 565 | N | ALA | A | 74 | −17.927 | 40.494 | 56.112 | 1.00 | 45.37 |
| ATOM | 566 | CA | ALA | A | 74 | −18.180 | 40.999 | 57.433 | 1.00 | 42.62 |
| ATOM | 567 | C | ALA | A | 74 | −16.892 | 41.265 | 58.222 | 1.00 | 47.81 |
| ATOM | 568 | O | ALA | A | 74 | −15.894 | 40.554 | 58.133 | 1.00 | 45.50 |
| ATOM | 569 | CB | ALA | A | 74 | −19.111 | 40.035 | 58.170 | 1.00 | 40.75 |
| ATOM | 570 | N | LEU | A | 75 | −16.930 | 42.323 | 59.005 | 1.00 | 49.02 |
| ATOM | 571 | CA | LEU | A | 75 | −15.829 | 42.693 | 59.869 | 1.00 | 48.85 |
| ATOM | 572 | C | LEU | A | 75 | −16.319 | 42.464 | 61.281 | 1.00 | 47.18 |
| ATOM | 573 | O | LEU | A | 75 | −17.309 | 43.021 | 61.687 | 1.00 | 44.35 |
| ATOM | 574 | CB | LEU | A | 75 | −15.332 | 44.136 | 59.675 | 1.00 | 49.64 |
| ATOM | 575 | CG | LEU | A | 75 | −14.789 | 44.357 | 58.270 | 1.00 | 58.09 |
| ATOM | 576 | CD1 | LEU | A | 75 | −14.524 | 45.841 | 58.023 | 1.00 | 61.34 |
| ATOM | 577 | CD2 | LEU | A | 75 | −13.512 | 43.565 | 58.069 | 1.00 | 62.34 |
| ATOM | 578 | N | GLY | A | 76 | −15.647 | 41.592 | 62.004 | 1.00 | 47.67 |
| ATOM | 579 | CA | GLY | A | 76 | −16.034 | 41.281 | 63.359 | 1.00 | 46.79 |
| ATOM | 580 | C | GLY | A | 76 | −15.495 | 42.337 | 64.279 | 1.00 | 47.74 |
| ATOM | 581 | O | GLY | A | 76 | −14.656 | 43.171 | 63.882 | 1.00 | 42.87 |
| ATOM | 582 | N | GLU | A | 77 | −15.988 | 42.311 | 65.502 | 1.00 | 48.32 |
| ATOM | 583 | CA | GLU | A | 77 | −15.526 | 43.300 | 66.431 | 1.00 | 52.14 |
| ATOM | 584 | C | GLU | A | 77 | −14.029 | 43.195 | 66.679 | 1.00 | 56.71 |
| ATOM | 585 | O | GLU | A | 77 | −13.418 | 42.120 | 66.591 | 1.00 | 55.78 |
| ATOM | 586 | CB | GLU | A | 77 | −16.357 | 43.341 | 67.732 | 1.00 | 55.55 |
| ATOM | 587 | CG | GLU | A | 77 | −17.198 | 42.063 | 67.969 | 1.00 | 79.57 |
| ATOM | 588 | CD | GLU | A | 77 | −17.440 | 41.739 | 69.427 | 1.00 | 100.00 |
| ATOM | 589 | OE1 | GLU | A | 77 | −16.537 | 41.435 | 70.211 | 1.00 | 100.00 |
| ATOM | 590 | OE2 | GLU | A | 77 | −18.712 | 41.799 | 69.770 | 1.00 | 100.00 |
| ATOM | 591 | N | ARG | A | 78 | −13.452 | 44.344 | 67.000 | 1.00 | 54.17 |
| ATOM | 592 | CA | ARG | A | 78 | −12.041 | 44.433 | 67.298 | 1.00 | 53.38 |
| ATOM | 593 | C | ARG | A | 78 | −11.627 | 43.656 | 68.579 | 1.00 | 58.88 |
| ATOM | 594 | O | ARG | A | 78 | −12.247 | 43.767 | 69.635 | 1.00 | 61.35 |
| ATOM | 595 | CB | ARG | A | 78 | −11.571 | 45.891 | 67.367 | 1.00 | 41.96 |
| ATOM | 596 | CG | ARG | A | 78 | −10.050 | 46.006 | 67.326 | 1.00 | 38.20 |
| ATOM | 597 | CD | ARG | A | 78 | −9.537 | 47.411 | 67.551 | 1.00 | 44.73 |
| ATOM | 598 | NE | ARG | A | 78 | −8.294 | 47.648 | 66.842 | 1.00 | 66.47 |
| ATOM | 599 | CZ | ARG | A | 78 | −7.250 | 48.247 | 67.389 | 1.00 | 97.61 |
| ATOM | 600 | NH1 | ARG | A | 78 | −7.276 | 48.692 | 68.645 | 1.00 | 100.00 |
| ATOM | 601 | NH2 | ARG | A | 78 | −6.151 | 48.413 | 66.663 | 1.00 | 80.10 |
| ATOM | 602 | N | GLN | A | 79 | −10.557 | 42.857 | 68.463 | 1.00 | 49.54 |
| ATOM | 603 | CA | GLN | A | 79 | −9.995 | 42.115 | 69.566 | 1.00 | 47.71 |
| ATOM | 604 | C | GLN | A | 79 | −8.664 | 42.789 | 69.865 | 1.00 | 49.77 |
| ATOM | 605 | O | GLN | A | 79 | −7.626 | 42.421 | 69.333 | 1.00 | 52.63 |
| ATOM | 606 | CB | GLN | A | 79 | −9.803 | 40.613 | 69.240 | 1.00 | 49.05 |
| ATOM | 607 | CG | GLN | A | 79 | −11.109 | 39.794 | 69.339 | 1.00 | 57.32 |
| ATOM | 608 | CD | GLN | A | 79 | −11.043 | 38.435 | 68.656 | 1.00 | 69.51 |
| ATOM | 609 | OE1 | GLN | A | 79 | −10.400 | 37.480 | 69.152 | 1.00 | 49.72 |
| ATOM | 610 | NE2 | GLN | A | 79 | −11.727 | 38.340 | 67.517 | 1.00 | 62.60 |
| ATOM | 611 | N | SER | A | 80 | −8.699 | 43.826 | 70.683 | 1.00 | 41.74 |
| ATOM | 612 | CA | SER | A | 80 | −7.490 | 44.543 | 71.022 | 1.00 | 37.90 |
| ATOM | 613 | C | SER | A | 80 | −6.437 | 44.559 | 69.920 | 1.00 | 35.98 |
| ATOM | 614 | O | SER | A | 80 | −6.736 | 44.939 | 68.801 | 1.00 | 34.52 |
| ATOM | 615 | CB | SER | A | 80 | −6.910 | 44.144 | 72.372 | 1.00 | 39.07 |
| ATOM | 616 | OG | SER | A | 80 | −7.255 | 42.803 | 72.684 | 1.00 | 61.32 |
| ATOM | 617 | N | TYR | A | 81 | −5.206 | 44.154 | 70.289 | 1.00 | 29.92 |

TABLE 9-continued

Structure coordinates of LTA₄ hydrolase-thiolamine complex
(The amino acid sequence set forth as residues 1-610 below correspond to SEQ ID NO:1.)

| ATOM | 618 | CA | TYR | A | 81 | −4.027 | 44.114 | 69.430 | 1.00 | 26.45 |
|---|---|---|---|---|---|---|---|---|---|---|
| ATOM | 619 | C | TYR | A | 81 | −4.163 | 43.116 | 68.285 | 1.00 | 30.82 |
| ATOM | 620 | O | TYR | A | 81 | −3.480 | 43.215 | 67.269 | 1.00 | 34.48 |
| ATOM | 621 | CB | TYR | A | 81 | −2.727 | 43.893 | 70.257 | 1.00 | 25.19 |
| ATOM | 622 | CG | TYR | A | 81 | −2.713 | 42.491 | 70.839 | 1.00 | 24.57 |
| ATOM | 623 | CD1 | TYR | A | 81 | −3.327 | 42.247 | 72.066 | 1.00 | 27.27 |
| ATOM | 624 | CD2 | TYR | A | 81 | −2.165 | 41.410 | 70.148 | 1.00 | 21.82 |
| ATOM | 625 | CE1 | TYR | A | 81 | −3.380 | 40.975 | 72.632 | 1.00 | 26.49 |
| ATOM | 626 | CE2 | TYR | A | 81 | −2.230 | 40.122 | 70.682 | 1.00 | 23.48 |
| ATOM | 627 | CZ | TYR | A | 81 | −2.827 | 39.908 | 71.930 | 1.00 | 38.28 |
| ATOM | 628 | OH | TYR | A | 81 | −2.889 | 38.653 | 72.493 | 1.00 | 42.17 |
| ATOM | 629 | N | LYS | A | 82 | −5.038 | 42.136 | 68.415 | 1.00 | 26.97 |
| ATOM | 630 | CA | LYS | A | 82 | −5.170 | 41.229 | 67.293 | 1.00 | 27.99 |
| ATOM | 631 | C | LYS | A | 82 | −5.867 | 41.898 | 66.072 | 1.00 | 38.90 |
| ATOM | 632 | O | LYS | A | 82 | −5.614 | 41.541 | 64.900 | 1.00 | 37.15 |
| ATOM | 633 | CB | LYS | A | 82 | −5.785 | 39.918 | 67.708 | 1.00 | 27.59 |
| ATOM | 634 | CG | LYS | A | 82 | −5.169 | 39.451 | 69.008 | 1.00 | 39.68 |
| ATOM | 635 | CD | LYS | A | 82 | −5.435 | 37.993 | 69.350 | 1.00 | 46.78 |
| ATOM | 636 | CE | LYS | A | 82 | −6.414 | 37.819 | 70.492 | 1.00 | 59.84 |
| ATOM | 637 | NZ | LYS | A | 82 | −7.097 | 36.523 | 70.452 | 1.00 | 63.48 |
| ATOM | 638 | N | GLY | A | 83 | −6.738 | 42.894 | 66.367 | 1.00 | 35.64 |
| ATOM | 639 | CA | GLY | A | 83 | −7.512 | 43.620 | 65.368 | 1.00 | 33.65 |
| ATOM | 640 | C | GLY | A | 83 | −8.866 | 42.925 | 65.111 | 1.00 | 32.95 |
| ATOM | 641 | O | GLY | A | 83 | −9.297 | 42.063 | 65.870 | 1.00 | 28.28 |
| ATOM | 642 | N | SER | A | 84 | −9.535 | 43.300 | 64.026 | 1.00 | 34.51 |
| ATOM | 643 | CA | SER | A | 84 | −10.839 | 42.742 | 63.673 | 1.00 | 36.13 |
| ATOM | 644 | C | SER | A | 84 | −10.796 | 41.724 | 62.549 | 1.00 | 40.65 |
| ATOM | 645 | O | SER | A | 84 | −10.173 | 41.893 | 61.501 | 1.00 | 39.77 |
| ATOM | 646 | CB | SER | A | 84 | −11.883 | 43.808 | 63.383 | 1.00 | 37.68 |
| ATOM | 647 | OG | SER | A | 84 | −11.812 | 44.832 | 64.352 | 1.00 | 45.14 |
| ATOM | 648 | N | PRO | A | 85 | −11.491 | 40.656 | 62.791 | 1.00 | 37.01 |
| ATOM | 649 | CA | PRO | A | 85 | −11.573 | 39.559 | 61.863 | 1.00 | 34.91 |
| ATOM | 650 | C | PRO | A | 85 | −12.459 | 39.946 | 60.712 | 1.00 | 35.92 |
| ATOM | 651 | O | PRO | A | 85 | −13.514 | 40.522 | 60.941 | 1.00 | 35.30 |
| ATOM | 652 | CB | PRO | A | 85 | −12.227 | 38.406 | 62.647 | 1.00 | 37.00 |
| ATOM | 653 | CG | PRO | A | 85 | −12.714 | 38.981 | 63.974 | 1.00 | 44.97 |
| ATOM | 654 | CD | PRO | A | 85 | −12.325 | 40.462 | 64.004 | 1.00 | 40.72 |
| ATOM | 655 | N | MET | A | 86 | −12.018 | 39.642 | 59.487 | 1.00 | 30.47 |
| ATOM | 656 | CA | MET | A | 86 | −12.756 | 39.960 | 58.275 | 1.00 | 28.55 |
| ATOM | 657 | C | MET | A | 86 | −13.165 | 38.683 | 57.552 | 1.00 | 40.49 |
| ATOM | 658 | O | MET | A | 86 | −12.338 | 38.015 | 56.954 | 1.00 | 39.69 |
| ATOM | 659 | CB | MET | A | 86 | −11.921 | 40.829 | 57.337 | 1.00 | 29.51 |
| ATOM | 660 | CG | MET | A | 86 | −12.750 | 41.242 | 56.136 | 1.00 | 37.40 |
| ATOM | 661 | SD | MET | A | 86 | −11.816 | 41.878 | 54.701 | 1.00 | 47.84 |
| ATOM | 662 | CE | MET | A | 86 | −13.244 | 42.527 | 53.805 | 1.00 | 46.52 |
| ATOM | 663 | N | GLU | A | 87 | −14.441 | 38.324 | 57.610 | 1.00 | 44.31 |
| ATOM | 664 | CA | GLU | A | 87 | −14.912 | 37.107 | 56.950 | 1.00 | 47.21 |
| ATOM | 665 | C | GLU | A | 87 | −15.495 | 37.352 | 55.560 | 1.00 | 51.53 |
| ATOM | 666 | O | GLU | A | 87 | −16.425 | 38.129 | 55.424 | 1.00 | 53.92 |
| ATOM | 667 | CB | GLU | A | 87 | −15.942 | 36.390 | 57.813 | 1.00 | 49.46 |
| ATOM | 668 | CG | GLU | A | 87 | −16.144 | 34.937 | 57.389 | 1.00 | 56.39 |
| ATOM | 669 | CD | GLU | A | 87 | −17.300 | 34.316 | 58.104 | 1.00 | 80.78 |
| ATOM | 670 | OE1 | GLU | A | 87 | −18.439 | 34.738 | 57.994 | 1.00 | 86.69 |
| ATOM | 671 | OE2 | GLU | A | 87 | −16.943 | 33.301 | 58.868 | 1.00 | 68.69 |
| ATOM | 672 | N | ILE | A | 88 | −14.942 | 36.659 | 54.544 | 1.00 | 43.84 |
| ATOM | 673 | CA | ILE | A | 88 | −15.332 | 36.765 | 53.145 | 1.00 | 40.15 |
| ATOM | 674 | C | ILE | A | 88 | −16.145 | 35.610 | 52.613 | 1.00 | 46.72 |
| ATOM | 675 | O | ILE | A | 88 | −15.725 | 34.460 | 52.656 | 1.00 | 48.10 |
| ATOM | 676 | CB | ILE | A | 88 | −14.107 | 36.891 | 52.292 | 1.00 | 39.13 |
| ATOM | 677 | CG1 | ILE | A | 88 | −13.328 | 38.146 | 52.696 | 1.00 | 38.40 |
| ATOM | 678 | CG2 | ILE | A | 88 | −14.538 | 36.932 | 50.839 | 1.00 | 28.13 |
| ATOM | 679 | CD1 | ILE | A | 88 | −11.944 | 38.200 | 52.051 | 1.00 | 30.07 |
| ATOM | 680 | N | SER | A | 89 | −17.314 | 35.931 | 52.077 | 1.00 | 45.16 |
| ATOM | 681 | CA | SER | A | 89 | −18.181 | 34.893 | 51.559 | 1.00 | 44.76 |
| ATOM | 682 | C | SER | A | 89 | −17.902 | 34.531 | 50.131 | 1.00 | 46.01 |
| ATOM | 683 | O | SER | A | 89 | −18.048 | 35.347 | 49.243 | 1.00 | 44.34 |
| ATOM | 684 | CB | SER | A | 89 | −19.657 | 35.121 | 51.827 | 1.00 | 51.87 |
| ATOM | 685 | OG | SER | A | 89 | −19.942 | 34.834 | 53.198 | 1.00 | 69.07 |
| ATOM | 686 | N | LEU | A | 90 | −17.494 | 33.279 | 49.914 | 1.00 | 46.43 |
| ATOM | 687 | CA | LEU | A | 90 | −17.204 | 32.804 | 48.575 | 1.00 | 46.93 |
| ATOM | 688 | C | LEU | A | 90 | −18.450 | 32.235 | 47.935 | 1.00 | 55.26 |
| ATOM | 689 | O | LEU | A | 90 | −19.210 | 31.476 | 48.556 | 1.00 | 54.94 |
| ATOM | 690 | CB | LEU | A | 90 | −16.080 | 31.750 | 48.521 | 1.00 | 46.14 |
| ATOM | 691 | CG | LEU | A | 90 | −15.262 | 31.607 | 49.792 | 1.00 | 50.78 |
| ATOM | 692 | CD1 | LEU | A | 90 | −14.546 | 30.261 | 49.806 | 1.00 | 50.27 |
| ATOM | 693 | CD2 | LEU | A | 90 | −14.219 | 32.708 | 49.863 | 1.00 | 55.52 |

TABLE 9-continued

Structure coordinates of LTA₄ hydrolase-thiolamine complex
(The amino acid sequence set forth as residues 1-610 below correspond to SEQ ID NO:1.)

| ATOM | 694 | N   | PRO | A | 91  | −18.626 | 32.607 | 46.683 | 1.00 | 54.81  |
|------|-----|-----|-----|---|-----|---------|--------|--------|------|--------|
| ATOM | 695 | CA  | PRO | A | 91  | −19.756 | 32.183 | 45.870 | 1.00 | 58.45  |
| ATOM | 696 | C   | PRO | A | 91  | −19.585 | 30.782 | 45.254 | 1.00 | 67.78  |
| ATOM | 697 | O   | PRO | A | 91  | −20.500 | 30.250 | 44.623 | 1.00 | 68.64  |
| ATOM | 698 | CB  | PRO | A | 91  | −19.843 | 33.213 | 44.738 | 1.00 | 59.70  |
| ATOM | 699 | CG  | PRO | A | 91  | −18.503 | 33.952 | 44.711 | 1.00 | 61.25  |
| ATOM | 700 | CD  | PRO | A | 91  | −17.731 | 33.539 | 45.961 | 1.00 | 54.16  |
| ATOM | 701 | N   | ILE | A | 92  | −18.413 | 30.177 | 45.416 | 1.00 | 64.82  |
| ATOM | 702 | CA  | ILE | A | 92  | −18.210 | 28.863 | 44.850 | 1.00 | 65.03  |
| ATOM | 703 | C   | ILE | A | 92  | −17.485 | 27.948 | 45.801 | 1.00 | 66.34  |
| ATOM | 704 | O   | ILE | A | 92  | −16.258 | 27.984 | 45.865 | 1.00 | 70.20  |
| ATOM | 705 | CB  | ILE | A | 92  | −17.433 | 28.927 | 43.547 | 1.00 | 69.56  |
| ATOM | 706 | CG1 | ILE | A | 92  | −18.298 | 29.495 | 42.430 | 1.00 | 70.02  |
| ATOM | 707 | CG2 | ILE | A | 92  | −16.975 | 27.517 | 43.171 | 1.00 | 71.86  |
| ATOM | 708 | CD1 | ILE | A | 92  | −17.528 | 29.672 | 41.121 | 1.00 | 80.63  |
| ATOM | 709 | N   | ALA | A | 93  | −18.219 | 27.115 | 46.534 | 1.00 | 54.40  |
| ATOM | 710 | CA  | ALA | A | 93  | −17.526 | 26.247 | 47.452 | 1.00 | 51.74  |
| ATOM | 711 | C   | ALA | A | 93  | −16.265 | 25.750 | 46.804 | 1.00 | 52.66  |
| ATOM | 712 | O   | ALA | A | 93  | −16.288 | 25.319 | 45.662 | 1.00 | 49.87  |
| ATOM | 713 | CB  | ALA | A | 93  | −18.367 | 25.101 | 47.968 | 1.00 | 52.76  |
| ATOM | 714 | N   | LEU | A | 94  | −15.162 | 25.861 | 47.544 | 1.00 | 48.18  |
| ATOM | 715 | CA  | LEU | A | 94  | −13.862 | 25.425 | 47.067 | 1.00 | 43.27  |
| ATOM | 716 | C   | LEU | A | 94  | −13.566 | 24.066 | 47.581 | 1.00 | 43.98  |
| ATOM | 717 | O   | LEU | A | 94  | −14.086 | 23.633 | 48.601 | 1.00 | 44.63  |
| ATOM | 718 | CB  | LEU | A | 94  | −12.713 | 26.344 | 47.509 | 1.00 | 41.05  |
| ATOM | 719 | CG  | LEU | A | 94  | −12.685 | 27.638 | 46.739 | 1.00 | 40.03  |
| ATOM | 720 | CD1 | LEU | A | 94  | −11.272 | 28.200 | 46.751 | 1.00 | 36.88  |
| ATOM | 721 | CD2 | LEU | A | 94  | −13.115 | 27.343 | 45.311 | 1.00 | 44.98  |
| ATOM | 722 | N   | SER | A | 95  | −12.706 | 23.406 | 46.875 | 1.00 | 43.26  |
| ATOM | 723 | CA  | SER | A | 95  | −12.321 | 22.074 | 47.256 | 1.00 | 43.76  |
| ATOM | 724 | C   | SER | A | 95  | −10.807 | 21.991 | 47.344 | 1.00 | 38.58  |
| ATOM | 725 | O   | SER | A | 95  | −10.087 | 22.944 | 46.975 | 1.00 | 36.78  |
| ATOM | 726 | CB  | SER | A | 95  | −12.902 | 21.092 | 46.256 | 1.00 | 51.55  |
| ATOM | 727 | OG  | SER | A | 95  | −14.299 | 21.305 | 46.156 | 1.00 | 62.74  |
| ATOM | 728 | N   | LYS | A | 96  | −10.321 | 20.863 | 47.830 | 1.00 | 31.10  |
| ATOM | 729 | CA  | LYS | A | 96  | −8.883  | 20.723 | 47.958 | 1.00 | 34.92  |
| ATOM | 730 | C   | LYS | A | 96  | −8.058  | 21.238 | 46.777 | 1.00 | 45.63  |
| ATOM | 731 | O   | LYS | A | 96  | −8.400  | 21.063 | 45.612 | 1.00 | 49.35  |
| ATOM | 732 | CB  | LYS | A | 96  | −8.401  | 19.366 | 48.451 | 1.00 | 38.53  |
| ATOM | 733 | CG  | LYS | A | 96  | −9.189  | 18.871 | 49.651 | 1.00 | 68.97  |
| ATOM | 734 | CD  | LYS | A | 96  | −8.691  | 17.549 | 50.221 | 1.00 | 80.86  |
| ATOM | 735 | CE  | LYS | A | 96  | −9.596  | 17.011 | 51.330 | 1.00 | 92.53  |
| ATOM | 736 | NZ  | LYS | A | 96  | −9.049  | 15.833 | 52.029 | 1.00 | 100.00 |
| ATOM | 737 | N   | ASN | A | 97  | −6.944  | 21.873 | 47.108 | 1.00 | 41.92  |
| ATOM | 738 | CA  | ASN | A | 97  | −6.009  | 22.403 | 46.139 | 1.00 | 40.91  |
| ATOM | 739 | C   | ASN | A | 97  | −6.606  | 23.348 | 45.088 | 1.00 | 42.64  |
| ATOM | 740 | O   | ASN | A | 97  | −5.963  | 23.681 | 44.068 | 1.00 | 38.69  |
| ATOM | 741 | CB  | ASN | A | 97  | −5.084  | 21.304 | 45.583 | 1.00 | 28.16  |
| ATOM | 742 | CG  | ASN | A | 97  | −4.327  | 20.568 | 46.677 | 1.00 | 52.21  |
| ATOM | 743 | OD1 | ASN | A | 97  | −3.089  | 20.627 | 46.744 | 1.00 | 55.30  |
| ATOM | 744 | ND2 | ASN | A | 97  | −5.060  | 19.858 | 47.533 | 1.00 | 53.87  |
| ATOM | 745 | N   | GLN | A | 98  | −7.833  | 23.791 | 45.382 | 1.00 | 36.59  |
| ATOM | 746 | CA  | GLN | A | 98  | −8.557  | 24.718 | 44.536 | 1.00 | 38.44  |
| ATOM | 747 | C   | GLN | A | 98  | −8.288  | 26.181 | 44.951 | 1.00 | 43.30  |
| ATOM | 748 | O   | GLN | A | 98  | −8.248  | 26.526 | 46.138 | 1.00 | 43.40  |
| ATOM | 749 | CB  | GLN | A | 98  | −10.064 | 24.395 | 44.575 | 1.00 | 42.26  |
| ATOM | 750 | CG  | GLN | A | 98  | −10.553 | 23.538 | 43.385 | 1.00 | 68.24  |
| ATOM | 751 | CD  | GLN | A | 98  | −12.008 | 23.778 | 43.010 | 1.00 | 95.57  |
| ATOM | 752 | OE1 | GLN | A | 98  | −12.890 | 22.935 | 43.278 | 1.00 | 86.92  |
| ATOM | 753 | NE2 | GLN | A | 98  | −12.271 | 24.935 | 42.393 | 1.00 | 95.48  |
| ATOM | 754 | N   | GLU | A | 99  | −8.089  | 27.062 | 43.973 | 1.00 | 39.70  |
| ATOM | 755 | CA  | GLU | A | 99  | −7.817  | 28.468 | 44.280 | 1.00 | 40.49  |
| ATOM | 756 | C   | GLU | A | 99  | −8.750  | 29.536 | 43.683 | 1.00 | 47.84  |
| ATOM | 757 | O   | GLU | A | 99  | −9.330  | 29.394 | 42.606 | 1.00 | 46.85  |
| ATOM | 758 | CB  | GLU | A | 99  | −6.361  | 28.866 | 43.951 | 1.00 | 40.24  |
| ATOM | 759 | CG  | GLU | A | 99  | −5.608  | 27.861 | 43.080 | 1.00 | 44.16  |
| ATOM | 760 | CD  | GLU | A | 99  | −4.120  | 28.119 | 42.990 | 1.00 | 65.64  |
| ATOM | 761 | OE1 | GLU | A | 99  | −3.636  | 29.062 | 42.376 | 1.00 | 73.95  |
| ATOM | 762 | OE2 | GLU | A | 99  | −3.395  | 27.210 | 43.614 | 1.00 | 55.99  |
| ATOM | 763 | N   | ILE | A | 100 | −8.848  | 30.643 | 44.418 | 1.00 | 43.55  |
| ATOM | 764 | CA  | ILE | A | 100 | −9.595  | 31.800 | 44.005 | 1.00 | 43.46  |
| ATOM | 765 | C   | ILE | A | 100 | −8.701  | 32.992 | 44.238 | 1.00 | 53.31  |
| ATOM | 766 | O   | ILE | A | 100 | −7.725  | 32.927 | 45.004 | 1.00 | 55.16  |
| ATOM | 767 | CB  | ILE | A | 100 | −10.881 | 32.068 | 44.773 | 1.00 | 46.65  |
| ATOM | 768 | CG1 | ILE | A | 100 | −10.762 | 31.640 | 46.227 | 1.00 | 50.76  |
| ATOM | 769 | CG2 | ILE | A | 100 | −12.111 | 31.486 | 44.106 | 1.00 | 46.76  |

TABLE 9-continued

Structure coordinates of LTA₄ hydrolase-thiolamine complex
(The amino acid sequence set forth as residues 1-610 below correspond to SEQ ID NO:1.)

| ATOM | 770 | CD1 | ILE | A | 100 | −9.959 | 32.620 | 47.087 | 1.00 | 64.36 |
| --- | --- | --- | --- | --- | --- | --- | --- | --- | --- | --- |
| ATOM | 771 | N | VAL | A | 101 | −9.060 | 34.076 | 43.580 | 1.00 | 48.20 |
| ATOM | 772 | CA | VAL | A | 101 | −8.382 | 35.329 | 43.760 | 1.00 | 45.63 |
| ATOM | 773 | C | VAL | A | 101 | −9.383 | 36.351 | 44.295 | 1.00 | 48.59 |
| ATOM | 774 | O | VAL | A | 101 | −10.331 | 36.722 | 43.623 | 1.00 | 51.29 |
| ATOM | 775 | CB | VAL | A | 101 | −7.461 | 35.793 | 42.633 | 1.00 | 45.06 |
| ATOM | 776 | CG1 | VAL | A | 101 | −7.693 | 35.000 | 41.378 | 1.00 | 43.25 |
| ATOM | 777 | CG2 | VAL | A | 101 | −7.609 | 37.289 | 42.395 | 1.00 | 45.02 |
| ATOM | 778 | N | ILE | A | 102 | −9.182 | 36.738 | 45.546 | 1.00 | 41.15 |
| ATOM | 779 | CA | ILE | A | 102 | −10.023 | 37.690 | 46.238 | 1.00 | 39.43 |
| ATOM | 780 | C | ILE | A | 102 | −9.439 | 39.062 | 46.170 | 1.00 | 49.35 |
| ATOM | 781 | O | ILE | A | 102 | −8.331 | 39.274 | 46.659 | 1.00 | 53.80 |
| ATOM | 782 | CB | ILE | A | 102 | −10.097 | 37.319 | 47.694 | 1.00 | 39.19 |
| ATOM | 783 | CG1 | ILE | A | 102 | −10.180 | 35.800 | 47.809 | 1.00 | 35.28 |
| ATOM | 784 | CG2 | ILE | A | 102 | −11.300 | 37.992 | 48.341 | 1.00 | 35.25 |
| ATOM | 785 | CD1 | ILE | A | 102 | −10.962 | 35.392 | 49.044 | 1.00 | 47.09 |
| ATOM | 786 | N | GLU | A | 103 | −10.192 | 39.984 | 45.572 | 1.00 | 43.20 |
| ATOM | 787 | CA | GLU | A | 103 | −9.748 | 41.362 | 45.433 | 1.00 | 39.88 |
| ATOM | 788 | C | GLU | A | 103 | −10.378 | 42.299 | 46.425 | 1.00 | 44.03 |
| ATOM | 789 | O | GLU | A | 103 | −11.580 | 42.558 | 46.385 | 1.00 | 41.34 |
| ATOM | 790 | CB | GLU | A | 103 | −9.950 | 41.930 | 44.047 | 1.00 | 39.11 |
| ATOM | 791 | CG | GLU | A | 103 | −9.017 | 43.112 | 43.863 | 1.00 | 36.18 |
| ATOM | 792 | CD | GLU | A | 103 | −9.150 | 43.666 | 42.485 | 1.00 | 61.93 |
| ATOM | 793 | OE1 | GLU | A | 103 | −10.157 | 44.234 | 42.100 | 1.00 | 69.89 |
| ATOM | 794 | OE2 | GLU | A | 103 | −8.087 | 43.457 | 41.744 | 1.00 | 76.18 |
| ATOM | 795 | N | ILE | A | 104 | −9.534 | 42.797 | 47.322 | 1.00 | 42.69 |
| ATOM | 796 | CA | ILE | A | 104 | −9.969 | 43.718 | 48.346 | 1.00 | 40.72 |
| ATOM | 797 | C | ILE | A | 104 | −9.522 | 45.167 | 48.099 | 1.00 | 46.21 |
| ATOM | 798 | O | ILE | A | 104 | −8.346 | 45.478 | 47.866 | 1.00 | 42.68 |
| ATOM | 799 | CB | ILE | A | 104 | −9.578 | 43.283 | 49.754 | 1.00 | 41.75 |
| ATOM | 800 | CG1 | ILE | A | 104 | −10.006 | 41.855 | 50.032 | 1.00 | 39.85 |
| ATOM | 801 | CG2 | ILE | A | 104 | −10.225 | 44.222 | 50.768 | 1.00 | 41.53 |
| ATOM | 802 | CD1 | ILE | A | 104 | −8.839 | 40.995 | 50.485 | 1.00 | 34.17 |
| ATOM | 803 | N | SER | A | 105 | −10.506 | 46.056 | 48.173 | 1.00 | 47.94 |
| ATOM | 804 | CA | SER | A | 105 | −10.278 | 47.481 | 48.046 | 1.00 | 48.05 |
| ATOM | 805 | C | SER | A | 105 | −10.184 | 47.977 | 49.482 | 1.00 | 42.39 |
| ATOM | 806 | O | SER | A | 105 | −11.134 | 47.879 | 50.263 | 1.00 | 39.69 |
| ATOM | 807 | CB | SER | A | 105 | −11.399 | 48.180 | 47.290 | 1.00 | 53.77 |
| ATOM | 808 | OG | SER | A | 105 | −11.399 | 47.789 | 45.930 | 1.00 | 60.69 |
| ATOM | 809 | N | PHE | A | 106 | −9.020 | 48.445 | 49.857 | 1.00 | 35.07 |
| ATOM | 810 | CA | PHE | A | 106 | −8.844 | 48.890 | 51.223 | 1.00 | 34.98 |
| ATOM | 811 | C | PHE | A | 106 | −8.177 | 50.238 | 51.262 | 1.00 | 39.26 |
| ATOM | 812 | O | PHE | A | 106 | −7.607 | 50.730 | 50.265 | 1.00 | 34.24 |
| ATOM | 813 | CB | PHE | A | 106 | −8.015 | 47.864 | 52.060 | 1.00 | 36.05 |
| ATOM | 814 | CG | PHE | A | 106 | −6.581 | 47.815 | 51.556 | 1.00 | 37.24 |
| ATOM | 815 | CD1 | PHE | A | 106 | −6.251 | 47.073 | 50.422 | 1.00 | 39.71 |
| ATOM | 816 | CD2 | PHE | A | 106 | −5.579 | 48.579 | 52.161 | 1.00 | 36.44 |
| ATOM | 817 | CE1 | PHE | A | 106 | −4.950 | 47.086 | 49.920 | 1.00 | 41.48 |
| ATOM | 818 | CE2 | PHE | A | 106 | −4.273 | 48.609 | 51.672 | 1.00 | 38.19 |
| ATOM | 819 | CZ | PHE | A | 106 | −3.961 | 47.856 | 50.540 | 1.00 | 37.91 |
| ATOM | 820 | N | GLU | A | 107 | −8.284 | 50.794 | 52.453 | 1.00 | 40.64 |
| ATOM | 821 | CA | GLU | A | 107 | −7.711 | 52.064 | 52.848 | 1.00 | 43.81 |
| ATOM | 822 | C | GLU | A | 107 | −7.206 | 51.869 | 54.284 | 1.00 | 43.82 |
| ATOM | 823 | O | GLU | A | 107 | −7.933 | 51.303 | 55.121 | 1.00 | 38.38 |
| ATOM | 824 | CB | GLU | A | 107 | −8.737 | 53.234 | 52.753 | 1.00 | 46.93 |
| ATOM | 825 | CG | GLU | A | 107 | −8.107 | 54.637 | 52.467 | 1.00 | 67.21 |
| ATOM | 826 | CD | GLU | A | 107 | −9.086 | 55.715 | 52.042 | 1.00 | 100.00 |
| ATOM | 827 | OE1 | GLU | A | 107 | −10.208 | 55.504 | 51.599 | 1.00 | 100.00 |
| ATOM | 828 | OE2 | GLU | A | 107 | −8.631 | 56.938 | 52.221 | 1.00 | 93.72 |
| ATOM | 829 | N | THR | A | 108 | −5.963 | 52.294 | 54.551 | 1.00 | 39.12 |
| ATOM | 830 | CA | THR | A | 108 | −5.345 | 52.175 | 55.873 | 1.00 | 39.69 |
| ATOM | 831 | C | THR | A | 108 | −5.564 | 53.427 | 56.724 | 1.00 | 49.82 |
| ATOM | 832 | O | THR | A | 108 | −5.565 | 54.552 | 56.177 | 1.00 | 50.94 |
| ATOM | 833 | CB | THR | A | 108 | −3.810 | 52.095 | 55.722 | 1.00 | 40.40 |
| ATOM | 834 | OG1 | THR | A | 108 | −3.360 | 53.226 | 54.981 | 1.00 | 32.22 |
| ATOM | 835 | CG2 | THR | A | 108 | −3.371 | 50.802 | 55.042 | 1.00 | 46.43 |
| ATOM | 836 | N | SER | A | 109 | −5.698 | 53.217 | 58.065 | 1.00 | 42.02 |
| ATOM | 837 | CA | SER | A | 109 | −5.848 | 54.294 | 59.038 | 1.00 | 38.13 |
| ATOM | 838 | C | SER | A | 109 | −4.555 | 55.101 | 59.082 | 1.00 | 38.47 |
| ATOM | 839 | O | SER | A | 109 | −3.460 | 54.583 | 58.921 | 1.00 | 33.60 |
| ATOM | 840 | CB | SER | A | 109 | −6.166 | 53.759 | 60.437 | 1.00 | 41.44 |
| ATOM | 841 | OG | SER | A | 109 | −6.205 | 54.812 | 61.404 | 1.00 | 47.63 |
| ATOM | 842 | N | PRO | A | 110 | −4.655 | 56.392 | 59.308 | 1.00 | 41.64 |
| ATOM | 843 | CA | PRO | A | 110 | −3.419 | 57.116 | 59.393 | 1.00 | 40.75 |
| ATOM | 844 | C | PRO | A | 110 | −2.803 | 56.749 | 60.725 | 1.00 | 41.47 |
| ATOM | 845 | O | PRO | A | 110 | −1.676 | 57.080 | 61.009 | 1.00 | 42.30 |

TABLE 9-continued

Structure coordinates of LTA₄ hydrolase-thiolamine complex
(The amino acid sequence set forth as residues 1-610 below correspond to SEQ ID NO:1.)

| ATOM | 846 | CB | PRO | A | 110 | −3.721 | 58.605 | 59.298 | 1.00 | 42.09 |
|---|---|---|---|---|---|---|---|---|---|---|
| ATOM | 847 | CG | PRO | A | 110 | −5.224 | 58.719 | 59.132 | 1.00 | 48.77 |
| ATOM | 848 | CD | PRO | A | 110 | −5.811 | 57.318 | 59.269 | 1.00 | 44.58 |
| ATOM | 849 | N | LYS | A | 111 | −3.578 | 56.017 | 61.518 | 1.00 | 36.35 |
| ATOM | 850 | CA | LYS | A | 111 | −3.167 | 55.535 | 62.819 | 1.00 | 36.74 |
| ATOM | 851 | C | LYS | A | 111 | −2.669 | 54.083 | 62.720 | 1.00 | 40.19 |
| ATOM | 852 | O | LYS | A | 111 | −2.733 | 53.319 | 63.678 | 1.00 | 40.53 |
| ATOM | 853 | CB | LYS | A | 111 | −4.341 | 55.606 | 63.807 | 1.00 | 41.91 |
| ATOM | 854 | CG | LYS | A | 111 | −4.362 | 56.838 | 64.708 | 1.00 | 71.21 |
| ATOM | 855 | CD | LYS | A | 111 | −5.421 | 57.854 | 64.309 | 1.00 | 97.95 |
| ATOM | 856 | CE | LYS | A | 111 | −6.839 | 57.394 | 64.611 | 1.00 | 100.00 |
| ATOM | 857 | NZ | LYS | A | 111 | −7.853 | 58.120 | 63.819 | 1.00 | 100.00 |
| ATOM | 858 | N | SER | A | 112 | −2.184 | 53.670 | 61.550 | 1.00 | 36.84 |
| ATOM | 859 | CA | SER | A | 112 | −1.714 | 52.296 | 61.358 | 1.00 | 34.35 |
| ATOM | 860 | C | SER | A | 112 | −0.518 | 51.917 | 62.225 | 1.00 | 35.57 |
| ATOM | 861 | O | SER | A | 112 | 0.533 | 52.548 | 62.166 | 1.00 | 32.49 |
| ATOM | 862 | CB | SER | A | 112 | −1.449 | 51.995 | 59.883 | 1.00 | 35.16 |
| ATOM | 863 | OG | SER | A | 112 | −0.682 | 50.814 | 59.762 | 1.00 | 31.94 |
| ATOM | 864 | N | SER | A | 113 | −0.666 | 50.872 | 63.033 | 1.00 | 31.84 |
| ATOM | 865 | CA | SER | A | 113 | 0.445 | 50.460 | 63.866 | 1.00 | 29.27 |
| ATOM | 866 | C | SER | A | 113 | 1.601 | 49.927 | 63.040 | 1.00 | 33.37 |
| ATOM | 867 | O | SER | A | 113 | 2.715 | 49.792 | 63.497 | 1.00 | 32.95 |
| ATOM | 868 | CB | SER | A | 113 | 0.052 | 49.498 | 64.945 | 1.00 | 29.45 |
| ATOM | 869 | OG | SER | A | 113 | 0.045 | 48.169 | 64.462 | 1.00 | 34.27 |
| ATOM | 870 | N | ALA | A | 114 | 1.357 | 49.628 | 61.797 | 1.00 | 33.69 |
| ATOM | 871 | CA | ALA | A | 114 | 2.437 | 49.134 | 60.981 | 1.00 | 34.05 |
| ATOM | 872 | C | ALA | A | 114 | 3.239 | 50.287 | 60.388 | 1.00 | 37.83 |
| ATOM | 873 | O | ALA | A | 114 | 4.411 | 50.149 | 60.033 | 1.00 | 37.72 |
| ATOM | 874 | CB | ALA | A | 114 | 1.845 | 48.292 | 59.852 | 1.00 | 34.51 |
| ATOM | 875 | N | LEU | A | 115 | 2.580 | 51.432 | 60.259 | 1.00 | 32.19 |
| ATOM | 876 | CA | LEU | A | 115 | 3.201 | 52.595 | 59.662 | 1.00 | 30.48 |
| ATOM | 877 | C | LEU | A | 115 | 3.509 | 53.745 | 60.565 | 1.00 | 35.32 |
| ATOM | 878 | O | LEU | A | 115 | 2.902 | 54.012 | 61.604 | 1.00 | 35.25 |
| ATOM | 879 | CB | LEU | A | 115 | 2.358 | 53.156 | 58.507 | 1.00 | 30.53 |
| ATOM | 880 | CG | LEU | A | 115 | 1.787 | 52.064 | 57.602 | 1.00 | 35.51 |
| ATOM | 881 | CD1 | LEU | A | 115 | 0.812 | 52.710 | 56.637 | 1.00 | 35.12 |
| ATOM | 882 | CD2 | LEU | A | 115 | 2.903 | 51.387 | 56.821 | 1.00 | 33.88 |
| ATOM | 883 | N | GLN | A | 116 | 4.490 | 54.457 | 60.096 | 1.00 | 34.00 |
| ATOM | 884 | CA | GLN | A | 116 | 4.926 | 55.656 | 60.737 | 1.00 | 32.52 |
| ATOM | 885 | C | GLN | A | 116 | 5.066 | 56.689 | 59.645 | 1.00 | 31.34 |
| ATOM | 886 | O | GLN | A | 116 | 5.880 | 56.552 | 58.729 | 1.00 | 28.29 |
| ATOM | 887 | CB | GLN | A | 116 | 6.232 | 55.540 | 61.496 | 1.00 | 32.66 |
| ATOM | 888 | CG | GLN | A | 116 | 6.419 | 56.813 | 62.322 | 1.00 | 41.25 |
| ATOM | 889 | CD | GLN | A | 116 | 7.777 | 56.897 | 62.952 | 1.00 | 50.08 |
| ATOM | 890 | OE1 | GLN | A | 116 | 8.515 | 55.905 | 63.017 | 1.00 | 55.36 |
| ATOM | 891 | NE2 | GLN | A | 116 | 8.090 | 58.081 | 63.438 | 1.00 | 38.23 |
| ATOM | 892 | N | TRP | A | 117 | 4.210 | 57.680 | 59.748 | 1.00 | 26.66 |
| ATOM | 893 | CA | TRP | A | 117 | 4.148 | 58.785 | 58.827 | 1.00 | 26.04 |
| ATOM | 894 | C | TRP | A | 117 | 4.912 | 59.978 | 59.375 | 1.00 | 34.56 |
| ATOM | 895 | O | TRP | A | 117 | 4.467 | 60.589 | 60.364 | 1.00 | 36.83 |
| ATOM | 896 | CB | TRP | A | 117 | 2.669 | 59.188 | 58.630 | 1.00 | 23.15 |
| ATOM | 897 | CG | TRP | A | 117 | 1.826 | 58.209 | 57.863 | 1.00 | 23.02 |
| ATOM | 898 | CD1 | TRP | A | 117 | 1.052 | 57.224 | 58.397 | 1.00 | 26.39 |
| ATOM | 899 | CD2 | TRP | A | 117 | 1.640 | 58.135 | 56.433 | 1.00 | 21.06 |
| ATOM | 900 | NE1 | TRP | A | 117 | 0.395 | 56.534 | 57.393 | 1.00 | 26.40 |
| ATOM | 901 | CE2 | TRP | A | 117 | 0.735 | 57.087 | 56.184 | 1.00 | 27.99 |
| ATOM | 902 | CE3 | TRP | A | 117 | 2.121 | 58.872 | 55.361 | 1.00 | 20.95 |
| ATOM | 903 | CZ2 | TRP | A | 117 | 0.352 | 56.753 | 54.886 | 1.00 | 28.21 |
| ATOM | 904 | CZ3 | TRP | A | 117 | 1.750 | 58.560 | 54.079 | 1.00 | 22.43 |
| ATOM | 905 | CH2 | TRP | A | 117 | 0.872 | 57.512 | 53.847 | 1.00 | 24.28 |
| ATOM | 906 | N | LEU | A | 118 | 6.043 | 60.340 | 58.756 | 1.00 | 31.44 |
| ATOM | 907 | CA | LEU | A | 118 | 6.745 | 61.506 | 59.276 | 1.00 | 36.67 |
| ATOM | 908 | C | LEU | A | 118 | 6.584 | 62.774 | 58.432 | 1.00 | 46.93 |
| ATOM | 909 | O | LEU | A | 118 | 6.434 | 62.705 | 57.210 | 1.00 | 51.17 |
| ATOM | 910 | CB | LEU | A | 118 | 8.250 | 61.327 | 59.577 | 1.00 | 38.83 |
| ATOM | 911 | CG | LEU | A | 118 | 8.881 | 59.939 | 59.398 | 1.00 | 44.33 |
| ATOM | 912 | CD1 | LEU | A | 118 | 10.392 | 60.065 | 59.569 | 1.00 | 42.12 |
| ATOM | 913 | CD2 | LEU | A | 118 | 8.351 | 58.950 | 60.426 | 1.00 | 49.99 |
| ATOM | 914 | N | THR | A | 119 | 6.524 | 63.939 | 59.109 | 1.00 | 41.34 |
| ATOM | 915 | CA | THR | A | 119 | 6.449 | 65.260 | 58.468 | 1.00 | 38.89 |
| ATOM | 916 | C | THR | A | 119 | 7.847 | 65.633 | 58.034 | 1.00 | 40.14 |
| ATOM | 917 | O | THR | A | 119 | 8.841 | 65.165 | 58.605 | 1.00 | 44.03 |
| ATOM | 918 | CB | THR | A | 119 | 5.932 | 66.300 | 59.467 | 1.00 | 42.63 |
| ATOM | 919 | OG1 | THR | A | 119 | 6.994 | 66.605 | 60.362 | 1.00 | 50.01 |
| ATOM | 920 | CG2 | THR | A | 119 | 4.769 | 65.668 | 60.224 | 1.00 | 36.78 |
| ATOM | 921 | N | PRO | A | 120 | 7.963 | 66.440 | 57.020 | 1.00 | 33.41 |

TABLE 9-continued

Structure coordinates of LTA₄ hydrolase-thiolamine complex
(The amino acid sequence set forth as residues 1-610 below correspond to SEQ ID NO:1.)

| ATOM | 922 | CA | PRO | A | 120 | 9.275 | 66.781 | 56.517 | 1.00 | 33.18 |
|---|---|---|---|---|---|---|---|---|---|---|
| ATOM | 923 | C | PRO | A | 120 | 10.260 | 67.209 | 57.599 | 1.00 | 38.27 |
| ATOM | 924 | O | PRO | A | 120 | 11.433 | 66.829 | 57.566 | 1.00 | 34.42 |
| ATOM | 925 | CB | PRO | A | 120 | 9.068 | 67.840 | 55.416 | 1.00 | 33.54 |
| ATOM | 926 | CG | PRO | A | 120 | 7.582 | 67.823 | 55.097 | 1.00 | 34.86 |
| ATOM | 927 | CD | PRO | A | 120 | 6.891 | 67.180 | 56.300 | 1.00 | 30.86 |
| ATOM | 928 | N | GLU | A | 121 | 9.751 | 67.982 | 58.563 | 1.00 | 38.03 |
| ATOM | 929 | CA | GLU | A | 121 | 10.534 | 68.474 | 59.681 | 1.00 | 41.03 |
| ATOM | 930 | C | GLU | A | 121 | 11.212 | 67.361 | 60.411 | 1.00 | 50.88 |
| ATOM | 931 | O | GLU | A | 121 | 12.279 | 67.548 | 60.977 | 1.00 | 54.97 |
| ATOM | 932 | CB | GLU | A | 121 | 9.742 | 69.325 | 60.699 | 1.00 | 43.28 |
| ATOM | 933 | CG | GLU | A | 121 | 8.220 | 69.071 | 60.702 | 1.00 | 64.72 |
| ATOM | 934 | CD | GLU | A | 121 | 7.398 | 70.118 | 59.988 | 1.00 | 86.07 |
| ATOM | 935 | OE1 | GLU | A | 121 | 7.007 | 71.131 | 60.538 | 1.00 | 100.00 |
| ATOM | 936 | OE2 | GLU | A | 121 | 7.108 | 69.803 | 58.739 | 1.00 | 59.72 |
| ATOM | 937 | N | GLN | A | 122 | 10.569 | 66.202 | 60.394 | 1.00 | 44.09 |
| ATOM | 938 | CA | GLN | A | 122 | 11.083 | 65.019 | 61.041 | 1.00 | 40.20 |
| ATOM | 939 | C | GLN | A | 122 | 12.170 | 64.373 | 60.232 | 1.00 | 47.73 |
| ATOM | 940 | O | GLN | A | 122 | 12.711 | 63.343 | 60.643 | 1.00 | 53.29 |
| ATOM | 941 | CB | GLN | A | 122 | 9.965 | 63.992 | 61.224 | 1.00 | 39.31 |
| ATOM | 942 | CG | GLN | A | 122 | 9.057 | 64.441 | 62.361 | 1.00 | 30.23 |
| ATOM | 943 | CD | GLN | A | 122 | 7.756 | 63.691 | 62.438 | 1.00 | 38.25 |
| ATOM | 944 | OE1 | GLN | A | 122 | 6.899 | 63.804 | 61.548 | 1.00 | 53.34 |
| ATOM | 945 | NE2 | GLN | A | 122 | 7.592 | 62.938 | 63.521 | 1.00 | 18.98 |
| ATOM | 946 | N | THR | A | 123 | 12.486 | 64.942 | 59.074 | 1.00 | 38.99 |
| ATOM | 947 | CA | THR | A | 123 | 13.490 | 64.319 | 58.229 | 1.00 | 36.00 |
| ATOM | 948 | C | THR | A | 123 | 14.755 | 65.034 | 58.264 | 1.00 | 35.30 |
| ATOM | 949 | O | THR | A | 123 | 14.842 | 66.074 | 58.875 | 1.00 | 34.95 |
| ATOM | 950 | CB | THR | A | 123 | 13.067 | 64.145 | 56.759 | 1.00 | 38.25 |
| ATOM | 951 | OG1 | THR | A | 123 | 13.144 | 65.374 | 56.046 | 1.00 | 43.75 |
| ATOM | 952 | CG2 | THR | A | 123 | 11.643 | 63.616 | 56.725 | 1.00 | 40.72 |
| ATOM | 953 | N | SER | A | 124 | 15.699 | 64.447 | 57.557 | 1.00 | 32.18 |
| ATOM | 954 | CA | SER | A | 124 | 17.025 | 64.996 | 57.442 | 1.00 | 33.71 |
| ATOM | 955 | C | SER | A | 124 | 17.007 | 66.216 | 56.553 | 1.00 | 39.04 |
| ATOM | 956 | O | SER | A | 124 | 17.537 | 67.268 | 56.883 | 1.00 | 39.07 |
| ATOM | 957 | CB | SER | A | 124 | 18.023 | 63.992 | 56.859 | 1.00 | 37.73 |
| ATOM | 958 | OG | SER | A | 124 | 18.359 | 62.978 | 57.796 | 1.00 | 36.28 |
| ATOM | 959 | N | GLY | A | 125 | 16.389 | 66.025 | 55.414 | 1.00 | 38.59 |
| ATOM | 960 | CA | GLY | A | 125 | 16.280 | 67.034 | 54.396 | 1.00 | 39.90 |
| ATOM | 961 | C | GLY | A | 125 | 15.290 | 68.094 | 54.749 | 1.00 | 46.83 |
| ATOM | 962 | O | GLY | A | 125 | 15.347 | 69.171 | 54.172 | 1.00 | 49.78 |
| ATOM | 963 | N | LYS | A | 126 | 14.391 | 67.788 | 55.678 | 1.00 | 41.09 |
| ATOM | 964 | CA | LYS | A | 126 | 13.396 | 68.761 | 56.126 | 1.00 | 41.26 |
| ATOM | 965 | C | LYS | A | 126 | 12.498 | 69.307 | 55.020 | 1.00 | 47.42 |
| ATOM | 966 | O | LYS | A | 126 | 11.617 | 70.141 | 55.279 | 1.00 | 48.94 |
| ATOM | 967 | CB | LYS | A | 126 | 14.024 | 69.936 | 56.894 | 1.00 | 41.98 |
| ATOM | 968 | CG | LYS | A | 126 | 15.094 | 69.555 | 57.913 | 1.00 | 45.84 |
| ATOM | 969 | CD | LYS | A | 126 | 14.535 | 68.838 | 59.135 | 1.00 | 58.74 |
| ATOM | 970 | CE | LYS | A | 126 | 15.612 | 68.500 | 60.151 | 1.00 | 72.12 |
| ATOM | 971 | NZ | LYS | A | 126 | 15.395 | 67.218 | 60.839 | 1.00 | 88.38 |
| ATOM | 972 | N | GLU | A | 127 | 12.722 | 68.858 | 53.792 | 1.00 | 41.82 |
| ATOM | 973 | CA | GLU | A | 127 | 11.921 | 69.344 | 52.708 | 1.00 | 41.98 |
| ATOM | 974 | C | GLU | A | 127 | 10.899 | 68.334 | 52.239 | 1.00 | 45.14 |
| ATOM | 975 | O | GLU | A | 127 | 9.994 | 68.683 | 51.496 | 1.00 | 46.95 |
| ATOM | 976 | CB | GLU | A | 127 | 12.727 | 70.015 | 51.543 | 1.00 | 44.39 |
| ATOM | 977 | CG | GLU | A | 127 | 13.198 | 71.499 | 51.820 | 1.00 | 57.99 |
| ATOM | 978 | CD | GLU | A | 127 | 12.331 | 72.659 | 51.301 | 1.00 | 100.00 |
| ATOM | 979 | OE1 | GLU | A | 127 | 11.652 | 72.611 | 50.286 | 1.00 | 100.00 |
| ATOM | 980 | OE2 | GLU | A | 127 | 12.387 | 73.758 | 52.054 | 1.00 | 100.00 |
| ATOM | 981 | N | HIS | A | 128 | 11.027 | 67.077 | 52.653 | 1.00 | 39.18 |
| ATOM | 982 | CA | HIS | A | 128 | 10.068 | 66.072 | 52.210 | 1.00 | 39.43 |
| ATOM | 983 | C | HIS | A | 128 | 9.636 | 65.148 | 53.316 | 1.00 | 42.09 |
| ATOM | 984 | O | HIS | A | 128 | 10.366 | 64.955 | 54.281 | 1.00 | 45.34 |
| ATOM | 985 | CB | HIS | A | 128 | 10.628 | 65.194 | 51.097 | 1.00 | 42.16 |
| ATOM | 986 | CG | HIS | A | 128 | 10.947 | 65.936 | 49.854 | 1.00 | 47.24 |
| ATOM | 987 | ND1 | HIS | A | 128 | 9.943 | 66.423 | 49.029 | 1.00 | 49.12 |
| ATOM | 988 | CD2 | HIS | A | 128 | 12.159 | 66.262 | 49.322 | 1.00 | 51.13 |
| ATOM | 989 | CE1 | HIS | A | 128 | 10.559 | 67.031 | 48.026 | 1.00 | 49.97 |
| ATOM | 990 | NE2 | HIS | A | 128 | 11.888 | 66.953 | 48.166 | 1.00 | 50.87 |
| ATOM | 991 | N | PRO | A | 129 | 8.447 | 64.572 | 53.171 | 1.00 | 32.55 |
| ATOM | 992 | CA | PRO | A | 129 | 7.968 | 63.650 | 54.163 | 1.00 | 31.15 |
| ATOM | 993 | C | PRO | A | 129 | 8.636 | 62.328 | 53.900 | 1.00 | 34.90 |
| ATOM | 994 | O | PRO | A | 129 | 9.481 | 62.214 | 53.021 | 1.00 | 35.46 |
| ATOM | 995 | CB | PRO | A | 129 | 6.466 | 63.490 | 53.986 | 1.00 | 31.94 |
| ATOM | 996 | CG | PRO | A | 129 | 6.133 | 64.104 | 52.649 | 1.00 | 36.83 |
| ATOM | 997 | CD | PRO | A | 129 | 7.384 | 64.850 | 52.185 | 1.00 | 32.71 |

TABLE 9-continued

Structure coordinates of LTA₄ hydrolase-thiolamine complex
(The amino acid sequence set forth as residues 1-610 below correspond to SEQ ID NO:1.)

| ATOM | 998 | N | TYR | A | 130 | 8.248 | 61.342 | 54.659 | 1.00 | 29.47 |
|---|---|---|---|---|---|---|---|---|---|---|
| ATOM | 999 | CA | TYR | A | 130 | 8.826 | 60.025 | 54.548 | 1.00 | 29.35 |
| ATOM | 1000 | C | TYR | A | 130 | 7.856 | 59.046 | 55.156 | 1.00 | 31.83 |
| ATOM | 1001 | O | TYR | A | 130 | 7.138 | 59.375 | 56.093 | 1.00 | 29.84 |
| ATOM | 1002 | CB | TYR | A | 130 | 10.098 | 60.029 | 55.433 | 1.00 | 30.54 |
| ATOM | 1003 | CG | TYR | A | 130 | 11.083 | 58.886 | 55.285 | 1.00 | 29.76 |
| ATOM | 1004 | CD1 | TYR | A | 130 | 10.845 | 57.630 | 55.845 | 1.00 | 26.16 |
| ATOM | 1005 | CD2 | TYR | A | 130 | 12.290 | 59.110 | 54.619 | 1.00 | 30.28 |
| ATOM | 1006 | CE1 | TYR | A | 130 | 11.795 | 56.621 | 55.721 | 1.00 | 17.87 |
| ATOM | 1007 | CE2 | TYR | A | 130 | 13.253 | 58.114 | 54.479 | 1.00 | 27.75 |
| ATOM | 1008 | CZ | TYR | A | 130 | 12.983 | 56.866 | 55.031 | 1.00 | 25.76 |
| ATOM | 1009 | OH | TYR | A | 130 | 13.899 | 55.864 | 54.894 | 1.00 | 40.52 |
| ATOM | 1010 | N | LEU | A | 131 | 7.832 | 57.842 | 54.647 | 1.00 | 31.12 |
| ATOM | 1011 | CA | LEU | A | 131 | 6.994 | 56.868 | 55.303 | 1.00 | 30.43 |
| ATOM | 1012 | C | LEU | A | 131 | 7.691 | 55.568 | 55.289 | 1.00 | 33.91 |
| ATOM | 1013 | O | LEU | A | 131 | 8.398 | 55.257 | 54.397 | 1.00 | 33.68 |
| ATOM | 1014 | CB | LEU | A | 131 | 5.679 | 56.761 | 54.530 | 1.00 | 26.16 |
| ATOM | 1015 | CG | LEU | A | 131 | 5.065 | 55.367 | 54.600 | 1.00 | 21.68 |
| ATOM | 1016 | CD1 | LEU | A | 131 | 4.163 | 55.206 | 55.797 | 1.00 | 17.56 |
| ATOM | 1017 | CD2 | LEU | A | 131 | 4.222 | 55.008 | 53.380 | 1.00 | 13.86 |
| ATOM | 1018 | N | PHE | A | 132 | 7.533 | 54.828 | 56.348 | 1.00 | 29.24 |
| ATOM | 1019 | CA | PHE | A | 132 | 8.129 | 53.527 | 56.323 | 1.00 | 33.44 |
| ATOM | 1020 | C | PHE | A | 132 | 7.299 | 52.519 | 57.157 | 1.00 | 41.08 |
| ATOM | 1021 | O | PHE | A | 132 | 6.344 | 52.889 | 57.837 | 1.00 | 46.05 |
| ATOM | 1022 | CB | PHE | A | 132 | 9.621 | 53.670 | 56.791 | 1.00 | 36.40 |
| ATOM | 1023 | CG | PHE | A | 132 | 9.763 | 53.895 | 58.256 | 1.00 | 38.11 |
| ATOM | 1024 | CD1 | PHE | A | 132 | 9.601 | 52.821 | 59.053 | 1.00 | 37.18 |
| ATOM | 1025 | CD2 | PHE | A | 132 | 10.123 | 55.158 | 58.803 | 1.00 | 43.89 |
| ATOM | 1026 | CE1 | PHE | A | 132 | 9.771 | 52.936 | 60.422 | 1.00 | 41.04 |
| ATOM | 1027 | CE2 | PHE | A | 132 | 10.289 | 55.258 | 60.174 | 1.00 | 47.72 |
| ATOM | 1028 | CZ | PHE | A | 132 | 10.131 | 54.143 | 60.986 | 1.00 | 44.34 |
| ATOM | 1029 | N | SER | A | 133 | 7.612 | 51.221 | 57.002 | 1.00 | 33.47 |
| ATOM | 1030 | CA | SER | A | 133 | 6.744 | 50.228 | 57.629 | 1.00 | 29.86 |
| ATOM | 1031 | C | SER | A | 133 | 7.499 | 49.221 | 58.504 | 1.00 | 31.53 |
| ATOM | 1032 | O | SER | A | 133 | 8.724 | 49.146 | 58.531 | 1.00 | 33.16 |
| ATOM | 1033 | CB | SER | A | 133 | 5.942 | 49.481 | 56.535 | 1.00 | 33.19 |
| ATOM | 1034 | OG | SER | A | 133 | 6.757 | 48.480 | 55.926 | 1.00 | 50.66 |
| ATOM | 1035 | N | GLN | A | 134 | 6.703 | 48.466 | 59.294 | 1.00 | 24.61 |
| ATOM | 1036 | CA | GLN | A | 134 | 7.283 | 47.422 | 60.134 | 1.00 | 22.55 |
| ATOM | 1037 | C | GLN | A | 134 | 6.268 | 46.321 | 60.398 | 1.00 | 27.28 |
| ATOM | 1038 | O | GLN | A | 134 | 5.161 | 46.566 | 60.809 | 1.00 | 25.09 |
| ATOM | 1039 | CB | GLN | A | 134 | 7.711 | 48.041 | 61.464 | 1.00 | 23.29 |
| ATOM | 1040 | CG | GLN | A | 134 | 8.218 | 46.987 | 62.454 | 1.00 | 25.96 |
| ATOM | 1041 | CD | GLN | A | 134 | 9.423 | 46.290 | 61.872 | 1.00 | 25.65 |
| ATOM | 1042 | OE1 | GLN | A | 134 | 10.296 | 46.876 | 61.263 | 1.00 | 26.36 |
| ATOM | 1043 | NE2 | GLN | A | 134 | 9.445 | 44.965 | 62.095 | 1.00 | 21.75 |
| ATOM | 1044 | N | CYS | A | 135 | 6.435 | 45.124 | 59.820 | 1.00 | 29.60 |
| ATOM | 1045 | CA | CYS | A | 135 | 5.291 | 44.220 | 59.755 | 1.00 | 32.30 |
| ATOM | 1046 | C | CYS | A | 135 | 5.442 | 43.006 | 60.662 | 1.00 | 39.58 |
| ATOM | 1047 | O | CYS | A | 135 | 4.597 | 42.144 | 60.739 | 1.00 | 40.94 |
| ATOM | 1048 | CB | CYS | A | 135 | 5.098 | 43.794 | 58.320 | 1.00 | 35.40 |
| ATOM | 1049 | SG | CYS | A | 135 | 3.976 | 44.922 | 57.445 | 1.00 | 41.22 |
| ATOM | 1050 | N | GLN | A | 136 | 6.582 | 42.949 | 61.345 | 1.00 | 37.37 |
| ATOM | 1051 | CA | GLN | A | 136 | 6.715 | 41.982 | 62.417 | 1.00 | 35.71 |
| ATOM | 1052 | C | GLN | A | 136 | 6.589 | 42.645 | 63.797 | 1.00 | 31.90 |
| ATOM | 1053 | O | GLN | A | 136 | 6.878 | 43.803 | 63.981 | 1.00 | 30.54 |
| ATOM | 1054 | CB | GLN | A | 136 | 8.077 | 41.311 | 62.295 | 1.00 | 37.24 |
| ATOM | 1055 | CG | GLN | A | 136 | 8.076 | 39.878 | 62.847 | 1.00 | 29.70 |
| ATOM | 1056 | CD | GLN | A | 136 | 9.483 | 39.511 | 63.235 | 1.00 | 36.48 |
| ATOM | 1057 | OE1 | GLN | A | 136 | 10.366 | 40.328 | 63.356 | 1.00 | 24.49 |
| ATOM | 1058 | NE2 | GLN | A | 136 | 9.665 | 38.201 | 63.443 | 1.00 | 22.19 |
| ATOM | 1059 | N | ALA | A | 137 | 5.850 | 41.899 | 64.648 | 1.00 | 28.56 |
| ATOM | 1060 | CA | ALA | A | 137 | 5.235 | 40.581 | 64.351 | 1.00 | 28.89 |
| ATOM | 1061 | C | ALA | A | 137 | 3.860 | 40.503 | 63.630 | 1.00 | 31.83 |
| ATOM | 1062 | O | ALA | A | 137 | 3.679 | 39.688 | 62.738 | 1.00 | 29.67 |
| ATOM | 1063 | CB | ALA | A | 137 | 5.091 | 39.742 | 65.625 | 1.00 | 28.91 |
| ATOM | 1064 | N | ILE | A | 138 | 2.863 | 41.285 | 64.070 | 1.00 | 27.07 |
| ATOM | 1065 | CA | ILE | A | 138 | 1.553 | 41.176 | 63.445 | 1.00 | 23.90 |
| ATOM | 1066 | C | ILE | A | 138 | 0.960 | 42.492 | 63.053 | 1.00 | 28.69 |
| ATOM | 1067 | O | ILE | A | 138 | −0.144 | 42.822 | 63.426 | 1.00 | 31.92 |
| ATOM | 1068 | CB | ILE | A | 138 | 0.641 | 40.357 | 64.339 | 1.00 | 25.41 |
| ATOM | 1069 | CG1 | ILE | A | 138 | 0.871 | 40.811 | 65.801 | 1.00 | 27.32 |
| ATOM | 1070 | CG2 | ILE | A | 138 | 1.162 | 38.938 | 64.191 | 1.00 | 16.34 |
| ATOM | 1071 | CD1 | ILE | A | 138 | −0.275 | 40.615 | 66.826 | 1.00 | 20.22 |
| ATOM | 1072 | N | HIS | A | 139 | 1.718 | 43.223 | 62.265 | 1.00 | 24.05 |
| ATOM | 1073 | CA | HIS | A | 139 | 1.322 | 44.511 | 61.824 | 1.00 | 24.05 |

TABLE 9-continued

Structure coordinates of LTA₄ hydrolase-thiolamine complex
(The amino acid sequence set forth as residues 1-610 below correspond to SEQ ID NO:1.)

| ATOM | 1074 | C | HIS | A | 139 | 0.982 | 44.579 | 60.351 | 1.00 | 34.40 |
|------|------|-----|-----|---|-----|--------|--------|--------|------|-------|
| ATOM | 1075 | O | HIS | A | 139 | 0.539 | 45.625 | 59.888 | 1.00 | 35.89 |
| ATOM | 1076 | CB | HIS | A | 139 | 2.439 | 45.519 | 62.173 | 1.00 | 24.63 |
| ATOM | 1077 | CG | HIS | A | 139 | 2.689 | 45.619 | 63.657 | 1.00 | 27.97 |
| ATOM | 1078 | ND1 | HIS | A | 139 | 1.679 | 45.970 | 64.571 | 1.00 | 27.75 |
| ATOM | 1079 | CD2 | HIS | A | 139 | 3.835 | 45.437 | 64.356 | 1.00 | 28.42 |
| ATOM | 1080 | CE1 | HIS | A | 139 | 2.222 | 45.983 | 65.770 | 1.00 | 26.19 |
| ATOM | 1081 | NE2 | HIS | A | 139 | 3.517 | 45.668 | 65.671 | 1.00 | 27.42 |
| ATOM | 1082 | N | CYS | A | 140 | 1.181 | 43.490 | 59.598 | 1.00 | 30.28 |
| ATOM | 1083 | CA | CYS | A | 140 | 0.832 | 43.517 | 58.181 | 1.00 | 28.08 |
| ATOM | 1084 | C | CYS | A | 140 | −0.671 | 43.765 | 58.011 | 1.00 | 28.98 |
| ATOM | 1085 | O | CYS | A | 140 | −1.111 | 44.449 | 57.066 | 1.00 | 30.00 |
| ATOM | 1086 | CB | CYS | A | 140 | 1.181 | 42.213 | 57.447 | 1.00 | 28.82 |
| ATOM | 1087 | SG | CYS | A | 140 | 1.330 | 42.483 | 55.661 | 1.00 | 34.37 |
| ATOM | 1088 | N | ARG | A | 141 | −1.440 | 43.168 | 58.949 | 1.00 | 20.78 |
| ATOM | 1089 | CA | ARG | A | 141 | −2.884 | 43.252 | 58.996 | 1.00 | 20.33 |
| ATOM | 1090 | C | ARG | A | 141 | −3.286 | 44.684 | 59.003 | 1.00 | 32.37 |
| ATOM | 1091 | O | ARG | A | 141 | −4.355 | 45.032 | 58.510 | 1.00 | 35.81 |
| ATOM | 1092 | CB | ARG | A | 141 | −3.557 | 42.498 | 60.156 | 1.00 | 14.60 |
| ATOM | 1093 | CG | ARG | A | 141 | −3.081 | 42.891 | 61.568 | 1.00 | 20.94 |
| ATOM | 1094 | CD | ARG | A | 141 | −3.576 | 41.978 | 62.715 | 1.00 | 19.99 |
| ATOM | 1095 | NE | ARG | A | 141 | −2.911 | 40.690 | 62.786 | 1.00 | 18.24 |
| ATOM | 1096 | CZ | ARG | A | 141 | −3.140 | 39.707 | 63.648 | 1.00 | 18.77 |
| ATOM | 1097 | NH1 | ARG | A | 141 | −4.029 | 39.739 | 64.634 | 1.00 | 20.76 |
| ATOM | 1098 | NH2 | ARG | A | 141 | −2.415 | 38.640 | 63.508 | 1.00 | 24.20 |
| ATOM | 1099 | N | ALA | A | 142 | −2.408 | 45.511 | 59.580 | 1.00 | 28.35 |
| ATOM | 1100 | CA | ALA | A | 142 | −2.668 | 46.940 | 59.657 | 1.00 | 27.60 |
| ATOM | 1101 | C | ALA | A | 142 | −2.369 | 47.652 | 58.345 | 1.00 | 34.33 |
| ATOM | 1102 | O | ALA | A | 142 | −2.620 | 48.835 | 58.203 | 1.00 | 34.36 |
| ATOM | 1103 | CB | ALA | A | 142 | −1.994 | 47.616 | 60.843 | 1.00 | 27.67 |
| ATOM | 1104 | N | ILE | A | 143 | −1.824 | 46.922 | 57.382 | 1.00 | 32.39 |
| ATOM | 1105 | CA | ILE | A | 143 | −1.537 | 47.499 | 56.099 | 1.00 | 30.38 |
| ATOM | 1106 | C | ILE | A | 143 | −2.520 | 46.994 | 55.067 | 1.00 | 37.79 |
| ATOM | 1107 | O | ILE | A | 143 | −2.885 | 47.709 | 54.152 | 1.00 | 42.65 |
| ATOM | 1108 | CB | ILE | A | 143 | −0.142 | 47.228 | 55.613 | 1.00 | 32.06 |
| ATOM | 1109 | CG1 | ILE | A | 143 | 0.827 | 48.062 | 56.414 | 1.00 | 31.71 |
| ATOM | 1110 | CG2 | ILE | A | 143 | −0.074 | 47.654 | 54.143 | 1.00 | 34.02 |
| ATOM | 1111 | CD1 | ILE | A | 143 | 2.258 | 47.774 | 55.988 | 1.00 | 42.10 |
| ATOM | 1112 | N | LEU | A | 144 | −2.939 | 45.749 | 55.218 | 1.00 | 32.50 |
| ATOM | 1113 | CA | LEU | A | 144 | −3.873 | 45.142 | 54.291 | 1.00 | 32.36 |
| ATOM | 1114 | C | LEU | A | 144 | −4.435 | 43.838 | 54.849 | 1.00 | 40.36 |
| ATOM | 1115 | O | LEU | A | 144 | −3.959 | 43.278 | 55.852 | 1.00 | 33.27 |
| ATOM | 1116 | CB | LEU | A | 144 | −3.250 | 44.936 | 52.894 | 1.00 | 31.58 |
| ATOM | 1117 | CG | LEU | A | 144 | −1.923 | 44.170 | 52.917 | 1.00 | 33.31 |
| ATOM | 1118 | CD1 | LEU | A | 144 | −2.147 | 42.770 | 52.352 | 1.00 | 32.07 |
| ATOM | 1119 | CD2 | LEU | A | 144 | −0.836 | 44.897 | 52.110 | 1.00 | 28.67 |
| ATOM | 1120 | N | PRO | A | 145 | −5.490 | 43.347 | 54.213 | 1.00 | 40.02 |
| ATOM | 1121 | CA | PRO | A | 145 | −6.080 | 42.129 | 54.715 | 1.00 | 37.86 |
| ATOM | 1122 | C | PRO | A | 145 | −5.264 | 40.941 | 54.286 | 1.00 | 37.87 |
| ATOM | 1123 | O | PRO | A | 145 | −4.819 | 40.831 | 53.144 | 1.00 | 35.27 |
| ATOM | 1124 | CB | PRO | A | 145 | −7.530 | 42.080 | 54.220 | 1.00 | 38.81 |
| ATOM | 1125 | CG | PRO | A | 145 | −7.778 | 43.393 | 53.492 | 1.00 | 41.34 |
| ATOM | 1126 | CD | PRO | A | 145 | −6.432 | 44.093 | 53.341 | 1.00 | 36.69 |
| ATOM | 1127 | N | CYS | A | 146 | −5.041 | 40.056 | 55.233 | 1.00 | 36.18 |
| ATOM | 1128 | CA | CYS | A | 146 | −4.250 | 38.882 | 54.958 | 1.00 | 35.60 |
| ATOM | 1129 | C | CYS | A | 146 | −4.358 | 37.859 | 56.069 | 1.00 | 33.04 |
| ATOM | 1130 | O | CYS | A | 146 | −5.067 | 38.062 | 57.050 | 1.00 | 30.78 |
| ATOM | 1131 | CB | CYS | A | 146 | −2.761 | 39.287 | 54.813 | 1.00 | 36.08 |
| ATOM | 1132 | SG | CYS | A | 146 | −2.087 | 40.108 | 56.302 | 1.00 | 39.43 |
| ATOM | 1133 | N | GLN | A | 147 | −3.637 | 36.755 | 55.883 | 1.00 | 29.33 |
| ATOM | 1134 | CA | GLN | A | 147 | −3.517 | 35.703 | 56.875 | 1.00 | 29.71 |
| ATOM | 1135 | C | GLN | A | 147 | −2.254 | 36.131 | 57.628 | 1.00 | 38.75 |
| ATOM | 1136 | O | GLN | A | 147 | −1.141 | 35.926 | 57.135 | 1.00 | 40.79 |
| ATOM | 1137 | CB | GLN | A | 147 | −3.322 | 34.352 | 56.206 | 1.00 | 28.99 |
| ATOM | 1138 | CG | GLN | A | 147 | −4.672 | 33.707 | 55.894 | 1.00 | 25.73 |
| ATOM | 1139 | CD | GLN | A | 147 | −4.562 | 32.532 | 54.960 | 1.00 | 39.92 |
| ATOM | 1140 | OE1 | GLN | A | 147 | −4.217 | 32.668 | 53.775 | 1.00 | 43.89 |
| ATOM | 1141 | NE2 | GLN | A | 147 | −4.828 | 31.368 | 55.499 | 1.00 | 26.36 |
| ATOM | 1142 | N | ASP | A | 148 | −2.425 | 36.834 | 58.765 | 1.00 | 32.68 |
| ATOM | 1143 | CA | ASP | A | 148 | −1.287 | 37.362 | 59.474 | 1.00 | 33.50 |
| ATOM | 1144 | C | ASP | A | 148 | −0.629 | 36.377 | 60.371 | 1.00 | 33.13 |
| ATOM | 1145 | O | ASP | A | 148 | −0.622 | 36.563 | 61.584 | 1.00 | 31.30 |
| ATOM | 1146 | CB | ASP | A | 148 | −1.633 | 38.642 | 60.253 | 1.00 | 37.78 |
| ATOM | 1147 | CG | ASP | A | 148 | −0.535 | 39.666 | 60.332 | 1.00 | 45.10 |
| ATOM | 1148 | OD1 | ASP | A | 148 | 0.564 | 39.540 | 59.836 | 1.00 | 47.89 |
| ATOM | 1149 | OD2 | ASP | A | 148 | −0.913 | 40.737 | 60.952 | 1.00 | 48.63 |

TABLE 9-continued

Structure coordinates of LTA$_4$ hydrolase-thiolamine complex
(The amino acid sequence set forth as residues 1-610 below correspond to SEQ ID NO:1.)

| ATOM | 1150 | N | THR | A | 149 | −0.080 | 35.345 | 59.742 | 1.00 | 29.15 |
|---|---|---|---|---|---|---|---|---|---|---|
| ATOM | 1151 | CA | THR | A | 149 | 0.584 | 34.251 | 60.422 | 1.00 | 28.25 |
| ATOM | 1152 | C | THR | A | 149 | 1.805 | 33.831 | 59.625 | 1.00 | 34.92 |
| ATOM | 1153 | O | THR | A | 149 | 1.757 | 33.764 | 58.410 | 1.00 | 34.47 |
| ATOM | 1154 | CB | THR | A | 149 | −0.403 | 33.087 | 60.674 | 1.00 | 24.79 |
| ATOM | 1155 | OG1 | THR | A | 149 | 0.241 | 32.059 | 61.352 | 1.00 | 37.15 |
| ATOM | 1156 | CG2 | THR | A | 149 | −0.905 | 32.527 | 59.345 | 1.00 | 26.56 |
| ATOM | 1157 | N | PRO | A | 150 | 2.910 | 33.575 | 60.323 | 1.00 | 34.69 |
| ATOM | 1158 | CA | PRO | A | 150 | 4.142 | 33.217 | 59.659 | 1.00 | 31.06 |
| ATOM | 1159 | C | PRO | A | 150 | 4.087 | 31.813 | 59.131 | 1.00 | 36.66 |
| ATOM | 1160 | O | PRO | A | 150 | 4.995 | 31.356 | 58.450 | 1.00 | 36.37 |
| ATOM | 1161 | CB | PRO | A | 150 | 5.245 | 33.327 | 60.712 | 1.00 | 31.18 |
| ATOM | 1162 | CG | PRO | A | 150 | 4.570 | 33.471 | 62.077 | 1.00 | 36.95 |
| ATOM | 1163 | CD | PRO | A | 150 | 3.078 | 33.589 | 61.823 | 1.00 | 34.62 |
| ATOM | 1164 | N | SER | A | 151 | 2.992 | 31.150 | 59.452 | 1.00 | 31.62 |
| ATOM | 1165 | CA | SER | A | 151 | 2.778 | 29.791 | 59.029 | 1.00 | 27.35 |
| ATOM | 1166 | C | SER | A | 151 | 2.357 | 29.738 | 57.564 | 1.00 | 32.97 |
| ATOM | 1167 | O | SER | A | 151 | 2.344 | 28.703 | 56.928 | 1.00 | 34.25 |
| ATOM | 1168 | CB | SER | A | 151 | 1.714 | 29.203 | 59.905 | 1.00 | 25.95 |
| ATOM | 1169 | OG | SER | A | 151 | 0.483 | 29.685 | 59.439 | 1.00 | 49.35 |
| ATOM | 1170 | N | VAL | A | 152 | 1.997 | 30.887 | 57.024 | 1.00 | 34.36 |
| ATOM | 1171 | CA | VAL | A | 152 | 1.595 | 31.015 | 55.623 | 1.00 | 33.74 |
| ATOM | 1172 | C | VAL | A | 152 | 2.705 | 31.764 | 54.847 | 1.00 | 37.45 |
| ATOM | 1173 | O | VAL | A | 152 | 3.295 | 32.761 | 55.313 | 1.00 | 37.63 |
| ATOM | 1174 | CB | VAL | A | 152 | 0.203 | 31.697 | 55.427 | 1.00 | 32.61 |
| ATOM | 1175 | CG1 | VAL | A | 152 | −0.184 | 31.767 | 53.963 | 1.00 | 31.50 |
| ATOM | 1176 | CG2 | VAL | A | 152 | −0.915 | 30.975 | 56.149 | 1.00 | 31.29 |
| ATOM | 1177 | N | LYS | A | 153 | 2.999 | 31.289 | 53.654 | 1.00 | 26.98 |
| ATOM | 1178 | CA | LYS | A | 153 | 4.002 | 31.927 | 52.866 | 1.00 | 25.81 |
| ATOM | 1179 | C | LYS | A | 153 | 3.469 | 32.141 | 51.473 | 1.00 | 33.94 |
| ATOM | 1180 | O | LYS | A | 153 | 2.826 | 31.251 | 50.936 | 1.00 | 32.91 |
| ATOM | 1181 | CB | LYS | A | 153 | 5.252 | 31.091 | 52.841 | 1.00 | 24.70 |
| ATOM | 1182 | CG | LYS | A | 153 | 6.383 | 31.760 | 53.583 | 1.00 | 34.68 |
| ATOM | 1183 | CD | LYS | A | 153 | 7.641 | 30.893 | 53.616 | 1.00 | 39.37 |
| ATOM | 1184 | CE | LYS | A | 153 | 8.121 | 30.506 | 55.015 | 1.00 | 29.09 |
| ATOM | 1185 | NZ | LYS | A | 153 | 9.556 | 30.152 | 55.112 | 1.00 | 26.03 |
| ATOM | 1186 | N | LEU | A | 154 | 3.732 | 33.321 | 50.896 | 1.00 | 32.13 |
| ATOM | 1187 | CA | LEU | A | 154 | 3.285 | 33.639 | 49.544 | 1.00 | 30.67 |
| ATOM | 1188 | C | LEU | A | 154 | 4.279 | 34.475 | 48.789 | 1.00 | 40.67 |
| ATOM | 1189 | O | LEU | A | 154 | 5.264 | 35.000 | 49.344 | 1.00 | 42.56 |
| ATOM | 1190 | CB | LEU | A | 154 | 1.966 | 34.432 | 49.515 | 1.00 | 30.10 |
| ATOM | 1191 | CG | LEU | A | 154 | 2.084 | 35.793 | 50.207 | 1.00 | 35.20 |
| ATOM | 1192 | CD1 | LEU | A | 154 | 0.989 | 36.716 | 49.690 | 1.00 | 37.21 |
| ATOM | 1193 | CD2 | LEU | A | 154 | 1.934 | 35.608 | 51.715 | 1.00 | 33.07 |
| ATOM | 1194 | N | THR | A | 155 | 3.963 | 34.610 | 47.499 | 1.00 | 37.82 |
| ATOM | 1195 | CA | THR | A | 155 | 4.728 | 35.449 | 46.596 | 1.00 | 38.44 |
| ATOM | 1196 | C | THR | A | 155 | 3.934 | 36.730 | 46.389 | 1.00 | 41.52 |
| ATOM | 1197 | O | THR | A | 155 | 2.738 | 36.775 | 46.674 | 1.00 | 43.95 |
| ATOM | 1198 | CB | THR | A | 155 | 5.041 | 34.814 | 45.230 | 1.00 | 36.99 |
| ATOM | 1199 | OG1 | THR | A | 155 | 3.886 | 34.281 | 44.584 | 1.00 | 32.59 |
| ATOM | 1200 | CG2 | THR | A | 155 | 6.133 | 33.790 | 45.404 | 1.00 | 18.24 |
| ATOM | 1201 | N | TYR | A | 156 | 4.563 | 37.768 | 45.892 | 1.00 | 33.87 |
| ATOM | 1202 | CA | TYR | A | 156 | 3.835 | 39.003 | 45.683 | 1.00 | 32.49 |
| ATOM | 1203 | C | TYR | A | 156 | 4.509 | 39.922 | 44.717 | 1.00 | 37.91 |
| ATOM | 1204 | O | TYR | A | 156 | 5.725 | 39.940 | 44.562 | 1.00 | 39.04 |
| ATOM | 1205 | CB | TYR | A | 156 | 3.534 | 39.795 | 46.983 | 1.00 | 31.16 |
| ATOM | 1206 | CG | TYR | A | 156 | 4.642 | 40.731 | 47.471 | 1.00 | 28.94 |
| ATOM | 1207 | CD1 | TYR | A | 156 | 4.817 | 42.021 | 46.969 | 1.00 | 30.33 |
| ATOM | 1208 | CD2 | TYR | A | 156 | 5.525 | 40.303 | 48.465 | 1.00 | 30.43 |
| ATOM | 1209 | CE1 | TYR | A | 156 | 5.829 | 42.853 | 47.459 | 1.00 | 36.89 |
| ATOM | 1210 | CE2 | TYR | A | 156 | 6.553 | 41.104 | 48.960 | 1.00 | 31.47 |
| ATOM | 1211 | CZ | TYR | A | 156 | 6.690 | 42.396 | 48.462 | 1.00 | 43.34 |
| ATOM | 1212 | OH | TYR | A | 156 | 7.701 | 43.180 | 48.956 | 1.00 | 36.86 |
| ATOM | 1213 | N | THR | A | 157 | 3.657 | 40.689 | 44.101 | 1.00 | 36.75 |
| ATOM | 1214 | CA | THR | A | 157 | 4.036 | 41.691 | 43.171 | 1.00 | 38.49 |
| ATOM | 1215 | C | THR | A | 157 | 3.346 | 42.942 | 43.611 | 1.00 | 42.61 |
| ATOM | 1216 | O | THR | A | 157 | 2.228 | 42.913 | 44.143 | 1.00 | 38.45 |
| ATOM | 1217 | CB | THR | A | 157 | 3.631 | 41.316 | 41.751 | 1.00 | 39.73 |
| ATOM | 1218 | OG1 | THR | A | 157 | 2.380 | 40.655 | 41.803 | 1.00 | 55.71 |
| ATOM | 1219 | CG2 | THR | A | 157 | 4.680 | 40.370 | 41.212 | 1.00 | 26.71 |
| ATOM | 1220 | N | ALA | A | 158 | 4.037 | 44.025 | 43.404 | 1.00 | 41.36 |
| ATOM | 1221 | CA | ALA | A | 158 | 3.488 | 45.273 | 43.789 | 1.00 | 41.08 |
| ATOM | 1222 | C | ALA | A | 158 | 3.869 | 46.401 | 42.839 | 1.00 | 50.77 |
| ATOM | 1223 | O | ALA | A | 158 | 4.919 | 46.390 | 42.179 | 1.00 | 53.47 |
| ATOM | 1224 | CB | ALA | A | 158 | 3.910 | 45.570 | 45.212 | 1.00 | 39.87 |
| ATOM | 1225 | N | GLU | A | 159 | 2.974 | 47.376 | 42.788 | 1.00 | 43.90 |

TABLE 9-continued

Structure coordinates of LTA₄ hydrolase-thiolamine complex
(The amino acid sequence set forth as residues 1-610 below correspond to SEQ ID NO:1.)

| ATOM | 1226 | CA  | GLU | A | 159 | 3.107  | 48.604 | 42.023 | 1.00 | 42.27  |
|------|------|-----|-----|---|-----|--------|--------|--------|------|--------|
| ATOM | 1227 | C   | GLU | A | 159 | 2.451  | 49.705 | 42.843 | 1.00 | 42.17  |
| ATOM | 1228 | O   | GLU | A | 159 | 1.257  | 49.630 | 43.227 | 1.00 | 41.00  |
| ATOM | 1229 | CB  | GLU | A | 159 | 2.641  | 48.521 | 40.571 | 1.00 | 43.72  |
| ATOM | 1230 | CG  | GLU | A | 159 | 1.943  | 47.197 | 40.255 | 1.00 | 62.90  |
| ATOM | 1231 | CD  | GLU | A | 159 | 1.502  | 47.156 | 38.835 | 1.00 | 91.28  |
| ATOM | 1232 | OE1 | GLU | A | 159 | 2.202  | 46.696 | 37.955 | 1.00 | 77.84  |
| ATOM | 1233 | OE2 | GLU | A | 159 | 0.322  | 47.707 | 38.644 | 1.00 | 100.00 |
| ATOM | 1234 | N   | VAL | A | 160 | 3.263  | 50.686 | 43.197 | 1.00 | 34.67  |
| ATOM | 1235 | CA  | VAL | A | 160 | 2.738  | 51.717 | 44.044 | 1.00 | 36.57  |
| ATOM | 1236 | C   | VAL | A | 160 | 3.024  | 53.091 | 43.533 | 1.00 | 43.02  |
| ATOM | 1237 | O   | VAL | A | 160 | 4.121  | 53.380 | 43.050 | 1.00 | 42.71  |
| ATOM | 1238 | CB  | VAL | A | 160 | 3.180  | 51.530 | 45.500 | 1.00 | 40.73  |
| ATOM | 1239 | CG1 | VAL | A | 160 | 3.988  | 50.239 | 45.644 | 1.00 | 38.56  |
| ATOM | 1240 | CG2 | VAL | A | 160 | 4.006  | 52.728 | 45.963 | 1.00 | 40.46  |
| ATOM | 1241 | N   | SER | A | 161 | 2.002  | 53.922 | 43.653 | 1.00 | 41.79  |
| ATOM | 1242 | CA  | SER | A | 161 | 2.076  | 55.292 | 43.185 | 1.00 | 42.07  |
| ATOM | 1243 | C   | SER | A | 161 | 2.532  | 56.204 | 44.270 | 1.00 | 44.28  |
| ATOM | 1244 | O   | SER | A | 161 | 2.047  | 56.121 | 45.403 | 1.00 | 43.60  |
| ATOM | 1245 | CB  | SER | A | 161 | 0.751  | 55.801 | 42.635 | 1.00 | 43.32  |
| ATOM | 1246 | OG  | SER | A | 161 | 0.971  | 56.850 | 41.726 | 1.00 | 49.40  |
| ATOM | 1247 | N   | VAL | A | 162 | 3.447  | 57.080 | 43.896 | 1.00 | 36.49  |
| ATOM | 1248 | CA  | VAL | A | 162 | 3.979  | 58.019 | 44.838 | 1.00 | 34.99  |
| ATOM | 1249 | C   | VAL | A | 162 | 4.273  | 59.319 | 44.148 | 1.00 | 42.57  |
| ATOM | 1250 | O   | VAL | A | 162 | 4.470  | 59.354 | 42.932 | 1.00 | 44.41  |
| ATOM | 1251 | CB  | VAL | A | 162 | 5.300  | 57.498 | 45.402 | 1.00 | 35.97  |
| ATOM | 1252 | CG1 | VAL | A | 162 | 5.084  | 56.219 | 46.188 | 1.00 | 36.12  |
| ATOM | 1253 | CG2 | VAL | A | 162 | 6.222  | 57.194 | 44.239 | 1.00 | 35.42  |
| ATOM | 1254 | N   | PRO | A | 163 | 4.332  | 60.377 | 44.942 | 1.00 | 32.95  |
| ATOM | 1255 | CA  | PRO | A | 163 | 4.664  | 61.662 | 44.400 | 1.00 | 31.07  |
| ATOM | 1256 | C   | PRO | A | 163 | 5.966  | 61.496 | 43.652 | 1.00 | 39.67  |
| ATOM | 1257 | O   | PRO | A | 163 | 6.919  | 60.892 | 44.142 | 1.00 | 42.78  |
| ATOM | 1258 | CB  | PRO | A | 163 | 4.780  | 62.562 | 45.618 | 1.00 | 31.62  |
| ATOM | 1259 | CG  | PRO | A | 163 | 3.946  | 61.893 | 46.714 | 1.00 | 33.93  |
| ATOM | 1260 | CD  | PRO | A | 163 | 3.652  | 60.480 | 46.259 | 1.00 | 28.53  |
| ATOM | 1261 | N   | LYS | A | 164 | 5.962  | 61.978 | 42.436 | 1.00 | 38.52  |
| ATOM | 1262 | CA  | LYS | A | 164 | 7.086  | 61.860 | 41.539 | 1.00 | 39.97  |
| ATOM | 1263 | C   | LYS | A | 164 | 8.451  | 62.222 | 42.088 | 1.00 | 42.75  |
| ATOM | 1264 | O   | LYS | A | 164 | 9.453  | 61.708 | 41.593 | 1.00 | 44.47  |
| ATOM | 1265 | CB  | LYS | A | 164 | 6.828  | 62.479 | 40.177 | 1.00 | 44.67  |
| ATOM | 1266 | CG  | LYS | A | 164 | 6.004  | 63.758 | 40.257 | 1.00 | 78.05  |
| ATOM | 1267 | CD  | LYS | A | 164 | 6.651  | 64.918 | 39.497 | 1.00 | 100.00 |
| ATOM | 1268 | CE  | LYS | A | 164 | 6.016  | 66.289 | 39.772 | 1.00 | 100.00 |
| ATOM | 1269 | NZ  | LYS | A | 164 | 6.679  | 67.075 | 40.835 | 1.00 | 100.00 |
| ATOM | 1270 | N   | GLU | A | 165 | 8.519  | 63.097 | 43.082 | 1.00 | 37.25  |
| ATOM | 1271 | CA  | GLU | A | 165 | 9.814  | 63.489 | 43.665 | 1.00 | 39.56  |
| ATOM | 1272 | C   | GLU | A | 165 | 10.333 | 62.462 | 44.677 | 1.00 | 46.39  |
| ATOM | 1273 | O   | GLU | A | 165 | 11.531 | 62.318 | 44.927 | 1.00 | 48.93  |
| ATOM | 1274 | CB  | GLU | A | 165 | 9.797  | 64.902 | 44.297 | 1.00 | 42.10  |
| ATOM | 1275 | CG  | GLU | A | 165 | 8.602  | 65.156 | 45.257 | 1.00 | 58.16  |
| ATOM | 1276 | CD  | GLU | A | 165 | 7.214  | 64.970 | 44.664 | 1.00 | 88.01  |
| ATOM | 1277 | OE1 | GLU | A | 165 | 6.994  | 64.757 | 43.475 | 1.00 | 79.46  |
| ATOM | 1278 | OE2 | GLU | A | 165 | 6.266  | 65.050 | 45.575 | 1.00 | 70.27  |
| ATOM | 1279 | N   | LEU | A | 166 | 9.398  | 61.733 | 45.265 | 1.00 | 40.39  |
| ATOM | 1280 | CA  | LEU | A | 166 | 9.696  | 60.733 | 46.254 | 1.00 | 36.56  |
| ATOM | 1281 | C   | LEU | A | 166 | 9.934  | 59.377 | 45.640 | 1.00 | 47.57  |
| ATOM | 1282 | O   | LEU | A | 166 | 9.366  | 59.080 | 44.581 | 1.00 | 52.86  |
| ATOM | 1283 | CB  | LEU | A | 166 | 8.525  | 60.630 | 47.250 | 1.00 | 31.92  |
| ATOM | 1284 | CG  | LEU | A | 166 | 8.315  | 61.912 | 48.057 | 1.00 | 29.18  |
| ATOM | 1285 | CD1 | LEU | A | 166 | 7.363  | 61.590 | 49.189 | 1.00 | 25.96  |
| ATOM | 1286 | CD2 | LEU | A | 166 | 9.635  | 62.467 | 48.622 | 1.00 | 23.78  |
| ATOM | 1287 | N   | VAL | A | 167 | 10.769 | 58.564 | 46.328 | 1.00 | 34.75  |
| ATOM | 1288 | CA  | VAL | A | 167 | 11.077 | 57.218 | 45.908 | 1.00 | 30.00  |
| ATOM | 1289 | C   | VAL | A | 167 | 10.332 | 56.229 | 46.771 | 1.00 | 38.80  |
| ATOM | 1290 | O   | VAL | A | 167 | 9.902  | 56.532 | 47.879 | 1.00 | 40.91  |
| ATOM | 1291 | CB  | VAL | A | 167 | 12.549 | 56.860 | 46.048 | 1.00 | 31.28  |
| ATOM | 1292 | CG1 | VAL | A | 167 | 12.854 | 55.542 | 45.329 | 1.00 | 28.20  |
| ATOM | 1293 | CG2 | VAL | A | 167 | 13.456 | 57.964 | 45.565 | 1.00 | 31.06  |
| ATOM | 1294 | N   | ALA | A | 168 | 10.217 | 55.019 | 46.257 | 1.00 | 36.46  |
| ATOM | 1295 | CA  | ALA | A | 168 | 9.584  | 53.935 | 46.979 | 1.00 | 35.14  |
| ATOM | 1296 | C   | ALA | A | 168 | 10.418 | 52.662 | 46.836 | 1.00 | 43.27  |
| ATOM | 1297 | O   | ALA | A | 168 | 10.889 | 52.343 | 45.733 | 1.00 | 44.74  |
| ATOM | 1298 | CB  | ALA | A | 168 | 8.149  | 53.700 | 46.550 | 1.00 | 34.20  |
| ATOM | 1299 | N   | LEU | A | 169 | 10.603 | 51.960 | 47.975 | 1.00 | 35.27  |
| ATOM | 1300 | CA  | LEU | A | 169 | 11.323 | 50.696 | 48.069 | 1.00 | 29.39  |
| ATOM | 1301 | C   | LEU | A | 169 | 10.491 | 49.635 | 48.797 | 1.00 | 33.87  |

TABLE 9-continued

Structure coordinates of LTA₄ hydrolase-thiolamine complex
(The amino acid sequence set forth as residues 1-610 below correspond to SEQ ID NO:1.)

| ATOM | 1302 | O | LEU | A | 169 | 9.604 | 49.918 | 49.613 | 1.00 | 31.21 |
|---|---|---|---|---|---|---|---|---|---|---|
| ATOM | 1303 | CB | LEU | A | 169 | 12.721 | 50.835 | 48.656 | 1.00 | 28.62 |
| ATOM | 1304 | CG | LEU | A | 169 | 13.593 | 51.810 | 47.891 | 1.00 | 35.90 |
| ATOM | 1305 | CD1 | LEU | A | 169 | 14.953 | 51.819 | 48.558 | 1.00 | 39.38 |
| ATOM | 1306 | CD2 | LEU | A | 169 | 13.765 | 51.394 | 46.432 | 1.00 | 37.35 |
| ATOM | 1307 | N | MET | A | 170 | 10.758 | 48.381 | 48.479 | 1.00 | 34.23 |
| ATOM | 1308 | CA | MET | A | 170 | 10.012 | 47.291 | 49.069 | 1.00 | 31.07 |
| ATOM | 1309 | C | MET | A | 170 | 10.874 | 46.083 | 49.287 | 1.00 | 34.13 |
| ATOM | 1310 | O | MET | A | 170 | 11.995 | 45.973 | 48.775 | 1.00 | 35.20 |
| ATOM | 1311 | CB | MET | A | 170 | 8.842 | 46.882 | 48.154 | 1.00 | 31.95 |
| ATOM | 1312 | CG | MET | A | 170 | 7.751 | 47.934 | 48.116 | 1.00 | 33.13 |
| ATOM | 1313 | SD | MET | A | 170 | 6.105 | 47.253 | 47.815 | 1.00 | 34.54 |
| ATOM | 1314 | CE | MET | A | 170 | 5.820 | 46.349 | 49.363 | 1.00 | 32.25 |
| ATOM | 1315 | N | SER | A | 171 | 10.332 | 45.165 | 50.057 | 1.00 | 28.20 |
| ATOM | 1316 | CA | SER | A | 171 | 11.064 | 43.953 | 50.297 | 1.00 | 28.47 |
| ATOM | 1317 | C | SER | A | 171 | 10.929 | 43.054 | 49.049 | 1.00 | 32.01 |
| ATOM | 1318 | O | SER | A | 171 | 10.396 | 41.958 | 49.089 | 1.00 | 30.93 |
| ATOM | 1319 | CB | SER | A | 171 | 10.662 | 43.265 | 51.606 | 1.00 | 30.93 |
| ATOM | 1320 | OG | SER | A | 171 | 9.297 | 42.920 | 51.581 | 1.00 | 32.90 |
| ATOM | 1321 | N | ALA | A | 172 | 11.401 | 43.543 | 47.912 | 1.00 | 28.84 |
| ATOM | 1322 | CA | ALA | A | 172 | 11.286 | 42.773 | 46.691 | 1.00 | 29.48 |
| ATOM | 1323 | C | ALA | A | 172 | 12.241 | 43.258 | 45.644 | 1.00 | 37.63 |
| ATOM | 1324 | O | ALA | A | 172 | 13.060 | 44.147 | 45.881 | 1.00 | 35.07 |
| ATOM | 1325 | CB | ALA | A | 172 | 9.884 | 42.969 | 46.120 | 1.00 | 29.48 |
| ATOM | 1326 | N | ILE | A | 173 | 12.104 | 42.686 | 44.452 | 1.00 | 39.49 |
| ATOM | 1327 | CA | ILE | A | 173 | 12.966 | 43.120 | 43.382 | 1.00 | 38.64 |
| ATOM | 1328 | C | ILE | A | 173 | 12.418 | 44.343 | 42.648 | 1.00 | 44.83 |
| ATOM | 1329 | O | ILE | A | 173 | 11.269 | 44.394 | 42.193 | 1.00 | 40.97 |
| ATOM | 1330 | CB | ILE | A | 173 | 13.549 | 42.027 | 42.479 | 1.00 | 38.79 |
| ATOM | 1331 | CG1 | ILE | A | 173 | 14.258 | 40.970 | 43.302 | 1.00 | 37.40 |
| ATOM | 1332 | CG2 | ILE | A | 173 | 14.606 | 42.621 | 41.570 | 1.00 | 38.88 |
| ATOM | 1333 | CD1 | ILE | A | 173 | 15.770 | 41.069 | 43.193 | 1.00 | 25.93 |
| ATOM | 1334 | N | ARG | A | 174 | 13.286 | 45.345 | 42.584 | 1.00 | 43.21 |
| ATOM | 1335 | CA | ARG | A | 174 | 12.997 | 46.567 | 41.917 | 1.00 | 42.34 |
| ATOM | 1336 | C | ARG | A | 174 | 12.630 | 46.173 | 40.516 | 1.00 | 47.54 |
| ATOM | 1337 | O | ARG | A | 174 | 13.478 | 45.667 | 39.770 | 1.00 | 42.08 |
| ATOM | 1338 | CB | ARG | A | 174 | 14.254 | 47.422 | 41.937 | 1.00 | 42.47 |
| ATOM | 1339 | CG | ARG | A | 174 | 14.231 | 48.450 | 43.075 | 1.00 | 53.40 |
| ATOM | 1340 | CD | ARG | A | 174 | 15.617 | 48.917 | 43.515 | 1.00 | 33.80 |
| ATOM | 1341 | NE | ARG | A | 174 | 16.036 | 50.083 | 42.756 | 1.00 | 53.32 |
| ATOM | 1342 | CZ | ARG | A | 174 | 17.221 | 50.208 | 42.181 | 1.00 | 97.11 |
| ATOM | 1343 | NH1 | ARG | A | 174 | 18.132 | 49.243 | 42.266 | 1.00 | 100.00 |
| ATOM | 1344 | NH2 | ARG | A | 174 | 17.503 | 51.321 | 41.489 | 1.00 | 100.00 |
| ATOM | 1345 | N | ASP | A | 175 | 11.356 | 46.356 | 40.195 | 1.00 | 51.12 |
| ATOM | 1346 | CA | ASP | A | 175 | 10.858 | 45.981 | 38.882 | 1.00 | 53.89 |
| ATOM | 1347 | C | ASP | A | 175 | 10.778 | 47.128 | 37.885 | 1.00 | 58.32 |
| ATOM | 1348 | O | ASP | A | 175 | 10.455 | 46.901 | 36.727 | 1.00 | 56.00 |
| ATOM | 1349 | CB | ASP | A | 175 | 9.533 | 45.186 | 38.948 | 1.00 | 57.16 |
| ATOM | 1350 | CG | ASP | A | 175 | 9.196 | 44.446 | 37.675 | 1.00 | 81.25 |
| ATOM | 1351 | OD1 | ASP | A | 175 | 10.034 | 44.118 | 36.851 | 1.00 | 83.53 |
| ATOM | 1352 | OD2 | ASP | A | 175 | 7.910 | 44.176 | 37.558 | 1.00 | 92.45 |
| ATOM | 1353 | N | GLY | A | 176 | 11.062 | 48.356 | 38.331 | 1.00 | 58.24 |
| ATOM | 1354 | CA | GLY | A | 176 | 11.021 | 49.498 | 37.438 | 1.00 | 57.71 |
| ATOM | 1355 | C | GLY | A | 176 | 9.969 | 50.546 | 37.773 | 1.00 | 58.98 |
| ATOM | 1356 | O | GLY | A | 176 | 9.090 | 50.371 | 38.620 | 1.00 | 52.04 |
| ATOM | 1357 | N | GLU | A | 177 | 10.110 | 51.649 | 37.050 | 1.00 | 63.72 |
| ATOM | 1358 | CA | GLU | A | 177 | 9.267 | 52.812 | 37.172 | 1.00 | 67.79 |
| ATOM | 1359 | C | GLU | A | 177 | 8.874 | 53.388 | 35.817 | 1.00 | 86.22 |
| ATOM | 1360 | O | GLU | A | 177 | 9.614 | 53.364 | 34.830 | 1.00 | 91.14 |
| ATOM | 1361 | CB | GLU | A | 177 | 9.986 | 53.902 | 38.006 | 1.00 | 68.25 |
| ATOM | 1362 | CG | GLU | A | 177 | 11.432 | 54.145 | 37.519 | 1.00 | 71.58 |
| ATOM | 1363 | CD | GLU | A | 177 | 12.183 | 55.088 | 38.404 | 1.00 | 85.08 |
| ATOM | 1364 | OE1 | GLU | A | 177 | 13.045 | 54.733 | 39.198 | 1.00 | 100.00 |
| ATOM | 1365 | OE2 | GLU | A | 177 | 11.765 | 56.316 | 38.264 | 1.00 | 56.71 |
| ATOM | 1366 | N | THR | A | 178 | 7.671 | 53.924 | 35.835 | 1.00 | 84.76 |
| ATOM | 1367 | CA | THR | A | 178 | 6.684 | 54.686 | 35.042 | 1.00 | 84.81 |
| ATOM | 1368 | C | THR | A | 178 | 6.024 | 55.810 | 35.855 | 1.00 | 90.37 |
| ATOM | 1369 | O | THR | A | 178 | 5.664 | 55.655 | 36.996 | 1.00 | 91.10 |
| ATOM | 1370 | CB | THR | A | 178 | 5.618 | 53.713 | 34.561 | 1.00 | 89.82 |
| ATOM | 1371 | OG1 | THR | A | 178 | 5.283 | 52.830 | 35.636 | 1.00 | 80.25 |
| ATOM | 1372 | CG2 | THR | A | 178 | 6.161 | 52.898 | 33.396 | 1.00 | 93.46 |
| ATOM | 1373 | N | PRO | A | 179 | 5.921 | 56.984 | 35.217 | 1.00 | 87.05 |
| ATOM | 1374 | CA | PRO | A | 179 | 5.365 | 58.187 | 35.845 | 1.00 | 86.61 |
| ATOM | 1375 | C | PRO | A | 179 | 3.857 | 58.419 | 35.531 | 1.00 | 89.04 |
| ATOM | 1376 | O | PRO | A | 179 | 3.444 | 59.516 | 35.140 | 1.00 | 91.15 |

TABLE 9-continued

Structure coordinates of LTA$_4$ hydrolase-thiolamine complex
(The amino acid sequence set forth as residues 1-610 below correspond to SEQ ID NO:1.)

| ATOM | 1377 | CB | PRO | A | 179 | 6.176 | 59.345 | 35.301 | 1.00 | 88.63 |
|---|---|---|---|---|---|---|---|---|---|---|
| ATOM | 1378 | CG | PRO | A | 179 | 6.657 | 58.947 | 33.895 | 1.00 | 92.62 |
| ATOM | 1379 | CD | PRO | A | 179 | 6.426 | 57.345 | 33.902 | 1.00 | 87.63 |
| ATOM | 1380 | N | ASP | A | 180 | 3.020 | 57.347 | 35.694 | 1.00 | 82.31 |
| ATOM | 1381 | CA | ASP | A | 180 | 1.616 | 57.568 | 35.310 | 1.00 | 81.19 |
| ATOM | 1382 | C | ASP | A | 180 | 0.629 | 56.743 | 36.166 | 1.00 | 90.72 |
| ATOM | 1383 | O | ASP | A | 180 | 0.533 | 55.519 | 36.072 | 1.00 | 91.13 |
| ATOM | 1384 | CB | ASP | A | 180 | 1.458 | 57.196 | 33.827 | 1.00 | 82.12 |
| ATOM | 1385 | CG | ASP | A | 180 | 0.087 | 57.651 | 33.327 | 1.00 | 95.94 |
| ATOM | 1386 | OD1 | ASP | A | 180 | −0.155 | 58.858 | 33.337 | 1.00 | 100.00 |
| ATOM | 1387 | OD2 | ASP | A | 180 | −0.714 | 56.801 | 32.946 | 1.00 | 94.36 |
| ATOM | 1388 | N | PRO | A | 181 | −0.060 | 57.456 | 37.086 | 1.00 | 92.45 |
| ATOM | 1389 | CA | PRO | A | 181 | −1.212 | 56.934 | 37.795 | 1.00 | 92.02 |
| ATOM | 1390 | C | PRO | A | 181 | −2.519 | 57.566 | 37.284 | 1.00 | 100.00 |
| ATOM | 1391 | O | PRO | A | 181 | −2.605 | 58.114 | 36.192 | 1.00 | 100.00 |
| ATOM | 1392 | CB | PRO | A | 181 | −1.014 | 57.340 | 39.210 | 1.00 | 92.48 |
| ATOM | 1393 | CG | PRO | A | 181 | −0.362 | 58.734 | 39.152 | 1.00 | 98.39 |
| ATOM | 1394 | CD | PRO | A | 181 | 0.268 | 58.736 | 37.663 | 1.00 | 94.17 |
| ATOM | 1395 | N | GLU | A | 182 | −3.567 | 57.456 | 38.141 | 1.00 | 100.00 |
| ATOM | 1396 | CA | GLU | A | 182 | −4.822 | 58.161 | 37.876 | 1.00 | 98.21 |
| ATOM | 1397 | C | GLU | A | 182 | −5.359 | 58.856 | 39.154 | 1.00 | 100.00 |
| ATOM | 1398 | O | GLU | A | 182 | −6.404 | 59.497 | 39.167 | 1.00 | 99.44 |
| ATOM | 1399 | CB | GLU | A | 182 | −5.854 | 57.142 | 37.356 | 1.00 | 98.57 |
| ATOM | 1400 | CG | GLU | A | 182 | −5.880 | 57.077 | 35.816 | 1.00 | 100.00 |
| ATOM | 1401 | CD | GLU | A | 182 | −7.013 | 57.938 | 35.300 | 1.00 | 100.00 |
| ATOM | 1402 | OE1 | GLU | A | 182 | −7.817 | 58.385 | 36.105 | 1.00 | 100.00 |
| ATOM | 1403 | OE2 | GLU | A | 182 | −7.084 | 58.153 | 34.091 | 1.00 | 100.00 |
| ATOM | 1404 | N | ASP | A | 183 | −4.607 | 58.672 | 40.265 | 1.00 | 98.63 |
| ATOM | 1405 | CA | ASP | A | 183 | −5.021 | 59.257 | 41.552 | 1.00 | 97.49 |
| ATOM | 1406 | C | ASP | A | 183 | −4.126 | 60.472 | 41.932 | 1.00 | 100.00 |
| ATOM | 1407 | O | ASP | A | 183 | −3.464 | 61.061 | 41.079 | 1.00 | 100.00 |
| ATOM | 1408 | CB | ASP | A | 183 | −4.946 | 58.144 | 42.619 | 1.00 | 98.36 |
| ATOM | 1409 | CG | ASP | A | 183 | −3.612 | 57.409 | 42.547 | 1.00 | 100.00 |
| ATOM | 1410 | OD1 | ASP | A | 183 | −3.471 | 56.556 | 41.668 | 1.00 | 100.00 |
| ATOM | 1411 | OD2 | ASP | A | 183 | −2.741 | 57.688 | 43.364 | 1.00 | 100.00 |
| ATOM | 1412 | N | PRO | A | 184 | −4.187 | 60.906 | 43.237 | 1.00 | 97.96 |
| ATOM | 1413 | CA | PRO | A | 184 | −3.311 | 61.985 | 43.738 | 1.00 | 97.92 |
| ATOM | 1414 | C | PRO | A | 184 | −1.865 | 61.528 | 44.071 | 1.00 | 97.89 |
| ATOM | 1415 | O | PRO | A | 184 | −1.348 | 61.748 | 45.159 | 1.00 | 100.00 |
| ATOM | 1416 | CB | PRO | A | 184 | −3.973 | 62.561 | 44.992 | 1.00 | 98.86 |
| ATOM | 1417 | CG | PRO | A | 184 | −5.262 | 61.777 | 45.284 | 1.00 | 100.00 |
| ATOM | 1418 | CD | PRO | A | 184 | −5.122 | 60.532 | 44.284 | 1.00 | 97.20 |
| ATOM | 1419 | N | SER | A | 185 | −1.249 | 60.840 | 43.071 | 1.00 | 82.40 |
| ATOM | 1420 | CA | SER | A | 185 | 0.196 | 60.496 | 43.086 | 1.00 | 75.26 |
| ATOM | 1421 | C | SER | A | 185 | 0.748 | 60.563 | 41.623 | 1.00 | 71.84 |
| ATOM | 1422 | O | SER | A | 185 | −0.006 | 60.525 | 40.670 | 1.00 | 77.97 |
| ATOM | 1423 | CB | SER | A | 185 | 0.337 | 59.068 | 43.636 | 1.00 | 73.41 |
| ATOM | 1424 | OG | SER | A | 185 | 0.672 | 59.109 | 45.027 | 1.00 | 63.60 |
| ATOM | 1425 | N | ARG | A | 186 | 2.107 | 60.704 | 41.461 | 1.00 | 57.89 |
| ATOM | 1426 | CA | ARG | A | 186 | 2.650 | 60.971 | 40.088 | 1.00 | 56.00 |
| ATOM | 1427 | C | ARG | A | 186 | 3.725 | 59.943 | 39.633 | 1.00 | 59.64 |
| ATOM | 1428 | O | ARG | A | 186 | 4.473 | 60.157 | 38.688 | 1.00 | 60.30 |
| ATOM | 1429 | CB | ARG | A | 186 | 3.258 | 62.393 | 40.064 | 1.00 | 63.74 |
| ATOM | 1430 | CG | ARG | A | 186 | 2.339 | 63.457 | 40.677 | 1.00 | 80.44 |
| ATOM | 1431 | CD | ARG | A | 186 | 1.188 | 63.874 | 39.736 | 1.00 | 71.31 |
| ATOM | 1432 | NE | ARG | A | 186 | 1.316 | 63.215 | 38.436 | 1.00 | 79.64 |
| ATOM | 1433 | CZ | ARG | A | 186 | 0.185 | 62.862 | 37.784 | 1.00 | 95.30 |
| ATOM | 1434 | NH1 | ARG | A | 186 | −0.999 | 63.109 | 38.312 | 1.00 | 56.25 |
| ATOM | 1435 | NH2 | ARG | A | 186 | 0.276 | 62.232 | 36.603 | 1.00 | 89.98 |
| ATOM | 1436 | N | LYS | A | 187 | 3.892 | 58.778 | 40.265 | 1.00 | 54.50 |
| ATOM | 1437 | CA | LYS | A | 187 | 4.891 | 57.805 | 39.851 | 1.00 | 51.93 |
| ATOM | 1438 | C | LYS | A | 187 | 4.506 | 56.436 | 40.276 | 1.00 | 52.96 |
| ATOM | 1439 | O | LYS | A | 187 | 3.971 | 56.236 | 41.368 | 1.00 | 53.58 |
| ATOM | 1440 | CB | LYS | A | 187 | 6.247 | 58.047 | 40.470 | 1.00 | 53.78 |
| ATOM | 1441 | CG | LYS | A | 187 | 7.427 | 57.714 | 39.574 | 1.00 | 43.05 |
| ATOM | 1442 | CD | LYS | A | 187 | 8.517 | 58.761 | 39.762 | 1.00 | 53.36 |
| ATOM | 1443 | CE | LYS | A | 187 | 9.870 | 58.468 | 39.146 | 1.00 | 39.68 |
| ATOM | 1444 | NZ | LYS | A | 187 | 10.795 | 59.601 | 39.341 | 1.00 | 40.19 |
| ATOM | 1445 | N | ILE | A | 188 | 4.819 | 55.502 | 39.403 | 1.00 | 46.36 |
| ATOM | 1446 | CA | ILE | A | 188 | 4.565 | 54.128 | 39.700 | 1.00 | 43.57 |
| ATOM | 1447 | C | ILE | A | 188 | 5.824 | 53.311 | 39.851 | 1.00 | 42.64 |
| ATOM | 1448 | O | ILE | A | 188 | 6.647 | 53.189 | 38.937 | 1.00 | 41.55 |
| ATOM | 1449 | CB | ILE | A | 188 | 3.579 | 53.425 | 38.826 | 1.00 | 45.64 |
| ATOM | 1450 | CG1 | ILE | A | 188 | 2.193 | 54.021 | 39.047 | 1.00 | 45.82 |
| ATOM | 1451 | CG2 | ILE | A | 188 | 3.590 | 51.969 | 39.273 | 1.00 | 43.43 |
| ATOM | 1452 | CD1 | ILE | A | 188 | 1.448 | 53.505 | 40.276 | 1.00 | 62.08 |

TABLE 9-continued

Structure coordinates of LTA₄ hydrolase-thiolamine complex
(The amino acid sequence set forth as residues 1-610 below correspond to SEQ ID NO:1.)

| ATOM | 1453 | N | TYR | A | 189 | 5.950 | 52.757 | 41.042 | 1.00 | 35.58 |
|---|---|---|---|---|---|---|---|---|---|---|
| ATOM | 1454 | CA | TYR | A | 189 | 7.079 | 51.933 | 41.356 | 1.00 | 37.57 |
| ATOM | 1455 | C | TYR | A | 189 | 6.652 | 50.465 | 41.359 | 1.00 | 44.89 |
| ATOM | 1456 | O | TYR | A | 189 | 5.656 | 50.092 | 41.999 | 1.00 | 44.33 |
| ATOM | 1457 | CB | TYR | A | 189 | 7.752 | 52.392 | 42.661 | 1.00 | 37.85 |
| ATOM | 1458 | CG | TYR | A | 189 | 8.692 | 53.563 | 42.456 | 1.00 | 34.49 |
| ATOM | 1459 | CD1 | TYR | A | 189 | 9.968 | 53.375 | 41.930 | 1.00 | 35.93 |
| ATOM | 1460 | CD2 | TYR | A | 189 | 8.310 | 54.859 | 42.813 | 1.00 | 32.44 |
| ATOM | 1461 | CE1 | TYR | A | 189 | 10.843 | 54.449 | 41.753 | 1.00 | 36.88 |
| ATOM | 1462 | CE2 | TYR | A | 189 | 9.170 | 55.945 | 42.647 | 1.00 | 31.63 |
| ATOM | 1463 | CZ | TYR | A | 189 | 10.441 | 55.734 | 42.113 | 1.00 | 44.54 |
| ATOM | 1464 | OH | TYR | A | 189 | 11.296 | 56.788 | 41.929 | 1.00 | 57.77 |
| ATOM | 1465 | N | LYS | A | 190 | 7.413 | 49.651 | 40.608 | 1.00 | 42.91 |
| ATOM | 1466 | CA | LYS | A | 190 | 7.173 | 48.210 | 40.420 | 1.00 | 42.22 |
| ATOM | 1467 | C | LYS | A | 190 | 8.152 | 47.262 | 41.143 | 1.00 | 40.73 |
| ATOM | 1468 | O | LYS | A | 190 | 9.398 | 47.400 | 41.093 | 1.00 | 35.69 |
| ATOM | 1469 | CB | LYS | A | 190 | 7.007 | 47.839 | 38.944 | 1.00 | 45.87 |
| ATOM | 1470 | CG | LYS | A | 190 | 5.735 | 48.403 | 38.306 | 1.00 | 71.08 |
| ATOM | 1471 | CD | LYS | A | 190 | 5.758 | 48.384 | 36.779 | 1.00 | 84.62 |
| ATOM | 1472 | CE | LYS | A | 190 | 4.386 | 48.157 | 36.147 | 1.00 | 100.00 |
| ATOM | 1473 | NZ | LYS | A | 190 | 4.299 | 46.930 | 35.329 | 1.00 | 100.00 |
| ATOM | 1474 | N | PHE | A | 191 | 7.539 | 46.264 | 41.812 | 1.00 | 35.01 |
| ATOM | 1475 | CA | PHE | A | 191 | 8.276 | 45.304 | 42.592 | 1.00 | 31.57 |
| ATOM | 1476 | C | PHE | A | 191 | 7.792 | 43.871 | 42.465 | 1.00 | 30.89 |
| ATOM | 1477 | O | PHE | A | 191 | 6.603 | 43.584 | 42.377 | 1.00 | 25.06 |
| ATOM | 1478 | CB | PHE | A | 191 | 8.217 | 45.734 | 44.080 | 1.00 | 32.11 |
| ATOM | 1479 | CG | PHE | A | 191 | 8.570 | 47.190 | 44.372 | 1.00 | 29.24 |
| ATOM | 1480 | CD1 | PHE | A | 191 | 9.895 | 47.593 | 44.539 | 1.00 | 31.81 |
| ATOM | 1481 | CD2 | PHE | A | 191 | 7.565 | 48.147 | 44.508 | 1.00 | 30.17 |
| ATOM | 1482 | CE1 | PHE | A | 191 | 10.230 | 48.925 | 44.805 | 1.00 | 34.10 |
| ATOM | 1483 | CE2 | PHE | A | 191 | 7.866 | 49.483 | 44.776 | 1.00 | 33.69 |
| ATOM | 1484 | CZ | PHE | A | 191 | 9.201 | 49.860 | 44.928 | 1.00 | 33.32 |
| ATOM | 1485 | N | ILE | A | 192 | 8.764 | 42.961 | 42.505 | 1.00 | 35.75 |
| ATOM | 1486 | CA | ILE | A | 192 | 8.525 | 41.520 | 42.415 | 1.00 | 37.02 |
| ATOM | 1487 | C | ILE | A | 192 | 9.255 | 40.653 | 43.469 | 1.00 | 33.05 |
| ATOM | 1488 | O | ILE | A | 192 | 10.489 | 40.672 | 43.593 | 1.00 | 30.73 |
| ATOM | 1489 | CB | ILE | A | 192 | 8.850 | 40.970 | 41.025 | 1.00 | 42.45 |
| ATOM | 1490 | CG1 | ILE | A | 192 | 8.289 | 41.914 | 39.981 | 1.00 | 46.39 |
| ATOM | 1491 | CG2 | ILE | A | 192 | 8.251 | 39.567 | 40.859 | 1.00 | 44.02 |
| ATOM | 1492 | CD1 | ILE | A | 192 | 7.609 | 41.231 | 38.798 | 1.00 | 69.61 |
| ATOM | 1493 | N | GLN | A | 193 | 8.459 | 39.864 | 44.195 | 1.00 | 27.51 |
| ATOM | 1494 | CA | GLN | A | 193 | 8.954 | 38.908 | 45.177 | 1.00 | 32.05 |
| ATOM | 1495 | C | GLN | A | 193 | 8.626 | 37.488 | 44.757 | 1.00 | 44.32 |
| ATOM | 1496 | O | GLN | A | 193 | 7.583 | 36.926 | 45.120 | 1.00 | 43.11 |
| ATOM | 1497 | CB | GLN | A | 193 | 8.502 | 39.100 | 46.638 | 1.00 | 33.44 |
| ATOM | 1498 | CG | GLN | A | 193 | 9.285 | 38.203 | 47.632 | 1.00 | 22.34 |
| ATOM | 1499 | CD | GLN | A | 193 | 10.824 | 38.337 | 47.636 | 1.00 | 48.52 |
| ATOM | 1500 | OE1 | GLN | A | 193 | 11.557 | 37.537 | 47.016 | 1.00 | 45.24 |
| ATOM | 1501 | NE2 | GLN | A | 193 | 11.326 | 39.330 | 48.373 | 1.00 | 24.82 |
| ATOM | 1502 | N | LYS | A | 194 | 9.543 | 36.908 | 43.993 | 1.00 | 46.91 |
| ATOM | 1503 | CA | LYS | A | 194 | 9.384 | 35.540 | 43.529 | 1.00 | 47.56 |
| ATOM | 1504 | C | LYS | A | 194 | 9.456 | 34.524 | 44.666 | 1.00 | 49.56 |
| ATOM | 1505 | O | LYS | A | 194 | 8.777 | 33.520 | 44.598 | 1.00 | 50.85 |
| ATOM | 1506 | CB | LYS | A | 194 | 10.385 | 35.159 | 42.439 | 1.00 | 48.11 |
| ATOM | 1507 | CG | LYS | A | 194 | 9.884 | 35.443 | 41.031 | 1.00 | 55.70 |
| ATOM | 1508 | CD | LYS | A | 194 | 10.895 | 36.200 | 40.179 | 1.00 | 67.67 |
| ATOM | 1509 | CE | LYS | A | 194 | 10.614 | 36.122 | 38.682 | 1.00 | 81.92 |
| ATOM | 1510 | NZ | LYS | A | 194 | 11.284 | 37.185 | 37.910 | 1.00 | 88.34 |
| ATOM | 1511 | N | VAL | A | 195 | 10.308 | 34.753 | 45.689 | 1.00 | 39.55 |
| ATOM | 1512 | CA | VAL | A | 195 | 10.422 | 33.780 | 46.764 | 1.00 | 33.56 |
| ATOM | 1513 | C | VAL | A | 195 | 9.261 | 33.862 | 47.698 | 1.00 | 35.67 |
| ATOM | 1514 | O | VAL | A | 195 | 8.804 | 34.945 | 48.034 | 1.00 | 38.69 |
| ATOM | 1515 | CB | VAL | A | 195 | 11.716 | 33.844 | 47.560 | 1.00 | 32.62 |
| ATOM | 1516 | CG1 | VAL | A | 195 | 11.849 | 32.539 | 46.310 | 1.00 | 32.40 |
| ATOM | 1517 | CG2 | VAL | A | 195 | 12.933 | 34.029 | 46.667 | 1.00 | 30.55 |
| ATOM | 1518 | N | PRO | A | 196 | 8.770 | 32.717 | 48.126 | 1.00 | 27.75 |
| ATOM | 1519 | CA | PRO | A | 196 | 7.653 | 32.757 | 49.038 | 1.00 | 26.18 |
| ATOM | 1520 | C | PRO | A | 196 | 8.132 | 33.236 | 50.410 | 1.00 | 35.86 |
| ATOM | 1521 | O | PRO | A | 196 | 9.185 | 32.809 | 50.899 | 1.00 | 35.43 |
| ATOM | 1522 | CB | PRO | A | 196 | 7.022 | 31.359 | 49.044 | 1.00 | 26.04 |
| ATOM | 1523 | CG | PRO | A | 196 | 7.856 | 30.472 | 48.113 | 1.00 | 27.79 |
| ATOM | 1524 | CD | PRO | A | 196 | 8.964 | 31.352 | 47.546 | 1.00 | 25.40 |
| ATOM | 1525 | N | ILE | A | 197 | 7.388 | 34.171 | 51.009 | 1.00 | 29.92 |
| ATOM | 1526 | CA | ILE | A | 197 | 7.772 | 34.697 | 52.284 | 1.00 | 26.98 |
| ATOM | 1527 | C | ILE | A | 197 | 6.544 | 34.809 | 53.128 | 1.00 | 34.88 |
| ATOM | 1528 | O | ILE | A | 197 | 5.444 | 34.788 | 52.606 | 1.00 | 29.68 |

TABLE 9-continued

Structure coordinates of LTA₄ hydrolase-thiolamine complex
(The amino acid sequence set forth as residues 1-610 below correspond to SEQ ID NO:1.)

| ATOM | 1529 | CB | ILE | A | 197 | 8.334 | 36.100 | 52.094 | 1.00 | 27.90 |
|---|---|---|---|---|---|---|---|---|---|---|
| ATOM | 1530 | CG1 | ILE | A | 197 | 7.342 | 36.867 | 51.254 | 1.00 | 27.78 |
| ATOM | 1531 | CG2 | ILE | A | 197 | 9.659 | 36.091 | 51.337 | 1.00 | 28.12 |
| ATOM | 1532 | CD1 | ILE | A | 197 | 7.494 | 38.378 | 51.438 | 1.00 | 19.03 |
| ATOM | 1533 | N | PRO | A | 198 | 6.743 | 34.936 | 54.447 | 1.00 | 36.02 |
| ATOM | 1534 | CA | PRO | A | 198 | 5.647 | 35.110 | 55.410 | 1.00 | 31.31 |
| ATOM | 1535 | C | PRO | A | 198 | 5.299 | 36.583 | 55.308 | 1.00 | 28.27 |
| ATOM | 1536 | O | PRO | A | 198 | 6.212 | 37.391 | 55.115 | 1.00 | 22.70 |
| ATOM | 1537 | CB | PRO | A | 198 | 6.252 | 34.849 | 56.794 | 1.00 | 31.17 |
| ATOM | 1538 | CG | PRO | A | 198 | 7.768 | 34.768 | 56.615 | 1.00 | 34.94 |
| ATOM | 1539 | CD | PRO | A | 198 | 8.057 | 34.706 | 55.122 | 1.00 | 32.99 |
| ATOM | 1540 | N | CYS | A | 199 | 4.011 | 36.939 | 55.405 | 1.00 | 27.60 |
| ATOM | 1541 | CA | CYS | A | 199 | 3.555 | 38.360 | 55.289 | 1.00 | 27.66 |
| ATOM | 1542 | C | CYS | A | 199 | 4.255 | 39.390 | 56.187 | 1.00 | 30.13 |
| ATOM | 1543 | O | CYS | A | 199 | 4.294 | 40.596 | 55.895 | 1.00 | 29.50 |
| ATOM | 1544 | CB | CYS | A | 199 | 2.025 | 38.534 | 55.242 | 1.00 | 27.18 |
| ATOM | 1545 | SG | CYS | A | 199 | 1.232 | 38.279 | 56.841 | 1.00 | 30.85 |
| ATOM | 1546 | N | TYR | A | 200 | 4.847 | 38.903 | 57.270 | 1.00 | 26.15 |
| ATOM | 1547 | CA | TYR | A | 200 | 5.538 | 39.798 | 58.123 | 1.00 | 28.28 |
| ATOM | 1548 | C | TYR | A | 200 | 6.760 | 40.395 | 57.483 | 1.00 | 32.29 |
| ATOM | 1549 | O | TYR | A | 200 | 7.359 | 41.286 | 58.036 | 1.00 | 31.56 |
| ATOM | 1550 | CB | TYR | A | 200 | 5.844 | 39.215 | 59.489 | 1.00 | 30.59 |
| ATOM | 1551 | CG | TYR | A | 200 | 6.989 | 38.272 | 59.568 | 1.00 | 28.28 |
| ATOM | 1552 | CD1 | TYR | A | 200 | 8.288 | 38.733 | 59.689 | 1.00 | 29.48 |
| ATOM | 1553 | CD2 | TYR | A | 200 | 6.756 | 36.903 | 59.475 | 1.00 | 27.55 |
| ATOM | 1554 | CE1 | TYR | A | 200 | 9.377 | 37.862 | 59.825 | 1.00 | 21.42 |
| ATOM | 1555 | CE2 | TYR | A | 200 | 7.838 | 36.015 | 59.595 | 1.00 | 27.41 |
| ATOM | 1556 | CZ | TYR | A | 200 | 9.144 | 36.488 | 59.737 | 1.00 | 25.11 |
| ATOM | 1557 | OH | TYR | A | 200 | 10.215 | 35.614 | 59.880 | 1.00 | 27.62 |
| ATOM | 1558 | N | LEU | A | 201 | 7.113 | 39.897 | 56.313 | 1.00 | 31.66 |
| ATOM | 1559 | CA | LEU | A | 201 | 8.278 | 40.378 | 55.579 | 1.00 | 29.49 |
| ATOM | 1560 | C | LEU | A | 201 | 7.914 | 41.343 | 54.484 | 1.00 | 33.65 |
| ATOM | 1561 | O | LEU | A | 201 | 8.767 | 41.737 | 53.686 | 1.00 | 35.31 |
| ATOM | 1562 | CB | LEU | A | 201 | 9.225 | 39.275 | 55.035 | 1.00 | 27.04 |
| ATOM | 1563 | CG | LEU | A | 201 | 9.697 | 38.271 | 56.071 | 1.00 | 27.42 |
| ATOM | 1564 | CD1 | LEU | A | 201 | 10.254 | 37.030 | 55.390 | 1.00 | 23.71 |
| ATOM | 1565 | CD2 | LEU | A | 201 | 10.764 | 38.913 | 56.957 | 1.00 | 30.55 |
| ATOM | 1566 | N | ILE | A | 202 | 6.648 | 41.710 | 54.438 | 1.00 | 28.66 |
| ATOM | 1567 | CA | ILE | A | 202 | 6.249 | 42.674 | 53.433 | 1.00 | 29.57 |
| ATOM | 1568 | C | ILE | A | 202 | 6.636 | 44.074 | 53.951 | 1.00 | 40.28 |
| ATOM | 1569 | O | ILE | A | 202 | 6.192 | 44.493 | 55.027 | 1.00 | 40.75 |
| ATOM | 1570 | CB | ILE | A | 202 | 4.733 | 42.651 | 53.182 | 1.00 | 31.18 |
| ATOM | 1571 | CG1 | ILE | A | 202 | 4.250 | 41.429 | 52.405 | 1.00 | 28.21 |
| ATOM | 1572 | CG2 | ILE | A | 202 | 4.259 | 43.962 | 52.521 | 1.00 | 29.23 |
| ATOM | 1573 | CD1 | ILE | A | 202 | 2.724 | 41.288 | 52.449 | 1.00 | 23.01 |
| ATOM | 1574 | N | ALA | A | 203 | 7.445 | 44.813 | 53.197 | 1.00 | 39.14 |
| ATOM | 1575 | CA | ALA | A | 203 | 7.840 | 46.150 | 53.611 | 1.00 | 37.03 |
| ATOM | 1576 | C | ALA | A | 203 | 7.819 | 47.159 | 52.482 | 1.00 | 34.32 |
| ATOM | 1577 | O | ALA | A | 203 | 8.060 | 46.836 | 51.311 | 1.00 | 30.63 |
| ATOM | 1578 | CB | ALA | A | 203 | 9.180 | 46.143 | 54.309 | 1.00 | 38.22 |
| ATOM | 1579 | N | LEU | A | 204 | 7.514 | 48.388 | 52.910 | 1.00 | 33.64 |
| ATOM | 1580 | CA | LEU | A | 204 | 7.388 | 49.604 | 52.102 | 1.00 | 32.56 |
| ATOM | 1581 | C | LEU | A | 204 | 7.993 | 50.817 | 52.812 | 1.00 | 37.69 |
| ATOM | 1582 | O | LEU | A | 204 | 7.854 | 51.037 | 54.034 | 1.00 | 32.66 |
| ATOM | 1583 | CB | LEU | A | 204 | 5.906 | 49.929 | 51.718 | 1.00 | 29.74 |
| ATOM | 1584 | CG | LEU | A | 204 | 5.706 | 51.182 | 50.855 | 1.00 | 29.64 |
| ATOM | 1585 | CD1 | LEU | A | 204 | 6.263 | 50.994 | 49.445 | 1.00 | 29.47 |
| ATOM | 1586 | CD2 | LEU | A | 204 | 4.222 | 51.515 | 50.750 | 1.00 | 33.50 |
| ATOM | 1587 | N | VAL | A | 205 | 8.670 | 51.603 | 51.991 | 1.00 | 36.87 |
| ATOM | 1588 | CA | VAL | A | 205 | 9.305 | 52.821 | 52.415 | 1.00 | 35.15 |
| ATOM | 1589 | C | VAL | A | 205 | 9.224 | 53.795 | 51.284 | 1.00 | 38.41 |
| ATOM | 1590 | O | VAL | A | 205 | 9.575 | 53.462 | 50.148 | 1.00 | 39.50 |
| ATOM | 1591 | CB | VAL | A | 205 | 10.769 | 52.651 | 52.804 | 1.00 | 36.06 |
| ATOM | 1592 | CG1 | VAL | A | 205 | 11.466 | 51.794 | 51.757 | 1.00 | 35.08 |
| ATOM | 1593 | CG2 | VAL | A | 205 | 11.432 | 54.020 | 52.833 | 1.00 | 35.98 |
| ATOM | 1594 | N | VAL | A | 206 | 8.750 | 54.983 | 51.623 | 1.00 | 33.54 |
| ATOM | 1595 | CA | VAL | A | 206 | 8.623 | 56.104 | 50.687 | 1.00 | 31.81 |
| ATOM | 1596 | C | VAL | A | 206 | 9.300 | 57.343 | 51.249 | 1.00 | 31.62 |
| ATOM | 1597 | O | VAL | A | 206 | 9.076 | 57.722 | 52.406 | 1.00 | 34.81 |
| ATOM | 1598 | CB | VAL | A | 206 | 7.179 | 56.405 | 50.305 | 1.00 | 33.35 |
| ATOM | 1599 | CG1 | VAL | A | 206 | 7.129 | 57.243 | 49.029 | 1.00 | 33.44 |
| ATOM | 1600 | CG2 | VAL | A | 206 | 6.452 | 55.084 | 50.109 | 1.00 | 31.98 |
| ATOM | 1601 | N | GLY | A | 207 | 10.130 | 57.959 | 50.431 | 1.00 | 24.94 |
| ATOM | 1602 | CA | GLY | A | 207 | 10.807 | 59.168 | 50.861 | 1.00 | 27.25 |
| ATOM | 1603 | C | GLY | A | 207 | 11.802 | 59.632 | 49.838 | 1.00 | 38.81 |
| ATOM | 1604 | O | GLY | A | 207 | 12.046 | 58.966 | 48.840 | 1.00 | 39.82 |

TABLE 9-continued

Structure coordinates of LTA₄ hydrolase-thiolamine complex
(The amino acid sequence set forth as residues 1-610 below correspond to SEQ ID NO:1.)

| ATOM | 1605 | N   | ALA | A | 208 | 12.375 | 60.783 | 50.113 | 1.00 | 41.07 |
|------|------|-----|-----|---|-----|--------|--------|--------|------|-------|
| ATOM | 1606 | CA  | ALA | A | 208 | 13.370 | 61.354 | 49.233 | 1.00 | 42.72 |
| ATOM | 1607 | C   | ALA | A | 208 | 14.660 | 60.550 | 49.356 | 1.00 | 49.10 |
| ATOM | 1608 | O   | ALA | A | 208 | 15.651 | 60.997 | 49.957 | 1.00 | 51.30 |
| ATOM | 1609 | CB  | ALA | A | 208 | 13.605 | 62.810 | 49.589 | 1.00 | 42.95 |
| ATOM | 1610 | N   | LEU | A | 209 | 14.623 | 59.350 | 48.773 | 1.00 | 40.92 |
| ATOM | 1611 | CA  | LEU | A | 209 | 15.739 | 58.440 | 48.825 | 1.00 | 39.55 |
| ATOM | 1612 | C   | LEU | A | 209 | 16.756 | 58.575 | 47.743 | 1.00 | 47.96 |
| ATOM | 1613 | O   | LEU | A | 209 | 16.420 | 58.843 | 46.597 | 1.00 | 49.44 |
| ATOM | 1614 | CB  | LEU | A | 209 | 15.269 | 56.994 | 48.894 | 1.00 | 37.97 |
| ATOM | 1615 | CG  | LEU | A | 209 | 14.420 | 56.803 | 50.129 | 1.00 | 40.46 |
| ATOM | 1616 | CD1 | LEU | A | 209 | 13.713 | 55.469 | 50.075 | 1.00 | 36.99 |
| ATOM | 1617 | CD2 | LEU | A | 209 | 15.283 | 56.921 | 51.387 | 1.00 | 43.31 |
| ATOM | 1618 | N   | GLU | A | 210 | 17.999 | 58.317 | 48.182 | 1.00 | 42.68 |
| ATOM | 1619 | CA  | GLU | A | 210 | 19.205 | 58.311 | 47.381 | 1.00 | 40.30 |
| ATOM | 1620 | C   | GLU | A | 210 | 19.965 | 57.056 | 47.693 | 1.00 | 47.51 |
| ATOM | 1621 | O   | GLU | A | 210 | 19.708 | 56.432 | 48.721 | 1.00 | 47.89 |
| ATOM | 1622 | CB  | GLU | A | 210 | 20.084 | 59.553 | 47.613 | 1.00 | 42.01 |
| ATOM | 1623 | CG  | GLU | A | 210 | 19.699 | 60.734 | 46.697 | 1.00 | 58.26 |
| ATOM | 1624 | CD  | GLU | A | 210 | 20.524 | 61.970 | 46.897 | 1.00 | 100.00 |
| ATOM | 1625 | OE1 | GLU | A | 210 | 21.629 | 61.968 | 47.451 | 1.00 | 95.26 |
| ATOM | 1626 | OE2 | GLU | A | 210 | 19.935 | 63.047 | 46.486 | 1.00 | 100.00 |
| ATOM | 1627 | N   | SER | A | 211 | 20.895 | 56.662 | 46.805 | 1.00 | 45.01 |
| ATOM | 1628 | CA  | SER | A | 211 | 21.661 | 55.442 | 47.013 | 1.00 | 42.25 |
| ATOM | 1629 | C   | SER | A | 211 | 23.143 | 55.535 | 46.667 | 1.00 | 43.37 |
| ATOM | 1630 | O   | SER | A | 211 | 23.649 | 56.493 | 46.086 | 1.00 | 46.43 |
| ATOM | 1631 | CB  | SER | A | 211 | 21.025 | 54.233 | 46.346 | 1.00 | 44.33 |
| ATOM | 1632 | OG  | SER | A | 211 | 21.274 | 54.244 | 44.934 | 1.00 | 54.15 |
| ATOM | 1633 | N   | ARG | A | 212 | 23.829 | 54.497 | 47.053 | 1.00 | 34.85 |
| ATOM | 1634 | CA  | ARG | A | 212 | 25.229 | 54.328 | 46.791 | 1.00 | 35.41 |
| ATOM | 1635 | C   | ARG | A | 212 | 25.430 | 52.838 | 46.567 | 1.00 | 45.39 |
| ATOM | 1636 | O   | ARG | A | 212 | 24.840 | 52.027 | 47.276 | 1.00 | 48.85 |
| ATOM | 1637 | CB  | ARG | A | 212 | 26.101 | 54.846 | 47.915 | 1.00 | 37.25 |
| ATOM | 1638 | CG  | ARG | A | 212 | 27.151 | 55.827 | 47.402 | 1.00 | 68.10 |
| ATOM | 1639 | CD  | ARG | A | 212 | 26.532 | 56.962 | 46.587 | 1.00 | 76.55 |
| ATOM | 1640 | NE  | ARG | A | 212 | 26.695 | 58.307 | 47.148 | 1.00 | 55.19 |
| ATOM | 1641 | CZ  | ARG | A | 212 | 25.845 | 59.301 | 46.867 | 1.00 | 70.87 |
| ATOM | 1642 | NH1 | ARG | A | 212 | 24.806 | 59.105 | 46.059 | 1.00 | 35.71 |
| ATOM | 1643 | NH2 | ARG | A | 212 | 26.032 | 60.516 | 47.392 | 1.00 | 73.35 |
| ATOM | 1644 | N   | GLN | A | 213 | 26.210 | 52.442 | 45.567 | 1.00 | 40.74 |
| ATOM | 1645 | CA  | GLN | A | 213 | 26.408 | 51.021 | 45.331 | 1.00 | 39.90 |
| ATOM | 1646 | C   | GLN | A | 213 | 27.646 | 50.537 | 46.050 | 1.00 | 46.34 |
| ATOM | 1647 | O   | GLN | A | 213 | 28.740 | 50.981 | 45.741 | 1.00 | 53.77 |
| ATOM | 1648 | CB  | GLN | A | 213 | 26.545 | 50.741 | 43.846 | 1.00 | 40.99 |
| ATOM | 1649 | CG  | GLN | A | 213 | 26.976 | 49.296 | 43.532 | 1.00 | 55.79 |
| ATOM | 1650 | CD  | GLN | A | 213 | 26.292 | 48.743 | 42.301 | 1.00 | 76.04 |
| ATOM | 1651 | OE1 | GLN | A | 213 | 26.275 | 47.523 | 42.102 | 1.00 | 86.66 |
| ATOM | 1652 | NE2 | GLN | A | 213 | 25.700 | 49.618 | 41.489 | 1.00 | 55.45 |
| ATOM | 1653 | N   | ILE | A | 214 | 27.495 | 49.649 | 47.013 | 1.00 | 33.12 |
| ATOM | 1654 | CA  | ILE | A | 214 | 28.663 | 49.206 | 47.743 | 1.00 | 32.55 |
| ATOM | 1655 | C   | ILE | A | 214 | 28.911 | 47.765 | 47.536 | 1.00 | 39.29 |
| ATOM | 1656 | O   | ILE | A | 214 | 29.726 | 47.162 | 48.230 | 1.00 | 42.41 |
| ATOM | 1657 | CB  | ILE | A | 214 | 28.546 | 49.428 | 49.250 | 1.00 | 35.72 |
| ATOM | 1658 | CG1 | ILE | A | 214 | 27.395 | 48.573 | 49.791 | 1.00 | 36.13 |
| ATOM | 1659 | CG2 | ILE | A | 214 | 28.344 | 50.911 | 49.598 | 1.00 | 35.79 |
| ATOM | 1660 | CD1 | ILE | A | 214 | 27.067 | 48.841 | 51.260 | 1.00 | 46.69 |
| ATOM | 1661 | N   | GLY | A | 215 | 28.199 | 47.197 | 46.598 | 1.00 | 35.02 |
| ATOM | 1662 | CA  | GLY | A | 215 | 28.638 | 45.855 | 46.234 | 1.00 | 34.88 |
| ATOM | 1663 | C   | GLY | A | 215 | 27.970 | 45.405 | 44.950 | 1.00 | 41.09 |
| ATOM | 1664 | O   | GLY | A | 215 | 27.083 | 46.048 | 44.425 | 1.00 | 44.25 |
| ATOM | 1665 | N   | PRO | A | 216 | 28.448 | 44.262 | 44.410 | 1.00 | 39.62 |
| ATOM | 1666 | CA  | PRO | A | 216 | 27.890 | 43.720 | 43.197 | 1.00 | 39.69 |
| ATOM | 1667 | C   | PRO | A | 216 | 26.369 | 43.661 | 43.253 | 1.00 | 41.56 |
| ATOM | 1668 | O   | PRO | A | 216 | 25.655 | 43.817 | 42.240 | 1.00 | 44.35 |
| ATOM | 1669 | CB  | PRO | A | 216 | 28.448 | 42.311 | 42.996 | 1.00 | 39.91 |
| ATOM | 1670 | CG  | PRO | A | 216 | 29.377 | 41.993 | 44.164 | 1.00 | 41.54 |
| ATOM | 1671 | CD  | PRO | A | 216 | 29.514 | 43.411 | 44.897 | 1.00 | 37.70 |
| ATOM | 1672 | N   | ARG | A | 217 | 25.846 | 43.398 | 44.477 | 1.00 | 31.04 |
| ATOM | 1673 | CA  | ARG | A | 217 | 24.421 | 43.328 | 44.652 | 1.00 | 29.22 |
| ATOM | 1674 | C   | ARG | A | 217 | 23.928 | 44.109 | 45.872 | 1.00 | 38.24 |
| ATOM | 1675 | O   | ARG | A | 217 | 22.861 | 43.885 | 46.368 | 1.00 | 40.69 |
| ATOM | 1676 | CD  | ARG | A | 217 | 24.012 | 41.844 | 44.790 | 1.00 | 22.75 |
| ATOM | 1677 | CG  | ARG | A | 217 | 25.221 | 40.963 | 45.109 | 1.00 | 40.77 |
| ATOM | 1678 | CD  | ARG | A | 217 | 24.828 | 39.774 | 45.985 | 1.00 | 34.08 |
| ATOM | 1679 | NE  | ARG | A | 217 | 26.020 | 39.183 | 46.581 | 1.00 | 45.20 |
| ATOM | 1680 | CZ  | ARG | A | 217 | 25.955 | 37.894 | 46.911 | 1.00 | 65.13 |

TABLE 9-continued

Structure coordinates of LTA₄ hydrolase-thiolamine complex
(The amino acid sequence set forth as residues 1-610 below correspond to SEQ ID NO:1.)

| ATOM | 1681 | NH1 | ARG | A | 217 | 24.832 | 37.220 | 46.716 | 1.00 | 42.40 |
|------|------|-----|-----|---|-----|--------|--------|--------|------|-------|
| ATOM | 1682 | NH2 | ARG | A | 217 | 26.997 | 37.300 | 47.472 | 1.00 | 48.08 |
| ATOM | 1683 | N | THR | A | 218 | 24.784 | 45.022 | 46.404 | 1.00 | 31.00 |
| ATOM | 1684 | CA | THR | A | 218 | 24.309 | 45.886 | 47.487 | 1.00 | 31.00 |
| ATOM | 1685 | C | THR | A | 218 | 24.128 | 47.319 | 47.021 | 1.00 | 43.60 |
| ATOM | 1686 | O | THR | A | 218 | 25.065 | 47.930 | 46.512 | 1.00 | 48.42 |
| ATOM | 1687 | CB | THR | A | 218 | 25.315 | 45.845 | 48.640 | 1.00 | 36.95 |
| ATOM | 1688 | OG1 | THR | A | 218 | 25.430 | 44.517 | 49.139 | 1.00 | 45.66 |
| ATOM | 1689 | CG2 | THR | A | 218 | 24.826 | 46.751 | 49.766 | 1.00 | 34.17 |
| ATOM | 1690 | N | LEU | A | 219 | 23.099 | 48.018 | 47.431 | 1.00 | 39.19 |
| ATOM | 1691 | CA | LEU | A | 219 | 23.055 | 49.452 | 47.315 | 1.00 | 38.18 |
| ATOM | 1692 | C | LEU | A | 219 | 22.713 | 50.000 | 48.695 | 1.00 | 42.32 |
| ATOM | 1693 | O | LEU | A | 219 | 22.108 | 49.289 | 49.498 | 1.00 | 43.67 |
| ATOM | 1694 | CB | LEU | A | 219 | 21.927 | 49.841 | 46.356 | 1.00 | 37.05 |
| ATOM | 1695 | CG | LEU | A | 219 | 22.386 | 50.657 | 45.168 | 1.00 | 39.31 |
| ATOM | 1696 | CD1 | LEU | A | 219 | 23.670 | 50.064 | 44.613 | 1.00 | 40.57 |
| ATOM | 1697 | CD2 | LEU | A | 219 | 21.283 | 50.619 | 44.131 | 1.00 | 29.39 |
| ATOM | 1698 | N | VAL | A | 220 | 23.066 | 51.241 | 48.976 | 1.00 | 35.01 |
| ATOM | 1699 | CA | VAL | A | 220 | 22.741 | 51.830 | 50.253 | 1.00 | 36.98 |
| ATOM | 1700 | C | VAL | A | 220 | 21.736 | 52.923 | 50.043 | 1.00 | 44.08 |
| ATOM | 1701 | O | VAL | A | 220 | 21.959 | 53.835 | 49.256 | 1.00 | 46.60 |
| ATOM | 1702 | CB | VAL | A | 220 | 23.965 | 52.346 | 51.028 | 1.00 | 44.95 |
| ATOM | 1703 | CG1 | VAL | A | 220 | 23.675 | 52.428 | 52.516 | 1.00 | 43.16 |
| ATOM | 1704 | CG2 | VAL | A | 220 | 25.138 | 51.382 | 50.828 | 1.00 | 47.70 |
| ATOM | 1705 | N | TRP | A | 221 | 20.622 | 52.618 | 50.731 | 1.00 | 41.98 |
| ATOM | 1706 | CA | TRP | A | 221 | 19.605 | 53.828 | 50.602 | 1.00 | 41.64 |
| ATOM | 1707 | C | TRP | A | 221 | 19.464 | 54.612 | 51.872 | 1.00 | 42.40 |
| ATOM | 1708 | O | TRP | A | 221 | 19.461 | 54.060 | 52.960 | 1.00 | 45.56 |
| ATOM | 1709 | CB | TRP | A | 221 | 18.256 | 53.245 | 50.186 | 1.00 | 41.24 |
| ATOM | 1710 | CG | TRP | A | 221 | 18.353 | 52.459 | 48.918 | 1.00 | 42.59 |
| ATOM | 1711 | CD1 | TRP | A | 221 | 18.888 | 51.225 | 48.793 | 1.00 | 45.35 |
| ATOM | 1712 | CD2 | TRP | A | 221 | 17.949 | 52.873 | 47.590 | 1.00 | 41.62 |
| ATOM | 1713 | NE1 | TRP | A | 221 | 18.826 | 50.832 | 47.478 | 1.00 | 44.74 |
| ATOM | 1714 | CE2 | TRP | A | 221 | 18.243 | 51.821 | 46.720 | 1.00 | 45.31 |
| ATOM | 1715 | CE3 | TRP | A | 221 | 17.345 | 54.009 | 47.061 | 1.00 | 41.17 |
| ATOM | 1716 | CZ2 | TRP | A | 221 | 17.958 | 51.902 | 45.346 | 1.00 | 42.60 |
| ATOM | 1717 | CZ3 | TRP | A | 221 | 17.054 | 54.083 | 45.710 | 1.00 | 39.08 |
| ATOM | 1718 | CH2 | TRP | A | 221 | 17.360 | 53.040 | 44.864 | 1.00 | 38.48 |
| ATOM | 1719 | N | SER | A | 222 | 19.271 | 55.896 | 51.688 | 1.00 | 37.01 |
| ATOM | 1720 | CA | SER | A | 222 | 19.017 | 56.846 | 52.748 | 1.00 | 38.05 |
| ATOM | 1721 | C | SER | A | 222 | 18.853 | 58.251 | 52.205 | 1.00 | 45.28 |
| ATOM | 1722 | O | SER | A | 222 | 19.005 | 58.503 | 51.008 | 1.00 | 44.02 |
| ATOM | 1723 | CB | SER | A | 222 | 20.098 | 56.816 | 53.820 | 1.00 | 39.07 |
| ATOM | 1724 | OG | SER | A | 222 | 21.322 | 57.149 | 53.229 | 1.00 | 42.36 |
| ATOM | 1725 | N | GLU | A | 223 | 18.586 | 59.190 | 53.088 | 1.00 | 40.91 |
| ATOM | 1726 | CA | GLU | A | 223 | 18.465 | 60.527 | 52.584 | 1.00 | 41.97 |
| ATOM | 1727 | C | GLU | A | 223 | 19.843 | 61.042 | 52.234 | 1.00 | 50.17 |
| ATOM | 1728 | O | GLU | A | 223 | 20.829 | 60.701 | 52.863 | 1.00 | 52.02 |
| ATOM | 1729 | CB | GLU | A | 223 | 17.856 | 61.483 | 53.597 | 1.00 | 43.06 |
| ATOM | 1730 | CG | GLU | A | 223 | 16.364 | 61.262 | 53.861 | 1.00 | 51.71 |
| ATOM | 1731 | CD | GLU | A | 223 | 15.799 | 62.478 | 54.545 | 1.00 | 84.51 |
| ATOM | 1732 | OE1 | GLU | A | 223 | 15.905 | 63.610 | 54.085 | 1.00 | 56.82 |
| ATOM | 1733 | OE2 | GLU | A | 223 | 15.244 | 62.222 | 55.705 | 1.00 | 88.87 |
| ATOM | 1734 | N | LYS | A | 224 | 19.892 | 61.875 | 51.229 | 1.00 | 47.39 |
| ATOM | 1735 | CA | LYS | A | 224 | 21.139 | 62.456 | 50.792 | 1.00 | 48.51 |
| ATOM | 1736 | C | LYS | A | 224 | 22.163 | 62.683 | 51.930 | 1.00 | 50.90 |
| ATOM | 1737 | O | LYS | A | 224 | 23.382 | 62.569 | 51.736 | 1.00 | 51.55 |
| ATOM | 1738 | CB | LYS | A | 224 | 20.843 | 63.736 | 49.986 | 1.00 | 51.58 |
| ATOM | 1739 | CG | LYS | A | 224 | 22.039 | 64.648 | 49.723 | 1.00 | 81.16 |
| ATOM | 1740 | CD | LYS | A | 224 | 21.954 | 65.397 | 48.392 | 1.00 | 97.82 |
| ATOM | 1741 | CE | LYS | A | 224 | 21.646 | 66.891 | 48.530 | 1.00 | 100.00 |
| ATOM | 1742 | NZ | LYS | A | 224 | 22.056 | 67.700 | 47.362 | 1.00 | 100.00 |
| ATOM | 1743 | N | GLU | A | 225 | 21.683 | 63.011 | 53.123 | 1.00 | 45.77 |
| ATOM | 1744 | CA | GLU | A | 225 | 22.607 | 63.309 | 54.199 | 1.00 | 46.00 |
| ATOM | 1745 | C | GLU | A | 225 | 23.227 | 62.150 | 54.902 | 1.00 | 47.99 |
| ATOM | 1746 | O | GLU | A | 225 | 24.107 | 62.354 | 55.732 | 1.00 | 47.21 |
| ATOM | 1747 | CB | GLU | A | 225 | 22.057 | 64.296 | 55.210 | 1.00 | 47.71 |
| ATOM | 1748 | CG | GLU | A | 225 | 20.530 | 64.296 | 55.182 | 1.00 | 63.24 |
| ATOM | 1749 | CD | GLU | A | 225 | 19.931 | 65.219 | 54.150 | 1.00 | 75.13 |
| ATOM | 1750 | OE1 | GLU | A | 225 | 20.187 | 66.420 | 54.046 | 1.00 | 54.64 |
| ATOM | 1751 | OE2 | GLU | A | 225 | 19.039 | 64.578 | 53.420 | 1.00 | 49.64 |
| ATOM | 1752 | N | GLN | A | 226 | 22.798 | 60.949 | 54.564 | 1.00 | 43.92 |
| ATOM | 1753 | CA | GLN | A | 226 | 23.340 | 59.772 | 55.224 | 1.00 | 43.91 |
| ATOM | 1754 | C | GLN | A | 226 | 24.036 | 58.756 | 54.322 | 1.00 | 45.86 |
| ATOM | 1755 | O | GLN | A | 226 | 24.756 | 57.871 | 54.806 | 1.00 | 45.70 |
| ATOM | 1756 | CB | GLN | A | 226 | 22.252 | 59.084 | 56.063 | 1.00 | 45.27 |

TABLE 9-continued

Structure coordinates of LTA₄ hydrolase-thiolamine complex
(The amino acid sequence set forth as residues 1-610 below correspond to SEQ ID NO:1.)

| ATOM | 1757 | CG  | GLN | A | 226 | 21.965 | 59.790 | 57.400 | 1.00 | 31.17  |
|------|------|-----|-----|---|-----|--------|--------|--------|------|--------|
| ATOM | 1758 | CD  | GLN | A | 226 | 21.297 | 61.155 | 57.302 | 1.00 | 44.48  |
| ATOM | 1759 | OE1 | GLN | A | 226 | 21.823 | 62.149 | 57.820 | 1.00 | 37.36  |
| ATOM | 1760 | NE2 | GLN | A | 226 | 20.115 | 61.202 | 56.696 | 1.00 | 30.28  |
| ATOM | 1761 | N   | VAL | A | 227 | 23.814 | 58.871 | 53.021 | 1.00 | 41.20  |
| ATOM | 1762 | CA  | VAL | A | 227 | 24.406 | 57.947 | 52.071 | 1.00 | 43.13  |
| ATOM | 1763 | C   | VAL | A | 227 | 25.884 | 57.670 | 52.261 | 1.00 | 50.55  |
| ATOM | 1764 | O   | VAL | A | 227 | 26.298 | 56.518 | 52.480 | 1.00 | 53.01  |
| ATOM | 1765 | CB  | VAL | A | 227 | 24.155 | 58.293 | 50.604 | 1.00 | 49.39  |
| ATOM | 1766 | CG1 | VAL | A | 227 | 24.319 | 57.029 | 49.771 | 1.00 | 48.89  |
| ATOM | 1767 | CG2 | VAL | A | 227 | 22.752 | 58.851 | 50.421 | 1.00 | 50.47  |
| ATOM | 1768 | N   | GLU | A | 228 | 26.696 | 58.718 | 52.170 | 1.00 | 44.08  |
| ATOM | 1769 | CA  | GLU | A | 228 | 28.123 | 58.542 | 52.310 | 1.00 | 41.71  |
| ATOM | 1770 | C   | GLU | A | 228 | 28.514 | 57.871 | 53.583 | 1.00 | 44.20  |
| ATOM | 1771 | O   | GLU | A | 228 | 29.227 | 56.868 | 53.589 | 1.00 | 44.88  |
| ATOM | 1772 | CB  | GLU | A | 228 | 28.935 | 59.824 | 52.102 | 1.00 | 43.08  |
| ATOM | 1773 | CG  | GLU | A | 228 | 29.153 | 60.161 | 50.611 | 1.00 | 64.74  |
| ATOM | 1774 | CD  | GLU | A | 228 | 29.114 | 58.965 | 49.701 | 1.00 | 84.29  |
| ATOM | 1775 | OE1 | GLU | A | 228 | 29.975 | 58.107 | 49.685 | 1.00 | 84.36  |
| ATOM | 1776 | OE2 | GLU | A | 228 | 28.064 | 58.951 | 48.917 | 1.00 | 73.81  |
| ATOM | 1777 | N   | LYS | A | 229 | 28.066 | 58.423 | 54.685 | 1.00 | 39.79  |
| ATOM | 1778 | CA  | LYS | A | 229 | 28.449 | 57.796 | 55.922 | 1.00 | 39.04  |
| ATOM | 1779 | C   | LYS | A | 229 | 27.949 | 56.375 | 55.930 | 1.00 | 40.38  |
| ATOM | 1780 | O   | LYS | A | 229 | 28.639 | 55.433 | 56.346 | 1.00 | 43.63  |
| ATOM | 1781 | CB  | LYS | A | 229 | 28.129 | 58.585 | 57.187 | 1.00 | 39.79  |
| ATOM | 1782 | CG  | LYS | A | 229 | 28.903 | 58.072 | 58.394 | 1.00 | 63.75  |
| ATOM | 1783 | CD  | LYS | A | 229 | 28.498 | 58.763 | 59.685 | 1.00 | 77.46  |
| ATOM | 1784 | CE  | LYS | A | 229 | 29.677 | 59.084 | 60.593 | 1.00 | 94.73  |
| ATOM | 1785 | NZ  | LYS | A | 229 | 30.344 | 60.353 | 60.256 | 1.00 | 100.00 |
| ATOM | 1786 | N   | SER | A | 230 | 26.741 | 56.220 | 55.428 | 1.00 | 28.48  |
| ATOM | 1787 | CA  | SER | A | 230 | 26.174 | 54.891 | 55.377 | 1.00 | 25.93  |
| ATOM | 1788 | C   | SER | A | 230 | 27.089 | 53.988 | 54.587 | 1.00 | 30.26  |
| ATOM | 1789 | O   | SER | A | 230 | 27.469 | 52.855 | 54.955 | 1.00 | 28.48  |
| ATOM | 1790 | GB  | SER | A | 230 | 24.824 | 54.927 | 54.694 | 1.00 | 30.08  |
| ATOM | 1791 | OG  | SER | A | 230 | 23.822 | 55.293 | 55.605 | 1.00 | 41.60  |
| ATOM | 1792 | N   | ALA | A | 231 | 27.436 | 54.536 | 53.459 | 1.00 | 31.13  |
| ATOM | 1793 | CA  | ALA | A | 231 | 28.288 | 53.820 | 52.593 | 1.00 | 36.66  |
| ATOM | 1794 | C   | ALA | A | 231 | 29.597 | 53.383 | 53.270 | 1.00 | 47.68  |
| ATOM | 1795 | O   | ALA | A | 231 | 30.003 | 52.238 | 53.103 | 1.00 | 54.59  |
| ATOM | 1796 | CB  | ALA | A | 231 | 28.406 | 54.518 | 51.257 | 1.00 | 38.49  |
| ATOM | 1797 | N   | TYR | A | 232 | 30.256 | 54.246 | 54.060 | 1.00 | 40.77  |
| ATOM | 1798 | CA  | TYR | A | 232 | 31.500 | 53.830 | 54.730 | 1.00 | 38.40  |
| ATOM | 1799 | C   | TYR | A | 232 | 31.265 | 52.721 | 55.753 | 1.00 | 39.70  |
| ATOM | 1800 | O   | TYR | A | 232 | 32.041 | 51.772 | 55.862 | 1.00 | 36.46  |
| ATOM | 1801 | CB  | TYR | A | 232 | 32.311 | 54.981 | 55.414 | 1.00 | 38.27  |
| ATOM | 1802 | CG  | TYR | A | 232 | 33.497 | 54.525 | 56.303 | 1.00 | 42.36  |
| ATOM | 1803 | CD1 | TYR | A | 232 | 34.755 | 54.238 | 55.753 | 1.00 | 46.41  |
| ATOM | 1804 | CD2 | TYR | A | 232 | 33.373 | 54.394 | 57.691 | 1.00 | 40.99  |
| ATOM | 1805 | CE1 | TYR | A | 232 | 35.835 | 53.815 | 56.534 | 1.00 | 47.23  |
| ATOM | 1806 | CE2 | TYR | A | 232 | 34.441 | 53.979 | 58.496 | 1.00 | 40.10  |
| ATOM | 1807 | CZ  | TYR | A | 232 | 35.680 | 53.695 | 57.916 | 1.00 | 48.59  |
| ATOM | 1808 | OH  | TYR | A | 232 | 36.734 | 53.282 | 58.698 | 1.00 | 51.92  |
| ATOM | 1809 | N   | GLU | A | 233 | 30.191 | 52.883 | 56.519 | 1.00 | 35.75  |
| ATOM | 1810 | CA  | GLU | A | 233 | 29.835 | 51.984 | 57.606 | 1.00 | 34.55  |
| ATOM | 1811 | C   | GLU | A | 233 | 29.633 | 50.498 | 57.252 | 1.00 | 38.39  |
| ATOM | 1812 | O   | GLU | A | 233 | 30.152 | 49.576 | 57.892 | 1.00 | 38.55  |
| ATOM | 1813 | CB  | GLU | A | 233 | 28.673 | 52.623 | 58.414 | 1.00 | 34.48  |
| ATOM | 1814 | CG  | GLU | A | 233 | 28.666 | 52.262 | 59.912 | 1.00 | 24.95  |
| ATOM | 1815 | CD  | GLU | A | 233 | 29.463 | 53.183 | 60.787 | 1.00 | 37.55  |
| ATOM | 1816 | OE1 | GLU | A | 233 | 29.408 | 54.410 | 60.741 | 1.00 | 55.33  |
| ATOM | 1817 | OE2 | GLU | A | 233 | 30.216 | 52.518 | 61.619 | 1.00 | 40.65  |
| ATOM | 1818 | N   | PHE | A | 234 | 28.867 | 50.282 | 56.202 | 1.00 | 33.02  |
| ATOM | 1819 | CA  | PHE | A | 234 | 28.493 | 48.974 | 55.719 | 1.00 | 29.90  |
| ATOM | 1820 | C   | PHE | A | 234 | 29.341 | 48.398 | 54.592 | 1.00 | 34.69  |
| ATOM | 1821 | O   | PHE | A | 234 | 28.883 | 47.521 | 53.823 | 1.00 | 34.21  |
| ATOM | 1822 | CB  | PHE | A | 234 | 27.020 | 49.081 | 55.293 | 1.00 | 30.23  |
| ATOM | 1823 | CG  | PHE | A | 234 | 26.215 | 49.752 | 56.394 | 1.00 | 30.32  |
| ATOM | 1824 | CD1 | PHE | A | 234 | 26.518 | 49.521 | 57.739 | 1.00 | 31.50  |
| ATOM | 1825 | CD2 | PHE | A | 234 | 25.151 | 50.605 | 56.102 | 1.00 | 28.66  |
| ATOM | 1826 | CE1 | PHE | A | 234 | 25.780 | 50.103 | 58.772 | 1.00 | 30.43  |
| ATOM | 1827 | CE2 | PHE | A | 234 | 24.407 | 51.203 | 57.121 | 1.00 | 29.60  |
| ATOM | 1828 | CZ  | PHE | A | 234 | 24.725 | 50.959 | 58.458 | 1.00 | 27.47  |
| ATOM | 1829 | N   | SER | A | 235 | 30.571 | 48.874 | 54.476 | 1.00 | 29.55  |
| ATOM | 1830 | CA  | SER | A | 235 | 31.428 | 48.366 | 53.412 | 1.00 | 28.64  |
| ATOM | 1831 | C   | SER | A | 235 | 31.387 | 46.858 | 53.338 | 1.00 | 30.38  |
| ATOM | 1832 | O   | SER | A | 235 | 31.166 | 46.252 | 52.282 | 1.00 | 32.37  |

TABLE 9-continued

Structure coordinates of LTA₄ hydrolase-thiolamine complex
(The amino acid sequence set forth as residues 1-610 below correspond to SEQ ID NO:1.)

| ATOM | 1833 | CB  | SER | A | 235 | 32.861 | 48.787 | 53.604 | 1.00 | 31.15  |
|------|------|-----|-----|---|-----|--------|--------|--------|------|--------|
| ATOM | 1834 | OG  | SER | A | 235 | 33.028 | 49.368 | 54.873 | 1.00 | 39.32  |
| ATOM | 1835 | N   | GLU | A | 236 | 31.698 | 46.299 | 54.504 | 1.00 | 22.49  |
| ATOM | 1836 | CA  | GLU | A | 236 | 31.815 | 44.873 | 54.737 | 1.00 | 23.79  |
| ATOM | 1837 | C   | GLU | A | 236 | 30.627 | 43.992 | 54.380 | 1.00 | 32.37  |
| ATOM | 1838 | O   | GLU | A | 236 | 30.697 | 42.772 | 54.545 | 1.00 | 29.91  |
| ATOM | 1839 | CB  | GLU | A | 236 | 32.305 | 44.529 | 56.134 | 1.00 | 24.06  |
| ATOM | 1840 | CG  | GLU | A | 236 | 33.491 | 45.403 | 56.585 | 1.00 | 22.96  |
| ATOM | 1841 | CD  | GLU | A | 236 | 33.600 | 45.492 | 58.090 | 1.00 | 66.18  |
| ATOM | 1842 | OE1 | GLU | A | 236 | 32.633 | 45.482 | 58.849 | 1.00 | 37.01  |
| ATOM | 1843 | OE2 | GLU | A | 236 | 34.848 | 45.518 | 58.494 | 1.00 | 78.68  |
| ATOM | 1844 | N   | THR | A | 237 | 29.560 | 44.593 | 53.891 | 1.00 | 34.11  |
| ATOM | 1845 | CA  | THR | A | 237 | 28.384 | 43.823 | 53.539 | 1.00 | 33.69  |
| ATOM | 1846 | C   | THR | A | 237 | 28.644 | 42.609 | 52.644 | 1.00 | 33.33  |
| ATOM | 1847 | O   | THR | A | 237 | 28.517 | 41.451 | 53.048 | 1.00 | 31.09  |
| ATOM | 1848 | CB  | THR | A | 237 | 27.218 | 44.710 | 53.057 | 1.00 | 37.99  |
| ATOM | 1849 | OG1 | THR | A | 237 | 26.899 | 45.675 | 54.048 | 1.00 | 33.49  |
| ATOM | 1850 | CG2 | THR | A | 237 | 25.995 | 43.862 | 52.744 | 1.00 | 25.66  |
| ATOM | 1851 | N   | GLU | A | 238 | 29.020 | 42.854 | 51.409 | 1.00 | 29.69  |
| ATOM | 1852 | CA  | GLU | A | 238 | 29.267 | 41.734 | 50.520 | 1.00 | 27.05  |
| ATOM | 1853 | C   | GLU | A | 238 | 30.071 | 40.638 | 51.146 | 1.00 | 33.17  |
| ATOM | 1854 | O   | GLU | A | 238 | 29.660 | 39.497 | 51.055 | 1.00 | 38.50  |
| ATOM | 1855 | CB  | GLU | A | 238 | 29.851 | 42.080 | 49.161 | 1.00 | 27.50  |
| ATOM | 1856 | CG  | GLU | A | 238 | 30.116 | 40.813 | 48.320 | 1.00 | 18.83  |
| ATOM | 1857 | CD  | GLU | A | 238 | 28.902 | 40.297 | 47.596 | 1.00 | 41.67  |
| ATOM | 1858 | OE1 | GLU | A | 238 | 27.848 | 40.909 | 47.464 | 1.00 | 33.59  |
| ATOM | 1859 | OE2 | GLU | A | 238 | 29.085 | 39.089 | 47.138 | 1.00 | 46.30  |
| ATOM | 1860 | N   | SER | A | 239 | 31.203 | 40.973 | 51.772 | 1.00 | 24.44  |
| ATOM | 1861 | CA  | SER | A | 239 | 32.045 | 39.957 | 52.387 | 1.00 | 24.60  |
| ATOM | 1862 | C   | SER | A | 239 | 31.245 | 39.060 | 53.344 | 1.00 | 35.72  |
| ATOM | 1863 | O   | SER | A | 239 | 31.379 | 37.830 | 53.360 | 1.00 | 35.25  |
| ATOM | 1864 | CB  | SER | A | 239 | 33.231 | 40.601 | 53.074 | 1.00 | 29.14  |
| ATOM | 1865 | OG  | SER | A | 239 | 32.747 | 41.590 | 53.961 | 1.00 | 54.60  |
| ATOM | 1866 | N   | MET | A | 240 | 30.382 | 39.703 | 54.154 | 1.00 | 33.13  |
| ATOM | 1867 | CA  | MET | A | 240 | 29.529 | 38.993 | 55.091 | 1.00 | 28.55  |
| ATOM | 1868 | C   | MET | A | 240 | 28.603 | 38.075 | 54.325 | 1.00 | 35.65  |
| ATOM | 1869 | O   | MET | A | 240 | 28.435 | 36.926 | 54.689 | 1.00 | 35.99  |
| ATOM | 1870 | CB  | MET | A | 240 | 28.736 | 39.945 | 55.993 | 1.00 | 26.50  |
| ATOM | 1871 | CG  | MET | A | 240 | 29.691 | 40.675 | 56.910 | 1.00 | 27.57  |
| ATOM | 1872 | SD  | MET | A | 240 | 28.871 | 41.986 | 57.833 | 1.00 | 32.91  |
| ATOM | 1873 | CE  | MET | A | 240 | 30.040 | 42.085 | 59.183 | 1.00 | 28.47  |
| ATOM | 1874 | N   | LEU | A | 241 | 28.019 | 38.603 | 53.243 | 1.00 | 32.77  |
| ATOM | 1875 | CA  | LEU | A | 241 | 27.120 | 37.859 | 52.381 | 1.00 | 29.87  |
| ATOM | 1876 | C   | LEU | A | 241 | 27.848 | 36.615 | 51.878 | 1.00 | 36.76  |
| ATOM | 1877 | O   | LEU | A | 241 | 27.302 | 35.509 | 51.858 | 1.00 | 36.97  |
| ATOM | 1878 | CB  | LEU | A | 241 | 26.715 | 38.753 | 51.196 | 1.00 | 29.71  |
| ATOM | 1879 | CG  | LEU | A | 241 | 25.283 | 39.289 | 51.237 | 1.00 | 37.68  |
| ATOM | 1880 | CD1 | LEU | A | 241 | 25.174 | 40.552 | 50.389 | 1.00 | 35.76  |
| ATOM | 1881 | CD2 | LEU | A | 241 | 24.309 | 38.257 | 50.673 | 1.00 | 45.60  |
| ATOM | 1882 | N   | LYS | A | 242 | 29.114 | 36.806 | 51.468 | 1.00 | 34.76  |
| ATOM | 1883 | CA  | LYS | A | 242 | 29.908 | 35.702 | 50.972 | 1.00 | 33.62  |
| ATOM | 1884 | C   | LYS | A | 242 | 30.072 | 34.690 | 52.039 | 1.00 | 32.18  |
| ATOM | 1885 | O   | LYS | A | 242 | 29.887 | 33.512 | 51.795 | 1.00 | 32.56  |
| ATOM | 1886 | CB  | LYS | A | 242 | 31.292 | 36.069 | 50.468 | 1.00 | 38.43  |
| ATOM | 1887 | CG  | LYS | A | 242 | 31.406 | 36.263 | 48.961 | 1.00 | 49.23  |
| ATOM | 1888 | CD  | LYS | A | 242 | 31.160 | 37.721 | 48.536 | 1.00 | 88.36  |
| ATOM | 1889 | CE  | LYS | A | 242 | 32.371 | 38.456 | 47.943 | 1.00 | 100.00 |
| ATOM | 1890 | NZ  | LYS | A | 242 | 32.033 | 39.411 | 46.862 | 1.00 | 100.00 |
| ATOM | 1891 | N   | ILE | A | 243 | 30.428 | 35.154 | 53.227 | 1.00 | 30.87  |
| ATOM | 1892 | CA  | ILE | A | 243 | 30.627 | 34.229 | 54.359 | 1.00 | 31.70  |
| ATOM | 1893 | C   | ILE | A | 243 | 29.381 | 33.458 | 54.764 | 1.00 | 36.50  |
| ATOM | 1894 | O   | ILE | A | 243 | 29.458 | 32.303 | 55.119 | 1.00 | 39.33  |
| ATOM | 1895 | CB  | ILE | A | 243 | 31.227 | 34.886 | 55.579 | 1.00 | 32.36  |
| ATOM | 1896 | CG1 | ILE | A | 243 | 32.630 | 35.337 | 55.222 | 1.00 | 32.09  |
| ATOM | 1897 | CG2 | ILE | A | 243 | 31.243 | 33.891 | 56.718 | 1.00 | 28.26  |
| ATOM | 1898 | CD1 | ILE | A | 243 | 33.035 | 36.578 | 55.981 | 1.00 | 20.09  |
| ATOM | 1899 | N   | ALA | A | 244 | 28.237 | 34.120 | 54.708 | 1.00 | 32.10  |
| ATOM | 1900 | CA  | ALA | A | 244 | 26.968 | 33.519 | 55.066 | 1.00 | 32.95  |
| ATOM | 1901 | C   | ALA | A | 244 | 26.600 | 32.392 | 54.127 | 1.00 | 36.35  |
| ATOM | 1902 | O   | ALA | A | 244 | 26.074 | 31.358 | 54.546 | 1.00 | 36.88  |
| ATOM | 1903 | CB  | ALA | A | 244 | 25.858 | 34.576 | 55.123 | 1.00 | 34.02  |
| ATOM | 1904 | N   | GLU | A | 245 | 26.890 | 32.617 | 52.846 | 1.00 | 31.20  |
| ATOM | 1905 | CA  | GLU | A | 245 | 26.614 | 31.635 | 51.818 | 1.00 | 29.26  |
| ATOM | 1906 | C   | GLU | A | 245 | 27.360 | 30.354 | 52.092 | 1.00 | 35.18  |
| ATOM | 1907 | O   | GLU | A | 245 | 26.849 | 29.276 | 51.800 | 1.00 | 36.21  |
| ATOM | 1908 | CB  | GLU | A | 245 | 26.908 | 32.177 | 50.421 | 1.00 | 30.22  |

TABLE 9-continued

Structure coordinates of LTA$_4$ hydrolase-thiolamine complex
(The amino acid sequence set forth as residues 1-610 below correspond to SEQ ID NO:1.)

| ATOM | 1909 | CG | GLU | A | 245 | 25.701 | 32.938 | 49.842 | 1.00 | 39.79 |
|------|------|-----|-----|---|-----|--------|--------|--------|------|-------|
| ATOM | 1910 | CD | GLU | A | 245 | 26.026 | 33.564 | 48.529 | 1.00 | 51.91 |
| ATOM | 1911 | OE1 | GLU | A | 245 | 26.945 | 34.351 | 48.358 | 1.00 | 34.19 |
| ATOM | 1912 | OE2 | GLU | A | 245 | 25.246 | 33.142 | 47.585 | 1.00 | 47.48 |
| ATOM | 1913 | N | ASP | A | 246 | 28.570 | 30.484 | 52.680 | 1.00 | 32.29 |
| ATOM | 1914 | CA | ASP | A | 246 | 29.417 | 29.350 | 53.033 | 1.00 | 30.70 |
| ATOM | 1915 | C | ASP | A | 246 | 28.848 | 28.645 | 54.230 | 1.00 | 35.47 |
| ATOM | 1916 | O | ASP | A | 246 | 28.881 | 27.417 | 54.347 | 1.00 | 37.08 |
| ATOM | 1917 | CB | ASP | A | 246 | 30.873 | 29.717 | 53.355 | 1.00 | 33.17 |
| ATOM | 1918 | CG | ASP | A | 246 | 31.709 | 28.473 | 53.413 | 1.00 | 64.49 |
| ATOM | 1919 | OD1 | ASP | A | 246 | 31.934 | 27.789 | 52.437 | 1.00 | 67.15 |
| ATOM | 1920 | OD2 | ASP | A | 246 | 32.118 | 28.167 | 54.622 | 1.00 | 79.01 |
| ATOM | 1921 | N | LEU | A | 247 | 28.323 | 29.434 | 55.134 | 1.00 | 33.59 |
| ATOM | 1922 | CA | LEU | A | 247 | 27.731 | 28.868 | 56.334 | 1.00 | 36.70 |
| ATOM | 1923 | C | LEU | A | 247 | 26.355 | 28.208 | 56.083 | 1.00 | 35.92 |
| ATOM | 1924 | O | LEU | A | 247 | 26.060 | 27.110 | 56.551 | 1.00 | 30.77 |
| ATOM | 1925 | CB | LEU | A | 247 | 27.562 | 29.954 | 57.435 | 1.00 | 38.34 |
| ATOM | 1926 | CG | LEU | A | 247 | 28.732 | 30.100 | 58.394 | 1.00 | 44.30 |
| ATOM | 1927 | CD1 | LEU | A | 247 | 29.341 | 28.738 | 58.641 | 1.00 | 48.20 |
| ATOM | 1928 | CD2 | LEU | A | 247 | 29.779 | 31.013 | 57.815 | 1.00 | 35.25 |
| ATOM | 1929 | N | GLY | A | 248 | 25.471 | 28.887 | 55.353 | 1.00 | 34.97 |
| ATOM | 1930 | CA | GLY | A | 248 | 24.160 | 28.315 | 55.181 | 1.00 | 36.00 |
| ATOM | 1931 | C | GLY | A | 248 | 23.754 | 27.976 | 53.778 | 1.00 | 37.99 |
| ATOM | 1932 | O | GLY | A | 248 | 22.637 | 27.524 | 53.526 | 1.00 | 38.13 |
| ATOM | 1933 | N | GLY | A | 249 | 24.637 | 28.158 | 52.849 | 1.00 | 30.74 |
| ATOM | 1934 | CA | GLY | A | 249 | 24.203 | 27.852 | 51.526 | 1.00 | 30.15 |
| ATOM | 1935 | C | GLY | A | 249 | 23.918 | 29.131 | 50.759 | 1.00 | 38.91 |
| ATOM | 1936 | O | GLY | A | 249 | 24.126 | 30.240 | 51.238 | 1.00 | 41.32 |
| ATOM | 1937 | N | PRO | A | 250 | 23.453 | 28.946 | 49.547 | 1.00 | 38.93 |
| ATOM | 1938 | CA | PRO | A | 250 | 23.173 | 30.021 | 48.639 | 1.00 | 38.03 |
| ATOM | 1939 | C | PRO | A | 250 | 22.203 | 31.078 | 49.096 | 1.00 | 42.17 |
| ATOM | 1940 | O | PRO | A | 250 | 21.258 | 30.823 | 49.840 | 1.00 | 45.20 |
| ATOM | 1941 | CB | PRO | A | 250 | 22.663 | 29.357 | 47.352 | 1.00 | 39.18 |
| ATOM | 1942 | CG | PRO | A | 250 | 22.952 | 27.864 | 47.436 | 1.00 | 41.01 |
| ATOM | 1943 | CD | PRO | A | 250 | 23.396 | 27.610 | 48.865 | 1.00 | 38.57 |
| ATOM | 1944 | N | TYR | A | 251 | 22.486 | 32.275 | 48.600 | 1.00 | 35.37 |
| ATOM | 1945 | CA | TYR | A | 251 | 21.692 | 33.461 | 48.817 | 1.00 | 34.87 |
| ATOM | 1946 | C | TYR | A | 251 | 20.740 | 33.479 | 47.649 | 1.00 | 39.55 |
| ATOM | 1947 | O | TYR | A | 251 | 21.125 | 33.794 | 46.535 | 1.00 | 42.57 |
| ATOM | 1948 | CB | TYR | A | 251 | 22.540 | 34.759 | 48.790 | 1.00 | 35.07 |
| ATOM | 1949 | CG | TYR | A | 251 | 21.711 | 35.980 | 49.119 | 1.00 | 35.25 |
| ATOM | 1950 | CD1 | TYR | A | 251 | 21.341 | 36.229 | 50.441 | 1.00 | 33.14 |
| ATOM | 1951 | CD2 | TYR | A | 251 | 21.260 | 36.846 | 48.121 | 1.00 | 37.98 |
| ATOM | 1952 | CE1 | TYR | A | 251 | 20.575 | 37.341 | 50.781 | 1.00 | 28.05 |
| ATOM | 1953 | CE2 | TYR | A | 251 | 20.492 | 37.967 | 48.443 | 1.00 | 40.05 |
| ATOM | 1954 | CZ | TYR | A | 251 | 20.160 | 38.213 | 49.777 | 1.00 | 42.84 |
| ATOM | 1955 | OH | TYR | A | 251 | 19.409 | 39.307 | 50.112 | 1.00 | 39.70 |
| ATOM | 1956 | N | VAL | A | 252 | 19.510 | 33.102 | 47.914 | 1.00 | 32.21 |
| ATOM | 1957 | CA | VAL | A | 252 | 18.495 | 33.003 | 46.899 | 1.00 | 30.05 |
| ATOM | 1958 | C | VAL | A | 252 | 17.708 | 34.279 | 46.631 | 1.00 | 38.47 |
| ATOM | 1959 | O | VAL | A | 252 | 17.000 | 34.340 | 45.640 | 1.00 | 40.65 |
| ATOM | 1960 | CB | VAL | A | 252 | 17.560 | 31.845 | 47.253 | 1.00 | 31.27 |
| ATOM | 1961 | CG1 | VAL | A | 252 | 18.378 | 30.605 | 47.643 | 1.00 | 28.15 |
| ATOM | 1962 | CG2 | VAL | A | 252 | 16.614 | 32.234 | 48.405 | 1.00 | 30.93 |
| ATOM | 1963 | N | TRP | A | 253 | 17.800 | 35.292 | 47.504 | 1.00 | 32.44 |
| ATOM | 1964 | CA | TRP | A | 253 | 17.041 | 36.509 | 47.309 | 1.00 | 30.93 |
| ATOM | 1965 | C | TRP | A | 253 | 17.468 | 37.341 | 46.119 | 1.00 | 43.56 |
| ATOM | 1966 | O | TRP | A | 253 | 16.690 | 38.119 | 45.568 | 1.00 | 46.70 |
| ATOM | 1967 | CB | TRP | A | 253 | 16.898 | 37.302 | 48.606 | 1.00 | 29.65 |
| ATOM | 1968 | CG | TRP | A | 253 | 16.364 | 36.369 | 49.625 | 1.00 | 30.19 |
| ATOM | 1969 | CD1 | TRP | A | 253 | 17.086 | 35.546 | 50.413 | 1.00 | 32.81 |
| ATOM | 1970 | CD2 | TRP | A | 253 | 14.989 | 36.110 | 49.913 | 1.00 | 29.63 |
| ATOM | 1971 | NE1 | TRP | A | 253 | 16.251 | 34.794 | 51.194 | 1.00 | 30.69 |
| ATOM | 1972 | CE2 | TRP | A | 253 | 14.955 | 35.128 | 50.912 | 1.00 | 31.50 |
| ATOM | 1973 | CE3 | TRP | A | 253 | 13.789 | 36.637 | 49.450 | 1.00 | 30.18 |
| ATOM | 1974 | CZ2 | TRP | A | 253 | 13.746 | 34.657 | 51.433 | 1.00 | 30.31 |
| ATOM | 1975 | CZ3 | TRP | A | 253 | 12.600 | 36.164 | 49.958 | 1.00 | 31.14 |
| ATOM | 1976 | CH2 | TRP | A | 253 | 12.579 | 35.176 | 50.946 | 1.00 | 31.37 |
| ATOM | 1977 | N | GLY | A | 254 | 18.697 | 37.182 | 45.675 | 1.00 | 42.35 |
| ATOM | 1978 | CA | GLY | A | 254 | 19.101 | 37.944 | 44.509 | 1.00 | 41.34 |
| ATOM | 1979 | C | GLY | A | 254 | 19.875 | 39.192 | 44.858 | 1.00 | 45.47 |
| ATOM | 1980 | O | GLY | A | 254 | 21.079 | 39.236 | 44.671 | 1.00 | 45.89 |
| ATOM | 1981 | N | GLN | A | 255 | 19.160 | 40.210 | 45.351 | 1.00 | 41.86 |
| ATOM | 1982 | CA | GLN | A | 255 | 19.746 | 41.488 | 45.675 | 1.00 | 38.67 |
| ATOM | 1983 | C | GLN | A | 255 | 19.576 | 41.776 | 47.153 | 1.00 | 40.18 |
| ATOM | 1984 | O | GLN | A | 255 | 18.494 | 41.811 | 47.659 | 1.00 | 38.67 |

TABLE 9-continued

Structure coordinates of LTA₄ hydrolase-thiolamine complex
(The amino acid sequence set forth as residues 1-610 below correspond to SEQ ID NO:1.)

| ATOM | 1985 | CB | GLN | A | 255 | 19.023 | 42.552 | 44.836 | 1.00 | 37.82 |
|---|---|---|---|---|---|---|---|---|---|---|
| ATOM | 1986 | CG | GLN | A | 255 | 19.455 | 43.979 | 45.169 | 1.00 | 50.17 |
| ATOM | 1987 | CD | GLN | A | 255 | 20.618 | 44.368 | 44.283 | 1.00 | 62.88 |
| ATOM | 1988 | OE1 | GLN | A | 255 | 21.104 | 43.612 | 43.463 | 1.00 | 55.76 |
| ATOM | 1989 | NE2 | GLN | A | 255 | 21.057 | 45.625 | 44.479 | 1.00 | 34.97 |
| ATOM | 1990 | N | TYR | A | 256 | 20.716 | 41.900 | 47.866 | 1.00 | 33.01 |
| ATOM | 1991 | CA | TYR | A | 256 | 20.651 | 42.361 | 49.258 | 1.00 | 28.69 |
| ATOM | 1992 | C | TYR | A | 256 | 20.891 | 43.854 | 49.329 | 1.00 | 26.72 |
| ATOM | 1993 | O | TYR | A | 256 | 21.963 | 44.321 | 49.225 | 1.00 | 24.22 |
| ATOM | 1994 | CB | TYR | A | 256 | 21.743 | 41.629 | 50.075 | 1.00 | 29.99 |
| ATOM | 1995 | CG | TYR | A | 256 | 21.567 | 41.867 | 51.556 | 1.00 | 35.47 |
| ATOM | 1996 | CD1 | TYR | A | 256 | 20.582 | 41.200 | 52.250 | 1.00 | 35.76 |
| ATOM | 1997 | CD2 | TYR | A | 256 | 22.405 | 42.746 | 52.239 | 1.00 | 37.52 |
| ATOM | 1998 | CE1 | TYR | A | 256 | 20.436 | 41.396 | 53.599 | 1.00 | 25.80 |
| ATOM | 1999 | CE2 | TYR | A | 256 | 22.255 | 42.946 | 53.588 | 1.00 | 39.10 |
| ATOM | 2000 | CZ | TYR | A | 256 | 21.283 | 42.275 | 54.268 | 1.00 | 31.78 |
| ATOM | 2001 | OH | TYR | A | 256 | 21.153 | 42.433 | 55.631 | 1.00 | 37.35 |
| ATOM | 2002 | N | ASP | A | 257 | 19.834 | 44.613 | 49.463 | 1.00 | 23.26 |
| ATOM | 2003 | CA | ASP | A | 257 | 20.077 | 46.027 | 49.621 | 1.00 | 23.47 |
| ATOM | 2004 | C | ASP | A | 257 | 19.977 | 46.444 | 51.071 | 1.00 | 35.90 |
| ATOM | 2005 | O | ASP | A | 257 | 19.729 | 45.661 | 51.967 | 1.00 | 39.48 |
| ATOM | 2006 | CB | ASP | A | 257 | 19.073 | 46.803 | 48.758 | 1.00 | 24.13 |
| ATOM | 2007 | CG | ASP | A | 257 | 19.689 | 47.030 | 47.388 | 1.00 | 38.50 |
| ATOM | 2008 | OD1 | ASP | A | 257 | 20.843 | 46.675 | 47.220 | 1.00 | 42.61 |
| ATOM | 2009 | OD2 | ASP | A | 257 | 19.020 | 47.555 | 46.517 | 1.00 | 29.02 |
| ATOM | 2010 | N | LEU | A | 258 | 20.370 | 47.661 | 51.386 | 1.00 | 30.86 |
| ATOM | 2011 | CA | LEU | A | 258 | 20.306 | 48.159 | 52.735 | 1.00 | 27.50 |
| ATOM | 2012 | C | LEU | A | 258 | 19.526 | 49.466 | 52.765 | 1.00 | 36.37 |
| ATOM | 2013 | O | LEU | A | 258 | 19.620 | 50.302 | 51.840 | 1.00 | 37.98 |
| ATOM | 2014 | CB | LEU | A | 258 | 21.727 | 48.442 | 53.274 | 1.00 | 24.71 |
| ATOM | 2015 | CG | LEU | A | 258 | 22.552 | 47.191 | 53.491 | 1.00 | 31.13 |
| ATOM | 2016 | CD1 | LEU | A | 258 | 23.913 | 47.567 | 54.043 | 1.00 | 30.89 |
| ATOM | 2017 | CD2 | LEU | A | 258 | 21.854 | 46.282 | 54.500 | 1.00 | 33.65 |
| ATOM | 2018 | N | LEU | A | 259 | 18.762 | 49.632 | 53.838 | 1.00 | 29.87 |
| ATOM | 2019 | CA | LEU | A | 259 | 18.006 | 50.849 | 54.052 | 1.00 | 28.43 |
| ATOM | 2020 | C | LEU | A | 259 | 18.283 | 51.453 | 55.446 | 1.00 | 31.30 |
| ATOM | 2021 | O | LEU | A | 259 | 18.055 | 50.819 | 56.477 | 1.00 | 31.19 |
| ATOM | 2022 | CB | LEU | A | 259 | 16.500 | 50.809 | 53.693 | 1.00 | 27.63 |
| ATOM | 2023 | CG | LEU | A | 259 | 15.706 | 51.980 | 54.298 | 1.00 | 31.51 |
| ATOM | 2024 | CD1 | LEU | A | 259 | 16.026 | 53.300 | 53.605 | 1.00 | 32.32 |
| ATOM | 2025 | CD2 | LEU | A | 259 | 14.212 | 51.731 | 54.253 | 1.00 | 26.87 |
| ATOM | 2026 | N | VAL | A | 260 | 18.807 | 52.683 | 55.447 | 1.00 | 25.88 |
| ATOM | 2027 | CA | VAL | A | 260 | 19.105 | 53.435 | 56.638 | 1.00 | 25.99 |
| ATOM | 2028 | C | VAL | A | 260 | 17.896 | 54.336 | 56.796 | 1.00 | 34.83 |
| ATOM | 2029 | O | VAL | A | 260 | 17.647 | 55.187 | 55.959 | 1.00 | 41.92 |
| ATOM | 2030 | CB | VAL | A | 260 | 20.390 | 54.234 | 56.408 | 1.00 | 29.97 |
| ATOM | 2031 | CG1 | VAL | A | 260 | 20.701 | 55.179 | 57.592 | 1.00 | 32.08 |
| ATOM | 2032 | CG2 | VAL | A | 260 | 21.563 | 53.295 | 56.130 | 1.00 | 26.15 |
| ATOM | 2033 | N | LEU | A | 261 | 17.098 | 54.120 | 57.815 | 1.00 | 28.41 |
| ATOM | 2034 | CA | LEU | A | 261 | 15.865 | 54.878 | 58.024 | 1.00 | 25.52 |
| ATOM | 2035 | C | LEU | A | 261 | 16.016 | 56.054 | 58.948 | 1.00 | 29.42 |
| ATOM | 2036 | O | LEU | A | 261 | 17.090 | 56.300 | 59.489 | 1.00 | 29.96 |
| ATOM | 2037 | CB | LEU | A | 261 | 14.874 | 53.921 | 58.706 | 1.00 | 25.70 |
| ATOM | 2038 | CG | LEU | A | 261 | 14.387 | 52.877 | 57.740 | 1.00 | 33.14 |
| ATOM | 2039 | CD1 | LEU | A | 261 | 15.161 | 51.571 | 57.929 | 1.00 | 32.73 |
| ATOM | 2040 | CD2 | LEU | A | 261 | 12.900 | 52.686 | 57.935 | 1.00 | 43.74 |
| ATOM | 2041 | N | PRO | A | 262 | 14.903 | 56.758 | 59.142 | 1.00 | 28.52 |
| ATOM | 2042 | CA | PRO | A | 262 | 14.894 | 57.870 | 60.047 | 1.00 | 28.50 |
| ATOM | 2043 | C | PRO | A | 262 | 15.152 | 57.294 | 61.432 | 1.00 | 35.36 |
| ATOM | 2044 | O | PRO | A | 262 | 14.866 | 56.124 | 61.683 | 1.00 | 34.52 |
| ATOM | 2045 | CB | PRO | A | 262 | 13.512 | 58.512 | 59.971 | 1.00 | 29.19 |
| ATOM | 2046 | CG | PRO | A | 262 | 12.707 | 57.719 | 58.964 | 1.00 | 34.34 |
| ATOM | 2047 | CD | PRO | A | 262 | 13.581 | 56.575 | 58.492 | 1.00 | 30.63 |
| ATOM | 2048 | N | PRO | A | 263 | 15.706 | 58.105 | 62.327 | 1.00 | 31.50 |
| ATOM | 2049 | CA | PRO | A | 263 | 16.060 | 57.657 | 63.673 | 1.00 | 28.77 |
| ATOM | 2050 | C | PRO | A | 263 | 14.966 | 57.021 | 64.493 | 1.00 | 29.15 |
| ATOM | 2051 | O | PRO | A | 263 | 15.256 | 56.335 | 65.434 | 1.00 | 26.36 |
| ATOM | 2052 | CB | PRO | A | 263 | 16.652 | 58.867 | 64.392 | 1.00 | 29.16 |
| ATOM | 2053 | CG | PRO | A | 263 | 16.851 | 59.954 | 63.335 | 1.00 | 31.55 |
| ATOM | 2054 | CD | PRO | A | 263 | 15.994 | 59.558 | 62.138 | 1.00 | 29.17 |
| ATOM | 2055 | N | SER | A | 264 | 13.712 | 57.258 | 64.143 | 1.00 | 33.87 |
| ATOM | 2056 | CA | SER | A | 264 | 12.578 | 56.703 | 64.864 | 1.00 | 33.81 |
| ATOM | 2057 | C | SER | A | 264 | 12.403 | 55.223 | 64.604 | 1.00 | 37.36 |
| ATOM | 2058 | O | SER | A | 264 | 11.529 | 54.570 | 65.201 | 1.00 | 39.61 |
| ATOM | 2059 | CB | SER | A | 264 | 11.280 | 57.423 | 64.576 | 1.00 | 35.61 |
| ATOM | 2060 | OG | SER | A | 264 | 10.955 | 57.276 | 63.201 | 1.00 | 53.45 |

TABLE 9-continued

Structure coordinates of LTA₄ hydrolase-thiolamine complex
(The amino acid sequence set forth as residues 1-610 below correspond to SEQ ID NO:1.)

| ATOM | 2061 | N | PHE | A | 265 | 13.213 | 54.684 | 63.710 | 1.00 | 29.00 |
|------|------|------|-----|---|-----|--------|--------|--------|------|-------|
| ATOM | 2062 | CA | PHE | A | 265 | 13.136 | 53.256 | 63.453 | 1.00 | 28.56 |
| ATOM | 2063 | C | PHE | A | 265 | 13.260 | 52.491 | 64.787 | 1.00 | 28.49 |
| ATOM | 2064 | O | PHE | A | 265 | 14.208 | 52.675 | 65.533 | 1.00 | 27.36 |
| ATOM | 2065 | CB | PHE | A | 265 | 14.200 | 52.833 | 62.454 | 1.00 | 31.40 |
| ATOM | 2066 | CG | PHE | A | 265 | 13.875 | 51.458 | 62.028 | 1.00 | 34.51 |
| ATOM | 2067 | CD1 | PHE | A | 265 | 12.601 | 51.174 | 61.543 | 1.00 | 35.11 |
| ATOM | 2068 | CD2 | PHE | A | 265 | 14.814 | 50.435 | 62.156 | 1.00 | 38.94 |
| ATOM | 2069 | CE1 | PHE | A | 265 | 12.282 | 49.876 | 61.154 | 1.00 | 37.42 |
| ATOM | 2070 | CE2 | PHE | A | 265 | 14.511 | 49.131 | 61.772 | 1.00 | 42.65 |
| ATOM | 2071 | CZ | PHE | A | 265 | 13.236 | 48.860 | 61.274 | 1.00 | 40.14 |
| ATOM | 2072 | N | PRO | A | 266 | 12.272 | 51.650 | 65.128 | 1.00 | 24.06 |
| ATOM | 2073 | CA | PRO | A | 266 | 12.249 | 50.945 | 66.419 | 1.00 | 20.62 |
| ATOM | 2074 | C | PRO | A | 266 | 13.231 | 49.794 | 66.701 | 1.00 | 29.34 |
| ATOM | 2075 | O | PRO | A | 266 | 13.343 | 49.364 | 67.847 | 1.00 | 28.17 |
| ATOM | 2076 | CB | PRO | A | 266 | 10.808 | 50.463 | 66.593 | 1.00 | 19.16 |
| ATOM | 2077 | CG | PRO | A | 266 | 10.076 | 50.686 | 65.281 | 1.00 | 21.07 |
| ATOM | 2078 | CD | PRO | A | 266 | 11.046 | 51.355 | 64.325 | 1.00 | 19.44 |
| ATOM | 2079 | N | TYR | A | 267 | 13.922 | 49.280 | 65.676 | 1.00 | 27.23 |
| ATOM | 2080 | CA | TYR | A | 267 | 14.849 | 48.160 | 65.817 | 1.00 | 25.74 |
| ATOM | 2081 | C | TYR | A | 267 | 16.181 | 48.454 | 65.189 | 1.00 | 32.57 |
| ATOM | 2082 | O | TYR | A | 267 | 16.281 | 49.316 | 64.324 | 1.00 | 32.48 |
| ATOM | 2083 | CB | TYR | A | 267 | 14.298 | 46.903 | 65.121 | 1.00 | 25.07 |
| ATOM | 2084 | CG | TYR | A | 267 | 12.968 | 46.502 | 65.674 | 1.00 | 24.45 |
| ATOM | 2085 | CD1 | TYR | A | 267 | 12.915 | 45.765 | 66.856 | 1.00 | 27.05 |
| ATOM | 2086 | CD2 | TYR | A | 267 | 11.776 | 46.851 | 65.037 | 1.00 | 22.15 |
| ATOM | 2087 | CE1 | TYR | A | 267 | 11.697 | 45.387 | 67.419 | 1.00 | 25.01 |
| ATOM | 2088 | CE2 | TYR | A | 267 | 10.548 | 46.496 | 65.596 | 1.00 | 19.09 |
| ATOM | 2089 | CZ | TYR | A | 267 | 10.510 | 45.767 | 66.786 | 1.00 | 17.98 |
| ATOM | 2090 | OH | TYR | A | 267 | 9.302 | 45.416 | 67.353 | 1.00 | 19.51 |
| ATOM | 2091 | N | GLY | A | 268 | 17.196 | 47.698 | 65.627 | 1.00 | 30.22 |
| ATOM | 2092 | CA | GLY | A | 268 | 18.547 | 47.826 | 65.114 | 1.00 | 27.29 |
| ATOM | 2093 | C | GLY | A | 268 | 18.485 | 47.620 | 63.614 | 1.00 | 29.82 |
| ATOM | 2094 | O | GLY | A | 268 | 19.136 | 48.297 | 62.836 | 1.00 | 32.99 |
| ATOM | 2095 | N | GLY | A | 269 | 17.637 | 46.676 | 63.228 | 1.00 | 23.19 |
| ATOM | 2096 | CA | GLY | A | 269 | 17.393 | 46.320 | 61.853 | 1.00 | 21.62 |
| ATOM | 2097 | C | GLY | A | 269 | 16.187 | 45.402 | 61.777 | 1.00 | 27.53 |
| ATOM | 2098 | O | GLY | A | 269 | 15.681 | 44.948 | 62.820 | 1.00 | 20.14 |
| ATOM | 2099 | N | MET | A | 270 | 15.735 | 45.154 | 60.528 | 1.00 | 27.81 |
| ATOM | 2100 | CA | MET | A | 270 | 14.615 | 44.267 | 60.176 | 1.00 | 25.61 |
| ATOM | 2101 | C | MET | A | 270 | 14.956 | 43.585 | 58.874 | 1.00 | 33.56 |
| ATOM | 2102 | O | MET | A | 270 | 15.221 | 44.247 | 57.867 | 1.00 | 34.67 |
| ATOM | 2103 | CB | MET | A | 270 | 13.247 | 44.936 | 60.028 | 1.00 | 26.07 |
| ATOM | 2104 | CG | MET | A | 270 | 12.195 | 43.937 | 59.602 | 1.00 | 28.81 |
| ATOM | 2105 | SD | MET | A | 270 | 11.875 | 42.742 | 60.929 | 1.00 | 37.39 |
| ATOM | 2106 | CE | MET | A | 270 | 10.720 | 41.621 | 60.082 | 1.00 | 35.30 |
| ATOM | 2107 | N | GLU | A | 271 | 14.995 | 42.263 | 58.904 | 1.00 | 32.20 |
| ATOM | 2108 | CA | GLU | A | 271 | 15.393 | 41.459 | 57.753 | 1.00 | 33.32 |
| ATOM | 2109 | C | GLU | A | 271 | 14.419 | 41.382 | 56.567 | 1.00 | 40.86 |
| ATOM | 2110 | O | GLU | A | 271 | 14.087 | 40.285 | 56.107 | 1.00 | 42.02 |
| ATOM | 2111 | CB | GLU | A | 271 | 15.802 | 40.054 | 58.230 | 1.00 | 35.05 |
| ATOM | 2112 | CG | GLU | A | 271 | 14.607 | 39.218 | 58.760 | 1.00 | 33.55 |
| ATOM | 2113 | CD | GLU | A | 271 | 14.291 | 39.428 | 60.219 | 1.00 | 25.52 |
| ATOM | 2114 | OE1 | GLU | A | 271 | 14.586 | 40.436 | 60.844 | 1.00 | 37.23 |
| ATOM | 2115 | OE2 | GLU | A | 271 | 13.699 | 38.393 | 60.757 | 1.00 | 25.86 |
| ATOM | 2116 | N | ASN | A | 272 | 13.978 | 42.535 | 56.052 | 1.00 | 35.34 |
| ATOM | 2117 | CA | ASN | A | 272 | 13.057 | 42.544 | 54.928 | 1.00 | 33.26 |
| ATOM | 2118 | C | ASN | A | 272 | 13.787 | 42.048 | 53.702 | 1.00 | 34.47 |
| ATOM | 2119 | O | ASN | A | 272 | 14.811 | 42.613 | 53.351 | 1.00 | 33.64 |
| ATOM | 2120 | CB | ASN | A | 272 | 12.441 | 43.947 | 54.719 | 1.00 | 30.65 |
| ATOM | 2121 | CG | ASN | A | 272 | 11.667 | 44.453 | 55.935 | 1.00 | 42.50 |
| ATOM | 2122 | OD1 | ASN | A | 272 | 11.908 | 45.554 | 56.475 | 1.00 | 47.09 |
| ATOM | 2123 | ND2 | ASN | A | 272 | 10.716 | 43.661 | 56.371 | 1.00 | 24.31 |
| ATOM | 2124 | N | PRO | A | 273 | 13.281 | 40.983 | 53.078 | 1.00 | 29.63 |
| ATOM | 2125 | CA | PRO | A | 273 | 13.935 | 40.373 | 51.910 | 1.00 | 28.47 |
| ATOM | 2126 | C | PRO | A | 273 | 14.303 | 41.345 | 50.819 | 1.00 | 30.43 |
| ATOM | 2127 | O | PRO | A | 273 | 13.457 | 42.089 | 50.372 | 1.00 | 31.65 |
| ATOM | 2128 | CB | PRO | A | 273 | 12.991 | 39.305 | 51.381 | 1.00 | 30.16 |
| ATOM | 2129 | CG | PRO | A | 273 | 11.829 | 39.237 | 52.365 | 1.00 | 36.65 |
| ATOM | 2130 | CD | PRO | A | 273 | 11.927 | 40.440 | 53.310 | 1.00 | 30.84 |
| ATOM | 2131 | N | CYS | A | 274 | 15.571 | 41.333 | 50.431 | 1.00 | 27.40 |
| ATOM | 2132 | CA | CYS | A | 274 | 16.069 | 42.206 | 49.373 | 1.00 | 28.17 |
| ATOM | 2133 | C | CYS | A | 274 | 16.327 | 43.604 | 49.860 | 1.00 | 27.35 |
| ATOM | 2134 | O | CYS | A | 274 | 17.114 | 44.345 | 49.248 | 1.00 | 28.53 |
| ATOM | 2135 | CB | CYS | A | 274 | 15.121 | 42.347 | 48.145 | 1.00 | 32.00 |
| ATOM | 2136 | SG | CYS | A | 274 | 14.659 | 40.798 | 47.340 | 1.00 | 38.42 |

TABLE 9-continued

Structure coordinates of LTA₄ hydrolase-thiolamine complex
(The amino acid sequence set forth as residues 1-610 below correspond to SEQ ID NO:1.)

| ATOM | 2137 | N | LEU | A | 275 | 15.658 | 43.972 | 50.947 | 1.00 | 26.20 |
|---|---|---|---|---|---|---|---|---|---|---|
| ATOM | 2138 | CA | LEU | A | 275 | 15.789 | 45.315 | 51.535 | 1.00 | 29.54 |
| ATOM | 2139 | C | LEU | A | 275 | 15.857 | 45.279 | 53.059 | 1.00 | 32.52 |
| ATOM | 2140 | O | LEU | A | 275 | 14.859 | 45.250 | 53.772 | 1.00 | 32.44 |
| ATOM | 2141 | CB | LEU | A | 275 | 14.657 | 46.253 | 51.005 | 1.00 | 28.58 |
| ATOM | 2142 | CG | LEU | A | 275 | 14.847 | 47.735 | 51.239 | 1.00 | 26.78 |
| ATOM | 2143 | CD1 | LEU | A | 275 | 16.191 | 48.183 | 50.698 | 1.00 | 21.90 |
| ATOM | 2144 | CD2 | LEU | A | 275 | 13.712 | 48.478 | 50.554 | 1.00 | 31.48 |
| ATOM | 2145 | N | THR | A | 276 | 17.062 | 45.244 | 53.570 | 1.00 | 29.67 |
| ATOM | 2146 | CA | THR | A | 276 | 17.225 | 45.198 | 54.996 | 1.00 | 30.47 |
| ATOM | 2147 | C | THR | A | 276 | 17.120 | 46.624 | 55.597 | 1.00 | 34.60 |
| ATOM | 2148 | O | THR | A | 276 | 17.766 | 47.588 | 55.129 | 1.00 | 31.01 |
| ATOM | 2149 | CB | THR | A | 276 | 18.508 | 44.397 | 55.387 | 1.00 | 30.98 |
| ATOM | 2150 | OG1 | THR | A | 276 | 18.224 | 43.030 | 55.512 | 1.00 | 42.01 |
| ATOM | 2151 | CG2 | THR | A | 276 | 19.124 | 44.835 | 56.694 | 1.00 | 29.43 |
| ATOM | 2152 | N | PHE | A | 277 | 16.280 | 46.759 | 56.622 | 1.00 | 27.69 |
| ATOM | 2153 | CA | PHE | A | 277 | 16.164 | 48.034 | 57.274 | 1.00 | 28.92 |
| ATOM | 2154 | C | PHE | A | 277 | 17.184 | 48.065 | 58.403 | 1.00 | 36.07 |
| ATOM | 2155 | O | PHE | A | 277 | 17.337 | 47.088 | 59.131 | 1.00 | 34.57 |
| ATOM | 2156 | CB | PHE | A | 277 | 14.791 | 48.265 | 57.901 | 1.00 | 30.17 |
| ATOM | 2157 | CG | PHE | A | 277 | 13.774 | 48.458 | 56.848 | 1.00 | 30.72 |
| ATOM | 2158 | CD1 | PHE | A | 277 | 14.011 | 47.966 | 55.568 | 1.00 | 30.73 |
| ATOM | 2159 | CD2 | PHE | A | 277 | 12.573 | 49.114 | 57.105 | 1.00 | 30.61 |
| ATOM | 2160 | CE1 | PHE | A | 277 | 13.072 | 48.135 | 54.552 | 1.00 | 29.30 |
| ATOM | 2161 | CE2 | PHE | A | 277 | 11.619 | 49.276 | 56.101 | 1.00 | 32.26 |
| ATOM | 2162 | CZ | PHE | A | 277 | 11.862 | 48.772 | 54.824 | 1.00 | 27.48 |
| ATOM | 2163 | N | VAL | A | 278 | 17.864 | 49.186 | 58.562 | 1.00 | 32.97 |
| ATOM | 2164 | CA | VAL | A | 278 | 18.839 | 49.338 | 59.614 | 1.00 | 32.66 |
| ATOM | 2165 | C | VAL | A | 278 | 18.696 | 50.698 | 60.248 | 1.00 | 37.01 |
| ATOM | 2166 | O | VAL | A | 278 | 18.251 | 51.635 | 59.599 | 1.00 | 37.16 |
| ATOM | 2167 | CB | VAL | A | 278 | 20.246 | 49.088 | 59.109 | 1.00 | 36.51 |
| ATOM | 2168 | CG1 | VAL | A | 278 | 20.173 | 47.967 | 58.086 | 1.00 | 37.40 |
| ATOM | 2169 | CG2 | VAL | A | 278 | 20.791 | 50.356 | 58.444 | 1.00 | 34.87 |
| ATOM | 2170 | N | THR | A | 279 | 19.066 | 50.778 | 61.515 | 1.00 | 32.36 |
| ATOM | 2171 | CA | THR | A | 279 | 18.948 | 51.994 | 62.264 | 1.00 | 31.03 |
| ATOM | 2172 | C | THR | A | 279 | 20.121 | 52.883 | 62.035 | 1.00 | 37.42 |
| ATOM | 2173 | O | THR | A | 279 | 21.243 | 52.397 | 61.920 | 1.00 | 39.87 |
| ATOM | 2174 | CB | THR | A | 279 | 18.885 | 51.695 | 63.759 | 1.00 | 31.39 |
| ATOM | 2175 | OG1 | THR | A | 279 | 19.110 | 52.895 | 64.472 | 1.00 | 34.21 |
| ATOM | 2176 | CG2 | THR | A | 279 | 19.989 | 50.706 | 64.083 | 1.00 | 23.69 |
| ATOM | 2177 | N | PRO | A | 280 | 19.845 | 54.187 | 62.000 | 1.00 | 30.07 |
| ATOM | 2178 | CA | PRO | A | 280 | 20.903 | 55.132 | 61.802 | 1.00 | 27.00 |
| ATOM | 2179 | C | PRO | A | 280 | 21.823 | 55.110 | 63.005 | 1.00 | 30.60 |
| ATOM | 2180 | O | PRO | A | 280 | 22.951 | 55.588 | 62.934 | 1.00 | 30.20 |
| ATOM | 2181 | CB | PRO | A | 280 | 20.249 | 56.497 | 61.601 | 1.00 | 26.23 |
| ATOM | 2182 | CG | PRO | A | 280 | 18.769 | 56.337 | 61.889 | 1.00 | 28.07 |
| ATOM | 2183 | CD | PRO | A | 280 | 18.499 | 54.848 | 61.984 | 1.00 | 26.11 |
| ATOM | 2184 | N | THR | A | 281 | 21.348 | 54.509 | 64.112 | 1.00 | 27.82 |
| ATOM | 2185 | CA | THR | A | 281 | 22.199 | 54.426 | 65.302 | 1.00 | 27.48 |
| ATOM | 2186 | C | THR | A | 281 | 23.372 | 53.523 | 65.073 | 1.00 | 31.37 |
| ATOM | 2187 | O | THR | A | 281 | 24.226 | 53.385 | 65.944 | 1.00 | 31.93 |
| ATOM | 2188 | CB | THR | A | 281 | 21.499 | 54.016 | 66.601 | 1.00 | 21.45 |
| ATOM | 2189 | OG1 | THR | A | 281 | 21.021 | 52.681 | 66.524 | 1.00 | 33.18 |
| ATOM | 2190 | CG2 | THR | A | 281 | 20.388 | 54.994 | 66.874 | 1.00 | 9.89 |
| ATOM | 2191 | N | LEU | A | 282 | 23.378 | 52.881 | 63.913 | 1.00 | 25.29 |
| ATOM | 2192 | CA | LEU | A | 282 | 24.473 | 51.993 | 63.586 | 1.00 | 24.04 |
| ATOM | 2193 | C | LEU | A | 282 | 25.682 | 52.790 | 63.049 | 1.00 | 34.74 |
| ATOM | 2194 | O | LEU | A | 282 | 26.787 | 52.279 | 62.884 | 1.00 | 34.84 |
| ATOM | 2195 | CB | LEU | A | 282 | 24.063 | 51.038 | 62.464 | 1.00 | 22.14 |
| ATOM | 2196 | CG | LEU | A | 282 | 23.104 | 49.916 | 62.819 | 1.00 | 26.88 |
| ATOM | 2197 | CD1 | LEU | A | 282 | 23.312 | 48.809 | 61.791 | 1.00 | 27.77 |
| ATOM | 2198 | CD2 | LEU | A | 282 | 23.322 | 49.404 | 64.249 | 1.00 | 21.75 |
| ATOM | 2199 | N | LEU | A | 283 | 25.465 | 54.063 | 62.744 | 1.00 | 32.05 |
| ATOM | 2200 | CA | LEU | A | 283 | 26.501 | 54.903 | 62.159 | 1.00 | 31.43 |
| ATOM | 2201 | C | LEU | A | 283 | 27.659 | 55.324 | 63.055 | 1.00 | 41.94 |
| ATOM | 2202 | O | LEU | A | 283 | 27.907 | 56.525 | 63.196 | 1.00 | 49.19 |
| ATOM | 2203 | CB | LEU | A | 283 | 25.861 | 56.117 | 61.418 | 1.00 | 29.55 |
| ATOM | 2204 | CG | LEU | A | 283 | 24.720 | 55.661 | 60.488 | 1.00 | 32.94 |
| ATOM | 2205 | CD1 | LEU | A | 283 | 23.933 | 56.811 | 59.869 | 1.00 | 33.48 |
| ATOM | 2206 | CD2 | LEU | A | 283 | 25.232 | 54.716 | 59.409 | 1.00 | 28.39 |
| ATOM | 2207 | N | ALA | A | 284 | 28.387 | 54.370 | 63.638 | 1.00 | 33.18 |
| ATOM | 2208 | CA | ALA | A | 284 | 29.488 | 54.728 | 64.532 | 1.00 | 30.20 |
| ATOM | 2209 | C | ALA | A | 284 | 30.655 | 55.492 | 63.922 | 1.00 | 31.97 |
| ATOM | 2210 | O | ALA | A | 284 | 31.411 | 56.165 | 64.642 | 1.00 | 31.40 |
| ATOM | 2211 | CB | ALA | A | 284 | 29.973 | 53.544 | 65.336 | 1.00 | 29.60 |
| ATOM | 2212 | N | GLY | A | 285 | 30.801 | 55.371 | 62.605 | 1.00 | 27.10 |

TABLE 9-continued

Structure coordinates of LTA$_4$ hydrolase-thiolamine complex
(The amino acid sequence set forth as residues 1-610 below correspond to SEQ ID NO:1.)

| ATOM | 2213 | CA | GLY | A | 285 | 31.882 | 56.018 | 61.867 | 1.00 | 29.77 |
|------|------|-----|-----|---|-----|--------|--------|--------|------|-------|
| ATOM | 2214 | C | GLY | A | 285 | 33.174 | 55.194 | 61.910 | 1.00 | 39.25 |
| ATOM | 2215 | O | GLY | A | 285 | 34.264 | 55.649 | 61.544 | 1.00 | 41.21 |
| ATOM | 2216 | N | ASP | A | 286 | 33.022 | 53.951 | 62.363 | 1.00 | 34.57 |
| ATOM | 2217 | CA | ASP | A | 286 | 34.144 | 53.057 | 62.473 | 1.00 | 32.57 |
| ATOM | 2218 | C | ASP | A | 286 | 33.805 | 51.625 | 62.130 | 1.00 | 31.59 |
| ATOM | 2219 | O | ASP | A | 286 | 34.609 | 50.743 | 62.325 | 1.00 | 29.27 |
| ATOM | 2220 | CD | ASP | A | 286 | 34.812 | 53.163 | 63.860 | 1.00 | 34.65 |
| ATOM | 2221 | CG | ASP | A | 286 | 34.081 | 52.447 | 64.945 | 1.00 | 41.93 |
| ATOM | 2222 | OD1 | ASP | A | 286 | 33.008 | 51.893 | 64.765 | 1.00 | 45.21 |
| ATOM | 2223 | OD2 | ASP | A | 286 | 34.714 | 52.492 | 66.087 | 1.00 | 35.67 |
| ATOM | 2224 | N | LYS | A | 287 | 32.590 | 51.395 | 61.641 | 1.00 | 29.46 |
| ATOM | 2225 | CA | LYS | A | 287 | 32.199 | 50.038 | 61.272 | 1.00 | 31.62 |
| ATOM | 2226 | C | LYS | A | 287 | 31.976 | 49.060 | 62.437 | 1.00 | 37.91 |
| ATOM | 2227 | O | LYS | A | 287 | 31.761 | 47.879 | 62.240 | 1.00 | 37.91 |
| ATOM | 2228 | CD | LYS | A | 287 | 33.215 | 49.447 | 60.304 | 1.00 | 32.17 |
| ATOM | 2229 | CG | LYS | A | 287 | 33.510 | 50.358 | 59.119 | 1.00 | 51.60 |
| ATOM | 2230 | CD | LYS | A | 287 | 33.960 | 49.601 | 57.877 | 1.00 | 50.74 |
| ATOM | 2231 | CE | LYS | A | 287 | 35.290 | 50.105 | 57.328 | 1.00 | 63.80 |
| ATOM | 2232 | NZ | LYS | A | 287 | 35.167 | 50.866 | 56.069 | 1.00 | 71.91 |
| ATOM | 2233 | N | SER | A | 288 | 32.168 | 49.575 | 63.647 | 1.00 | 31.58 |
| ATOM | 2234 | CA | SER | A | 288 | 32.079 | 48.737 | 64.810 | 1.00 | 27.15 |
| ATOM | 2235 | C | SER | A | 288 | 30.742 | 48.137 | 65.142 | 1.00 | 36.08 |
| ATOM | 2236 | O | SER | A | 288 | 30.676 | 47.318 | 66.057 | 1.00 | 37.87 |
| ATOM | 2237 | CB | SER | A | 288 | 32.618 | 49.463 | 66.005 | 1.00 | 16.31 |
| ATOM | 2238 | OG | SER | A | 288 | 31.659 | 50.443 | 66.312 | 1.00 | 29.71 |
| ATOM | 2239 | N | LEU | A | 289 | 29.669 | 48.529 | 64.460 | 1.00 | 29.34 |
| ATOM | 2240 | CA | LEU | A | 289 | 28.351 | 47.979 | 64.794 | 1.00 | 24.70 |
| ATOM | 2241 | C | LEU | A | 289 | 27.792 | 47.105 | 63.686 | 1.00 | 32.97 |
| ATOM | 2242 | O | LEU | A | 289 | 26.591 | 46.766 | 63.648 | 1.00 | 30.35 |
| ATOM | 2243 | CB | LEU | A | 289 | 27.385 | 49.090 | 65.191 | 1.00 | 21.45 |
| ATOM | 2244 | CG | LEU | A | 289 | 27.954 | 49.887 | 66.347 | 1.00 | 22.99 |
| ATOM | 2245 | CD1 | LEU | A | 289 | 26.881 | 50.769 | 66.950 | 1.00 | 20.66 |
| ATOM | 2246 | CD2 | LEU | A | 289 | 28.381 | 48.881 | 67.394 | 1.00 | 29.65 |
| ATOM | 2247 | N | SER | A | 290 | 28.723 | 46.753 | 62.801 | 1.00 | 31.21 |
| ATOM | 2248 | CA | SER | A | 290 | 28.453 | 45.941 | 61.645 | 1.00 | 29.89 |
| ATOM | 2249 | C | SER | A | 290 | 27.861 | 44.582 | 62.006 | 1.00 | 30.57 |
| ATOM | 2250 | O | SER | A | 290 | 27.299 | 43.872 | 61.153 | 1.00 | 29.73 |
| ATOM | 2251 | CD | SER | A | 290 | 29.704 | 45.800 | 60.783 | 1.00 | 29.27 |
| ATOM | 2252 | OG | SER | A | 290 | 30.470 | 44.725 | 61.266 | 1.00 | 38.77 |
| ATOM | 2253 | N | ASN | A | 291 | 27.980 | 44.207 | 63.282 | 1.00 | 26.55 |
| ATOM | 2254 | CA | ASN | A | 291 | 27.449 | 42.909 | 63.706 | 1.00 | 25.78 |
| ATOM | 2255 | C | ASN | A | 291 | 26.006 | 42.773 | 63.355 | 1.00 | 30.89 |
| ATOM | 2256 | O | ASN | A | 291 | 25.576 | 41.702 | 62.975 | 1.00 | 29.73 |
| ATOM | 2257 | CB | ASN | A | 291 | 27.725 | 42.503 | 65.157 | 1.00 | 28.48 |
| ATOM | 2258 | CG | ASN | A | 291 | 26.910 | 43.313 | 66.119 | 1.00 | 33.33 |
| ATOM | 2259 | OD1 | ASN | A | 291 | 27.065 | 44.529 | 66.198 | 1.00 | 34.48 |
| ATOM | 2260 | ND2 | ASN | A | 291 | 26.001 | 42.653 | 66.818 | 1.00 | 28.96 |
| ATOM | 2261 | N | VAL | A | 292 | 25.277 | 43.885 | 63.476 | 1.00 | 30.68 |
| ATOM | 2262 | CA | VAL | A | 292 | 23.865 | 43.924 | 63.142 | 1.00 | 30.27 |
| ATOM | 2263 | C | VAL | A | 292 | 23.667 | 43.619 | 61.669 | 1.00 | 32.61 |
| ATOM | 2264 | O | VAL | A | 292 | 22.644 | 43.082 | 61.255 | 1.00 | 33.31 |
| ATOM | 2265 | CB | VAL | A | 292 | 23.288 | 45.289 | 63.505 | 1.00 | 35.13 |
| ATOM | 2266 | CG1 | VAL | A | 292 | 21.877 | 45.486 | 62.946 | 1.00 | 33.48 |
| ATOM | 2267 | CG2 | VAL | A | 292 | 23.328 | 45.478 | 65.014 | 1.00 | 35.02 |
| ATOM | 2268 | N | ILE | A | 293 | 24.653 | 43.975 | 60.861 | 1.00 | 27.92 |
| ATOM | 2269 | CA | ILE | A | 293 | 24.527 | 43.685 | 59.461 | 1.00 | 28.71 |
| ATOM | 2270 | C | ILE | A | 293 | 24.658 | 42.159 | 59.296 | 1.00 | 35.03 |
| ATOM | 2271 | O | ILE | A | 293 | 23.860 | 41.475 | 58.624 | 1.00 | 38.34 |
| ATOM | 2272 | CB | ILE | A | 293 | 25.554 | 44.438 | 58.606 | 1.00 | 33.84 |
| ATOM | 2273 | CG1 | ILE | A | 293 | 25.608 | 45.952 | 58.898 | 1.00 | 34.55 |
| ATOM | 2274 | CG2 | ILE | A | 293 | 25.305 | 44.186 | 57.121 | 1.00 | 36.50 |
| ATOM | 2275 | CD1 | ILE | A | 293 | 24.265 | 46.680 | 58.808 | 1.00 | 30.49 |
| ATOM | 2276 | N | ALA | A | 294 | 25.668 | 41.584 | 59.934 | 1.00 | 23.76 |
| ATOM | 2277 | CA | ALA | A | 294 | 25.836 | 40.138 | 59.809 | 1.00 | 19.95 |
| ATOM | 2278 | C | ALA | A | 294 | 24.559 | 39.409 | 60.165 | 1.00 | 27.33 |
| ATOM | 2279 | O | ALA | A | 294 | 24.183 | 38.422 | 59.505 | 1.00 | 25.48 |
| ATOM | 2280 | CB | ALA | A | 294 | 26.984 | 39.644 | 60.688 | 1.00 | 19.24 |
| ATOM | 2281 | N | HIS | A | 295 | 23.917 | 39.934 | 61.244 | 1.00 | 27.63 |
| ATOM | 2282 | CA | HIS | A | 295 | 22.666 | 39.414 | 61.797 | 1.00 | 26.83 |
| ATOM | 2283 | C | HIS | A | 295 | 21.611 | 39.383 | 60.734 | 1.00 | 28.61 |
| ATOM | 2284 | O | HIS | A | 295 | 21.169 | 38.301 | 60.348 | 1.00 | 25.72 |
| ATOM | 2285 | CB | HIS | A | 295 | 22.148 | 40.175 | 63.028 | 1.00 | 27.98 |
| ATOM | 2286 | CG | HIS | A | 295 | 20.937 | 39.534 | 63.657 | 1.00 | 31.62 |
| ATOM | 2287 | ND1 | HIS | A | 295 | 21.047 | 38.675 | 64.763 | 1.00 | 32.66 |
| ATOM | 2288 | CD2 | HIS | A | 295 | 19.602 | 39.643 | 63.338 | 1.00 | 30.92 |

TABLE 9-continued

Structure coordinates of LTA$_4$ hydrolase-thiolamine complex
(The amino acid sequence set forth as residues 1-610 below correspond to SEQ ID NO:1.)

| ATOM | 2289 | CE1 | HIS | A | 295 | 19.802 | 38.298 | 65.088 | 1.00 | 30.14 |
|---|---|---|---|---|---|---|---|---|---|---|
| ATOM | 2290 | NE2 | HIS | A | 295 | 18.916 | 38.860 | 64.254 | 1.00 | 30.24 |
| ATOM | 2291 | N | GLU | A | 296 | 21.257 | 40.590 | 60.251 | 1.00 | 27.23 |
| ATOM | 2292 | CA | GLU | A | 296 | 20.266 | 40.749 | 59.195 | 1.00 | 25.98 |
| ATOM | 2293 | C | GLU | A | 296 | 20.533 | 39.790 | 58.056 | 1.00 | 32.73 |
| ATOM | 2294 | O | GLU | A | 296 | 19.628 | 39.081 | 57.561 | 1.00 | 31.88 |
| ATOM | 2295 | CB | GLU | A | 296 | 20.046 | 42.203 | 58.728 | 1.00 | 24.55 |
| ATOM | 2296 | CG | GLU | A | 296 | 19.892 | 43.148 | 59.936 | 1.00 | 23.16 |
| ATOM | 2297 | CD | GLU | A | 296 | 18.939 | 42.632 | 60.991 | 1.00 | 53.50 |
| ATOM | 2298 | OE1 | GLU | A | 296 | 17.964 | 41.956 | 60.700 | 1.00 | 23.99 |
| ATOM | 2299 | OE2 | GLU | A | 296 | 19.237 | 43.006 | 62.233 | 1.00 | 32.77 |
| ATOM | 2300 | N | ILE | A | 297 | 21.803 | 39.745 | 57.675 | 1.00 | 25.37 |
| ATOM | 2301 | CA | ILE | A | 297 | 22.195 | 38.870 | 56.599 | 1.00 | 22.64 |
| ATOM | 2302 | C | ILE | A | 297 | 21.812 | 37.445 | 56.859 | 1.00 | 27.47 |
| ATOM | 2303 | O | ILE | A | 297 | 21.175 | 36.799 | 56.048 | 1.00 | 26.25 |
| ATOM | 2304 | CB | ILE | A | 297 | 23.672 | 38.963 | 56.302 | 1.00 | 24.19 |
| ATOM | 2305 | CG1 | ILE | A | 297 | 23.920 | 40.140 | 55.355 | 1.00 | 25.28 |
| ATOM | 2306 | CG2 | ILE | A | 297 | 24.079 | 37.686 | 55.626 | 1.00 | 20.77 |
| ATOM | 2307 | CD1 | ILE | A | 297 | 25.325 | 40.705 | 55.435 | 1.00 | 16.26 |
| ATOM | 2308 | N | SER | A | 298 | 22.226 | 36.947 | 58.012 | 1.00 | 28.23 |
| ATOM | 2309 | CA | SER | A | 298 | 21.939 | 35.569 | 58.377 | 1.00 | 25.04 |
| ATOM | 2310 | C | SER | A | 298 | 20.467 | 35.235 | 58.298 | 1.00 | 26.21 |
| ATOM | 2311 | O | SER | A | 298 | 20.118 | 34.097 | 58.000 | 1.00 | 26.30 |
| ATOM | 2312 | CB | SER | A | 298 | 22.520 | 35.209 | 59.714 | 1.00 | 27.82 |
| ATOM | 2313 | OG | SER | A | 298 | 23.890 | 35.552 | 59.714 | 1.00 | 35.98 |
| ATOM | 2314 | N | HIS | A | 299 | 19.599 | 36.230 | 58.562 | 1.00 | 22.17 |
| ATOM | 2315 | CA | HIS | A | 299 | 18.205 | 36.092 | 58.719 | 1.00 | 22.77 |
| ATOM | 2316 | C | HIS | A | 299 | 17.614 | 35.710 | 57.387 | 1.00 | 29.10 |
| ATOM | 2317 | O | HIS | A | 299 | 16.553 | 35.162 | 57.290 | 1.00 | 31.50 |
| ATOM | 2318 | CB | HIS | A | 299 | 17.662 | 37.432 | 59.200 | 1.00 | 24.67 |
| ATOM | 2319 | CG | HIS | A | 299 | 17.053 | 37.338 | 60.602 | 1.00 | 29.10 |
| ATOM | 2320 | ND1 | HIS | A | 299 | 16.190 | 36.368 | 60.975 | 1.00 | 30.70 |
| ATOM | 2321 | CD2 | HIS | A | 299 | 17.196 | 38.233 | 61.667 | 1.00 | 32.39 |
| ATOM | 2322 | CE1 | HIS | A | 299 | 15.811 | 36.675 | 62.233 | 1.00 | 30.41 |
| ATOM | 2323 | NE2 | HIS | A | 299 | 16.397 | 37.783 | 62.674 | 1.00 | 31.74 |
| ATOM | 2324 | N | SER | A | 300 | 18.356 | 36.048 | 56.315 | 1.00 | 23.31 |
| ATOM | 2325 | CA | SER | A | 300 | 17.942 | 35.581 | 55.010 | 1.00 | 24.24 |
| ATOM | 2326 | C | SER | A | 300 | 17.879 | 34.050 | 54.977 | 1.00 | 34.13 |
| ATOM | 2327 | O | SER | A | 300 | 17.075 | 33.463 | 54.305 | 1.00 | 33.28 |
| ATOM | 2328 | CB | SER | A | 300 | 18.941 | 36.092 | 53.965 | 1.00 | 27.31 |
| ATOM | 2329 | OG | SER | A | 300 | 18.947 | 37.519 | 53.962 | 1.00 | 49.96 |
| ATOM | 2330 | N | TRP | A | 301 | 18.773 | 33.411 | 55.752 | 1.00 | 33.09 |
| ATOM | 2331 | CA | TRP | A | 301 | 18.702 | 31.969 | 55.829 | 1.00 | 31.84 |
| ATOM | 2332 | C | TRP | A | 301 | 17.740 | 31.511 | 56.895 | 1.00 | 32.15 |
| ATOM | 2333 | O | TRP | A | 301 | 16.764 | 30.876 | 56.620 | 1.00 | 27.05 |
| ATOM | 2334 | CB | TRP | A | 301 | 20.095 | 31.429 | 56.082 | 1.00 | 30.16 |
| ATOM | 2335 | CG | TRP | A | 301 | 20.791 | 31.421 | 54.801 | 1.00 | 32.02 |
| ATOM | 2336 | CD1 | TRP | A | 301 | 20.787 | 30.393 | 53.859 | 1.00 | 35.05 |
| ATOM | 2337 | CD2 | TRP | A | 301 | 21.496 | 32.520 | 54.202 | 1.00 | 30.84 |
| ATOM | 2338 | NE1 | TRP | A | 301 | 21.415 | 30.732 | 52.722 | 1.00 | 33.29 |
| ATOM | 2339 | CE2 | TRP | A | 301 | 21.886 | 32.112 | 52.921 | 1.00 | 33.44 |
| ATOM | 2340 | CE3 | TRP | A | 301 | 21.811 | 33.790 | 54.631 | 1.00 | 32.65 |
| ATOM | 2341 | CZ2 | TRP | A | 301 | 22.577 | 32.970 | 52.108 | 1.00 | 32.21 |
| ATOM | 2342 | CZ3 | TRP | A | 301 | 22.503 | 34.652 | 53.812 | 1.00 | 36.10 |
| ATOM | 2343 | CH2 | TRP | A | 301 | 22.888 | 34.239 | 52.544 | 1.00 | 36.83 |
| ATOM | 2344 | N | THR | A | 302 | 18.042 | 31.864 | 58.146 | 1.00 | 31.77 |
| ATOM | 2345 | CA | THR | A | 302 | 17.125 | 31.488 | 59.215 | 1.00 | 33.55 |
| ATOM | 2346 | C | THR | A | 302 | 16.276 | 32.690 | 59.695 | 1.00 | 36.35 |
| ATOM | 2347 | O | THR | A | 302 | 16.759 | 33.590 | 60.330 | 1.00 | 36.56 |
| ATOM | 2348 | CB | THR | A | 302 | 17.963 | 30.920 | 60.366 | 1.00 | 31.04 |
| ATOM | 2349 | OG1 | THR | A | 302 | 19.047 | 31.807 | 60.639 | 1.00 | 38.50 |
| ATOM | 2350 | CG2 | THR | A | 302 | 18.544 | 29.555 | 59.967 | 1.00 | 17.10 |
| ATOM | 2351 | N | GLY | A | 303 | 15.053 | 32.418 | 59.250 | 1.00 | 25.28 |
| ATOM | 2352 | CA | GLY | A | 303 | 13.908 | 33.236 | 59.483 | 1.00 | 21.59 |
| ATOM | 2353 | C | GLY | A | 303 | 13.202 | 33.382 | 58.163 | 1.00 | 26.99 |
| ATOM | 2354 | O | GLY | A | 303 | 12.040 | 33.040 | 57.994 | 1.00 | 26.18 |
| ATOM | 2355 | N | ASN | A | 304 | 13.936 | 33.891 | 57.195 | 1.00 | 28.05 |
| ATOM | 2356 | CA | ASN | A | 304 | 13.363 | 34.101 | 55.875 | 1.00 | 28.17 |
| ATOM | 2357 | C | ASN | A | 304 | 13.141 | 32.839 | 55.056 | 1.00 | 28.99 |
| ATOM | 2358 | O | ASN | A | 304 | 12.118 | 32.715 | 54.415 | 1.00 | 24.87 |
| ATOM | 2359 | CB | ASN | A | 304 | 14.091 | 35.176 | 55.047 | 1.00 | 23.55 |
| ATOM | 2360 | CG | ASN | A | 304 | 14.133 | 36.499 | 55.757 | 1.00 | 37.80 |
| ATOM | 2361 | OD1 | ASN | A | 304 | 13.630 | 36.613 | 56.892 | 1.00 | 20.66 |
| ATOM | 2362 | ND2 | ASN | A | 304 | 14.752 | 37.488 | 55.093 | 1.00 | 24.17 |
| ATOM | 2363 | N | LEU | A | 305 | 14.110 | 31.919 | 55.055 | 1.00 | 27.24 |
| ATOM | 2364 | CA | LEU | A | 305 | 13.987 | 30.677 | 54.306 | 1.00 | 27.34 |

TABLE 9-continued

Structure coordinates of LTA₄ hydrolase-thiolamine complex
(The amino acid sequence set forth as residues 1-610 below correspond to SEQ ID NO:1.)

| ATOM | 2365 | C   | LEU | A | 305 | 13.218 | 29.665 | 55.121 | 1.00 | 31.29 |
|------|------|-----|-----|---|-----|--------|--------|--------|------|-------|
| ATOM | 2366 | O   | LEU | A | 305 | 12.235 | 29.051 | 54.678 | 1.00 | 29.23 |
| ATOM | 2367 | CB  | LEU | A | 305 | 15.371 | 30.119 | 53.967 | 1.00 | 27.62 |
| ATOM | 2368 | CG  | LEU | A | 305 | 15.805 | 30.593 | 52.603 | 1.00 | 32.23 |
| ATOM | 2369 | CD1 | LEU | A | 305 | 17.289 | 30.293 | 52.412 | 1.00 | 28.91 |
| ATOM | 2370 | CD2 | LEU | A | 305 | 14.951 | 29.887 | 51.549 | 1.00 | 41.51 |
| ATOM | 2371 | N   | VAL | A | 306 | 13.711 | 29.528 | 56.347 | 1.00 | 27.75 |
| ATOM | 2372 | CA  | VAL | A | 306 | 13.134 | 28.652 | 57.327 | 1.00 | 29.99 |
| ATOM | 2373 | C   | VAL | A | 306 | 12.578 | 29.527 | 58.403 | 1.00 | 31.78 |
| ATOM | 2374 | O   | VAL | A | 306 | 13.306 | 30.217 | 59.110 | 1.00 | 28.32 |
| ATOM | 2375 | CB  | VAL | A | 306 | 14.092 | 27.593 | 57.827 | 1.00 | 37.24 |
| ATOM | 2376 | CG1 | VAL | A | 306 | 15.479 | 28.180 | 57.969 | 1.00 | 38.36 |
| ATOM | 2377 | CG2 | VAL | A | 306 | 13.602 | 27.107 | 59.164 | 1.00 | 37.56 |
| ATOM | 2378 | N   | THR | A | 307 | 11.259 | 29.517 | 58.440 | 1.00 | 29.40 |
| ATOM | 2379 | CA  | THR | A | 307 | 10.499 | 30.358 | 59.320 | 1.00 | 28.14 |
| ATOM | 2380 | C   | THR | A | 307 | 9.729  | 29.712 | 60.446 | 1.00 | 34.06 |
| ATOM | 2381 | O   | THR | A | 307 | 9.029  | 28.706 | 60.277 | 1.00 | 36.72 |
| ATOM | 2382 | CB  | THR | A | 307 | 9.474  | 31.115 | 58.460 | 1.00 | 23.03 |
| ATOM | 2383 | OG1 | THR | A | 307 | 10.124 | 31.811 | 57.422 | 1.00 | 28.56 |
| ATOM | 2384 | CG2 | THR | A | 307 | 8.665  | 32.068 | 59.336 | 1.00 | 12.55 |
| ATOM | 2385 | N   | ASN | A | 308 | 9.802  | 30.347 | 61.608 | 1.00 | 29.29 |
| ATOM | 2386 | CA  | ASN | A | 308 | 9.042  | 29.862 | 62.724 | 1.00 | 27.82 |
| ATOM | 2387 | C   | ASN | A | 308 | 7.576  | 29.716 | 62.234 | 1.00 | 31.42 |
| ATOM | 2388 | O   | ASN | A | 308 | 7.072  | 30.535 | 61.450 | 1.00 | 32.96 |
| ATOM | 2389 | CB  | ASN | A | 308 | 9.194  | 30.790 | 63.972 | 1.00 | 23.57 |
| ATOM | 2390 | CG  | ASN | A | 308 | 8.935  | 32.298 | 63.745 | 1.00 | 30.38 |
| ATOM | 2391 | OD1 | ASN | A | 308 | 9.505  | 33.190 | 64.400 | 1.00 | 23.70 |
| ATOM | 2392 | ND2 | ASN | A | 308 | 8.056  | 32.608 | 62.818 | 1.00 | 41.34 |
| ATOM | 2393 | N   | LYS | A | 309 | 6.890  | 28.658 | 62.640 | 1.00 | 24.10 |
| ATOM | 2394 | CA  | LYS | A | 309 | 5.502  | 28.433 | 62.230 | 1.00 | 23.40 |
| ATOM | 2395 | C   | LYS | A | 309 | 4.514  | 29.380 | 62.964 | 1.00 | 28.17 |
| ATOM | 2396 | O   | LYS | A | 309 | 3.430  | 29.756 | 62.474 | 1.00 | 22.88 |
| ATOM | 2397 | CB  | LYS | A | 309 | 5.151  | 26.975 | 62.459 | 1.00 | 24.26 |
| ATOM | 2398 | CG  | LYS | A | 309 | 4.036  | 26.478 | 61.555 | 1.00 | 28.57 |
| ATOM | 2399 | CD  | LYS | A | 309 | 3.543  | 25.075 | 61.924 | 1.00 | 38.25 |
| ATOM | 2400 | CE  | LYS | A | 309 | 3.475  | 24.112 | 60.739 | 1.00 | 78.39 |
| ATOM | 2401 | NZ  | LYS | A | 309 | 4.389  | 22.953 | 60.849 | 1.00 | 98.22 |
| ATOM | 2402 | N   | THR | A | 310 | 4.917  | 29.744 | 64.179 | 1.00 | 23.46 |
| ATOM | 2403 | CA  | THR | A | 310 | 4.179  | 30.616 | 65.037 | 1.00 | 22.98 |
| ATOM | 2404 | C   | THR | A | 310 | 5.142  | 31.336 | 65.922 | 1.00 | 31.43 |
| ATOM | 2405 | O   | THR | A | 310 | 6.223  | 30.836 | 66.230 | 1.00 | 31.51 |
| ATOM | 2406 | CB  | THR | A | 310 | 3.104  | 29.917 | 65.871 | 1.00 | 34.01 |
| ATOM | 2407 | OG1 | THR | A | 310 | 3.684  | 29.148 | 66.945 | 1.00 | 27.97 |
| ATOM | 2408 | CG2 | THR | A | 310 | 2.174  | 29.114 | 64.956 | 1.00 | 24.58 |
| ATOM | 2409 | N   | TRP | A | 311 | 4.733  | 32.527 | 66.299 | 1.00 | 29.82 |
| ATOM | 2410 | CA  | TRP | A | 311 | 5.559  | 33.371 | 67.120 | 1.00 | 30.49 |
| ATOM | 2411 | C   | TRP | A | 311 | 6.044  | 32.692 | 68.381 | 1.00 | 26.99 |
| ATOM | 2412 | O   | TRP | A | 311 | 7.015  | 33.101 | 68.971 | 1.00 | 25.15 |
| ATOM | 2413 | CB  | TRP | A | 311 | 4.933  | 34.768 | 67.320 | 1.00 | 30.34 |
| ATOM | 2414 | CG  | TRP | A | 311 | 4.706  | 35.412 | 66.001 | 1.00 | 30.63 |
| ATOM | 2415 | CD1 | TRP | A | 311 | 3.514  | 35.785 | 65.490 | 1.00 | 32.07 |
| ATOM | 2416 | CD2 | TRP | A | 311 | 5.705  | 35.723 | 65.008 | 1.00 | 31.31 |
| ATOM | 2417 | NE1 | TRP | A | 311 | 3.703  | 36.335 | 64.250 | 1.00 | 29.97 |
| ATOM | 2418 | CE2 | TRP | A | 311 | 5.033  | 36.317 | 63.931 | 1.00 | 32.88 |
| ATOM | 2419 | CE3 | TRP | A | 311 | 7.099  | 35.586 | 64.943 | 1.00 | 31.44 |
| ATOM | 2420 | CZ2 | TRP | A | 311 | 5.721  | 36.771 | 62.804 | 1.00 | 31.56 |
| ATOM | 2421 | CZ3 | TRP | A | 311 | 7.779  | 36.059 | 63.848 | 1.00 | 30.39 |
| ATOM | 2422 | CH2 | TRP | A | 311 | 7.089  | 36.639 | 62.789 | 1.00 | 30.58 |
| ATOM | 2423 | N   | ASP | A | 312 | 5.366  | 31.632 | 68.770 | 1.00 | 27.36 |
| ATOM | 2424 | CA  | ASP | A | 312 | 5.757  | 30.868 | 69.950 | 1.00 | 27.38 |
| ATOM | 2425 | C   | ASP | A | 312 | 7.149  | 30.213 | 69.757 | 1.00 | 31.25 |
| ATOM | 2426 | O   | ASP | A | 312 | 7.826  | 29.802 | 70.718 | 1.00 | 27.07 |
| ATOM | 2427 | CB  | ASP | A | 312 | 4.697  | 29.750 | 70.217 | 1.00 | 25.96 |
| ATOM | 2428 | CG  | ASP | A | 312 | 3.432  | 30.230 | 70.872 | 1.00 | 27.42 |
| ATOM | 2429 | OD1 | ASP | A | 312 | 3.197  | 31.396 | 71.102 | 1.00 | 28.97 |
| ATOM | 2430 | OD2 | ASP | A | 312 | 2.623  | 29.265 | 71.208 | 1.00 | 29.33 |
| ATOM | 2431 | N   | HIS | A | 313 | 7.562  | 30.089 | 68.487 | 1.00 | 25.04 |
| ATOM | 2432 | CA  | HIS | A | 313 | 8.820  | 29.454 | 68.164 | 1.00 | 23.48 |
| ATOM | 2433 | C   | HIS | A | 313 | 9.864  | 30.452 | 67.737 | 1.00 | 25.38 |
| ATOM | 2434 | O   | HIS | A | 313 | 10.929 | 30.139 | 67.214 | 1.00 | 29.97 |
| ATOM | 2435 | CB  | HIS | A | 313 | 8.588  | 28.245 | 67.209 | 1.00 | 25.00 |
| ATOM | 2436 | CG  | HIS | A | 313 | 7.641  | 27.230 | 67.837 | 1.00 | 29.77 |
| ATOM | 2437 | ND1 | HIS | A | 313 | 8.087  | 26.183 | 68.635 | 1.00 | 31.37 |
| ATOM | 2438 | CD2 | HIS | A | 313 | 6.279  | 27.152 | 67.808 | 1.00 | 31.31 |
| ATOM | 2439 | CE1 | HIS | A | 313 | 7.015  | 25.509 | 69.039 | 1.00 | 28.91 |
| ATOM | 2440 | NE2 | HIS | A | 313 | 5.913  | 26.066 | 68.559 | 1.00 | 29.40 |

TABLE 9-continued

Structure coordinates of LTA₄ hydrolase-thiolamine complex
(The amino acid sequence set forth as residues 1-610 below correspond to SEQ ID NO:1.)

| ATOM | 2441 | N | PHE | A | 314 | 9.521 | 31.682 | 68.005 | 1.00 | 17.43 |
|------|------|------|-----|---|-----|--------|--------|--------|------|-------|
| ATOM | 2442 | CA | PHE | A | 314 | 10.345 | 32.810 | 67.701 | 1.00 | 17.16 |
| ATOM | 2443 | C | PHE | A | 314 | 11.852 | 32.523 | 67.812 | 1.00 | 26.01 |
| ATOM | 2444 | O | PHE | A | 314 | 12.669 | 32.922 | 66.963 | 1.00 | 30.40 |
| ATOM | 2445 | CB | PHE | A | 314 | 9.908 | 34.056 | 68.517 | 1.00 | 18.63 |
| ATOM | 2446 | CG | PHE | A | 314 | 10.592 | 35.351 | 68.113 | 1.00 | 20.10 |
| ATOM | 2447 | CD1 | PHE | A | 314 | 10.712 | 35.697 | 66.768 | 1.00 | 21.80 |
| ATOM | 2448 | CD2 | PHE | A | 314 | 11.129 | 36.214 | 69.070 | 1.00 | 22.60 |
| ATOM | 2449 | CE1 | PHE | A | 314 | 11.337 | 36.890 | 66.400 | 1.00 | 24.74 |
| ATOM | 2450 | CE2 | PHE | A | 314 | 11.750 | 37.416 | 68.716 | 1.00 | 27.24 |
| ATOM | 2451 | CZ | PHE | A | 314 | 11.857 | 37.756 | 67.368 | 1.00 | 24.97 |
| ATOM | 2452 | N | TRP | A | 315 | 12.235 | 31.828 | 68.861 | 1.00 | 19.66 |
| ATOM | 2453 | CA | TRP | A | 315 | 13.639 | 31.541 | 69.068 | 1.00 | 17.87 |
| ATOM | 2454 | C | TRP | A | 315 | 14.292 | 30.775 | 67.953 | 1.00 | 28.55 |
| ATOM | 2455 | O | TRP | A | 315 | 15.518 | 30.769 | 67.830 | 1.00 | 29.23 |
| ATOM | 2456 | CB | TRP | A | 315 | 13.860 | 30.842 | 70.362 | 1.00 | 16.03 |
| ATOM | 2457 | CG | TRP | A | 315 | 13.613 | 29.408 | 70.161 | 1.00 | 19.64 |
| ATOM | 2458 | CD1 | TRP | A | 315 | 12.428 | 28.787 | 70.247 | 1.00 | 22.39 |
| ATOM | 2459 | CD2 | TRP | A | 315 | 14.599 | 28.430 | 69.876 | 1.00 | 21.70 |
| ATOM | 2460 | NE1 | TRP | A | 315 | 12.597 | 27.457 | 70.033 | 1.00 | 24.22 |
| ATOM | 2461 | CE2 | TRP | A | 315 | 13.934 | 27.205 | 69.801 | 1.00 | 27.96 |
| ATOM | 2462 | CE3 | TRP | A | 315 | 15.976 | 28.481 | 69.681 | 1.00 | 22.89 |
| ATOM | 2463 | CZ2 | TRP | A | 315 | 14.631 | 26.018 | 69.547 | 1.00 | 27.76 |
| ATOM | 2464 | CZ3 | TRP | A | 315 | 16.651 | 27.321 | 69.421 | 1.00 | 23.16 |
| ATOM | 2465 | CH2 | TRP | A | 315 | 15.991 | 26.108 | 69.341 | 1.00 | 23.94 |
| ATOM | 2466 | N | LEU | A | 316 | 13.488 | 30.114 | 67.144 | 1.00 | 26.33 |
| ATOM | 2467 | CA | LEU | A | 316 | 14.092 | 29.400 | 66.067 | 1.00 | 25.44 |
| ATOM | 2468 | C | LEU | A | 316 | 14.666 | 30.443 | 65.129 | 1.00 | 33.21 |
| ATOM | 2469 | O | LEU | A | 316 | 15.737 | 30.252 | 64.530 | 1.00 | 37.80 |
| ATOM | 2470 | CB | LEU | A | 316 | 13.050 | 28.567 | 65.311 | 1.00 | 24.82 |
| ATOM | 2471 | CG | LEU | A | 316 | 12.663 | 27.242 | 65.956 | 1.00 | 27.62 |
| ATOM | 2472 | CD1 | LEU | A | 316 | 11.574 | 26.552 | 65.106 | 1.00 | 22.30 |
| ATOM | 2473 | CD2 | LEU | A | 316 | 13.897 | 26.344 | 66.097 | 1.00 | 27.03 |
| ATOM | 2474 | N | ASN | A | 317 | 13.931 | 31.555 | 64.997 | 1.00 | 20.55 |
| ATOM | 2475 | CA | ASN | A | 317 | 14.354 | 32.624 | 64.115 | 1.00 | 19.34 |
| ATOM | 2476 | C | ASN | A | 317 | 15.603 | 33.333 | 64.531 | 1.00 | 30.38 |
| ATOM | 2477 | O | ASN | A | 317 | 16.553 | 33.425 | 63.766 | 1.00 | 32.04 |
| ATOM | 2478 | CB | ASN | A | 317 | 13.273 | 33.682 | 63.838 | 1.00 | 14.82 |
| ATOM | 2479 | CG | ASN | A | 317 | 12.330 | 33.177 | 62.793 | 1.00 | 31.14 |
| ATOM | 2480 | OD1 | ASN | A | 317 | 12.151 | 31.966 | 62.657 | 1.00 | 38.42 |
| ATOM | 2481 | ND2 | ASN | A | 317 | 11.724 | 34.074 | 62.049 | 1.00 | 17.34 |
| ATOM | 2482 | N | GLU | A | 318 | 15.562 | 33.870 | 65.750 | 1.00 | 26.15 |
| ATOM | 2483 | CA | GLU | A | 318 | 16.624 | 34.648 | 66.358 | 1.00 | 20.23 |
| ATOM | 2484 | C | GLU | A | 318 | 17.860 | 33.884 | 66.816 | 1.00 | 23.53 |
| ATOM | 2485 | O | GLU | A | 318 | 19.006 | 34.273 | 66.554 | 1.00 | 26.34 |
| ATOM | 2486 | CB | GLU | A | 318 | 15.998 | 35.484 | 67.456 | 1.00 | 19.11 |
| ATOM | 2487 | CG | GLU | A | 318 | 14.999 | 36.480 | 66.800 | 1.00 | 24.06 |
| ATOM | 2488 | CD | GLU | A | 318 | 15.615 | 37.391 | 65.758 | 1.00 | 40.32 |
| ATOM | 2489 | OE1 | GLU | A | 318 | 16.833 | 37.559 | 65.612 | 1.00 | 21.24 |
| ATOM | 2490 | OE2 | GLU | A | 318 | 14.703 | 38.025 | 65.062 | 1.00 | 24.23 |
| ATOM | 2491 | N | GLY | A | 319 | 17.621 | 32.782 | 67.494 | 1.00 | 17.17 |
| ATOM | 2492 | CA | GLY | A | 319 | 18.681 | 31.955 | 68.016 | 1.00 | 15.31 |
| ATOM | 2493 | C | GLY | A | 319 | 19.673 | 31.601 | 66.953 | 1.00 | 24.07 |
| ATOM | 2494 | O | GLY | A | 319 | 20.860 | 31.897 | 67.080 | 1.00 | 28.47 |
| ATOM | 2495 | N | HIS | A | 320 | 19.165 | 30.956 | 65.907 | 1.00 | 20.24 |
| ATOM | 2496 | CA | HIS | A | 320 | 19.977 | 30.556 | 64.790 | 1.00 | 20.13 |
| ATOM | 2497 | C | HIS | A | 320 | 20.678 | 31.759 | 64.142 | 1.00 | 24.97 |
| ATOM | 2498 | O | HIS | A | 320 | 21.855 | 31.700 | 63.739 | 1.00 | 23.54 |
| ATOM | 2499 | CB | HIS | A | 320 | 19.143 | 29.737 | 63.791 | 1.00 | 20.57 |
| ATOM | 2500 | CG | HIS | A | 320 | 18.662 | 28.426 | 64.349 | 1.00 | 22.57 |
| ATOM | 2501 | ND1 | HIS | A | 320 | 17.471 | 28.332 | 65.058 | 1.00 | 22.98 |
| ATOM | 2502 | CD2 | HIS | A | 320 | 19.217 | 27.176 | 64.286 | 1.00 | 19.52 |
| ATOM | 2503 | CE1 | HIS | A | 320 | 17.336 | 27.046 | 65.385 | 1.00 | 19.18 |
| ATOM | 2504 | NE2 | HIS | A | 320 | 18.368 | 26.329 | 64.952 | 1.00 | 18.12 |
| ATOM | 2505 | N | THR | A | 321 | 19.958 | 32.875 | 64.053 | 1.00 | 21.61 |
| ATOM | 2506 | CA | THR | A | 321 | 20.543 | 34.056 | 63.478 | 1.00 | 22.16 |
| ATOM | 2507 | C | THR | A | 321 | 21.697 | 34.552 | 64.342 | 1.00 | 27.47 |
| ATOM | 2508 | O | THR | A | 321 | 22.789 | 34.825 | 63.836 | 1.00 | 26.64 |
| ATOM | 2509 | CB | THR | A | 321 | 19.470 | 35.097 | 63.113 | 1.00 | 27.88 |
| ATOM | 2510 | OG1 | THR | A | 321 | 18.403 | 34.392 | 62.523 | 1.00 | 27.92 |
| ATOM | 2511 | CG2 | THR | A | 321 | 19.999 | 36.088 | 62.087 | 1.00 | 18.05 |
| ATOM | 2512 | N | VAL | A | 322 | 21.496 | 34.634 | 65.659 | 1.00 | 21.90 |
| ATOM | 2513 | CA | VAL | A | 322 | 22.610 | 35.054 | 66.470 | 1.00 | 19.44 |
| ATOM | 2514 | C | VAL | A | 322 | 23.762 | 34.071 | 66.285 | 1.00 | 24.43 |
| ATOM | 2515 | O | VAL | A | 322 | 24.926 | 34.414 | 66.188 | 1.00 | 21.48 |
| ATOM | 2516 | CB | VAL | A | 322 | 22.218 | 35.185 | 67.928 | 1.00 | 20.92 |

TABLE 9-continued

Structure coordinates of LTA₄ hydrolase-thiolamine complex
(The amino acid sequence set forth as residues 1-610 below correspond to SEQ ID NO:1.)

| ATOM | 2517 | CG1 | VAL | A | 322 | 23.406 | 35.644 | 68.772 | 1.00 | 18.37 |
|---|---|---|---|---|---|---|---|---|---|---|
| ATOM | 2518 | CG2 | VAL | A | 322 | 21.093 | 36.200 | 68.048 | 1.00 | 20.01 |
| ATOM | 2519 | N | TYR | A | 323 | 23.427 | 32.811 | 66.197 | 1.00 | 27.08 |
| ATOM | 2520 | CA | TYR | A | 323 | 24.446 | 31.803 | 66.013 | 1.00 | 26.26 |
| ATOM | 2521 | C | TYR | A | 323 | 25.222 | 32.036 | 64.728 | 1.00 | 28.26 |
| ATOM | 2522 | O | TYR | A | 323 | 26.431 | 31.894 | 64.643 | 1.00 | 27.51 |
| ATOM | 2523 | CB | TYR | A | 323 | 23.804 | 30.407 | 66.020 | 1.00 | 25.74 |
| ATOM | 2524 | CG | TYR | A | 323 | 24.867 | 29.341 | 65.987 | 1.00 | 26.66 |
| ATOM | 2525 | CD1 | TYR | A | 323 | 25.539 | 28.957 | 67.150 | 1.00 | 29.09 |
| ATOM | 2526 | CD2 | TYR | A | 323 | 25.199 | 28.713 | 64.789 | 1.00 | 24.52 |
| ATOM | 2527 | CE1 | TYR | A | 323 | 26.530 | 27.974 | 67.157 | 1.00 | 22.56 |
| ATOM | 2528 | CE2 | TYR | A | 323 | 26.178 | 27.722 | 64.770 | 1.00 | 25.31 |
| ATOM | 2529 | CZ | TYR | A | 323 | 26.846 | 27.370 | 65.944 | 1.00 | 29.19 |
| ATOM | 2530 | OH | TYR | A | 323 | 27.823 | 26.434 | 65.895 | 1.00 | 27.51 |
| ATOM | 2531 | N | LEU | A | 324 | 24.497 | 32.408 | 63.702 | 1.00 | 24.82 |
| ATOM | 2532 | CA | LEU | A | 324 | 25.135 | 32.638 | 62.439 | 1.00 | 26.04 |
| ATOM | 2533 | C | LEU | A | 324 | 25.832 | 33.952 | 62.417 | 1.00 | 30.92 |
| ATOM | 2534 | O | LEU | A | 324 | 26.903 | 34.045 | 61.851 | 1.00 | 33.76 |
| ATOM | 2535 | CB | LEU | A | 324 | 24.176 | 32.537 | 61.235 | 1.00 | 26.21 |
| ATOM | 2536 | CG | LEU | A | 324 | 23.916 | 31.112 | 60.778 | 1.00 | 28.46 |
| ATOM | 2537 | CD1 | LEU | A | 324 | 22.752 | 31.109 | 59.791 | 1.00 | 28.95 |
| ATOM | 2538 | CD2 | LEU | A | 324 | 25.169 | 30.508 | 60.151 | 1.00 | 26.54 |
| ATOM | 2539 | N | GLU | A | 325 | 25.234 | 34.976 | 63.033 | 1.00 | 27.04 |
| ATOM | 2540 | CA | GLU | A | 325 | 25.870 | 36.303 | 63.064 | 1.00 | 22.88 |
| ATOM | 2541 | C | GLU | A | 325 | 27.282 | 36.210 | 63.624 | 1.00 | 28.76 |
| ATOM | 2542 | O | GLU | A | 325 | 28.250 | 36.722 | 63.026 | 1.00 | 26.24 |
| ATOM | 2543 | CB | GLU | A | 325 | 25.016 | 37.365 | 63.759 | 1.00 | 22.01 |
| ATOM | 2544 | CG | GLU | A | 325 | 25.827 | 38.411 | 64.524 | 1.00 | 41.55 |
| ATOM | 2545 | CD | GLU | A | 325 | 25.035 | 39.040 | 65.646 | 1.00 | 72.11 |
| ATOM | 2546 | OE1 | GLU | A | 325 | 23.866 | 38.764 | 65.862 | 1.00 | 41.88 |
| ATOM | 2547 | OE2 | GLU | A | 325 | 25.719 | 39.922 | 66.350 | 1.00 | 67.15 |
| ATOM | 2548 | N | ARG | A | 326 | 27.349 | 35.479 | 64.755 | 1.00 | 27.84 |
| ATOM | 2549 | CA | ARG | A | 326 | 28.551 | 35.213 | 65.511 | 1.00 | 28.10 |
| ATOM | 2550 | C | ARG | A | 326 | 29.604 | 34.457 | 64.771 | 1.00 | 30.90 |
| ATOM | 2551 | O | ARG | A | 326 | 30.763 | 34.747 | 64.976 | 1.00 | 33.93 |
| ATOM | 2552 | CB | ARG | A | 326 | 28.334 | 34.761 | 66.947 | 1.00 | 31.52 |
| ATOM | 2553 | CG | ARG | A | 326 | 27.645 | 35.864 | 67.726 | 1.00 | 22.20 |
| ATOM | 2554 | CD | ARG | A | 326 | 27.462 | 35.572 | 69.203 | 1.00 | 28.71 |
| ATOM | 2555 | NE | ARG | A | 326 | 26.727 | 36.673 | 69.830 | 1.00 | 23.82 |
| ATOM | 2556 | CZ | ARG | A | 326 | 25.805 | 36.556 | 70.780 | 1.00 | 26.09 |
| ATOM | 2557 | NH1 | ARG | A | 326 | 25.443 | 35.388 | 71.305 | 1.00 | 23.16 |
| ATOM | 2558 | NH2 | ARG | A | 326 | 25.220 | 37.655 | 71.222 | 1.00 | 24.77 |
| ATOM | 2559 | N | HIS | A | 327 | 29.221 | 33.511 | 63.918 | 1.00 | 29.85 |
| ATOM | 2560 | CA | HIS | A | 327 | 30.207 | 32.777 | 63.120 | 1.00 | 30.52 |
| ATOM | 2561 | C | HIS | A | 327 | 30.778 | 33.738 | 62.085 | 1.00 | 35.50 |
| ATOM | 2562 | O | HIS | A | 327 | 31.966 | 33.777 | 61.822 | 1.00 | 36.74 |
| ATOM | 2563 | CB | HIS | A | 327 | 29.591 | 31.555 | 62.407 | 1.00 | 31.59 |
| ATOM | 2564 | CG | HIS | A | 327 | 29.764 | 30.259 | 63.176 | 1.00 | 34.51 |
| ATOM | 2565 | ND1 | HIS | A | 327 | 30.963 | 29.913 | 63.788 | 1.00 | 36.17 |
| ATOM | 2566 | CD2 | HIS | A | 327 | 28.875 | 29.263 | 63.432 | 1.00 | 35.58 |
| ATOM | 2567 | CE1 | HIS | A | 327 | 30.778 | 28.740 | 64.384 | 1.00 | 35.27 |
| ATOM | 2568 | NE2 | HIS | A | 327 | 29.532 | 28.322 | 64.191 | 1.003 | 5.56 |
| ATOM | 2569 | N | ILE | A | 328 | 29.902 | 34.549 | 61.511 | 1.00 | 31.10 |
| ATOM | 2570 | CA | ILE | A | 328 | 30.328 | 35.517 | 60.528 | 1.00 | 31.66 |
| ATOM | 2571 | C | ILE | A | 328 | 31.416 | 36.407 | 61.086 | 1.00 | 40.12 |
| ATOM | 2572 | O | ILE | A | 328 | 32.451 | 36.615 | 60.465 | 1.00 | 40.81 |
| ATOM | 2573 | CB | ILE | A | 328 | 29.175 | 36.379 | 59.998 | 1.00 | 32.94 |
| ATOM | 2574 | CG1 | ILE | A | 328 | 28.220 | 35.570 | 59.114 | 1.00 | 29.53 |
| ATOM | 2575 | CG2 | ILE | A | 328 | 29.694 | 37.591 | 59.201 | 1.00 | 30.91 |
| ATOM | 2576 | CD1 | ILE | A | 328 | 27.119 | 36.463 | 58.535 | 1.00 | 32.98 |
| ATOM | 2577 | N | CYS | A | 329 | 31.179 | 36.948 | 62.266 | 1.00 | 37.88 |
| ATOM | 2578 | CA | CYS | A | 329 | 32.170 | 37.810 | 62.851 | 1.00 | 39.54 |
| ATOM | 2579 | C | CYS | A | 329 | 33.475 | 37.092 | 63.157 | 1.00 | 40.19 |
| ATOM | 2580 | O | CYS | A | 329 | 34.567 | 37.642 | 62.971 | 1.00 | 38.44 |
| ATOM | 2581 | CB | CYS | A | 329 | 31.607 | 38.509 | 64.083 | 1.00 | 42.61 |
| ATOM | 2582 | SG | CYS | A | 329 | 30.241 | 39.595 | 63.619 | 1.00 | 48.14 |
| ATOM | 2583 | N | GLY | A | 330 | 33.332 | 35.852 | 63.632 | 1.00 | 34.74 |
| ATOM | 2584 | CA | GLY | A | 330 | 34.471 | 35.030 | 63.980 | 1.00 | 35.20 |
| ATOM | 2585 | C | GLY | A | 330 | 35.359 | 34.854 | 62.778 | 1.00 | 43.66 |
| ATOM | 2586 | O | GLY | A | 330 | 36.581 | 34.857 | 62.891 | 1.00 | 46.79 |
| ATOM | 2587 | N | ARG | A | 331 | 34.709 | 34.725 | 61.622 | 1.00 | 34.99 |
| ATOM | 2588 | CA | ARG | A | 331 | 35.416 | 34.562 | 60.392 | 1.00 | 33.19 |
| ATOM | 2589 | C | ARG | A | 331 | 36.086 | 35.863 | 60.017 | 1.00 | 40.63 |
| ATOM | 2590 | O | ARG | A | 331 | 37.238 | 35.914 | 59.586 | 1.00 | 44.40 |
| ATOM | 2591 | CB | ARG | A | 331 | 34.494 | 34.101 | 59.269 | 1.00 | 31.29 |
| ATOM | 2592 | CG | ARG | A | 331 | 33.987 | 32.685 | 59.450 | 1.00 | 47.66 |

TABLE 9-continued

Structure coordinates of LTA₄ hydrolase-thiolamine complex
(The amino acid sequence set forth as residues 1-610 below correspond to SEQ ID NO:1.)

| ATOM | 2593 | CD  | ARG | A | 331 | 34.812 | 31.722 | 58.622 | 1.00 | 70.36  |
|------|------|-----|-----|---|-----|--------|--------|--------|------|--------|
| ATOM | 2594 | NE  | ARG | A | 331 | 34.461 | 31.851 | 57.221 | 1.00 | 80.25  |
| ATOM | 2595 | CZ  | ARG | A | 331 | 33.615 | 31.023 | 56.628 | 1.00 | 100.00 |
| ATOM | 2596 | NH1 | ARG | A | 331 | 33.055 | 29.999 | 57.279 | 1.00 | 79.12  |
| ATOM | 2597 | NH2 | ARG | A | 331 | 33.334 | 31.216 | 55.341 | 1.00 | 89.33  |
| ATOM | 2598 | N   | LEU | A | 332 | 35.342 | 36.926 | 60.172 | 1.00 | 32.14  |
| ATOM | 2599 | CA  | LEU | A | 332 | 35.885 | 38.198 | 59.820 | 1.00 | 30.02  |
| ATOM | 2600 | C   | LEU | A | 332 | 37.013 | 38.612 | 60.761 | 1.00 | 40.33  |
| ATOM | 2601 | O   | LEU | A | 332 | 38.084 | 38.972 | 60.286 | 1.00 | 40.10  |
| ATOM | 2602 | CB  | LEU | A | 332 | 34.772 | 39.262 | 59.822 | 1.00 | 28.20  |
| ATOM | 2603 | CG  | LEU | A | 332 | 34.451 | 39.896 | 58.469 | 1.00 | 28.82  |
| ATOM | 2604 | CD1 | LEU | A | 332 | 35.007 | 39.063 | 57.341 | 1.00 | 23.73  |
| ATOM | 2605 | CD2 | LEU | A | 332 | 32.947 | 40.114 | 58.306 | 1.00 | 29.76  |
| ATOM | 2606 | N   | PHE | A | 333 | 36.744 | 38.557 | 62.091 | 1.00 | 37.69  |
| ATOM | 2607 | CA  | PHE | A | 333 | 37.657 | 38.997 | 63.143 | 1.00 | 34.12  |
| ATOM | 2608 | C   | PHE | A | 333 | 38.251 | 37.956 | 64.035 | 1.00 | 37.99  |
| ATOM | 2609 | O   | PHE | A | 333 | 39.015 | 38.293 | 64.925 | 1.00 | 41.67  |
| ATOM | 2610 | CB  | PHE | A | 333 | 36.970 | 40.058 | 64.024 | 1.00 | 35.62  |
| ATOM | 2611 | CG  | PHE | A | 333 | 36.209 | 41.003 | 63.138 | 1.00 | 39.09  |
| ATOM | 2612 | CD1 | PHE | A | 333 | 36.887 | 41.923 | 62.332 | 1.00 | 43.22  |
| ATOM | 2613 | CD2 | PHE | A | 333 | 34.818 | 40.941 | 63.045 | 1.00 | 42.78  |
| ATOM | 2614 | CE1 | PHE | A | 333 | 36.205 | 42.781 | 61.464 | 1.00 | 44.14  |
| ATOM | 2615 | CE2 | PHE | A | 333 | 34.123 | 41.806 | 62.194 | 1.00 | 46.56  |
| ATOM | 2616 | CZ  | PHE | A | 333 | 34.814 | 42.716 | 61.389 | 1.00 | 43.20  |
| ATOM | 2617 | N   | GLY | A | 334 | 37.908 | 36.706 | 63.865 | 1.00 | 34.36  |
| ATOM | 2618 | CA  | GLY | A | 334 | 38.507 | 35.705 | 64.763 | 1.00 | 32.89  |
| ATOM | 2619 | C   | GLY | A | 334 | 37.582 | 34.985 | 65.767 | 1.00 | 32.67  |
| ATOM | 2620 | O   | GLY | A | 334 | 36.641 | 35.540 | 66.340 | 1.00 | 33.48  |
| ATOM | 2621 | N   | GLU | A | 335 | 37.908 | 33.726 | 66.003 | 1.00 | 23.52  |
| ATOM | 2622 | CA  | GLU | A | 335 | 37.196 | 32.875 | 66.931 | 1.00 | 18.13  |
| ATOM | 2623 | C   | GLU | A | 335 | 37.278 | 33.384 | 68.346 | 1.00 | 29.15  |
| ATOM | 2624 | O   | GLU | A | 335 | 36.357 | 33.124 | 69.112 | 1.00 | 34.14  |
| ATOM | 2625 | CB  | GLU | A | 335 | 37.782 | 31.488 | 66.929 | 1.00 | 17.35  |
| ATOM | 2626 | CG  | GLU | A | 335 | 37.041 | 30.591 | 67.929 | 1.00 | 32.97  |
| ATOM | 2627 | CD  | GLU | A | 335 | 35.642 | 30.305 | 67.473 | 1.00 | 46.14  |
| ATOM | 2628 | OE1 | GLU | A | 335 | 35.093 | 30.944 | 66.588 | 1.00 | 39.31  |
| ATOM | 2629 | OE2 | GLU | A | 335 | 35.080 | 29.317 | 68.132 | 1.00 | 32.80  |
| ATOM | 2630 | N   | LYS | A | 336 | 38.370 | 34.077 | 68.706 | 1.00 | 24.53  |
| ATOM | 2631 | CA  | LYS | A | 336 | 38.468 | 34.609 | 70.061 | 1.00 | 25.38  |
| ATOM | 2632 | C   | LYS | A | 336 | 37.445 | 35.726 | 70.169 | 1.00 | 35.32  |
| ATOM | 2633 | O   | LYS | A | 336 | 36.908 | 36.004 | 71.233 | 1.00 | 38.14  |
| ATOM | 2634 | CB  | LYS | A | 336 | 39.820 | 35.199 | 70.421 | 1.00 | 25.45  |
| ATOM | 2635 | CG  | LYS | A | 336 | 40.871 | 34.188 | 70.825 | 1.00 | 25.43  |
| ATOM | 2636 | CD  | LYS | A | 336 | 42.207 | 34.846 | 71.189 | 1.00 | 47.10  |
| ATOM | 2637 | CE  | LYS | A | 336 | 43.325 | 34.600 | 70.172 | 1.00 | 68.74  |
| ATOM | 2638 | NZ  | LYS | A | 336 | 44.566 | 34.072 | 70.767 | 1.00 | 77.62  |
| ATOM | 2639 | N   | PHE | A | 337 | 37.174 | 36.364 | 69.029 | 1.00 | 31.52  |
| ATOM | 2640 | CA  | PHE | A | 337 | 36.186 | 37.442 | 68.967 | 1.00 | 29.34  |
| ATOM | 2641 | C   | PHE | A | 337 | 34.783 | 36.869 | 69.083 | 1.00 | 31.73  |
| ATOM | 2642 | O   | PHE | A | 337 | 33.908 | 37.424 | 69.742 | 1.00 | 35.53  |
| ATOM | 2643 | CB  | PHE | A | 337 | 36.304 | 38.336 | 67.709 | 1.00 | 30.04  |
| ATOM | 2644 | CG  | PHE | A | 337 | 35.435 | 39.589 | 67.747 | 1.00 | 35.16  |
| ATOM | 2645 | CD1 | PHE | A | 337 | 35.468 | 40.459 | 68.843 | 1.00 | 43.88  |
| ATOM | 2646 | CD2 | PHE | A | 337 | 34.550 | 39.893 | 66.709 | 1.00 | 40.16  |
| ATOM | 2647 | CE1 | PHE | A | 337 | 34.688 | 41.617 | 68.913 | 1.00 | 46.53  |
| ATOM | 2648 | CE2 | PHE | A | 337 | 33.753 | 41.040 | 66.760 | 1.00 | 45.62  |
| ATOM | 2649 | CZ  | PHE | A | 337 | 33.830 | 41.908 | 67.852 | 1.00 | 45.57  |
| ATOM | 2650 | N   | ARG | A | 338 | 34.566 | 35.733 | 68.452 | 1.00 | 25.52  |
| ATOM | 2651 | CA  | ARG | A | 338 | 33.266 | 35.119 | 68.508 | 1.00 | 25.23  |
| ATOM | 2652 | C   | ARG | A | 338 | 32.944 | 34.759 | 69.922 | 1.00 | 29.77  |
| ATOM | 2653 | O   | ARG | A | 338 | 31.854 | 35.025 | 70.415 | 1.00 | 31.81  |
| ATOM | 2654 | CB  | ARG | A | 338 | 33.186 | 33.920 | 67.606 | 1.00 | 24.04  |
| ATOM | 2655 | CG  | ARG | A | 338 | 31.839 | 33.228 | 67.623 | 1.00 | 21.31  |
| ATOM | 2656 | CD  | ARG | A | 338 | 31.807 | 32.086 | 66.599 | 1.00 | 30.62  |
| ATOM | 2657 | NE  | ARG | A | 338 | 32.518 | 30.892 | 67.040 | 1.00 | 29.87  |
| ATOM | 2658 | CZ  | ARG | A | 338 | 31.919 | 29.781 | 67.466 | 1.00 | 26.37  |
| ATOM | 2659 | NH1 | ARG | A | 338 | 30.616 | 29.687 | 67.518 | 1.00 | 20.26  |
| ATOM | 2660 | NH2 | ARG | A | 338 | 32.632 | 28.737 | 67.864 | 1.00 | 18.57  |
| ATOM | 2661 | N   | HIS | A | 339 | 33.934 | 34.190 | 70.577 | 1.00 | 25.88  |
| ATOM | 2662 | CA  | HIS | A | 339 | 33.813 | 33.797 | 71.982 | 1.00 | 25.59  |
| ATOM | 2663 | C   | HIS | A | 339 | 33.455 | 34.972 | 72.892 | 1.00 | 27.61  |
| ATOM | 2664 | O   | HIS | A | 339 | 32.615 | 34.912 | 73.793 | 1.00 | 25.27  |
| ATOM | 2665 | CB  | HIS | A | 339 | 35.065 | 33.045 | 72.462 | 1.00 | 25.06  |
| ATOM | 2666 | CG  | HIS | A | 339 | 34.923 | 31.587 | 72.155 | 1.00 | 28.13  |
| ATOM | 2667 | ND1 | HIS | A | 339 | 35.049 | 30.612 | 73.127 | 1.00 | 30.52  |

TABLE 9-continued

Structure coordinates of LTA₄ hydrolase-thiolamine complex
(The amino acid sequence set forth as residues 1-610 below correspond to SEQ ID NO:1.)

| ATOM | 2668 | CD2 | HIS | A | 339 | 34.586 | 30.970 | 70.981 | 1.00 | 30.89 |
|---|---|---|---|---|---|---|---|---|---|---|
| ATOM | 2669 | CE1 | HIS | A | 339 | 34.843 | 29.442 | 72.535 | 1.00 | 30.89 |
| ATOM | 2670 | NE2 | HIS | A | 339 | 34.546 | 29.616 | 71.245 | 1.00 | 31.36 |
| ATOM | 2671 | N | PHE | A | 340 | 34.103 | 36.065 | 72.608 | 1.00 | 24.54 |
| ATOM | 2672 | CA | PHE | A | 340 | 33.892 | 37.278 | 73.334 | 1.00 | 25.36 |
| ATOM | 2673 | C | PHE | A | 340 | 32.452 | 37.762 | 73.216 | 1.00 | 32.47 |
| ATOM | 2674 | O | PHE | A | 340 | 31.822 | 38.222 | 74.190 | 1.00 | 32.78 |
| ATOM | 2675 | CB | PHE | A | 340 | 34.876 | 38.309 | 72.801 | 1.00 | 26.03 |
| ATOM | 2676 | CG | PHE | A | 340 | 34.654 | 39.671 | 73.346 | 1.00 | 26.47 |
| ATOM | 2677 | CD1 | PHE | A | 340 | 35.238 | 40.047 | 74.559 | 1.00 | 24.59 |
| ATOM | 2678 | CD2 | PHE | A | 340 | 33.902 | 40.592 | 72.616 | 1.00 | 28.22 |
| ATOM | 2679 | CE1 | PHE | A | 340 | 35.063 | 41.330 | 75.072 | 1.00 | 21.58 |
| ATOM | 2680 | CE2 | PHE | A | 340 | 33.715 | 41.879 | 73.115 | 1.00 | 29.13 |
| ATOM | 2681 | CZ | PHE | A | 340 | 34.280 | 42.225 | 74.345 | 1.00 | 25.28 |
| ATOM | 2682 | N | ASN | A | 341 | 31.944 | 37.663 | 72.004 | 1.00 | 28.41 |
| ATOM | 2683 | CA | ASN | A | 341 | 30.600 | 38.084 | 71.728 | 1.00 | 29.60 |
| ATOM | 2684 | C | ASN | A | 341 | 29.665 | 37.110 | 72.379 | 1.00 | 38.52 |
| ATOM | 2685 | O | ASN | A | 341 | 28.699 | 37.511 | 73.029 | 1.00 | 42.88 |
| ATOM | 2686 | CB | ASN | A | 341 | 30.322 | 38.274 | 70.224 | 1.00 | 30.01 |
| ATOM | 2687 | CG | ASN | A | 341 | 31.159 | 39.374 | 69.587 | 1.00 | 52.80 |
| ATOM | 2688 | OD1 | ASN | A | 341 | 31.528 | 39.284 | 68.404 | 1.00 | 60.88 |
| ATOM | 2689 | ND2 | ASN | A | 341 | 31.442 | 40.427 | 70.359 | 1.00 | 41.02 |
| ATOM | 2690 | N | ALA | A | 342 | 29.994 | 35.826 | 72.239 | 1.00 | 28.24 |
| ATOM | 2691 | CA | ALA | A | 342 | 29.195 | 34.800 | 72.877 | 1.00 | 26.95 |
| ATOM | 2692 | C | ALA | A | 342 | 29.013 | 35.134 | 74.393 | 1.00 | 35.98 |
| ATOM | 2693 | O | ALA | A | 342 | 27.877 | 35.261 | 74.897 | 1.00 | 35.09 |
| ATOM | 2694 | CB | ALA | A | 342 | 29.837 | 33.422 | 72.671 | 1.00 | 25.45 |
| ATOM | 2695 | N | LEU | A | 343 | 30.153 | 35.304 | 75.122 | 1.00 | 29.16 |
| ATOM | 2696 | CA | LEU | A | 343 | 30.162 | 35.633 | 76.560 | 1.00 | 22.58 |
| ATOM | 2697 | C | LEU | A | 343 | 29.310 | 36.854 | 76.831 | 1.00 | 27.48 |
| ATOM | 2698 | O | LEU | A | 343 | 28.452 | 36.821 | 77.696 | 1.00 | 32.73 |
| ATOM | 2699 | CB | LEU | A | 343 | 31.583 | 35.786 | 77.147 | 1.00 | 18.70 |
| ATOM | 2700 | CG | LEU | A | 343 | 31.647 | 35.693 | 78.671 | 1.00 | 20.08 |
| ATOM | 2701 | CD1 | LEU | A | 343 | 30.842 | 34.510 | 79.204 | 1.00 | 17.76 |
| ATOM | 2702 | CD2 | LEU | A | 343 | 33.091 | 35.522 | 79.111 | 1.00 | 21.94 |
| ATOM | 2703 | N | GLY | A | 344 | 29.512 | 37.936 | 76.080 | 1.00 | 22.60 |
| ATOM | 2704 | CA | GLY | A | 344 | 28.670 | 39.146 | 76.278 | 1.00 | 24.15 |
| ATOM | 2705 | C | GLY | A | 344 | 27.157 | 38.824 | 76.136 | 1.00 | 31.38 |
| ATOM | 2706 | O | GLY | A | 344 | 26.339 | 39.260 | 76.943 | 1.00 | 32.44 |
| ATOM | 2707 | N | GLY | A | 345 | 26.806 | 38.017 | 75.094 | 1.00 | 22.79 |
| ATOM | 2708 | CA | GLY | A | 345 | 25.451 | 37.587 | 74.801 | 1.00 | 19.88 |
| ATOM | 2709 | C | GLY | A | 345 | 24.787 | 36.994 | 76.034 | 1.00 | 28.37 |
| ATOM | 2710 | O | GLY | A | 345 | 23.632 | 37.294 | 76.325 | 1.00 | 27.56 |
| ATOM | 2711 | N | TRP | A | 346 | 25.547 | 36.153 | 76.765 | 1.00 | 25.41 |
| ATOM | 2712 | CA | TRP | A | 346 | 25.082 | 35.520 | 77.994 | 1.00 | 23.90 |
| ATOM | 2713 | C | TRP | A | 346 | 24.825 | 36.541 | 79.071 | 1.00 | 31.54 |
| ATOM | 2714 | O | TRP | A | 346 | 23.957 | 36.379 | 79.924 | 1.00 | 29.57 |
| ATOM | 2715 | CB | TRP | A | 346 | 26.122 | 34.556 | 78.562 | 1.00 | 21.53 |
| ATOM | 2716 | CG | TRP | A 346 | 25.680 | 33.880 | 79.837 | 1.00 | 21.92 | |
| ATOM | 2717 | CD1 | TRP | A | 346 | 25.933 | 34.335 | 81.079 | 1.00 | 24.36 |
| ATOM | 2718 | CD2 | TRP | A | 346 | 25.004 | 32.597 | 80.010 | 1.00 | 20.97 |
| ATOM | 2719 | NE1 | TRP | A | 346 | 25.450 | 33.453 | 82.008 | 1.00 | 23.95 |
| ATOM | 2720 | CE2 | TRP | A | 346 | 24.859 | 32.388 | 81.391 | 1.00 | 24.13 |
| ATOM | 2721 | CE3 | TRP | A | 346 | 24.488 | 31.611 | 79.144 | 1.00 | 21.46 |
| ATOM | 2722 | CZ2 | TRP | A | 346 | 24.225 | 31.244 | 81.921 | 1.00 | 22.89 |
| ATOM | 2723 | CZ3 | TRP | A | 346 | 23.872 | 30.477 | 79.662 | 1.00 | 22.03 |
| ATOM | 2724 | CH2 | TRP | A | 346 | 23.747 | 30.286 | 81.046 | 1.00 | 21.87 |
| ATOM | 2725 | N | GLY | A | 347 | 25.627 | 37.593 | 79.039 | 1.00 | 29.66 |
| ATOM | 2726 | CA | GLY | A | 347 | 25.465 | 38.625 | 80.042 | 1.00 | 29.03 |
| ATOM | 2727 | C | GLY | A | 347 | 24.156 | 39.333 | 79.844 | 1.00 | 33.01 |
| ATOM | 2728 | O | GLY | A | 347 | 23.491 | 39.647 | 80.799 | 1.00 | 34.17 |
| ATOM | 2729 | N | GLU | A | 348 | 23.797 | 39.574 | 78.581 | 1.00 | 30.57 |
| ATOM | 2730 | CA | GLU | A | 348 | 22.535 | 40.220 | 78.250 | 1.00 | 29.17 |
| ATOM | 2731 | C | GLU | A | 348 | 21.423 | 39.282 | 78.664 | 1.00 | 31.25 |
| ATOM | 2732 | O | GLU | A | 348 | 20.373 | 39.663 | 79.142 | 1.00 | 33.71 |
| ATOM | 2733 | CB | GLU | A | 348 | 22.432 | 40.606 | 76.757 | 1.00 | 30.33 |
| ATOM | 2734 | CG | GLU | A | 348 | 23.432 | 41.715 | 76.336 | 1.00 | 49.41 |
| ATOM | 2735 | CD | GLU | A | 348 | 23.209 | 43.088 | 76.964 | 1.00 | 73.39 |
| ATOM | 2736 | OE1 | GLU | A | 348 | 22.295 | 43.846 | 76.656 | 1.00 | 71.22 |
| ATOM | 2737 | OE2 | GLU | A | 348 | 24.119 | 43.395 | 77.857 | 1.00 | 44.23 |
| ATOM | 2738 | N | LEU | A | 349 | 21.682 | 38.011 | 78.541 | 1.00 | 27.36 |
| ATOM | 2739 | CA | LEU | A | 349 | 20.677 | 37.081 | 78.976 | 1.00 | 26.89 |
| ATOM | 2740 | C | LEU | A | 349 | 20.429 | 37.250 | 80.485 | 1.00 | 24.87 |
| ATOM | 2741 | O | LEU | A | 349 | 19.299 | 37.403 | 80.914 | 1.00 | 28.31 |
| ATOM | 2742 | CB | LEU | A | 349 | 20.984 | 35.630 | 78.529 | 1.00 | 27.18 |
| ATOM | 2743 | CG | LEU | A | 349 | 19.943 | 34.565 | 78.942 | 1.00 | 32.45 |

TABLE 9-continued

Structure coordinates of LTA₄ hydrolase-thiolamine complex
(The amino acid sequence set forth as residues 1-610 below correspond to SEQ ID NO:1.)

| ATOM | 2744 | CD1 | LEU | A | 349 | 18.611 | 34.704 | 78.154 | 1.00 | 30.09 |
|---|---|---|---|---|---|---|---|---|---|---|
| ATOM | 2745 | CD2 | LEU | A | 349 | 20.541 | 33.169 | 78.749 | 1.00 | 27.10 |
| ATOM | 2746 | N | GLN | A | 350 | 21.460 | 37.255 | 81.315 | 1.00 | 14.78 |
| ATOM | 2747 | CA | GLN | A | 350 | 21.188 | 37.428 | 82.727 | 1.00 | 18.51 |
| ATOM | 2748 | C | GLN | A | 350 | 20.442 | 38.722 | 82.953 | 1.00 | 25.53 |
| ATOM | 2749 | O | GLN | A | 350 | 19.495 | 38.833 | 83.737 | 1.00 | 28.35 |
| ATOM | 2750 | CB | GLN | A | 350 | 22.469 | 37.369 | 83.536 | 1.00 | 22.22 |
| ATOM | 2751 | CG | GLN | A | 350 | 23.512 | 36.426 | 82.919 | 1.00 | 22.37 |
| ATOM | 2752 | CD | GLN | A | 350 | 24.871 | 36.673 | 83.547 | 1.00 | 34.49 |
| ATOM | 2753 | OE1 | GLN | A | 350 | 25.261 | 35.932 | 84.417 | 1.00 | 24.01 |
| ATOM | 2754 | NE2 | GLN | A | 350 | 25.588 | 37.727 | 83.127 | 1.00 | 36.58 |
| ATOM | 2755 | N | ASN | A | 351 | 20.838 | 39.696 | 82.201 | 1.00 | 22.64 |
| ATOM | 2756 | CA | ASN | A | 351 | 20.163 | 40.960 | 82.273 | 1.00 | 26.10 |
| ATOM | 2757 | C | ASN | A | 351 | 18.661 | 40.780 | 82.083 | 1.00 | 37.49 |
| ATOM | 2758 | O | ASN | A | 351 | 17.890 | 41.098 | 82.977 | 1.00 | 41.41 |
| ATOM | 2759 | CB | ASN | A | 351 | 20.769 | 42.021 | 81.341 | 1.00 | 20.74 |
| ATOM | 2760 | CG | ASN | A | 351 | 22.118 | 42.477 | 81.847 | 1.00 | 23.25 |
| ATOM | 2761 | OD1 | ASN | A | 351 | 22.692 | 41.875 | 82.771 | 1.00 | 26.88 |
| ATOM | 2762 | ND2 | ASN | A | 351 | 22.644 | 43.530 | 81.247 | 1.00 | 32.93 |
| ATOM | 2763 | N | SER | A | 352 | 18.228 | 40.252 | 80.938 | 1.00 | 32.84 |
| ATOM | 2764 | CA | SER | A | 352 | 16.784 | 40.041 | 80.715 | 1.00 | 34.27 |
| ATOM | 2765 | C | SER | A | 352 | 16.107 | 39.135 | 81.784 | 1.00 | 31.72 |
| ATOM | 2766 | O | SER | A | 352 | 14.927 | 39.266 | 82.189 | 1.00 | 28.64 |
| ATOM | 2767 | CB | SER | A | 352 | 16.503 | 39.531 | 79.301 | 1.00 | 42.57 |
| ATOM | 2768 | OG | SER | A | 352 | 17.506 | 39.979 | 78.407 | 1.00 | 49.17 |
| ATOM | 2769 | N | VAL | A | 353 | 16.874 | 38.188 | 82.247 | 1.00 | 22.90 |
| ATOM | 2770 | CA | VAL | A | 353 | 16.322 | 37.351 | 83.234 | 1.00 | 22.13 |
| ATOM | 2771 | C | VAL | A | 353 | 16.068 | 38.122 | 84.516 | 1.00 | 36.22 |
| ATOM | 2772 | O | VAL | A | 353 | 14.958 | 38.076 | 85.052 | 1.00 | 37.69 |
| ATOM | 2773 | CB | VAL | A | 353 | 17.137 | 36.070 | 83.419 | 1.00 | 20.84 |
| ATOM | 2774 | CG1 | VAL | A | 353 | 16.632 | 35.256 | 84.634 | 1.00 | 15.06 |
| ATOM | 2775 | CG2 | VAL | A | 353 | 16.968 | 35.284 | 82.105 | 1.00 | 20.93 |
| ATOM | 2776 | N | LYS | A | 354 | 17.086 | 38.847 | 85.002 | 1.00 | 30.67 |
| ATOM | 2777 | CA | LYS | A | 354 | 16.880 | 39.587 | 86.221 | 1.00 | 31.71 |
| ATOM | 2778 | C | LYS | A | 354 | 15.660 | 40.474 | 86.098 | 1.00 | 36.17 |
| ATOM | 2779 | O | LYS | A | 354 | 14.808 | 40.582 | 86.980 | 1.00 | 35.80 |
| ATOM | 2780 | CB | LYS | A | 354 | 18.099 | 40.396 | 86.624 | 1.00 | 35.28 |
| ATOM | 2781 | CG | LYS | A | 354 | 17.841 | 41.303 | 87.818 | 1.00 | 51.51 |
| ATOM | 2782 | CD | LYS | A | 354 | 19.038 | 41.405 | 88.749 | 1.00 | 60.46 |
| ATOM | 2783 | CE | LYS | A | 354 | 19.198 | 42.780 | 89.383 | 1.00 | 50.09 |
| ATOM | 2784 | NZ | LYS | A | 354 | 20.596 | 43.133 | 89.657 | 1.00 | 63.77 |
| ATOM | 2785 | N | THR | A | 355 | 15.608 | 41.108 | 84.962 | 1.00 | 32.63 |
| ATOM | 2786 | CA | THR | A | 355 | 14.562 | 42.025 | 84.610 | 1.00 | 34.03 |
| ATOM | 2787 | C | THR | A | 355 | 13.129 | 41.422 | 84.578 | 1.00 | 42.11 |
| ATOM | 2788 | O | THR | A | 355 | 12.216 | 42.006 | 85.154 | 1.00 | 40.96 |
| ATOM | 2789 | CB | THR | A | 355 | 14.974 | 42.736 | 83.308 | 1.00 | 41.11 |
| ATOM | 2790 | OG1 | THR | A | 355 | 16.071 | 43.615 | 83.542 | 1.00 | 29.85 |
| ATOM | 2791 | CG2 | THR | A | 355 | 13.798 | 43.438 | 82.656 | 1.00 | 45.50 |
| ATOM | 2792 | N | PHE | A | 356 | 12.895 | 40.273 | 83.908 | 1.00 | 33.89 |
| ATOM | 2793 | CA | PHE | A | 356 | 11.556 | 39.729 | 83.860 | 1.00 | 29.29 |
| ATOM | 2794 | C | PHE | A | 356 | 11.209 | 39.070 | 85.147 | 1.00 | 31.93 |
| ATOM | 2795 | O | PHE | A | 356 | 10.089 | 39.152 | 85.642 | 1.00 | 33.85 |
| ATOM | 2796 | CB | PHE | A | 356 | 11.460 | 38.645 | 82.785 | 1.00 | 33.30 |
| ATOM | 2797 | CG | PHE | A | 356 | 11.187 | 39.196 | 81.416 | 1.00 | 36.54 |
| ATOM | 2798 | CD1 | PHE | A | 356 | 10.106 | 40.054 | 81.224 | 1.00 | 42.38 |
| ATOM | 2799 | CD2 | PHE | A | 356 | 11.985 | 38.858 | 80.320 | 1.00 | 38.62 |
| ATOM | 2800 | CE1 | PHE | A | 356 | 9.831 | 40.596 | 79.968 | 1.00 | 44.75 |
| ATOM | 2801 | CE2 | PHE | A | 356 | 11.723 | 39.384 | 79.055 | 1.00 | 43.46 |
| ATOM | 2802 | CZ | PHE | A | 356 | 10.649 | 40.261 | 78.890 | 1.00 | 43.86 |
| ATOM | 2803 | N | GLY | A | 357 | 12.212 | 38.386 | 85.661 | 1.00 | 30.41 |
| ATOM | 2804 | CA | GLY | A | 357 | 12.152 | 37.564 | 86.864 | 1.00 | 29.17 |
| ATOM | 2805 | C | GLY | A | 357 | 12.446 | 36.100 | 86.438 | 1.00 | 28.92 |
| ATOM | 2806 | O | GLY | A | 357 | 12.008 | 35.642 | 85.372 | 1.00 | 27.33 |
| ATOM | 2807 | N | GLU | A | 358 | 13.211 | 35.382 | 87.243 | 1.00 | 21.27 |
| ATOM | 2808 | CA | GLU | A | 358 | 13.590 | 34.040 | 86.898 | 1.00 | 23.10 |
| ATOM | 2809 | C | GLU | A | 358 | 12.424 | 33.104 | 86.747 | 1.00 | 31.53 |
| ATOM | 2810 | O | GLU | A | 358 | 12.581 | 31.972 | 86.294 | 1.00 | 30.92 |
| ATOM | 2811 | CB | GLU | A | 358 | 14.596 | 33.473 | 87.880 | 1.00 | 25.36 |
| ATOM | 2812 | CG | GLU | A | 358 | 14.011 | 33.436 | 89.301 | 1.00 | 38.73 |
| ATOM | 2813 | CD | GLU | A | 358 | 15.011 | 33.037 | 90.345 | 1.00 | 56.34 |
| ATOM | 2814 | OE1 | GLU | A | 358 | 16.026 | 32.446 | 90.071 | 1.00 | 50.55 |
| ATOM | 2815 | OE2 | GLU | A | 358 | 14.678 | 33.403 | 91.564 | 1.00 | 75.65 |
| ATOM | 2816 | N | THR | A | 359 | 11.246 | 33.542 | 87.139 | 1.00 | 27.87 |

TABLE 9-continued

Structure coordinates of LTA₄ hydrolase-thiolamine complex
(The amino acid sequence set forth as residues 1-610 below correspond to SEQ ID NO:1.)

| ATOM | 2817 | CA  | THR | A | 359 | 10.154 | 32.625 | 86.970 | 1.00 | 25.66 |
|------|------|-----|-----|---|-----|--------|--------|--------|------|-------|
| ATOM | 2818 | C   | THR | A | 359 | 9.236  | 33.152 | 85.906 | 1.00 | 25.96 |
| ATOM | 2819 | O   | THR | A | 359 | 8.247  | 32.528 | 85.533 | 1.00 | 25.58 |
| ATOM | 2820 | CB  | THR | A | 359 | 9.423  | 32.341 | 88.253 | 1.00 | 25.00 |
| ATOM | 2821 | OG1 | THR | A | 359 | 8.908  | 33.565 | 88.692 | 1.00 | 33.10 |
| ATOM | 2822 | CG2 | THR | A | 359 | 10.406 | 31.785 | 89.273 | 1.00 | 14.43 |
| ATOM | 2823 | N   | HIS | A | 360 | 9.602  | 34.310 | 85.407 | 1.00 | 20.75 |
| ATOM | 2824 | CA  | HIS | A | 360 | 8.837  | 34.902 | 84.363 | 1.00 | 22.77 |
| ATOM | 2825 | C   | HIS | A | 360 | 8.823  | 34.034 | 83.130 | 1.00 | 35.30 |
| ATOM | 2826 | O   | HIS | A | 360 | 9.858  | 33.611 | 82.620 | 1.00 | 37.42 |
| ATOM | 2827 | CB  | HIS | A | 360 | 9.294  | 36.291 | 83.982 | 1.00 | 23.18 |
| ATOM | 2828 | CG  | HIS | A | 360 | 8.207  | 36.908 | 83.219 | 1.00 | 27.05 |
| ATOM | 2829 | ND1 | HIS | A | 360 | 7.532  | 38.009 | 83.691 | 1.00 | 29.34 |
| ATOM | 2830 | CD2 | HIS | A | 360 | 7.651  | 36.545 | 82.059 | 1.00 | 29.91 |
| ATOM | 2831 | CE1 | HIS | A | 360 | 6.596  | 38.315 | 82.806 | 1.00 | 27.94 |
| ATOM | 2832 | NE2 | HIS | A | 360 | 6.651  | 37.440 | 81.812 | 1.00 | 29.60 |
| ATOM | 2833 | N   | PRO | A | 361 | 7.606  | 33.817 | 82.666 | 1.00 | 32.40 |
| ATOM | 2834 | CA  | PRO | A | 361 | 7.301  | 32.999 | 81.519 | 1.00 | 29.46 |
| ATOM | 2835 | C   | PRO | A | 361 | 7.862  | 33.478 | 80.224 | 1.00 | 30.59 |
| ATOM | 2836 | O   | PRO | A | 361 | 7.907  | 32.737 | 79.248 | 1.00 | 33.00 |
| ATOM | 2837 | CB  | PRO | A | 361 | 5.770  | 32.963 | 81.478 | 1.00 | 30.74 |
| ATOM | 2838 | CG  | PRO | A | 361 | 5.311  | 33.172 | 82.927 | 1.00 | 34.96 |
| ATOM | 2839 | CD  | PRO | A | 361 | 6.463  | 33.869 | 83.627 | 1.00 | 31.82 |
| ATOM | 2840 | N   | PHE | A | 362 | 8.289  | 34.712 | 80.179 | 1.00 | 26.32 |
| ATOM | 2841 | CA  | PHE | A | 362 | 8.823  | 35.173 | 78.933 | 1.00 | 25.68 |
| ATOM | 2842 | C   | PHE | A | 362 | 10.261 | 34.781 | 78.829 | 1.00 | 29.73 |
| ATOM | 2843 | O   | PHE | A | 362 | 10.906 | 35.131 | 77.870 | 1.00 | 32.02 |
| ATOM | 2844 | CB  | PHE | A | 362 | 8.643  | 36.677 | 78.723 | 1.00 | 28.12 |
| ATOM | 2845 | CG  | PHE | A | 362 | 7.194  | 37.105 | 78.629 | 1.00 | 30.03 |
| ATOM | 2846 | CD1 | PHE | A | 362 | 6.204  | 36.276 | 78.098 | 1.00 | 30.92 |
| ATOM | 2847 | CD2 | PHE | A | 362 | 6.804  | 38.372 | 79.051 | 1.00 | 32.04 |
| ATOM | 2848 | CE1 | PHE | A | 362 | 4.864  | 36.655 | 77.998 | 1.00 | 26.59 |
| ATOM | 2849 | CE2 | PHE | A | 362 | 5.470  | 38.773 | 78.952 | 1.00 | 32.40 |
| ATOM | 2914 | C   | ASP | A | 371 | −2.557 | 37.636 | 75.255 | 1.00 | 40.92 |
| ATOM | 2915 | O   | ASP | A | 371 | −2.784 | 38.625 | 75.933 | 1.00 | 41.63 |
| ATOM | 2916 | CB  | ASP | A | 371 | −4.519 | 36.375 | 76.245 | 1.00 | 39.88 |
| ATOM | 2917 | CG  | ASP | A | 371 | −5.805 | 35.733 | 75.798 | 1.00 | 51.30 |
| ATOM | 2918 | OD1 | ASP | A | 371 | −6.373 | 36.072 | 74.761 | 1.00 | 50.39 |
| ATOM | 2919 | OD2 | ASP | A | 371 | −6.206 | 34.754 | 76.583 | 1.00 | 48.61 |
| ATOM | 2920 | N   | ILE | A | 372 | −1.387 | 37.398 | 74.664 | 1.00 | 36.37 |
| ATOM | 2921 | CA  | ILE | A | 372 | −0.259 | 38.283 | 74.817 | 1.00 | 34.61 |
| ATOM | 2922 | C   | ILE | A | 372 | 0.203  | 39.018 | 73.555 | 1.00 | 35.46 |
| ATOM | 2923 | O   | ILE | A | 372 | 0.545  | 38.400 | 72.548 | 1.00 | 36.69 |
| ATOM | 2924 | CB  | ILE | A | 372 | 0.920  | 37.511 | 75.381 | 1.00 | 36.51 |
| ATOM | 2925 | CG1 | ILE | A | 372 | 0.658  | 37.195 | 76.842 | 1.00 | 37.01 |
| ATOM | 2926 | CG2 | ILE | A | 372 | 2.121  | 38.441 | 75.281 | 1.00 | 35.52 |
| ATOM | 2927 | CD1 | ILE | A | 372 | 1.268  | 38.261 | 77.747 | 1.00 | 54.33 |
| ATOM | 2928 | N   | ASP | A | 373 | 0.254  | 40.345 | 73.601 | 1.00 | 25.92 |
| ATOM | 2929 | CA  | ASP | A | 373 | 0.747  | 41.053 | 72.450 | 1.00 | 23.77 |
| ATOM | 2930 | C   | ASP | A | 373 | 2.263  | 40.781 | 72.360 | 1.00 | 31.40 |
| ATOM | 2931 | O   | ASP | A | 373 | 3.040  | 41.002 | 73.305 | 1.00 | 32.80 |
| ATOM | 2932 | CB  | ASP | A | 373 | 0.408  | 42.543 | 72.519 | 1.00 | 25.08 |
| ATOM | 2933 | CG  | ASP | A | 373 | 1.064  | 43.356 | 71.418 | 1.00 | 43.24 |
| ATOM | 2934 | OD1 | ASP | A | 373 | 1.861  | 42.894 | 70.616 | 1.00 | 45.30 |
| ATOM | 2935 | OD2 | ASP | A | 373 | 0.668  | 44.610 | 71.395 | 1.00 | 38.59 |
| ATOM | 2936 | N   | PRO | A | 374 | 2.709  | 40.267 | 71.225 | 1.00 | 29.51 |
| ATOM | 2937 | CA  | PRO | A | 374 | 4.123  | 39.943 | 71.132 | 1.00 | 28.52 |
| ATOM | 2938 | C   | PRO | A | 374 | 5.029  | 41.090 | 71.506 | 1.00 | 32.54 |
| ATOM | 2939 | O   | PRO | A | 374 | 6.019  | 40.905 | 72.217 | 1.00 | 29.62 |
| ATOM | 2940 | CB  | PRO | A | 374 | 4.390  | 39.421 | 69.714 | 1.00 | 28.88 |
| ATOM | 2941 | CG  | PRO | A | 374 | 3.028  | 39.278 | 69.032 | 1.00 | 32.27 |
| ATOM | 2942 | CD  | PRO | A | 374 | 1.966  | 39.786 | 70.008 | 1.00 | 28.84 |
| ATOM | 2943 | N   | ASP | A | 375 | 4.660  | 42.257 | 70.981 | 1.00 | 26.85 |
| ATOM | 2944 | CA  | ASP | A | 375 | 5.357  | 43.511 | 71.154 | 1.00 | 24.25 |
| ATOM | 2945 | C   | ASP | A | 375 | 5.695  | 43.783 | 72.628 | 1.00 | 33.10 |
| ATOM | 2946 | O   | ASP | A | 375 | 6.648  | 44.494 | 72.988 | 1.00 | 30.67 |
| ATOM | 2947 | CB  | ASP | A | 375 | 4.507  | 44.617 | 70.509 | 1.00 | 24.46 |
| ATOM | 2948 | CG  | ASP | A | 375 | 4.753  | 44.836 | 69.033 | 1.00 | 30.08 |
| ATOM | 2949 | OD1 | ASP | A | 375 | 5.703  | 44.393 | 68.411 | 1.00 | 33.47 |
| ATOM | 2950 | OD2 | ASP | A | 375 | 3.852  | 45.609 | 68.491 | 1.00 | 38.41 |
| ATOM | 2951 | N   | VAL | A | 376 | 4.885  | 43.161 | 73.477 | 1.00 | 30.21 |
| ATOM | 2952 | CA  | VAL | A | 376 | 5.001  | 43.232 | 74.904 | 1.00 | 25.40 |
| ATOM | 2953 | C   | VAL | A | 376 | 5.879  | 42.106 | 75.431 | 1.00 | 37.27 |
| ATOM | 2954 | O   | VAL | A | 376 | 6.599  | 42.299 | 76.394 | 1.00 | 42.46 |
| ATOM | 2955 | CB  | VAL | A | 376 | 3.638  | 43.099 | 75.550 | 1.00 | 22.48 |
| ATOM | 2956 | CG1 | VAL | A | 376 | 3.799  | 42.533 | 76.975 | 1.00 | 21.25 |

TABLE 9-continued

Structure coordinates of LTA₄ hydrolase-thiolamine complex
(The amino acid sequence set forth as residues 1-610 below correspond to SEQ ID NO:1.)

| ATOM | 2957 | CG2 | VAL | A | 376 | 2.926 | 44.440 | 75.547 | 1.00 | 18.29 |
|------|------|-----|-----|---|-----|-------|--------|--------|------|-------|
| ATOM | 2958 | N | ALA | A | 377 | 5.811 | 40.905 | 74.831 | 1.00 | 30.48 |
| ATOM | 2959 | CA | ALA | A | 377 | 6.671 | 39.793 | 75.288 | 1.00 | 27.04 |
| ATOM | 2960 | C | ALA | A | 377 | 8.149 | 39.911 | 74.797 | 1.00 | 28.15 |
| ATOM | 2961 | O | ALA | A | 377 | 9.077 | 39.325 | 75.312 | 1.00 | 27.36 |
| ATOM | 2962 | CB | ALA | A | 377 | 6.091 | 38.433 | 74.891 | 1.00 | 26.74 |
| ATOM | 2963 | N | TYR | A | 378 | 8.376 | 40.692 | 73.768 | 1.00 | 25.81 |
| ATOM | 2964 | CA | TYR | A | 378 | 9.683 | 40.876 | 73.161 | 1.00 | 25.43 |
| ATOM | 2965 | C | TYR | A | 378 | 10.862 | 41.194 | 74.057 | 1.00 | 30.49 |
| ATOM | 2966 | O | TYR | A | 378 | 10.873 | 42.204 | 74.747 | 1.00 | 32.35 |
| ATOM | 2967 | CB | TYR | A | 378 | 9.549 | 41.924 | 72.068 | 1.00 | 26.20 |
| ATOM | 2968 | CG | TYR | A | 378 | 10.804 | 42.168 | 71.327 | 1.00 | 19.90 |
| ATOM | 2969 | CD1 | TYR | A | 378 | 11.256 | 41.231 | 70.406 | 1.00 | 18.53 |
| ATOM | 2970 | CD2 | TYR | A | 378 | 11.536 | 43.331 | 71.543 | 1.00 | 18.47 |
| ATOM | 2971 | CE1 | TYR | A | 378 | 12.444 | 41.436 | 69.716 | 1.00 | 15.98 |
| ATOM | 2972 | CE2 | TYR | A | 378 | 12.719 | 43.555 | 70.840 | 1.00 | 18.77 |
| ATOM | 2973 | CZ | TYR | A | 378 | 13.161 | 42.609 | 69.920 | 1.00 | 16.37 |
| ATOM | 2974 | OH | TYR | A | 378 | 14.309 | 42.811 | 69.212 | 1.00 | 32.30 |
| ATOM | 2975 | N | SER | A | 379 | 11.879 | 40.317 | 73.977 | 1.00 | 23.03 |
| ATOM | 2976 | CA | SER | A | 379 | 13.115 | 40.430 | 74.725 | 1.00 | 18.13 |
| ATOM | 2977 | C | SER | A | 379 | 14.267 | 39.777 | 73.970 | 1.00 | 20.60 |
| ATOM | 2850 | CZ | PHE | A | 362 | 4.495 | 37.920 | 78.435 | 1.00 | 26.37 |
| ATOM | 2851 | N | THR | A | 363 | 10.730 | 34.049 | 79.843 | 1.00 | 27.22 |
| ATOM | 2852 | CA | THR | A | 363 | 12.102 | 33.575 | 79.943 | 1.00 | 27.52 |
| ATOM | 2853 | C | THR | A | 363 | 12.251 | 32.132 | 79.504 | 1.00 | 29.28 |
| ATOM | 2854 | O | THR | A | 363 | 13.331 | 31.560 | 79.524 | 1.00 | 29.42 |
| ATOM | 2855 | CB | THR | A | 363 | 12.697 | 33.777 | 81.360 | 1.00 | 31.67 |
| ATOM | 2856 | OG1 | THR | A | 363 | 12.279 | 32.745 | 82.218 | 1.00 | 26.17 |
| ATOM | 2857 | CG2 | THR | A | 363 | 12.278 | 35.118 | 81.930 | 1.00 | 31.62 |
| ATOM | 2858 | N | LYS | A | 364 | 11.148 | 31.530 | 79.113 | 1.00 | 23.08 |
| ATOM | 2859 | CA | LYS | A | 364 | 11.174 | 30.160 | 78.664 | 1.00 | 20.50 |
| ATOM | 2860 | C | LYS | A | 364 | 11.556 | 30.270 | 77.217 | 1.00 | 28.83 |
| ATOM | 2861 | O | LYS | A | 364 | 11.139 | 31.239 | 76.570 | 1.00 | 29.80 |
| ATOM | 2862 | CB | LYS | A | 364 | 9.766 | 29.584 | 78.667 | 1.00 | 23.55 |
| ATOM | 2863 | CG | LYS | A | 364 | 9.252 | 29.134 | 80.022 | 1.00 | 40.85 |
| ATOM | 2864 | CD | LYS | A | 364 | 7.761 | 29.369 | 80.162 | 1.00 | 44.83 |
| ATOM | 2865 | CE | LYS | A | 364 | 7.131 | 28.492 | 81.224 | 1.00 | 66.38 |
| ATOM | 2866 | NZ | LYS | A | 364 | 6.063 | 27.638 | 80.691 | 1.00 | 91.70 |
| ATOM | 2867 | N | LEU | A | 365 | 12.332 | 29.328 | 76.698 | 1.00 | 23.57 |
| ATOM | 2868 | CA | LEU | A | 365 | 12.699 | 29.420 | 75.312 | 1.00 | 23.95 |
| ATOM | 2869 | C | LEU | A | 365 | 11.414 | 29.419 | 74.445 | 1.00 | 35.57 |
| ATOM | 2870 | O | LEU | A | 365 | 11.166 | 30.369 | 73.708 | 1.00 | 34.58 |
| ATOM | 2871 | CB | LEU | A | 365 | 13.702 | 28.303 | 75.021 | 1.00 | 25.08 |
| ATOM | 2872 | CG | LEU | A | 365 | 14.456 | 28.372 | 73.702 | 1.00 | 31.15 |
| ATOM | 2873 | CD1 | LEU | A | 365 | 14.987 | 29.778 | 73.466 | 1.00 | 33.16 |
| ATOM | 2874 | CD2 | LEU | A | 365 | 15.609 | 27.353 | 73.781 | 1.00 | 30.62 |
| ATOM | 2875 | N | VAL | A | 366 | 10.572 | 28.360 | 74.564 | 1.00 | 35.62 |
| ATOM | 2876 | CA | VAL | A | 366 | 9.294 | 28.232 | 73.840 | 1.00 | 32.10 |
| ATOM | 2877 | C | VAL | A | 366 | 8.211 | 28.911 | 74.694 | 1.00 | 33.14 |
| ATOM | 2878 | O | VAL | A | 366 | 7.982 | 28.470 | 75.808 | 1.00 | 34.20 |
| ATOM | 2879 | CB | VAL | A | 366 | 8.936 | 26.739 | 73.568 | 1.00 | 34.73 |
| ATOM | 2880 | CG1 | VAL | A | 366 | 7.558 | 26.605 | 72.933 | 1.00 | 34.88 |
| ATOM | 2881 | CG2 | VAL | A | 366 | 9.922 | 26.012 | 72.649 | 1.00 | 32.65 |
| ATOM | 2882 | N | VAL | A | 367 | 7.562 | 29.990 | 74.211 | 1.00 | 28.76 |
| ATOM | 2883 | CA | VAL | A | 367 | 6.532 | 30.700 | 74.987 | 1.00 | 28.27 |
| ATOM | 2884 | C | VAL | A | 367 | 5.161 | 30.613 | 74.420 | 1.00 | 30.62 |
| ATOM | 2885 | O | VAL | A | 367 | 4.994 | 30.509 | 73.235 | 1.00 | 34.30 |
| ATOM | 2886 | CB | VAL | A | 367 | 6.773 | 32.185 | 75.061 | 1.00 | 33.45 |
| ATOM | 2887 | CG1 | VAL | A | 367 | 8.178 | 32.478 | 75.565 | 1.00 | 33.03 |
| ATOM | 2888 | CG2 | VAL | A | 367 | 6.498 | 32.804 | 73.693 | 1.00 | 33.18 |
| ATOM | 2889 | N | ASP | A | 368 | 4.168 | 30.722 | 75.290 | 1.00 | 29.27 |
| ATOM | 2890 | CA | ASP | A | 368 | 2.764 | 30.771 | 74.984 | 1.00 | 27.67 |
| ATOM | 2891 | C | ASP | A | 368 | 2.315 | 32.207 | 74.862 | 1.00 | 26.94 |
| ATOM | 2892 | O | ASP | A | 368 | 2.283 | 32.975 | 75.830 | 1.00 | 23.11 |
| ATOM | 2893 | CB | ASP | A | 368 | 1.990 | 30.073 | 76.100 | 1.00 | 26.80 |
| ATOM | 2894 | CG | ASP | A | 368 | 0.572 | 29.781 | 75.613 | 1.00 | 37.90 |
| ATOM | 2895 | OD1 | ASP | A | 368 | 0.276 | 30.123 | 74.481 | 1.00 | 38.93 |
| ATOM | 2896 | OD2 | ASP | A | 368 | −0.215 | 29.217 | 76.380 | 1.00 | 38.59 |
| ATOM | 2897 | N | LEU | A | 369 | 2.027 | 32.588 | 73.622 | 1.00 | 26.55 |
| ATOM | 2898 | CA | LEU | A | 369 | 1.643 | 33.953 | 73.373 | 1.00 | 27.39 |
| ATOM | 2899 | C | LEU | A | 369 | 0.138 | 34.105 | 73.301 | 1.00 | 30.74 |
| ATOM | 2900 | O | LEU | A | 369 | −0.372 | 34.979 | 72.648 | 1.00 | 30.68 |
| ATOM | 2901 | CB | LEU | A | 369 | 2.281 | 34.395 | 72.064 | 1.00 | 26.06 |
| ATOM | 2902 | CG | LEU | A | 369 | 3.759 | 34.760 | 72.229 | 1.00 | 26.80 |
| ATOM | 2903 | CD1 | LEU | A | 369 | 4.343 | 35.415 | 70.994 | 1.00 | 24.30 |
| ATOM | 2904 | CD2 | LEU | A | 369 | 4.014 | 35.728 | 73.384 | 1.00 | 21.81 |

TABLE 9-continued

Structure coordinates of LTA₄ hydrolase-thiolamine complex
(The amino acid sequence set forth as residues 1-610 below correspond to SEQ ID NO:1.)

| ATOM | 2905 | N | THR | A | 370 | −0.577 | 33.154 | 73.953 | 1.00 | 30.26 |
|------|------|-----|-----|---|-----|--------|--------|--------|------|-------|
| ATOM | 2906 | CA | THR | A | 370 | −2.022 | 33.306 | 74.093 | 1.00 | 31.38 |
| ATOM | 2907 | C | THR | A | 370 | −2.355 | 34.519 | 74.941 | 1.00 | 38.62 |
| ATOM | 2908 | O | THR | A | 370 | −1.821 | 34.714 | 76.027 | 1.00 | 38.84 |
| ATOM | 2909 | CB | THR | A | 370 | −2.601 | 32.056 | 74.750 | 1.00 | 34.04 |
| ATOM | 2910 | OG1 | THR | A | 370 | −2.472 | 30.949 | 73.873 | 1.00 | 29.99 |
| ATOM | 2911 | CG2 | THR | A | 370 | −4.091 | 32.266 | 75.052 | 1.00 | 26.40 |
| ATOM | 2912 | N | ASP | A | 371 | −3.173 | 35.387 | 74.363 | 1.00 | 37.89 |
| ATOM | 2913 | CA | ASP | A | 371 | −3.641 | 36.612 | 75.012 | 1.00 | 37.85 |
| ATOM | 2978 | O | SER | A | 379 | 14.100 | 39.334 | 72.843 | 1.00 | 18.46 |
| ATOM | 2979 | CB | SER | A | 379 | 12.976 | 39.740 | 76.067 | 1.00 | 23.56 |
| ATOM | 2980 | OG | SER | A | 379 | 12.805 | 38.329 | 75.883 | 1.00 | 37.26 |
| ATOM | 2981 | N | SER | A | 380 | 15.424 | 39.697 | 74.651 | 1.00 | 23.65 |
| ATOM | 2982 | CA | SER | A | 380 | 16.701 | 39.084 | 74.222 | 1.00 | 26.09 |
| ATOM | 2983 | C | SER | A | 380 | 16.669 | 37.571 | 74.457 | 1.00 | 28.37 |
| ATOM | 2984 | O | SER | A | 380 | 17.480 | 36.785 | 73.975 | 1.00 | 30.81 |
| ATOM | 2985 | CB | SER | A | 380 | 17.889 | 39.588 | 75.062 | 1.00 | 31.60 |
| ATOM | 2986 | OG | SER | A | 380 | 18.036 | 41.000 | 75.033 | 1.00 | 42.48 |
| ATOM | 2987 | N | VAL | A | 381 | 15.718 | 37.188 | 75.260 | 1.00 | 18.04 |
| ATOM | 2288 | CA | VAL | A | 381 | 15.595 | 35.812 | 75.598 | 1.00 | 14.91 |
| ATOM | 2989 | C | VAL | A | 381 | 15.708 | 34.897 | 74.419 | 1.00 | 20.31 |
| ATOM | 2990 | O | VAL | A | 381 | 16.620 | 34.091 | 74.330 | 1.00 | 27.64 |
| ATOM | 2991 | CB | VAL | A | 381 | 14.408 | 35.546 | 76.501 | 1.00 | 16.34 |
| ATOM | 2992 | CG1 | VAL | A | 381 | 14.284 | 34.062 | 76.734 | 1.00 | 17.26 |
| ATOM | 2993 | CG2 | VAL | A | 381 | 14.687 | 36.204 | 77.829 | 1.00 | 13.94 |
| ATOM | 2994 | N | PRO | A | 382 | 14.797 | 35.005 | 73.489 | 1.00 | 16.53 |
| ATOM | 2995 | CA | PRO | A | 382 | 14.886 | 34.139 | 72.324 | 1.00 | 17.21 |
| ATOM | 2996 | C | PRO | A | 382 | 16.222 | 34.230 | 71.634 | 1.00 | 24.01 |
| ATOM | 2997 | O | PRO | A | 382 | 16.709 | 33.192 | 71.207 | 1.00 | 27.79 |
| ATOM | 2998 | CB | PRO | A | 382 | 13.777 | 34.514 | 71.351 | 1.00 | 17.20 |
| ATOM | 2999 | CG | PRO | A | 382 | 13.003 | 35.618 | 72.033 | 1.00 | 18.32 |
| ATOM | 3000 | CD | PRO | A | 382 | 13.627 | 35.873 | 73.399 | 1.00 | 12.12 |
| ATOM | 3001 | N | TYR | A | 383 | 16.809 | 35.447 | 71.542 | 1.00 | 19.33 |
| ATOM | 3002 | CA | TYR | A | 383 | 18.112 | 35.648 | 70.902 | 1.00 | 19.70 |
| ATOM | 3003 | C | TYR | A | 383 | 19.246 | 34.953 | 71.651 | 1.00 | 28.79 |
| ATOM | 3004 | O | TYR | A | 383 | 19.980 | 34.117 | 71.104 | 1.00 | 31.38 |
| ATOM | 3005 | CB | TYR | A | 383 | 18.468 | 37.135 | 70.894 | 1.00 | 21.02 |
| ATOM | 3006 | CG | TYR | A | 383 | 17.593 | 37.968 | 70.011 | 1.00 | 23.86 |
| ATOM | 3007 | CD1 | TYR | A | 383 | 16.290 | 38.277 | 70.404 | 1.00 | 28.36 |
| ATOM | 3008 | CD2 | TYR | A | 383 | 18.067 | 38.450 | 68.784 | 1.00 | 20.93 |
| ATOM | 3009 | CE1 | TYR | A | 383 | 15.473 | 39.054 | 69.576 | 1.00 | 30.88 |
| ATOM | 3010 | CE2 | TYR | A | 383 | 17.272 | 39.244 | 67.957 | 1.00 | 18.71 |
| ATOM | 3011 | CZ | TYR | A | 383 | 15.967 | 39.533 | 68.358 | 1.00 | 25.95 |
| ATOM | 3012 | OH | TYR | A | 383 | 15.171 | 40.294 | 67.556 | 1.00 | 30.84 |
| ATOM | 3013 | N | GLU | A | 384 | 19.389 | 35.333 | 72.921 | 1.00 | 20.17 |
| ATOM | 3014 | CA | GLU | A | 384 | 20.419 | 34.857 | 73.803 | 1.00 | 17.57 |
| ATOM | 3015 | C | GLU | A | 384 | 20.188 | 33.506 | 74.405 | 1.00 | 22.88 |
| ATOM | 3016 | O | GLU | A | 384 | 21.151 | 32.775 | 74.669 | 1.00 | 25.65 |
| ATOM | 3017 | CB | GLU | A | 384 | 20.833 | 35.973 | 74.773 | 1.00 | 20.44 |
| ATOM | 3018 | CG | GLU | A | 384 | 21.263 | 37.202 | 73.944 | 1.00 | 15.21 |
| ATOM | 3019 | CD | GLU | A | 384 | 22.539 | 36.937 | 73.184 | 1.00 | 26.58 |
| ATOM | 3020 | OE1 | GLU | A | 384 | 23.185 | 35.915 | 73.293 | 1.00 | 17.84 |
| ATOM | 3021 | OE2 | GLU | A | 384 | 22.887 | 37.915 | 72.400 | 1.00 | 21.88 |
| ATOM | 3022 | N | LYS | A | 385 | 18.935 | 33.116 | 74.610 | 1.00 | 20.33 |
| ATOM | 3023 | CA | LYS | A | 385 | 18.736 | 31.767 | 75.146 | 1.00 | 20.05 |
| ATOM | 3024 | C | LYS | A | 385 | 18.865 | 30.716 | 74.028 | 1.00 | 27.19 |
| ATOM | 3025 | O | LYS | A | 385 | 19.420 | 29.621 | 74.219 | 1.00 | 31.66 |
| ATOM | 3026 | CB | LYS | A | 385 | 17.507 | 31.577 | 76.014 | 1.00 | 21.51 |
| ATOM | 3027 | CG | LYS | A | 385 | 17.676 | 30.384 | 76.953 | 1.00 | 22.29 |
| ATOM | 3028 | CD | LYS | A | 385 | 16.386 | 29.820 | 77.518 | 1.00 | 19.87 |
| ATOM | 3029 | CE | LYS | A | 385 | 16.049 | 30.277 | 78.937 | 1.00 | 31.60 |
| ATOM | 3030 | NZ | LYS | A | 385 | 14.783 | 29.694 | 79.441 | 1.00 | 30.38 |
| ATOM | 3031 | N | GLY | A | 386 | 18.364 | 31.084 | 72.832 | 1.00 | 20.72 |
| ATOM | 3032 | CA | GLY | A | 386 | 18.453 | 30.248 | 71.637 | 1.00 | 17.41 |
| ATOM | 3033 | C | GLY | A | 386 | 19.924 | 30.106 | 71.298 | 1.00 | 20.81 |
| ATOM | 3034 | O | GLY | A | 386 | 20.396 | 29.001 | 71.225 | 1.00 | 22.50 |
| ATOM | 3035 | N | PHE | A | 387 | 20.683 | 31.228 | 71.163 | 1.00 | 20.30 |
| ATOM | 3036 | CA | PHE | A | 387 | 22.137 | 31.158 | 70.900 | 1.00 | 19.92 |
| ATOM | 3037 | C | PHE | A | 387 | 22.840 | 30.263 | 71.905 | 1.00 | 29.09 |
| ATOM | 3038 | O | PHE | A | 387 | 23.685 | 29.478 | 71.530 | 1.00 | 32.80 |
| ATOM | 3039 | CB | PHE | A | 387 | 22.852 | 32.519 | 70.955 | 1.00 | 20.07 |
| ATOM | 3040 | CG | PHE | A | 387 | 24.344 | 32.358 | 70.872 | 1.00 | 19.41 |
| ATOM | 3041 | CD1 | PHE | A | 387 | 24.949 | 32.163 | 69.631 | 1.00 | 19.67 |
| ATOM | 3042 | CD2 | PHE | A | 387 | 25.157 | 32.373 | 72.007 | 1.00 | 25.27 |
| ATOM | 3043 | CE1 | PHE | A | 387 | 26.329 | 31.977 | 69.525 | 1.00 | 20.88 |
| ATOM | 3044 | CE2 | PHE | A | 387 | 26.542 | 32.202 | 71.916 | 1.00 | 28.83 |

TABLE 9-continued

Structure coordinates of LTA₄ hydrolase-thiolamine complex
(The amino acid sequence set forth as residues 1-610 below correspond to SEQ ID NO:1.)

| ATOM | 3045 | CZ | PHE | A | 387 | 27.131 | 31.981 | 70.668 | 1.00 | 23.24 |
|------|------|-----|-----|---|-----|--------|--------|--------|------|-------|
| ATOM | 3046 | N | ALA | A | 388 | 22.495 | 30.381 | 73.203 | 1.00 | 25.48 |
| ATOM | 3047 | CA | ALA | A | 388 | 23.133 | 29.556 | 74.242 | 1.00 | 23.14 |
| ATOM | 3048 | C | ALA | A | 388 | 22.872 | 28.108 | 74.055 | 1.00 | 32.10 |
| ATOM | 3049 | O | ALA | A | 388 | 23.757 | 27.282 | 74.258 | 1.00 | 37.82 |
| ATOM | 3050 | CB | ALA | A | 388 | 22.717 | 29.932 | 75.633 | 1.00 | 23.02 |
| ATOM | 3051 | N | LEU | A | 389 | 21.636 | 27.793 | 73.691 | 1.00 | 26.31 |
| ATOM | 3052 | CA | LEU | A | 389 | 21.275 | 26.405 | 73.460 | 1.00 | 21.42 |
| ATOM | 3053 | C | LEU | A | 389 | 22.189 | 25.906 | 72.372 | 1.00 | 27.91 |
| ATOM | 3054 | O | LEU | A | 389 | 22.865 | 24.900 | 72.532 | 1.00 | 29.25 |
| ATOM | 3055 | CB | LEU | A | 389 | 19.841 | 26.300 | 72.937 | 1.00 | 19.24 |
| ATOM | 3056 | CG | LEU | A | 389 | 19.427 | 24.868 | 72.632 | 1.00 | 17.17 |
| ATOM | 3057 | CD1 | LEU | A | 389 | 19.717 | 24.017 | 73.844 | 1.00 | 14.63 |
| ATOM | 3058 | CD2 | LEU | A | 389 | 17.943 | 24.808 | 72.328 | 1.00 | 10.16 |
| ATOM | 3059 | N | LEU | A | 390 | 22.217 | 26.659 | 71.262 | 1.00 | 24.49 |
| ATOM | 3060 | CA | LEU | A | 390 | 23.050 | 26.340 | 70.107 | 1.00 | 25.05 |
| ATOM | 3061 | C | LEU | A | 390 | 24.531 | 26.256 | 70.383 | 1.00 | 32.31 |
| ATOM | 3062 | O | LEU | A | 390 | 25.183 | 25.301 | 69.932 | 1.00 | 33.60 |
| ATOM | 3063 | CB | LEU | A | 390 | 22.765 | 27.152 | 68.844 | 1.00 | 23.33 |
| ATOM | 3064 | CG | LEU | A | 390 | 21.307 | 27.026 | 68.442 | 1.00 | 23.38 |
| ATOM | 3065 | CD1 | LEU | A | 390 | 20.986 | 28.025 | 67.334 | 1.00 | 20.84 |
| ATOM | 3066 | CD2 | LEU | A | 390 | 20.988 | 25.591 | 68.017 | 1.00 | 18.86 |
| ATOM | 3067 | N | PHE | A | 391 | 25.058 | 27.231 | 71.127 | 1.00 | 28.52 |
| ATOM | 3068 | CA | PHE | A | 391 | 26.480 | 27.236 | 71.494 | 1.00 | 27.82 |
| ATOM | 3069 | C | PHE | A | 391 | 26.813 | 25.992 | 72.312 | 1.00 | 28.67 |
| ATOM | 3070 | O | PHE | A | 391 | 27.839 | 25.331 | 72.148 | 1.00 | 26.96 |
| ATOM | 3071 | CB | PHE | A | 391 | 26.834 | 28.455 | 72.341 | 1.00 | 28.60 |
| ATOM | 3072 | CG | PHE | A | 391 | 28.296 | 28.786 | 72.283 | 1.00 | 30.53 |
| ATOM | 3073 | CD1 | PHE | A | 391 | 28.967 | 28.816 | 71.064 | 1.00 | 35.08 |
| ATOM | 3074 | CD2 | PHE | A | 391 | 29.020 | 29.063 | 73.440 | 1.00 | 36.52 |
| ATOM | 3075 | CE1 | PHE | A | 391 | 30.320 | 29.142 | 70.983 | 1.00 | 37.61 |
| ATOM | 3076 | CE2 | PHE | A | 391 | 30.378 | 29.383 | 73.382 | 1.00 | 40.61 |
| ATOM | 3077 | CZ | PHE | A | 391 | 31.026 | 29.432 | 72.148 | 1.00 | 37.64 |
| ATOM | 3078 | N | TYR | A | 392 | 25.913 | 25.699 | 73.225 | 1.00 | 24.90 |
| ATOM | 3079 | CA | TYR | A | 392 | 26.044 | 24.550 | 74.065 | 1.00 | 24.66 |
| ATOM | 3080 | C | TYR | A | 392 | 26.106 | 23.298 | 73.186 | 1.00 | 34.30 |
| ATOM | 3081 | O | TYR | A | 392 | 27.058 | 22.558 | 73.268 | 1.00 | 37.51 |
| ATOM | 3082 | CB | TYR | A | 392 | 24.821 | 24.501 | 74.967 | 1.00 | 26.39 |
| ATOM | 3083 | CG | TYR | A | 392 | 24.631 | 23.181 | 75.678 | 1.00 | 31.99 |
| ATOM | 3084 | CD1 | TYR | A | 392 | 25.546 | 22.715 | 76.625 | 1.00 | 35.17 |
| ATOM | 3085 | CD2 | TYR | A | 392 | 23.501 | 22.397 | 75.432 | 1.00 | 32.49 |
| ATOM | 3086 | CE1 | TYR | A | 392 | 25.341 | 21.512 | 77.306 | 1.00 | 39.01 |
| ATOM | 3087 | CE2 | TYR | A | 392 | 23.281 | 21.184 | 76.094 | 1.00 | 31.50 |
| ATOM | 3088 | CZ | TYR | A | 392 | 24.206 | 20.743 | 77.035 | 1.00 | 34.08 |
| ATOM | 3089 | OH | TYR | A | 392 | 23.986 | 19.564 | 77.683 | 1.00 | 36.46 |
| ATOM | 3090 | N | LEU | A | 393 | 25.101 | 23.067 | 72.310 | 1.00 | 31.02 |
| ATOM | 3091 | CA | LEU | A | 393 | 25.043 | 21.889 | 71.410 | 1.00 | 29.65 |
| ATOM | 3092 | C | LEU | A | 393 | 26.274 | 21.616 | 70.507 | 1.00 | 32.03 |
| ATOM | 3093 | O | LEU | A | 393 | 26.664 | 20.468 | 70.267 | 1.00 | 27.90 |
| ATOM | 3094 | CB | LEU | A | 393 | 23.758 | 21.905 | 70.552 | 1.00 | 28.85 |
| ATOM | 3095 | CG | LEU | A | 393 | 22.489 | 21.688 | 71.375 | 1.00 | 30.33 |
| ATOM | 3096 | CD1 | LEU | A | 393 | 21.256 | 22.047 | 70.559 | 1.00 | 27.38 |
| ATOM | 3097 | CD2 | LEU | A 393 | | 22.400 | 20.246 | 71.865 | 1.00 | 29.76 |
| ATOM | 3098 | N | GLU | A | 394 | 26.841 | 22.701 | 69.980 | 1.00 | 30.84 |
| ATOM | 3099 | CA | GLU | A | 394 | 28.000 | 22.727 | 69.118 | 1.00 | 30.05 |
| ATOM | 3100 | C | GLU | A | 394 | 29.210 | 22.214 | 69.868 | 1.00 | 39.16 |
| ATOM | 3101 | O | GLU | A | 394 | 30.089 | 21.595 | 69.299 | 1.00 | 42.14 |
| ATOM | 3102 | CB | GLU | A | 394 | 28.300 | 24.204 | 68.756 | 1.00 | 31.03 |
| ATOM | 3103 | CG | GLU | A | 394 | 29.776 | 24.406 | 68.376 | 1.00 | 37.11 |
| ATOM | 3104 | CD | GLU | A | 394 | 30.182 | 25.830 | 68.208 | 1.00 | 45.20 |
| ATOM | 3105 | OE1 | GLU | A | 394 | 29.614 | 26.609 | 67.471 | 1.00 | 56.77 |
| ATOM | 3106 | OE2 | GLU | A | 394 | 31.229 | 26.133 | 68.927 | 1.00 | 39.77 |
| ATOM | 3107 | N | GLN | A | 395 | 29.256 | 22.534 | 71.160 | 1.00 | 34.20 |
| ATOM | 3108 | CA | GLN | A | 395 | 30.342 | 22.139 | 72.029 | 1.00 | 32.86 |
| ATOM | 3109 | C | GLN | A | 395 | 30.143 | 20.690 | 72.435 | 1.00 | 38.65 |
| ATOM | 3110 | O | GLN | A | 395 | 31.066 | 19.899 | 72.507 | 1.00 | 38.67 |
| ATOM | 3111 | CB | GLN | A | 395 | 30.474 | 23.051 | 73.287 | 1.00 | 33.17 |
| ATOM | 3112 | CG | GLN | A | 395 | 30.831 | 24.540 | 72.996 | 1.00 | 13.79 |
| ATOM | 3113 | CD | GLN | A | 395 | 31.176 | 25.354 | 74.247 | 1.00 | 37.45 |
| ATOM | 3114 | OE1 | GLN | A | 395 | 30.909 | 24.959 | 75.407 | 1.00 | 26.89 |
| ATOM | 3115 | NE2 | GLN | A | 395 | 31.758 | 26.523 | 74.010 | 1.00 | 31.99 |
| ATOM | 3116 | N | LEU | A | 396 | 28.903 | 20.352 | 72.682 | 1.00 | 38.68 |
| ATOM | 3117 | CA | LEU | A | 396 | 28.514 | 19.015 | 73.083 | 1.00 | 38.49 |
| ATOM | 3118 | C | LEU | A | 396 | 28.633 | 18.017 | 71.924 | 1.00 | 39.28 |
| ATOM | 3119 | O | LEU | A | 396 | 29.012 | 16.871 | 72.100 | 1.00 | 42.17 |

TABLE 9-continued

Structure coordinates of LTA₄ hydrolase-thiolamine complex
(The amino acid sequence set forth as residues 1-610 below correspond to SEQ ID NO:1.)

| ATOM | 3120 | CB  | LEU | A | 396 | 27.055 | 19.072 | 73.628 | 1.00 | 37.93 |
|------|------|-----|-----|---|-----|--------|--------|--------|------|-------|
| ATOM | 3121 | CG  | LEU | A | 396 | 26.389 | 17.732 | 73.946 | 1.00 | 42.72 |
| ATOM | 3122 | CD1 | LEU | A | 396 | 26.436 | 17.489 | 75.445 | 1.00 | 45.42 |
| ATOM | 3123 | CD2 | LEU | A | 396 | 24.917 | 17.709 | 73.527 | 1.00 | 43.81 |
| ATOM | 3124 | N   | LEU | A | 397 | 28.303 | 18.456 | 70.730 | 1.00 | 28.48 |
| ATOM | 3125 | CA  | LEU | A | 397 | 28.337 | 17.595 | 69.589 | 1.00 | 25.49 |
| ATOM | 3126 | C   | LEU | A | 397 | 29.620 | 17.609 | 68.771 | 1.00 | 36.86 |
| ATOM | 3127 | O   | LEU | A | 397 | 29.596 | 17.220 | 67.599 | 1.00 | 39.85 |
| ATOM | 3128 | CB  | LEU | A | 397 | 27.156 | 17.924 | 68.686 | 1.00 | 23.73 |
| ATOM | 3129 | CG  | LEU | A | 397 | 25.843 | 17.773 | 69.401 | 1.00 | 25.82 |
| ATOM | 3130 | CD1 | LEU | A | 397 | 24.740 | 18.559 | 68.669 | 1.00 | 22.99 |
| ATOM | 3131 | CD2 | LEU | A | 397 | 25.525 | 16.272 | 69.452 | 1.00 | 27.30 |
| ATOM | 3132 | N   | GLY | A | 398 | 30.731 | 18.069 | 69.342 | 1.00 | 33.98 |
| ATOM | 3133 | CA  | GLY | A | 398 | 31.993 | 18.038 | 68.617 | 1.00 | 34.14 |
| ATOM | 3134 | C   | GLY | A | 398 | 32.547 | 19.260 | 67.889 | 1.00 | 38.92 |
| ATOM | 3135 | O   | GLY | A | 398 | 33.502 | 19.097 | 67.115 | 1.00 | 39.98 |
| ATOM | 3136 | N   | GLY | A | 399 | 32.001 | 20.457 | 68.105 | 1.00 | 33.01 |
| ATOM | 3137 | CA  | GLY | A | 399 | 32.543 | 21.650 | 67.440 | 1.00 | 30.35 |
| ATOM | 3138 | C   | GLY | A | 399 | 31.713 | 22.336 | 66.365 | 1.00 | 31.72 |
| ATOM | 3139 | O   | GLY | A | 399 | 30.800 | 21.823 | 65.762 | 1.00 | 34.57 |
| ATOM | 3140 | N   | PRO | A | 400 | 32.076 | 23.550 | 66.124 | 1.00 | 33.01 |
| ATOM | 3141 | CA  | PRO | A | 400 | 31.429 | 24.406 | 65.151 | 1.00 | 35.02 |
| ATOM | 3142 | C   | PRO | A | 400 | 31.379 | 23.794 | 63.750 | 1.00 | 43.93 |
| ATOM | 3143 | O   | PRO | A | 400 | 30.360 | 23.838 | 63.045 | 1.00 | 40.14 |
| ATOM | 3144 | CB  | PRO | A | 400 | 32.293 | 25.672 | 65.111 | 1.00 | 35.73 |
| ATOM | 3145 | CG  | PRO | A | 400 | 33.539 | 25.411 | 65.948 | 1.00 | 38.03 |
| ATOM | 3146 | CD  | PRO | A | 400 | 33.423 | 24.010 | 66.517 | 1.00 | 33.92 |
| ATOM | 3147 | N   | GLU | A | 401 | 32.512 | 23.237 | 63.345 | 1.00 | 43.85 |
| ATOM | 3148 | CA  | GLU | A | 401 | 32.597 | 22.620 | 62.042 | 1.00 | 42.92 |
| ATOM | 3149 | C   | GLU | A | 401 | 31.491 | 21.587 | 61.878 | 1.00 | 37.92 |
| ATOM | 3150 | O   | GLU | A | 401 | 30.810 | 21.588 | 60.866 | 1.00 | 33.79 |
| ATOM | 3151 | CB  | GLU | A | 401 | 33.996 | 22.034 | 61.789 | 1.00 | 45.93 |
| ATOM | 3152 | CG  | GLU | A | 401 | 34.578 | 22.372 | 60.398 | 1.00 | 69.62 |
| ATOM | 3153 | CD  | GLU | A | 401 | 35.603 | 21.373 | 59.911 | 1.00 | 100.00 |
| ATOM | 3154 | OE1 | GLU | A | 401 | 36.702 | 21.236 | 60.427 | 1.00 | 100.00 |
| ATOM | 3155 | OE2 | GLU | A | 401 | 35.195 | 20.689 | 58.865 | 1.00 | 93.16 |
| ATOM | 3156 | N   | ILE | A | 402 | 31.317 | 20.720 | 62.902 | 1.00 | 34.58 |
| ATOM | 3157 | CA  | ILE | A | 402 | 30.281 | 19.681 | 62.922 | 1.00 | 33.20 |
| ATOM | 3158 | C   | ILE | A | 402 | 28.898 | 20.291 | 62.938 | 1.00 | 39.09 |
| ATOM | 3159 | O   | ILE | A | 402 | 28.065 | 19.896 | 62.133 | 1.00 | 41.43 |
| ATOM | 3160 | CB  | ILE | A | 402 | 30.391 | 18.673 | 64.078 | 1.00 | 33.82 |
| ATOM | 3161 | CG1 | ILE | A | 402 | 31.490 | 17.661 | 63.811 | 1.00 | 34.70 |
| ATOM | 3162 | CG2 | ILE | A | 402 | 29.080 | 17.900 | 64.287 | 1.00 | 23.32 |
| ATOM | 3163 | CD1 | ILE | A | 402 | 31.878 | 16.896 | 65.080 | 1.00 | 49.20 |
| ATOM | 3164 | N   | PHE | A | 403 | 28.668 | 21.246 | 63.868 | 1.00 | 32.73 |
| ATOM | 3165 | CA  | PHE | A | 403 | 27.390 | 21.952 | 64.044 | 1.00 | 29.52 |
| ATOM | 3166 | C   | PHE | A | 403 | 27.032 | 22.816 | 62.836 | 1.00 | 33.94 |
| ATOM | 3167 | O   | PHE | A | 403 | 25.866 | 23.022 | 62.469 | 1.00 | 34.15 |
| ATOM | 3168 | CB  | PHE | A | 403 | 27.319 | 22.719 | 65.381 | 1.00 | 29.03 |
| ATOM | 3169 | CG  | PHE | A | 403 | 25.917 | 22.783 | 65.929 | 1.00 | 28.54 |
| ATOM | 3170 | CD1 | PHE | A | 403 | 25.323 | 21.643 | 66.484 | 1.00 | 29.91 |
| ATOM | 3171 | CD2 | PHE | A | 403 | 25.176 | 23.964 | 65.873 | 1.00 | 27.62 |
| ATOM | 3172 | CE1 | PHE | A | 403 | 24.021 | 21.667 | 66.990 | 1.00 | 27.38 |
| ATOM | 3173 | CE2 | PHE | A | 403 | 23.881 | 24.017 | 66.393 | 1.00 | 28.82 |
| ATOM | 3174 | CZ  | PHE | A | 403 | 23.304 | 22.863 | 66.932 | 1.00 | 25.72 |
| ATOM | 3175 | N   | LEU | A | 404 | 28.040 | 23.327 | 62.165 | 1.00 | 31.31 |
| ATOM | 3176 | CA  | LEU | A | 404 | 27.687 | 24.080 | 60.983 | 1.00 | 32.95 |
| ATOM | 3177 | C   | LEU | A | 404 | 27.068 | 23.099 | 59.952 | 1.00 | 32.89 |
| ATOM | 3178 | O   | LEU | A | 404 | 26.050 | 23.361 | 59.315 | 1.00 | 37.36 |
| ATOM | 3179 | CB  | LEU | A | 404 | 28.798 | 25.045 | 60.464 | 1.00 | 33.15 |
| ATOM | 3180 | CG  | LEU | A | 404 | 29.029 | 26.208 | 61.444 | 1.00 | 36.96 |
| ATOM | 3181 | CD1 | LEU | A | 404 | 30.454 | 26.717 | 61.353 | 1.00 | 37.13 |
| ATOM | 3182 | CD2 | LEU | A | 404 | 28.083 | 27.362 | 61.163 | 1.00 | 39.27 |
| ATOM | 3183 | N   | GLY | A | 405 | 27.670 | 21.921 | 59.826 | 1.00 | 22.02 |
| ATOM | 3184 | CA  | GLY | A | 405 | 27.167 | 20.908 | 58.928 | 1.00 | 22.77 |
| ATOM | 3185 | C   | GLY | A | 405 | 25.698 | 20.676 | 59.206 | 1.00 | 31.85 |
| ATOM | 3186 | O   | GLY | A | 405 | 24.885 | 20.438 | 58.297 | 1.00 | 33.01 |
| ATOM | 3187 | N   | PHE | A | 406 | 25.364 | 20.747 | 60.493 | 1.00 | 26.28 |
| ATOM | 3188 | CA  | PHE | A | 406 | 23.992 | 20.565 | 60.863 | 1.00 | 25.27 |
| ATOM | 3189 | C   | PHE | A | 406 | 23.188 | 21.757 | 60.365 | 1.00 | 34.80 |
| ATOM | 3190 | O   | PHE | A | 406 | 22.195 | 21.629 | 59.638 | 1.00 | 36.22 |
| ATOM | 3191 | CB  | PHE | A | 406 | 23.798 | 20.268 | 62.351 | 1.00 | 24.52 |
| ATOM | 3192 | CG  | PHE | A | 406 | 22.388 | 20.525 | 62.798 | 1.00 | 24.82 |
| ATOM | 3193 | CD1 | PHE | A | 406 | 21.328 | 19.734 | 62.353 | 1.00 | 28.50 |
| ATOM | 3194 | CD2 | PHE | A | 406 | 22.107 | 21.579 | 63.669 | 1.00 | 30.12 |
| ATOM | 3195 | CE1 | PHE | A | 406 | 20.025 | 19.977 | 62.793 | 1.00 | 31.40 |

TABLE 9-continued

Structure coordinates of LTA$_4$ hydrolase-thiolamine complex
(The amino acid sequence set forth as residues 1-610 below correspond to SEQ ID NO:1.)

| ATOM | 3196 | CE2 | PHE | A | 406 | 20.810 | 21.862 | 64.105 | 1.00 | 32.57 |
|---|---|---|---|---|---|---|---|---|---|---|
| ATOM | 3197 | CZ | PHE | A | 406 | 19.771 | 21.037 | 63.669 | 1.00 | 31.88 |
| ATOM | 3198 | N | LEU | A | 407 | 23.661 | 22.934 | 60.708 | 1.00 | 32.11 |
| ATOM | 3199 | CA | LEU | A | 407 | 22.972 | 24.132 | 60.269 | 1.00 | 33.11 |
| ATOM | 3200 | C | LEU | A | 407 | 22.706 | 24.204 | 58.767 | 1.00 | 34.74 |
| ATOM | 3201 | O | LEU | A | 407 | 21.635 | 24.615 | 58.341 | 1.00 | 35.21 |
| ATOM | 3202 | CB | LEU | A | 407 | 23.589 | 25.420 | 60.840 | 1.00 | 35.36 |
| ATOM | 3203 | CG | LEU | A | 407 | 22.597 | 26.577 | 60.855 | 1.00 | 41.79 |
| ATOM | 3204 | CD1 | LEU | A | 407 | 23.048 | 27.626 | 61.833 | 1.00 | 40.45 |
| ATOM | 3205 | CD2 | LEU | A | 407 | 22.513 | 27.197 | 59.461 | 1.00 | 49.57 |
| ATOM | 3206 | N | LYS | A | 408 | 23.667 | 23.804 | 57.948 | 1.00 | 34.92 |
| ATOM | 3207 | CA | LYS | A | 408 | 23.476 | 23.826 | 56.490 | 1.00 | 36.29 |
| ATOM | 3208 | C | LYS | A | 408 | 22.378 | 22.876 | 56.037 | 1.00 | 38.15 |
| ATOM | 3209 | O | LYS | A | 408 | 21.568 | 23.191 | 55.160 | 1.00 | 35.09 |
| ATOM | 3210 | CB | LYS | A | 408 | 24.747 | 23.517 | 55.707 | 1.00 | 40.54 |
| ATOM | 3211 | CG | LYS | A | 408 | 24.633 | 23.873 | 54.214 | 1.00 | 43.41 |
| ATOM | 3212 | CD | LYS | A | 408 | 25.950 | 23.796 | 53.422 | 1.00 | 49.26 |
| ATOM | 3213 | CE | LYS | A | 408 | 26.808 | 25.059 | 53.459 | 1.00 | 61.45 |
| ATOM | 3214 | NZ | LYS | A | 408 | 28.014 | 24.994 | 52.606 | 1.00 | 73.78 |
| ATOM | 3215 | N | ALA | A | 409 | 22.352 | 21.690 | 56.655 | 1.00 | 35.34 |
| ATOM | 3216 | CA | ALA | A | 409 | 21.333 | 20.698 | 56.298 | 1.00 | 36.14 |
| ATOM | 3217 | C | ALA | A | 409 | 19.927 | 21.041 | 56.814 | 1.00 | 38.45 |
| ATOM | 3218 | O | ALA | A | 409 | 18.913 | 20.821 | 56.134 | 1.00 | 37.39 |
| ATOM | 3219 | CB | ALA | A | 409 | 21.762 | 19.273 | 56.626 | 1.00 | 36.66 |
| ATOM | 3220 | N | TYR | A | 410 | 19.902 | 21.597 | 58.030 | 1.00 | 33.14 |
| ATOM | 3221 | CA | TYR | A | 410 | 18.693 | 22.059 | 58.682 | 1.00 | 29.65 |
| ATOM | 3222 | C | TYR | A | 410 | 18.028 | 23.051 | 57.730 | 1.00 | 35.55 |
| ATOM | 3223 | O | TYR | A | 410 | 16.855 | 22.976 | 57.399 | 1.00 | 37.26 |
| ATOM | 3224 | CB | TYR | A | 410 | 19.117 | 22.762 | 59.970 | 1.00 | 24.67 |
| ATOM | 3225 | CG | TYR | A | 410 | 18.069 | 23.643 | 60.541 | 1.00 | 26.95 |
| ATOM | 3226 | CD1 | TYR | A | 410 | 16.861 | 23.112 | 60.990 | 0.00 | 28.10 |
| ATOM | 3227 | CD2 | TYR | A | 410 | 18.288 | 25.015 | 60.663 | 1.00 | 29.66 |
| ATOM | 3228 | CE1 | TYR | A | 410 | 15.883 | 23.924 | 61.571 | 1.00 | 26.98 |
| ATOM | 3229 | CE2 | TYR | A | 410 | 17.316 | 25.839 | 61.230 | 1.00 | 31.84 |
| ATOM | 3230 | CZ | TYR | A | 410 | 16.112 | 25.294 | 61.685 | 1.00 | 37.49 |
| ATOM | 3231 | OH | TYR | A | 410 | 15.156 | 26.110 | 62.241 | 1.00 | 33.48 |
| ATOM | 3232 | N | VAL | A | 411 | 18.848 | 23.961 | 57.262 | 1.00 | 28.75 |
| ATOM | 3233 | CA | VAL | A | 411 | 18.457 | 24.984 | 56.341 | 1.00 | 29.23 |
| ATOM | 3234 | C | VAL | A | 411 | 18.013 | 24.469 | 54.992 | 1.00 | 34.00 |
| ATOM | 3235 | O | VAL | A | 411 | 17.060 | 24.982 | 54.401 | 1.00 | 30.00 |
| ATOM | 3236 | CB | VAL | A | 411 | 19.617 | 25.922 | 56.139 | 1.00 | 32.22 |
| ATOM | 3237 | CG1 | VAL | A | 411 | 19.331 | 26.821 | 54.950 | 1.00 | 29.86 |
| ATOM | 3238 | CG2 | VAL | A | 411 | 19.850 | 26.708 | 57.431 | 1.00 | 31.69 |
| ATOM | 3239 | N | GLU | A | 412 | 18.730 | 23.479 | 54.488 | 1.00 | 33.14 |
| ATOM | 3240 | CA | GLU | A | 412 | 18.402 | 22.900 | 53.217 | 1.00 | 31.91 |
| ATOM | 3241 | C | GLU | A | 412 | 17.068 | 22.163 | 53.355 | 1.00 | 30.32 |
| ATOM | 3242 | O | GLU | A | 412 | 16.182 | 22.225 | 52.531 | 1.00 | 31.89 |
| ATOM | 3243 | CB | GLU | A | 412 | 19.502 | 21.883 | 52.932 | 1.00 | 36.48 |
| ATOM | 3244 | CG | GLU | A | 412 | 20.443 | 22.174 | 51.737 | 1.00 | 67.01 |
| ATOM | 3245 | CD | GLU | A | 412 | 21.872 | 21.699 | 51.962 | 1.00 | 100.00 |
| ATOM | 3246 | OE1 | GLU | A | 412 | 22.193 | 20.782 | 52.716 | 1.00 | 100.00 |
| ATOM | 3247 | OE2 | GLU | A | 412 | 22.750 | 22.396 | 51.277 | 1.00 | 94.73 |
| ATOM | 3248 | N | LYS | A | 413 | 16.922 | 21.444 | 54.444 | 1.00 | 22.18 |
| ATOM | 3249 | CA | LYS | A | 413 | 15.729 | 20.692 | 54.714 | 1.00 | 17.91 |
| ATOM | 3250 | C | LYS | A | 413 | 14.463 | 21.486 | 54.855 | 1.00 | 23.75 |
| ATOM | 3251 | O | LYS | A | 413 | 13.417 | 20.978 | 54.503 | 1.00 | 25.92 |
| ATOM | 3252 | CB | LYS | A | 413 | 15.890 | 19.911 | 55.988 | 1.00 | 15.65 |
| ATOM | 3253 | CG | LYS | A | 413 | 14.554 | 19.422 | 56.503 | 1.00 | 38.69 |
| ATOM | 3254 | CD | LYS | A | 413 | 14.150 | 18.089 | 55.903 | 1.00 | 58.11 |
| ATOM | 3255 | CE | LYS | A | 413 | 13.634 | 17.099 | 56.937 | 1.00 | 64.98 |
| ATOM | 3256 | NZ | LYS | A | 413 | 13.457 | 15.751 | 56.381 | 1.00 | 73.89 |
| ATOM | 3257 | N | PHE | A | 414 | 14.530 | 22.688 | 55.424 | 1.00 | 25.40 |
| ATOM | 3258 | CA | PHE | A | 414 | 13.316 | 23.479 | 55.640 | 1.00 | 27.80 |
| ATOM | 3259 | C | PHE | A | 414 | 13.151 | 24.748 | 54.821 | 1.00 | 35.82 |
| ATOM | 3260 | O | PHE | A | 414 | 12.276 | 25.557 | 55.122 | 1.00 | 35.17 |
| ATOM | 3261 | CB | PHE | A | 414 | 13.063 | 23.791 | 57.118 | 1.00 | 30.46 |
| ATOM | 3262 | CG | PHE | A | 414 | 12.936 | 22.553 | 57.964 | 1.00 | 33.88 |
| ATOM | 3263 | CD1 | PHE | A | 414 | 11.746 | 21.826 | 57.996 | 1.00 | 35.94 |
| ATOM | 3264 | CD2 | PHE | A | 414 | 14.005 | 22.110 | 58.742 | 1.00 | 37.75 |
| ATOM | 3265 | CE1 | PHE | A | 414 | 11.629 | 20.664 | 58.761 | 1.00 | 37.77 |
| ATOM | 3266 | CE2 | PHE | A | 414 | 13.888 | 20.962 | 59.526 | 1.00 | 42.23 |
| ATOM | 3267 | CZ | PHE | A | 414 | 12.698 | 20.231 | 59.542 | 1.00 | 39.10 |
| ATOM | 3268 | N | SER | A | 415 | 13.970 | 24.933 | 53.795 | 1.00 | 36.12 |
| ATOM | 3269 | CA | SER | A | 415 | 13.858 | 26.115 | 52.945 | 1.00 | 36.36 |
| ATOM | 3270 | C | SER | A | 415 | 12.412 | 26.295 | 52.510 | 1.00 | 38.99 |
| ATOM | 3271 | O | SER | A | 415 | 11.730 | 25.315 | 52.243 | 1.00 | 41.04 |

TABLE 9-continued

Structure coordinates of LTA₄ hydrolase-thiolamine complex
(The amino acid sequence set forth as residues 1-610 below correspond to SEQ ID NO:1.)

| ATOM | 3272 | CB | SER | A | 415 | 14.773 | 26.008 | 51.736 | 1.00 | 37.43 |
|---|---|---|---|---|---|---|---|---|---|---|
| ATOM | 3273 | OG | SER | A | 415 | 16.036 | 26.566 | 52.046 | 1.00 | 46.73 |
| ATOM | 3274 | N | TYR | A | 416 | 11.928 | 27.537 | 52.475 | 1.00 | 33.40 |
| ATOM | 3275 | CA | TYR | A | 416 | 10.541 | 27.832 | 52.072 | 1.00 | 30.88 |
| ATOM | 3276 | C | TYR | A | 416 | 9.453 | 27.183 | 52.947 | 1.00 | 33.62 |
| ATOM | 3277 | O | TYR | A | 416 | 8.295 | 27.095 | 52.546 | 1.00 | 33.44 |
| ATOM | 3278 | CB | TYR | A | 416 | 10.292 | 27.479 | 50.584 | 1.00 | 28.42 |
| ATOM | 3279 | CG | TYR | A | 416 | 11.496 | 27.782 | 49.723 | 1.00 | 24.76 |
| ATOM | 3280 | CD1 | TYR | A | 416 | 11.791 | 29.087 | 49.338 | 1.00 | 26.55 |
| ATOM | 3281 | CD2 | TYR | A | 416 | 12.375 | 26.778 | 49.335 | 1.00 | 21.68 |
| ATOM | 3282 | CE1 | TYR | A | 416 | 12.914 | 29.384 | 48.570 | 1.00 | 25.16 |
| ATOM | 3283 | CE2 | TYR | A | 416 | 13.504 | 27.052 | 48.572 | 1.00 | 20.15 |
| ATOM | 3284 | CZ | TYR | A | 416 | 13.780 | 28.360 | 48.189 | 1.00 | 30.62 |
| ATOM | 3285 | OH | TYR | A | 416 | 14.892 | 28.616 | 47.399 | 1.00 | 35.15 |
| ATOM | 3286 | N | LYS | A | 417 | 9.823 | 26.713 | 54.122 | 1.00 | 27.67 |
| ATOM | 3287 | CA | LYS | A | 417 | 8.889 | 26.065 | 55.008 | 1.00 | 28.02 |
| ATOM | 3288 | C | LYS | A | 417 | 8.733 | 26.830 | 56.317 | 1.00 | 31.36 |
| ATOM | 3289 | O | LYS | A | 417 | 9.547 | 27.671 | 56.682 | 1.00 | 33.15 |
| ATOM | 3290 | CB | LYS | A | 417 | 9.335 | 24.615 | 55.252 | 1.00 | 33.86 |
| ATOM | 3291 | CG | LYS | A | 417 | 8.449 | 23.792 | 56.201 | 1.00 | 86.28 |
| ATOM | 3292 | CD | LYS | A | 417 | 8.742 | 22.275 | 56.232 | 1.00 | 100.00 |
| ATOM | 3293 | CE | LYS | A | 417 | 7.924 | 21.471 | 57.265 | 1.00 | 72.28 |
| ATOM | 3294 | NZ | LYS | A | 417 | 8.280 | 20.033 | 57.323 | 1.00 | 41.88 |
| ATOM | 3295 | N | SER | A | 418 | 7.668 | 26.557 | 57.033 | 1.00 | 28.88 |
| ATOM | 3296 | CA | SER | A | 418 | 7.455 | 27.195 | 58.335 | 1.00 | 30.04 |
| ATOM | 3297 | C | SER | A | 418 | 7.425 | 26.064 | 59.332 | 1.00 | 34.09 |
| ATOM | 3298 | O | SER | A | 418 | 6.614 | 25.145 | 59.193 | 1.00 | 31.54 |
| ATOM | 3299 | CB | SER | A | 418 | 6.261 | 28.126 | 58.410 | 1.00 | 31.46 |
| ATOM | 3300 | OG | SER | A | 418 | 6.417 | 29.106 | 57.399 | 1.00 | 35.01 |
| ATOM | 3301 | N | ILE | A | 419 | 8.356 | 26.077 | 60.281 | 1.00 | 28.50 |
| ATOM | 3302 | CA | ILE | A | 419 | 8.446 | 24.971 | 61.205 | 1.00 | 23.86 |
| ATOM | 3303 | C | ILE | A | 419 | 8.272 | 25.342 | 62.641 | 1.00 | 25.06 |
| ATOM | 3304 | O | ILE | A | 419 | 8.122 | 26.500 | 63.002 | 1.00 | 21.64 |
| ATOM | 3305 | CB | ILE | A | 419 | 9.803 | 24.314 | 61.026 | 1.00 | 25.02 |
| ATOM | 3306 | CG1 | ILE | A | 419 | 10.863 | 25.325 | 61.399 | 1.00 | 23.63 |
| ATOM | 3307 | CG2 | ILE | A | 419 | 10.051 | 23.937 | 59.565 | 1.00 | 23.22 |
| ATOM | 3308 | CD1 | ILE | A | 419 | 12.236 | 24.688 | 61.253 | 1.00 | 23.48 |
| ATOM | 3309 | N | THR | A | 420 | 8.321 | 24.302 | 63.455 | 1.00 | 24.71 |
| ATOM | 3310 | CA | THR | A | 420 | 8.201 | 24.417 | 64.895 | 1.00 | 24.36 |
| ATOM | 3311 | C | THR | A | 420 | 9.416 | 23.795 | 65.538 | 1.00 | 28.90 |
| ATOM | 3312 | O | THR | A | 420 | 10.190 | 23.112 | 64.863 | 1.00 | 23.38 |
| ATOM | 3313 | CB | THR | A | 420 | 6.979 | 23.691 | 65.448 | 1.00 | 24.92 |
| ATOM | 3314 | OG1 | THR | A | 420 | 7.190 | 22.313 | 65.291 | 1.00 | 26.43 |
| ATOM | 3315 | CG2 | THR | A | 420 | 5.728 | 24.082 | 64.694 | 1.00 | 31.57 |
| ATOM | 3316 | N | THR | A | 421 | 9.542 | 24.051 | 66.855 | 1.00 | 29.30 |
| ATOM | 3317 | CA | THR | A | 421 | 10.610 | 23.549 | 67.709 | 1.00 | 27.78 |
| ATOM | 3318 | C | THR | A | 421 | 10.831 | 22.035 | 67.585 | 1.00 | 30.99 |
| ATOM | 3319 | O | THR | A | 421 | 11.975 | 21.594 | 67.489 | 1.00 | 33.28 |
| ATOM | 3320 | CB | THR | A | 421 | 10.394 | 23.969 | 69.166 | 1.00 | 21.94 |
| ATOM | 3321 | OG1 | THR | A | 421 | 10.567 | 25.369 | 69.263 | 1.00 | 24.52 |
| ATOM | 3322 | CG2 | THR | A | 421 | 11.399 | 23.221 | 70.045 | 1.00 | 20.12 |
| ATOM | 3323 | N | ASP | A | 422 | 9.721 | 21.272 | 67.575 | 1.00 | 21.94 |
| ATOM | 3324 | CA | ASP | A | 422 | 9.706 | 19.823 | 67.430 | 1.00 | 21.08 |
| ATOM | 3325 | C | ASP | A | 422 | 10.323 | 19.401 | 66.104 | 1.00 | 31.16 |
| ATOM | 3326 | O | ASP | A | 422 | 11.110 | 18.427 | 66.027 | 1.00 | 31.95 |
| ATOM | 3327 | CB | ASP | A | 422 | 8.276 | 19.278 | 67.561 | 1.00 | 19.49 |
| ATOM | 3328 | CG | ASP | A | 422 | 8.236 | 17.802 | 67.298 | 1.00 | 31.85 |
| ATOM | 3329 | OD1 | ASP | A | 422 | 9.130 | 17.040 | 67.654 | 1.00 | 29.73 |
| ATOM | 3330 | OD2 | ASP | A | 422 | 7.197 | 17.415 | 66.598 | 1.00 | 56.60 |
| ATOM | 3331 | N | ASP | A | 423 | 9.957 | 20.146 | 65.049 | 1.00 | 26.75 |
| ATOM | 3332 | CA | ASP | A | 423 | 10.505 | 19.876 | 63.729 | 1.00 | 26.01 |
| ATOM | 3333 | C | ASP | A | 423 | 12.027 | 19.957 | 63.830 | 1.00 | 40.09 |
| ATOM | 3334 | O | ASP | A | 423 | 12.753 | 19.020 | 63.500 | 1.00 | 47.09 |
| ATOM | 3335 | CB | ASP | A | 423 | 10.000 | 20.833 | 62.631 | 1.00 | 24.86 |
| ATOM | 3336 | CG | ASP | A | 423 | 8.538 | 20.722 | 62.343 | 1.00 | 39.90 |
| ATOM | 3337 | OD1 | ASP | A | 423 | 7.968 | 19.649 | 62.299 | 1.00 | 45.03 |
| ATOM | 3338 | OD2 | ASP | A | 423 | 7.943 | 21.887 | 62.113 | 1.00 | 40.43 |
| ATOM | 3339 | N | TRP | A | 424 | 12.493 | 21.099 | 64.320 | 1.00 | 31.92 |
| ATOM | 3340 | CA | TRP | A | 424 | 13.903 | 21.372 | 64.495 | 1.00 | 29.69 |
| ATOM | 3341 | C | TRP | A | 424 | 14.611 | 20.271 | 65.282 | 1.00 | 33.81 |
| ATOM | 3342 | O | TRP | A | 424 | 15.537 | 19.616 | 64.824 | 1.00 | 35.87 |
| ATOM | 3343 | CB | TRP | A | 424 | 14.056 | 22.711 | 65.239 | 1.00 | 26.11 |
| ATOM | 3344 | CG | TRP | A | 424 | 15.431 | 22.869 | 65.786 | 1.00 | 27.05 |
| ATOM | 3345 | CD1 | TRP | A | 424 | 16.518 | 23.302 | 65.101 | 1.00 | 29.65 |
| ATOM | 3346 | CD2 | TRP | A | 424 | 15.885 | 22.587 | 67.119 | 1.00 | 26.62 |
| ATOM | 3347 | NE1 | TRP | A | 424 | 17.612 | 23.321 | 65.922 | 1.00 | 27.83 |

TABLE 9-continued

Structure coordinates of LTA$_4$ hydrolase-thiolamine complex
(The amino acid sequence set forth as residues 1-610 below correspond to SEQ ID NO:1.)

| ATOM | 3348 | CE2 | TRP | A | 424 | 17.257 | 22.891 | 67.163 | 1.00 | 28.62 |
|------|------|-----|-----|---|-----|--------|--------|--------|------|-------|
| ATOM | 3349 | CE3 | TRP | A | 424 | 15.260 | 22.138 | 68.269 | 1.00 | 29.69 |
| ATOM | 3350 | CZ2 | TRP | A | 424 | 18.010 | 22.758 | 68.319 | 1.00 | 29.28 |
| ATOM | 3351 | CZ3 | TRP | A | 424 | 16.000 | 21.993 | 69.429 | 1.00 | 33.50 |
| ATOM | 3352 | CH2 | TRP | A | 424 | 17.362 | 22.317 | 69.459 | 1.00 | 33.93 |
| ATOM | 3353 | N | LYS | A | 425 | 14.156 | 20.090 | 66.497 | 1.00 | 28.75 |
| ATOM | 3354 | CA | LYS | A | 425 | 14.723 | 19.105 | 67.373 | 1.00 | 29.43 |
| ATOM | 3355 | C | LYS | A | 425 | 14.697 | 17.691 | 66.808 | 1.00 | 29.49 |
| ATOM | 3356 | O | LYS | A | 425 | 15.627 | 16.928 | 67.030 | 1.00 | 27.65 |
| ATOM | 3357 | CB | LYS | A | 425 | 14.078 | 19.171 | 68.744 | 1.00 | 29.70 |
| ATOM | 3358 | CG | LYS | A | 425 | 14.860 | 18.414 | 69.787 | 1.00 | 28.11 |
| ATOM | 3359 | CD | LYS | A | 425 | 14.161 | 18.409 | 71.132 | 1.00 | 23.57 |
| ATOM | 3360 | CE | LYS | A | 425 | 14.300 | 17.063 | 71.815 | 1.00 | 36.16 |
| ATOM | 3361 | NZ | LYS | A | 425 | 13.042 | 16.302 | 71.768 | 1.00 | 58.08 |
| ATOM | 3362 | N | ASP | A | 426 | 13.606 | 17.361 | 66.107 | 1.00 | 19.05 |
| ATOM | 3363 | CA | ASP | A | 426 | 13.417 | 16.070 | 65.516 | 1.00 | 18.43 |
| ATOM | 3364 | C | ASP | A | 426 | 14.453 | 15.879 | 64.387 | 1.00 | 28.33 |
| ATOM | 3365 | O | ASP | A | 426 | 15.070 | 14.832 | 64.232 | 1.00 | 31.25 |
| ATOM | 3366 | CB | ASP | A | 426 | 11.920 | 15.840 | 65.098 | 1.00 | 19.79 |
| ATOM | 3367 | CG | ASP | A | 426 | 10.998 | 15.575 | 66.274 | 1.00 | 25.54 |
| ATOM | 3368 | OD1 | ASP | A | 426 | 11.341 | 15.466 | 67.409 | 1.00 | 29.73 |
| ATOM | 3369 | OD2 | ASP | A | 426 | 9.804 | 15.611 | 65.938 | 1.00 | 20.67 |
| ATOM | 3370 | N | PHE | A | 427 | 14.674 | 16.926 | 63.612 | 1.00 | 25.09 |
| ATOM | 3371 | CA | PHE | A | 427 | 15.654 | 16.899 | 62.540 | 1.00 | 25.81 |
| ATOM | 3372 | C | PHE | A | 427 | 17.066 | 16.718 | 63.159 | 1.00 | 34.01 |
| ATOM | 3373 | O | PHE | A | 427 | 17.843 | 15.851 | 62.773 | 1.00 | 36.25 |
| ATOM | 3374 | CB | PHE | A | 427 | 15.589 | 18.197 | 61.704 | 1.00 | 26.35 |
| ATOM | 3375 | CG | PHE | A | 427 | 16.698 | 18.202 | 60.702 | 1.00 | 27.40 |
| ATOM | 3376 | CD1 | PHE | A | 427 | 16.714 | 17.247 | 59.686 | 1.00 | 29.97 |
| ATOM | 3377 | CD2 | PHE | A | 427 | 17.773 | 19.084 | 60.805 | 1.00 | 28.71 |
| ATOM | 3378 | CE1 | PHE | A | 427 | 17.730 | 17.194 | 58.733 | 1.00 | 27.72 |
| ATOM | 3379 | CE2 | PHE | A | 427 | 18.806 | 19.046 | 59.867 | 1.00 | 30.37 |
| ATOM | 3380 | CZ | PHE | A | 427 | 18.780 | 18.104 | 58.837 | 1.00 | 26.34 |
| ATOM | 3381 | N | LEU | A | 428 | 17.369 | 17.544 | 64.160 | 1.00 | 28.94 |
| ATOM | 3382 | CA | LEU | A | 428 | 18.622 | 17.496 | 64.924 | 1.00 | 27.74 |
| ATOM | 3383 | C | LEU | A | 428 | 18.989 | 16.047 | 65.303 | 1.00 | 32.08 |
| ATOM | 3384 | O | LEU | A | 428 | 20.145 | 15.647 | 65.209 | 1.00 | 36.38 |
| ATOM | 3385 | CB | LEU | A | 428 | 18.510 | 18.362 | 66.223 | 1.00 | 24.68 |
| ATOM | 3386 | CG | LEU | A | 428 | 19.778 | 18.377 | 67.079 | 1.00 | 24.30 |
| ATOM | 3387 | CD1 | LEU | A | 428 | 20.855 | 19.278 | 66.467 | 1.00 | 23.00 |
| ATOM | 3388 | CD2 | LEU | A | 428 | 19.446 | 18.856 | 68.481 | 1.00 | 16.41 |
| ATOM | 3389 | N | TYR | A | 429 | 17.991 | 15.271 | 65.735 | 1.00 | 23.71 |
| ATOM | 3390 | CA | TYR | A | 429 | 18.148 | 13.896 | 66.144 | 1.00 | 23.18 |
| ATOM | 3391 | C | TYR | A | 429 | 18.311 | 12.967 | 64.976 | 1.00 | 26.62 |
| ATOM | 3392 | O | TYR | A | 429 | 18.911 | 11.910 | 65.076 | 1.00 | 28.43 |
| ATOM | 3393 | CB | TYR | A | 429 | 16.921 | 13.453 | 66.914 | 1.00 | 25.59 |
| ATOM | 3394 | CG | TYR | A | 429 | 17.069 | 13.526 | 68.414 | 1.00 | 29.53 |
| ATOM | 3395 | CD1 | TYR | A | 429 | 16.823 | 14.714 | 69.114 | 1.00 | 31.11 |
| ATOM | 3396 | CD2 | TYR | A | 429 | 17.361 | 12.383 | 69.156 | 1.00 | 32.70 |
| ATOM | 3397 | CE1 | TYR | A | 429 | 16.916 | 14.769 | 70.510 | 1.00 | 32.23 |
| ATOM | 3398 | CE2 | TYR | A | 429 | 17.485 | 12.420 | 70.551 | 1.00 | 35.30 |
| ATOM | 3399 | CZ | TYR | A | 429 | 17.251 | 13.623 | 71.231 | 1.00 | 41.02 |
| ATOM | 3400 | OH | TYR | A | 429 | 17.339 | 13.679 | 72.609 | 1.00 | 30.02 |
| ATOM | 3401 | N | SER | A | 430 | 17.748 | 13.342 | 63.854 | 1.00 | 21.68 |
| ATOM | 3402 | CA | SER | A | 430 | 17.914 | 12.469 | 62.730 | 1.00 | 23.42 |
| ATOM | 3403 | C | SER | A | 430 | 19.264 | 12.722 | 62.050 | 1.00 | 32.87 |
| ATOM | 3404 | O | SER | A | 430 | 19.879 | 11.819 | 61.467 | 1.00 | 35.11 |
| ATOM | 3405 | CB | SER | A | 430 | 16.756 | 12.541 | 61.773 | 1.00 | 28.79 |
| ATOM | 3406 | OG | SER | A | 430 | 17.089 | 13.475 | 60.777 | 1.00 | 49.56 |
| ATOM | 3407 | N | TYR | A | 431 | 19.748 | 13.955 | 62.132 | 1.00 | 27.18 |
| ATOM | 3408 | CA | TYR | A | 431 | 21.017 | 14.296 | 61.537 | 1.00 | 27.14 |
| ATOM | 3409 | C | TYR | A | 431 | 22.152 | 13.702 | 62.316 | 1.00 | 32.52 |
| ATOM | 3410 | O | TYR | A | 431 | 23.155 | 13.242 | 61.771 | 1.00 | 33.64 |
| ATOM | 3411 | CB | TYR | A | 431 | 21.216 | 15.818 | 61.385 | 1.00 | 31.07 |
| ATOM | 3412 | CG | TYR | A | 431 | 22.566 | 16.265 | 60.812 | 1.00 | 35.63 |
| ATOM | 3413 | CD1 | TYR | A | 431 | 23.663 | 16.492 | 61.650 | 1.00 | 36.88 |
| ATOM | 3414 | CD2 | TYR | A | 431 | 22.735 | 16.496 | 59.444 | 1.00 | 36.92 |
| ATOM | 3415 | CE1 | TYR | A | 431 | 24.894 | 16.924 | 61.157 | 1.00 | 33.78 |
| ATOM | 3416 | CE2 | TYR | A | 431 | 23.964 | 16.916 | 58.924 | 1.00 | 37.86 |
| ATOM | 3417 | CZ | TYR | A | 431 | 25.038 | 17.143 | 59.786 | 1.00 | 46.01 |
| ATOM | 3418 | OH | TYR | A | 431 | 26.247 | 17.573 | 59.294 | 1.00 | 51.28 |
| ATOM | 3419 | N | PHE | A | 432 | 21.964 | 13.728 | 63.606 | 1.00 | 29.66 |
| ATOM | 3420 | CA | PHE | A | 432 | 22.939 | 13.215 | 64.526 | 1.00 | 29.12 |
| ATOM | 3421 | C | PHE | A | 432 | 22.522 | 11.865 | 65.007 | 1.00 | 42.64 |
| ATOM | 3422 | O | PHE | A | 432 | 22.499 | 11.593 | 66.197 | 1.00 | 46.77 |
| ATOM | 3423 | CB | PHE | A | 432 | 23.063 | 14.157 | 65.719 | 1.00 | 30.24 |

TABLE 9-continued

Structure coordinates of LTA$_4$ hydrolase-thiolamine complex
(The amino acid sequence set forth as residues 1-610 below correspond to SEQ ID NO:1.)

| ATOM | 3424 | CG | PHE | A | 432 | 23.962 | 15.327 | 65.401 | 1.00 | 33.03 |
|---|---|---|---|---|---|---|---|---|---|---|
| ATOM | 3425 | CD1 | PHE | A | 432 | 25.336 | 15.113 | 65.277 | 1.00 | 37.22 |
| ATOM | 3426 | CD2 | PHE | A | 432 | 23.470 | 16.624 | 65.232 | 1.00 | 30.70 |
| ATOM | 3427 | CE1 | PHE | A | 432 | 26.223 | 16.153 | 64.999 | 1.00 | 34.27 |
| ATOM | 3428 | CE2 | PHE | A | 432 | 24.349 | 17.667 | 64.938 | 1.00 | 31.71 |
| ATOM | 3429 | CZ | PHE | A | 432 | 25.722 | 17.438 | 64.823 | 1.00 | 27.82 |
| ATOM | 3430 | N | LYS | A | 433 | 22.174 | 11.029 | 64.063 | 1.00 | 42.50 |
| ATOM | 3431 | CA | LYS | A | 433 | 21.669 | 9.670 | 64.270 | 1.00 | 40.87 |
| ATOM | 3432 | C | LYS | A | 433 | 22.718 | 8.751 | 64.908 | 1.00 | 46.17 |
| ATOM | 3433 | O | LYS | A | 433 | 22.405 | 7.734 | 65.513 | 1.00 | 48.48 |
| ATOM | 3434 | CB | LYS | A | 433 | 21.245 | 9.106 | 62.917 | 1.00 | 39.25 |
| ATOM | 3435 | CG | LYS | A | 433 | 19.988 | 8.241 | 63.017 | 1.00 | 84.17 |
| ATOM | 3436 | CD | LYS | A | 433 | 18.925 | 8.660 | 62.000 | 1.00 | 100.00 |
| ATOM | 3437 | CE | LYS | A | 433 | 17.523 | 8.172 | 62.384 | 1.00 | 100.00 |
| ATOM | 3438 | NZ | LYS | A | 433 | 16.525 | 9.119 | 61.884 | 1.00 | 100.00 |
| ATOM | 3439 | N | ASP | A | 434 | 24.002 | 9.112 | 64.697 | 1.00 | 45.20 |
| ATOM | 3440 | CA | ASP | A | 434 | 25.083 | 8.349 | 65.321 | 1.00 | 47.80 |
| ATOM | 3441 | C | ASP | A | 434 | 25.201 | 8.684 | 66.802 | 1.00 | 50.78 |
| ATOM | 3442 | O | ASP | A | 434 | 25.474 | 7.845 | 67.653 | 1.00 | 55.76 |
| ATOM | 3443 | CB | ASP | A | 434 | 26.405 | 8.567 | 64.562 | 1.00 | 53.91 |
| ATOM | 3444 | CG | ASP | A | 434 | 26.123 | 8.474 | 63.069 | 1.00 | 93.32 |
| ATOM | 3445 | OD1 | ASP | A | 434 | 25.744 | 7.573 | 62.325 | 1.00 | 96.22 |
| ATOM | 3446 | OD2 | ASP | A | 434 | 26.119 | 9.664 | 62.753 | 1.00 | 100.00 |
| ATOM | 3447 | N | LYS | A | 435 | 25.015 | 9.978 | 67.085 | 1.00 | 38.82 |
| ATOM | 3448 | CA | LYS | A | 435 | 24.974 | 10.404 | 68.468 | 1.00 | 34.57 |
| ATOM | 3449 | C | LYS | A | 435 | 23.549 | 10.749 | 68.881 | 1.00 | 39.87 |
| ATOM | 3450 | O | LYS | A | 435 | 23.070 | 11.840 | 68.693 | 1.00 | 40.34 |
| ATOM | 3451 | CB | LYS | A | 435 | 25.864 | 11.631 | 68.615 | 1.00 | 34.69 |
| ATOM | 3452 | CG | LYS | A | 435 | 27.064 | 11.595 | 67.679 | 1.00 | 40.86 |
| ATOM | 3453 | CD | LYS | A | 435 | 27.703 | 12.975 | 67.532 | 1.00 | 51.04 |
| ATOM | 3454 | CE | LYS | A | 435 | 29.242 | 12.904 | 67.557 | 1.00 | 24.08 |
| ATOM | 3455 | NZ | LYS | A | 435 | 29.822 | 13.990 | 66.760 | 1.00 | 45.26 |
| ATOM | 3456 | N | VAL | A | 436 | 22.843 | 9.728 | 69.414 | 1.00 | 38.07 |
| ATOM | 3457 | CA | VAL | A | 436 | 21.601 | 10.036 | 70.111 | 1.00 | 36.86 |
| ATOM | 3458 | C | VAL | A | 436 | 21.846 | 10.129 | 71.608 | 1.00 | 44.88 |
| ATOM | 3459 | O | VAL | A | 436 | 21.289 | 10.948 | 72.300 | 1.00 | 46.42 |
| ATOM | 3460 | CB | VAL | A | 436 | 20.567 | 8.923 | 69.816 | 1.00 | 37.37 |
| ATOM | 3461 | CG1 | VAL | A | 436 | 19.944 | 9.143 | 68.446 | 1.00 | 36.24 |
| ATOM | 3462 | CG2 | VAL | A | 436 | 21.227 | 7.556 | 69.854 | 1.00 | 36.80 |
| ATOM | 3463 | N | ASP | A | 437 | 22.718 | 9.232 | 72.099 | 1.00 | 43.61 |
| ATOM | 3464 | CA | ASP | A | 437 | 23.044 | 9.222 | 73.522 | 1.00 | 41.43 |
| ATOM | 3465 | C | ASP | A | 437 | 23.657 | 10.546 | 73.958 | 1.00 | 45.71 |
| ATOM | 3466 | O | ASP | A | 437 | 23.554 | 10.956 | 75.107 | 1.00 | 49.89 |
| ATOM | 3467 | CB | ASP | A | 437 | 24.022 | 8.082 | 73.776 | 1.00 | 43.84 |
| ATOM | 3468 | CG | ASP | A | 437 | 23.281 | 6.752 | 73.691 | 1.00 | 72.47 |
| ATOM | 3469 | OD1 | ASP | A | 437 | 22.062 | 6.769 | 73.823 | 1.00 | 74.64 |
| ATOM | 3470 | OD2 | ASP | A | 437 | 23.933 | 5.730 | 73.481 | 1.00 | 86.09 |
| ATOM | 3471 | N | VAL | A | 438 | 24.333 | 11.324 | 73.122 | 1.00 | 40.21 |
| ATOM | 3472 | CA | VAL | A | 438 | 24.807 | 12.624 | 73.577 | 1.00 | 40.97 |
| ATOM | 3473 | C | VAL | A | 438 | 23.621 | 13.582 | 73.668 | 1.00 | 41.86 |
| ATOM | 3474 | O | VAL | A | 438 | 23.368 | 14.276 | 74.657 | 1.00 | 39.95 |
| ATOM | 3475 | CB | VAL | A | 438 | 25.875 | 13.165 | 72.615 | 1.00 | 47.47 |
| ATOM | 3476 | CG1 | VAL | A | 438 | 26.438 | 14.523 | 73.051 | 1.00 | 47.51 |
| ATOM | 3477 | CG2 | VAL | A | 438 | 26.996 | 12.149 | 72.440 | 1.00 | 47.51 |
| ATOM | 3478 | N | LEU | A | 439 | 22.876 | 13.595 | 72.585 | 1.00 | 37.91 |
| ATOM | 3479 | CA | LEU | A | 439 | 21.729 | 14.442 | 72.507 | 1.00 | 36.21 |
| ATOM | 3480 | C | LEU | A | 439 | 20.850 | 14.190 | 73.695 | 1.00 | 40.03 |
| ATOM | 3481 | O | LEU | A | 439 | 20.214 | 15.064 | 74.255 | 1.00 | 42.22 |
| ATOM | 3482 | CB | LEU | A | 439 | 20.949 | 14.180 | 71.210 | 1.00 | 33.84 |
| ATOM | 3483 | CG | LEU | A | 439 | 21.552 | 14.939 | 70.039 | 1.00 | 32.80 |
| ATOM | 3484 | CD1 | LEU | A | 439 | 20.813 | 14.538 | 68.775 | 1.00 | 34.08 |
| ATOM | 3485 | CD2 | LEU | A | 439 | 21.435 | 16.434 | 70.258 | 1.00 | 23.80 |
| ATOM | 3486 | N | ASN | A | 440 | 20.810 | 12.953 | 74.076 | 1.00 | 34.03 |
| ATOM | 3487 | CA | ASN | A | 440 | 19.971 | 12.603 | 75.187 | 1.00 | 34.00 |
| ATOM | 3488 | C | ASN | A | 440 | 20.494 | 13.093 | 76.532 | 1.00 | 40.95 |
| ATOM | 3489 | O | ASN | A | 440 | 19.816 | 12.995 | 77.544 | 1.00 | 42.09 |
| ATOM | 3490 | CB | ASN | A | 440 | 19.681 | 11.095 | 75.178 | 1.00 | 24.89 |
| ATOM | 3491 | CG | ASN | A | 440 | 18.790 | 10.635 | 74.028 | 1.00 | 46.52 |
| ATOM | 3492 | OD1 | ASN | A | 440 | 19.005 | 9.537 | 73.480 | 1.00 | 58.82 |
| ATOM | 3493 | ND2 | ASN | A | 440 | 17.769 | 11.440 | 73.680 | 1.00 | 31.11 |
| ATOM | 3494 | N | GLN | A | 441 | 21.707 | 13.623 | 76.531 | 1.00 | 36.98 |
| ATOM | 3495 | CA | GLN | A | 441 | 22.339 | 14.095 | 77.744 | 1.00 | 35.47 |
| ATOM | 3496 | C | GLN | A | 441 | 21.879 | 15.478 | 78.067 | 1.00 | 36.00 |
| ATOM | 3497 | O | GLN | A | 441 | 22.137 | 16.029 | 79.142 | 1.00 | 34.96 |
| ATOM | 3498 | CB | GLN | A | 441 | 23.878 | 14.109 | 77.581 | 1.00 | 38.10 |
| ATOM | 3499 | CG | GLN | A | 441 | 24.504 | 12.692 | 77.422 | 1.00 | 52.06 |

TABLE 9-continued

Structure coordinates of LTA₄ hydrolase-thiolamine complex
(The amino acid sequence set forth as residues 1-610 below correspond to SEQ ID NO:1.)

| ATOM | 3500 | CD | GLN | A | 441 | 25.954 | 12.730 | 76.955 | 1.00 | 81.69 |
|---|---|---|---|---|---|---|---|---|---|---|
| ATOM | 3501 | OE1 | GLN | A | 441 | 26.476 | 13.796 | 76.609 | 1.00 | 74.46 |
| ATOM | 3502 | NE2 | GLN | A | 441 | 26.616 | 11.574 | 76.972 | 1.00 | 91.09 |
| ATOM | 3503 | N | VAL | A | 442 | 21.197 | 16.067 | 77.112 | 1.00 | 31.86 |
| ATOM | 3504 | CA | VAL | A | 442 | 20.753 | 17.411 | 77.384 | 1.00 | 32.78 |
| ATOM | 3505 | C | VAL | A | 442 | 19.354 | 17.468 | 77.970 | 1.00 | 38.24 |
| ATOM | 3506 | O | VAL | A | 442 | 18.468 | 16.700 | 77.588 | 1.00 | 42.83 |
| ATOM | 3507 | CB | VAL | A | 442 | 20.845 | 18.277 | 76.159 | 1.00 | 34.84 |
| ATOM | 3508 | CG1 | VAL | A | 442 | 21.430 | 17.435 | 75.020 | 1.00 | 34.65 |
| ATOM | 3509 | CG2 | VAL | A | 442 | 19.441 | 18.705 | 75.811 | 1.00 | 33.21 |
| ATOM | 3510 | N | ASP | A | 443 | 19.172 | 18.388 | 78.908 | 1.00 | 25.60 |
| ATOM | 3511 | CA | ASP | A | 443 | 17.931 | 18.634 | 79.616 | 1.00 | 24.57 |
| ATOM | 3512 | C | ASP | A | 443 | 16.996 | 19.533 | 78.791 | 1.00 | 32.14 |
| ATOM | 3513 | O | ASP | A | 443 | 16.744 | 20.732 | 79.073 | 1.00 | 34.77 |
| ATOM | 3514 | CB | ASP | A | 443 | 18.332 | 19.272 | 80.957 | 1.00 | 27.11 |
| ATOM | 3515 | CG | ASP | A | 443 | 17.216 | 19.413 | 81.901 | 1.00 | 39.99 |
| ATOM | 3516 | OD1 | ASP | A | 443 | 16.063 | 19.234 | 81.573 | 1.00 | 44.78 |
| ATOM | 3517 | OD2 | ASP | A | 443 | 17.631 | 19.753 | 83.094 | 1.00 | 56.66 |
| ATOM | 3518 | N | TRP | A | 444 | 16.525 | 18.914 | 77.722 | 1.00 | 28.30 |
| ATOM | 3519 | CA | TRP | A | 444 | 15.614 | 19.507 | 76.757 | 1.00 | 26.27 |
| ATOM | 3520 | C | TRP | A | 444 | 14.460 | 20.296 | 77.416 | 1.00 | 31.52 |
| ATOM | 3521 | O | TRP | A | 444 | 14.102 | 21.409 | 76.988 | 1.00 | 34.63 |
| ATOM | 3522 | CB | TRP | A | 444 | 15.067 | 18.398 | 75.799 | 1.00 | 21.47 |
| ATOM | 3523 | CG | TRP | A | 444 | 16.095 | 17.951 | 74.806 | 1.00 | 22.03 |
| ATOM | 3524 | CD1 | TRP | A | 444 | 16.675 | 16.718 | 74.736 | 1.00 | 25.16 |
| ATOM | 3525 | CD2 | TRP | A | 444 | 16.733 | 18.738 | 73.776 | 1.00 | 20.36 |
| ATOM | 3526 | NE1 | TRP | A | 444 | 17.623 | 16.677 | 73.738 | 1.00 | 23.97 |
| ATOM | 3527 | CE2 | TRP | A | 444 | 17.688 | 17.906 | 73.138 | 1.00 | 24.71 |
| ATOM | 3528 | CE3 | TRP | A | 444 | 16.596 | 20.045 | 73.342 | 1.00 | 20.86 |
| ATOM | 3529 | CZ2 | TRP | A | 444 | 18.448 | 18.345 | 72.060 | 1.00 | 24.51 |
| ATOM | 3530 | CZ3 | TRP | A | 444 | 17.353 | 20.471 | 72.264 | 1.00 | 22.88 |
| ATOM | 3531 | CH2 | TRP | A | 444 | 18.281 | 19.643 | 71.643 | 1.00 | 23.48 |
| ATOM | 3532 | N | ASN | A | 445 | 13.855 | 19.711 | 78.457 | 1.00 | 24.92 |
| ATOM | 3533 | CA | ASN | A | 445 | 12.723 | 20.326 | 79.113 | 1.00 | 26.30 |
| ATOM | 3534 | C | ASN | A | 445 | 13.040 | 21.677 | 79.729 | 1.00 | 30.17 |
| ATOM | 3535 | O | ASN | A | 445 | 12.291 | 22.660 | 79.547 | 1.00 | 31.86 |
| ATOM | 3536 | CB | ASN | A | 445 | 11.987 | 19.382 | 80.094 | 1.00 | 40.83 |
| ATOM | 3537 | CG | ASN | A | 445 | 10.946 | 20.033 | 81.020 | 1.00 | 87.07 |
| ATOM | 3538 | OD1 | ASN | A | 445 | 11.271 | 20.635 | 82.065 | 1.00 | 86.38 |
| ATOM | 3539 | ND2 | ASN | A | 445 | 9.670 | 19.848 | 80.688 | 1.00 | 71.65 |
| ATOM | 3540 | N | ALA | A | 446 | 14.147 | 21.687 | 80.436 | 1.00 | 22.70 |
| ATOM | 3541 | CA | ALA | A | 446 | 14.583 | 22.886 | 81.073 | 1.00 | 24.45 |
| ATOM | 3542 | C | ALA | A | 446 | 14.886 | 23.896 | 79.990 | 1.00 | 30.52 |
| ATOM | 3543 | O | ALA | A | 446 | 14.324 | 25.001 | 79.936 | 1.00 | 33.92 |
| ATOM | 3544 | CB | ALA | A | 446 | 15.814 | 22.543 | 81.900 | 1.00 | 25.68 |
| ATOM | 3545 | N | TRP | A | 447 | 15.776 | 23.494 | 79.102 | 1.00 | 25.24 |
| ATOM | 3546 | CA | TRP | A | 447 | 16.162 | 24.384 | 78.034 | 1.00 | 26.83 |
| ATOM | 3547 | C | TRP | A | 447 | 14.989 | 24.912 | 77.223 | 1.00 | 31.32 |
| ATOM | 3548 | O | TRP | A | 447 | 14.971 | 26.089 | 76.875 | 1.00 | 30.48 |
| ATOM | 3549 | CB | TRP | A | 447 | 17.166 | 23.725 | 77.062 | 1.00 | 25.78 |
| ATOM | 3550 | CG | TRP | A | 447 | 18.625 | 23.815 | 77.421 | 1.00 | 26.60 |
| ATOM | 3551 | CD1 | TRP | A | 447 | 19.343 | 22.840 | 78.046 | 1.00 | 28.89 |
| ATOM | 3552 | CD2 | TRP | A | 447 | 19.554 | 24.896 | 77.165 | 1.00 | 26.16 |
| ATOM | 3553 | NE1 | TRP | A | 447 | 20.654 | 23.217 | 78.197 | 1.00 | 27.23 |
| ATOM | 3554 | CE2 | TRP | A | 447 | 20.822 | 24.476 | 77.660 | 1.00 | 29.00 |
| ATOM | 3555 | CE3 | TRP | A | 447 | 19.435 | 26.162 | 76.607 | 1.00 | 27.56 |
| ATOM | 3556 | CZ2 | TRP | A | 447 | 21.954 | 25.290 | 77.583 | 1.00 | 27.95 |
| ATOM | 3557 | CZ3 | TRP | A | 447 | 20.554 | 26.966 | 76.538 | 1.00 | 29.93 |
| ATOM | 3558 | CH2 | TRP | A | 447 | 21.792 | 26.539 | 77.035 | 1.00 | 30.16 |
| ATOM | 3559 | N | LEU | A | 448 | 14.029 | 24.034 | 76.893 | 1.00 | 26.54 |
| ATOM | 3560 | CA | LEU | A | 448 | 12.896 | 24.421 | 76.052 | 1.00 | 26.92 |
| ATOM | 3561 | C | LEU | A | 448 | 11.734 | 25.064 | 76.779 | 1.00 | 36.15 |
| ATOM | 3562 | O | LEU | A | 448 | 11.089 | 26.031 | 76.304 | 1.00 | 31.19 |
| ATOM | 3563 | CB | LEU | A | 448 | 12.338 | 23.197 | 75.307 | 1.00 | 25.26 |
| ATOM | 3564 | CG | LEU | A | 448 | 13.311 | 22.545 | 74.332 | 1.00 | 28.29 |
| ATOM | 3565 | CD1 | LEU | A | 448 | 12.597 | 21.455 | 73.530 | 1.00 | 30.49 |
| ATOM | 3566 | CD2 | LEU | A | 448 | 13.879 | 23.576 | 73.375 | 1.00 | 21.94 |
| ATOM | 3567 | N | TYR | A | 449 | 11.472 | 24.455 | 77.924 | 1.00 | 33.14 |
| ATOM | 3568 | CA | TYR | A | 449 | 10.373 | 24.835 | 78.747 | 1.00 | 30.64 |
| ATOM | 3569 | C | TYR | A | 449 | 10.646 | 25.525 | 80.041 | 1.00 | 34.31 |
| ATOM | 3570 | O | TYR | A | 449 | 9.750 | 26.191 | 80.529 | 1.00 | 41.98 |
| ATOM | 3571 | CB | TYR | A | 449 | 9.400 | 23.674 | 78.916 | 1.00 | 29.14 |
| ATOM | 3572 | CG | TYR | A | 449 | 9.212 | 23.089 | 77.556 | 1.00 | 26.50 |
| ATOM | 3573 | CD1 | TYR | A | 449 | 8.762 | 23.869 | 76.485 | 1.00 | 24.36 |
| ATOM | 3574 | CD2 | TYR | A | 449 | 9.560 | 21.762 | 77.325 | 1.00 | 28.48 |
| ATOM | 3575 | CE1 | TYR | A | 449 | 8.626 | 23.331 | 75.202 | 1.00 | 17.56 |

TABLE 9-continued

Structure coordinates of LTA₄ hydrolase-thiolamine complex
(The amino acid sequence set forth as residues 1-610 below correspond to SEQ ID NO:1.)

| ATOM | 3576 | CE2 | TYR | A | 449 | 9.427 | 21.205 | 76.054 | 1.00 | 29.93 |
|---|---|---|---|---|---|---|---|---|---|---|
| ATOM | 3577 | CZ | TYR | A | 449 | 8.959 | 21.988 | 74.998 | 1.00 | 33.65 |
| ATOM | 3578 | OH | TYR | A | 449 | 8.840 | 21.415 | 73.762 | 1.00 | 39.47 |
| ATOM | 3579 | N | SER | A | 450 | 11.806 | 25.413 | 80.644 | 1.00 | 22.72 |
| ATOM | 3580 | CA | SER | A | 450 | 11.902 | 26.149 | 81.900 | 1.00 | 21.21 |
| ATOM | 3581 | C | SER | A | 450 | 12.278 | 27.625 | 81.749 | 1.00 | 23.98 |
| ATOM | 3582 | O | SER | A | 450 | 12.966 | 28.035 | 80.810 | 1.00 | 27.17 |
| ATOM | 3583 | CB | SER | A | 450 | 12.666 | 25.436 | 83.010 | 1.00 | 24.83 |
| ATOM | 3584 | OG | SER | A | 450 | 12.540 | 24.046 | 82.871 | 1.00 | 36.29 |
| ATOM | 3585 | N | PRO | A | 451 | 11.806 | 28.430 | 82.689 | 1.00 | 19.76 |
| ATOM | 3586 | CA | PRO | A | 451 | 12.111 | 29.840 | 82.669 | 1.00 | 18.20 |
| ATOM | 3587 | C | PRO | A | 451 | 13.461 | 29.988 | 83.271 | 1.00 | 21.72 |
| ATOM | 3588 | O | PRO | A | 451 | 14.022 | 29.015 | 83.742 | 1.00 | 24.34 |
| ATOM | 3589 | CB | PRO | A | 451 | 11.185 | 30.485 | 83.695 | 1.00 | 18.85 |
| ATOM | 3590 | CG | PRO | A | 451 | 10.836 | 29.390 | 84.677 | 1.00 | 23.13 |
| ATOM | 3591 | CD | PRO | A | 451 | 11.002 | 28.078 | 83.900 | 1.00 | 19.61 |
| ATOM | 3592 | N | GLY | A | 452 | 13.959 | 31.212 | 83.307 | 1.00 | 18.97 |
| ATOM | 3593 | CA | GLY | A | 452 | 15.241 | 31.444 | 83.922 | 1.00 | 19.09 |
| ATOM | 3594 | C | GLY | A | 452 | 16.382 | 31.107 | 83.016 | 1.00 | 26.20 |
| ATOM | 3595 | O | GLY | A | 452 | 16.191 | 30.916 | 81.819 | 1.00 | 27.37 |
| ATOM | 3596 | N | LEU | A | 453 | 17.557 | 31.057 | 83.650 | 1.00 | 25.48 |
| ATOM | 3597 | CA | LEU | A | 453 | 18.843 | 30.750 | 83.029 | 1.00 | 25.32 |
| ATOM | 3598 | C | LEU | A | 453 | 18.906 | 29.322 | 82.629 | 1.00 | 26.21 |
| ATOM | 3599 | O | LEU | A | 453 | 18.400 | 28.458 | 83.322 | 1.00 | 25.04 |
| ATOM | 3600 | CB | LEU | A | 453 | 20.042 | 31.119 | 83.938 | 1.00 | 25.46 |
| ATOM | 3601 | CG | LEU | A | 453 | 20.280 | 32.632 | 83.904 | 1.00 | 31.82 |
| ATOM | 3602 | CD1 | LEU | A | 453 | 21.019 | 33.087 | 85.119 | 1.00 | 31.78 |
| ATOM | 3603 | CD2 | LEU | A | 453 | 21.046 | 33.056 | 82.651 | 1.00 | 41.50 |
| ATOM | 3604 | N | PRO | A | 454 | 19.510 | 29.082 | 81.489 | 1.00 | 22.97 |
| ATOM | 3605 | CA | PRO | A | 454 | 19.585 | 27.747 | 81.003 | 1.00 | 21.60 |
| ATOM | 3606 | C | PRO | A | 454 | 20.145 | 26.890 | 82.075 | 1.00 | 26.94 |
| ATOM | 3607 | O | PRO | A | 454 | 20.923 | 27.359 | 82.893 | 1.00 | 29.09 |
| ATOM | 3608 | CB | PRO | A | 454 | 20.489 | 27.780 | 79.768 | 1.00 | 22.34 |
| ATOM | 3609 | CG | PRO | A | 454 | 20.777 | 29.232 | 79.470 | 1.00 | 23.69 |
| ATOM | 3610 | CD | PRO | A | 454 | 20.136 | 30.054 | 80.556 | 1.00 | 20.82 |
| ATOM | 3611 | N | PRO | A | 455 | 19.721 | 25.648 | 82.067 | 1.00 | 25.61 |
| ATOM | 3612 | CA | PRO | A | 455 | 20.167 | 24.683 | 83.031 | 1.00 | 24.27 |
| ATOM | 3613 | C | PRO | A | 455 | 21.661 | 24.568 | 82.991 | 1.00 | 30.95 |
| ATOM | 3614 | O | PRO | A | 455 | 22.225 | 24.062 | 83.920 | 1.00 | 33.47 |
| ATOM | 3615 | CB | PRO | A | 455 | 19.631 | 23.320 | 82.592 | 1.00 | 25.04 |
| ATOM | 3616 | CG | PRO | A | 455 | 19.149 | 23.497 | 81.162 | 1.00 | 33.02 |
| ATOM | 3617 | CD | PRO | A | 455 | 19.111 | 25.005 | 80.888 | 1.00 | 28.49 |
| ATOM | 3618 | N | ILE | A | 456 | 22.305 | 25.002 | 81.911 | 1.00 | 27.91 |
| ATOM | 3619 | CA | ILE | A | 456 | 23.764 | 24.893 | 81.821 | 1.00 | 27.82 |
| ATOM | 3620 | C | ILE | A | 456 | 24.395 | 26.057 | 81.077 | 1.00 | 34.73 |
| ATOM | 3621 | O | ILE | A | 456 | 23.737 | 26.769 | 80.293 | 1.00 | 37.01 |
| ATOM | 3622 | CB | ILE | A | 456 | 24.228 | 23.540 | 81.259 | 1.00 | 31.34 |
| ATOM | 3623 | CG1 | ILE | A | 456 | 25.721 | 23.305 | 81.417 | 1.00 | 29.78 |
| ATOM | 3624 | CG2 | ILE | A | 456 | 23.865 | 23.369 | 79.788 | 1.00 | 32.96 |
| ATOM | 3625 | CD1 | ILE | A | 456 | 26.054 | 21.852 | 81.116 | 1.00 | 23.94 |
| ATOM | 3626 | N | LYS | A | 457 | 25.680 | 26.252 | 81.334 | 1.00 | 30.52 |
| ATOM | 3627 | CA | LYS | A | 457 | 26.405 | 27.335 | 80.707 | 1.00 | 30.21 |
| ATOM | 3628 | C | LYS | A | 457 | 27.515 | 26.808 | 79.835 | 1.00 | 32.14 |
| ATOM | 3629 | O | LYS | A | 457 | 28.328 | 26.037 | 80.273 | 1.00 | 33.07 |
| ATOM | 3630 | CB | LYS | A | 457 | 26.953 | 28.264 | 81.749 | 1.00 | 32.38 |
| ATOM | 3631 | CG | LYS | A | 457 | 27.818 | 29.327 | 81.121 | 1.00 | 34.64 |
| ATOM | 3632 | CD | LYS | A | 457 | 28.288 | 30.306 | 82.166 | 1.00 | 13.41 |
| ATOM | 3633 | CE | LYS | A | 457 | 28.803 | 31.596 | 81.565 | 1.00 | 18.04 |
| ATOM | 3634 | NZ | LYS | A | 457 | 28.974 | 32.643 | 82.595 | 1.00 | 26.77 |
| ATOM | 3635 | N | PRO | A | 458 | 27.567 | 27.208 | 78.589 | 1.00 | 27.50 |
| ATOM | 3636 | CA | PRO | A | 458 | 28.630 | 26.675 | 77.737 | 1.00 | 26.85 |
| ATOM | 3637 | C | PRO | A | 458 | 29.994 | 27.147 | 78.185 | 1.00 | 26.89 |
| ATOM | 3638 | O | PRO | A | 458 | 30.128 | 27.876 | 79.167 | 1.00 | 24.86 |
| ATOM | 3639 | CB | PRO | A | 458 | 28.335 | 27.191 | 76.316 | 1.00 | 29.41 |
| ATOM | 3640 | CG | PRO | A | 458 | 26.952 | 27.864 | 76.375 | 1.00 | 33.24 |
| ATOM | 3641 | CD | PRO | A | 458 | 26.574 | 28.044 | 77.848 | 1.00 | 26.12 |
| ATOM | 3642 | N | ASN | A | 459 | 31.005 | 26.754 | 77.440 | 1.00 | 22.13 |
| ATOM | 3643 | CA | ASN | A | 459 | 32.359 | 27.191 | 77.735 | 1.00 | 22.29 |
| ATOM | 3644 | C | ASN | A | 459 | 32.751 | 28.325 | 76.820 | 1.00 | 30.27 |
| ATOM | 3645 | O | ASN | A | 459 | 32.451 | 28.296 | 75.617 | 1.00 | 32.89 |
| ATOM | 3646 | CB | ASN | A | 459 | 33.315 | 26.060 | 77.494 | 1.00 | 25.03 |
| ATOM | 3647 | CG | ASN | A | 459 | 32.766 | 24.846 | 78.155 | 1.00 | 49.54 |
| ATOM | 3648 | OD1 | ASN | A | 459 | 32.618 | 24.822 | 79.383 | 1.00 | 50.09 |
| ATOM | 3649 | ND2 | ASN | A | 459 | 32.411 | 23.870 | 77.332 | 1.00 | 38.39 |
| ATOM | 3650 | N | TYR | A | 460 | 33.448 | 29.316 | 77.380 | 1.00 | 25.58 |

TABLE 9-continued

Structure coordinates of LTA₄ hydrolase-thiolamine complex
(The amino acid sequence set forth as residues 1-610 below correspond to SEQ ID NO:1.)

| ATOM | 3651 | CA | TYR | A | 460 | 33.851 | 30.493 | 76.625 | 1.00 | 23.89 |
|------|------|-----|-----|---|-----|--------|--------|--------|------|-------|
| ATOM | 3652 | C | TYR | A | 460 | 35.298 | 30.853 | 76.745 | 1.00 | 34.20 |
| ATOM | 3653 | O | TYR | A | 460 | 35.849 | 30.862 | 77.839 | 1.00 | 35.27 |
| ATOM | 3654 | CB | TYR | A | 460 | 33.120 | 31.708 | 77.171 | 1.00 | 24.38 |
| ATOM | 3655 | CG | TYR | A | 460 | 31.636 | 31.631 | 77.024 | 1.00 | 26.98 |
| ATOM | 3656 | CD1 | TYR | A | 460 | 31.029 | 32.011 | 75.829 | 1.00 | 30.69 |
| ATOM | 3657 | CD2 | TYR | A | 460 | 30.838 | 31.168 | 78.064 | 1.00 | 25.70 |
| ATOM | 3658 | CE1 | TYR | A | 460 | 29.644 | 31.952 | 75.684 | 1.00 | 28.77 |
| ATOM | 3659 | CE2 | TYR | A | 460 | 29.453 | 31.096 | 77.938 | 1.00 | 25.24 |
| ATOM | 3660 | CZ | TYR | A | 460 | 28.863 | 31.496 | 76.741 | 1.00 | 24.49 |
| ATOM | 3661 | OH | TYR | A | 460 | 27.519 | 31.443 | 76.587 | 1.00 | 28.39 |
| ATOM | 3662 | N | ASP | A | 461 | 35.893 | 31.227 | 75.616 | 1.00 | 30.58 |
| ATOM | 3663 | CA | ASP | A | 461 | 37.268 | 31.640 | 75.654 | 1.00 | 27.51 |
| ATOM | 3664 | C | ASP | A | 461 | 37.319 | 32.941 | 76.464 | 1.00 | 23.53 |
| ATOM | 3665 | O | ASP | A | 461 | 36.377 | 33.704 | 76.396 | 1.00 | 26.62 |
| ATOM | 3666 | CB | ASP | A | 461 | 37.821 | 31.784 | 74.218 | 1.00 | 27.30 |
| ATOM | 3667 | CG | ASP | A | 461 | 39.137 | 32.466 | 74.260 | 1.00 | 32.53 |
| ATOM | 3668 | OD1 | ASP | A | 461 | 39.262 | 33.672 | 74.334 | 1.00 | 39.66 |
| ATOM | 3669 | OD2 | ASP | A | 461 | 40.130 | 31.628 | 74.306 | 1.00 | 44.34 |
| ATOM | 3670 | N | MET | A | 462 | 38.375 | 33.234 | 77.224 | 1.00 | 17.26 |
| ATOM | 3671 | CA | MET | A | 462 | 38.396 | 34.511 | 78.008 | 1.00 | 18.66 |
| ATOM | 3672 | C | MET | A | 462 | 39.299 | 35.634 | 77.485 | 1.00 | 24.02 |
| ATOM | 3673 | O | MET | A | 462 | 39.336 | 36.738 | 78.011 | 1.00 | 24.56 |
| ATOM | 3674 | CB | MET | A | 462 | 38.818 | 34.186 | 79.431 | 1.00 | 22.99 |
| ATOM | 3675 | CG | MET | A | 462 | 37.808 | 33.209 | 80.025 | 1.00 | 28.98 |
| ATOM | 3676 | SD | MET | A | 462 | 36.166 | 33.969 | 79.951 | 1.00 | 33.22 |
| ATOM | 3677 | CE | MET | A | 462 | 36.420 | 35.300 | 81.153 | 1.00 | 27.89 |
| ATOM | 3678 | N | THR | A | 463 | 40.067 | 35.348 | 76.461 | 1.00 | 22.57 |
| ATOM | 3679 | CA | THR | A | 463 | 41.015 | 36.285 | 75.911 | 1.00 | 22.64 |
| ATOM | 3680 | C | THR | A | 463 | 40.690 | 37.738 | 75.961 | 1.00 | 33.12 |
| ATOM | 3681 | O | THR | A | 463 | 41.372 | 38.493 | 76.640 | 1.00 | 35.27 |
| ATOM | 3682 | CB | THR | A | 463 | 41.574 | 35.929 | 74.536 | 1.00 | 29.80 |
| ATOM | 3683 | OG1 | THR | A | 463 | 41.939 | 34.576 | 74.509 | 1.00 | 26.74 |
| ATOM | 3684 | CG2 | THR | A | 463 | 42.797 | 36.793 | 74.224 | 1.00 | 18.79 |
| ATOM | 3685 | N | LEU | A | 464 | 39.700 | 38.141 | 75.177 | 1.00 | 30.50 |
| ATOM | 3686 | CA | LEU | A | 464 | 39.293 | 39.533 | 75.061 | 1.00 | 29.15 |
| ATOM | 3687 | C | LEU | A | 464 | 38.490 | 40.067 | 76.216 | 1.00 | 34.24 |
| ATOM | 3688 | O | LEU | A | 464 | 38.439 | 41.270 | 76.422 | 1.00 | 37.12 |
| ATOM | 3689 | CB | LEU | A | 464 | 38.537 | 39.767 | 73.743 | 1.00 | 29.20 |
| ATOM | 3690 | CG | LEU | A | 464 | 39.393 | 39.394 | 72.527 | 1.00 | 33.73 |
| ATOM | 3691 | CD1 | LEU | A | 464 | 38.609 | 39.565 | 71.217 | 1.00 | 32.72 |
| ATOM | 3692 | CD2 | LEU | A | 464 | 40.648 | 40.261 | 72.499 | 1.00 | 26.22 |
| ATOM | 3693 | N | THR | A | 465 | 37.855 | 39.167 | 76.964 | 1.00 | 30.71 |
| ATOM | 3694 | CA | THR | A | 465 | 37.005 | 39.496 | 78.103 | 1.00 | 28.58 |
| ATOM | 3695 | C | THR | A | 465 | 37.800 | 39.893 | 79.324 | 1.00 | 30.69 |
| ATOM | 3696 | O | THR | A | 465 | 37.530 | 40.865 | 80.030 | 1.00 | 31.27 |
| ATOM | 3697 | CB | THR | A | 465 | 36.016 | 38.328 | 78.372 | 1.00 | 35.85 |
| ATOM | 3698 | OG1 | THR | A | 465 | 35.101 | 38.212 | 77.296 | 1.00 | 50.93 |
| ATOM | 3699 | CG2 | THR | A | 465 | 35.255 | 38.451 | 79.690 | 1.00 | 26.34 |
| ATOM | 3700 | N | ASN | A | 466 | 38.802 | 39.111 | 79.568 | 1.00 | 24.40 |
| ATOM | 3701 | CA | ASN | A | 466 | 39.635 | 39.375 | 80.688 | 1.00 | 23.11 |
| ATOM | 3702 | C | ASN | A | 466 | 39.899 | 40.856 | 80.967 | 1.00 | 28.37 |
| ATOM | 3703 | O | ASN | A | 466 | 39.763 | 41.270 | 82.120 | 1.00 | 27.03 |
| ATOM | 3704 | CB | ASN | A | 466 | 40.921 | 38.543 | 80.629 | 1.00 | 20.30 |
| ATOM | 3705 | CG | ASN | A | 466 | 40.709 | 37.145 | 81.155 | 1.00 | 32.26 |
| ATOM | 3706 | OD1 | ASN | A | 466 | 41.384 | 36.191 | 80.723 | 1.00 | 29.29 |
| ATOM | 3707 | ND2 | ASN | A | 466 | 39.775 | 37.015 | 82.111 | 1.00 | 28.19 |
| ATOM | 3708 | N | ALA | A | 467 | 40.306 | 41.666 | 79.967 | 1.00 | 27.97 |
| ATOM | 3709 | CA | ALA | A | 467 | 40.587 | 43.079 | 80.295 | 1.00 | 26.66 |
| ATOM | 3710 | C | ALA | A | 467 | 39.352 | 43.827 | 80.720 | 1.00 | 31.78 |
| ATOM | 3711 | O | ALA | A | 467 | 39.406 | 44.845 | 81.393 | 1.00 | 31.71 |
| ATOM | 3712 | CB | ALA | A | 467 | 41.365 | 43.837 | 79.256 | 1.00 | 25.99 |
| ATOM | 3713 | N | CYS | A | 468 | 38.217 | 43.277 | 80.336 | 1.00 | 28.06 |
| ATOM | 3714 | CA | CYS | A | 468 | 36.942 | 43.862 | 80.693 | 1.00 | 25.80 |
| ATOM | 3715 | C | CYS | A | 468 | 36.668 | 43.619 | 82.165 | 1.00 | 26.47 |
| ATOM | 3716 | O | CYS | A | 468 | 36.469 | 44.517 | 82.963 | 1.00 | 27.99 |
| ATOM | 3717 | CB | CYS | A | 468 | 35.882 | 43.376 | 79.696 | 1.00 | 24.56 |
| ATOM | 3718 | SG | CYS | A | 468 | 36.455 | 43.873 | 78.049 | 1.00 | 27.76 |
| ATOM | 3719 | N | ILE | A | 469 | 36.752 | 42.384 | 82.540 | 1.00 | 24.34 |
| ATOM | 3720 | CA | ILE | A | 469 | 36.599 | 42.052 | 83.921 | 1.00 | 25.23 |
| ATOM | 3721 | C | ILE | A | 469 | 37.560 | 42.800 | 84.876 | 1.00 | 28.13 |
| ATOM | 3722 | O | ILE | A | 469 | 37.175 | 43.220 | 85.950 | 1.00 | 29.54 |
| ATOM | 3723 | CB | ILE | A | 469 | 36.858 | 40.574 | 84.068 | 1.00 | 27.23 |
| ATOM | 3724 | CG1 | ILE | A | 469 | 35.956 | 39.801 | 83.112 | 1.00 | 26.94 |
| ATOM | 3725 | CG2 | ILE | A | 469 | 36.537 | 40.208 | 85.496 | 1.00 | 25.56 |
| ATOM | 3726 | CD1 | ILE | A | 469 | 36.247 | 38.298 | 83.085 | 1.00 | 45.50 |

TABLE 9-continued

Structure coordinates of LTA₄ hydrolase-thiolamine complex
(The amino acid sequence set forth as residues 1-610 below correspond to SEQ ID NO:1.)

| ATOM | 3727 | N | ALA | A | 470 | 38.830 | 42.960 | 84.534 | 1.00 | 23.28 |
|---|---|---|---|---|---|---|---|---|---|---|
| ATOM | 3728 | CA | ALA | A | 470 | 39.749 | 43.621 | 85.461 | 1.00 | 22.23 |
| ATOM | 3729 | C | ALA | A | 470 | 39.392 | 45.038 | 85.808 | 1.00 | 30.29 |
| ATOM | 3730 | O | ALA | A | 470 | 39.474 | 45.451 | 86.986 | 1.00 | 32.82 |
| ATOM | 3731 | CB | ALA | A | 470 | 41.218 | 43.502 | 85.074 | 1.00 | 21.98 |
| ATOM | 3732 | N | LEU | A | 471 | 39.007 | 45.760 | 84.759 | 1.00 | 23.53 |
| ATOM | 3733 | CA | LEU | A | 471 | 38.643 | 47.173 | 84.834 | 1.00 | 18.39 |
| ATOM | 3734 | C | LEU | A | 471 | 37.333 | 47.373 | 85.569 | 1.00 | 26.57 |
| ATOM | 3735 | O | LEU | A | 471 | 37.210 | 48.208 | 86.462 | 1.00 | 30.48 |
| ATOM | 3736 | CB | LEU | A | 471 | 38.676 | 47.827 | 83.444 | 1.00 | 15.51 |
| ATOM | 3737 | CG | LEU | A | 471 | 38.671 | 49.325 | 83.539 | 1.00 | 24.20 |
| ATOM | 3738 | CD1 | LEU | A | 471 | 39.754 | 49.795 | 84.513 | 1.00 | 24.86 |
| ATOM | 3739 | CD2 | LEU | A | 471 | 38.876 | 49.941 | 82.156 | 1.00 | 26.35 |
| ATOM | 3740 | N | SER | A | 472 | 36.351 | 46.570 | 85.222 | 1.00 | 25.31 |
| ATOM | 3741 | CA | SER | A | 472 | 35.080 | 46.674 | 85.901 | 1.00 | 27.56 |
| ATOM | 3742 | C | SER | A | 472 | 35.260 | 46.477 | 87.396 | 1.00 | 33.46 |
| ATOM | 3743 | O | SER | A | 472 | 34.800 | 47.292 | 88.214 | 1.00 | 32.85 |
| ATOM | 3744 | CB | SER | A | 472 | 33.989 | 45.714 | 85.393 | 1.00 | 32.06 |
| ATOM | 3745 | OG | SER | A | 472 | 34.492 | 44.774 | 84.470 | 1.00 | 48.56 |
| ATOM | 3746 | N | GLN | A | 473 | 35.911 | 45.350 | 87.736 | 1.00 | 27.52 |
| ATOM | 3747 | CA | GLN | A | 473 | 36.170 | 44.971 | 89.108 | 1.00 | 24.10 |
| ATOM | 3748 | C | GLN | A | 473 | 36.866 | 46.096 | 89.836 | 1.00 | 25.18 |
| ATOM | 3749 | O | GLN | A | 473 | 36.534 | 46.458 | 90.969 | 1.00 | 21.62 |
| ATOM | 3750 | CB | GLN | A | 473 | 36.994 | 43.671 | 89.148 | 1.00 | 25.86 |
| ATOM | 3751 | CG | GLN | A | 473 | 36.128 | 42.402 | 89.118 | 1.00 | 32.72 |
| ATOM | 3752 | CD | GLN | A | 473 | 34.970 | 42.504 | 90.090 | 1.00 | 46.08 |
| ATOM | 3753 | OE1 | GLN | A | 473 | 35.165 | 42.422 | 91.308 | 1.00 | 40.73 |
| ATOM | 3754 | NE2 | GLN | A | 473 | 33.761 | 42.692 | 89.559 | 1.00 | 28.28 |
| ATOM | 3755 | N | ARG | A | 474 | 37.855 | 46.656 | 89.161 | 1.00 | 24.00 |
| ATOM | 3756 | CA | ARG | A | 474 | 38.562 | 47.765 | 89.779 | 1.00 | 24.46 |
| ATOM | 3757 | C | ARG | A | 474 | 37.609 | 48.893 | 90.141 | 1.00 | 29.31 |
| ATOM | 3758 | O | ARG | A | 474 | 37.620 | 49.447 | 91.242 | 1.00 | 33.13 |
| ATOM | 3759 | CB | ARG | A | 474 | 39.682 | 48.290 | 88.898 | 1.00 | 20.19 |
| ATOM | 3760 | CG | ARG | A | 474 | 40.866 | 47.352 | 88.831 | 1.00 | 28.48 |
| ATOM | 3761 | CD | ARG | A | 474 | 41.871 | 47.869 | 87.832 | 1.00 | 34.41 |
| ATOM | 3762 | NE | ARG | A | 474 | 42.258 | 49.245 | 88.093 | 1.00 | 40.09 |
| ATOM | 3763 | CZ | ARG | A | 474 | 42.927 | 49.938 | 87.185 | 1.00 | 51.25 |
| ATOM | 3764 | NH1 | ARG | A | 474 | 43.220 | 49.376 | 86.019 | 1.00 | 24.79 |
| ATOM | 3765 | NH2 | ARG | A | 474 | 43.316 | 51.199 | 87.444 | 1.00 | 20.43 |
| ATOM | 3766 | N | TRP | A | 475 | 36.791 | 49.259 | 89.178 | 1.00 | 25.32 |
| ATOM | 3767 | CA | TRP | A | 475 | 35.862 | 50.332 | 89.400 | 1.00 | 26.77 |
| ATOM | 3768 | C | TRP | A | 475 | 34.881 | 49.962 | 90.474 | 1.00 | 27.52 |
| ATOM | 3769 | O | TRP | A | 475 | 34.749 | 50.633 | 91.475 | 1.00 | 29.64 |
| ATOM | 3770 | CB | TRP | A | 475 | 35.199 | 50.804 | 88.093 | 1.00 | 27.95 |
| ATOM | 3771 | CG | TRP | A | 475 | 36.047 | 51.819 | 87.361 | 1.00 | 32.11 |
| ATOM | 3772 | CD1 | TRP | A | 475 | 36.873 | 51.592 | 86.298 | 1.00 | 35.65 |
| ATOM | 3773 | CD2 | TRP | A | 475 | 36.161 | 53.217 | 87.648 | 1.00 | 31.62 |
| ATOM | 3774 | NE1 | TRP | A | 475 | 37.484 | 52.748 | 85.904 | 1.00 | 34.92 |
| ATOM | 3775 | CE2 | TRP | A | 475 | 37.054 | 53.763 | 86.707 | 1.00 | 36.16 |
| ATOM | 3776 | CE3 | TRP | A | 475 | 35.588 | 54.040 | 88.606 | 1.00 | 32.63 |
| ATOM | 3777 | CZ2 | TRP | A | 475 | 37.372 | 55.112 | 86.719 | 1.00 | 36.24 |
| ATOM | 3778 | CH3 | TRP | A | 475 | 35.897 | 55.375 | 88.616 | 1.00 | 34.74 |
| ATOM | 3779 | CH2 | TRP | A | 475 | 36.777 | 55.901 | 87.685 | 1.00 | 35.77 |
| ATOM | 3780 | N | ILE | A | 476 | 34.234 | 48.847 | 90.279 | 1.00 | 26.36 |
| ATOM | 3781 | CA | ILE | A | 476 | 33.268 | 48.386 | 91.235 | 1.00 | 28.33 |
| ATOM | 3782 | C | ILE | A | 476 | 33.771 | 48.315 | 92.681 | 1.00 | 34.20 |
| ATOM | 3783 | O | ILE | A | 476 | 33.056 | 48.595 | 93.637 | 1.00 | 36.89 |
| ATOM | 3784 | CB | ILE | A | 476 | 32.722 | 47.070 | 90.761 | 1.00 | 32.23 |
| ATOM | 3785 | CG1 | ILE | A | 476 | 31.993 | 47.308 | 89.443 | 1.00 | 30.49 |
| ATOM | 3786 | CG2 | ILE | A | 476 | 31.864 | 46.376 | 91.851 | 1.00 | 34.86 |
| ATOM | 3787 | CD1 | ILE | A | 476 | 31.595 | 46.005 | 88.756 | 1.00 | 33.04 |
| ATOM | 3788 | N | THR | A | 477 | 35.010 | 47.934 | 92.860 | 1.00 | 27.27 |
| ATOM | 3789 | CA | THR | A | 477 | 35.558 | 47.846 | 94.194 | 1.00 | 24.15 |
| ATOM | 3790 | C | THR | A | 477 | 36.416 | 49.052 | 94.523 | 1.00 | 27.30 |
| ATOM | 3791 | O | THR | A | 477 | 37.120 | 49.065 | 95.519 | 1.00 | 27.36 |
| ATOM | 3792 | CB | THR | A | 477 | 36.402 | 46.578 | 94.257 | 1.00 | 32.13 |
| ATOM | 3793 | OG1 | THR | A | 477 | 37.593 | 46.848 | 93.557 | 1.00 | 29.48 |
| ATOM | 3794 | CG2 | THR | A | 477 | 35.634 | 45.470 | 93.530 | 1.00 | 16.94 |
| ATOM | 3795 | N | ALA | A | 478 | 36.371 | 50.097 | 93.695 | 1.00 | 22.33 |
| ATOM | 3796 | CA | ALA | A | 478 | 37.164 | 51.260 | 93.988 | 1.00 | 20.44 |
| ATOM | 3797 | C | ALA | A | 478 | 36.890 | 51.843 | 95.390 | 1.00 | 32.94 |
| ATOM | 3798 | O | ALA | A | 478 | 35.786 | 51.756 | 95.922 | 1.00 | 34.38 |
| ATOM | 3799 | CB | ALA | A | 478 | 36.938 | 52.343 | 92.942 | 1.00 | 19.26 |
| ATOM | 3800 | N | LYS | A | 479 | 37.931 | 52.469 | 95.970 | 1.00 | 29.65 |
| ATOM | 3801 | CA | LYS | A | 479 | 37.899 | 53.168 | 97.243 | 1.00 | 27.30 |
| ATOM | 3802 | C | LYS | A | 479 | 38.575 | 54.512 | 97.051 | 1.00 | 36.54 |

TABLE 9-continued

Structure coordinates of LTA₄ hydrolase-thiolamine complex
(The amino acid sequence set forth as residues 1-610 below correspond to SEQ ID NO:1.)

| ATOM | 3803 | O   | LYS | A | 479 | 39.378 | 54.692 | 96.118  | 1.00 | 34.13  |
|------|------|-----|-----|---|-----|--------|--------|---------|------|--------|
| ATOM | 3804 | CB  | LYS | A | 479 | 38.457 | 52.410 | 98.417  | 1.00 | 28.01  |
| ATOM | 3805 | CG  | LYS | A | 479 | 37.696 | 51.116 | 98.631  | 1.00 | 51.38  |
| ATOM | 3806 | CD  | LYS | A | 479 | 37.115 | 50.880 | 100.021 | 1.00 | 67.24  |
| ATOM | 3807 | CE  | LYS | A | 479 | 35.804 | 50.103 | 99.931  | 1.00 | 87.12  |
| ATOM | 3808 | NZ  | LYS | A | 479 | 35.711 | 48.948 | 100.841 | 1.00 | 85.55  |
| ATOM | 3809 | N   | GLU | A | 480 | 38.241 | 55.477 | 97.900  | 1.00 | 36.30  |
| ATOM | 3810 | CA  | GLU | A | 480 | 38.843 | 56.793 | 97.751  | 1.00 | 34.79  |
| ATOM | 3811 | C   | GLU | A | 480 | 40.261 | 56.707 | 97.220  | 1.00 | 34.79  |
| ATOM | 3812 | O   | GLU | A | 480 | 40.613 | 57.332 | 96.234  | 1.00 | 34.10  |
| ATOM | 3813 | CB  | GLU | A | 480 | 38.899 | 57.565 | 99.078  | 1.00 | 36.21  |
| ATOM | 3814 | CG  | GLU | A | 480 | 37.709 | 58.500 | 99.303  | 1.00 | 63.85  |
| ATOM | 3815 | CD  | GLU | A | 480 | 37.601 | 59.511 | 98.214  | 1.00 | 100.00 |
| ATOM | 3816 | OE1 | GLU | A | 480 | 38.457 | 59.648 | 97.357  | 1.00 | 100.00 |
| ATOM | 3817 | OE2 | GLU | A | 480 | 36.491 | 60.209 | 98.288  | 1.00 | 100.00 |
| ATOM | 3818 | N   | ASP | A | 481 | 41.080 | 55.946 | 97.904  | 1.00 | 24.69  |
| ATOM | 3819 | CA  | ASP | A | 481 | 42.451 | 55.860 | 97.519  | 1.00 | 23.87  |
| ATOM | 3820 | C   | ASP | A | 401 | 42.771 | 55.314 | 96.132  | 1.00 | 34.51  |
| ATOM | 3821 | O   | ASP | A | 481 | 43.925 | 55.312 | 95.721  | 1.00 | 39.44  |
| ATOM | 3822 | CB  | ASP | A | 481 | 43.262 | 55.155 | 98.611  | 1.00 | 25.29  |
| ATOM | 3823 | CG  | ASP | A | 481 | 43.072 | 53.668 | 98.575  | 1.00 | 39.58  |
| ATOM | 3824 | OD1 | ASP | A | 481 | 42.471 | 53.029 | 97.708  | 1.00 | 46.00  |
| ATOM | 3825 | OD2 | ASP | A | 481 | 43.698 | 53.107 | 99.567  | 1.00 | 39.59  |
| ATOM | 3826 | N   | ASP | A | 482 | 41.788 | 54.881 | 95.373  | 1.00 | 30.70  |
| ATOM | 3827 | CA  | ASP | A | 482 | 42.098 | 54.379 | 94.024  | 1.00 | 31.73  |
| ATOM | 3828 | C   | ASP | A | 482 | 41.725 | 55.307 | 92.859  | 1.00 | 34.17  |
| ATOM | 3829 | O   | ASP | A | 482 | 42.158 | 55.150 | 91.717  | 1.00 | 35.45  |
| ATOM | 3830 | CB  | ASP | A | 482 | 41.399 | 53.022 | 93.756  | 1.00 | 33.31  |
| ATOM | 3831 | CG  | ASP | A | 482 | 41.686 | 51.970 | 94.779  | 1.00 | 38.90  |
| ATOM | 3832 | OD1 | ASP | A | 482 | 42.810 | 51.514 | 94.992  | 1.00 | 42.45  |
| ATOM | 3833 | OD2 | ASP | A | 482 | 40.606 | 51.625 | 95.440  | 1.00 | 40.17  |
| ATOM | 3834 | N   | LEU | A | 483 | 40.863 | 56.246 | 93.146  | 1.00 | 29.93  |
| ATOM | 3835 | CA  | LEU | A | 483 | 40.352 | 57.159 | 92.160  | 1.00 | 27.80  |
| ATOM | 3836 | C   | LEU | A | 483 | 41.434 | 57.943 | 91.410  | 1.00 | 40.70  |
| ATOM | 3837 | O   | LEU | A | 483 | 41.386 | 58.102 | 90.180  | 1.00 | 40.76  |
| ATOM | 3838 | CB  | LEU | A | 483 | 39.265 | 58.049 | 92.819  | 1.00 | 22.54  |
| ATOM | 3839 | CG  | LEU | A | 483 | 38.148 | 57.240 | 93.488  | 1.00 | 20.75  |
| ATOM | 3840 | CD1 | LEU | A | 483 | 37.170 | 58.165 | 94.197  | 1.00 | 19.29  |
| ATOM | 3841 | CD2 | LEU | A | 483 | 37.389 | 56.467 | 92.414  | 1.00 | 21.46  |
| ATOM | 3842 | N   | ASN | A | 484 | 42.410 | 58.446 | 92.162  | 1.00 | 36.15  |
| ATOM | 3843 | CA  | ASN | A | 484 | 43.459 | 59.225 | 91.571  | 1.00 | 34.08  |
| ATOM | 3844 | C   | ASN | A | 484 | 44.168 | 58.524 | 90.429  | 1.00 | 39.51  |
| ATOM | 3845 | O   | ASN | A | 484 | 44.456 | 59.091 | 89.359  | 1.00 | 38.59  |
| ATOM | 3846 | CB  | ASN | A | 484 | 44.495 | 59.602 | 92.618  | 1.00 | 34.26  |
| ATOM | 3847 | CG  | ASN | A | 484 | 45.807 | 59.955 | 91.941  | 1.00 | 100.00 |
| ATOM | 3848 | OD1 | ASN | A | 484 | 45.878 | 60.940 | 91.171  | 1.00 | 100.00 |
| ATOM | 3849 | ND2 | ASN | A | 484 | 46.836 | 59.134 | 92.186  | 1.00 | 100.00 |
| ATOM | 3850 | N   | SER | A | 485 | 44.472 | 57.268 | 90.698  | 1.00 | 35.37  |
| ATOM | 3851 | CA  | SER | A | 485 | 45.202 | 56.417 | 89.791  | 1.00 | 32.79  |
| ATOM | 3852 | C   | SER | A | 485 | 44.522 | 56.140 | 88.484  | 1.00 | 32.26  |
| ATOM | 3853 | O   | SER | A | 485 | 45.159 | 55.925 | 87.463  | 1.00 | 32.44  |
| ATOM | 3854 | CB  | SER | A | 485 | 45.565 | 55.132 | 90.477  | 1.00 | 38.65  |
| ATOM | 3855 | OG  | SER | A | 485 | 46.040 | 55.437 | 91.777  | 1.00 | 62.66  |
| ATOM | 3856 | N   | PHE | A | 486 | 43.222 | 56.110 | 88.491  | 1.00 | 27.13  |
| ATOM | 3857 | CA  | PHE | A | 486 | 42.631 | 55.809 | 87.233  | 1.00 | 28.26  |
| ATOM | 3858 | C   | PHE | A | 486 | 43.193 | 56.772 | 86.264  | 1.00 | 32.12  |
| ATOM | 3859 | O   | PHE | A | 486 | 43.423 | 57.910 | 86.604  | 1.00 | 32.02  |
| ATOM | 3860 | CB  | PHE | A | 486 | 41.101 | 55.819 | 87.198  | 1.00 | 31.01  |
| ATOM | 3861 | CG  | PHE | A | 486 | 40.471 | 54.807 | 88.132  | 1.00 | 27.04  |
| ATOM | 3862 | CD1 | PHE | A | 486 | 40.504 | 53.425 | 87.911  | 1.00 | 22.43  |
| ATOM | 3863 | CD2 | PHE | A | 486 | 39.805 | 55.293 | 89.253  | 1.00 | 21.40  |
| ATOM | 3864 | CE1 | PHE | A | 486 | 39.896 | 52.538 | 88.804  | 1.00 | 19.69  |
| ATOM | 3865 | CE2 | PHE | A | 486 | 39.224 | 54.426 | 90.174  | 1.00 | 19.20  |
| ATOM | 3866 | CZ  | PHE | A | 486 | 39.245 | 53.051 | 89.927  | 1.00 | 15.13  |
| ATOM | 3867 | N   | ASN | A | 487 | 43.455 | 56.279 | 85.089  | 1.00 | 34.97  |
| ATOM | 3868 | CA  | ASN | A | 487 | 44.032 | 57.092 | 84.070  | 1.00 | 38.06  |
| ATOM | 3869 | C   | ASN | A | 487 | 43.491 | 56.622 | 82.758  | 1.00 | 43.55  |
| ATOM | 3870 | O   | ASN | A | 487 | 42.951 | 55.537 | 82.604  | 1.00 | 46.30  |
| ATOM | 3871 | CB  | ASN | A | 487 | 45.591 | 57.038 | 84.085  | 1.00 | 43.93  |
| ATOM | 3872 | CG  | ASN | A | 487 | 46.196 | 58.169 | 83.302  | 1.00 | 56.10  |
| ATOM | 3873 | OD1 | ASN | A | 487 | 46.057 | 58.189 | 82.077  | 1.00 | 42.12  |
| ATOM | 3874 | ND2 | ASN | A | 487 | 46.829 | 59.112 | 84.007  | 1.00 | 65.62  |
| ATOM | 3875 | N   | ALA | A | 488 | 43.662 | 57.435 | 81.781  | 1.00 | 39.34  |
| ATOM | 3876 | CA  | ALA | A | 488 | 43.201 | 57.055 | 80.472  | 1.00 | 38.25  |
| ATOM | 3877 | C   | ALA | A | 488 | 44.024 | 55.900 | 79.809  | 1.00 | 43.58  |
| ATOM | 3878 | O   | ALA | A | 488 | 43.596 | 55.317 | 78.834  | 1.00 | 44.11  |

TABLE 9-continued

Structure coordinates of LTA₄ hydrolase-thiolamine complex
(The amino acid sequence set forth as residues 1-610 below correspond to SEQ ID NO:1.)

| ATOM | 3879 | CB | ALA | A | 488 | 43.153 | 58.314 | 79.621 | 1.00 | 37.54 |
|------|------|-----|-----|---|-----|--------|--------|--------|------|-------|
| ATOM | 3880 | N | THR | A | 489 | 45.207 | 55.555 | 80.314 | 1.00 | 38.34 |
| ATOM | 3881 | CA | THR | A | 489 | 45.996 | 54.499 | 79.715 | 1.00 | 36.16 |
| ATOM | 3882 | C | THR | A | 489 | 45.270 | 53.181 | 79.792 | 1.00 | 45.74 |
| ATOM | 3883 | O | THR | A | 489 | 45.476 | 52.233 | 79.057 | 1.00 | 47.78 |
| ATOM | 3884 | CB | THR | A | 489 | 47.296 | 54.458 | 80.503 | 1.00 | 31.01 |
| ATOM | 3885 | OG1 | THR | A | 489 | 46.961 | 54.457 | 81.872 | 1.00 | 35.33 |
| ATOM | 3886 | CG2 | THR | A | 489 | 47.993 | 55.771 | 80.229 | 1.00 | 28.28 |
| ATOM | 3887 | N | ASP | A | 490 | 44.337 | 53.182 | 80.708 | 1.00 | 46.75 |
| ATOM | 3888 | CA | ASP | A | 490 | 43.560 | 52.018 | 80.972 | 1.00 | 51.49 |
| ATOM | 3889 | C | ASP | A | 490 | 42.759 | 51.515 | 79.786 | 1.00 | 52.21 |
| ATOM | 3890 | O | ASP | A | 490 | 42.396 | 50.342 | 79.651 | 1.00 | 54.75 |
| ATOM | 3891 | CB | ASP | A | 490 | 42.676 | 52.345 | 82.184 | 1.00 | 54.04 |
| ATOM | 3892 | CG | ASP | A | 490 | 43.413 | 52.884 | 83.380 | 1.00 | 53.83 |
| ATOM | 3893 | OD1 | ASP | A | 490 | 44.621 | 52.777 | 83.616 | 1.00 | 62.93 |
| ATOM | 3894 | OD2 | ASP | A | 490 | 42.565 | 53.446 | 84.165 | 1.00 | 35.66 |
| ATOM | 3895 | N | LEU | A | 491 | 42.486 | 52.450 | 78.938 | 1.00 | 42.42 |
| ATOM | 3896 | CA | LEU | A | 491 | 41.752 | 52.250 | 77.723 | 1.00 | 43.54 |
| ATOM | 3897 | C | LEU | A | 491 | 42.712 | 51.977 | 76.585 | 1.00 | 43.97 |
| ATOM | 3898 | O | LEU | A | 491 | 42.340 | 51.438 | 75.588 | 1.00 | 42.53 |
| ATOM | 3899 | CB | LEU | A | 491 | 40.984 | 53.528 | 77.421 | 1.00 | 44.89 |
| ATOM | 3900 | CG | LEU | A | 491 | 39.794 | 53.747 | 78.338 | 1.00 | 48.31 |
| ATOM | 3901 | CD1 | LEU | A | 491 | 38.558 | 54.171 | 77.552 | 1.00 | 49.16 |
| ATOM | 3902 | CD2 | LEU | A | 491 | 39.377 | 52.494 | 79.125 | 1.00 | 39.24 |
| ATOM | 3903 | N | LYS | A | 492 | 43.958 | 52.403 | 76.754 | 1.00 | 42.32 |
| ATOM | 3904 | CA | LYS | A | 492 | 44.999 | 52.320 | 75.696 | 1.00 | 44.57 |
| ATOM | 3905 | C | LYS | A | 492 | 44.826 | 51.165 | 74.680 | 1.00 | 49.08 |
| ATOM | 3906 | O | LYS | A | 492 | 44.810 | 51.343 | 73.473 | 1.00 | 49.66 |
| ATOM | 3907 | CB | LYS | A | 492 | 46.359 | 52.177 | 76.401 | 1.00 | 48.47 |
| ATOM | 3908 | CG | LYS | A | 492 | 47.487 | 52.883 | 75.629 | 1.00 | 88.73 |
| ATOM | 3909 | CD | LYS | A | 492 | 48.852 | 52.537 | 76.197 | 1.00 | 100.00 |
| ATOM | 3910 | CE | LYS | A | 492 | 48.786 | 51.460 | 77.300 | 1.00 | 100.00 |
| ATOM | 3911 | NZ | LYS | A | 492 | 50.103 | 50.896 | 77.541 | 1.00 | 100.00 |
| ATOM | 3912 | N | ASP | A | 493 | 44.711 | 49.917 | 75.227 | 1.00 | 41.86 |
| ATOM | 3913 | CA | ASP | A | 493 | 44.664 | 48.740 | 74.372 | 1.00 | 40.17 |
| ATOM | 3914 | C | ASP | A | 493 | 43.220 | 48.162 | 74.215 | 1.00 | 44.29 |
| ATOM | 3915 | O | ASP | A | 493 | 43.031 | 46.973 | 73.889 | 1.00 | 42.00 |
| ATOM | 3916 | CB | ASP | A | 493 | 45.560 | 47.699 | 75.015 | 1.00 | 41.52 |
| ATOM | 3917 | CG | ASP | A | 493 | 47.021 | 48.130 | 74.956 | 1.00 | 67.01 |
| ATOM | 3918 | OD1 | ASP | A | 493 | 47.467 | 48.451 | 73.856 | 1.00 | 77.10 |
| ATOM | 3919 | OD2 | ASP | A | 493 | 47.678 | 48.131 | 75.984 | 1.00 | 57.19 |
| ATOM | 3920 | N | LEU | A | 494 | 42.193 | 49.005 | 74.475 | 1.00 | 40.69 |
| ATOM | 3921 | CA | LEU | A | 494 | 40.789 | 48.512 | 74.526 | 1.00 | 36.32 |
| ATOM | 3922 | C | LEU | A | 494 | 39.992 | 48.877 | 73.245 | 1.00 | 37.76 |
| ATOM | 3923 | O | LEU | A | 494 | 39.897 | 50.029 | 72.863 | 1.00 | 38.93 |
| ATOM | 3924 | CB | LEU | A | 494 | 40.098 | 49.125 | 75.733 | 1.00 | 32.52 |
| ATOM | 3925 | CG | LEU | A | 494 | 40.376 | 48.433 | 77.063 | 1.00 | 30.66 |
| ATOM | 3926 | CD1 | LEU | A | 494 | 39.229 | 48.580 | 78.052 | 1.00 | 30.39 |
| ATOM | 3927 | CD2 | LEU | A | 494 | 40.611 | 46.925 | 76.918 | 1.00 | 23.54 |
| ATOM | 3928 | N | SER | A | 495 | 39.477 | 47.825 | 72.631 | 1.00 | 25.56 |
| ATOM | 3929 | CA | SER | A | 495 | 38.674 | 48.017 | 71.457 | 1.00 | 22.23 |
| ATOM | 3930 | C | SER | A | 495 | 37.344 | 48.670 | 71.856 | 1.00 | 31.27 |
| ATOM | 3931 | O | SER | A | 495 | 36.968 | 48.706 | 73.038 | 1.00 | 31.21 |
| ATOM | 3932 | CB | SER | A | 495 | 38.380 | 46.705 | 70.795 | 1.00 | 20.88 |
| ATOM | 3933 | OG | SER | A | 495 | 37.192 | 46.143 | 71.317 | 1.00 | 33.60 |
| ATOM | 3934 | N | SER | A | 496 | 36.627 | 49.184 | 70.865 | 1.00 | 29.48 |
| ATOM | 3935 | CA | SER | A | 496 | 35.363 | 49.821 | 71.139 | 1.00 | 26.67 |
| ATOM | 3936 | C | SER | A | 496 | 34.495 | 48.747 | 71.744 | 1.00 | 29.54 |
| ATOM | 3937 | O | SER | A | 496 | 33.744 | 48.960 | 72.697 | 1.00 | 24.80 |
| ATOM | 3938 | CB | SER | A | 496 | 34.760 | 50.441 | 69.894 | 1.00 | 24.67 |
| ATOM | 3939 | OG | SER | A | 496 | 33.749 | 49.597 | 69.397 | 1.00 | 48.80 |
| ATOM | 3940 | N | HIS | A | 497 | 34.674 | 47.547 | 71.219 | 1.00 | 26.61 |
| ATOM | 3941 | CA | HIS | A | 497 | 33.949 | 46.383 | 71.750 | 1.00 | 29.22 |
| ATOM | 3942 | C | HIS | A | 497 | 34.156 | 46.148 | 73.275 | 1.00 | 37.24 |
| ATOM | 3943 | O | HIS | A | 497 | 33.238 | 45.863 | 74.041 | 1.00 | 38.21 |
| ATOM | 3944 | CB | HIS | A | 497 | 34.364 | 45.106 | 70.978 | 1.00 | 30.69 |
| ATOM | 3945 | CG | HIS | A | 497 | 34.182 | 45.348 | 69.545 | 1.00 | 34.29 |
| ATOM | 3946 | ND1 | HIS | A | 497 | 32.943 | 45.204 | 68.962 | 1.00 | 35.42 |
| ATOM | 3947 | CD2 | HIS | A | 497 | 35.054 | 45.833 | 68.622 | 1.00 | 36.68 |
| ATOM | 3948 | CE1 | HIS | A | 497 | 33.075 | 45.531 | 67.702 | 1.00 | 35.05 |
| ATOM | 3949 | NE2 | HIS | A | 497 | 34.330 | 45.932 | 67.462 | 1.00 | 35.88 |
| ATOM | 3950 | N | GLN | A | 498 | 35.406 | 46.243 | 73.715 | 1.00 | 33.56 |
| ATOM | 3951 | CA | GLN | A | 498 | 35.737 | 46.008 | 75.094 | 1.00 | 29.69 |
| ATOM | 3952 | C | GLN | A | 498 | 35.263 | 47.122 | 75.965 | 1.00 | 27.11 |
| ATOM | 3953 | O | GLN | A | 498 | 34.842 | 46.930 | 77.089 | 1.00 | 23.92 |
| ATOM | 3954 | CB | GLN | A | 498 | 37.221 | 45.659 | 75.248 | 1.00 | 29.95 |

TABLE 9-continued

Structure coordinates of LTA$_4$ hydrolase-thiolamine complex
(The amino acid sequence set forth as residues 1-610 below correspond to SEQ ID NO:1.)

| ATOM | 3955 | CG | GLN | A | 498 | 37.582 | 44.317 | 74.544 | 1.00 | 25.78 |
|------|------|-----|-----|---|-----|--------|--------|--------|------|-------|
| ATOM | 3956 | CD | GLN | A | 498 | 39.074 | 44.084 | 74.535 | 1.00 | 28.64 |
| ATOM | 3957 | OE1 | GLN | A | 498 | 39.796 | 44.891 | 73.960 | 1.00 | 26.62 |
| ATOM | 3958 | NE2 | GLN | A | 498 | 39.561 | 43.049 | 75.218 | 1.00 | 20.96 |
| ATOM | 3959 | N | LEU | A | 499 | 35.289 | 48.301 | 75.431 | 1.00 | 27.13 |
| ATOM | 3960 | CA | LEU | A | 499 | 34.819 | 49.396 | 76.229 | 1.00 | 29.32 |
| ATOM | 3961 | C | LEU | A | 499 | 33.351 | 49.162 | 76.632 | 1.00 | 28.39 |
| ATOM | 3962 | O | LEU | A | 499 | 32.893 | 49.361 | 77.780 | 1.00 | 29.41 |
| ATOM | 3963 | CB | LEU | A | 499 | 34.991 | 50.709 | 75.436 | 1.00 | 31.70 |
| ATOM | 3964 | CG | LEU | A | 499 | 36.242 | 51.512 | 75.788 | 1.00 | 39.76 |
| ATOM | 3965 | CD1 | LEU | A | 499 | 37.335 | 50.572 | 76.278 | 1.00 | 42.91 |
| ATOM | 3966 | CD2 | LEU | A | 499 | 36.718 | 52.268 | 74.555 | 1.00 | 39.08 |
| ATOM | 3967 | N | ASN | A | 500 | 32.606 | 48.737 | 75.642 | 1.00 | 15.23 |
| ATOM | 3968 | CA | ASN | A | 500 | 31.213 | 48.508 | 75.828 | 1.00 | 13.44 |
| ATOM | 3969 | C | ASN | A | 500 | 30.919 | 47.455 | 76.864 | 1.00 | 18.98 |
| ATOM | 3970 | O | ASN | A | 500 | 29.997 | 47.602 | 77.705 | 1.00 | 19.01 |
| ATOM | 3971 | CB | ASN | A | 500 | 30.604 | 48.129 | 74.476 | 1.00 | 12.21 |
| ATOM | 3972 | CG | ASN | A | 500 | 29.093 | 48.214 | 74.426 | 1.00 | 37.49 |
| ATOM | 3973 | OD1 | ASN | A | 500 | 28.433 | 49.151 | 74.930 | 1.00 | 36.17 |
| ATOM | 3974 | ND2 | ASN | A | 500 | 28.542 | 47.218 | 73.787 | 1.00 | 18.34 |
| ATOM | 3975 | N | GLU | A | 501 | 31.699 | 46.366 | 76.743 | 1.00 | 14.20 |
| ATOM | 3976 | CA | GLU | A | 501 | 31.626 | 45.224 | 77.625 | 1.00 | 13.27 |
| ATOM | 3977 | C | GLU | A | 501 | 31.948 | 45.676 | 79.063 | 1.00 | 21.59 |
| ATOM | 3978 | O | GLU | A | 501 | 31.175 | 45.463 | 80.009 | 1.00 | 25.02 |
| ATOM | 3979 | CB | GLU | A | 501 | 32.446 | 44.057 | 77.053 | 1.00 | 14.95 |
| ATOM | 3980 | CD | GLU | A | 501 | 32.371 | 42.827 | 77.989 | 1.00 | 30.40 |
| ATOM | 3981 | CD | GLU | A | 501 | 30.946 | 42.399 | 78.199 | 1.00 | 39.28 |
| ATOM | 3982 | OE1 | GLU | A | 501 | 30.050 | 42.672 | 77.413 | 1.00 | 76.70 |
| ATOM | 3983 | OE2 | GLU | A | 501 | 30.780 | 41.694 | 79.292 | 1.00 | 46.10 |
| ATOM | 3984 | N | PHE | A | 502 | 33.059 | 46.400 | 79.226 | 1.00 | 18.07 |
| ATOM | 3985 | CA | PHE | A | 502 | 33.395 | 46.952 | 80.530 | 1.00 | 21.54 |
| ATOM | 3986 | C | PHE | A | 502 | 32.179 | 47.679 | 81.125 | 1.00 | 23.38 |
| ATOM | 3987 | O | PHE | A | 502 | 31.786 | 47.491 | 82.301 | 1.00 | 21.47 |
| ATOM | 3988 | CB | PHE | A | 502 | 34.507 | 48.012 | 80.327 | 1.00 | 26.05 |
| ATOM | 3989 | CG | PHE | A | 502 | 34.590 | 49.082 | 81.393 | 1.00 | 30.41 |
| ATOM | 3990 | CD1 | PHE | A | 502 | 35.085 | 48.781 | 82.662 | 1.00 | 29.68 |
| ATOM | 3991 | CD2 | PHE | A | 502 | 34.211 | 50.402 | 81.132 | 1.00 | 39.16 |
| ATOM | 3992 | CE1 | PHE | A | 502 | 35.183 | 49.773 | 83.638 | 1.00 | 31.12 |
| ATOM | 3993 | CE2 | PHE | A | 502 | 34.305 | 51.414 | 82.096 | 1.00 | 40.46 |
| ATOM | 3994 | CZ | PHE | A | 502 | 34.812 | 51.090 | 83.352 | 1.00 | 35.41 |
| ATOM | 3995 | N | LEU | A | 503 | 31.613 | 48.557 | 80.288 | 1.00 | 18.39 |
| ATOM | 3996 | CA | LEU | A | 503 | 30.487 | 49.343 | 80.692 | 1.00 | 22.78 |
| ATOM | 3997 | C | LEU | A | 503 | 29.337 | 48.491 | 81.178 | 1.00 | 31.04 |
| ATOM | 3998 | O | LEU | A | 503 | 28.768 | 48.784 | 82.243 | 1.00 | 29.23 |
| ATOM | 3999 | CB | LEU | A | 503 | 30.002 | 50.325 | 79.619 | 1.00 | 24.68 |
| ATOM | 4000 | CG | LEU | A | 503 | 30.888 | 51.571 | 79.465 | 1.00 | 27.47 |
| ATOM | 4001 | CD1 | LEU | A | 503 | 30.415 | 52.376 | 78.259 | 1.00 | 24.86 |
| ATOM | 4002 | CD2 | LEU | A | 503 | 30.860 | 52.420 | 80.733 | 1.00 | 20.54 |
| ATOM | 4003 | N | ALA | A | 504 | 29.012 | 47.444 | 80.378 | 1.00 | 27.79 |
| ATOM | 4004 | CA | ALA | A | 504 | 27.911 | 46.474 | 80.643 | 1.00 | 24.63 |
| ATOM | 4005 | C | ALA | A | 504 | 28.140 | 45.752 | 81.939 | 1.00 | 27.71 |
| ATOM | 4006 | O | ALA | A | 504 | 27.265 | 45.577 | 82.817 | 1.00 | 28.62 |
| ATOM | 4007 | CB | ALA | A | 504 | 27.762 | 45.482 | 79.496 | 1.00 | 23.87 |
| ATOM | 4008 | N | GLN | A | 505 | 29.382 | 45.344 | 82.066 | 1.00 | 22.16 |
| ATOM | 4009 | CA | GLN | A | 505 | 29.738 | 44.710 | 83.299 | 1.00 | 21.02 |
| ATOM | 4010 | C | GLN | A | 505 | 29.489 | 45.737 | 84.423 | 1.00 | 31.26 |
| ATOM | 4011 | O | GLN | A | 505 | 28.787 | 45.507 | 85.413 | 1.00 | 32.31 |
| ATOM | 4012 | CB | GLN | A | 505 | 31.202 | 44.209 | 83.270 | 1.00 | 18.95 |
| ATOM | 4013 | CG | GLN | A | 505 | 31.367 | 42.881 | 82.495 | 1.00 | 13.72 |
| ATOM | 4014 | CD | GLN | A | 505 | 32.806 | 42.549 | 82.236 | 1.00 | 31.75 |
| ATOM | 4015 | OE1 | GLN | A | 505 | 33.796 | 42.969 | 82.768 | 1.00 | 43.14 |
| ATOM | 4016 | NE2 | GLN | A | 505 | 32.923 | 41.781 | 81.085 | 1.00 | 39.34 |
| ATOM | 4017 | N | THR | A | 506 | 30.056 | 46.918 | 84.263 | 1.00 | 25.95 |
| ATOM | 4018 | CA | THR | A | 506 | 29.855 | 47.864 | 85.302 | 1.00 | 23.64 |
| ATOM | 4019 | C | THR | A | 506 | 28.411 | 48.101 | 85.579 | 1.00 | 23.89 |
| ATOM | 4020 | O | THR | A | 506 | 27.923 | 47.999 | 86.696 | 1.00 | 22.75 |
| ATOM | 4021 | CB | THR | A | 506 | 30.600 | 49.130 | 85.008 | 1.00 | 23.72 |
| ATOM | 4022 | OG1 | THR | A | 506 | 31.938 | 48.749 | 84.742 | 1.00 | 27.18 |
| ATOM | 4023 | CG2 | THR | A | 506 | 30.502 | 49.961 | 86.260 | 1.00 | 11.12 |
| ATOM | 4024 | N | LEU | A | 507 | 27.727 | 48.408 | 84.518 | 1.00 | 17.92 |
| ATOM | 4025 | CA | LEU | A | 507 | 26.334 | 48.683 | 84.604 | 1.00 | 17.22 |
| ATOM | 4026 | C | LEU | A | 507 | 25.618 | 47.683 | 85.442 | 1.00 | 25.65 |
| ATOM | 4027 | O | LEU | A | 507 | 24.816 | 48.073 | 86.266 | 1.00 | 27.85 |
| ATOM | 4028 | CB | LEU | A | 507 | 25.693 | 48.686 | 83.224 | 1.00 | 17.85 |
| ATOM | 4029 | CG | LEU | A | 507 | 24.207 | 48.930 | 83.336 | 1.00 | 21.02 |
| ATOM | 4030 | CD1 | LEU | A | 507 | 23.974 | 50.290 | 83.970 | 1.00 | 22.48 |

TABLE 9-continued

Structure coordinates of LTA$_4$ hydrolase-thiolamine complex
(The amino acid sequence set forth as residues 1-610 below correspond to SEQ ID NO:1.)

| ATOM | 4031 | CD2 | LEU | A | 507 | 23.599 | 48.919 | 81.949 | 1.00 | 15.25 |
|------|------|-----|-----|---|-----|--------|--------|--------|------|-------|
| ATOM | 4032 | N | GLN | A | 508 | 25.878 | 46.395 | 85.194 | 1.00 | 21.35 |
| ATOM | 4033 | CA | GLN | A | 508 | 25.215 | 45.333 | 85.979 | 1.00 | 18.08 |
| ATOM | 4034 | C | GLN | A | 508 | 25.386 | 45.561 | 87.508 | 1.00 | 34.24 |
| ATOM | 4035 | O | GLN | A | 508 | 24.653 | 45.017 | 88.343 | 1.00 | 34.04 |
| ATOM | 4036 | CB | GLN | A | 508 | 25.713 | 43.917 | 85.608 | 1.00 | 10.94 |
| ATOM | 4037 | CG | GLN | A | 508 | 25.366 | 43.446 | 84.191 | 1.00 | 26.42 |
| ATOM | 4038 | CD | GLN | A | 508 | 25.635 | 41.944 | 84.002 | 1.00 | 52.93 |
| ATOM | 4039 | OE1 | GLN | A | 508 | 26.550 | 41.396 | 84.628 | 1.00 | 32.89 |
| ATOM | 4040 | NE2 | GLN | A | 508 | 24.864 | 41.252 | 83.147 | 1.00 | 34.36 |
| ATOM | 4041 | N | ARG | A | 509 | 26.380 | 46.361 | 87.901 | 1.00 | 33.73 |
| ATOM | 4042 | CA | ARG | A | 509 | 26.600 | 46.614 | 89.328 | 1.00 | 32.53 |
| ATOM | 4043 | C | ARG | A | 509 | 26.153 | 40.016 | 89.727 | 1.00 | 33.63 |
| ATOM | 4044 | O | ARG | A | 509 | 26.509 | 48.522 | 90.777 | 1.00 | 31.08 |
| ATOM | 4045 | CB | ARG | A | 509 | 28.055 | 46.440 | 89.760 | 1.00 | 29.22 |
| ATOM | 4046 | CG | ARG | A | 509 | 28.553 | 45.014 | 89.733 | 1.00 | 29.78 |
| ATOM | 4047 | CD | ARG | A | 509 | 27.744 | 44.054 | 90.609 | 1.00 | 30.86 |
| ATOM | 4048 | NE | ARG | A | 509 | 28.533 | 43.602 | 91.756 | 1.00 | 82.23 |
| ATOM | 4049 | CZ | ARG | A | 509 | 29.842 | 43.274 | 91.726 | 1.00 | 100.00 |
| ATOM | 4050 | NH1 | ARG | A | 509 | 30.579 | 43.315 | 90.613 | 1.00 | 92.85 |
| ATOM | 4051 | NH2 | ARG | A | 509 | 30.430 | 42.881 | 92.855 | 1.00 | 91.85 |
| ATOM | 4052 | N | ALA | A | 510 | 25.384 | 48.659 | 88.880 | 1.00 | 32.59 |
| ATOM | 4053 | CA | ALA | A | 510 | 24.952 | 49.985 | 89.215 | 1.00 | 32.51 |
| ATOM | 4054 | C | ALA | A | 510 | 24.151 | 49.845 | 90.479 | 1.00 | 34.97 |
| ATOM | 4055 | O | ALA | A | 510 | 23.601 | 48.785 | 90.693 | 1.00 | 37.57 |
| ATOM | 4056 | CB | ALA | A | 510 | 24.189 | 50.622 | 88.063 | 1.00 | 32.91 |
| ATOM | 4057 | N | PRO | A | 511 | 24.174 | 50.856 | 91.334 | 1.00 | 25.14 |
| ATOM | 4058 | CA | PRO | A | 511 | 24.867 | 52.102 | 91.052 | 1.00 | 21.00 |
| ATOM | 4059 | C | PRO | A | 511 | 26.217 | 52.178 | 91.694 | 1.00 | 29.23 |
| ATOM | 4060 | O | PRO | A | 511 | 26.445 | 51.601 | 92.723 | 1.00 | 28.16 |
| ATOM | 4061 | CB | PRO | A | 511 | 24.102 | 53.169 | 91.818 | 1.00 | 21.55 |
| ATOM | 4062 | CG | PRO | A | 511 | 23.316 | 52.432 | 92.886 | 1.00 | 28.68 |
| ATOM | 4063 | CD | PRO | A | 511 | 23.169 | 50.995 | 92.407 | 1.00 | 25.16 |
| ATOM | 4064 | N | LEU | A | 512 | 27.094 | 52.968 | 91.109 | 1.00 | 32.95 |
| ATOM | 4065 | CA | LEU | A | 512 | 28.394 | 53.188 | 91.686 | 1.00 | 33.42 |
| ATOM | 4066 | C | LEU | A | 512 | 28.287 | 54.512 | 92.397 | 1.00 | 38.65 |
| ATOM | 4067 | O | LEU | A | 512 | 27.388 | 55.305 | 92.114 | 1.00 | 40.69 |
| ATOM | 4068 | CB | LEU | A | 512 | 29.453 | 53.350 | 90.587 | 1.00 | 34.40 |
| ATOM | 4069 | CG | LEU | A | 512 | 30.178 | 52.049 | 90.216 | 1.00 | 40.13 |
| ATOM | 4070 | CD1 | LEU | A | 512 | 29.222 | 51.086 | 89.508 | 1.00 | 39.04 |
| ATOM | 4071 | CD2 | LEU | A | 512 | 31.322 | 52.385 | 89.273 | 1.00 | 44.61 |
| ATOM | 4072 | N | PRO | A | 513 | 29.196 | 54.781 | 93.312 | 1.00 | 31.05 |
| ATOM | 4073 | CA | PRO | A | 513 | 29.167 | 56.058 | 94.008 | 1.00 | 27.16 |
| ATOM | 4074 | C | PRO | A | 513 | 29.296 | 57.203 | 93.019 | 1.00 | 23.76 |
| ATOM | 4075 | O | PRO | A | 513 | 30.121 | 57.182 | 92.118 | 1.00 | 27.17 |
| ATOM | 4076 | CB | PRO | A | 513 | 30.387 | 56.013 | 94.948 | 1.00 | 25.59 |
| ATOM | 4077 | CG | PRO | A | 513 | 30.702 | 54.542 | 95.149 | 1.00 | 27.14 |
| ATOM | 4078 | CD | PRO | A | 513 | 30.030 | 53.779 | 94.032 | 1.00 | 25.00 |
| ATOM | 4079 | N | LEU | A | 514 | 28.478 | 58.203 | 93.185 | 1.00 | 22.92 |
| ATOM | 4080 | CA | LEU | A | 514 | 28.516 | 59.350 | 92.279 | 1.00 | 27.55 |
| ATOM | 4081 | C | LEU | A | 514 | 29.930 | 59.766 | 91.940 | 1.00 | 31.95 |
| ATOM | 4082 | O | LEU | A | 514 | 30.287 | 59.908 | 90.765 | 1.00 | 37.11 |
| ATOM | 4083 | CB | LEU | A | 514 | 27.673 | 60.564 | 92.741 | 1.00 | 30.03 |
| ATOM | 4084 | CG | LEU | A | 514 | 27.428 | 61.626 | 91.648 | 1.00 | 32.87 |
| ATOM | 4085 | CD1 | LEU | A | 514 | 26.648 | 61.082 | 90.440 | 1.00 | 28.48 |
| ATOM | 4086 | CD2 | LEU | A | 514 | 26.699 | 62.780 | 92.272 | 1.00 | 31.16 |
| ATOM | 4087 | N | GLY | A | 515 | 30.731 | 59.989 | 92.979 | 1.00 | 24.42 |
| ATOM | 4088 | CA | GLY | A | 515 | 32.131 | 60.384 | 92.811 | 1.00 | 25.59 |
| ATOM | 4089 | C | GLY | A | 515 | 32.902 | 59.472 | 91.835 | 1.00 | 33.83 |
| ATOM | 4090 | O | GLY | A | 515 | 33.746 | 59.914 | 91.035 | 1.00 | 35.67 |
| ATOM | 4091 | N | HIS | A | 516 | 32.602 | 58.180 | 91.891 | 1.00 | 26.40 |
| ATOM | 4092 | CA | HIS | A | 516 | 33.257 | 57.255 | 90.998 | 1.00 | 25.86 |
| ATOM | 4093 | C | HIS | A | 516 | 32.911 | 57.578 | 89.560 | 1.00 | 27.62 |
| ATOM | 4094 | O | HIS | A | 516 | 33.786 | 57.596 | 88.695 | 1.00 | 28.67 |
| ATOM | 4095 | CB | HIS | A | 516 | 32.826 | 55.814 | 91.282 | 1.00 | 25.39 |
| ATOM | 4096 | CG | HIS | A | 516 | 33.452 | 55.283 | 92.505 | 1.00 | 27.96 |
| ATOM | 4097 | ND1 | HIS | A | 516 | 33.635 | 56.092 | 93.602 | 1.00 | 30.14 |
| ATOM | 4098 | CD2 | HIS | A | 516 | 33.929 | 54.037 | 92.791 | 1.00 | 27.79 |
| ATOM | 4099 | CE1 | HIS | A | 516 | 34.205 | 55.336 | 94.534 | 1.00 | 27.58 |
| ATOM | 4100 | NE2 | HIS | A | 516 | 34.390 | 54.099 | 94.085 | 1.00 | 27.02 |
| ATOM | 4101 | N | ILE | A | 517 | 31.617 | 57.815 | 89.315 | 1.00 | 21.40 |
| ATOM | 4102 | CA | ILE | A | 517 | 31.137 | 58.107 | 87.973 | 1.00 | 22.75 |
| ATOM | 4103 | C | ILE | A | 517 | 31.706 | 59.424 | 87.462 | 1.00 | 31.09 |
| ATOM | 4104 | O | ILE | A | 517 | 32.246 | 59.558 | 86.352 | 1.00 | 28.78 |
| ATOM | 4105 | CB | ILE | A | 517 | 29.601 | 58.024 | 87.930 | 1.00 | 27.12 |
| ATOM | 4106 | CG1 | ILE | A | 517 | 29.225 | 56.610 | 88.312 | 1.00 | 29.40 |

TABLE 9-continued

Structure coordinates of LTA$_4$ hydrolase-thiolamine complex
(The amino acid sequence set forth as residues 1-610 below correspond to SEQ ID NO:1.)

| ATOM | 4107 | CG2 | ILE | A | 517 | 29.013 | 58.285 | 86.536 | 1.00 | 25.49 |
|------|------|-----|-----|---|-----|--------|--------|--------|------|-------|
| ATOM | 4108 | CD1 | ILE | A | 517 | 29.305 | 55.665 | 87.105 | 1.00 | 34.77 |
| ATOM | 4109 | N | LYS | A | 518 | 31.589 | 60.416 | 88.308 | 1.00 | 27.28 |
| ATOM | 4110 | CA | LYS | A | 518 | 32.108 | 61.690 | 87.955 | 1.00 | 23.77 |
| ATOM | 4111 | C | LYS | A | 518 | 33.558 | 61.482 | 87.485 | 1.00 | 24.03 |
| ATOM | 4112 | O | LYS | A | 518 | 33.982 | 61.831 | 86.391 | 1.00 | 26.08 |
| ATOM | 4113 | CB | LYS | A | 518 | 32.038 | 62.557 | 89.210 | 1.00 | 24.00 |
| ATOM | 4114 | CG | LYS | A | 518 | 30.641 | 63.060 | 89.591 | 1.00 | 19.24 |
| ATOM | 4115 | CD | LYS | A | 518 | 30.721 | 64.276 | 90.537 | 1.00 | 27.93 |
| ATOM | 4116 | CE | LYS | A | 518 | 29.379 | 64.877 | 90.962 | 1.00 | 37.11 |
| ATOM | 4117 | NZ | LYS | A | 518 | 28.924 | 65.988 | 90.104 | 1.00 | 52.30 |
| ATOM | 4118 | N | ARG | A | 519 | 34.322 | 60.899 | 88.361 | 1.00 | 17.90 |
| ATOM | 4119 | CA | ARG | A | 519 | 35.703 | 60.636 | 88.098 | 1.00 | 20.80 |
| ATOM | 4120 | C | ARG | A | 519 | 35.862 | 59.874 | 86.802 | 1.00 | 28.98 |
| ATOM | 4121 | O | ARG | A | 519 | 36.812 | 60.084 | 86.051 | 1.00 | 29.86 |
| ATOM | 4122 | CB | ARG | A | 519 | 36.313 | 59.844 | 89.276 | 1.00 | 20.56 |
| ATOM | 4123 | CG | ARG | A | 519 | 37.721 | 59.308 | 89.036 | 1.00 | 29.02 |
| ATOM | 4124 | CD | ARG | A | 519 | 38.668 | 60.320 | 88.404 | 1.00 | 41.17 |
| ATOM | 4125 | NE | ARG | A | 519 | 40.086 | 60.008 | 88.616 | 1.00 | 59.84 |
| ATOM | 4126 | CZ | ARG | A | 519 | 41.076 | 60.858 | 88.349 | 1.00 | 50.77 |
| ATOM | 4127 | NH1 | ARG | A | 519 | 40.838 | 62.073 | 87.880 | 1.00 | 31.21 |
| ATOM | 4128 | NH2 | ARG | A | 519 | 42.329 | 60.486 | 88.543 | 1.00 | 31.86 |
| ATOM | 4129 | N | MET | A | 520 | 34.937 | 58.956 | 86.565 | 1.00 | 25.08 |
| ATOM | 4130 | CA | MET | A | 520 | 34.979 | 58.121 | 85.379 | 1.00 | 24.56 |
| ATOM | 4131 | C | MET | A | 520 | 34.906 | 58.918 | 84.086 | 1.00 | 29.37 |
| ATOM | 4132 | O | MET | A | 520 | 35.651 | 58.687 | 83.114 | 1.00 | 27.92 |
| ATOM | 4133 | CB | MET | A | 520 | 33.905 | 57.007 | 85.442 | 1.00 | 26.98 |
| ATOM | 4134 | CG | MET | A | 520 | 34.082 | 55.902 | 84.399 | 1.00 | 28.02 |
| ATOM | 4135 | SD | MET | A | 520 | 32.830 | 54.591 | 84.479 | 1.00 | 27.87 |
| ATOM | 4136 | CE | MET | A | 520 | 33.246 | 53.825 | 86.070 | 1.00 | 22.09 |
| ATOM | 4137 | N | GLN | A | 521 | 33.982 | 59.864 | 84.067 | 1.00 | 28.32 |
| ATOM | 4138 | CA | GLN | A | 521 | 33.838 | 60.672 | 82.886 | 1.00 | 28.34 |
| ATOM | 4139 | C | GLN | A | 521 | 35.067 | 61.540 | 82.785 | 1.00 | 36.52 |
| ATOM | 4140 | O | GLN | A | 521 | 33.514 | 61.879 | 81.707 | 1.00 | 35.87 |
| ATOM | 4141 | CB | GLN | A | 521 | 32.514 | 61.451 | 82.863 | 1.00 | 28.34 |
| ATOM | 4142 | CG | GLN | A | 521 | 32.564 | 62.774 | 82.079 | 1.00 | 9.68 |
| ATOM | 4143 | CD | GLN | A | 521 | 32.890 | 62.572 | 80.616 | 1.00 | 27.55 |
| ATOM | 4144 | OE1 | GLN | A | 521 | 33.382 | 63.491 | 79.924 | 1.00 | 28.25 |
| ATOM | 4145 | NE2 | GLN | A | 521 | 32.657 | 61.368 | 80.142 | 1.00 | 25.70 |
| ATOM | 4146 | N | GLU | A | 522 | 35.626 | 61.827 | 83.963 | 1.00 | 36.19 |
| ATOM | 4147 | CA | GLU | A | 522 | 36.818 | 62.648 | 84.171 | 1.00 | 36.13 |
| ATOM | 4148 | C | GLU | A | 522 | 38.136 | 62.046 | 83.662 | 1.00 | 42.48 |
| ATOM | 4149 | O | GLU | A | 522 | 39.099 | 62.735 | 83.335 | 1.00 | 42.40 |
| ATOM | 4150 | CB | GLU | A | 522 | 36.857 | 63.035 | 85.641 | 1.00 | 37.79 |
| ATOM | 4151 | CG | GLU | A | 522 | 38.233 | 63.196 | 86.273 | 1.00 | 58.85 |
| ATOM | 4152 | CD | GLU | A | 522 | 38.046 | 64.040 | 87.493 | 1.00 | 73.64 |
| ATOM | 4153 | OE1 | GLU | A | 522 | 37.006 | 64.641 | 87.709 | 1.00 | 45.66 |
| ATOM | 4154 | OE2 | GLU | A | 522 | 39.081 | 64.037 | 88.289 | 1.00 | 47.91 |
| ATOM | 4155 | N | VAL | A | 523 | 38.188 | 60.739 | 83.552 | 1.00 | 40.13 |
| ATOM | 4156 | CA | VAL | A | 523 | 39.401 | 60.136 | 83.058 | 1.00 | 37.49 |
| ATOM | 4157 | C | VAL | A | 523 | 39.205 | 59.351 | 81.778 | 1.00 | 38.88 |
| ATOM | 4158 | O | VAL | A | 523 | 40.195 | 59.016 | 81.138 | 1.00 | 40.21 |
| ATOM | 4159 | CB | VAL | A | 523 | 40.184 | 59.370 | 84.102 | 1.00 | 40.01 |
| ATOM | 4160 | CG1 | VAL | A | 523 | 40.231 | 60.165 | 85.413 | 1.00 | 39.12 |
| ATOM | 4161 | CG2 | VAL | A | 523 | 39.534 | 58.017 | 84.320 | 1.00 | 39.82 |
| ATOM | 4162 | N | TYR | A | 524 | 37.952 | 59.048 | 81.379 | 1.00 | 30.35 |
| ATOM | 4163 | CA | TYR | A | 524 | 37.801 | 58.330 | 80.114 | 1.00 | 28.11 |
| ATOM | 4164 | C | TYR | A | 524 | 37.061 | 59.144 | 79.074 | 1.00 | 33.14 |
| ATOM | 4165 | O | TYR | A | 524 | 37.076 | 58.802 | 77.908 | 1.00 | 35.84 |
| ATOM | 4166 | CB | TYR | A | 524 | 37.281 | 56.878 | 80.119 | 1.00 | 25.56 |
| ATOM | 4167 | CG | TYR | A | 524 | 37.941 | 55.960 | 81.111 | 1.00 | 20.87 |
| ATOM | 4168 | CD1 | TYR | A | 524 | 39.324 | 55.938 | 81.258 | 1.00 | 21.59 |
| ATOM | 4169 | CD2 | TYR | A | 524 | 37.170 | 55.083 | 81.879 | 1.00 | 19.80 |
| ATOM | 4170 | CE1 | TYR | A | 524 | 39.905 | 55.063 | 82.176 | 1.00 | 25.64 |
| ATOM | 4171 | CE2 | TYR | A | 524 | 37.731 | 54.227 | 82.827 | 1.00 | 18.61 |
| ATOM | 4172 | CZ | TYR | A | 524 | 39.116 | 54.231 | 82.969 | 1.00 | 19.81 |
| ATOM | 4173 | OH | TYR | A | 524 | 39.706 | 53.402 | 83.863 | 1.00 | 23.92 |
| ATOM | 4174 | N | ASN | A | 525 | 36.416 | 60.221 | 79.496 | 1.00 | 25.98 |
| ATOM | 4175 | CA | ASN | A | 525 | 35.687 | 61.088 | 78.588 | 1.00 | 25.01 |
| ATOM | 4176 | C | ASN | A | 525 | 34.661 | 60.354 | 77.735 | 1.00 | 29.86 |
| ATOM | 4177 | O | ASN | A | 525 | 34.533 | 60.535 | 76.499 | 1.00 | 29.39 |
| ATOM | 4178 | CB | ASN | A | 525 | 36.637 | 61.922 | 77.739 | 1.00 | 29.55 |
| ATOM | 4179 | CG | ASN | A | 525 | 35.949 | 62.980 | 76.894 | 1.00 | 30.32 |
| ATOM | 4180 | OD1 | ASN | A | 525 | 36.460 | 63.332 | 75.850 | 1.00 | 32.77 |
| ATOM | 4181 | ND2 | ASN | A | 525 | 34.822 | 63.527 | 77.344 | 1.00 | 13.80 |
| ATOM | 4182 | N | PHE | A | 526 | 33.924 | 59.512 | 78.436 | 1.00 | 24.21 |

TABLE 9-continued

Structure coordinates of LTA₄ hydrolase-thiolamine complex
(The amino acid sequence set forth as residues 1-610 below correspond to SEQ ID NO:1.)

| ATOM | 4183 | CA | PHE | A | 526 | 32.900 | 58.745 | 77.807 | 1.00 | 25.14 |
|------|------|-----|-----|---|-----|--------|--------|--------|------|-------|
| ATOM | 4184 | C | PHE | A | 526 | 31.846 | 59.631 | 77.214 | 1.00 | 31.74 |
| ATOM | 4185 | O | PHE | A | 526 | 31.161 | 59.241 | 76.272 | 1.00 | 34.99 |
| ATOM | 4186 | CB | PHE | A | 526 | 32.256 | 57.732 | 78.781 | 1.00 | 26.60 |
| ATOM | 4187 | CG | PHE | A | 526 | 33.115 | 56.499 | 78.978 | 1.00 | 23.82 |
| ATOM | 4188 | CD1 | PHE | A | 526 | 34.017 | 56.080 | 78.000 | 1.00 | 25.00 |
| ATOM | 4189 | CD2 | PHE | A | 526 | 33.031 | 55.767 | 80.159 | 1.00 | 21.74 |
| ATOM | 4190 | CE1 | PHE | A | 526 | 34.783 | 54.927 | 78.173 | 1.00 | 27.63 |
| ATOM | 4191 | CE2 | PHE | A | 526 | 33.817 | 54.634 | 80.370 | 1.00 | 25.42 |
| ATOM | 4192 | CZ | PHE | A | 526 | 34.683 | 54.202 | 79.364 | 1.00 | 25.28 |
| ATOM | 4193 | N | ASN | A | 527 | 31.689 | 60.815 | 77.760 | 1.00 | 28.22 |
| ATOM | 4194 | CA | ASN | A | 527 | 30.657 | 61.688 | 77.214 | 1.00 | 31.18 |
| ATOM | 4195 | C | ASN | A | 527 | 30.884 | 62.046 | 75.744 | 1.00 | 33.17 |
| ATOM | 4196 | O | ASN | A | 527 | 29.965 | 62.394 | 74.999 | 1.00 | 30.80 |
| ATOM | 4197 | CB | ASN | A | 527 | 30.479 | 62.967 | 78.052 | 1.00 | 36.41 |
| ATOM | 4198 | CG | ASN | A | 527 | 29.638 | 62.752 | 79.292 | 1.00 | 46.99 |
| ATOM | 4199 | OD1 | ASN | A | 527 | 29.647 | 63.571 | 80.209 | 1.00 | 36.82 |
| ATOM | 4200 | ND2 | ASN | A | 527 | 28.922 | 61.636 | 79.338 | 1.00 | 43.55 |
| ATOM | 4201 | N | ALA | A | 528 | 32.136 | 61.947 | 75.348 | 1.00 | 27.46 |
| ATOM | 4202 | CA | ALA | A | 528 | 32.581 | 62.278 | 74.005 | 1.00 | 26.48 |
| ATOM | 4203 | C | ALA | A | 528 | 32.335 | 61.188 | 72.950 | 1.00 | 32.09 |
| ATOM | 4204 | O | ALA | A | 528 | 32.420 | 61.404 | 71.753 | 1.00 | 32.09 |
| ATOM | 4205 | CB | ALA | A | 528 | 34.076 | 62.584 | 74.105 | 1.00 | 26.04 |
| ATOM | 4206 | N | ILE | A | 529 | 32.067 | 59.983 | 73.402 | 1.00 | 31.35 |
| ATOM | 4207 | CA | ILE | A | 529 | 31.854 | 58.859 | 72.529 | 1.00 | 28.47 |
| ATOM | 4208 | C | ILE | A | 529 | 30.492 | 58.904 | 71.887 | 1.00 | 35.96 |
| ATOM | 4209 | O | ILE | A | 529 | 29.486 | 59.023 | 72.578 | 1.00 | 38.79 |
| ATOM | 4210 | CB | ILE | A | 529 | 32.103 | 57.544 | 73.264 | 1.00 | 30.17 |
| ATOM | 4211 | CG1 | ILE | A | 529 | 33.622 | 57.291 | 73.392 | 1.00 | 31.37 |
| ATOM | 4212 | CG2 | ILE | A | 529 | 31.428 | 56.411 | 72.489 | 1.00 | 27.63 |
| ATOM | 4213 | CD1 | ILE | A | 529 | 34.059 | 56.515 | 74.635 | 1.00 | 33.41 |
| ATOM | 4214 | N | ASN | A | 530 | 30.462 | 58.806 | 70.559 | 1.00 | 34.86 |
| ATOM | 4215 | CA | ASN | A | 530 | 29.196 | 58.841 | 69.852 | 1.00 | 36.44 |
| ATOM | 4216 | C | ASN | A | 530 | 28.596 | 57.495 | 69.473 | 1.00 | 39.90 |
| ATOM | 4217 | O | ASN | A | 530 | 27.452 | 57.437 | 69.043 | 1.00 | 41.37 |
| ATOM | 4218 | CB | ASN | A | 530 | 28.951 | 60.044 | 68.928 | 1.00 | 51.44 |
| ATOM | 4219 | CG | ASN | A | 530 | 28.461 | 61.253 | 69.732 | 1.00 | 100.00 |
| ATOM | 4220 | OD1 | ASN | A | 530 | 27.652 | 61.109 | 70.665 | 1.00 | 100.00 |
| ATOM | 4221 | ND2 | ASN | A | 530 | 28.955 | 62.442 | 69.392 | 1.00 | 91.39 |
| ATOM | 4222 | N | ASN | A | 531 | 29.368 | 56.403 | 69.688 | 1.00 | 30.37 |
| ATOM | 4223 | CA | ASN | A | 531 | 28.912 | 55.030 | 69.446 | 1.00 | 28.14 |
| ATOM | 4224 | C | ASN | A | 531 | 27.696 | 54.753 | 70.360 | 1.00 | 32.80 |
| ATOM | 4225 | O | ASN | A | 531 | 27.746 | 54.887 | 71.611 | 1.00 | 36.74 |
| ATOM | 4226 | CB | ASN | A | 531 | 30.092 | 54.066 | 69.690 | 1.00 | 24.31 |
| ATOM | 4227 | CG | ASN | A | 531 | 29.770 | 52.601 | 69.730 | 1.00 | 34.44 |
| ATOM | 4228 | OD1 | ASN | A | 531 | 28.795 | 52.182 | 70.359 | 1.00 | 36.49 |
| ATOM | 4229 | ND2 | ASN | A | 531 | 30.643 | 51.810 | 69.099 | 1.00 | 30.57 |
| ATOM | 4230 | N | SER | A | 532 | 26.570 | 54.403 | 69.734 | 1.00 | 22.02 |
| ATOM | 4231 | CA | SER | A | 532 | 25.325 | 54.183 | 70.459 | 1.00 | 19.67 |
| ATOM | 4232 | C | SER | A | 532 | 25.323 | 53.208 | 71.627 | 1.00 | 26.15 |
| ATOM | 4233 | O | SER | A | 532 | 24.767 | 53.475 | 72.680 | 1.00 | 26.64 |
| ATOM | 4234 | CB | SER | A | 532 | 24.090 | 54.034 | 69.582 | 1.00 | 26.92 |
| ATOM | 4235 | OG | SER | A | 532 | 24.294 | 53.211 | 68.452 | 1.00 | 23.59 |
| ATOM | 4236 | N | GLU | A | 533 | 25.929 | 52.062 | 71.423 | 1.00 | 22.68 |
| ATOM | 4237 | CA | GLU | A | 533 | 25.995 | 51.036 | 72.420 | 1.00 | 22.97 |
| ATOM | 4238 | C | GLU | A | 533 | 26.677 | 51.569 | 73.635 | 1.00 | 30.48 |
| ATOM | 4239 | O | GLU | A | 533 | 26.125 | 51.539 | 74.749 | 1.00 | 31.13 |
| ATOM | 4240 | CB | GLU | A | 533 | 26.683 | 49.779 | 71.850 | 1.00 | 23.96 |
| ATOM | 4241 | CG | GLU | A | 533 | 25.827 | 49.146 | 70.733 | 1.00 | 20.82 |
| ATOM | 4242 | CD | GLU | A | 533 | 24.611 | 48.450 | 71.276 | 1.00 | 40.65 |
| ATOM | 4243 | OE1 | GLU | A | 533 | 24.432 | 48.256 | 72.476 | 1.00 | 36.25 |
| ATOM | 4244 | OE2 | GLU | A | 533 | 23.782 | 48.038 | 70.339 | 1.00 | 25.87 |
| ATOM | 4245 | N | ILE | A | 534 | 27.872 | 52.101 | 73.392 | 1.00 | 26.20 |
| ATOM | 4246 | CA | ILE | A | 534 | 28.622 | 52.672 | 74.484 | 1.00 | 26.32 |
| ATOM | 4247 | C | ILE | A | 534 | 27.900 | 53.849 | 75.121 | 1.00 | 27.83 |
| ATOM | 4248 | O | ILE | A | 534 | 27.697 | 53.911 | 76.326 | 1.00 | 26.54 |
| ATOM | 4249 | CB | ILE | A | 534 | 30.051 | 53.022 | 74.102 | 1.00 | 29.16 |
| ATOM | 4250 | CG1 | ILE | A | 534 | 30.738 | 51.808 | 73.479 | 1.00 | 29.47 |
| ATOM | 4251 | CG2 | ILE | A | 534 | 30.801 | 53.458 | 75.353 | 1.00 | 28.28 |
| ATOM | 4252 | CD1 | ILE | A | 534 | 32.038 | 52.184 | 72.765 | 1.00 | 34.99 |
| ATOM | 4253 | N | ARG | A | 535 | 27.480 | 54.805 | 74.320 | 1.00 | 24.30 |
| ATOM | 4254 | CA | ARG | A | 535 | 26.804 | 55.898 | 74.949 | 1.00 | 22.51 |
| ATOM | 4255 | C | ARG | A | 535 | 25.573 | 55.401 | 75.701 | 1.00 | 28.19 |
| ATOM | 4256 | O | ARG | A | 535 | 25.212 | 55.808 | 76.791 | 1.00 | 32.61 |
| ATOM | 4257 | CB | ARG | A | 535 | 26.457 | 56.942 | 73.913 | 1.00 | 24.83 |
| ATOM | 4258 | CG | ARG | A | 535 | 25.970 | 58.229 | 74.541 | 1.00 | 21.49 |

TABLE 9-continued

Structure coordinates of LTA$_4$ hydrolase-thiolamine complex
(The amino acid sequence set forth as residues 1-610 below correspond to SEQ ID NO:1.)

| ATOM | 4259 | CD  | ARG | A | 535 | 25.327 | 59.183 | 73.554 | 1.00 | 13.79 |
|------|------|-----|-----|---|-----|--------|--------|--------|------|-------|
| ATOM | 4260 | NE  | ARG | A | 535 | 25.194 | 60.457 | 74.213 | 1.00 | 31.38 |
| ATOM | 4261 | CZ  | ARG | A | 535 | 26.256 | 61.140 | 74.554 | 1.00 | 29.41 |
| ATOM | 4262 | NH1 | ARG | A | 535 | 27.463 | 60.677 | 74.259 | 1.00 | 26.45 |
| ATOM | 4263 | NH2 | ARG | A | 535 | 26.110 | 62.302 | 75.195 | 1.00 | 19.99 |
| ATOM | 4264 | N   | PHE | A | 536 | 24.911 | 54.466 | 75.126 | 1.00 | 23.44 |
| ATOM | 4265 | CA  | PHE | A | 536 | 23.740 | 53.980 | 75.770 | 1.00 | 22.05 |
| ATOM | 4266 | C   | PHE | A | 536 | 23.976 | 53.555 | 77.199 | 1.00 | 22.74 |
| ATOM | 4267 | O   | PHE | A | 536 | 23.349 | 54.113 | 78.105 | 1.00 | 22.06 |
| ATOM | 4268 | CB  | PHE | A | 536 | 23.117 | 52.865 | 74.919 | 1.00 | 23.17 |
| ATOM | 4269 | CG  | PHE | A | 536 | 22.040 | 52.153 | 75.658 | 1.00 | 21.92 |
| ATOM | 4270 | CD1 | PHE | A | 536 | 20.933 | 52.845 | 76.150 | 1.00 | 22.66 |
| ATOM | 4271 | CD2 | PHE | A | 536 | 22.145 | 50.783 | 75.882 | 1.00 | 23.25 |
| ATOM | 4272 | CE1 | PHE | A | 536 | 19.926 | 52.181 | 76.847 | 1.00 | 21.23 |
| ATOM | 4273 | CE2 | PHE | A | 536 | 21.147 | 50.101 | 76.576 | 1.00 | 24.70 |
| ATOM | 4274 | CZ  | PHE | A | 536 | 20.047 | 50.811 | 77.065 | 1.00 | 20.57 |
| ATOM | 4275 | N   | ARG | A | 537 | 24.863 | 52.560 | 77.364 | 1.00 | 18.22 |
| ATOM | 4276 | CA  | ARG | A | 537 | 25.239 | 51.995 | 78.665 | 1.00 | 19.20 |
| ATOM | 4277 | C   | ARG | A | 537 | 25.932 | 52.963 | 79.618 | 1.00 | 27.62 |
| ATOM | 4278 | O   | ARG | A | 537 | 25.803 | 52.845 | 80.837 | 1.00 | 26.73 |
| ATOM | 4279 | CB  | ARG | A | 537 | 26.035 | 50.709 | 78.556 | 1.00 | 18.91 |
| ATOM | 4280 | CG  | ARG | A | 537 | 25.318 | 49.656 | 77.708 | 1.00 | 16.55 |
| ATOM | 4281 | CD  | ARG | A | 537 | 26.181 | 48.426 | 77.387 | 1.00 | 21.58 |
| ATOM | 4282 | NE  | ARG | A | 537 | 25.341 | 47.357 | 76.886 | 1.00 | 28.42 |
| ATOM | 4283 | CZ  | ARG | A | 537 | 25.060 | 47.206 | 75.609 | 1.00 | 18.29 |
| ATOM | 4284 | NH1 | ARG | A | 537 | 25.569 | 48.004 | 74.703 | 1.00 | 22.46 |
| ATOM | 4285 | NH2 | ARG | A | 537 | 24.240 | 46.236 | 75.224 | 1.00 | 25.22 |
| ATOM | 4286 | N   | TRP | A | 538 | 26.668 | 53.930 | 79.064 | 1.00 | 24.21 |
| ATOM | 4287 | CA  | TRP | A | 538 | 27.337 | 54.918 | 79.867 | 1.00 | 22.11 |
| ATOM | 4288 | C   | TRP | A | 538 | 26.274 | 55.719 | 80.550 | 1.00 | 28.09 |
| ATOM | 4289 | O   | TRP | A | 538 | 26.320 | 55.951 | 81.741 | 1.00 | 27.39 |
| ATOM | 4290 | CB  | TRP | A | 538 | 28.064 | 55.888 | 78.949 | 1.00 | 20.48 |
| ATOM | 4291 | CG  | TRP | A | 538 | 28.606 | 57.157 | 79.580 | 1.00 | 21.29 |
| ATOM | 4292 | CD1 | TRP | A | 538 | 28.641 | 58.345 | 78.968 | 1.00 | 22.86 |
| ATOM | 4293 | CD2 | TRP | A | 538 | 29.286 | 57.352 | 80.845 | 1.00 | 21.79 |
| ATOM | 4294 | NE1 | TRP | A | 538 | 29.228 | 59.270 | 79.769 | 1.00 | 22.70 |
| ATOM | 4295 | CE2 | TRP | A | 538 | 29.643 | 58.696 | 80.911 | 1.00 | 24.79 |
| ATOM | 4296 | CE3 | TRP | A | 538 | 29.574 | 56.535 | 81.946 | 1.00 | 23.35 |
| ATOM | 4297 | CZ2 | TRP | A | 538 | 30.280 | 59.248 | 82.025 | 1.00 | 25.89 |
| ATOM | 4298 | CZ3 | TRP | A | 538 | 30.203 | 57.056 | 83.046 | 1.00 | 23.35 |
| ATOM | 4299 | CH2 | TRP | A | 538 | 30.562 | 58.405 | 83.081 | 1.00 | 24.89 |
| ATOM | 4300 | N   | LEU | A | 539 | 25.303 | 56.161 | 79.758 | 1.00 | 27.31 |
| ATOM | 4301 | CA  | LEU | A | 539 | 24.229 | 56.974 | 80.306 | 1.00 | 27.18 |
| ATOM | 4302 | C   | LEU | A | 539 | 23.369 | 56.245 | 81.332 | 1.00 | 28.25 |
| ATOM | 4303 | O   | LEU | A | 539 | 22.857 | 56.822 | 82.266 | 1.00 | 27.19 |
| ATOM | 4304 | CB  | LEU | A | 539 | 23.428 | 57.812 | 79.262 | 1.00 | 26.37 |
| ATOM | 4305 | CG  | LEU | A | 539 | 24.269 | 58.682 | 78.279 | 1.00 | 25.71 |
| ATOM | 4306 | CD1 | LEU | A | 539 | 23.369 | 59.424 | 77.290 | 1.00 | 21.79 |
| ATOM | 4307 | CD2 | LEU | A | 539 | 25.146 | 59.680 | 79.011 | 1.00 | 23.51 |
| ATOM | 4308 | N   | ARG | A | 540 | 23.199 | 54.960 | 81.188 | 1.00 | 27.56 |
| ATOM | 4309 | CA  | ARG | A | 540 | 22.390 | 54.283 | 82.170 | 1.00 | 26.88 |
| ATOM | 4310 | C   | ARG | A | 540 | 23.145 | 54.229 | 83.453 | 1.00 | 31.82 |
| ATOM | 4311 | O   | ARG | A | 540 | 22.618 | 54.448 | 84.539 | 1.00 | 32.72 |
| ATOM | 4312 | CB  | ARG | A | 540 | 22.034 | 52.888 | 81.732 | 1.00 | 24.48 |
| ATOM | 4313 | CG  | ARG | A | 540 | 21.447 | 52.885 | 80.331 | 1.00 | 32.96 |
| ATOM | 4314 | CD  | ARG | A | 540 | 20.695 | 51.597 | 80.090 | 1.00 | 33.19 |
| ATOM | 4315 | NE  | ARG | A | 540 | 19.660 | 51.414 | 81.085 | 1.00 | 33.95 |
| ATOM | 4316 | CZ  | ARG | A | 540 | 19.151 | 50.242 | 81.409 | 1.00 | 30.83 |
| ATOM | 4317 | NH1 | ARG | A | 540 | 19.564 | 49.132 | 80.849 | 1.00 | 25.37 |
| ATOM | 4318 | NH2 | ARG | A | 540 | 18.186 | 50.186 | 82.317 | 1.00 | 30.30 |
| ATOM | 4319 | N   | LEU | A | 541 | 24.414 | 53.948 | 83.318 | 1.00 | 28.93 |
| ATOM | 4320 | CA  | LEU | A | 541 | 25.239 | 53.895 | 84.505 | 1.00 | 26.36 |
| ATOM | 4321 | C   | LEU | A | 541 | 25.036 | 55.210 | 85.277 | 1.00 | 31.00 |
| ATOM | 4322 | O   | LEU | A | 541 | 24.632 | 55.246 | 86.439 | 1.00 | 31.62 |
| ATOM | 4323 | CB  | LEU | A | 541 | 26.702 | 53.586 | 84.094 | 1.00 | 23.61 |
| ATOM | 4324 | CG  | LEU | A | 541 | 27.730 | 53.533 | 85.212 | 1.00 | 24.67 |
| ATOM | 4325 | CD1 | LEU | A | 541 | 27.387 | 52.411 | 86.190 | 1.00 | 25.02 |
| ATOM | 4326 | CD2 | LEU | A | 541 | 29.098 | 53.245 | 84.621 | 1.00 | 19.31 |
| ATOM | 4327 | N   | CYS | A | 542 | 25.254 | 56.307 | 84.570 | 1.00 | 30.52 |
| ATOM | 4328 | CA  | CYS | A | 542 | 25.115 | 57.661 | 85.105 | 1.00 | 31.76 |
| ATOM | 4329 | C   | CYS | A | 542 | 23.808 | 57.996 | 85.805 | 1.00 | 32.71 |
| ATOM | 4330 | O   | CYS | A | 542 | 23.801 | 58.536 | 86.914 | 1.00 | 33.97 |
| ATOM | 4331 | CB  | CYS | A | 542 | 25.461 | 58.744 | 84.073 | 1.00 | 31.30 |
| ATOM | 4332 | SG  | CYS | A | 542 | 27.085 | 58.488 | 83.347 | 1.00 | 34.39 |
| ATOM | 4333 | N   | ILE | A | 543 | 22.711 | 57.708 | 85.125 | 1.00 | 25.61 |
| ATOM | 4334 | CA  | ILE | A | 543 | 21.382 | 57.982 | 85.643 | 1.00 | 23.12 |

TABLE 9-continued

Structure coordinates of LTA$_4$ hydrolase-thiolamine complex
(The amino acid sequence set forth as residues 1-610 below correspond to SEQ ID NO:1.)

| ATOM | 4335 | C | ILE | A | 543 | 21.199 | 57.161 | 86.885 | 1.00 | 30.15 |
|------|------|-----|-----|---|-----|--------|--------|--------|------|-------|
| ATOM | 4336 | O | ILE | A | 543 | 20.900 | 57.645 | 87.972 | 1.00 | 30.73 |
| ATOM | 4337 | CB | ILE | A | 543 | 20.340 | 57.627 | 84.585 | 1.00 | 23.75 |
| ATOM | 4338 | CG1 | ILE | A | 543 | 20.369 | 58.664 | 83.468 | 1.00 | 24.09 |
| ATOM | 4339 | CG2 | ILE | A | 543 | 18.955 | 57.572 | 85.182 | 1.00 | 22.99 |
| ATOM | 4340 | CD1 | ILE | A | 543 | 20.386 | 60.109 | 83.982 | 1.00 | 27.34 |
| ATOM | 4341 | N | GLN | A | 544 | 21.440 | 55.884 | 86.695 | 1.00 | 27.99 |
| ATOM | 4342 | CA | GLN | A | 544 | 21.320 | 54.929 | 87.756 | 1.00 | 25.72 |
| ATOM | 4343 | C | GLN | A | 544 | 22.243 | 55.269 | 88.901 | 1.00 | 26.34 |
| ATOM | 4344 | O | GLN | A | 544 | 22.029 | 54.826 | 90.014 | 1.00 | 26.24 |
| ATOM | 4345 | CB | GLN | A | 544 | 21.562 | 53.512 | 87.210 | 1.00 | 26.76 |
| ATOM | 4346 | CG | GLN | A | 544 | 20.355 | 52.955 | 86.432 | 1.00 | 17.74 |
| ATOM | 4347 | CD | GLN | A | 544 | 20.598 | 51.604 | 85.743 | 1.00 | 32.62 |
| ATOM | 4348 | OE1 | GLN | A | 544 | 20.326 | 51.432 | 84.551 | 1.00 | 38.66 |
| ATOM | 4349 | NE2 | GLN | A | 544 | 21.063 | 50.627 | 86.494 | 1.00 | 14.93 |
| ATOM | 4350 | N | SER | A | 545 | 23.286 | 56.033 | 88.625 | 1.00 | 21.73 |
| ATOM | 4351 | CA | SER | A | 545 | 24.187 | 56.392 | 89.685 | 1.00 | 22.42 |
| ATOM | 4352 | C | SER | A | 545 | 23.819 | 57.726 | 90.287 | 1.00 | 33.67 |
| ATOM | 4353 | O | SER | A | 545 | 24.567 | 58.257 | 91.133 | 1.00 | 37.22 |
| ATOM | 4354 | CB | SER | A | 545 | 25.646 | 56.322 | 89.338 | 1.00 | 21.57 |
| ATOM | 4355 | OG | SER | A | 545 | 25.980 | 54.968 | 89.163 | 1.00 | 31.72 |
| ATOM | 4356 | N | LYS | A | 546 | 22.662 | 58.251 | 89.841 | 1.00 | 23.09 |
| ATOM | 4357 | CA | LYS | A | 546 | 22.135 | 59.490 | 90.356 | 1.00 | 20.79 |
| ATOM | 4358 | C | LYS | A | 546 | 22.887 | 60.738 | 89.961 | 1.00 | 27.55 |
| ATOM | 4359 | O | LYS | A | 546 | 23.001 | 61.655 | 90.771 | 1.00 | 27.95 |
| ATOM | 4360 | CB | LYS | A | 546 | 22.126 | 59.449 | 91.881 | 1.00 | 21.71 |
| ATOM | 4361 | CG | LYS | A | 546 | 21.498 | 58.195 | 92.484 | 1.00 | 15.90 |
| ATOM | 4362 | CD | LYS | A | 546 | 20.245 | 57.814 | 91.731 | 1.00 | 39.84 |
| ATOM | 4363 | CE | LYS | A | 546 | 19.355 | 56.850 | 92.498 | 1.00 | 45.16 |
| ATOM | 4364 | NZ | LYS | A | 546 | 18.197 | 56.399 | 91.704 | 1.00 | 40.14 |
| ATOM | 4365 | N | TRP | A | 547 | 23.414 | 60.776 | 88.753 | 1.00 | 23.26 |
| ATOM | 4366 | CA | TRP | A | 547 | 24.141 | 61.931 | 88.289 | 1.00 | 21.90 |
| ATOM | 4367 | C | TRP | A | 547 | 23.221 | 62.901 | 87.570 | 1.00 | 29.82 |
| ATOM | 4368 | O | TRP | A | 547 | 22.808 | 62.679 | 86.432 | 1.00 | 34.91 |
| ATOM | 4369 | CB | TRP | A | 547 | 25.262 | 61.500 | 87.361 | 1.00 | 21.04 |
| ATOM | 4370 | CG | TRP | A | 547 | 26.254 | 62.591 | 87.206 | 1.00 | 22.57 |
| ATOM | 4371 | CD1 | TRP | A | 547 | 26.224 | 63.769 | 87.844 | 1.00 | 25.87 |
| ATOM | 4372 | CD2 | TRP | A | 547 | 27.437 | 62.588 | 86.417 | 1.00 | 23.40 |
| ATOM | 4373 | NE1 | TRP | A | 547 | 27.316 | 64.511 | 87.517 | 1.00 | 25.64 |
| ATOM | 4374 | CE2 | TRP | A | 547 | 28.081 | 63.819 | 86.635 | 1.00 | 27.46 |
| ATOM | 4375 | CE3 | TRP | A | 547 | 28.014 | 61.668 | 85.547 | 1.00 | 26.21 |
| ATOM | 4376 | CZ2 | TRP | A | 547 | 29.279 | 64.162 | 85.995 | 1.00 | 27.44 |
| ATOM | 4377 | CZ3 | TRP | A | 547 | 29.195 | 62.009 | 84.923 | 1.00 | 28.70 |
| ATOM | 4378 | CH2 | TRP | A | 547 | 29.822 | 63.236 | 85.138 | 1.00 | 28.41 |
| ATOM | 4379 | N | GLU | A | 548 | 22.888 | 63.995 | 88.227 | 1.00 | 22.95 |
| ATOM | 4380 | CA | GLU | A | 548 | 21.979 | 64.970 | 87.649 | 1.00 | 20.70 |
| ATOM | 4381 | C | GLU | A | 548 | 22.419 | 65.473 | 86.305 | 1.00 | 28.32 |
| ATOM | 4382 | O | GLU | A | 548 | 21.598 | 65.735 | 85.391 | 1.00 | 29.41 |
| ATOM | 4383 | CB | GLU | A | 548 | 21.635 | 66.144 | 88.607 | 1.00 | 22.45 |
| ATOM | 4384 | CG | GLU | A | 548 | 20.884 | 65.709 | 89.919 | 1.00 | 30.56 |
| ATOM | 4385 | CD | GLU | A | 548 | 20.337 | 66.848 | 90.765 | 1.00 | 59.35 |
| ATOM | 4386 | OE1 | GLU | A | 548 | 20.336 | 68.021 | 90.413 | 1.00 | 81.52 |
| ATOM | 4387 | OE2 | GLU | A | 548 | 19.888 | 66.450 | 91.925 | 1.00 | 57.05 |
| ATOM | 4388 | N | ASP | A | 549 | 23.728 | 65.661 | 86.201 | 1.00 | 24.72 |
| ATOM | 4389 | CA | ASP | A | 549 | 24.276 | 66.190 | 84.981 | 1.00 | 21.48 |
| ATOM | 4390 | C | ASP | A | 549 | 23.914 | 65.359 | 83.795 | 1.00 | 30.08 |
| ATOM | 4391 | O | ASP | A | 549 | 23.760 | 65.869 | 82.697 | 1.00 | 32.05 |
| ATOM | 4392 | CB | ASP | A | 549 | 25.775 | 66.480 | 85.048 | 1.00 | 21.28 |
| ATOM | 4393 | CG | ASP | A | 549 | 26.076 | 67.463 | 86.130 | 1.00 | 37.74 |
| ATOM | 4394 | OD1 | ASP | A | 549 | 25.432 | 68.479 | 86.297 | 1.00 | 48.21 |
| ATOM | 4395 | OD2 | ASP | A | 549 | 27.076 | 67.115 | 86.882 | 1.00 | 46.51 |
| ATOM | 4396 | N | ALA | A | 550 | 23.766 | 64.073 | 84.032 | 1.00 | 27.68 |
| ATOM | 4397 | CA | ALA | A | 550 | 23.445 | 63.133 | 82.965 | 1.00 | 26.74 |
| ATOM | 4398 | C | ALA | A | 550 | 22.019 | 63.171 | 82.431 | 1.00 | 32.35 |
| ATOM | 4399 | O | ALA | A | 550 | 21.745 | 62.615 | 81.361 | 1.00 | 31.95 |
| ATOM | 4400 | CB | ALA | A | 550 | 23.812 | 61.713 | 83.372 | 1.00 | 25.48 |
| ATOM | 4401 | N | ILE | A | 551 | 21.123 | 63.795 | 83.192 | 1.00 | 28.71 |
| ATOM | 4402 | CA | ILE | A | 551 | 19.716 | 63.882 | 82.832 | 1.00 | 28.20 |
| ATOM | 4403 | C | ILE | A | 551 | 19.461 | 64.355 | 81.411 | 1.00 | 32.04 |
| ATOM | 4404 | O | ILE | A | 551 | 18.833 | 63.679 | 80.619 | 1.00 | 31.75 |
| ATOM | 4405 | CB | ILE | A | 551 | 18.876 | 64.641 | 83.868 | 1.00 | 30.29 |
| ATOM | 4406 | CG1 | ILE | A | 551 | 19.038 | 63.985 | 85.226 | 1.00 | 31.50 |
| ATOM | 4407 | CG2 | ILE | A | 551 | 17.391 | 64.661 | 83.475 | 1.00 | 24.75 |
| ATOM | 4408 | CD1 | ILE | A | 551 | 18.072 | 64.561 | 86.253 | 1.00 | 31.62 |
| ATOM | 4409 | N | PRO | A | 552 | 19.969 | 65.529 | 81.099 | 1.00 | 33.75 |
| ATOM | 4410 | CA | PRO | A | 552 | 19.793 | 66.121 | 79.796 | 1.00 | 32.60 |

TABLE 9-continued

Structure coordinates of LTA₄ hydrolase-thiolamine complex
(The amino acid sequence set forth as residues 1-610 below correspond to SEQ ID NO:1.)

| ATOM | 4411 | C   | PRO | A | 552 | 20.240 | 65.224 | 78.669 | 1.00 | 30.34 |
|------|------|-----|-----|---|-----|--------|--------|--------|------|-------|
| ATOM | 4412 | O   | PRO | A | 552 | 19.583 | 65.119 | 77.622 | 1.00 | 27.23 |
| ATOM | 4413 | CB  | PRO | A | 552 | 20.659 | 67.383 | 79.787 | 1.00 | 34.45 |
| ATOM | 4414 | CG  | PRO | A | 552 | 21.348 | 67.500 | 81.139 | 1.00 | 38.39 |
| ATOM | 4415 | CD  | PRO | A | 552 | 20.934 | 66.296 | 81.950 | 1.00 | 34.48 |
| ATOM | 4416 | N   | LEU | A | 553 | 21.391 | 64.616 | 78.891 | 1.00 | 23.74 |
| ATOM | 4417 | CA  | LEU | A | 553 | 21.997 | 63.727 | 77.931 | 1.00 | 22.72 |
| ATOM | 4418 | C   | LEU | A | 553 | 21.138 | 62.522 | 77.670 | 1.00 | 32.68 |
| ATOM | 4419 | O   | LEU | A | 553 | 21.015 | 62.087 | 76.523 | 1.00 | 35.70 |
| ATOM | 4420 | CB  | LEU | A | 553 | 23.362 | 63.281 | 78.439 | 1.00 | 21.57 |
| ATOM | 4421 | CG  | LEU | A | 553 | 24.196 | 64.496 | 78.818 | 1.00 | 24.02 |
| ATOM | 4422 | CD1 | LEU | A | 553 | 25.608 | 64.071 | 79.174 | 1.00 | 19.59 |
| ATOM | 4423 | CD2 | LEU | A | 553 | 24.188 | 65.479 | 77.630 | 1.00 | 18.60 |
| ATOM | 4424 | N   | ALA | A | 554 | 20.563 | 61.973 | 78.754 | 1.00 | 30.05 |
| ATOM | 4425 | CA  | ALA | A | 554 | 19.726 | 60.779 | 78.669 | 1.00 | 27.72 |
| ATOM | 4426 | C   | ALA | A | 554 | 18.432 | 61.107 | 77.988 | 1.00 | 36.03 |
| ATOM | 4427 | O   | ALA | A | 554 | 17.944 | 60.332 | 77.163 | 1.00 | 37.08 |
| ATOM | 4428 | CB  | ALA | A | 554 | 19.475 | 60.165 | 80.017 | 1.00 | 26.78 |
| ATOM | 4429 | N   | LEU | A | 555 | 17.898 | 62.283 | 78.320 | 1.00 | 29.70 |
| ATOM | 4430 | CA  | LEU | A | 555 | 16.644 | 62.724 | 77.720 | 1.00 | 28.32 |
| ATOM | 4431 | C   | LEU | A | 555 | 16.803 | 62.902 | 76.229 | 1.00 | 29.19 |
| ATOM | 4432 | O   | LEU | A | 555 | 15.970 | 62.506 | 75.385 | 1.00 | 26.13 |
| ATOM | 4433 | CB  | LEU | A | 555 | 16.110 | 64.027 | 78.342 | 1.00 | 28.26 |
| ATOM | 4434 | CG  | LEU | A | 555 | 15.371 | 63.814 | 79.666 | 1.00 | 32.76 |
| ATOM | 4435 | CD1 | LEU | A | 555 | 15.360 | 65.118 | 80.464 | 1.00 | 34.66 |
| ATOM | 4436 | CD2 | LEU | A | 555 | 13.938 | 63.334 | 79.427 | 1.00 | 27.50 |
| ATOM | 4437 | N   | LYS | A | 556 | 17.922 | 63.524 | 75.950 | 1.00 | 28.45 |
| ATOM | 4438 | CA  | LYS | A | 556 | 18.325 | 63.839 | 74.615 | 1.00 | 28.76 |
| ATOM | 4439 | C   | LYS | A | 556 | 18.369 | 62.591 | 73.800 | 1.00 | 35.11 |
| ATOM | 4440 | O   | LYS | A | 556 | 17.670 | 62.491 | 72.796 | 1.00 | 41.80 |
| ATOM | 4441 | CB  | LYS | A | 556 | 19.645 | 64.592 | 74.599 | 1.00 | 31.79 |
| ATOM | 4442 | CG  | LYS | A | 556 | 20.101 | 65.139 | 73.250 | 1.00 | 63.55 |
| ATOM | 4443 | CD  | LYS | A | 556 | 21.585 | 65.518 | 73.254 | 1.00 | 81.77 |
| ATOM | 4444 | CE  | LYS | A | 556 | 22.046 | 66.270 | 72.011 | 1.00 | 79.68 |
| ATOM | 4445 | NZ  | LYS | A | 556 | 23.239 | 65.661 | 71.401 | 1.00 | 73.00 |
| ATOM | 4446 | N   | MET | A | 557 | 19.154 | 61.623 | 74.248 | 1.00 | 26.96 |
| ATOM | 4447 | CA  | MET | A | 557 | 19.305 | 60.364 | 73.514 | 1.00 | 23.97 |
| ATOM | 4448 | C   | MET | A | 557 | 18.033 | 59.553 | 73.287 | 1.00 | 30.96 |
| ATOM | 4449 | O   | MET | A | 557 | 17.811 | 58.907 | 72.263 | 1.00 | 23.24 |
| ATOM | 4450 | CB  | MET | A | 557 | 20.401 | 59.488 | 74.104 | 1.00 | 24.89 |
| ATOM | 4451 | CG  | MET | A | 557 | 20.533 | 58.163 | 73.368 | 1.00 | 29.37 |
| ATOM | 4452 | SD  | MET | A | 557 | 22.029 | 57.276 | 73.864 | 1.00 | 33.21 |
| ATOM | 4453 | CE  | MET | A | 557 | 21.939 | 55.812 | 72.793 | 1.00 | 30.16 |
| ATOM | 4454 | N   | ALA | A | 558 | 17.203 | 59.568 | 74.287 | 1.00 | 33.42 |
| ATOM | 4455 | CA  | ALA | A | 558 | 16.000 | 58.816 | 74.194 | 1.00 | 33.03 |
| ATOM | 4456 | C   | ALA | A | 558 | 15.042 | 59.345 | 73.163 | 1.00 | 38.12 |
| ATOM | 4457 | O   | ALA | A | 558 | 14.349 | 58.568 | 72.543 | 1.00 | 37.09 |
| ATOM | 4458 | CB  | ALA | A | 558 | 15.317 | 58.780 | 75.553 | 1.00 | 32.89 |
| ATOM | 4459 | N   | THR | A | 559 | 14.994 | 60.665 | 73.032 | 1.00 | 36.76 |
| ATOM | 4460 | CA  | THR | A | 559 | 14.067 | 61.326 | 72.144 | 1.00 | 36.43 |
| ATOM | 4461 | C   | THR | A | 559 | 14.588 | 61.590 | 70.794 | 1.00 | 41.71 |
| ATOM | 4462 | O   | THR | A | 559 | 13.788 | 61.768 | 69.891 | 1.00 | 44.66 |
| ATOM | 4463 | CB  | THR | A | 559 | 13.615 | 62.705 | 72.694 | 1.00 | 43.70 |
| ATOM | 4464 | OG1 | THR | A | 559 | 14.728 | 63.545 | 72.957 | 1.00 | 38.88 |
| ATOM | 4465 | CG2 | THR | A | 559 | 12.764 | 62.549 | 73.942 | 1.00 | 44.95 |
| ATOM | 4466 | N   | GLU | A | 560 | 15.897 | 61.695 | 70.674 | 1.00 | 37.38 |
| ATOM | 4467 | CA  | GLU | A | 560 | 16.495 | 62.018 | 69.395 | 1.00 | 36.51 |
| ATOM | 4468 | C   | GLU | A | 560 | 16.652 | 60.846 | 68.448 | 1.00 | 40.11 |
| ATOM | 4469 | O   | GLU | A | 560 | 17.003 | 61.052 | 67.300 | 1.00 | 43.23 |
| ATOM | 4470 | CB  | GLU | A | 560 | 17.799 | 62.820 | 69.519 | 1.00 | 38.13 |
| ATOM | 4471 | CG  | GLU | A | 560 | 17.653 | 64.142 | 70.292 | 1.00 | 54.29 |
| ATOM | 4472 | CD  | GLU | A | 560 | 18.857 | 65.043 | 70.127 | 1.00 | 78.42 |
| ATOM | 4473 | OE1 | GLU | A | 560 | 19.960 | 64.639 | 69.812 | 1.00 | 32.69 |
| ATOM | 4474 | OE2 | GLU | A | 560 | 18.593 | 66.303 | 70.380 | 1.00 | 85.90 |
| ATOM | 4475 | N   | GLN | A | 561 | 16.425 | 59.627 | 68.955 | 1.00 | 30.45 |
| ATOM | 4476 | CA  | GLN | A | 561 | 16.467 | 58.356 | 68.230 | 1.00 | 22.57 |
| ATOM | 4477 | C   | GLN | A | 561 | 15.398 | 57.523 | 68.878 | 1.00 | 26.95 |
| ATOM | 4478 | O   | GLN | A | 561 | 14.978 | 57.814 | 69.975 | 1.00 | 27.79 |
| ATOM | 4479 | CB  | GLN | A | 561 | 17.829 | 57.661 | 68.128 | 1.00 | 20.64 |
| ATOM | 4480 | CG  | GLN | A | 561 | 18.470 | 57.290 | 69.491 | 1.00 | 22.59 |
| ATOM | 4481 | CD  | GLN | A | 561 | 17.802 | 56.121 | 70.184 | 1.00 | 28.22 |
| ATOM | 4482 | OE1 | GLN | A | 561 | 17.524 | 56.156 | 71.400 | 1.00 | 37.44 |
| ATOM | 4483 | NE2 | GLN | A | 561 | 17.556 | 55.069 | 69.419 | 1.00 | 31.92 |
| ATOM | 4484 | N   | GLY | A | 562 | 14.888 | 56.535 | 68.209 | 1.00 | 26.16 |
| ATOM | 4485 | CA  | GLY | A | 562 | 13.801 | 55.810 | 68.858 | 1.00 | 27.83 |
| ATOM | 4486 | C   | GLY | A | 562 | 13.932 | 54.320 | 68.761 | 1.00 | 41.56 |

TABLE 9-continued

Structure coordinates of LTA₄ hydrolase-thiolamine complex
(The amino acid sequence set forth as residues 1-610 below correspond to SEQ ID NO:1.)

| ATOM | 4487 | O | GLY | A | 562 | 12.936 | 53.614 | 68.677 | 1.00 | 45.37 |
|------|------|------|------|---|-----|--------|--------|--------|------|-------|
| ATOM | 4488 | N | ARG | A | 563 | 15.171 | 53.864 | 68.742 | 1.00 | 37.40 |
| ATOM | 4489 | CA | ARG | A | 563 | 15.457 | 52.453 | 68.689 | 1.00 | 34.41 |
| ATOM | 4490 | C | ARG | A | 563 | 15.121 | 51.939 | 70.109 | 1.00 | 39.48 |
| ATOM | 4491 | O | ARG | A | 563 | 15.832 | 52.221 | 71.087 | 1.00 | 40.29 |
| ATOM | 4492 | CB | ARG | A | 563 | 16.932 | 52.231 | 68.284 | 1.00 | 18.23 |
| ATOM | 4493 | CG | ARG | A | 563 | 17.309 | 50.755 | 68.169 | 1.00 | 20.07 |
| ATOM | 4494 | CD | ARG | A | 563 | 18.779 | 50.514 | 68.512 | 1.00 | 25.07 |
| ATOM | 4495 | NE | ARG | A | 563 | 19.234 | 49.139 | 68.320 | 1.00 | 25.66 |
| ATOM | 4496 | CZ | ARG | A | 563 | 20.425 | 48.891 | 67.821 | 1.00 | 26.35 |
| ATOM | 4497 | NH1 | ARG | A | 563 | 21.257 | 49.860 | 67.430 | 1.00 | 12.96 |
| ATOM | 4498 | NH2 | ARG | A | 563 | 20.804 | 47.636 | 67.656 | 1.00 | 30.31 |
| ATOM | 4499 | N | MET | A | 564 | 13.989 | 51.228 | 70.239 | 1.00 | 33.12 |
| ATOM | 4500 | CA | MET | A | 564 | 13.487 | 50.695 | 71.526 | 1.00 | 31.84 |
| ATOM | 4501 | C | MET | A | 564 | 14.565 | 50.247 | 72.532 | 1.00 | 31.42 |
| ATOM | 4502 | O | MET | A | 564 | 14.494 | 50.501 | 73.744 | 1.00 | 25.72 |
| ATOM | 4503 | CB | MET | A | 564 | 12.323 | 49.682 | 71.365 | 1.00 | 32.45 |
| ATOM | 4504 | CG | MET | A | 564 | 11.196 | 50.225 | 70.487 | 1.00 | 35.78 |
| ATOM | 4505 | SD | MET | A | 564 | 9.695 | 49.205 | 70.533 | 1.00 | 40.85 |
| ATOM | 4506 | CE | MET | A | 564 | 10.177 | 47.892 | 69.382 | 1.00 | 35.87 |
| ATOM | 4507 | N | LYS | A | 565 | 15.562 | 49.581 | 71.966 | 1.00 | 31.68 |
| ATOM | 4508 | CA | LYS | A | 565 | 16.699 | 49.041 | 72.668 | 1.00 | 29.04 |
| ATOM | 4509 | C | LYS | A | 565 | 17.281 | 50.089 | 73.562 | 1.00 | 26.36 |
| ATOM | 4510 | O | LYS | A | 565 | 17.648 | 49.782 | 74.673 | 1.00 | 21.19 |
| ATOM | 4511 | CB | LYS | A | 565 | 17.747 | 48.494 | 71.697 | 1.00 | 29.06 |
| ATOM | 4512 | CG | LYS | A | 565 | 18.864 | 47.715 | 72.359 | 1.00 | 23.89 |
| ATOM | 4513 | CD | LYS | A | 565 | 19.982 | 47.355 | 71.392 | 1.00 | 35.75 |
| ATOM | 4514 | CE | LYS | A | 565 | 20.796 | 46.153 | 71.842 | 1.00 | 36.31 |
| ATOM | 4515 | NZ | LYS | A | 565 | 22.233 | 46.311 | 71.577 | 1.00 | 44.91 |
| ATOM | 4516 | N | PHE | A | 566 | 17.321 | 51.321 | 73.073 | 1.00 | 22.91 |
| ATOM | 4517 | CA | PHE | A | 566 | 17.866 | 52.423 | 73.833 | 1.00 | 24.36 |
| ATOM | 4518 | C | PHE | A | 566 | 16.814 | 53.253 | 74.571 | 1.00 | 30.37 |
| ATOM | 4519 | O | PHE | A | 566 | 16.882 | 53.540 | 75.758 | 1.00 | 30.52 |
| ATOM | 4520 | CB | PHE | A | 566 | 18.622 | 53.355 | 72.857 | 1.00 | 25.26 |
| ATOM | 4521 | CG | PHE | A | 566 | 19.738 | 52.677 | 72.088 | 1.00 | 24.09 |
| ATOM | 4522 | CD1 | PHE | A | 566 | 20.392 | 51.559 | 72.609 | 1.00 | 23.51 |
| ATOM | 4523 | CD2 | PHE | A | 566 | 20.165 | 53.187 | 70.858 | 1.00 | 24.48 |
| ATOM | 4524 | CE1 | PHE | A | 566 | 21.432 | 50.958 | 71.900 | 1.00 | 23.73 |
| ATOM | 4525 | CE2 | PHE | A | 566 | 21.211 | 52.620 | 70.129 | 1.00 | 24.75 |
| ATOM | 4526 | CZ | PHE | A | 566 | 21.828 | 51.491 | 70.668 | 1.00 | 25.20 |
| ATOM | 4527 | N | THR | A | 567 | 15.860 | 53.679 | 73.801 | 1.00 | 31.17 |
| ATOM | 4528 | CA | THR | A | 567 | 14.783 | 54.533 | 74.239 | 1.00 | 31.74 |
| ATOM | 4529 | C | THR | A | 567 | 13.985 | 54.037 | 75.458 | 1.00 | 33.79 |
| ATOM | 4530 | O | THR | A | 567 | 13.657 | 54.818 | 76.373 | 1.00 | 26.01 |
| ATOM | 4531 | CB | THR | A | 567 | 13.895 | 54.892 | 73.017 | 1.00 | 36.51 |
| ATOM | 4532 | OG1 | THR | A | 567 | 14.527 | 55.844 | 72.138 | 1.00 | 24.12 |
| ATOM | 4533 | CG2 | THR | A | 567 | 12.522 | 55.361 | 73.473 | 1.00 | 34.94 |
| ATOM | 4534 | N | ARG | A | 568 | 13.663 | 52.726 | 75.469 | 1.00 | 30.74 |
| ATOM | 4535 | CA | ARG | A | 568 | 12.864 | 52.166 | 76.545 | 1.00 | 26.30 |
| ATOM | 4536 | C | ARG | A | 568 | 13.486 | 52.226 | 77.882 | 1.00 | 28.61 |
| ATOM | 4537 | O | ARG | A | 568 | 12.876 | 52.667 | 78.832 | 1.00 | 30.84 |
| ATOM | 4538 | CB | ARG | A | 568 | 12.315 | 50.798 | 76.251 | 1.00 | 18.11 |
| ATOM | 4539 | CG | ARG | A | 568 | 11.342 | 50.919 | 75.088 | 1.00 | 29.19 |
| ATOM | 4540 | CD | ARG | A | 568 | 10.550 | 49.660 | 74.799 | 1.00 | 19.19 |
| ATOM | 4541 | NE | ARG | A | 568 | 9.707 | 49.343 | 75.917 | 1.00 | 28.72 |
| ATOM | 4542 | CZ | ARG | A | 568 | 9.254 | 48.138 | 76.133 | 1.00 | 32.39 |
| ATOM | 4543 | NH1 | ARG | A | 568 | 9.528 | 47.144 | 75.291 | 1.00 | 29.79 |
| ATOM | 4544 | NH2 | ARG | A | 568 | 8.507 | 47.930 | 77.208 | 1.00 | 16.44 |
| ATOM | 4545 | N | PRO | A | 569 | 14.705 | 51.774 | 77.925 | 1.00 | 28.41 |
| ATOM | 4546 | CA | PRO | A | 569 | 15.447 | 51.709 | 79.154 | 1.00 | 28.01 |
| ATOM | 4547 | C | PRO | A | 569 | 15.890 | 53.042 | 79.663 | 1.00 | 32.18 |
| ATOM | 4548 | O | PRO | A | 569 | 15.974 | 53.256 | 80.869 | 1.00 | 29.25 |
| ATOM | 4549 | CB | PRO | A | 569 | 16.607 | 50.732 | 78.919 | 1.00 | 28.83 |
| ATOM | 4550 | CG | PRO | A | 569 | 16.330 | 50.034 | 77.592 | 1.00 | 32.42 |
| ATOM | 4551 | CD | PRO | A | 569 | 15.234 | 50.829 | 76.893 | 1.00 | 29.82 |
| ATOM | 4552 | N | LEU | A | 570 | 16.143 | 53.949 | 78.741 | 1.00 | 31.95 |
| ATOM | 4553 | CA | LEU | A | 570 | 16.560 | 55.270 | 79.160 | 1.00 | 35.11 |
| ATOM | 4554 | C | LEU | A | 570 | 15.407 | 55.962 | 79.897 | 1.00 | 36.24 |
| ATOM | 4555 | O | LEU | A | 570 | 15.532 | 56.506 | 81.028 | 1.00 | 34.02 |
| ATOM | 4556 | CB | LEU | A | 570 | 17.021 | 56.110 | 77.932 | 1.00 | 37.06 |
| ATOM | 4557 | CG | LEU | A | 570 | 18.387 | 55.701 | 77.343 | 1.00 | 41.39 |
| ATOM | 4558 | CD1 | LEU | A | 570 | 18.678 | 56.462 | 76.050 | 1.00 | 41.06 |
| ATOM | 4559 | CD2 | LEU | A | 570 | 19.497 | 55.984 | 78.353 | 1.00 | 37.42 |
| ATOM | 4560 | N | PHE | A | 571 | 14.262 | 55.944 | 79.211 | 1.00 | 30.06 |
| ATOM | 4561 | CA | PHE | A | 571 | 13.084 | 56.541 | 79.758 | 1.00 | 27.27 |

TABLE 9-continued

Structure coordinates of LTA₄ hydrolase-thiolamine complex
(The amino acid sequence set forth as residues 1-610 below correspond to SEQ ID NO:1.)

| ATOM | 4562 | C   | PHE | A | 571 | 12.813 | 55.899 | 81.095 | 1.00 | 25.94 |
|------|------|-----|-----|---|-----|--------|--------|--------|------|-------|
| ATOM | 4563 | O   | PHE | A | 571 | 12.399 | 56.536 | 82.030 | 1.00 | 27.16 |
| ATOM | 4564 | CB  | PHE | A | 571 | 11.888 | 56.375 | 78.828 | 1.00 | 27.60 |
| ATOM | 4565 | CG  | PHE | A | 571 | 11.546 | 57.616 | 78.042 | 1.00 | 27.70 |
| ATOM | 4566 | CD1 | PHE | A | 571 | 11.193 | 58.820 | 78.651 | 1.00 | 29.97 |
| ATOM | 4567 | CD2 | PHE | A | 571 | 11.557 | 57.570 | 76.651 | 1.00 | 28.87 |
| ATOM | 4568 | CE1 | PHE | A | 571 | 10.861 | 59.953 | 77.910 | 1.00 | 28.24 |
| ATOM | 4569 | CE2 | PHE | A | 571 | 11.233 | 58.684 | 75.886 | 1.00 | 30.43 |
| ATOM | 4570 | CZ  | PHE | A | 571 | 10.877 | 59.875 | 76.520 | 1.00 | 29.55 |
| ATOM | 4571 | N   | LYS | A | 572 | 13.089 | 54.618 | 81.196 | 1.00 | 22.77 |
| ATOM | 4572 | CA  | LYS | A | 572 | 12.845 | 53.946 | 82.468 | 1.00 | 25.43 |
| ATOM | 4573 | C   | LYS | A | 572 | 13.783 | 54.425 | 83.561 | 1.00 | 34.48 |
| ATOM | 4574 | O   | LYS | A | 572 | 13.351 | 54.920 | 84.602 | 1.00 | 35.11 |
| ATOM | 4575 | CB  | LYS | A | 572 | 12.736 | 52.428 | 82.392 | 1.00 | 26.89 |
| ATOM | 4576 | CG  | LYS | A | 572 | 11.303 | 51.911 | 82.326 | 1.00 | 44.03 |
| ATOM | 4577 | CD  | LYS | A | 572 | 11.219 | 50.426 | 81.922 | 1.00 | 57.87 |
| ATOM | 4578 | CE  | LYS | A | 572 | 10.975 | 50.204 | 80.422 | 1.00 | 65.25 |
| ATOM | 4579 | NZ  | LYS | A | 572 | 11.535 | 48.954 | 79.850 | 1.00 | 61.06 |
| ATOM | 4580 | N   | ASP | A | 573 | 15.074 | 54.292 | 83.319 | 1.00 | 31.94 |
| ATOM | 4581 | CA  | ASP | A | 573 | 16.032 | 54.751 | 84.291 | 1.00 | 30.55 |
| ATOM | 4582 | C   | ASP | A | 573 | 15.684 | 56.166 | 84.712 | 1.00 | 32.26 |
| ATOM | 4583 | O   | ASP | A | 573 | 15.693 | 56.453 | 85.895 | 1.00 | 31.85 |
| ATOM | 4584 | CB  | ASP | A | 573 | 17.453 | 54.788 | 83.718 | 1.00 | 32.87 |
| ATOM | 4585 | CG  | ASP | A | 573 | 18.051 | 53.443 | 83.487 | 1.00 | 33.43 |
| ATOM | 4586 | OD1 | ASP | A | 573 | 17.517 | 52.422 | 83.853 | 1.00 | 29.11 |
| ATOM | 4587 | OD2 | ASP | A | 573 | 19.206 | 53.501 | 82.864 | 1.00 | 35.22 |
| ATOM | 4588 | N   | LEU | A | 574 | 15.387 | 57.071 | 83.745 | 1.00 | 29.50 |
| ATOM | 4589 | CA  | LEU | A | 574 | 15.062 | 58.461 | 84.109 | 1.00 | 27.65 |
| ATOM | 4590 | C   | LEU | A | 574 | 13.887 | 58.577 | 85.075 | 1.00 | 32.88 |
| ATOM | 4591 | O   | LEU | A | 574 | 13.864 | 59.411 | 85.962 | 1.00 | 31.04 |
| ATOM | 4592 | CB  | LEU | A | 574 | 14.844 | 59.385 | 82.909 | 1.00 | 26.24 |
| ATOM | 4593 | CG  | LEU | A | 574 | 16.068 | 59.567 | 82.027 | 1.00 | 30.41 |
| ATOM | 4594 | CD1 | LEU | A | 574 | 15.644 | 59.922 | 80.582 | 1.00 | 28.47 |
| ATOM | 4595 | CD2 | LEU | A | 574 | 16.974 | 60.659 | 82.604 | 1.00 | 27.06 |
| ATOM | 4596 | N   | ALA | A | 575 | 12.895 | 57.723 | 84.874 | 1.00 | 32.80 |
| ATOM | 4597 | CA  | ALA | A | 575 | 11.709 | 57.713 | 85.711 | 1.00 | 31.11 |
| ATOM | 4598 | C   | ALA | A | 575 | 12.002 | 57.140 | 87.083 | 1.00 | 35.71 |
| ATOM | 4599 | O   | ALA | A | 575 | 11.309 | 57.362 | 88.055 | 1.00 | 39.91 |
| ATOM | 4600 | CB  | ALA | A | 575 | 10.631 | 56.890 | 85.024 | 1.00 | 30.56 |
| ATOM | 4601 | N   | ALA | A | 576 | 13.049 | 56.364 | 87.170 | 1.00 | 28.55 |
| ATOM | 4602 | CA  | ALA | A | 576 | 13.390 | 55.778 | 88.448 | 1.00 | 22.80 |
| ATOM | 4603 | C   | ALA | A | 576 | 14.258 | 56.724 | 89.266 | 1.00 | 26.93 |
| ATOM | 4604 | O   | ALA | A | 576 | 14.444 | 56.591 | 90.461 | 1.00 | 30.45 |
| ATOM | 4605 | CB  | ALA | A | 576 | 14.023 | 54.415 | 88.245 | 1.00 | 20.31 |
| ATOM | 4606 | N   | PHE | A | 577 | 14.787 | 57.686 | 88.584 | 1.00 | 22.86 |
| ATOM | 4607 | CA  | PHE | A | 577 | 15.604 | 58.673 | 89.194 | 1.00 | 22.71 |
| ATOM | 4608 | C   | PHE | A | 577 | 14.651 | 59.751 | 89.673 | 1.00 | 32.25 |
| ATOM | 4609 | O   | PHE | A | 577 | 13.930 | 60.334 | 88.863 | 1.00 | 34.17 |
| ATOM | 4610 | CB  | PHE | A | 577 | 16.640 | 59.188 | 88.154 | 1.00 | 22.89 |
| ATOM | 4611 | CG  | PHE | A | 577 | 17.704 | 60.076 | 88.741 | 1.00 | 23.16 |
| ATOM | 4612 | CD1 | PHE | A | 577 | 17.847 | 60.231 | 90.120 | 1.00 | 26.60 |
| ATOM | 4613 | CD2 | PHE | A | 577 | 18.561 | 60.806 | 87.914 | 1.00 | 23.46 |
| ATOM | 4614 | CE1 | PHE | A | 577 | 18.818 | 61.082 | 90.661 | 1.00 | 27.55 |
| ATOM | 4615 | CE2 | PHE | A | 577 | 19.543 | 61.657 | 88.431 | 1.00 | 23.88 |
| ATOM | 4616 | CZ  | PHE | A | 577 | 19.669 | 61.791 | 89.813 | 1.00 | 23.59 |
| ATOM | 4617 | N   | ASP | A | 578 | 14.625 | 60.008 | 90.990 | 1.00 | 29.70 |
| ATOM | 4618 | CA  | ASP | A | 578 | 13.717 | 61.018 | 91.533 | 1.00 | 28.65 |
| ATOM | 4619 | C   | ASP | A | 578 | 13.862 | 62.357 | 90.881 | 1.00 | 28.55 |
| ATOM | 4620 | O   | ASP | A | 578 | 12.877 | 63.004 | 90.599 | 1.00 | 32.65 |
| ATOM | 4621 | CB  | ASP | A | 578 | 13.804 | 61.192 | 93.055 | 1.00 | 32.60 |
| ATOM | 4622 | CG  | ASP | A | 578 | 15.153 | 61.647 | 93.550 | 1.00 | 53.21 |
| ATOM | 4623 | OD1 | ASP | A | 578 | 16.175 | 61.594 | 92.872 | 1.00 | 51.81 |
| ATOM | 4624 | OD2 | ASP | A | 578 | 15.104 | 62.072 | 94.796 | 1.00 | 64.93 |
| ATOM | 4625 | N   | LYS | A | 579 | 15.104 | 62.750 | 90.674 | 1.00 | 20.12 |
| ATOM | 4626 | CA  | LYS | A | 579 | 15.470 | 64.012 | 90.084 | 1.00 | 21.01 |
| ATOM | 4627 | C   | LYS | A | 579 | 14.934 | 64.270 | 88.697 | 1.00 | 30.25 |
| ATOM | 4628 | O   | LYS | A | 579 | 14.620 | 65.413 | 88.368 | 1.00 | 35.12 |
| ATOM | 4629 | CB  | LYS | A | 579 | 16.982 | 64.223 | 90.104 | 1.00 | 24.11 |
| ATOM | 4630 | CG  | LYS | A | 579 | 17.552 | 64.202 | 91.512 | 1.00 | 48.98 |
| ATOM | 4631 | CD  | LYS | A | 579 | 17.252 | 65.488 | 92.286 | 1.00 | 76.92 |
| ATOM | 4632 | CE  | LYS | A | 579 | 16.495 | 65.258 | 93.588 | 1.00 | 87.93 |
| ATOM | 4633 | NZ  | LYS | A | 579 | 17.282 | 64.550 | 94.611 | 1.00 | 89.56 |
| ATOM | 4634 | N   | SER | A | 580 | 14.838 | 63.244 | 87.857 | 1.00 | 28.66 |
| ATOM | 4635 | CA  | SER | A | 580 | 14.368 | 63.437 | 86.459 | 1.00 | 28.56 |
| ATOM | 4636 | C   | SER | A | 580 | 13.007 | 62.829 | 86.129 | 1.00 | 32.95 |

TABLE 9-continued

Structure coordinates of LTA₄ hydrolase-thiolamine complex
(The amino acid sequence set forth as residues 1-610 below correspond to SEQ ID NO:1.)

| ATOM | 4637 | O | SER | A | 580 | 12.561 | 62.870 | 84.992 | 1.00 | 35.30 |
|------|------|------|-----|---|-----|--------|--------|--------|------|-------|
| ATOM | 4638 | CB | SER | A | 580 | 15.337 | 62.774 | 85.517 | 1.00 | 25.69 |
| ATOM | 4639 | OG | SER | A | 580 | 15.476 | 61.424 | 85.969 | 1.00 | 25.12 |
| ATOM | 4640 | N | HIS | A | 581 | 12.364 | 62.230 | 87.098 | 1.00 | 26.81 |
| ATOM | 4641 | CA | HIS | A | 581 | 11.100 | 61.595 | 86.850 | 1.00 | 28.26 |
| ATOM | 4642 | C | HIS | A | 581 | 10.067 | 62.399 | 86.042 | 1.00 | 36.50 |
| ATOM | 4643 | O | HIS | A | 581 | 9.644 | 62.031 | 84.927 | 1.00 | 34.71 |
| ATOM | 4644 | CB | HIS | A | 581 | 10.553 | 61.047 | 88.152 | 1.00 | 29.76 |
| ATOM | 4645 | CG | HIS | A | 581 | 9.148 | 60.588 | 87.968 | 1.00 | 35.31 |
| ATOM | 4646 | ND1 | HIS | A | 581 | 8.111 | 61.494 | 87.899 | 1.00 | 38.92 |
| ATOM | 4647 | CD2 | HIS | A | 581 | 8.634 | 59.338 | 87.891 | 1.00 | 36.84 |
| ATOM | 4648 | CE1 | HIS | A | 581 | 6.999 | 60.783 | 87.817 | 1.00 | 38.85 |
| ATOM | 4649 | NE2 | HIS | A | 581 | 7.280 | 59.488 | 87.734 | 1.00 | 38.13 |
| ATOM | 4650 | N | ASP | A | 582 | 9.656 | 63.502 | 86.639 | 1.00 | 35.79 |
| ATOM | 4651 | CA | ASP | A | 582 | 8.680 | 64.388 | 86.064 | 1.00 | 34.39 |
| ATOM | 4652 | C | ASP | A | 582 | 9.035 | 64.807 | 84.659 | 1.00 | 37.82 |
| ATOM | 4653 | O | ASP | A | 582 | 8.220 | 64.704 | 83.735 | 1.00 | 37.01 |
| ATOM | 4654 | CB | ASP | A | 582 | 8.428 | 65.552 | 87.001 | 1.00 | 36.57 |
| ATOM | 4655 | CG | ASP | A | 582 | 7.597 | 65.110 | 88.167 | 1.00 | 58.09 |
| ATOM | 4656 | OD1 | ASP | A | 582 | 6.708 | 64.289 | 88.070 | 1.00 | 63.17 |
| ATOM | 4657 | OD2 | ASP | A | 582 | 7.920 | 65.708 | 89.279 | 1.00 | 73.96 |
| ATOM | 4658 | N | GLN | A | 583 | 10.272 | 65.255 | 84.488 | 1.00 | 32.88 |
| ATOM | 4659 | CA | GLN | A | 583 | 10.750 | 65.648 | 83.169 | 1.00 | 29.92 |
| ATOM | 4660 | C | GLN | A | 583 | 10.690 | 64.464 | 82.168 | 1.00 | 37.12 |
| ATOM | 4661 | O | GLN | A | 583 | 10.362 | 64.624 | 80.990 | 1.00 | 37.42 |
| ATOM | 4662 | CB | GLN | A | 583 | 12.172 | 66.182 | 83.287 | 1.00 | 28.54 |
| ATOM | 4663 | CG | GLN | A | 583 | 12.704 | 66.648 | 81.929 | 1.00 | 48.12 |
| ATOM | 4664 | CD | GLN | A | 583 | 13.957 | 67.475 | 82.081 | 1.00 | 64.09 |
| ATOM | 4665 | OE1 | GLN | A | 583 | 14.736 | 67.248 | 83.015 | 1.00 | 59.43 |
| ATOM | 4666 | NE2 | GLN | A | 583 | 14.130 | 68.461 | 81.201 | 1.00 | 55.34 |
| ATOM | 4667 | N | ALA | A | 584 | 11.009 | 63.250 | 82.638 | 1.00 | 33.22 |
| ATOM | 4668 | CA | ALA | A | 584 | 10.964 | 62.062 | 81.780 | 1.00 | 32.22 |
| ATOM | 4669 | C | ALA | A | 584 | 9.557 | 61.841 | 81.315 | 1.00 | 37.45 |
| ATOM | 4670 | O | ALA | A | 584 | 9.319 | 61.526 | 80.152 | 1.00 | 40.05 |
| ATOM | 4671 | CB | ALA | A | 584 | 11.389 | 60.793 | 82.504 | 1.00 | 31.62 |
| ATOM | 4672 | N | VAL | A | 585 | 8.622 | 61.995 | 82.261 | 1.00 | 30.42 |
| ATOM | 4673 | CA | VAL | A | 585 | 7.217 | 61.806 | 81.946 | 1.00 | 29.16 |
| ATOM | 4674 | C | VAL | A | 585 | 6.647 | 62.909 | 81.024 | 1.00 | 36.53 |
| ATOM | 4675 | O | VAL | A | 585 | 5.933 | 62.690 | 80.052 | 1.00 | 36.22 |
| ATOM | 4676 | CB | VAL | A | 585 | 6.408 | 61.567 | 83.209 | 1.00 | 29.78 |
| ATOM | 4677 | CG1 | VAL | A | 585 | 4.959 | 61.947 | 82.955 | 1.00 | 30.03 |
| ATOM | 4678 | CG2 | VAL | A | 585 | 6.464 | 60.085 | 83.539 | 1.00 | 27.82 |
| ATOM | 4679 | N | ARG | A | 586 | 7.000 | 64.123 | 81.333 | 1.00 | 35.76 |
| ATOM | 4680 | CA | ARG | A | 586 | 6.574 | 65.242 | 80.562 | 1.00 | 36.20 |
| ATOM | 4681 | C | ARG | A | 586 | 7.146 | 65.125 | 79.180 | 1.00 | 44.65 |
| ATOM | 4682 | O | ARG | A | 586 | 6.459 | 65.355 | 78.197 | 1.00 | 48.32 |
| ATOM | 4683 | CB | ARG | A | 586 | 7.116 | 66.498 | 81.208 | 1.00 | 38.13 |
| ATOM | 4684 | CG | ARG | A | 586 | 6.744 | 67.799 | 80.518 | 1.00 | 61.01 |
| ATOM | 4685 | CD | ARG | A | 586 | 7.077 | 69.029 | 81.354 | 1.00 | 73.03 |
| ATOM | 4686 | NE | ARG | A | 586 | 8.491 | 69.128 | 81.711 | 1.00 | 86.05 |
| ATOM | 4687 | CZ | ARG | A | 586 | 8.961 | 69.001 | 82.957 | 1.00 | 98.46 |
| ATOM | 4688 | NH1 | ARG | A | 586 | 8.167 | 68.741 | 84.004 | 1.00 | 79.75 |
| ATOM | 4689 | NH2 | ARG | A | 586 | 10.268 | 69.103 | 83.159 | 1.00 | 77.55 |
| ATOM | 4690 | N | THR | A | 587 | 8.426 | 64.769 | 79.110 | 1.00 | 39.49 |
| ATOM | 4691 | CA | THR | A | 587 | 9.099 | 64.646 | 77.822 | 1.00 | 36.80 |
| ATOM | 4692 | C | THR | A | 587 | 8.387 | 63.690 | 76.869 | 1.00 | 37.11 |
| ATOM | 4693 | O | THR | A | 587 | 8.229 | 63.931 | 75.678 | 1.00 | 36.91 |
| ATOM | 4694 | CB | THR | A | 587 | 10.634 | 64.384 | 77.917 | 1.00 | 39.40 |
| ATOM | 4695 | OG1 | THR | A | 587 | 11.303 | 65.334 | 78.717 | 1.00 | 46.27 |
| ATOM | 4696 | CG2 | THR | A | 587 | 11.233 | 64.460 | 76.529 | 1.00 | 32.60 |
| ATOM | 4697 | N | TYR | A | 588 | 7.934 | 62.587 | 77.393 | 1.00 | 33.33 |
| ATOM | 4698 | CA | TYR | A | 588 | 7.252 | 61.639 | 76.555 | 1.00 | 33.94 |
| ATOM | 4699 | C | TYR | A | 588 | 5.890 | 62.146 | 76.090 | 1.00 | 37.02 |
| ATOM | 4700 | O | TYR | A | 588 | 5.428 | 61.880 | 74.988 | 1.00 | 41.55 |
| ATOM | 4701 | CB | TYR | A | 588 | 7.042 | 60.383 | 77.396 | 1.00 | 33.96 |
| ATOM | 4702 | CG | TYR | A | 588 | 6.017 | 59.440 | 76.851 | 1.00 | 33.08 |
| ATOM | 4703 | CD1 | TYR | A | 588 | 6.331 | 58.640 | 75.754 | 1.00 | 35.64 |
| ATOM | 4704 | CD2 | TYR | A | 588 | 4.758 | 59.288 | 77.437 | 1.00 | 34.09 |
| ATOM | 4705 | CE1 | TYR | A | 588 | 5.424 | 57.703 | 75.251 | 1.00 | 34.36 |
| ATOM | 4706 | CE2 | TYR | A | 588 | 3.822 | 58.378 | 76.932 | 1.00 | 34.05 |
| ATOM | 4707 | CZ | TYR | A | 588 | 4.162 | 57.581 | 75.834 | 1.00 | 33.89 |
| ATOM | 4708 | OH | TYR | A | 588 | 3.275 | 56.674 | 75.322 | 1.00 | 23.43 |
| ATOM | 4709 | N | GLN | A | 589 | 5.216 | 62.853 | 76.959 | 1.00 | 25.04 |
| ATOM | 4710 | CA | GLN | A | 589 | 3.914 | 63.339 | 76.612 | 1.00 | 21.41 |
| ATOM | 4711 | C | GLN | A | 589 | 3.992 | 64.304 | 75.481 | 1.00 | 28.78 |
| ATOM | 4712 | O | GLN | A | 589 | 3.099 | 64.410 | 74.678 | 1.00 | 31.24 |

TABLE 9-continued

Structure coordinates of LTA₄ hydrolase-thiolamine complex
(The amino acid sequence set forth as residues 1-610 below correspond to SEQ ID NO:1.)

| ATOM | 4713 | CB | GLN | A | 589 | 3.241 | 63.935 | 77.832 | 1.00 | 21.73 |
|------|------|-----|-----|---|-----|--------|--------|--------|------|-------|
| ATOM | 4714 | CG | GLN | A | 589 | 2.878 | 62.820 | 78.827 | 1.00 | 22.30 |
| ATOM | 4715 | CD | GLN | A | 589 | 1.695 | 62.069 | 78.293 | 1.00 | 52.83 |
| ATOM | 4716 | OE1 | GLN | A | 589 | 1.511 | 62.003 | 77.075 | 1.00 | 60.15 |
| ATOM | 4717 | NE2 | GLN | A | 589 | 0.864 | 61.542 | 79.182 | 1.00 | 53.04 |
| ATOM | 4718 | N | GLU | A | 590 | 5.099 | 65.001 | 75.409 | 1.00 | 28.36 |
| ATOM | 4719 | CA | GLU | A | 590 | 5.276 | 65.966 | 74.355 | 1.00 | 26.87 |
| ATOM | 4720 | C | GLU | A | 590 | 5.840 | 65.338 | 73.140 | 1.00 | 35.10 |
| ATOM | 4721 | O | GLU | A | 590 | 6.096 | 66.059 | 72.171 | 1.00 | 40.28 |
| ATOM | 4722 | CB | GLU | A | 590 | 6.323 | 67.011 | 74.747 | 1.00 | 27.61 |
| ATOM | 4723 | CG | GLU | A | 590 | 5.846 | 67.954 | 75.847 | 1.00 | 44.11 |
| ATOM | 4724 | CD | GLU | A | 590 | 6.981 | 68.759 | 76.388 | 1.00 | 75.35 |
| ATOM | 4725 | OE1 | GLU | A | 590 | 8.120 | 68.689 | 75.925 | 1.00 | 54.78 |
| ATOM | 4726 | OE2 | GLU | A | 590 | 6.609 | 69.516 | 77.403 | 1.00 | 59.46 |
| ATOM | 4727 | N | HIS | A | 591 | 6.091 | 64.031 | 73.207 | 1.00 | 27.57 |
| ATOM | 4728 | CA | HIS | A | 591 | 6.713 | 63.384 | 72.086 | 1.00 | 25.58 |
| ATOM | 4729 | C | HIS | A | 591 | 5.928 | 62.249 | 71.578 | 1.00 | 32.34 |
| ATOM | 4730 | O | HIS | A | 591 | 6.184 | 61.751 | 70.496 | 1.00 | 38.53 |
| ATOM | 4731 | CB | HIS | A | 591 | 8.094 | 62.851 | 72.487 | 1.00 | 26.32 |
| ATOM | 4732 | CG | HIS | A | 591 | 9.219 | 63.809 | 72.268 | 1.00 | 31.06 |
| ATOM | 4733 | ND1 | HIS | A | 591 | 9.630 | 64.680 | 73.255 | 1.00 | 32.65 |
| ATOM | 4734 | CD2 | HIS | A | 591 | 9.998 | 64.032 | 71.169 | 1.00 | 34.91 |
| ATOM | 4735 | CE1 | HIS | A | 591 | 10.635 | 65.404 | 72.756 | 1.00 | 32.01 |
| ATOM | 4736 | NE2 | HIS | A | 591 | 10.884 | 65.037 | 71.508 | 1.00 | 33.36 |
| ATOM | 4737 | N | LYS | A | 592 | 4.978 | 61.812 | 72.337 | 1.00 | 28.34 |
| ATOM | 4738 | CA | LYS | A | 592 | 4.254 | 60.643 | 71.849 | 1.00 | 29.96 |
| ATOM | 4739 | C | LYS | A | 592 | 3.654 | 60.692 | 70.432 | 1.00 | 33.41 |
| ATOM | 4740 | O | LYS | A | 592 | 3.819 | 59.769 | 69.592 | 1.00 | 29.05 |
| ATOM | 4741 | CB | LYS | A | 592 | 3.362 | 59.983 | 72.888 | 1.00 | 32.83 |
| ATOM | 4742 | CG | LYS | A | 592 | 2.435 | 60.930 | 73.615 | 1.00 | 31.14 |
| ATOM | 4743 | CD | LYS | A | 592 | 1.677 | 60.203 | 74.704 | 1.00 | 38.97 |
| ATOM | 4744 | CE | LYS | A | 592 | 0.253 | 60.691 | 74.890 | 1.00 | 25.02 |
| ATOM | 4745 | NZ | LYS | A | 592 | −0.157 | 60.632 | 76.302 | 1.00 | 45.83 |
| ATOM | 4746 | N | ALA | A | 593 | 2.934 | 61.782 | 70.187 | 1.00 | 30.97 |
| ATOM | 4747 | CA | ALA | A | 593 | 2.260 | 62.026 | 68.917 | 1.00 | 28.47 |
| ATOM | 4748 | C | ALA | A | 593 | 3.169 | 61.943 | 67.703 | 1.00 | 32.66 |
| ATOM | 4749 | O | ALA | A | 593 | 2.775 | 61.488 | 66.639 | 1.00 | 36.77 |
| ATOM | 4750 | CB | ALA | A | 593 | 1.571 | 63.379 | 60.954 | 1.00 | 27.35 |
| ATOM | 4751 | N | SER | A | 594 | 4.384 | 62.405 | 67.869 | 1.00 | 27.08 |
| ATOM | 4752 | CA | SER | A | 594 | 5.345 | 62.417 | 66.794 | 1.00 | 30.04 |
| ATOM | 4753 | C | SER | A | 594 | 6.185 | 61.169 | 66.760 | 1.00 | 36.80 |
| ATOM | 4754 | O | SER | A | 594 | 6.995 | 60.991 | 65.848 | 1.00 | 37.94 |
| ATOM | 4755 | CB | SER | A | 594 | 6.292 | 63.596 | 66.977 | 1.00 | 37.69 |
| ATOM | 4756 | OG | SER | A | 594 | 7.199 | 63.340 | 68.043 | 1.00 | 54.55 |
| ATOM | 4757 | N | MET | A | 595 | 6.015 | 60.340 | 67.776 | 1.00 | 33.12 |
| ATOM | 4758 | CA | MET | A | 595 | 6.794 | 59.115 | 67.898 | 1.00 | 33.96 |
| ATOM | 4759 | C | MET | A | 595 | 6.200 | 57.936 | 67.125 | 1.00 | 40.91 |
| ATOM | 4760 | O | MET | A | 595 | 5.019 | 57.927 | 66.809 | 1.00 | 50.82 |
| ATOM | 4761 | CB | MET | A | 595 | 6.716 | 58.686 | 69.382 | 1.00 | 34.22 |
| ATOM | 4762 | CG | MET | A | 595 | 7.621 | 59.371 | 70.399 | 1.00 | 34.61 |
| ATOM | 4763 | SD | MET | A | 595 | 7.606 | 58.440 | 71.962 | 1.00 | 39.24 |
| ATOM | 4764 | CE | MET | A | 595 | 7.145 | 59.779 | 73.084 | 1.00 | 36.72 |
| ATOM | 4765 | N | HIS | A | 596 | 6.987 | 56.897 | 66.886 | 1.00 | 26.19 |
| ATOM | 4766 | CA | HIS | A | 596 | 6.496 | 55.657 | 66.246 | 1.00 | 23.19 |
| ATOM | 4767 | C | HIS | A | 596 | 5.438 | 54.964 | 67.120 | 1.00 | 25.21 |
| ATOM | 4768 | O | HIS | A | 596 | 5.621 | 54.728 | 68.311 | 1.00 | 22.59 |
| ATOM | 4769 | CB | HIS | A | 596 | 7.657 | 54.655 | 66.077 | 1.00 | 24.43 |
| ATOM | 4770 | CG | HIS | A | 596 | 7.222 | 53.366 | 65.493 | 1.00 | 30.13 |
| ATOM | 4771 | ND1 | HIS | A | 596 | 7.606 | 52.995 | 64.214 | 1.00 | 32.86 |
| ATOM | 4772 | CD2 | HIS | A | 596 | 6.421 | 52.385 | 66.005 | 1.00 | 30.90 |
| ATOM | 4773 | CE1 | HIS | A | 596 | 7.047 | 51.824 | 63.974 | 1.00 | 30.05 |
| ATOM | 4774 | NE2 | HIS | A | 596 | 6.325 | 51.441 | 65.031 | 1.00 | 30.20 |
| ATOM | 4775 | N | PRO | A | 597 | 4.334 | 54.587 | 66.512 | 1.00 | 27.08 |
| ATOM | 4776 | CA | PRO | A | 597 | 3.217 | 53.912 | 67.173 | 1.00 | 26.35 |
| ATOM | 4777 | C | PRO | A | 597 | 3.513 | 52.851 | 68.248 | 1.00 | 37.51 |
| ATOM | 4778 | O | PRO | A | 597 | 2.979 | 52.900 | 69.348 | 1.00 | 41.16 |
| ATOM | 4779 | CB | PRO | A | 597 | 2.334 | 53.307 | 66.076 | 1.00 | 26.17 |
| ATOM | 4780 | CG | PRO | A | 597 | 3.140 | 53.426 | 64.792 | 1.00 | 34.56 |
| ATOM | 4781 | CD | PRO | A | 597 | 4.285 | 54.418 | 65.050 | 1.00 | 30.06 |
| ATOM | 4782 | N | VAL | A | 598 | 4.311 | 51.850 | 67.939 | 1.00 | 33.08 |
| ATOM | 4783 | CA | VAL | A | 598 | 4.585 | 50.802 | 68.911 | 1.00 | 28.39 |
| ATOM | 4784 | C | VAL | A | 598 | 5.444 | 51.307 | 70.029 | 1.00 | 29.32 |
| ATOM | 4785 | O | VAL | A | 598 | 5.168 | 51.096 | 71.217 | 1.00 | 29.13 |
| ATOM | 4786 | CB | VAL | A | 598 | 5.196 | 49.599 | 68.210 | 1.00 | 27.99 |
| ATOM | 4787 | CG1 | VAL | A | 598 | 5.806 | 48.608 | 69.187 | 1.00 | 26.98 |
| ATOM | 4788 | CG2 | VAL | A | 598 | 4.144 | 48.944 | 67.296 | 1.00 | 26.13 |

TABLE 9-continued

Structure coordinates of LTA$_4$ hydrolase-thiolamine complex
(The amino acid sequence set forth as residues 1-610 below correspond to SEQ ID NO:1.)

| ATOM | 4789 | N   | THR | A | 599 | 6.480  | 52.021 | 69.635 | 1.00 | 26.10  |
|------|------|-----|-----|---|-----|--------|--------|--------|------|--------|
| ATOM | 4790 | CA  | THR | A | 599 | 7.370  | 52.573 | 70.631 | 1.00 | 26.95  |
| ATOM | 4791 | C   | THR | A | 599 | 6.650  | 53.404 | 71.669 | 1.00 | 30.81  |
| ATOM | 4792 | O   | THR | A | 599 | 6.863  | 53.327 | 72.871 | 1.00 | 31.33  |
| ATOM | 4793 | CB  | THR | A | 599 | 8.413  | 53.455 | 69.975 | 1.00 | 26.67  |
| ATOM | 4794 | OG1 | THR | A | 599 | 9.092  | 52.725 | 68.958 | 1.00 | 27.92  |
| ATOM | 4795 | CG2 | THR | A | 599 | 9.358  | 53.884 | 71.092 | 1.00 | 20.69  |
| ATOM | 4796 | N   | ALA | A | 600 | 5.801  | 54.218 | 71.135 | 1.00 | 26.41  |
| ATOM | 4797 | CA  | ALA | A | 600 | 4.997  | 55.111 | 71.878 | 1.00 | 26.39  |
| ATOM | 4798 | C   | ALA | A | 600 | 4.176  | 54.339 | 72.860 | 1.00 | 32.00  |
| ATOM | 4799 | O   | ALA | A | 600 | 4.162  | 54.597 | 74.057 | 1.00 | 35.37  |
| ATOM | 4800 | CB  | ALA | A | 600 | 4.090  | 55.774 | 70.856 | 1.00 | 27.56  |
| ATOM | 4801 | N   | MET | A | 601 | 3.470  | 53.380 | 72.332 | 1.00 | 26.26  |
| ATOM | 4802 | CA  | MET | A | 601 | 2.627  | 52.585 | 73.167 | 1.00 | 26.60  |
| ATOM | 4803 | C   | MET | A | 601 | 3.439  | 51.909 | 74.225 | 1.00 | 25.73  |
| ATOM | 4804 | O   | MET | A | 601 | 3.099  | 51.964 | 75.381 | 1.00 | 25.77  |
| ATOM | 4805 | CB  | MET | A | 601 | 1.752  | 51.625 | 72.353 | 1.00 | 30.49  |
| ATOM | 4806 | CG  | MET | A | 601 | 1.024  | 50.594 | 73.176 | 1.00 | 36.00  |
| ATOM | 4807 | SD  | MET | A | 601 | 2.043  | 49.146 | 73.554 | 1.00 | 42.41  |
| ATOM | 4808 | CE  | MET | A | 601 | 1.693  | 48.128 | 72.111 | 1.00 | 37.75  |
| ATOM | 4809 | N   | LEU | A | 602 | 4.538  | 51.310 | 73.848 | 1.00 | 21.64  |
| ATOM | 4810 | CA  | LEU | A | 602 | 5.339  | 50.671 | 74.873 | 1.00 | 22.59  |
| ATOM | 4811 | C   | LEU | A | 602 | 6.010  | 51.650 | 75.870 | 1.00 | 29.61  |
| ATOM | 4812 | O   | LEU | A | 602 | 6.137  | 51.346 | 77.039 | 1.00 | 27.62  |
| ATOM | 4813 | CB  | LEU | A | 602 | 6.418  | 49.760 | 74.294 | 1.00 | 22.14  |
| ATOM | 4814 | CG  | LEU | A | 602 | 5.916  | 48.529 | 73.575 | 1.00 | 25.78  |
| ATOM | 4815 | CD1 | LEU | A | 602 | 7.021  | 48.087 | 72.609 | 1.00 | 26.02  |
| ATOM | 4816 | CD2 | LEU | A | 602 | 5.651  | 47.445 | 74.613 | 1.00 | 21.01  |
| ATOM | 4817 | N   | VAL | A | 603 | 6.508  | 52.805 | 75.445 | 1.00 | 27.15  |
| ATOM | 4818 | CA  | VAL | A | 603 | 7.145  | 53.684 | 76.413 | 1.00 | 26.39  |
| ATOM | 4819 | C   | VAL | A | 603 | 6.121  | 54.157 | 77.438 | 1.00 | 32.60  |
| ATOM | 4820 | O   | VAL | A | 603 | 6.436  | 54.235 | 78.621 | 1.00 | 35.31  |
| ATOM | 4821 | CB  | VAL | A | 603 | 7.917  | 54.832 | 75.760 | 1.00 | 27.78  |
| ATOM | 4822 | CG1 | VAL | A | 603 | 8.286  | 55.887 | 76.774 | 1.00 | 24.54  |
| ATOM | 4823 | CG2 | VAL | A | 603 | 9.172  | 54.286 | 75.094 | 1.00 | 27.29  |
| ATOM | 4824 | N   | GLY | A | 604 | 4.878  | 54.434 | 76.976 | 1.00 | 27.44  |
| ATOM | 4825 | CA  | GLY | A | 604 | 3.759  | 54.856 | 77.819 | 1.00 | 27.58  |
| ATOM | 4826 | C   | GLY | A | 604 | 3.418  | 53.797 | 78.905 | 1.00 | 37.00  |
| ATOM | 4827 | O   | GLY | A | 604 | 3.088  | 54.102 | 80.072 | 1.00 | 36.56  |
| ATOM | 4828 | N   | LYS | A | 605 | 3.511  | 52.522 | 78.520 | 1.00 | 32.54  |
| ATOM | 4829 | CA  | LYS | A | 605 | 3.250  | 51.415 | 79.459 | 1.00 | 32.17  |
| ATOM | 4830 | C   | LYS | A | 605 | 4.312  | 51.405 | 80.539 | 1.00 | 35.15  |
| ATOM | 4831 | O   | LYS | A | 605 | 4.040  | 51.347 | 81.734 | 1.00 | 33.77  |
| ATOM | 4832 | CB  | LYS | A | 605 | 3.231  | 50.034 | 78.782 | 1.00 | 33.59  |
| ATOM | 4833 | CG  | LYS | A | 605 | 1.837  | 49.438 | 78.576 | 1.00 | 42.45  |
| ATOM | 4834 | CD  | LYS | A | 605 | 1.846  | 48.115 | 77.815 | 1.00 | 60.83  |
| ATOM | 4835 | CE  | LYS | A | 605 | 1.223  | 46.946 | 78.578 | 1.00 | 86.38  |
| ATOM | 4836 | NZ  | LYS | A | 605 | 2.188  | 46.179 | 79.385 | 1.00 | 93.05  |
| ATOM | 4837 | N   | ASP | A | 606 | 5.544  | 51.470 | 80.056 | 1.00 | 32.91  |
| ATOM | 4838 | CA  | ASP | A | 606 | 6.715  | 51.510 | 80.878 | 1.00 | 31.82  |
| ATOM | 4839 | C   | ASP | A | 606 | 6.549  | 52.667 | 81.833 | 1.00 | 36.24  |
| ATOM | 4840 | O   | ASP | A | 606 | 6.652  | 52.503 | 83.045 | 1.00 | 35.19  |
| ATOM | 4841 | CB  | ASP | A | 606 | 7.983  | 51.702 | 80.027 | 1.00 | 32.52  |
| ATOM | 4842 | CG  | ASP | A | 606 | 8.302  | 50.525 | 79.134 | 1.00 | 40.01  |
| ATOM | 4843 | OD1 | ASP | A | 606 | 7.934  | 49.378 | 79.344 | 1.00 | 40.49  |
| ATOM | 4844 | OD2 | ASP | A | 606 | 9.038  | 50.869 | 78.111 | 1.00 | 41.73  |
| ATOM | 4845 | N   | LEU | A | 607 | 6.240  | 53.833 | 81.266 | 1.00 | 34.45  |
| ATOM | 4846 | CA  | LEU | A | 607 | 6.152  | 54.972 | 82.185 | 1.00 | 36.03  |
| ATOM | 4847 | C   | LEU | A | 607 | 4.814  | 55.018 | 82.968 | 1.00 | 42.35  |
| ATOM | 4848 | O   | LEU | A | 607 | 4.600  | 55.872 | 83.824 | 1.00 | 41.57  |
| ATOM | 4849 | CB  | LEU | A | 607 | 6.321  | 56.250 | 81.364 | 1.00 | 36.90  |
| ATOM | 4850 | CG  | LEU | A | 607 | 7.779  | 56.490 | 80.974 | 1.00 | 38.75  |
| ATOM | 4851 | CD1 | LEU | A | 607 | 7.954  | 57.746 | 80.132 | 1.00 | 34.34  |
| ATOM | 4852 | CD2 | LEU | A | 607 | 8.695  | 56.653 | 82.183 | 1.00 | 41.97  |
| ATOM | 4853 | N   | LYS | A | 608 | 3.895  | 54.062 | 82.586 | 1.00 | 45.01  |
| ATOM | 4854 | CA  | LYS | A | 608 | 2.576  | 53.874 | 83.264 | 1.00 | 46.99  |
| ATOM | 4855 | C   | LYS | A | 608 | 1.625  | 55.088 | 83.181 | 1.00 | 51.31  |
| ATOM | 4856 | O   | LYS | A | 608 | 0.988  | 55.467 | 84.151 | 1.00 | 51.35  |
| ATOM | 4857 | CB  | LYS | A | 608 | 2.813  | 53.510 | 84.750 | 1.00 | 50.83  |
| ATOM | 4858 | CG  | LYS | A | 608 | 3.331  | 52.093 | 84.949 | 1.00 | 63.57  |
| ATOM | 4859 | CD  | LYS | A | 608 | 4.405  | 52.019 | 86.031 | 1.00 | 77.03  |
| ATOM | 4860 | CE  | LYS | A | 608 | 5.341  | 50.825 | 85.858 | 1.00 | 96.40  |
| ATOM | 4861 | NZ  | LYS | A | 608 | 6.034  | 50.554 | 87.117 | 1.00 | 100.00 |
| ATOM | 4862 | N   | VAL | A | 609 | 1.560  | 55.724 | 81.991 | 1.00 | 50.28  |
| ATOM | 4863 | CA  | VAL | A | 609 | 0.688  | 56.901 | 81.852 | 1.00 | 50.89  |
| ATOM | 4864 | C   | VAL | A | 609 | -0.494 | 56.660 | 80.897 | 1.00 | 60.23  |

TABLE 9-continued

Structure coordinates of LTA₄ hydrolase-thiolamine complex
(The amino acid sequence set forth as residues 1-610 below correspond to SEQ ID NO:1.)

| ATOM | 4865 | O | VAL | A | 609 | −1.640 | 56.952 | 81.194 | 1.00 | 63.02 |
|---|---|---|---|---|---|---|---|---|---|---|
| ATOM | 4866 | CB | VAL | A | 609 | 1.533 | 58.091 | 81.364 | 1.00 | 54.72 |
| ATOM | 4867 | CG1 | VAL | A | 609 | 1.996 | 58.926 | 82.551 | 1.00 | 54.87 |
| ATOM | 4868 | CG2 | VAL | A | 609 | 2.744 | 57.607 | 80.605 | 1.00 | 54.46 |
| ATOM | 4869 | N | ASP | A | 610 | −0.177 | 56.152 | 79.687 | 1.00 | 58.84 |
| ATOM | 4870 | CA | ASP | A | 610 | −1.238 | 55.949 | 78.699 | 1.00 | 99.84 |
| ATOM | 4871 | C | ASP | A | 610 | −2.062 | 54.695 | 79.001 | 1.00 | 100.00 |
| ATOM | 4872 | O | ASP | A | 610 | −3.247 | 54.615 | 78.711 | 1.00 | 69.75 |
| ATOM | 4873 | CB | ASP | A | 610 | −0.594 | 55.818 | 77.316 | 1.00 | 100.00 |
| ATOM | 4874 | CG | ASP | A | 610 | −0.637 | 57.161 | 76.610 | 1.00 | 92.61 |
| ATOM | 4875 | OD1 | ASP | A | 610 | −1.449 | 57.999 | 77.018 | 1.00 | 90.49 |
| ATOM | 4876 | OD2 | ASP | A | 610 | 0.134 | 57.355 | 75.670 | 1.00 | 89.29 |
| ATOM | 4877 | ZN2+ | ZN | Z | 1 | 17.003 | 38.803 | 64.180 | 1.00 | 28.37 |
| ATOM | 4878 | YB3+ | YB | Y | 1 | 43.011 | 51.068 | 98.864 | 1.00 | 34.70 |
| ATOM | 4879 | YB3+ | YB | Y | 2 | −13.786 | 56.771 | 52.040 | 0.50 | 57.25 |
| ATOM | 4880 | YB3+ | YB | Y | 3 | −10.537 | 57.860 | 52.381 | 0.50 | 36.57 |
| ATOM | 4881 | CG | IMD | I | 1 | 26.249 | 42.039 | 80.754 | 1.00 | 28.44 |
| ATOM | 4882 | ND1 | IMD | I | 1 | 26.057 | 42.254 | 79.400 | 1.00 | 28.35 |
| ATOM | 4883 | CD2 | IMD | I | 1 | 27.562 | 41.726 | 80.902 | 1.00 | 17.99 |
| ATOM | 4884 | CE1 | IMD | I | 1 | 27.201 | 42.063 | 78.760 | 1.00 | 29.77 |
| ATOM | 4885 | NE2 | IMD | I | 1 | 28.130 | 41.745 | 79.647 | 1.00 | 35.02 |
| ATOM | 4886 | CB | ACE | C | 1 | 13.616 | 12.333 | 68.475 | 1.00 | 59.33 |
| ATOM | 4887 | CG | ACE | C | 1 | 12.871 | 13.331 | 69.306 | 1.00 | 42.98 |
| ATOM | 4888 | OD1 | ACE | C | 1 | 12.958 | 14.536 | 69.146 | 1.00 | 39.66 |
| ATOM | 4889 | OD2 | ACE | C | 1 | 12.142 | 12.759 | 70.236 | 1.00 | 47.21 |
| ATOM | 4890 | C6 | INH | V | 1 | 7.422 | 38.514 | 70.154 | 1.00 | 38.70 |
| ATOM | 4891 | C5 | INH | V | 1 | 7.571 | 39.820 | 69.689 | 1.00 | 37.05 |
| ATOM | 4892 | C4 | INH | V | 1 | 7.901 | 40.062 | 68.354 | 1.00 | 31.41 |
| ATOM | 4893 | C3 | INH | V | 1 | 8.091 | 38.967 | 67.505 | 1.00 | 35.48 |
| ATOM | 4894 | C2 | INH | V | 1 | 7.944 | 37.650 | 67.949 | 1.00 | 31.90 |
| ATOM | 4895 | C1 | INH | V | 1 | 7.611 | 37.434 | 69.286 | 1.00 | 36.93 |
| ATOM | 4896 | C7 | INH | V | 1 | 8.071 | 41.463 | 67.833 | 1.00 | 32.28 |
| ATOM | 4897 | O1 | INH | V | 1 | 8.288 | 41.443 | 66.485 | 1.00 | 37.06 |
| ATOM | 4898 | C8 | INH | V | 1 | 9.584 | 41.740 | 66.129 | 1.00 | 32.34 |
| ATOM | 4899 | C9 | INH | V | 1 | 9.825 | 42.911 | 65.416 | 1.00 | 31.03 |
| ATOM | 4900 | C10 | INH | V | 1 | 11.127 | 43.216 | 65.023 | 1.00 | 33.64 |
| ATOM | 4901 | C11 | INH | V | 1 | 12.194 | 42.381 | 65.339 | 1.00 | 31.88 |
| ATOM | 4902 | C12 | INH | V | 1 | 11.928 | 41.198 | 66.028 | 1.00 | 31.07 |
| ATOM | 4903 | C13 | INH | V | 1 | 10.630 | 40.858 | 66.412 | 1.00 | 28.70 |
| ATOM | 4904 | C14 | INH | V | 1 | 13.587 | 42.710 | 64.882 | 1.00 | 32.51 |
| ATOM | 4905 | C15 | INH | V | 1 | 14.260 | 41.560 | 64.121 | 1.00 | 34.69 |
| ATOM | 4906 | C16 | INH | V | 1 | 15.683 | 41.849 | 63.754 | 1.00 | 28.88 |
| ATOM | 4907 | S1 | INH | V | 1 | 16.605 | 40.755 | 64.790 | 1.00 | 29.16 |
| ATOM | 4908 | N1 | INH | V | 1 | 13.497 | 40.805 | 63.099 | 1.00 | 30.69 |
| ATOM | 4909 | O | HOH | W | 1 | 44.463 | 49.888 | 77.523 | 1.00 | 46.91 |
| ATOM | 4910 | O | HOH | W | 2 | 13.469 | 27.803 | 78.018 | 1.00 | 20.07 |
| ATOM | 4911 | O | HOH | W | 3 | 4.225 | 69.721 | 58.393 | 1.00 | 27.76 |
| ATOM | 4912 | O | HOH | W | 4 | 15.603 | 28.826 | 61.823 | 1.00 | 22.81 |
| ATOM | 4913 | O | HOH | W | 5 | 22.862 | 26.624 | 42.874 | 1.00 | 53.05 |
| ATOM | 4914 | O | HOH | W | 6 | 8.423 | 46.452 | 57.584 | 1.00 | 32.22 |
| ATOM | 4915 | O | HOH | W | 7 | 17.904 | 46.550 | 68.524 | 1.00 | 31.91 |
| ATOM | 4916 | O | HOH | W | 8 | 22.979 | 45.895 | 83.716 | 1.00 | 39.37 |
| ATOM | 4917 | O | HOH | W | 9 | 17.707 | 39.158 | 55.643 | 1.00 | 25.27 |
| ATOM | 4918 | O | HOH | W | 10 | 12.439 | 36.303 | 59.209 | 1.00 | 31.46 |
| ATOM | 4919 | O | HOH | W | 11 | 17.367 | 62.730 | 50.320 | 1.00 | 37.74 |
| ATOM | 4920 | O | HOH | W | 12 | 42.823 | 52.642 | 90.552 | 1.00 | 53.80 |
| ATOM | 4921 | O | HOH | W | 13 | 34.337 | 45.508 | 97.419 | 1.00 | 57.99 |
| ATOM | 4922 | O | HOH | W | 14 | 6.726 | 27.119 | 48.459 | 1.00 | 62.29 |
| ATOM | 4923 | O | HOH | W | 15 | −0.093 | 30.159 | 71.746 | 1.00 | 29.96 |
| ATOM | 4924 | O | HOH | W | 16 | −19.673 | 44.016 | 58.682 | 1.00 | 58.64 |
| ATOM | 4925 | O | HOH | W | 17 | 16.563 | 26.790 | 80.837 | 1.00 | 38.62 |
| ATOM | 4926 | O | HOH | W | 18 | 10.281 | 35.677 | 88.518 | 1.00 | 26.01 |
| ATOM | 4927 | O | HOH | W | 19 | 20.973 | 35.691 | 44.774 | 1.00 | 49.50 |
| ATOM | 4928 | O | HOH | W | 20 | 0.996 | 19.571 | 53.713 | 1.00 | 67.39 |
| ATOM | 4929 | O | HOH | W | 21 | 20.424 | 37.014 | 85.845 | 1.00 | 39.54 |
| ATOM | 4930 | O | HOH | W | 22 | −2.498 | 35.905 | 53.781 | 1.00 | 51.70 |
| ATOM | 4931 | O | HOH | W | 23 | 39.807 | 49.718 | 92.595 | 1.00 | 37.39 |
| ATOM | 4932 | O | HOH | W | 24 | 16.431 | 58.267 | 93.127 | 1.00 | 47.45 |
| ATOM | 4933 | O | HOH | W | 25 | 6.935 | 45.104 | 66.012 | 1.00 | 18.12 |
| ATOM | 4934 | O | HOH | W | 26 | 40.479 | 54.713 | 100.253 | 1.00 | 28.72 |
| ATOM | 4935 | O | HOH | W | 27 | 22.369 | 40.324 | 67.919 | 1.00 | 46.36 |
| ATOM | 4936 | O | HOH | W | 28 | 37.289 | 49.457 | 68.016 | 1.00 | 61.37 |
| ATOM | 4937 | O | HOH | W | 29 | 2.611 | 35.015 | 55.709 | 1.00 | 24.45 |
| ATOM | 4938 | O | HOH | W | 30 | 41.088 | 62.590 | 98.644 | 1.00 | 65.38 |
| ATOM | 4939 | O | HOH | W | 31 | 17.369 | 55.024 | 87.465 | 1.00 | 24.22 |
| ATOM | 4940 | O | HOH | W | 32 | 25.433 | 20.198 | 55.692 | 1.00 | 44.61 |

TABLE 9-continued

Structure coordinates of LTA₄ hydrolase-thiolamine complex
(The amino acid sequence set forth as residues 1-610 below correspond to SEQ ID NO:1.)

| ATOM | 4941 | O | HOH | W | 33 | 3.890 | 42.770 | 66.651 | 1.00 | 22.34 |
|---|---|---|---|---|---|---|---|---|---|---|
| ATOM | 4942 | O | HOH | W | 34 | 3.934 | 63.391 | 62.592 | 1.00 | 60.69 |
| ATOM | 4943 | O | HOH | W | 35 | 22.280 | 41.610 | 86.289 | 1.00 | 74.20 |
| ATOM | 4944 | O | HOH | W | 36 | 22.631 | 46.401 | 90.078 | 1.00 | 47.44 |
| ATOM | 4945 | O | HOH | W | 37 | 33.442 | 20.227 | 64.569 | 1.00 | 55.41 |
| ATOM | 4946 | O | HOH | W | 38 | 39.834 | 28.974 | 75.602 | 1.00 | 41.72 |
| ATOM | 4947 | O | HOH | W | 39 | 35.232 | 47.140 | 54.186 | 1.00 | 37.08 |
| ATOM | 4948 | O | HOH | W | 40 | 36.003 | 57.784 | 57.893 | 1.00 | 43.05 |
| ATOM | 4949 | O | HOH | W | 41 | 37.216 | 27.438 | 74.564 | 1.00 | 50.79 |
| ATOM | 4950 | O | HOH | W | 42 | 17.770 | 67.012 | 77.183 | 1.00 | 45.78 |
| ATOM | 4951 | O | HOH | W | 43 | 5.341 | 31.286 | 78.127 | 1.00 | 25.34 |
| ATOM | 4952 | O | HOH | W | 44 | 33.535 | 32.503 | 52.063 | 1.00 | 56.13 |
| ATOM | 4953 | O | HOH | W | 45 | 25.477 | 33.146 | 44.610 | 1.00 | 65.43 |
| ATOM | 4954 | O | HOH | W | 46 | 16.235 | 37.438 | 52.628 | 1.00 | 32.10 |
| ATOM | 4955 | O | HOH | W | 47 | 28.791 | 14.101 | 63.316 | 1.00 | 46.67 |
| ATOM | 4956 | O | HOH | W | 48 | 10.230 | 24.992 | 86.967 | 1.00 | 38.63 |
| ATOM | 4957 | O | HOH | W | 49 | 30.821 | 38.856 | 79.630 | 1.00 | 40.44 |
| ATOM | 4958 | O | HOH | W | 50 | 12.621 | 37.226 | 62.944 | 1.00 | 26.70 |
| ATOM | 4959 | O | HOH | W | 51 | 27.987 | 30.609 | 66.612 | 1.00 | 33.55 |
| ATOM | 4960 | O | HOH | W | 52 | 34.459 | 28.696 | 64.242 | 1.00 | 51.01 |
| ATOM | 4961 | O | HOH | W | 53 | 34.969 | 62.270 | 91.179 | 1.00 | 68.20 |
| ATOM | 4962 | O | HOH | W | 54 | 33.631 | 30.717 | 62.396 | 1.00 | 41.64 |
| ATOM | 4963 | O | HOH | W | 55 | 43.987 | 48.530 | 91.269 | 1.00 | 50.99 |
| ATOM | 4964 | O | HOH | W | 56 | 23.412 | 28.584 | 85.186 | 1.00 | 69.23 |
| ATOM | 4965 | O | HOH | W | 57 | 39.834 | 28.057 | 72.257 | 1.00 | 81.00 |
| ATOM | 4966 | O | HOH | W | 58 | 2.892 | 25.685 | 69.907 | 1.00 | 38.96 |
| ATOM | 4967 | O | HOH | W | 59 | 10.284 | 47.120 | 72.671 | 1.00 | 40.28 |
| ATOM | 4968 | O | HOH | W | 60 | 32.645 | 39.037 | 76.746 | 1.00 | 21.71 |
| ATOM | 4969 | O | HOH | W | 61 | 43.535 | 48.019 | 95.228 | 1.00 | 37.69 |
| ATOM | 4970 | O | HOH | W | 62 | 11.991 | 51.053 | 43.479 | 1.00 | 41.05 |
| ATOM | 4971 | O | HOH | W | 63 | 18.329 | 56.527 | 89.388 | 1.00 | 28.51 |
| ATOM | 4972 | O | HOH | W | 64 | 16.555 | 9.309 | 68.875 | 1.00 | 89.05 |
| ATOM | 4973 | O | HOH | W | 65 | 23.741 | 44.759 | 73.150 | 1.00 | 38.43 |
| ATOM | 4974 | O | HOH | W | 66 | 19.093 | 53.805 | 41.239 | 1.00 | 55.25 |
| ATOM | 4975 | O | HOH | W | 67 | 31.750 | 60.369 | 56.933 | 1.00 | 92.26 |
| ATOM | 4976 | O | HOH | W | 68 | 24.836 | 68.428 | 80.926 | 1.00 | 59.25 |
| ATOM | 4977 | O | HOH | W | 69 | −21.014 | 19.446 | 48.342 | 1.00 | 52.24 |
| ATOM | 4978 | O | HOH | W | 70 | 11.318 | 68.028 | 86.566 | 1.00 | 77.81 |
| ATOM | 4979 | O | HOH | W | 71 | 5.312 | 60.076 | 63.511 | 1.00 | 36.83 |
| ATOM | 4980 | O | HOH | W | 72 | 7.689 | 20.219 | 84.680 | 1.00 | 32.24 |
| ATOM | 4981 | O | HOH | W | 73 | 34.988 | 44.708 | 64.746 | 1.00 | 40.73 |
| ATOM | 4982 | O | HOH | W | 74 | 10.614 | 49.644 | 41.337 | 1.00 | 38.90 |
| ATOM | 4983 | O | HOH | W | 75 | 19.349 | 42.973 | 64.739 | 1.00 | 54.53 |
| ATOM | 4984 | O | HOH | W | 76 | 35.916 | 30.862 | 80.753 | 1.00 | 55.38 |
| ATOM | 4985 | O | HOH | W | 77 | 9.666 | 26.046 | 46.603 | 1.00 | 40.09 |
| ATOM | 4986 | O | HOH | W | 78 | −10.171 | 46.751 | 60.237 | 1.00 | 29.78 |
| ATOM | 4987 | O | HOH | W | 79 | 46.751 | 58.883 | 86.875 | 1.00 | 35.92 |
| ATOM | 4988 | O | HOH | W | 80 | 19.320 | 32.528 | 51.000 | 1.00 | 33.36 |
| ATOM | 4989 | O | HOH | W | 81 | 28.815 | 39.568 | 66.176 | 1.00 | 59.19 |
| ATOM | 4990 | O | HOH | W | 82 | 38.207 | 35.773 | 73.585 | 1.00 | 17.81 |
| ATOM | 4991 | O | HOH | W | 83 | 23.802 | 33.925 | 75.175 | 1.00 | 25.19 |
| ATOM | 4992 | O | HOH | W | 84 | 42.241 | 51.290 | 99.896 | 1.00 | 15.88 |
| ATOM | 4993 | O | HOH | W | 85 | 3.751 | 36.678 | 58.842 | 1.00 | 24.97 |
| ATOM | 4994 | O | HOH | W | 86 | −7.009 | 40.341 | 62.580 | 1.00 | 25.39 |
| ATOM | 4995 | O | HOH | W | 87 | 11.735 | 58.910 | 68.155 | 1.00 | 39.70 |
| ATOM | 4996 | O | HOH | W | 88 | 13.986 | 52.835 | 42.224 | 1.00 | 50.91 |
| ATOM | 4997 | O | HOH | W | 89 | 1.452 | 46.541 | 69.459 | 1.00 | 35.03 |
| ATOM | 4998 | O | HOH | W | 90 | −1.938 | 55.310 | 56.971 | 1.00 | 28.10 |
| ATOM | 4999 | O | HOH | W | 91 | 13.801 | 66.947 | 52.600 | 1.00 | 38.65 |
| ATOM | 5000 | O | HOH | W | 92 | 21.594 | 47.218 | 79.203 | 1.00 | 30.31 |
| ATOM | 5001 | O | HOH | W | 93 | 10.639 | 58.632 | 90.827 | 1.00 | 43.78 |
| ATOM | 5002 | O | HOH | W | 94 | 33.335 | 53.550 | 68.086 | 1.00 | 37.04 |
| ATOM | 5003 | O | HOH | W | 95 | −1.984 | 28.738 | 60.212 | 1.00 | 31.56 |
| ATOM | 5004 | O | HOH | W | 96 | −4.958 | 51.055 | 59.250 | 1.00 | 34.00 |
| ATOM | 5005 | O | HOH | W | 97 | 17.610 | 39.701 | 51.503 | 1.00 | 28.27 |
| ATOM | 5006 | O | HOH | W | 98 | 10.686 | 54.166 | 67.565 | 1.00 | 37.68 |
| ATOM | 5007 | O | HOH | W | 99 | 20.567 | 43.859 | 78.621 | 1.00 | 41.57 |
| ATOM | 5008 | O | HOH | W | 100 | 7.013 | 22.332 | 69.109 | 1.00 | 28.72 |
| ATOM | 5009 | O | HOH | W | 101 | 10.097 | 53.225 | 78.477 | 1.00 | 35.68 |
| ATOM | 5010 | O | HOH | W | 102 | 10.849 | 31.404 | 53.014 | 1.00 | 32.22 |
| ATOM | 5011 | O | HOH | W | 103 | 42.381 | 59.035 | 94.728 | 1.00 | 36.00 |
| ATOM | 5012 | O | HOH | W | 104 | 17.234 | 41.111 | 54.082 | 1.00 | 33.65 |
| ATOM | 5013 | O | HOH | W | 105 | 26.902 | 62.025 | 81.989 | 1.00 | 34.70 |
| ATOM | 5014 | O | HOH | W | 106 | −14.313 | 49.559 | 56.204 | 1.00 | 54.36 |
| ATOM | 5015 | O | HOH | W | 107 | 41.646 | 57.501 | 101.015 | 1.00 | 68.12 |
| ATOM | 5016 | O | HOH | W | 108 | 26.759 | 43.000 | 47.219 | 1.00 | 32.69 |

TABLE 9-continued

Structure coordinates of LTA₄ hydrolase-thiolamine complex
(The amino acid sequence set forth as residues 1-610 below correspond to SEQ ID NO:1.)

| ATOM | 5017 | O | HOH | W | 109 | 16.624 | 48.119 | 46.545 | 1.00 | 38.64 |
|---|---|---|---|---|---|---|---|---|---|---|
| ATOM | 5018 | O | HOH | W | 110 | 26.159 | 32.793 | 75.230 | 1.00 | 24.77 |
| ATOM | 5019 | O | HOH | W | 111 | 2.101 | 33.468 | 67.006 | 1.00 | 31.50 |
| ATOM | 5020 | O | HOH | W | 112 | 38.114 | 36.374 | 87.451 | 1.00 | 44.06 |
| ATOM | 5021 | O | HOH | W | 113 | 13.211 | 29.810 | 61.356 | 1.00 | 33.81 |
| ATOM | 5022 | O | HOH | W | 114 | −3.064 | 37.863 | 40.673 | 1.00 | 37.92 |
| ATOM | 5023 | O | HOH | W | 115 | 15.007 | 47.948 | 69.488 | 1.00 | 28.23 |
| ATOM | 5024 | O | HOH | W | 116 | 27.101 | 66.633 | 80.518 | 1.00 | 41.24 |
| ATOM | 5025 | O | HOH | W | 117 | 11.870 | 38.304 | 43.174 | 1.00 | 40.85 |
| ATOM | 5026 | O | HOH | W | 118 | −13.844 | 25.597 | 58.258 | 1.00 | 53.75 |
| ATOM | 5027 | O | HOH | W | 119 | 2.929 | 41.135 | 59.858 | 1.00 | 36.49 |
| ATOM | 5028 | O | HOH | W | 120 | 24.890 | 45.490 | 82.167 | 1.00 | 41.65 |
| ATOM | 5029 | O | HOH | W | 121 | 36.062 | 59.335 | 75.090 | 1.00 | 38.82 |
| ATOM | 5030 | O | HOH | W | 122 | −10.715 | 32.037 | 61.699 | 1.00 | 78.82 |
| ATOM | 5031 | O | HOH | W | 123 | −2.646 | 25.492 | 60.812 | 1.00 | 48.40 |
| ATOM | 5032 | O | HOH | W | 124 | −8.948 | 46.831 | 63.556 | 1.00 | 48.06 |
| ATOM | 5033 | O | HOH | W | 125 | −17.843 | 39.367 | 36.020 | 1.00 | 35.80 |
| ATOM | 5034 | O | HOH | W | 126 | 2.218 | 57.766 | 62.253 | 1.00 | 44.61 |
| ATOM | 5035 | O | HOH | W | 127 | 10.736 | 62.766 | 64.366 | 1.00 | 55.84 |
| ATOM | 5036 | O | HOH | W | 128 | 0.884 | 35.562 | 63.963 | 1.00 | 44.14 |
| ATOM | 5037 | O | HOH | W | 129 | 19.165 | 59.557 | 60.644 | 1.00 | 47.82 |
| ATOM | 5038 | O | HOH | W | 131 | 1.546 | 27.875 | 68.443 | 1.00 | 39.69 |
| ATOM | 5039 | O | HOH | W | 131 | 5.497 | 26.285 | 76.668 | 1.00 | 44.47 |
| ATOM | 5040 | O | HOH | W | 132 | 14.505 | 36.538 | 88.996 | 1.00 | 40.00 |
| ATOM | 5041 | O | HOH | W | 133 | 8.534 | 28.713 | 88.519 | 1.00 | 46.55 |
| ATOM | 5042 | O | HOH | W | 134 | 6.125 | 45.267 | 77.959 | 1.00 | 45.57 |
| ATOM | 5043 | O | HOH | W | 135 | 26.016 | 18.543 | 78.878 | 1.00 | 51.65 |
| ATOM | 5044 | O | HOH | W | 136 | 33.880 | 23.025 | 70.739 | 1.00 | 46.95 |
| ATOM | 5045 | O | HOH | W | 137 | 19.230 | 26.073 | 49.998 | 1.00 | 51.97 |
| ATOM | 5046 | O | HOH | W | 138 | 41.563 | 41.085 | 77.326 | 1.00 | 43.14 |
| ATOM | 5047 | O | HOH | W | 139 | 39.187 | 63.067 | 75.380 | 1.00 | 56.52 |
| ATOM | 5048 | O | HOH | W | 140 | 26.878 | 54.491 | 67.203 | 1.00 | 42.14 |
| ATOM | 5049 | O | HOH | W | 141 | 22.988 | 62.189 | 74.174 | 1.00 | 48.31 |
| ATOM | 5050 | O | HOH | W | 142 | 25.190 | 62.803 | 71.067 | 1.00 | 67.16 |
| ATOM | 5051 | O | HOH | W | 143 | 18.598 | 45.126 | 81.949 | 1.00 | 53.80 |
| ATOM | 5052 | O | HOH | W | 144 | 19.782 | 53.129 | 90.556 | 1.00 | 48.73 |
| ATOM | 5053 | O | HOH | W | 145 | 21.735 | 48.367 | 86.454 | 1.00 | 40.39 |
| ATOM | 5054 | O | HOH | W | 146 | 25.707 | 57.012 | 93.476 | 1.00 | 53.61 |
| ATOM | 5055 | O | HOH | W | 147 | 22.832 | 62.085 | 93.149 | 1.00 | 46.02 |
| ATOM | 5056 | O | HOH | W | 148 | 25.725 | 67.203 | 89.990 | 1.00 | 75.23 |
| ATOM | 5057 | O | HOH | W | 149 | 10.773 | 53.653 | 85.697 | 1.00 | 50.65 |
| ATOM | 5058 | O | HOH | W | 150 | 4.221 | 58.449 | 86.608 | 1.00 | 49.23 |
| ATOM | 5059 | O | HOH | W | 151 | 7.790 | 72.096 | 84.410 | 1.00 | 51.10 |
| ATOM | 5060 | O | HOH | W | 152 | 2.387 | 58.282 | 67.835 | 1.00 | 33.29 |
| ATOM | 5061 | O | HOH | W | 153 | 0.921 | 49.551 | 69.095 | 1.00 | 59.60 |
| ATOM | 5062 | O | HOH | W | 154 | 8.722 | 45.171 | 71.561 | 1.00 | 46.56 |
| ATOM | 5063 | O | HOH | W | 155 | 6.422 | 47.947 | 81.081 | 1.00 | 57.56 |
| ATOM | 5064 | O | HOH | W | 156 | 15.936 | 56.908 | 55.129 | 1.00 | 43.33 |
| ATOM | 5065 | O | HOH | W | 157 | 3.032 | 19.635 | 62.453 | 1.00 | 80.38 |
| ATOM | 5066 | O | HOH | W | 158 | −4.228 | 58.058 | 47.057 | 1.00 | 39.66 |
| ATOM | 5067 | O | HOH | W | 159 | 1.197 | 41.002 | 78.942 | 1.00 | 57.22 |
| ATOM | 5068 | O | HOH | W | 160 | 1.259 | 43.651 | 68.100 | 1.00 | 37.94 |
| ATOM | 5069 | O | HOH | W | 161 | 25.799 | 64.833 | 56.690 | 1.00 | 38.96 |
| ATOM | 5070 | O | HOH | W | 162 | −11.853 | 45.054 | 45.070 | 1.00 | 38.38 |
| ATOM | 5071 | O | HOH | W | 163 | 40.159 | 31.033 | 78.548 | 1.00 | 75.36 |
| ATOM | 5072 | O | HOH | W | 164 | 21.477 | 20.377 | 79.349 | 1.00 | 35.96 |
| ATOM | 5073 | O | HOH | W | 165 | 26.347 | 44.558 | 72.803 | 1.00 | 42.21 |
| ATOM | 5074 | O | HOH | W | 166 | 16.446 | 61.207 | 59.687 | 1.00 | 39.70 |
| ATOM | 5075 | O | HOH | W | 167 | 27.695 | 64.216 | 82.410 | 1.00 | 44.71 |
| ATOM | 5076 | O | HOH | W | 168 | −2.998 | 57.511 | 34.738 | 1.00 | 45.35 |
| ATOM | 5077 | O | HOH | W | 169 | 6.608 | 51.527 | 60.826 | 1.00 | 39.48 |
| ATOM | 5078 | O | HOH | W | 170 | 31.104 | 28.934 | 81.337 | 1.00 | 43.19 |
| ATOM | 5079 | O | HOH | W | 171 | 10.135 | 28.233 | 45.533 | 1.00 | 41.24 |
| ATOM | 5080 | O | HOH | W | 172 | 8.201 | 43.960 | 75.322 | 1.00 | 37.71 |
| ATOM | 5081 | O | HOH | W | 173 | 13.799 | 66.601 | 85.597 | 1.00 | 34.74 |
| ATOM | 5082 | O | HOH | W | 174 | 16.664 | 53.670 | 65.006 | 1.00 | 43.69 |
| ATOM | 5083 | O | HOH | W | 175 | 18.301 | 47.296 | 43.793 | 1.00 | 45.84 |
| ATOM | 5084 | O | HOH | W | 176 | 11.717 | 61.868 | 52.648 | 1.00 | 34.93 |
| ATOM | 5085 | O | HOH | W | 177 | 29.516 | 23.822 | 76.838 | 1.00 | 51.50 |
| ATOM | 5086 | O | HOH | W | 178 | 39.940 | 60.509 | 78.535 | 1.00 | 46.33 |
| ATOM | 5087 | O | HOH | W | 179 | −1.803 | 44.974 | 37.278 | 1.00 | 52.56 |
| ATOM | 5088 | O | HOH | W | 180 | 7.343 | 47.305 | 65.468 | 1.00 | 47.27 |
| ATOM | 5089 | O | HOH | W | 181 | 17.912 | 15.338 | 81.793 | 1.00 | 50.08 |
| ATOM | 5090 | O | HOH | W | 182 | −4.631 | 55.917 | 82.183 | 1.00 | 65.36 |
| ATOM | 5091 | O | HOH | W | 183 | 32.973 | 42.656 | 86.667 | 1.00 | 43.97 |

TABLE 9-continued

Structure coordinates of LTA$_4$ hydrolase-thiolamine complex
(The amino acid sequence set forth as residues 1-610 below correspond to SEQ ID NO:1.)

| ATOM | 5092 | O | HOH | W | 184 | −1.834 | 36.784 | 71.040 | 1.00 | 45.10 |
|---|---|---|---|---|---|---|---|---|---|---|
| ATOM | 5093 | O | HOH | W | 185 | −4.519 | 34.633 | 71.838 | 1.00 | 43.99 |
| ATOM | 5094 | O | HOH | W | 186 | 4.518 | 68.554 | 71.661 | 1.00 | 46.99 |
| ATOM | 5095 | O | HOH | W | 187 | 2.774 | 37.503 | 61.490 | 1.00 | 45.81 |
| ATOM | 5096 | O | HOH | W | 188 | 31.770 | 43.526 | 51.410 | 1.00 | 58.02 |
| ATOM | 5097 | O | HOH | W | 189 | 5.471 | 43.861 | 38.891 | 1.00 | 49.43 |
| ATOM | 5098 | O | HOH | W | 190 | 11.934 | 58.219 | 70.811 | 1.00 | 49.96 |
| ATOM | 5099 | O | HOH | W | 191 | 33.112 | 26.203 | 70.484 | 1.00 | 60.03 |
| ATOM | 5100 | O | HOH | W | 192 | 30.914 | 43.017 | 70.613 | 1.00 | 73.23 |
| ATOM | 5101 | O | HOH | W | 193 | 0.400 | 39.300 | 39.714 | 1.00 | 65.37 |
| ATOM | 5102 | O | HOH | W | 194 | 48.247 | 56.159 | 86.370 | 1.00 | 60.09 |
| ATOM | 5103 | O | HOH | W | 195 | 12.359 | 59.992 | 62.698 | 1.00 | 53.57 |
| ATOM | 5104 | O | HOH | W | 196 | 11.149 | 17.504 | 78.264 | 1.00 | 54.43 |
| ATOM | 5105 | O | HOH | W | 197 | −4.284 | 31.953 | 60.991 | 1.00 | 47.12 |
| ATOM | 5106 | O | HOH | W | 198 | 29.888 | 35.624 | 82.772 | 1.00 | 52.16 |
| ATOM | 5107 | O | HOH | W | 199 | 14.388 | 39.115 | 89.656 | 1.00 | 47.93 |
| ATOM | 5108 | O | HOH | W | 200 | −8.529 | 51.475 | 47.745 | 1.00 | 61.00 |
| ATOM | 5109 | O | HOH | W | 201 | −15.572 | 53.338 | 52.008 | 1.00 | 72.42 |
| ATOM | 5110 | O | HOH | W | 202 | 24.319 | 38.590 | 87.128 | 1.00 | 50.03 |
| ATOM | 5111 | O | HOH | W | 203 | 25.366 | 70.670 | 82.839 | 1.00 | 49.01 |
| ATOM | 5112 | O | HOH | W | 204 | 18.531 | 27.749 | 86.236 | 1.00 | 48.64 |
| ATOM | 5113 | O | HOH | W | 205 | 21.694 | 20.030 | 81.796 | 1.00 | 49.04 |
| ATOM | 5114 | O | HOH | W | 206 | 23.953 | 47.993 | 67.580 | 1.00 | 40.39 |
| ATOM | 5115 | O | HOH | W | 207 | 22.012 | 40.217 | 90.228 | 1.00 | 42.29 |
| ATOM | 5116 | O | HOH | W | 208 | 16.197 | 45.094 | 43.427 | 1.00 | 48.00 |
| ATOM | 5117 | O | HOH | W | 209 | 21.019 | 68.985 | 84.382 | 1.00 | 56.50 |
| ATOM | 5118 | O | HOH | W | 210 | −7.134 | 33.015 | 71.591 | 1.00 | 56.31 |
| ATOM | 5119 | O | HOH | W | 211 | 40.843 | 44.050 | 89.284 | 1.00 | 43.07 |
| ATOM | 5120 | O | HOH | W | 212 | 20.374 | 14.856 | 56.642 | 1.00 | 50.07 |
| ATOM | 5121 | O | HOH | W | 213 | 12.723 | 46.277 | 73.748 | 1.00 | 59.15 |
| ATOM | 5122 | O | HOH | W | 214 | 8.956 | 43.704 | 58.706 | 1.00 | 45.56 |
| ATOM | 5123 | O | HOH | W | 215 | −2.433 | 36.012 | 80.232 | 1.00 | 54.12 |
| ATOM | 5124 | O | HOH | W | 216 | 5.257 | 25.271 | 55.914 | 1.00 | 53.23 |
| ATOM | 5125 | O | HOH | W | 217 | 13.354 | 64.403 | 53.862 | 1.00 | 47.27 |
| ATOM | 5126 | O | HOH | W | 218 | 30.477 | 42.517 | 67.472 | 1.00 | 48.17 |
| ATOM | 5127 | O | HOH | W | 219 | 14.139 | 47.479 | 76.123 | 1.00 | 79.04 |
| ATOM | 5128 | O | HOH | W | 220 | 0.829 | 29.563 | 50.769 | 1.00 | 48.10 |
| ATOM | 5129 | O | HOH | W | 221 | 32.979 | 51.667 | 96.624 | 1.00 | 51.30 |
| ATOM | 5130 | O | HOH | W | 222 | 14.677 | 45.948 | 71.756 | 1.00 | 52.31 |
| ATOM | 5131 | O | HOH | W | 223 | 33.890 | 24.505 | 58.094 | 1.00 | 43.65 |
| ATOM | 5132 | O | HOH | W | 224 | 17.853 | 9.519 | 65.560 | 1.00 | 55.94 |
| ATOM | 5133 | O | HOH | W | 225 | 37.794 | 31.473 | 62.305 | 1.00 | 50.38 |
| ATOM | 5134 | O | HOH | W | 226 | 29.206 | 50.335 | 62.673 | 1.00 | 45.43 |
| ATOM | 5135 | O | HOH | W | 227 | 4.932 | 48.808 | 63.354 | 1.00 | 42.45 |
| ATOM | 5136 | O | HOH | W | 228 | 18.933 | 59.070 | 55.899 | 1.00 | 50.29 |
| ATOM | 5137 | O | HOH | W | 229 | 13.849 | 18.833 | 83.641 | 1.00 | 55.89 |
| ATOM | 5138 | O | HOH | W | 230 | 25.919 | 46.022 | 68.076 | 1.00 | 35.63 |
| ATOM | 5139 | O | HOH | W | 231 | 27.565 | 65.098 | 75.153 | 1.00 | 73.11 |
| ATOM | 5140 | O | HOH | W | 232 | 27.128 | 39.012 | 68.497 | 1.00 | 40.77 |
| ATOM | 5141 | O | HOH | W | 233 | 40.706 | 52.468 | 74.641 | 1.00 | 51.60 |
| ATOM | 5142 | O | HOH | W | 234 | 21.689 | 65.312 | 58.080 | 1.00 | 66.72 |
| ATOM | 5143 | O | HOH | W | 235 | 9.121 | 17.615 | 59.271 | 1.00 | 51.98 |
| ATOM | 5144 | O | HOH | W | 236 | 17.931 | 36.565 | 88.091 | 1.00 | 54.77 |
| ATOM | 5145 | O | HOH | W | 237 | 33.843 | 36.707 | 52.576 | 1.00 | 61.60 |
| ATOM | 5146 | O | HOH | W | 238 | −3.693 | 50.074 | 63.986 | 1.00 | 43.64 |
| ATOM | 5147 | O | HOH | W | 239 | 44.272 | 44.279 | 81.461 | 1.00 | 69.21 |
| ATOM | 5148 | O | HOH | W | 240 | 2.092 | 28.868 | 52.894 | 1.00 | 54.01 |
| ATOM | 5149 | O | HOH | W | 241 | 8.309 | 33.518 | 71.442 | 1.00 | 68.05 |
| ATOM | 5150 | O | HOH | W | 242 | 1.051 | 31.947 | 69.204 | 1.00 | 52.88 |
| ATOM | 5151 | O | HOH | W | 243 | 44.255 | 51.162 | 96.650 | 1.00 | 20.00 |
| ATOM | 5152 | O | HOH | W | 244 | 16.173 | 45.408 | 46.636 | 1.00 | 20.00 |
| ATOM | 5153 | O | HOH | W | 245 | 41.130 | 50.734 | 97.991 | 1.00 | 20.00 |
| ATOM | 5154 | O | HOH | W | 246 | 36.912 | 36.263 | 75.911 | 1.00 | 20.00 |
| ATOM | 5155 | O | HOH | W | 247 | −17.107 | 27.146 | 54.728 | 1.00 | 20.00 |
| ATOM | 5156 | O | HOH | W | 248 | 24.078 | 46.307 | 79.123 | 1.00 | 20.00 |
| ATOM | 5157 | O | HOH | W | 249 | −12.250 | 47.964 | 61.593 | 1.00 | 20.00 |
| ATOM | 5158 | O | HOH | W | 250 | 35.804 | 51.343 | 51.682 | 1.00 | 20.00 |
| ATOM | 5159 | O | HOH | W | 251 | 25.537 | 59.940 | 69.750 | 1.00 | 20.00 |
| ATOM | 5160 | O | HOH | W | 252 | 0.539 | 55.427 | 62.088 | 1.00 | 20.00 |
| END | | | | | | | | | | |

The invention claimed is:

1. A method of identifying compounds that bind to a leukotriene $A_4$ (LTA$_4$) hydrolase comprising the amino acid sequence of SEQ ID NO: 1, the method comprising the steps of:
   (a) crystallizing a purified LTA$_4$ hydrolase in the presence of bestatin to form a co-crystal of LTA$_4$ hydrolase and bestatin, wherein crystallization is performed by liquid-liquid diffusion in a capillary using equal volumes of a buffer:
   enzyme solution consisting of:
   i) a buffer solution consisting of 28% PEG8000, 0.1 M Na-acetate, 0.1 M imidazole at a pH of 6.8 and with 5 mM YbCl$_3$ as an additive; and
   ii) an enzyme solution consisting of 5 mg/ml LTA$_4$ hydrolase comprising the amino acid sequence of SEQ ID NO:1 in 10 mM Tris-HCl at a pH of 8, supplemented with 1 mM bestatin; wherein the crystallization results in a LTA$_4$ hydrolase crystal having the space group P2$_1$2$_1$2 and the unit cell dimensions a=67.59 Å, b=133.51 Å, and c=83.40 Å and wherein α=β=γ=90°;
   (b) determining the atomic coordinates of LTA$_4$ hydrolase from the co-crystal obtained in step (a); and
   (c) screening the atomic coordinates of a set of candidate compounds against the atomic coordinates obtained in step (b) to identify compounds that bind to the LTA$_4$ hydrolase.

2. The method of claim 1, wherein the LTA$_4$ hydrolase is purified by adsorption chromatography on hydroxyapatite and anion-exchange chromatography.

3. The method of claim 1, wherein the atomic coordinates obtained in step (b) correspond to the atomic coordinates defining atom 1 to atom 4876 as set forth in Table 9.

4. A method of identifying an inhibitor of LTA$_4$ hydrolase comprising the amino acid sequence of SEQ ID NO:1, the method comprising the steps of:
   (a) crystallizing a purified LTA$_4$ hydrolase in the presence of bestatin to form a co-crystal of LTA$_4$ hydrolase and bestatin and thereafter determining its three-dimensional structure, wherein the crystallization is performed by liquid-liquid diffusion in a capillary using equal volumes of a buffer: enzyme solution consisting of:

i) a buffer solution consisting of 28% PEG8000, 0.1 M Na-acetate, 0.1 M imidazole at a pH of 6.8 and with 5 mM YbCl$_3$ as an additive; and ii) an enzyme solution consisting of 5 mg/ml LTA$_4$ hydrolase comprising the amino acid sequence of SEQ ID NO:1 in 10 mM Tris-HCl at a pH of 8, supplemented with 1 mM bestatin; wherein the crystallization results in a LTA$_4$ hydrolase crystal having the space group P2$_1$2$_1$2 and the unit cell dimensions a=67.59 Å, b=133.51 Å, and c=83.40 Å and wherein α=β=γ=90°; and iii) determining the atomic coordinates of the LTA$_4$ hydrolase from the co-crystal;

(b) identifying at least one potential inhibitor that is at least in part complementary to the LTA$_4$ hydrolase by the use of the atomic coordinates of the LTA$_4$ hydrolase crystal;

(c) soaking a co-crystallized LTA$_4$ hydrolase as obtained in step (a) with a solution of the potential inhibitor identified in step (b) to obtain a complex of the crystal of said LTA$_4$ hydrolase and said potential inhibitor; and (d) determining the atomic coordinates of the crystal complex of LTA$_4$ hydrolase and said potential inhibitor in step (c) to determine the structure thereof, thereby identifying the potential inhibitor as an inhibitor of LTA$_4$ hydrolase.

5. The method of claim 4, wherein the LTA$_4$ hydrolase is purified by adsorption chromatography on hydroxyapatite and anion-exchange chromatography.

6. The method of claim 4, wherein the atomic coordinates obtained in step (a) correspond to the atomic coordinates defining atom 1 to atom 4876 as set forth in Table 9.

7. The method of claim 4, further comprising the step of refining the structure of the potential inhibitor obtained in step (d) via computer modeling using this refined data and repeating steps (b)-(d).

* * * * *